US012636360B2

(12) United States Patent
Graham et al.

(10) Patent No.: US 12,636,360 B2
(45) Date of Patent: May 26, 2026

(54) MUMPS AND MEASLES VIRUS IMMUNOGENS AND THEIR USE

(71) Applicant: The United States of America, as represented by the Secretary, Department of Health and Human Services, Bethesda, MD (US)

(72) Inventors: Barney Graham, Smyrna, GA (US); Guillaume Stewart-Jones, Cambridge, MA (US); Rebecca J. Loomis, Philadelphia, PA (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 1009 days.

(21) Appl. No.: 17/784,605

(22) PCT Filed: Dec. 11, 2020

(86) PCT No.: PCT/US2020/064619
§ 371 (c)(1),
(2) Date: Jun. 10, 2022

(87) PCT Pub. No.: WO2021/119497
PCT Pub. Date: Jun. 17, 2021

(65) Prior Publication Data
US 2023/0053555 A1 Feb. 23, 2023

Related U.S. Application Data

(60) Provisional application No. 62/946,902, filed on Dec. 11, 2019.

(51) Int. Cl.
| | |
|---|---|
| *A61K 39/165* | (2006.01) |
| *A61P 31/14* | (2006.01) |
| *C07K 14/12* | (2006.01) |
| *A61K 39/00* | (2006.01) |

(52) U.S. Cl.
CPC ............ *A61K 39/165* (2013.01); *A61P 31/14* (2018.01); *C07K 14/12* (2013.01); *A61K 2039/575* (2013.01); *C12N 2760/18032* (2013.01)

(58) Field of Classification Search
None
See application file for complete search history.

(56) References Cited

FOREIGN PATENT DOCUMENTS

| | | |
|---|---|---|
| JP | 2016202113 A | 12/2016 |
| WO | WO 94/25600 A1 | 11/1994 |
| WO | WO 1995/014083 A1 | 5/1995 |
| WO | WO 00/18929 A2 | 4/2000 |
| WO | WO 2012/116253 A2 | 8/2012 |
| WO | WO 2014/160463 A1 | 10/2014 |
| WO | WO 2016/103238 A1 | 6/2016 |
| WO | WO 2017/172890 A1 | 10/2017 |
| WO | WO 2018/081289 A2 | 5/2018 |
| WO | WO 2019/211630 A2 | 11/2019 |

OTHER PUBLICATIONS

Herren et al., "Regulatory Role of the Morbillivirus Attachment Protein Head-to- Stalk linker Module in Membrane Fusion Triggering," *Journal of Virology*, 92(18): 1-20, 2018.
Loomis et al., "Structure-based design of glycoprotein subunit vaccines for mumps," *Proceedings of the National Academy of Sciences of the United States of America* 121(47):e2404053121 E-Pub Nov. 11, 2024.
Bester, "Measles and Measles Vaccination: A Review," *JAMA Pediatr. 170.12*: 1209-1215, Dec. 2016.
Cardemil et al., "Effectiveness of a third dose of MMR vaccine for mumps outbreak control," *N Eng J Med. 377.10*: 947-956, Sep. 2017.
Dayan et al., "Recent Resurgence of Mumps in the United States," *N Engl J Med. 358.15*: 1580-1589, Apr. 2008.
Fiebelkorn et al., "Mumps antibody response in young adults after a third dose of Measles-Mumps-Rubella Vaccine," *OFID 1.3*: of4094, 2017 (9 pages).
Latner et al., "Estimates of mumps seroprevalence may be influenced by antibody specificity and serologic method," *Clin Vaccine Immunol. 21.3*: 286-297, Mar. 2014.
Liu et al., "Structural characterization of Mumps virus fusion protein core," *Biochemical and Biophysical Research Communications 348*: 916-922, 2006.
Mathieu et al., "Prevention of Measles Virus Infection by Intranasal Delivery of Fusion Inhibitor Peptides," *J Virol. 89.2*: 1143-1155, Jan. 2015.
(Continued)

*Primary Examiner* — Stacy B Chen
(74) *Attorney, Agent, or Firm* — Klarquist Sparkman, LLP

(57) ABSTRACT

Embodiments of immunogens comprising a recombinant Mumps (MuV) F ectodomain trimer stabilized in a prefusion conformation or a recombinant Measles (MeV) F ectodomain trimer stabilized in a prefusion conformation are provided. Also provided are embodiments of immunogens comprising chimeric proteins comprising the recombinant MuV or MeV F ectodomain trimer and one or more MuV HN or MeV H ectodomains. Also disclosed are nucleic acids encoding the immunogens and methods of their production. Methods for inducing an immune response in a subject by administering a disclosed immunogen to the subject are also provided. In some embodiments, the immune response treats or inhibits MuV and/or MeV infection in a subject.

35 Claims, 17 Drawing Sheets
Specification includes a Sequence Listing.

(56)          References Cited

OTHER PUBLICATIONS

May et al., "Emergent Lineages of Mumps Virus Suggest the Need for a Polyvalent Vaccine," *Int J Infect Dis. 66*: 1-4, Jan. 2018.

Plotkin, "Third Dose of MMR Vaccine for Mumps Control," *N Engl J Med. 377.24*: 2403, Dec. 2017.

Rasheed et al., "Decreased Humoral Immunity to Mumps in Young Adults Immunized with MMR Vaccine in Childhood," *Proc Natl Acad Sci. 116.38*: 19071-19076, Sep. 2019.

Rey and Lok, "Common features of enveloped viruses and implications for immunogen design for next-generation vaccines," *Cell 172*: 1319-1334, Mar. 2018.

Rubin et al., "Antibody induced by immunization with the Jeryl Lynn Mumps Vaccine strain effectively neutralizes a heterologous wild-type mumps virus associated with a large outbreak," *J Infectious Diseases* 198: 508-515, Aug. 2008.

Satoh et al., "A Residue Located at the Junction of the Head and Stalk Regions of Measles Virus Fusion Protein Regulates Membrane Fusion by Controlling Conformational Stability," *J Gen Virol. 98.2*: 143-154, Feb. 2017.

Shah et al., "Mumps Outbreak in a Highly Vaccinated University-Affiliated Setting Before and After a Measles-Mumps-Rubella Vaccination Campaign-Iowa, Jul. 2015-May 2016," *Clin Infect Dis. 66.1*; 81-88, Jan. 2018.

Stewart-Jones et al., "Structure-based design of a quadrivalent fusion glycoprotein vaccine for human parainfluenza virus types 1-4," *Proc Natl Acad Sci. 115.48*: 12265-12270, Nov. 2018.

Veneti et al. "Large Outbreak of Mumps Virus Genotype G Among Vaccinated Students in Norway, 2015 to 2016," *Euro Surveil. 23.38*: 1-9, Sep. 2018.

Welch et al., "Structure of the cleavage-activated prefusion form of the parainfluenza virus 5 fusion protein," *Proc Natl Acad Sci 109.41*: 16672-16677, Oct. 2012.

Xu et al., "Crystal structure of the pre-fusion Nipah virus fusion glycoprotein reveals a novel hexamer-of-trimers assembly," *PLOS Pathog. 11.12*: e1005322, Dec. 2015 (17 pages).

Zhang et al., "Canine distemper virus neutralization activity is low in human serum and it is sensitive to an amino acid substitution in the hemagglutinin protein," *Virology 482*: 218-22, 2015.

FIG. 1A
| Yield (mg/L) / % Prefusion | 483-GCN4 | 476-GCN4 | 469-GCN4 |
|---|---|---|---|
| A163C-V235C | 0 / n/a | 0 / n/a | 0 / n/a |
| V206C-A223C | 15.5 / 75 | 4.82 / 100 | 2.45 / 60 |
| N86C-A215C | 0.43 / 100 | 1.48 / 85 | 2.0 / 10 |
| P209C-P214C | 0.68 / 100 | 0.08 / 100 | 0 / n/a |
| K155C-L161C | 1.75 / 20 | 0.32 / 25 | 0.67 / 0 |
| V165C-M231C | 4.47 / 65 | 0.52 / 100 | 0.62 / 20 |
| I221C-M255C | 7.25 / 10 | 0.92 / 10 | 0.1 / 10 |
| S184P | 0 / n/a | 0 / n/a | 0 / n/a |
FIG. 1B
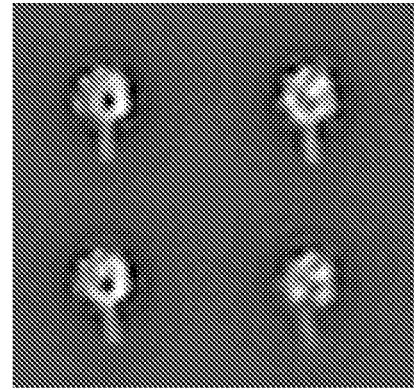
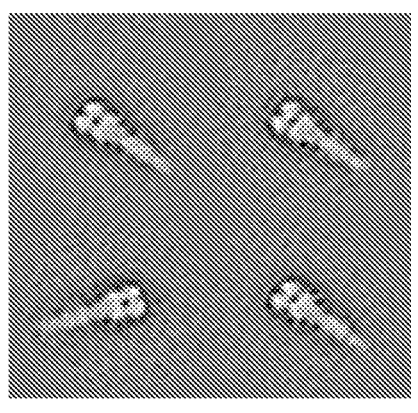

>5 Å movement to postfusion
<5 Å movement to postfusion

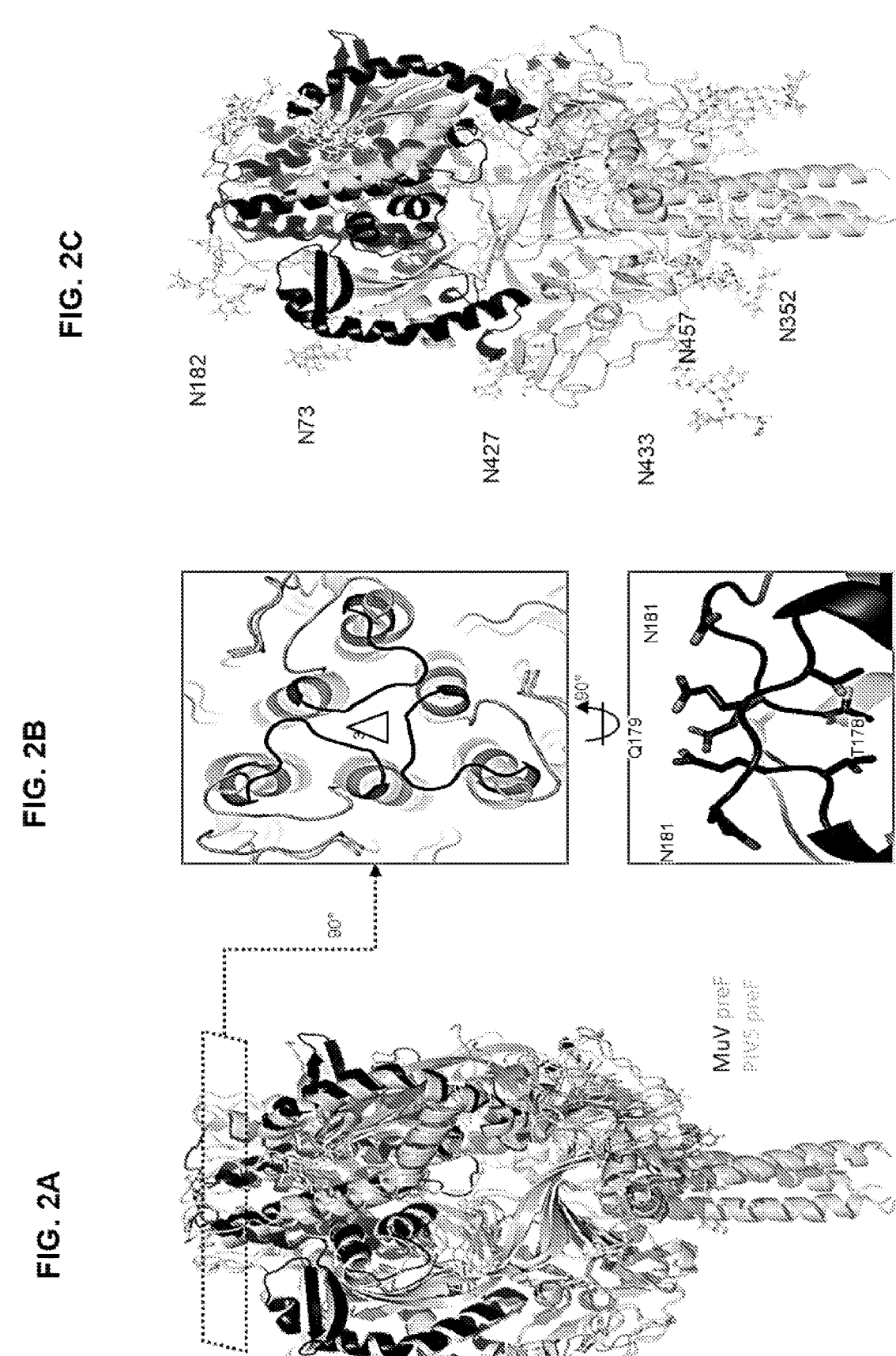

MeV 48C-284C          MeV 212C-236C

MeV 141C-270C          MeV postF-fd

MeV R165C-M171C

MeV H dimer

MeV H trimer

MuV HN trimer

MuV preF-MeV H

SEQUENCE LISTING

<160> NUMBER OF SEQ ID NOS: 106

<210> SEQ ID NO 1
<211> LENGTH: 538
<212> TYPE: PRT

<213> ORGANISM: Mumps virus

<400> SEQUENCE: 1

```
Met Lys Ala Phe Ser Val Thr Cys Leu Gly Phe Ala Val Phe Ser Ser
1               5                   10                  15

Ser Ile Cys Val Asn Ile Asn Ile Leu Gln Gln Ile Gly Tyr Ile Lys
            20                  25                  30

Gln Gln Val Arg Gln Leu Ser Tyr Tyr Ser Gln Ser Ser Ser Ser Tyr
            35                  40                  45

Ile Val Val Lys Leu Leu Pro Asn Ile Gln Pro Thr Asp Asn Ser Cys
        50                  55                  60

Glu Phe Lys Ser Val Thr Gln Tyr Asn Lys Thr Leu Ser Asn Leu Leu
65                  70                  75                  80

Leu Pro Ile Ala Glu Asn Ile Asn Asn Ile Ala Ser Pro Ser Pro Gly
                85                  90                  95

Ser Arg Arg His Lys Arg Phe Ala Gly Ile Ala Ile Gly Ile Ala Ala
            100                 105                 110

Leu Gly Val Ala Thr Ala Ala Gln Val Thr Ala Ala Val Ser Leu Val
        115                 120                 125

Gln Ala Gln Thr Asn Ala Arg Ala Ile Ala Ala Met Lys Asn Ser Ile
        130                 135                 140

Gln Ala Thr Asn Arg Ala Ile Phe Glu Val Lys Glu Gly Thr Gln Gln
145                 150                 155                 160

Leu Ala Ile Ala Val Gln Ala Ile Gln Asp His Ile Asn Thr Ile Met
                165                 170                 175

Asn Thr Gln Leu Asn Asn Met Ser Cys Gln Ile Leu Asp Asn Gln Leu
            180                 185                 190

Ala Thr Tyr Leu Gly Leu Tyr Leu Thr Glu Leu Thr Thr Val Phe Gln
            195                 200                 205

Pro Gln Leu Ile Asn Pro Ala Leu Ser Pro Ile Ser Ile Gln Ala Leu
        210                 215                 220

Arg Ser Leu Leu Gly Ser Met Thr Pro Ala Val Val Gln Ala Thr Leu
225                 230                 235                 240

Ser Thr Ser Ile Ser Ala Ala Glu Ile Leu Ser Ala Gly Leu Met Glu
                245                 250                 255

Gly Gln Ile Val Ser Val Leu Leu Asp Glu Met Gln Met Ile Val Lys
            260                 265                 270

Ile Asn Ile Pro Thr Ile Val Thr Gln Ser Asn Ala Leu Val Ile Asp
        275                 280                 285

Phe Tyr Ser Ile Ser Ser Phe Ile Asn Asn Gln Glu Ser Ile Ile Gln
        290                 295                 300

Leu Pro Asp Arg Ile Leu Glu Ile Gly Asn Glu Gln Trp Ser Tyr Pro
305                 310                 315                 320

Ala Lys Asn Cys Lys Leu Thr Arg His His Ile Phe Cys Gln Tyr Asn
            325                 330                 335

Glu Ala Glu Arg Leu Ser Leu Glu Ser Lys Leu Cys Leu Ala Gly Asn
            340                 345                 350

Ile Ser Ala Cys Val Phe Ser Pro Ile Ala Gly Ser Tyr Met Arg Arg
            355                 360                 365

Phe Val Ala Leu Asp Gly Thr Ile Val Ala Asn Cys Arg Ser Leu Thr
        370                 375                 380

Cys Leu Cys Lys Ser Pro Ser Tyr Pro Ile Tyr Gln Pro Asp His His
385                 390                 395                 400
```

```
Ala Val Thr Thr Ile Asp Leu Thr Thr Cys Gln Thr Leu Ser Leu Asp
            405             410             415

Gly Leu Asp Phe Ser Ile Val Ser Leu Ser Asn Ile Thr Tyr Ala Glu
            420             425             430

Asn Leu Thr Ile Ser Leu Ser Gln Thr Ile Asn Thr Gln Pro Ile Asp
            435             440             445

Ile Ser Thr Glu Leu Ser Lys Val Asn Ala Ser Leu Gln Asn Ala Val
        450             455             460

Lys Tyr Ile Lys Glu Ser Asn His Gln Leu Gln Ser Val Ser Val Asn
465             470             475             480

Ser Lys Ile Gly Ala Ile Ile Val Ala Ala Leu Val Leu Ser Ile Leu
            485             490             495

Ser Ile Ile Ile Ser Leu Leu Phe Cys Cys Trp Ala Tyr Ile Ala Thr
            500             505             510

Lys Glu Ile Arg Arg Ile Asn Phe Lys Thr Asn His Ile Asn Thr Ile
            515             520             525

Ser Ser Ser Val Asp Asp Leu Ile Arg Tyr
        530             535

<210> SEQ ID NO 2
<211> LENGTH: 513
<212> TYPE: PRT
<213> ORGANISM: Artificial sequence
<220> FEATURE:
<223> OTHER INFORMATION: Recombinant F protein

<400> SEQUENCE: 2

Met Lys Ala Phe Ser Val Thr Cys Leu Ser Phe Ala Val Phe Ser Ser
1               5               10              15

Ser Ile Cys Val Asn Ile Asn Ile Leu Gln Gln Ile Gly Tyr Ile Lys
            20              25              30

Gln Gln Val Arg Gln Leu Ser Tyr Tyr Ser Gln Ser Ser Ser Ser Tyr
            35              40              45

Ile Val Val Lys Leu Leu Pro Asn Ile Gln Pro Thr Asp Asp Ser Cys
        50              55              60

Glu Phe Lys Ser Val Thr Gln Tyr Asn Lys Thr Leu Ser Asn Leu Leu
65              70              75              80

Leu Pro Ile Ala Glu Asn Ile Asn Asn Ile Ala Ser Pro Ser Pro Gly
            85              90              95

Ser Arg Arg His Gly Gly Gly Ala Gly Ile Ala Ile Gly Ile Ala Ala
            100             105             110

Leu Gly Val Ala Thr Ala Ala Gln Val Thr Ala Ala Val Ser Leu Val
            115             120             125

Gln Ala Gln Thr Asn Ala Arg Ala Ile Ala Ala Met Lys Asn Ser Ile
        130             135             140

Gln Ala Thr Asn Arg Ala Val Phe Glu Val Lys Glu Gly Thr Gln Gln
145             150             155             160

Leu Ala Cys Ala Val Gln Ala Ile Gln Asp His Ile Asn Thr Ile Met
            165             170             175

Asn Thr Gln Leu Asn Asn Met Ser Cys Gln Ile Leu Asp Asn Gln Leu
            180             185             190

Ala Thr Ser Leu Gly Leu Tyr Leu Thr Glu Leu Thr Thr Val Phe Gln
            195             200             205

Pro Gln Leu Thr Asn Pro Ala Leu Ser Pro Ile Ser Ile Gln Ala Leu
        210             215             220
```

-continued

```
Arg Ser Leu Leu Gly Ser Met Thr Pro Ala Cys Val Gln Ala Thr Leu
225             230                 235                 240

Ser Thr Ser Ile Ser Ala Ala Glu Ile Leu Ser Ala Gly Leu Met Glu
                245                 250                 255

Gly Gln Ile Ile Ser Val Leu Leu Asp Glu Met Gln Met Ile Val Lys
                260                 265                 270

Ile Asn Ile Pro Thr Ile Val Thr Gln Ser Asn Ala Leu Val Ile Asp
                275                 280                 285

Phe Tyr Ser Ile Ser Ser Phe Ile Asn Asn Gln Glu Ser Ile Ile Gln
        290                 295                 300

Leu Pro Asp Arg Ile Leu Glu Ile Gly Asn Glu Gln Trp Ser Tyr Pro
305                 310                 315                 320

Ala Lys Asn Cys Lys Leu Thr Arg His His Ile Phe Cys Gln Tyr Asn
                325                 330                 335

Glu Ala Glu Arg Leu Ser Leu Glu Ser Lys Leu Cys Leu Ala Gly Asn
                340                 345                 350

Ile Ser Ala Cys Val Phe Ser Pro Ile Ala Gly Ser Tyr Met Arg Arg
        355                 360                 365

Phe Val Ala Leu Asp Gly Thr Ile Val Ala Asn Cys Arg Ser Leu Thr
        370                 375                 380

Cys Leu Cys Lys Ser Pro Ser Tyr Pro Ile Tyr Gln Pro Asp His His
385                 390                 395                 400

Ala Val Thr Thr Ile Asp Leu Thr Ala Cys Gln Thr Leu Ser Leu Asp
                405                 410                 415

Gly Leu Asp Phe Ser Ile Val Ser Leu Ser Asn Ile Thr Tyr Ala Glu
                420                 425                 430

Asn Leu Thr Ile Ser Leu Ser Gln Thr Ile Asn Thr Gln Pro Ile Asp
                435                 440                 445

Ile Ser Thr Glu Leu Ser Lys Val Asn Ala Ser Leu Gln Asn Ala Val
        450                 455                 460

Lys Tyr Ile Lys Glu Ser Asn His Gln Leu Gln Ser Val Ser Val Asn
465                 470                 475                 480

Ser Lys Ile Ile Glu Asp Lys Ile Glu Glu Ile Leu Ser Lys Ile Tyr
                485                 490                 495

His Ile Glu Asn Glu Ile Ala Arg Ile Lys Lys Leu Ile Gly Glu Ala
                500                 505                 510

Pro
```

<210> SEQ ID NO 3
<211> LENGTH: 513
<212> TYPE: PRT
<213> ORGANISM: Artificial sequence
<220> FEATURE:
<223> OTHER INFORMATION: Recombinant F protein

<400> SEQUENCE: 3

```
Met Lys Ala Phe Ser Val Thr Cys Leu Ser Phe Ala Val Phe Ser Ser
1               5                   10                  15

Ser Ile Cys Val Asn Ile Asn Ile Leu Gln Gln Ile Gly Tyr Ile Lys
                20                  25                  30

Gln Gln Val Arg Gln Leu Ser Tyr Tyr Ser Gln Ser Ser Ser Ser Tyr
        35                  40                  45

Ile Val Val Lys Leu Leu Pro Asn Ile Gln Pro Thr Asp Asp Ser Cys
        50                  55                  60

Glu Phe Lys Ser Val Thr Gln Tyr Asn Lys Thr Leu Ser Asn Leu Leu
```

```
65                    70                   75                    80

Leu Pro Ile Ala Glu Asn Ile Asn Asn Ile Ala Ser Pro Ser Pro Gly
                85                   90                   95

Ser Arg Arg His Gly Gly Gly Ala Gly Ile Ala Ile Gly Ile Ala Ala
                100                  105                  110

Leu Gly Val Ala Thr Ala Ala Gln Val Thr Ala Ala Val Ser Leu Val
                115                  120                  125

Gln Ala Gln Thr Asn Ala Arg Ala Ile Ala Ala Met Lys Asn Ser Ile
    130                  135                  140

Gln Ala Thr Asn Arg Ala Val Phe Glu Val Lys Glu Gly Thr Gln Gln
145                  150                  155                  160

Leu Ala Ile Ala Val Gln Ala Ile Gln Asp His Ile Asn Thr Ile Met
                165                  170                  175

Asn Thr Gln Leu Asn Asn Met Ser Cys Gln Ile Leu Asp Asn Gln Leu
                180                  185                  190

Ala Thr Ser Leu Gly Leu Tyr Leu Thr Glu Leu Thr Thr Cys Phe Gln
                195                  200                  205

Pro Gln Leu Thr Asn Pro Ala Leu Ser Pro Ile Ser Ile Gln Cys Leu
    210                  215                  220

Arg Ser Leu Leu Gly Ser Met Thr Pro Ala Val Val Gln Ala Thr Leu
225                  230                  235                  240

Ser Thr Ser Ile Ser Ala Ala Glu Ile Leu Ser Ala Gly Leu Met Glu
                245                  250                  255

Gly Gln Ile Ile Ser Val Leu Leu Asp Glu Met Gln Met Ile Val Lys
                260                  265                  270

Ile Asn Ile Pro Thr Ile Val Thr Gln Ser Asn Ala Leu Val Ile Asp
                275                  280                  285

Phe Tyr Ser Ile Ser Ser Phe Ile Asn Asn Gln Glu Ser Ile Ile Gln
    290                  295                  300

Leu Pro Asp Arg Ile Leu Glu Ile Gly Asn Glu Gln Trp Ser Tyr Pro
305                  310                  315                  320

Ala Lys Asn Cys Lys Leu Thr Arg His His Ile Phe Cys Gln Tyr Asn
                325                  330                  335

Glu Ala Glu Arg Leu Ser Leu Glu Ser Lys Leu Cys Leu Ala Gly Asn
                340                  345                  350

Ile Ser Ala Cys Val Phe Ser Pro Ile Ala Gly Ser Tyr Met Arg Arg
    355                  360                  365

Phe Val Ala Leu Asp Gly Thr Ile Val Ala Asn Cys Arg Ser Leu Thr
    370                  375                  380

Cys Leu Cys Lys Ser Pro Ser Tyr Pro Ile Tyr Gln Pro Asp His His
385                  390                  395                  400

Ala Val Thr Thr Ile Asp Leu Thr Ala Cys Gln Thr Leu Ser Leu Asp
                405                  410                  415

Gly Leu Asp Phe Ser Ile Val Ser Leu Ser Asn Ile Thr Tyr Ala Glu
                420                  425                  430

Asn Leu Thr Ile Ser Leu Ser Gln Thr Ile Asn Thr Gln Pro Ile Asp
    435                  440                  445

Ile Ser Thr Glu Leu Ser Lys Val Asn Ala Ser Leu Gln Asn Ala Val
    450                  455                  460

Lys Tyr Ile Lys Glu Ser Asn His Gln Leu Gln Ser Val Ser Val Asn
465                  470                  475                  480

Ser Lys Ile Ile Glu Asp Lys Ile Glu Glu Ile Leu Ser Lys Ile Tyr
                485                  490                  495
```

-continued

```
His Ile Glu Asn Glu Ile Ala Arg Ile Lys Lys Leu Ile Gly Glu Ala
            500                 505                 510

Pro

<210> SEQ ID NO 4
<211> LENGTH: 513
<212> TYPE: PRT
<213> ORGANISM: Artificial sequence
<220> FEATURE:
<223> OTHER INFORMATION: Recombinant F protein

<400> SEQUENCE: 4

Met Lys Ala Phe Ser Val Thr Cys Leu Ser Phe Ala Val Phe Ser Ser
1               5                   10                  15

Ser Ile Cys Val Asn Ile Asn Ile Leu Gln Gln Ile Gly Tyr Ile Lys
            20                  25                  30

Gln Gln Val Arg Gln Leu Ser Tyr Tyr Ser Gln Ser Ser Ser Ser Tyr
            35                  40                  45

Ile Val Val Lys Leu Leu Pro Asn Ile Gln Pro Thr Asp Asp Ser Cys
        50                  55                  60

Glu Phe Lys Ser Val Thr Gln Tyr Asn Lys Thr Leu Ser Asn Leu Leu
65                  70                  75                  80

Leu Pro Ile Ala Glu Cys Ile Asn Asn Ile Ala Ser Pro Ser Pro Gly
                85                  90                  95

Ser Arg Arg His Gly Gly Gly Ala Gly Ile Ala Ile Gly Ile Ala Ala
            100                 105                 110

Leu Gly Val Ala Thr Ala Ala Gln Val Thr Ala Ala Val Ser Leu Val
            115                 120                 125

Gln Ala Gln Thr Asn Ala Arg Ala Ile Ala Ala Met Lys Asn Ser Ile
        130                 135                 140

Gln Ala Thr Asn Arg Ala Val Phe Glu Val Lys Glu Gly Thr Gln Gln
145                 150                 155                 160

Leu Ala Ile Ala Val Gln Ala Ile Gln Asp His Ile Asn Thr Ile Met
                165                 170                 175

Asn Thr Gln Leu Asn Asn Met Ser Cys Gln Ile Leu Asp Asn Gln Leu
            180                 185                 190

Ala Thr Ser Leu Gly Leu Tyr Leu Thr Glu Leu Thr Thr Val Phe Gln
            195                 200                 205

Pro Gln Leu Thr Asn Pro Cys Leu Ser Pro Ile Ser Ile Gln Ala Leu
        210                 215                 220

Arg Ser Leu Leu Gly Ser Met Thr Pro Ala Val Val Gln Ala Thr Leu
225                 230                 235                 240

Ser Thr Ser Ile Ser Ala Ala Glu Ile Leu Ser Ala Gly Leu Met Glu
                245                 250                 255

Gly Gln Ile Ile Ser Val Leu Leu Asp Glu Met Gln Met Ile Val Lys
            260                 265                 270

Ile Asn Ile Pro Thr Ile Val Thr Gln Ser Asn Ala Leu Val Ile Asp
            275                 280                 285

Phe Tyr Ser Ile Ser Ser Phe Ile Asn Asn Gln Glu Ser Ile Ile Gln
        290                 295                 300

Leu Pro Asp Arg Ile Leu Glu Ile Gly Asn Glu Gln Trp Ser Tyr Pro
305                 310                 315                 320

Ala Lys Asn Cys Lys Leu Thr Arg His His Ile Phe Cys Gln Tyr Asn
                325                 330                 335
```

Glu Ala Glu Arg Leu Ser Leu Glu Ser Lys Leu Cys Leu Ala Gly Asn
                340                     345                 350

Ile Ser Ala Cys Val Phe Ser Pro Ile Ala Gly Ser Tyr Met Arg Arg
                355                 360                 365

Phe Val Ala Leu Asp Gly Thr Ile Val Ala Asn Cys Arg Ser Leu Thr
        370                 375                 380

Cys Leu Cys Lys Ser Pro Ser Tyr Pro Ile Tyr Gln Pro Asp His His
385                 390                 395                 400

Ala Val Thr Thr Ile Asp Leu Thr Ala Cys Gln Thr Leu Ser Leu Asp
                405                 410                 415

Gly Leu Asp Phe Ser Ile Val Ser Leu Ser Asn Ile Thr Tyr Ala Glu
                420                 425                 430

Asn Leu Thr Ile Ser Leu Ser Gln Thr Ile Asn Thr Gln Pro Ile Asp
                435                 440                 445

Ile Ser Thr Glu Leu Ser Lys Val Asn Ala Ser Leu Gln Asn Ala Val
        450                 455                 460

Lys Tyr Ile Lys Glu Ser Asn His Gln Leu Gln Ser Val Ser Val Asn
465                 470                 475                 480

Ser Lys Ile Ile Glu Asp Lys Ile Glu Glu Ile Leu Ser Lys Ile Tyr
                485                 490                 495

His Ile Glu Asn Glu Ile Ala Arg Ile Lys Lys Leu Ile Gly Glu Ala
                500                 505                 510

Pro

<210> SEQ ID NO 5
<211> LENGTH: 513
<212> TYPE: PRT
<213> ORGANISM: Artificial sequence
<220> FEATURE:
<223> OTHER INFORMATION: Recombinant F protein

<400> SEQUENCE: 5

Met Lys Ala Phe Ser Val Thr Cys Leu Ser Phe Ala Val Phe Ser Ser
1                   5                   10                  15

Ser Ile Cys Val Asn Ile Asn Ile Leu Gln Gln Ile Gly Tyr Ile Lys
                20                  25                  30

Gln Gln Val Arg Gln Leu Ser Tyr Tyr Ser Gln Ser Ser Ser Ser Tyr
            35                  40                  45

Ile Val Val Lys Leu Leu Pro Asn Ile Gln Pro Thr Asp Asp Ser Cys
        50                  55                  60

Glu Phe Lys Ser Val Thr Gln Tyr Asn Lys Thr Leu Ser Asn Leu Leu
65                  70                  75                  80

Leu Pro Ile Ala Glu Asn Ile Asn Asn Ile Ala Ser Pro Ser Pro Gly
                85                  90                  95

Ser Arg Arg His Gly Gly Gly Ala Gly Ile Ala Ile Gly Ile Ala Ala
            100                 105                 110

Leu Gly Val Ala Thr Ala Ala Gln Val Thr Ala Ala Val Ser Leu Val
            115                 120                 125

Gln Ala Gln Thr Asn Ala Arg Ala Ile Ala Ala Met Lys Asn Ser Ile
        130                 135                 140

Gln Ala Thr Asn Arg Ala Val Phe Glu Val Lys Glu Gly Thr Gln Gln
145                 150                 155                 160

Leu Ala Ile Ala Val Gln Ala Ile Gln Asp His Ile Asn Thr Ile Met
                165                 170                 175

Asn Thr Gln Leu Asn Asn Met Ser Cys Gln Ile Leu Asp Asn Gln Leu

-continued

```
                180                185                190

Ala Thr Ser Leu Gly Leu Tyr Leu Thr Glu Leu Thr Thr Val Phe Gln
        195                200                205

Cys Gln Leu Thr Asn Cys Ala Leu Ser Pro Ile Ser Ile Gln Ala Leu
    210                215                220

Arg Ser Leu Leu Gly Ser Met Thr Pro Ala Val Val Gln Ala Thr Leu
225                230                235                240

Ser Thr Ser Ile Ser Ala Ala Glu Ile Leu Ser Ala Gly Leu Met Glu
                245                250                255

Gly Gln Ile Ile Ser Val Leu Leu Asp Glu Met Gln Met Ile Val Lys
                260                265                270

Ile Asn Ile Pro Thr Ile Val Thr Gln Ser Asn Ala Leu Val Ile Asp
        275                280                285

Phe Tyr Ser Ile Ser Ser Phe Ile Asn Asn Gln Glu Ser Ile Ile Gln
    290                295                300

Leu Pro Asp Arg Ile Leu Glu Ile Gly Asn Glu Gln Trp Ser Tyr Pro
305                310                315                320

Ala Lys Asn Cys Lys Leu Thr Arg His His Ile Phe Cys Gln Tyr Asn
                325                330                335

Glu Ala Glu Arg Leu Ser Leu Glu Ser Lys Leu Cys Leu Ala Gly Asn
                340                345                350

Ile Ser Ala Cys Val Phe Ser Pro Ile Ala Gly Ser Tyr Met Arg Arg
        355                360                365

Phe Val Ala Leu Asp Gly Thr Ile Val Ala Asn Cys Arg Ser Leu Thr
    370                375                380

Cys Leu Cys Lys Ser Pro Ser Tyr Pro Ile Tyr Gln Pro Asp His His
385                390                395                400

Ala Val Thr Thr Ile Asp Leu Thr Ala Cys Gln Thr Leu Ser Leu Asp
                405                410                415

Gly Leu Asp Phe Ser Ile Val Ser Leu Ser Asn Ile Thr Tyr Ala Glu
                420                425                430

Asn Leu Thr Ile Ser Leu Ser Gln Thr Ile Asn Thr Gln Pro Ile Asp
        435                440                445

Ile Ser Thr Glu Leu Ser Lys Val Asn Ala Ser Leu Gln Asn Ala Val
    450                455                460

Lys Tyr Ile Lys Glu Ser Asn His Gln Leu Gln Ser Val Ser Val Asn
465                470                475                480

Ser Lys Ile Ile Glu Asp Lys Ile Glu Glu Ile Leu Ser Lys Ile Tyr
                485                490                495

His Ile Glu Asn Glu Ile Ala Arg Ile Lys Lys Leu Ile Gly Glu Ala
                500                505                510

Pro
```

<210> SEQ ID NO 6
<211> LENGTH: 513
<212> TYPE: PRT
<213> ORGANISM: Artificial sequence
<220> FEATURE:
<223> OTHER INFORMATION: Recombinant F protein

<400> SEQUENCE: 6

```
Met Lys Ala Phe Ser Val Thr Cys Leu Ser Phe Ala Val Phe Ser Ser
1                5                10                15

Ser Ile Cys Val Asn Ile Asn Ile Leu Gln Gln Ile Gly Tyr Ile Lys
        20                25                30
```

-continued

```
Gln Gln Val Arg Gln Leu Ser Tyr Tyr Ser Gln Ser Ser Ser Ser Tyr
        35              40              45

Ile Val Val Lys Leu Leu Pro Asn Ile Gln Pro Thr Asp Asp Ser Cys
        50              55              60

Glu Phe Lys Ser Val Thr Gln Tyr Asn Lys Thr Leu Ser Asn Leu Leu
65              70              75              80

Leu Pro Ile Ala Glu Asn Ile Asn Asn Ile Ala Ser Pro Ser Pro Gly
                85              90              95

Ser Arg Arg His Gly Gly Gly Ala Gly Ile Ala Ile Gly Ile Ala Ala
            100             105             110

Leu Gly Val Ala Thr Ala Ala Gln Val Thr Ala Ala Val Ser Leu Val
            115             120             125

Gln Ala Gln Thr Asn Ala Arg Ala Ile Ala Ala Met Lys Asn Ser Ile
        130             135             140

Gln Ala Thr Asn Arg Ala Val Phe Glu Val Cys Glu Gly Thr Gln Gln
145             150             155             160

Cys Ala Ile Ala Val Gln Ala Ile Gln Asp His Ile Asn Thr Ile Met
                165             170             175

Asn Thr Gln Leu Asn Asn Met Ser Cys Gln Ile Leu Asp Asn Gln Leu
            180             185             190

Ala Thr Ser Leu Gly Leu Tyr Leu Thr Glu Leu Thr Thr Val Phe Gln
            195             200             205

Pro Gln Leu Thr Asn Pro Ala Leu Ser Pro Ile Ser Ile Gln Ala Leu
        210             215             220

Arg Ser Leu Leu Gly Ser Met Thr Pro Ala Val Val Gln Ala Thr Leu
225             230             235             240

Ser Thr Ser Ile Ser Ala Ala Glu Ile Leu Ser Ala Gly Leu Met Glu
                245             250             255

Gly Gln Ile Ile Ser Val Leu Leu Asp Glu Met Gln Met Ile Val Lys
            260             265             270

Ile Asn Ile Pro Thr Ile Val Thr Gln Ser Asn Ala Leu Val Ile Asp
        275             280             285

Phe Tyr Ser Ile Ser Ser Phe Ile Asn Asn Gln Glu Ser Ile Ile Gln
        290             295             300

Leu Pro Asp Arg Ile Leu Glu Ile Gly Asn Glu Gln Trp Ser Tyr Pro
305             310             315             320

Ala Lys Asn Cys Lys Leu Thr Arg His His Ile Phe Cys Gln Tyr Asn
                325             330             335

Glu Ala Glu Arg Leu Ser Leu Glu Ser Lys Leu Cys Leu Ala Gly Asn
            340             345             350

Ile Ser Ala Cys Val Phe Ser Pro Ile Ala Gly Ser Tyr Met Arg Arg
            355             360             365

Phe Val Ala Leu Asp Gly Thr Ile Val Ala Asn Cys Arg Ser Leu Thr
        370             375             380

Cys Leu Cys Lys Ser Pro Ser Tyr Pro Ile Tyr Gln Pro Asp His His
385             390             395             400

Ala Val Thr Thr Ile Asp Leu Thr Ala Cys Gln Thr Leu Ser Leu Asp
                405             410             415

Gly Leu Asp Phe Ser Ile Val Ser Leu Ser Asn Ile Thr Tyr Ala Glu
            420             425             430

Asn Leu Thr Ile Ser Leu Ser Gln Thr Ile Asn Thr Gln Pro Ile Asp
            435             440             445
```

```
Ile Ser Thr Glu Leu Ser Lys Val Asn Ala Ser Leu Gln Asn Ala Val
    450             455             460

Lys Tyr Ile Lys Glu Ser Asn His Gln Leu Gln Ser Val Ser Val Asn
465             470             475             480

Ser Lys Ile Ile Glu Asp Lys Ile Glu Glu Ile Leu Ser Lys Ile Tyr
                485             490             495

His Ile Glu Asn Glu Ile Ala Arg Ile Lys Lys Leu Ile Gly Glu Ala
                500             505             510

Pro

<210> SEQ ID NO 7
<211> LENGTH: 513
<212> TYPE: PRT
<213> ORGANISM: Artificial sequence
<220> FEATURE:
<223> OTHER INFORMATION: Recombinant F protein

<400> SEQUENCE: 7

Met Lys Ala Phe Ser Val Thr Cys Leu Ser Phe Ala Val Phe Ser Ser
1               5               10              15

Ser Ile Cys Val Asn Ile Asn Ile Leu Gln Gln Ile Gly Tyr Ile Lys
                20              25              30

Gln Gln Val Arg Gln Leu Ser Tyr Tyr Ser Gln Ser Ser Ser Ser Tyr
        35              40              45

Ile Val Val Lys Leu Leu Pro Asn Ile Gln Pro Thr Asp Asp Ser Cys
    50              55              60

Glu Phe Lys Ser Val Thr Gln Tyr Asn Lys Thr Leu Ser Asn Leu Leu
65              70              75              80

Leu Pro Ile Ala Glu Asn Ile Asn Asn Ile Ala Ser Pro Ser Pro Gly
                85              90              95

Ser Arg Arg His Gly Gly Gly Ala Gly Ile Ala Ile Gly Ile Ala Ala
            100             105             110

Leu Gly Val Ala Thr Ala Ala Gln Val Thr Ala Ala Val Ser Leu Val
            115             120             125

Gln Ala Gln Thr Asn Ala Arg Ala Ile Ala Ala Met Lys Asn Ser Ile
    130             135             140

Gln Ala Thr Asn Arg Ala Val Phe Glu Val Lys Glu Gly Thr Gln Gln
145             150             155             160

Leu Ala Ile Ala Cys Gln Ala Ile Gln Asp His Ile Asn Thr Ile Met
                165             170             175

Asn Thr Gln Leu Asn Asn Met Ser Cys Gln Ile Leu Asp Asn Gln Leu
            180             185             190

Ala Thr Ser Leu Gly Leu Tyr Leu Thr Glu Leu Thr Thr Val Phe Gln
            195             200             205

Pro Gln Leu Thr Asn Pro Ala Leu Ser Pro Ile Ser Ile Gln Ala Leu
    210             215             220

Arg Ser Leu Leu Gly Ser Cys Thr Pro Ala Val Val Gln Ala Thr Leu
225             230             235             240

Ser Thr Ser Ile Ser Ala Ala Glu Ile Leu Ser Ala Gly Leu Met Glu
                245             250             255

Gly Gln Ile Ile Ser Val Leu Leu Asp Glu Met Gln Met Ile Val Lys
            260             265             270

Ile Asn Ile Pro Thr Ile Val Thr Gln Ser Asn Ala Leu Val Ile Asp
        275             280             285

Phe Tyr Ser Ile Ser Ser Phe Ile Asn Asn Gln Glu Ser Ile Ile Gln
```

-continued

```
        290              295              300

Leu Pro Asp Arg Ile Leu Glu Ile Gly Asn Glu Gln Trp Ser Tyr Pro
305                     310              315              320

Ala Lys Asn Cys Lys Leu Thr Arg His His Ile Phe Cys Gln Tyr Asn
                    325              330              335

Glu Ala Glu Arg Leu Ser Leu Glu Ser Lys Leu Cys Leu Ala Gly Asn
                    340              345              350

Ile Ser Ala Cys Val Phe Ser Pro Ile Ala Gly Ser Tyr Met Arg Arg
                355              360              365

Phe Val Ala Leu Asp Gly Thr Ile Val Ala Asn Cys Arg Ser Leu Thr
                370              375              380

Cys Leu Cys Lys Ser Pro Ser Tyr Pro Ile Tyr Gln Pro Asp His His
385                     390              395              400

Ala Val Thr Thr Ile Asp Leu Thr Ala Cys Gln Thr Leu Ser Leu Asp
                    405              410              415

Gly Leu Asp Phe Ser Ile Val Ser Leu Ser Asn Ile Thr Tyr Ala Glu
                420              425              430

Asn Leu Thr Ile Ser Leu Ser Gln Thr Ile Asn Thr Gln Pro Ile Asp
                435              440              445

Ile Ser Thr Glu Leu Ser Lys Val Asn Ala Ser Leu Gln Asn Ala Val
                450              455              460

Lys Tyr Ile Lys Glu Ser Asn His Gln Leu Gln Ser Val Ser Val Asn
465                     470              475              480

Ser Lys Ile Ile Glu Asp Lys Ile Glu Glu Ile Leu Ser Lys Ile Tyr
                485              490              495

His Ile Glu Asn Glu Ile Ala Arg Ile Lys Lys Leu Ile Gly Glu Ala
                500              505              510

Pro
```

```
<210> SEQ ID NO 8
<211> LENGTH: 513
<212> TYPE: PRT
<213> ORGANISM: Artificial sequence
<220> FEATURE:
<223> OTHER INFORMATION: Recombinant F protein

<400> SEQUENCE: 8

Met Lys Ala Phe Ser Val Thr Cys Leu Ser Phe Ala Val Phe Ser Ser
1               5               10              15

Ser Ile Cys Val Asn Ile Asn Ile Leu Gln Gln Ile Gly Tyr Ile Lys
                20              25              30

Gln Gln Val Arg Gln Leu Ser Tyr Tyr Ser Gln Ser Ser Ser Ser Tyr
            35              40              45

Ile Val Val Lys Leu Leu Pro Asn Ile Gln Pro Thr Asp Asp Ser Cys
        50              55              60

Glu Phe Lys Ser Val Thr Gln Tyr Asn Lys Thr Leu Ser Asn Leu Leu
65              70              75              80

Leu Pro Ile Ala Glu Asn Ile Asn Asn Ile Ala Ser Pro Ser Pro Gly
                85              90              95

Ser Arg Arg His Gly Gly Gly Ala Gly Ile Ala Ile Gly Ile Ala Ala
                100             105             110

Leu Gly Val Ala Thr Ala Ala Gln Val Thr Ala Ala Val Ser Leu Val
            115             120             125

Gln Ala Gln Thr Asn Ala Arg Ala Ile Ala Ala Met Lys Asn Ser Ile
            130             135             140
```

-continued

```
Gln Ala Thr Asn Arg Ala Val Phe Glu Val Lys Glu Gly Thr Gln Gln
145                 150                 155                 160

Leu Ala Ile Ala Val Gln Ala Ile Gln Asp His Ile Asn Thr Ile Met
                165                 170                 175

Asn Thr Gln Leu Asn Asn Met Ser Cys Gln Ile Leu Asp Asn Gln Leu
            180                 185                 190

Ala Thr Ser Leu Gly Leu Tyr Leu Thr Glu Leu Thr Thr Val Phe Gln
        195                 200                 205

Pro Gln Leu Thr Asn Pro Ala Leu Ser Pro Ile Ser Cys Gln Ala Leu
    210                 215                 220

Arg Ser Leu Leu Gly Ser Met Thr Pro Ala Val Val Gln Ala Thr Leu
225                 230                 235                 240

Ser Thr Ser Ile Ser Ala Ala Glu Ile Leu Ser Ala Gly Leu Cys Glu
                245                 250                 255

Gly Gln Ile Ile Ser Val Leu Leu Asp Glu Met Gln Met Ile Val Lys
            260                 265                 270

Ile Asn Ile Pro Thr Ile Val Thr Gln Ser Asn Ala Leu Val Ile Asp
        275                 280                 285

Phe Tyr Ser Ile Ser Ser Phe Ile Asn Asn Gln Glu Ser Ile Ile Gln
    290                 295                 300

Leu Pro Asp Arg Ile Leu Glu Ile Gly Asn Glu Gln Trp Ser Tyr Pro
305                 310                 315                 320

Ala Lys Asn Cys Lys Leu Thr Arg His His Ile Phe Cys Gln Tyr Asn
                325                 330                 335

Glu Ala Glu Arg Leu Ser Leu Glu Ser Lys Leu Cys Leu Ala Gly Asn
            340                 345                 350

Ile Ser Ala Cys Val Phe Ser Pro Ile Ala Gly Ser Tyr Met Arg Arg
        355                 360                 365

Phe Val Ala Leu Asp Gly Thr Ile Val Ala Asn Cys Arg Ser Leu Thr
    370                 375                 380

Cys Leu Cys Lys Ser Pro Ser Tyr Pro Ile Tyr Gln Pro Asp His His
385                 390                 395                 400

Ala Val Thr Thr Ile Asp Leu Thr Ala Cys Gln Thr Leu Ser Leu Asp
                405                 410                 415

Gly Leu Asp Phe Ser Ile Val Ser Leu Ser Asn Ile Thr Tyr Ala Glu
            420                 425                 430

Asn Leu Thr Ile Ser Leu Ser Gln Thr Ile Asn Thr Gln Pro Ile Asp
        435                 440                 445

Ile Ser Thr Glu Leu Ser Lys Val Asn Ala Ser Leu Gln Asn Ala Val
    450                 455                 460

Lys Tyr Ile Lys Glu Ser Asn His Gln Leu Gln Ser Val Ser Val Asn
465                 470                 475                 480

Ser Lys Ile Ile Glu Asp Lys Ile Glu Glu Ile Leu Ser Lys Ile Tyr
                485                 490                 495

His Ile Glu Asn Glu Ile Ala Arg Ile Lys Lys Leu Ile Gly Glu Ala
            500                 505                 510

Pro
```

<210> SEQ ID NO 9
<211> LENGTH: 513
<212> TYPE: PRT
<213> ORGANISM: Artificial sequence
<220> FEATURE:
<223> OTHER INFORMATION: Recombinant F protein -continued

<400> SEQUENCE: 9

Met Lys Ala Phe Ser Val Thr Cys Leu Ser Phe Ala Val Phe Ser Ser
1               5                   10                  15

Ser Ile Cys Val Asn Ile Asn Ile Leu Gln Gln Ile Gly Tyr Ile Lys
                20                  25                  30

Gln Gln Val Arg Gln Leu Ser Tyr Tyr Ser Gln Ser Ser Ser Ser Tyr
            35                  40                  45

Ile Val Val Lys Leu Leu Pro Asn Ile Gln Pro Thr Asp Asp Ser Cys
        50                  55                  60

Glu Phe Lys Ser Val Thr Gln Tyr Asn Lys Thr Leu Ser Asn Leu Leu
65                  70                  75                  80

Leu Pro Ile Ala Glu Asn Ile Asn Asn Ile Ala Ser Pro Ser Pro Gly
                85                  90                  95

Ser Arg Arg His Gly Gly Gly Ala Gly Ile Ala Ile Gly Ile Ala Ala
            100                 105                 110

Leu Gly Val Ala Thr Ala Ala Gln Val Thr Ala Ala Val Ser Leu Val
        115                 120                 125

Gln Ala Gln Thr Asn Ala Arg Ala Ile Ala Ala Met Lys Asn Ser Ile
    130                 135                 140

Gln Ala Thr Asn Arg Ala Val Phe Glu Val Lys Glu Gly Thr Gln Gln
145                 150                 155                 160

Leu Ala Ile Ala Val Gln Ala Ile Gln Asp His Ile Asn Thr Ile Met
                165                 170                 175

Asn Thr Gln Leu Asn Asn Met Pro Cys Gln Ile Leu Asp Asn Gln Leu
            180                 185                 190

Ala Thr Ser Leu Gly Leu Tyr Leu Thr Glu Leu Thr Thr Val Phe Gln
            195                 200                 205

Pro Gln Leu Thr Asn Pro Ala Leu Ser Pro Ile Ser Ile Gln Ala Leu
    210                 215                 220

Arg Ser Leu Leu Gly Ser Met Thr Pro Ala Val Val Gln Ala Thr Leu
225                 230                 235                 240

Ser Thr Ser Ile Ser Ala Ala Glu Ile Leu Ser Ala Gly Leu Met Glu
            245                 250                 255

Gly Gln Ile Ile Ser Val Leu Leu Asp Glu Met Gln Met Ile Val Lys
            260                 265                 270

Ile Asn Ile Pro Thr Ile Val Thr Gln Ser Asn Ala Leu Val Ile Asp
        275                 280                 285

Phe Tyr Ser Ile Ser Ser Phe Ile Asn Asn Gln Glu Ser Ile Ile Gln
    290                 295                 300

Leu Pro Asp Arg Ile Leu Glu Ile Gly Asn Glu Gln Trp Ser Tyr Pro
305                 310                 315                 320

Ala Lys Asn Cys Lys Leu Thr Arg His His Ile Phe Cys Gln Tyr Asn
            325                 330                 335

Glu Ala Glu Arg Leu Ser Leu Glu Ser Lys Leu Cys Leu Ala Gly Asn
            340                 345                 350

Ile Ser Ala Cys Val Phe Ser Pro Ile Ala Gly Ser Tyr Met Arg Arg
            355                 360                 365

Phe Val Ala Leu Asp Gly Thr Ile Val Ala Asn Cys Arg Ser Leu Thr
    370                 375                 380

Cys Leu Cys Lys Ser Pro Ser Tyr Pro Ile Tyr Gln Pro Asp His His
385                 390                 395                 400

Ala Val Thr Thr Ile Asp Leu Thr Ala Cys Gln Thr Leu Ser Leu Asp

-continued

```
                    405                 410                 415

Gly Leu Asp Phe Ser Ile Val Ser Leu Ser Asn Ile Thr Tyr Ala Glu
            420                 425                 430

Asn Leu Thr Ile Ser Leu Ser Gln Thr Ile Asn Thr Gln Pro Ile Asp
                435                 440                 445

Ile Ser Thr Glu Leu Ser Lys Val Asn Ala Ser Leu Gln Asn Ala Val
            450                 455                 460

Lys Tyr Ile Lys Glu Ser Asn His Gln Leu Gln Ser Val Ser Val Asn
465                 470                 475                 480

Ser Lys Ile Ile Glu Asp Lys Ile Glu Glu Ile Leu Ser Lys Ile Tyr
                485                 490                 495

His Ile Glu Asn Glu Ile Ala Arg Ile Lys Lys Leu Ile Gly Glu Ala
                500                 505                 510

Pro

<210> SEQ ID NO 10
<211> LENGTH: 506
<212> TYPE: PRT
<213> ORGANISM: Artificial sequence
<220> FEATURE:
<223> OTHER INFORMATION: Recombinant F protein

<400> SEQUENCE: 10

Met Lys Ala Phe Ser Val Thr Cys Leu Ser Phe Ala Val Phe Ser Ser
1               5                   10                  15

Ser Ile Cys Val Asn Ile Asn Ile Leu Gln Gln Ile Gly Tyr Ile Lys
                20                  25                  30

Gln Gln Val Arg Gln Leu Ser Tyr Tyr Ser Gln Ser Ser Ser Ser Tyr
            35                  40                  45

Ile Val Val Lys Leu Leu Pro Asn Ile Gln Pro Thr Asp Asp Ser Cys
    50                  55                  60

Glu Phe Lys Ser Val Thr Gln Tyr Asn Lys Thr Leu Ser Asn Leu Leu
65                  70                  75                  80

Leu Pro Ile Ala Glu Asn Ile Asn Asn Ile Ala Ser Pro Ser Pro Gly
                85                  90                  95

Ser Arg Arg His Gly Gly Gly Ala Gly Ile Ala Ile Gly Ile Ala Ala
                100                 105                 110

Leu Gly Val Ala Thr Ala Ala Gln Val Thr Ala Ala Val Ser Leu Val
            115                 120                 125

Gln Ala Gln Thr Asn Ala Arg Ala Ile Ala Ala Met Lys Asn Ser Ile
    130                 135                 140

Gln Ala Thr Asn Arg Ala Val Phe Glu Val Lys Glu Gly Thr Gln Gln
145                 150                 155                 160

Leu Ala Cys Ala Val Gln Ala Ile Gln Asp His Ile Asn Thr Ile Met
                165                 170                 175

Asn Thr Gln Leu Asn Asn Met Ser Cys Gln Ile Leu Asp Asn Gln Leu
                180                 185                 190

Ala Thr Ser Leu Gly Leu Tyr Leu Thr Glu Leu Thr Thr Val Phe Gln
            195                 200                 205

Pro Gln Leu Thr Asn Pro Ala Leu Ser Pro Ile Ser Ile Gln Ala Leu
            210                 215                 220

Arg Ser Leu Leu Gly Ser Met Thr Pro Ala Cys Val Gln Ala Thr Leu
225                 230                 235                 240

Ser Thr Ser Ile Ser Ala Ala Glu Ile Leu Ser Ala Gly Leu Met Glu
                245                 250                 255
```

```
Gly Gln Ile Ile Ser Val Leu Leu Asp Glu Met Gln Met Ile Val Lys
            260             265             270

Ile Asn Ile Pro Thr Ile Val Thr Gln Ser Asn Ala Leu Val Ile Asp
            275             280             285

Phe Tyr Ser Ile Ser Ser Phe Ile Asn Asn Gln Glu Ser Ile Ile Gln
            290             295             300

Leu Pro Asp Arg Ile Leu Glu Ile Gly Asn Glu Gln Trp Ser Tyr Pro
305             310             315             320

Ala Lys Asn Cys Lys Leu Thr Arg His His Ile Phe Cys Gln Tyr Asn
            325             330             335

Glu Ala Glu Arg Leu Ser Leu Glu Ser Lys Leu Cys Leu Ala Gly Asn
            340             345             350

Ile Ser Ala Cys Val Phe Ser Pro Ile Ala Gly Ser Tyr Met Arg Arg
            355             360             365

Phe Val Ala Leu Asp Gly Thr Ile Val Ala Asn Cys Arg Ser Leu Thr
            370             375             380

Cys Leu Cys Lys Ser Pro Ser Tyr Pro Ile Tyr Gln Pro Asp His His
385             390             395             400

Ala Val Thr Thr Ile Asp Leu Thr Ala Cys Gln Thr Leu Ser Leu Asp
            405             410             415

Gly Leu Asp Phe Ser Ile Val Ser Leu Ser Asn Ile Thr Tyr Ala Glu
            420             425             430

Asn Leu Thr Ile Ser Leu Ser Gln Thr Ile Asn Thr Gln Pro Ile Asp
            435             440             445

Ile Ser Thr Glu Leu Ser Lys Val Asn Ala Ser Leu Gln Asn Ala Val
            450             455             460

Lys Tyr Ile Lys Glu Ser Asn His Gln Leu Gln Ser Ile Glu Asp Lys
465             470             475             480

Ile Glu Glu Ile Leu Ser Lys Ile Tyr His Ile Glu Asn Glu Ile Ala
            485             490             495

Arg Ile Lys Lys Leu Ile Gly Glu Ala Pro
            500             505
```

<210> SEQ ID NO 11
<211> LENGTH: 506
<212> TYPE: PRT
<213> ORGANISM: Artificial sequence
<220> FEATURE:
<223> OTHER INFORMATION: Recombinant F protein

<400> SEQUENCE: 11

```
Met Lys Ala Phe Ser Val Thr Cys Leu Ser Phe Ala Val Phe Ser Ser
1               5               10              15

Ser Ile Cys Val Asn Ile Asn Ile Leu Gln Gln Ile Gly Tyr Ile Lys
            20              25              30

Gln Gln Val Arg Gln Leu Ser Tyr Tyr Ser Gln Ser Ser Ser Ser Tyr
            35              40              45

Ile Val Val Lys Leu Leu Pro Asn Ile Gln Pro Thr Asp Asp Ser Cys
            50              55              60

Glu Phe Lys Ser Val Thr Gln Tyr Asn Lys Thr Leu Ser Asn Leu Leu
65              70              75              80

Leu Pro Ile Ala Glu Asn Ile Asn Asn Ile Ala Ser Pro Ser Pro Gly
                85              90              95

Ser Arg Arg His Gly Gly Gly Ala Gly Ile Ala Ile Gly Ile Ala Ala
            100             105             110
```

-continued

```
Leu Gly Val Ala Thr Ala Ala Gln Val Thr Ala Ala Val Ser Leu Val
        115                 120                 125

Gln Ala Gln Thr Asn Ala Arg Ala Ile Ala Ala Met Lys Asn Ser Ile
    130                 135                 140

Gln Ala Thr Asn Arg Ala Val Phe Glu Val Lys Glu Gly Thr Gln Gln
145                 150                 155                 160

Leu Ala Ile Ala Val Gln Ala Ile Gln Asp His Ile Asn Thr Ile Met
                165                 170                 175

Asn Thr Gln Leu Asn Asn Met Ser Cys Gln Ile Leu Asp Asn Gln Leu
                180                 185                 190

Ala Thr Ser Leu Gly Leu Tyr Leu Thr Glu Leu Thr Thr Cys Phe Gln
                195                 200                 205

Pro Gln Leu Thr Asn Pro Ala Leu Ser Pro Ile Ser Ile Gln Cys Leu
    210                 215                 220

Arg Ser Leu Leu Gly Ser Met Thr Pro Ala Val Val Gln Ala Thr Leu
225                 230                 235                 240

Ser Thr Ser Ile Ser Ala Ala Glu Ile Leu Ser Ala Gly Leu Met Glu
                245                 250                 255

Gly Gln Ile Ile Ser Val Leu Leu Asp Glu Met Gln Met Ile Val Lys
                260                 265                 270

Ile Asn Ile Pro Thr Ile Val Thr Gln Ser Asn Ala Leu Val Ile Asp
                275                 280                 285

Phe Tyr Ser Ile Ser Ser Phe Ile Asn Asn Gln Glu Ser Ile Ile Gln
    290                 295                 300

Leu Pro Asp Arg Ile Leu Glu Ile Gly Asn Glu Gln Trp Ser Tyr Pro
305                 310                 315                 320

Ala Lys Asn Cys Lys Leu Thr Arg His His Ile Phe Cys Gln Tyr Asn
                325                 330                 335

Glu Ala Glu Arg Leu Ser Leu Glu Ser Lys Leu Cys Leu Ala Gly Asn
                340                 345                 350

Ile Ser Ala Cys Val Phe Ser Pro Ile Ala Gly Ser Tyr Met Arg Arg
                355                 360                 365

Phe Val Ala Leu Asp Gly Thr Ile Val Ala Asn Cys Arg Ser Leu Thr
    370                 375                 380

Cys Leu Cys Lys Ser Pro Ser Tyr Pro Ile Tyr Gln Pro Asp His His
385                 390                 395                 400

Ala Val Thr Thr Ile Asp Leu Thr Ala Cys Gln Thr Leu Ser Leu Asp
                405                 410                 415

Gly Leu Asp Phe Ser Ile Val Ser Leu Ser Asn Ile Thr Tyr Ala Glu
                420                 425                 430

Asn Leu Thr Ile Ser Leu Ser Gln Thr Ile Asn Thr Gln Pro Ile Asp
                435                 440                 445

Ile Ser Thr Glu Leu Ser Lys Val Asn Ala Ser Leu Gln Asn Ala Val
    450                 455                 460

Lys Tyr Ile Lys Glu Ser Asn His Gln Leu Gln Ser Ile Glu Asp Lys
465                 470                 475                 480

Ile Glu Glu Ile Leu Ser Lys Ile Tyr His Ile Glu Asn Glu Ile Ala
                485                 490                 495

Arg Ile Lys Lys Leu Ile Gly Glu Ala Pro
                500                 505
```

<210> SEQ ID NO 12
<211> LENGTH: 506

```
<212> TYPE: PRT
<213> ORGANISM: Artificial sequence
<220> FEATURE:
<223> OTHER INFORMATION: Recombinant F protein

<400> SEQUENCE: 12

Met Lys Ala Phe Ser Val Thr Cys Leu Ser Phe Ala Val Phe Ser Ser
1               5                   10                  15

Ser Ile Cys Val Asn Ile Asn Ile Leu Gln Gln Ile Gly Tyr Ile Lys
            20                  25                  30

Gln Gln Val Arg Gln Leu Ser Tyr Tyr Ser Gln Ser Ser Ser Ser Tyr
        35                  40                  45

Ile Val Val Lys Leu Leu Pro Asn Ile Gln Pro Thr Asp Asp Ser Cys
        50                  55                  60

Glu Phe Lys Ser Val Thr Gln Tyr Asn Lys Thr Leu Ser Asn Leu Leu
65                  70                  75                  80

Leu Pro Ile Ala Glu Cys Ile Asn Asn Ile Ala Ser Pro Ser Pro Gly
                85                  90                  95

Ser Arg Arg His Gly Gly Gly Ala Gly Ile Ala Ile Gly Ile Ala Ala
            100                 105                 110

Leu Gly Val Ala Thr Ala Ala Gln Val Thr Ala Ala Val Ser Leu Val
            115                 120                 125

Gln Ala Gln Thr Asn Ala Arg Ala Ile Ala Ala Met Lys Asn Ser Ile
        130                 135                 140

Gln Ala Thr Asn Arg Ala Val Phe Glu Val Lys Glu Gly Thr Gln Gln
145                 150                 155                 160

Leu Ala Ile Ala Val Gln Ala Ile Gln Asp His Ile Asn Thr Ile Met
                165                 170                 175

Asn Thr Gln Leu Asn Asn Met Ser Cys Gln Ile Leu Asp Asn Gln Leu
            180                 185                 190

Ala Thr Ser Leu Gly Leu Tyr Leu Thr Glu Leu Thr Thr Val Phe Gln
            195                 200                 205

Pro Gln Leu Thr Asn Pro Cys Leu Ser Pro Ile Ser Ile Gln Ala Leu
        210                 215                 220

Arg Ser Leu Leu Gly Ser Met Thr Pro Ala Val Val Gln Ala Thr Leu
225                 230                 235                 240

Ser Thr Ser Ile Ser Ala Ala Glu Ile Leu Ser Ala Gly Leu Met Glu
                245                 250                 255

Gly Gln Ile Ile Ser Val Leu Leu Asp Glu Met Gln Met Ile Val Lys
            260                 265                 270

Ile Asn Ile Pro Thr Ile Val Thr Gln Ser Asn Ala Leu Val Ile Asp
        275                 280                 285

Phe Tyr Ser Ile Ser Ser Phe Ile Asn Asn Gln Glu Ser Ile Ile Gln
        290                 295                 300

Leu Pro Asp Arg Ile Leu Glu Ile Gly Asn Glu Gln Trp Ser Tyr Pro
305                 310                 315                 320

Ala Lys Asn Cys Lys Leu Thr Arg His His Ile Phe Cys Gln Tyr Asn
                325                 330                 335

Glu Ala Glu Arg Leu Ser Leu Glu Ser Lys Leu Cys Leu Ala Gly Asn
            340                 345                 350

Ile Ser Ala Cys Val Phe Ser Pro Ile Ala Gly Ser Tyr Met Arg Arg
            355                 360                 365

Phe Val Ala Leu Asp Gly Thr Ile Val Ala Asn Cys Arg Ser Leu Thr
        370                 375                 380
```

```
Cys Leu Cys Lys Ser Pro Ser Tyr Pro Ile Tyr Gln Pro Asp His His
385             390             395             400

Ala Val Thr Thr Ile Asp Leu Thr Ala Cys Gln Thr Leu Ser Leu Asp
                405             410             415

Gly Leu Asp Phe Ser Ile Val Ser Leu Ser Asn Ile Thr Tyr Ala Glu
            420             425             430

Asn Leu Thr Ile Ser Leu Ser Gln Thr Ile Asn Thr Gln Pro Ile Asp
        435             440             445

Ile Ser Thr Glu Leu Ser Lys Val Asn Ala Ser Leu Gln Asn Ala Val
    450             455             460

Lys Tyr Ile Lys Glu Ser Asn His Gln Leu Gln Ser Ile Glu Asp Lys
465             470             475             480

Ile Glu Glu Ile Leu Ser Lys Ile Tyr His Ile Glu Asn Glu Ile Ala
            485             490             495

Arg Ile Lys Lys Leu Ile Gly Glu Ala Pro
            500             505
```

```
<210> SEQ ID NO 13
<211> LENGTH: 506
<212> TYPE: PRT
<213> ORGANISM: Artificial sequence
<220> FEATURE:
<223> OTHER INFORMATION: Recombinant F protein

<400> SEQUENCE: 13
```

```
Met Lys Ala Phe Ser Val Thr Cys Leu Ser Phe Ala Val Phe Ser Ser
1               5               10              15

Ser Ile Cys Val Asn Ile Asn Ile Leu Gln Gln Ile Gly Tyr Ile Lys
            20              25              30

Gln Gln Val Arg Gln Leu Ser Tyr Tyr Ser Gln Ser Ser Ser Ser Tyr
        35              40              45

Ile Val Val Lys Leu Leu Pro Asn Ile Gln Pro Thr Asp Asp Ser Cys
    50              55              60

Glu Phe Lys Ser Val Thr Gln Tyr Asn Lys Thr Leu Ser Asn Leu Leu
65              70              75              80

Leu Pro Ile Ala Glu Asn Ile Asn Asn Ile Ala Ser Pro Ser Pro Gly
                85              90              95

Ser Arg Arg His Gly Gly Gly Ala Gly Ile Ala Ile Gly Ile Ala Ala
            100             105             110

Leu Gly Val Ala Thr Ala Ala Gln Val Thr Ala Ala Val Ser Leu Val
            115             120             125

Gln Ala Gln Thr Asn Ala Arg Ala Ile Ala Ala Met Lys Asn Ser Ile
    130             135             140

Gln Ala Thr Asn Arg Ala Val Phe Glu Val Lys Glu Gly Thr Gln Gln
145             150             155             160

Leu Ala Ile Ala Val Gln Ala Ile Gln Asp His Ile Asn Thr Ile Met
            165             170             175

Asn Thr Gln Leu Asn Asn Met Ser Cys Gln Ile Leu Asp Asn Gln Leu
            180             185             190

Ala Thr Ser Leu Gly Leu Tyr Leu Thr Glu Leu Thr Thr Val Phe Gln
        195             200             205

Cys Gln Leu Thr Asn Cys Ala Leu Ser Pro Ile Ser Ile Gln Ala Leu
    210             215             220

Arg Ser Leu Leu Gly Ser Met Thr Pro Ala Val Val Gln Ala Thr Leu
225             230             235             240
```

```
Ser Thr Ser Ile Ser Ala Ala Glu Ile Leu Ser Ala Gly Leu Met Glu
            245                 250                 255

Gly Gln Ile Ile Ser Val Leu Leu Asp Glu Met Gln Met Ile Val Lys
            260                 265                 270

Ile Asn Ile Pro Thr Ile Val Thr Gln Ser Asn Ala Leu Val Ile Asp
            275                 280                 285

Phe Tyr Ser Ile Ser Ser Phe Ile Asn Asn Gln Glu Ser Ile Ile Gln
    290                 295                 300

Leu Pro Asp Arg Ile Leu Glu Ile Gly Asn Glu Gln Trp Ser Tyr Pro
305                 310                 315                 320

Ala Lys Asn Cys Lys Leu Thr Arg His His Ile Phe Cys Gln Tyr Asn
            325                 330                 335

Glu Ala Glu Arg Leu Ser Leu Glu Ser Lys Leu Cys Leu Ala Gly Asn
            340                 345                 350

Ile Ser Ala Cys Val Phe Ser Pro Ile Ala Gly Ser Tyr Met Arg Arg
            355                 360                 365

Phe Val Ala Leu Asp Gly Thr Ile Val Ala Asn Cys Arg Ser Leu Thr
    370                 375                 380

Cys Leu Cys Lys Ser Pro Ser Tyr Pro Ile Tyr Gln Pro Asp His His
385                 390                 395                 400

Ala Val Thr Thr Ile Asp Leu Thr Ala Cys Gln Thr Leu Ser Leu Asp
            405                 410                 415

Gly Leu Asp Phe Ser Ile Val Ser Leu Ser Asn Ile Thr Tyr Ala Glu
            420                 425                 430

Asn Leu Thr Ile Ser Leu Ser Gln Thr Ile Asn Thr Gln Pro Ile Asp
            435                 440                 445

Ile Ser Thr Glu Leu Ser Lys Val Asn Ala Ser Leu Gln Asn Ala Val
    450                 455                 460

Lys Tyr Ile Lys Glu Ser Asn His Gln Leu Gln Ser Ile Glu Asp Lys
465                 470                 475                 480

Ile Glu Glu Ile Leu Ser Lys Ile Tyr His Ile Glu Asn Glu Ile Ala
            485                 490                 495

Arg Ile Lys Lys Leu Ile Gly Glu Ala Pro
            500                 505
```

```
<210> SEQ ID NO 14
<211> LENGTH: 506
<212> TYPE: PRT
<213> ORGANISM: Artificial sequence
<220> FEATURE:
<223> OTHER INFORMATION: Recombinant F protein

<400> SEQUENCE: 14
```

```
Met Lys Ala Phe Ser Val Thr Cys Leu Ser Phe Ala Val Phe Ser Ser
1               5                   10                  15

Ser Ile Cys Val Asn Ile Asn Ile Leu Gln Gln Ile Gly Tyr Ile Lys
            20                  25                  30

Gln Gln Val Arg Gln Leu Ser Tyr Tyr Ser Gln Ser Ser Ser Ser Tyr
            35                  40                  45

Ile Val Val Lys Leu Leu Pro Asn Ile Gln Pro Thr Asp Asp Ser Cys
    50                  55                  60

Glu Phe Lys Ser Val Thr Gln Tyr Asn Lys Thr Leu Ser Asn Leu Leu
65                  70                  75                  80

Leu Pro Ile Ala Glu Asn Ile Asn Asn Ile Ala Ser Pro Ser Pro Gly
            85                  90                  95
```

```
Ser Arg Arg His Gly Gly Gly Ala Gly Ile Ala Ile Gly Ile Ala Ala
            100             105             110

Leu Gly Val Ala Thr Ala Ala Gln Val Thr Ala Ala Val Ser Leu Val
            115             120             125

Gln Ala Gln Thr Asn Ala Arg Ala Ile Ala Ala Met Lys Asn Ser Ile
    130             135             140

Gln Ala Thr Asn Arg Ala Val Phe Glu Val Cys Glu Gly Thr Gln Gln
145             150             155             160

Cys Ala Ile Ala Val Gln Ala Ile Gln Asp His Ile Asn Thr Ile Met
            165             170             175

Asn Thr Gln Leu Asn Asn Met Ser Cys Gln Ile Leu Asp Asn Gln Leu
            180             185             190

Ala Thr Ser Leu Gly Leu Tyr Leu Thr Glu Leu Thr Thr Val Phe Gln
            195             200             205

Pro Gln Leu Thr Asn Pro Ala Leu Ser Pro Ile Ser Ile Gln Ala Leu
    210             215             220

Arg Ser Leu Leu Gly Ser Met Thr Pro Ala Val Val Gln Ala Thr Leu
225             230             235             240

Ser Thr Ser Ile Ser Ala Ala Glu Ile Leu Ser Ala Gly Leu Met Glu
            245             250             255

Gly Gln Ile Ile Ser Val Leu Leu Asp Glu Met Gln Met Ile Val Lys
            260             265             270

Ile Asn Ile Pro Thr Ile Val Thr Gln Ser Asn Ala Leu Val Ile Asp
            275             280             285

Phe Tyr Ser Ile Ser Ser Phe Ile Asn Asn Gln Glu Ser Ile Ile Gln
    290             295             300

Leu Pro Asp Arg Ile Leu Glu Ile Gly Asn Glu Gln Trp Ser Tyr Pro
305             310             315             320

Ala Lys Asn Cys Lys Leu Thr Arg His His Ile Phe Cys Gln Tyr Asn
            325             330             335

Glu Ala Glu Arg Leu Ser Leu Glu Ser Lys Leu Cys Leu Ala Gly Asn
            340             345             350

Ile Ser Ala Cys Val Phe Ser Pro Ile Ala Gly Ser Tyr Met Arg Arg
            355             360             365

Phe Val Ala Leu Asp Gly Thr Ile Val Ala Asn Cys Arg Ser Leu Thr
    370             375             380

Cys Leu Cys Lys Ser Pro Ser Tyr Pro Ile Tyr Gln Pro Asp His His
385             390             395             400

Ala Val Thr Thr Ile Asp Leu Thr Ala Cys Gln Thr Leu Ser Leu Asp
            405             410             415

Gly Leu Asp Phe Ser Ile Val Ser Leu Ser Asn Ile Thr Tyr Ala Glu
            420             425             430

Asn Leu Thr Ile Ser Leu Ser Gln Thr Ile Asn Thr Gln Pro Ile Asp
            435             440             445

Ile Ser Thr Glu Leu Ser Lys Val Asn Ala Ser Leu Gln Asn Ala Val
    450             455             460

Lys Tyr Ile Lys Glu Ser Asn His Gln Leu Gln Ser Ile Glu Asp Lys
465             470             475             480

Ile Glu Glu Ile Leu Ser Lys Ile Tyr His Ile Glu Asn Glu Ile Ala
            485             490             495

Arg Ile Lys Lys Leu Ile Gly Glu Ala Pro
            500             505
```

-continued

<210> SEQ ID NO 15
<211> LENGTH: 506
<212> TYPE: PRT
<213> ORGANISM: Artificial sequence
<220> FEATURE:
<223> OTHER INFORMATION: Recombinant F protein

<400> SEQUENCE: 15

```
Met Lys Ala Phe Ser Val Thr Cys Leu Ser Phe Ala Val Phe Ser Ser
1               5                   10                  15

Ser Ile Cys Val Asn Ile Asn Ile Leu Gln Gln Ile Gly Tyr Ile Lys
            20                  25                  30

Gln Gln Val Arg Gln Leu Ser Tyr Tyr Ser Gln Ser Ser Ser Ser Tyr
        35                  40                  45

Ile Val Val Lys Leu Leu Pro Asn Ile Gln Pro Thr Asp Asp Ser Cys
    50                  55                  60

Glu Phe Lys Ser Val Thr Gln Tyr Asn Lys Thr Leu Ser Asn Leu Leu
65                  70                  75                  80

Leu Pro Ile Ala Glu Asn Ile Asn Asn Ile Ala Ser Pro Ser Pro Gly
                85                  90                  95

Ser Arg Arg His Gly Gly Gly Ala Gly Ile Ala Ile Gly Ile Ala Ala
            100                 105                 110

Leu Gly Val Ala Thr Ala Ala Gln Val Thr Ala Ala Val Ser Leu Val
        115                 120                 125

Gln Ala Gln Thr Asn Ala Arg Ala Ile Ala Ala Met Lys Asn Ser Ile
    130                 135                 140

Gln Ala Thr Asn Arg Ala Val Phe Glu Val Lys Glu Gly Thr Gln Gln
145                 150                 155                 160

Leu Ala Ile Ala Cys Gln Ala Ile Gln Asp His Ile Asn Thr Ile Met
                165                 170                 175

Asn Thr Gln Leu Asn Asn Met Ser Cys Gln Ile Leu Asp Asn Gln Leu
                180                 185                 190

Ala Thr Ser Leu Gly Leu Tyr Leu Thr Glu Leu Thr Thr Val Phe Gln
            195                 200                 205

Pro Gln Leu Thr Asn Pro Ala Leu Ser Pro Ile Ser Ile Gln Ala Leu
    210                 215                 220

Arg Ser Leu Leu Gly Ser Cys Thr Pro Ala Val Val Gln Ala Thr Leu
225                 230                 235                 240

Ser Thr Ser Ile Ser Ala Ala Glu Ile Leu Ser Ala Gly Leu Met Glu
                245                 250                 255

Gly Gln Ile Ile Ser Val Leu Leu Asp Glu Met Gln Met Ile Val Lys
            260                 265                 270

Ile Asn Ile Pro Thr Ile Val Thr Gln Ser Asn Ala Leu Val Ile Asp
        275                 280                 285

Phe Tyr Ser Ile Ser Ser Phe Ile Asn Asn Gln Glu Ser Ile Ile Gln
    290                 295                 300

Leu Pro Asp Arg Ile Leu Glu Ile Gly Asn Glu Gln Trp Ser Tyr Pro
305                 310                 315                 320

Ala Lys Asn Cys Lys Leu Thr Arg His His Ile Phe Cys Gln Tyr Asn
                325                 330                 335

Glu Ala Glu Arg Leu Ser Leu Glu Ser Lys Leu Cys Leu Ala Gly Asn
            340                 345                 350

Ile Ser Ala Cys Val Phe Ser Pro Ile Ala Gly Ser Tyr Met Arg Arg
        355                 360                 365

Phe Val Ala Leu Asp Gly Thr Ile Val Ala Asn Cys Arg Ser Leu Thr
```

```
              370               375               380
Cys Leu Cys Lys Ser Pro Ser Tyr Pro Ile Tyr Gln Pro Asp His His
385               390               395               400

Ala Val Thr Thr Ile Asp Leu Thr Ala Cys Gln Thr Leu Ser Leu Asp
                  405               410               415

Gly Leu Asp Phe Ser Ile Val Ser Leu Ser Asn Ile Thr Tyr Ala Glu
                  420               425               430

Asn Leu Thr Ile Ser Leu Ser Gln Thr Ile Asn Thr Gln Pro Ile Asp
              435               440               445

Ile Ser Thr Glu Leu Ser Lys Val Asn Ala Ser Leu Gln Asn Ala Val
          450               455               460

Lys Tyr Ile Lys Glu Ser Asn His Gln Leu Gln Ser Ile Glu Asp Lys
465               470               475               480

Ile Glu Glu Ile Leu Ser Lys Ile Tyr His Ile Glu Asn Glu Ile Ala
                  485               490               495

Arg Ile Lys Lys Leu Ile Gly Glu Ala Pro
              500               505

<210> SEQ ID NO 16
<211> LENGTH: 506
<212> TYPE: PRT
<213> ORGANISM: Artificial sequence
<220> FEATURE:
<223> OTHER INFORMATION: Recombinant F protein

<400> SEQUENCE: 16

Met Lys Ala Phe Ser Val Thr Cys Leu Ser Phe Ala Val Phe Ser Ser
1               5               10               15

Ser Ile Cys Val Asn Ile Asn Ile Leu Gln Gln Ile Gly Tyr Ile Lys
                  20               25               30

Gln Gln Val Arg Gln Leu Ser Tyr Tyr Ser Gln Ser Ser Ser Ser Tyr
              35               40               45

Ile Val Val Lys Leu Leu Pro Asn Ile Gln Pro Thr Asp Asp Ser Cys
          50               55               60

Glu Phe Lys Ser Val Thr Gln Tyr Asn Lys Thr Leu Ser Asn Leu Leu
65               70               75               80

Leu Pro Ile Ala Glu Asn Ile Asn Asn Ile Ala Ser Pro Ser Pro Gly
                  85               90               95

Ser Arg Arg His Gly Gly Gly Ala Gly Ile Ala Ile Gly Ile Ala Ala
                  100               105               110

Leu Gly Val Ala Thr Ala Ala Gln Val Thr Ala Ala Val Ser Leu Val
              115               120               125

Gln Ala Gln Thr Asn Ala Arg Ala Ile Ala Ala Met Lys Asn Ser Ile
          130               135               140

Gln Ala Thr Asn Arg Ala Val Phe Glu Val Lys Glu Gly Thr Gln Gln
145               150               155               160

Leu Ala Ile Ala Val Gln Ala Ile Gln Asp His Ile Asn Thr Ile Met
                  165               170               175

Asn Thr Gln Leu Asn Asn Met Ser Cys Gln Ile Leu Asp Asn Gln Leu
                  180               185               190

Ala Thr Ser Leu Gly Leu Tyr Leu Thr Glu Leu Thr Thr Val Phe Gln
                  195               200               205

Pro Gln Leu Thr Asn Pro Ala Leu Ser Pro Ile Ser Cys Gln Ala Leu
          210               215               220

Arg Ser Leu Leu Gly Ser Met Thr Pro Ala Val Val Gln Ala Thr Leu
```

-continued

```
225                 230                 235                 240

Ser Thr Ser Ile Ser Ala Ala Glu Ile Leu Ser Ala Gly Leu Cys Glu
                245                 250                 255

Gly Gln Ile Ile Ser Val Leu Leu Asp Glu Met Gln Met Ile Val Lys
                260                 265                 270

Ile Asn Ile Pro Thr Ile Val Thr Gln Ser Asn Ala Leu Val Ile Asp
                275                 280                 285

Phe Tyr Ser Ile Ser Ser Phe Ile Asn Asn Gln Glu Ser Ile Ile Gln
                290                 295                 300

Leu Pro Asp Arg Ile Leu Glu Ile Gly Asn Glu Gln Trp Ser Tyr Pro
305                 310                 315                 320

Ala Lys Asn Cys Lys Leu Thr Arg His His Ile Phe Cys Gln Tyr Asn
                325                 330                 335

Glu Ala Glu Arg Leu Ser Leu Glu Ser Lys Leu Cys Leu Ala Gly Asn
                340                 345                 350

Ile Ser Ala Cys Val Phe Ser Pro Ile Ala Gly Ser Tyr Met Arg Arg
                355                 360                 365

Phe Val Ala Leu Asp Gly Thr Ile Val Ala Asn Cys Arg Ser Leu Thr
                370                 375                 380

Cys Leu Cys Lys Ser Pro Ser Tyr Pro Ile Tyr Gln Pro Asp His His
385                 390                 395                 400

Ala Val Thr Thr Ile Asp Leu Thr Ala Cys Gln Thr Leu Ser Leu Asp
                405                 410                 415

Gly Leu Asp Phe Ser Ile Val Ser Leu Ser Asn Ile Thr Tyr Ala Glu
                420                 425                 430

Asn Leu Thr Ile Ser Leu Ser Gln Thr Ile Asn Thr Gln Pro Ile Asp
                435                 440                 445

Ile Ser Thr Glu Leu Ser Lys Val Asn Ala Ser Leu Gln Asn Ala Val
                450                 455                 460

Lys Tyr Ile Lys Glu Ser Asn His Gln Leu Gln Ser Ile Glu Asp Lys
465                 470                 475                 480

Ile Glu Glu Ile Leu Ser Lys Ile Tyr His Ile Glu Asn Glu Ile Ala
                485                 490                 495

Arg Ile Lys Lys Leu Ile Gly Glu Ala Pro
                500                 505
```

```
<210> SEQ ID NO 17
<211> LENGTH: 506
<212> TYPE: PRT
<213> ORGANISM: Artificial sequence
<220> FEATURE:
<223> OTHER INFORMATION: Recombinant F protein

<400> SEQUENCE: 17
```

```
Met Lys Ala Phe Ser Val Thr Cys Leu Ser Phe Ala Val Phe Ser Ser
1               5                   10                  15

Ser Ile Cys Val Asn Ile Asn Ile Leu Gln Gln Ile Gly Tyr Ile Lys
                20                  25                  30

Gln Gln Val Arg Gln Leu Ser Tyr Tyr Ser Gln Ser Ser Ser Ser Tyr
                35                  40                  45

Ile Val Val Lys Leu Leu Pro Asn Ile Gln Pro Thr Asp Asp Ser Cys
                50                  55                  60

Glu Phe Lys Ser Val Thr Gln Tyr Asn Lys Thr Leu Ser Asn Leu Leu
65                  70                  75                  80

Leu Pro Ile Ala Glu Asn Ile Asn Asn Ile Ala Ser Pro Ser Pro Gly
```

-continued

```
                    85               90               95

Ser Arg Arg His Gly Gly Gly Ala Gly Ile Ala Ile Gly Ile Ala Ala
            100             105             110

Leu Gly Val Ala Thr Ala Ala Gln Val Thr Ala Ala Val Ser Leu Val
            115             120             125

Gln Ala Gln Thr Asn Ala Arg Ala Ile Ala Ala Met Lys Asn Ser Ile
            130             135             140

Gln Ala Thr Asn Arg Ala Val Phe Glu Val Lys Glu Gly Thr Gln Gln
145             150             155             160

Leu Ala Ile Ala Val Gln Ala Ile Gln Asp His Ile Asn Thr Ile Met
                165             170             175

Asn Thr Gln Leu Asn Asn Met Pro Cys Gln Ile Leu Asp Asn Gln Leu
            180             185             190

Ala Thr Ser Leu Gly Leu Tyr Leu Thr Glu Leu Thr Thr Val Phe Gln
            195             200             205

Pro Gln Leu Thr Asn Pro Ala Leu Ser Pro Ile Ser Ile Gln Ala Leu
            210             215             220

Arg Ser Leu Leu Gly Ser Met Thr Pro Ala Val Val Gln Ala Thr Leu
225             230             235             240

Ser Thr Ser Ile Ser Ala Ala Glu Ile Leu Ser Ala Gly Leu Met Glu
                245             250             255

Gly Gln Ile Ile Ser Val Leu Leu Asp Glu Met Gln Met Ile Val Lys
            260             265             270

Ile Asn Ile Pro Thr Ile Val Thr Gln Ser Asn Ala Leu Val Ile Asp
            275             280             285

Phe Tyr Ser Ile Ser Ser Phe Ile Asn Asn Gln Glu Ser Ile Ile Gln
            290             295             300

Leu Pro Asp Arg Ile Leu Glu Ile Gly Asn Glu Gln Trp Ser Tyr Pro
305             310             315             320

Ala Lys Asn Cys Lys Leu Thr Arg His His Ile Phe Cys Gln Tyr Asn
                325             330             335

Glu Ala Glu Arg Leu Ser Leu Glu Ser Lys Leu Cys Leu Ala Gly Asn
            340             345             350

Ile Ser Ala Cys Val Phe Ser Pro Ile Ala Gly Ser Tyr Met Arg Arg
            355             360             365

Phe Val Ala Leu Asp Gly Thr Ile Val Ala Asn Cys Arg Ser Leu Thr
            370             375             380

Cys Leu Cys Lys Ser Pro Ser Tyr Pro Ile Tyr Gln Pro Asp His His
385             390             395             400

Ala Val Thr Thr Ile Asp Leu Thr Ala Cys Gln Thr Leu Ser Leu Asp
                405             410             415

Gly Leu Asp Phe Ser Ile Val Ser Leu Ser Asn Ile Thr Tyr Ala Glu
            420             425             430

Asn Leu Thr Ile Ser Leu Ser Gln Thr Ile Asn Thr Gln Pro Ile Asp
            435             440             445

Ile Ser Thr Glu Leu Ser Lys Val Asn Ala Ser Leu Gln Asn Ala Val
            450             455             460

Lys Tyr Ile Lys Glu Ser Asn His Gln Leu Gln Ser Ile Glu Asp Lys
465             470             475             480

Ile Glu Glu Ile Leu Ser Lys Ile Tyr His Ile Glu Asn Glu Ile Ala
                485             490             495

Arg Ile Lys Lys Leu Ile Gly Glu Ala Pro
            500             505
```

```
<210> SEQ ID NO 18
<211> LENGTH: 499
<212> TYPE: PRT
<213> ORGANISM: Artificial sequence
<220> FEATURE:
<223> OTHER INFORMATION: Recombinant F protein

<400> SEQUENCE: 18

Met Lys Ala Phe Ser Val Thr Cys Leu Ser Phe Ala Val Phe Ser Ser
1               5                   10                  15

Ser Ile Cys Val Asn Ile Asn Ile Leu Gln Gln Ile Gly Tyr Ile Lys
            20                  25                  30

Gln Gln Val Arg Gln Leu Ser Tyr Tyr Ser Gln Ser Ser Ser Ser Tyr
        35                  40                  45

Ile Val Val Lys Leu Leu Pro Asn Ile Gln Pro Thr Asp Asp Ser Cys
    50                  55                  60

Glu Phe Lys Ser Val Thr Gln Tyr Asn Lys Thr Leu Ser Asn Leu Leu
65                  70                  75                  80

Leu Pro Ile Ala Glu Asn Ile Asn Asn Ile Ala Ser Pro Ser Pro Gly
                85                  90                  95

Ser Arg Arg His Gly Gly Gly Ala Gly Ile Ala Ile Gly Ile Ala Ala
            100                 105                 110

Leu Gly Val Ala Thr Ala Ala Gln Val Thr Ala Ala Val Ser Leu Val
            115                 120                 125

Gln Ala Gln Thr Asn Ala Arg Ala Ile Ala Ala Met Lys Asn Ser Ile
        130                 135                 140

Gln Ala Thr Asn Arg Ala Val Phe Glu Val Lys Glu Gly Thr Gln Gln
145                 150                 155                 160

Leu Ala Cys Ala Val Gln Ala Ile Gln Asp His Ile Asn Thr Ile Met
                165                 170                 175

Asn Thr Gln Leu Asn Asn Met Ser Cys Gln Ile Leu Asp Asn Gln Leu
                180                 185                 190

Ala Thr Ser Leu Gly Leu Tyr Leu Thr Glu Leu Thr Thr Val Phe Gln
            195                 200                 205

Pro Gln Leu Thr Asn Pro Ala Leu Ser Pro Ile Ser Ile Gln Ala Leu
    210                 215                 220

Arg Ser Leu Leu Gly Ser Met Thr Pro Ala Cys Val Gln Ala Thr Leu
225                 230                 235                 240

Ser Thr Ser Ile Ser Ala Ala Glu Ile Leu Ser Ala Gly Leu Met Glu
                245                 250                 255

Gly Gln Ile Ile Ser Val Leu Leu Asp Glu Met Gln Met Ile Val Lys
            260                 265                 270

Ile Asn Ile Pro Thr Ile Val Thr Gln Ser Asn Ala Leu Val Ile Asp
            275                 280                 285

Phe Tyr Ser Ile Ser Ser Phe Ile Asn Asn Gln Glu Ser Ile Ile Gln
    290                 295                 300

Leu Pro Asp Arg Ile Leu Glu Ile Gly Asn Glu Gln Trp Ser Tyr Pro
305                 310                 315                 320

Ala Lys Asn Cys Lys Leu Thr Arg His His Ile Phe Cys Gln Tyr Asn
                325                 330                 335

Glu Ala Glu Arg Leu Ser Leu Glu Ser Lys Leu Cys Leu Ala Gly Asn
            340                 345                 350

Ile Ser Ala Cys Val Phe Ser Pro Ile Ala Gly Ser Tyr Met Arg Arg
            355                 360                 365
```

-continued

```
Phe Val Ala Leu Asp Gly Thr Ile Val Ala Asn Cys Arg Ser Leu Thr
    370             375             380

Cys Leu Cys Lys Ser Pro Ser Tyr Pro Ile Tyr Gln Pro Asp His His
385             390             395             400

Ala Val Thr Thr Ile Asp Leu Thr Ala Cys Gln Thr Leu Ser Leu Asp
                405             410             415

Gly Leu Asp Phe Ser Ile Val Ser Leu Ser Asn Ile Thr Tyr Ala Glu
                420             425             430

Asn Leu Thr Ile Ser Leu Ser Gln Thr Ile Asn Thr Gln Pro Ile Asp
            435             440             445

Ile Ser Thr Glu Leu Ser Lys Val Asn Ala Ser Leu Gln Asn Ala Val
    450             455             460

Lys Tyr Ile Lys Glu Ile Glu Asp Lys Ile Glu Glu Ile Leu Ser Lys
465             470             475             480

Ile Tyr His Ile Glu Asn Glu Ile Ala Arg Ile Lys Lys Leu Ile Gly
            485             490             495

Glu Ala Pro

<210> SEQ ID NO 19
<211> LENGTH: 499
<212> TYPE: PRT
<213> ORGANISM: Artificial sequence
<220> FEATURE:
<223> OTHER INFORMATION: Recombinant F protein

<400> SEQUENCE: 19

Met Lys Ala Phe Ser Val Thr Cys Leu Ser Phe Ala Val Phe Ser Ser
1               5               10              15

Ser Ile Cys Val Asn Ile Asn Ile Leu Gln Gln Ile Gly Tyr Ile Lys
            20              25              30

Gln Gln Val Arg Gln Leu Ser Tyr Tyr Ser Gln Ser Ser Ser Ser Tyr
        35              40              45

Ile Val Val Lys Leu Leu Pro Asn Ile Gln Pro Thr Asp Asp Ser Cys
    50              55              60

Glu Phe Lys Ser Val Thr Gln Tyr Asn Lys Thr Leu Ser Asn Leu Leu
65              70              75              80

Leu Pro Ile Ala Glu Asn Ile Asn Asn Ile Ala Ser Pro Ser Pro Gly
            85              90              95

Ser Arg Arg His Gly Gly Gly Ala Gly Ile Ala Ile Gly Ile Ala Ala
            100             105             110

Leu Gly Val Ala Thr Ala Ala Gln Val Thr Ala Ala Val Ser Leu Val
        115             120             125

Gln Ala Gln Thr Asn Ala Arg Ala Ile Ala Ala Met Lys Asn Ser Ile
    130             135             140

Gln Ala Thr Asn Arg Ala Val Phe Glu Val Lys Glu Gly Thr Gln Gln
145             150             155             160

Leu Ala Ile Ala Val Gln Ala Ile Gln Asp His Ile Asn Thr Ile Met
            165             170             175

Asn Thr Gln Leu Asn Asn Met Ser Cys Gln Ile Leu Asp Asn Gln Leu
            180             185             190

Ala Thr Ser Leu Gly Leu Tyr Leu Thr Glu Leu Thr Thr Cys Phe Gln
        195             200             205

Pro Gln Leu Thr Asn Pro Ala Leu Ser Pro Ile Ser Ile Gln Cys Leu
    210             215             220
```

```
Arg Ser Leu Leu Gly Ser Met Thr Pro Ala Val Val Gln Ala Thr Leu
225             230              235             240

Ser Thr Ser Ile Ser Ala Ala Glu Ile Leu Ser Ala Gly Leu Met Glu
                245             250             255

Gly Gln Ile Ile Ser Val Leu Leu Asp Glu Met Gln Met Ile Val Lys
                260             265             270

Ile Asn Ile Pro Thr Ile Val Thr Gln Ser Asn Ala Leu Val Ile Asp
                275             280             285

Phe Tyr Ser Ile Ser Ser Phe Ile Asn Asn Gln Glu Ser Ile Ile Gln
    290             295             300

Leu Pro Asp Arg Ile Leu Glu Ile Gly Asn Glu Gln Trp Ser Tyr Pro
305             310             315             320

Ala Lys Asn Cys Lys Leu Thr Arg His His Ile Phe Cys Gln Tyr Asn
                325             330             335

Glu Ala Glu Arg Leu Ser Leu Glu Ser Lys Leu Cys Leu Ala Gly Asn
                340             345             350

Ile Ser Ala Cys Val Phe Ser Pro Ile Ala Gly Ser Tyr Met Arg Arg
    355             360             365

Phe Val Ala Leu Asp Gly Thr Ile Val Ala Asn Cys Arg Ser Leu Thr
    370             375             380

Cys Leu Cys Lys Ser Pro Ser Tyr Pro Ile Tyr Gln Pro Asp His His
385             390             395             400

Ala Val Thr Thr Ile Asp Leu Thr Ala Cys Gln Thr Leu Ser Leu Asp
                405             410             415

Gly Leu Asp Phe Ser Ile Val Ser Leu Ser Asn Ile Thr Tyr Ala Glu
                420             425             430

Asn Leu Thr Ile Ser Leu Ser Gln Thr Ile Asn Thr Gln Pro Ile Asp
                435             440             445

Ile Ser Thr Glu Leu Ser Lys Val Asn Ala Ser Leu Gln Asn Ala Val
    450             455             460

Lys Tyr Ile Lys Glu Ile Glu Asp Lys Ile Glu Glu Ile Leu Ser Lys
465             470             475             480

Ile Tyr His Ile Glu Asn Glu Ile Ala Arg Ile Lys Lys Leu Ile Gly
                485             490             495

Glu Ala Pro
```

<210> SEQ ID NO 20
<211> LENGTH: 499
<212> TYPE: PRT
<213> ORGANISM: Artificial sequence
<220> FEATURE:
<223> OTHER INFORMATION: Recombinant F protein

<400> SEQUENCE: 20

```
Met Lys Ala Phe Ser Val Thr Cys Leu Ser Phe Ala Val Phe Ser Ser
1               5               10              15

Ser Ile Cys Val Asn Ile Asn Ile Leu Gln Gln Ile Gly Tyr Ile Lys
                20              25              30

Gln Gln Val Arg Gln Leu Ser Tyr Tyr Ser Gln Ser Ser Ser Ser Tyr
        35              40              45

Ile Val Val Lys Leu Leu Pro Asn Ile Gln Pro Thr Asp Asp Ser Cys
    50              55              60

Glu Phe Lys Ser Val Thr Gln Tyr Asn Lys Thr Leu Ser Asn Leu Leu
65              70              75              80

Leu Pro Ile Ala Glu Cys Ile Asn Asn Ile Ala Ser Pro Ser Pro Gly
```

-continued

```
                     85                    90                    95
Ser Arg Arg His Gly Gly Gly Ala Gly Ile Ala Ile Gly Ile Ala Ala
                100                   105                   110
Leu Gly Val Ala Thr Ala Ala Gln Val Thr Ala Ala Val Ser Leu Val
                115                   120                   125
Gln Ala Gln Thr Asn Ala Arg Ala Ile Ala Ala Met Lys Asn Ser Ile
        130                   135                   140
Gln Ala Thr Asn Arg Ala Val Phe Glu Val Lys Glu Gly Thr Gln Gln
145                   150                   155                   160
Leu Ala Ile Ala Val Gln Ala Ile Gln Asp His Ile Asn Thr Ile Met
                165                   170                   175
Asn Thr Gln Leu Asn Asn Met Ser Cys Gln Ile Leu Asp Asn Gln Leu
                180                   185                   190
Ala Thr Ser Leu Gly Leu Tyr Leu Thr Glu Leu Thr Thr Val Phe Gln
                195                   200                   205
Pro Gln Leu Thr Asn Pro Cys Leu Ser Pro Ile Ser Ile Gln Ala Leu
        210                   215                   220
Arg Ser Leu Leu Gly Ser Met Thr Pro Ala Val Val Gln Ala Thr Leu
225                   230                   235                   240
Ser Thr Ser Ile Ser Ala Ala Glu Ile Leu Ser Ala Gly Leu Met Glu
                245                   250                   255
Gly Gln Ile Ile Ser Val Leu Leu Asp Glu Met Gln Met Ile Val Lys
                260                   265                   270
Ile Asn Ile Pro Thr Ile Val Thr Gln Ser Asn Ala Leu Val Ile Asp
                275                   280                   285
Phe Tyr Ser Ile Ser Ser Phe Ile Asn Asn Gln Glu Ser Ile Ile Gln
        290                   295                   300
Leu Pro Asp Arg Ile Leu Glu Ile Gly Asn Glu Gln Trp Ser Tyr Pro
305                   310                   315                   320
Ala Lys Asn Cys Lys Leu Thr Arg His His Ile Phe Cys Gln Tyr Asn
                325                   330                   335
Glu Ala Glu Arg Leu Ser Leu Glu Ser Lys Leu Cys Leu Ala Gly Asn
                340                   345                   350
Ile Ser Ala Cys Val Phe Ser Pro Ile Ala Gly Ser Tyr Met Arg Arg
                355                   360                   365
Phe Val Ala Leu Asp Gly Thr Ile Val Ala Asn Cys Arg Ser Leu Thr
        370                   375                   380
Cys Leu Cys Lys Ser Pro Ser Tyr Pro Ile Tyr Gln Pro Asp His His
385                   390                   395                   400
Ala Val Thr Thr Ile Asp Leu Thr Ala Cys Gln Thr Leu Ser Leu Asp
                405                   410                   415
Gly Leu Asp Phe Ser Ile Val Ser Leu Ser Asn Ile Thr Tyr Ala Glu
                420                   425                   430
Asn Leu Thr Ile Ser Leu Ser Gln Thr Ile Asn Thr Gln Pro Ile Asp
                435                   440                   445
Ile Ser Thr Glu Leu Ser Lys Val Asn Ala Ser Leu Gln Asn Ala Val
        450                   455                   460
Lys Tyr Ile Lys Glu Ile Glu Asp Lys Ile Glu Glu Ile Leu Ser Lys
465                   470                   475                   480
Ile Tyr His Ile Glu Asn Glu Ile Ala Arg Ile Lys Lys Leu Ile Gly
                485                   490                   495
Glu Ala Pro
```

<210> SEQ ID NO 21
<211> LENGTH: 499
<212> TYPE: PRT
<213> ORGANISM: Artificial sequence
<220> FEATURE:
<223> OTHER INFORMATION: Recombinant F protein

<400> SEQUENCE: 21

```
Met Lys Ala Phe Ser Val Thr Cys Leu Ser Phe Ala Val Phe Ser Ser
1               5                   10                  15

Ser Ile Cys Val Asn Ile Asn Ile Leu Gln Gln Ile Gly Tyr Ile Lys
                20                  25                  30

Gln Gln Val Arg Gln Leu Ser Tyr Tyr Ser Gln Ser Ser Ser Ser Tyr
            35                  40                  45

Ile Val Val Lys Leu Leu Pro Asn Ile Gln Pro Thr Asp Asp Ser Cys
    50                  55                  60

Glu Phe Lys Ser Val Thr Gln Tyr Asn Lys Thr Leu Ser Asn Leu Leu
65                  70                  75                  80

Leu Pro Ile Ala Glu Asn Ile Asn Asn Ile Ala Ser Pro Ser Pro Gly
                85                  90                  95

Ser Arg Arg His Gly Gly Gly Ala Gly Ile Ala Ile Gly Ile Ala Ala
            100                 105                 110

Leu Gly Val Ala Thr Ala Ala Gln Val Thr Ala Ala Val Ser Leu Val
            115                 120                 125

Gln Ala Gln Thr Asn Ala Arg Ala Ile Ala Ala Met Lys Asn Ser Ile
    130                 135                 140

Gln Ala Thr Asn Arg Ala Val Phe Glu Val Lys Glu Gly Thr Gln Gln
145                 150                 155                 160

Leu Ala Ile Ala Val Gln Ala Ile Gln Asp His Ile Asn Thr Ile Met
                165                 170                 175

Asn Thr Gln Leu Asn Asn Met Ser Cys Gln Ile Leu Asp Asn Gln Leu
                180                 185                 190

Ala Thr Ser Leu Gly Leu Tyr Leu Thr Glu Leu Thr Thr Val Phe Gln
            195                 200                 205

Cys Gln Leu Thr Asn Cys Ala Leu Ser Pro Ile Ser Ile Gln Ala Leu
    210                 215                 220

Arg Ser Leu Leu Gly Ser Met Thr Pro Ala Val Val Gln Ala Thr Leu
225                 230                 235                 240

Ser Thr Ser Ile Ser Ala Ala Glu Ile Leu Ser Ala Gly Leu Met Glu
                245                 250                 255

Gly Gln Ile Ile Ser Val Leu Leu Asp Glu Met Gln Met Ile Val Lys
            260                 265                 270

Ile Asn Ile Pro Thr Ile Val Thr Gln Ser Asn Ala Leu Val Ile Asp
            275                 280                 285

Phe Tyr Ser Ile Ser Ser Phe Ile Asn Asn Gln Glu Ser Ile Ile Gln
    290                 295                 300

Leu Pro Asp Arg Ile Leu Glu Ile Gly Asn Glu Gln Trp Ser Tyr Pro
305                 310                 315                 320

Ala Lys Asn Cys Lys Leu Thr Arg His His Ile Phe Cys Gln Tyr Asn
                325                 330                 335

Glu Ala Glu Arg Leu Ser Leu Glu Ser Lys Leu Cys Leu Ala Gly Asn
            340                 345                 350

Ile Ser Ala Cys Val Phe Ser Pro Ile Ala Gly Ser Tyr Met Arg Arg
    355                 360                 365
```

```
Phe Val Ala Leu Asp Gly Thr Ile Val Ala Asn Cys Arg Ser Leu Thr
    370             375             380

Cys Leu Cys Lys Ser Pro Ser Tyr Pro Ile Tyr Gln Pro Asp His His
385             390             395             400

Ala Val Thr Thr Ile Asp Leu Thr Ala Cys Gln Thr Leu Ser Leu Asp
            405             410             415

Gly Leu Asp Phe Ser Ile Val Ser Leu Ser Asn Ile Thr Tyr Ala Glu
            420             425             430

Asn Leu Thr Ile Ser Leu Ser Gln Thr Ile Asn Thr Gln Pro Ile Asp
        435             440             445

Ile Ser Thr Glu Leu Ser Lys Val Asn Ala Ser Leu Gln Asn Ala Val
    450             455             460

Lys Tyr Ile Lys Glu Ile Glu Asp Lys Ile Glu Glu Ile Leu Ser Lys
465             470             475             480

Ile Tyr His Ile Glu Asn Glu Ile Ala Arg Ile Lys Lys Leu Ile Gly
            485             490             495

Glu Ala Pro
```

```
<210> SEQ ID NO 22
<211> LENGTH: 499
<212> TYPE: PRT
<213> ORGANISM: Artificial sequence
<220> FEATURE:
<223> OTHER INFORMATION: Recombinant F protein

<400> SEQUENCE: 22

Met Lys Ala Phe Ser Val Thr Cys Leu Ser Phe Ala Val Phe Ser Ser
1               5               10              15

Ser Ile Cys Val Asn Ile Asn Ile Leu Gln Gln Ile Gly Tyr Ile Lys
            20              25              30

Gln Gln Val Arg Gln Leu Ser Tyr Tyr Ser Gln Ser Ser Ser Ser Tyr
        35              40              45

Ile Val Val Lys Leu Leu Pro Asn Ile Gln Pro Thr Asp Asp Ser Cys
    50              55              60

Glu Phe Lys Ser Val Thr Gln Tyr Asn Lys Thr Leu Ser Asn Leu Leu
65              70              75              80

Leu Pro Ile Ala Glu Asn Ile Asn Asn Ile Ala Ser Pro Ser Pro Gly
            85              90              95

Ser Arg Arg His Gly Gly Gly Ala Gly Ile Ala Ile Gly Ile Ala Ala
            100             105             110

Leu Gly Val Ala Thr Ala Ala Gln Val Thr Ala Ala Val Ser Leu Val
        115             120             125

Gln Ala Gln Thr Asn Ala Arg Ala Ile Ala Ala Met Lys Asn Ser Ile
    130             135             140

Gln Ala Thr Asn Arg Ala Val Phe Glu Val Cys Glu Gly Thr Gln Gln
145             150             155             160

Cys Ala Ile Ala Val Gln Ala Ile Gln Asp His Ile Asn Thr Ile Met
            165             170             175

Asn Thr Gln Leu Asn Asn Met Ser Cys Gln Ile Leu Asp Asn Gln Leu
            180             185             190

Ala Thr Ser Leu Gly Leu Tyr Leu Thr Glu Leu Thr Thr Val Phe Gln
            195             200             205

Pro Gln Leu Thr Asn Pro Ala Leu Ser Pro Ile Ser Ile Gln Ala Leu
    210             215             220

Arg Ser Leu Leu Gly Ser Met Thr Pro Ala Val Val Gln Ala Thr Leu
```

-continued

```
225                 230                 235                 240

Ser Thr Ser Ile Ser Ala Ala Glu Ile Leu Ser Ala Gly Leu Met Glu
                245                 250                 255

Gly Gln Ile Ile Ser Val Leu Leu Asp Glu Met Gln Met Ile Val Lys
                260                 265                 270

Ile Asn Ile Pro Thr Ile Val Thr Gln Ser Asn Ala Leu Val Ile Asp
                275                 280                 285

Phe Tyr Ser Ile Ser Ser Phe Ile Asn Asn Gln Glu Ser Ile Ile Gln
                290                 295                 300

Leu Pro Asp Arg Ile Leu Glu Ile Gly Asn Glu Gln Trp Ser Tyr Pro
305                 310                 315                 320

Ala Lys Asn Cys Lys Leu Thr Arg His His Ile Phe Cys Gln Tyr Asn
                325                 330                 335

Glu Ala Glu Arg Leu Ser Leu Glu Ser Lys Leu Cys Leu Ala Gly Asn
                340                 345                 350

Ile Ser Ala Cys Val Phe Ser Pro Ile Ala Gly Ser Tyr Met Arg Arg
                355                 360                 365

Phe Val Ala Leu Asp Gly Thr Ile Val Ala Asn Cys Arg Ser Leu Thr
                370                 375                 380

Cys Leu Cys Lys Ser Pro Ser Tyr Pro Ile Tyr Gln Pro Asp His His
385                 390                 395                 400

Ala Val Thr Thr Ile Asp Leu Thr Ala Cys Gln Thr Leu Ser Leu Asp
                405                 410                 415

Gly Leu Asp Phe Ser Ile Val Ser Leu Ser Asn Ile Thr Tyr Ala Glu
                420                 425                 430

Asn Leu Thr Ile Ser Leu Ser Gln Thr Ile Asn Thr Gln Pro Ile Asp
                435                 440                 445

Ile Ser Thr Glu Leu Ser Lys Val Asn Ala Ser Leu Gln Asn Ala Val
                450                 455                 460

Lys Tyr Ile Lys Glu Ile Glu Asp Lys Ile Glu Glu Ile Leu Ser Lys
465                 470                 475                 480

Ile Tyr His Ile Glu Asn Glu Ile Ala Arg Ile Lys Lys Leu Ile Gly
                485                 490                 495

Glu Ala Pro
```

<210> SEQ ID NO 23
<211> LENGTH: 499
<212> TYPE: PRT
<213> ORGANISM: Artificial sequence
<220> FEATURE:
<223> OTHER INFORMATION: Recombinant F protein

<400> SEQUENCE: 23

```
Met Lys Ala Phe Ser Val Thr Cys Leu Ser Phe Ala Val Phe Ser Ser
1                   5                   10                  15

Ser Ile Cys Val Asn Ile Asn Ile Leu Gln Gln Ile Gly Tyr Ile Lys
                20                  25                  30

Gln Gln Val Arg Gln Leu Ser Tyr Tyr Ser Gln Ser Ser Ser Tyr
            35                  40                  45

Ile Val Val Lys Leu Leu Pro Asn Ile Gln Pro Thr Asp Asp Ser Cys
        50                  55                  60

Glu Phe Lys Ser Val Thr Gln Tyr Asn Lys Thr Leu Ser Asn Leu Leu
65                  70                  75                  80

Leu Pro Ile Ala Glu Asn Ile Asn Asn Ile Ala Ser Pro Ser Pro Gly
                85                  90                  95
```

```
Ser Arg Arg His Gly Gly Gly Ala Gly Ile Ala Ile Gly Ile Ala Ala
            100             105             110

Leu Gly Val Ala Thr Ala Ala Gln Val Thr Ala Ala Val Ser Leu Val
            115             120             125

Gln Ala Gln Thr Asn Ala Arg Ala Ile Ala Ala Met Lys Asn Ser Ile
        130             135             140

Gln Ala Thr Asn Arg Ala Val Phe Glu Val Lys Glu Gly Thr Gln Gln
    145             150             155             160

Leu Ala Ile Ala Cys Gln Ala Ile Gln Asp His Ile Asn Thr Ile Met
                165             170             175

Asn Thr Gln Leu Asn Asn Met Ser Cys Gln Ile Leu Asp Asn Gln Leu
            180             185             190

Ala Thr Ser Leu Gly Leu Tyr Leu Thr Glu Leu Thr Thr Val Phe Gln
            195             200             205

Pro Gln Leu Thr Asn Pro Ala Leu Ser Pro Ile Ser Ile Gln Ala Leu
        210             215             220

Arg Ser Leu Leu Gly Ser Cys Thr Pro Ala Val Val Gln Ala Thr Leu
225             230             235             240

Ser Thr Ser Ile Ser Ala Ala Glu Ile Leu Ser Ala Gly Leu Met Glu
                245             250             255

Gly Gln Ile Ile Ser Val Leu Leu Asp Glu Met Gln Met Ile Val Lys
            260             265             270

Ile Asn Ile Pro Thr Ile Val Thr Gln Ser Asn Ala Leu Val Ile Asp
            275             280             285

Phe Tyr Ser Ile Ser Ser Phe Ile Asn Asn Gln Glu Ser Ile Ile Gln
    290             295             300

Leu Pro Asp Arg Ile Leu Glu Ile Gly Asn Glu Gln Trp Ser Tyr Pro
305             310             315             320

Ala Lys Asn Cys Lys Leu Thr Arg His His Ile Phe Cys Gln Tyr Asn
            325             330             335

Glu Ala Glu Arg Leu Ser Leu Glu Ser Lys Leu Cys Leu Ala Gly Asn
            340             345             350

Ile Ser Ala Cys Val Phe Ser Pro Ile Ala Gly Ser Tyr Met Arg Arg
            355             360             365

Phe Val Ala Leu Asp Gly Thr Ile Val Ala Asn Cys Arg Ser Leu Thr
    370             375             380

Cys Leu Cys Lys Ser Pro Ser Tyr Pro Ile Tyr Gln Pro Asp His His
385             390             395             400

Ala Val Thr Thr Ile Asp Leu Thr Ala Cys Gln Thr Leu Ser Leu Asp
            405             410             415

Gly Leu Asp Phe Ser Ile Val Ser Leu Ser Asn Ile Thr Tyr Ala Glu
            420             425             430

Asn Leu Thr Ile Ser Leu Ser Gln Thr Ile Asn Thr Gln Pro Ile Asp
            435             440             445

Ile Ser Thr Glu Leu Ser Lys Val Asn Ala Ser Leu Gln Asn Ala Val
    450             455             460

Lys Tyr Ile Lys Glu Ile Glu Asp Lys Ile Glu Glu Ile Leu Ser Lys
465             470             475             480

Ile Tyr His Ile Glu Asn Glu Ile Ala Arg Ile Lys Lys Leu Ile Gly
            485             490             495

Glu Ala Pro
```

-continued

```
<210> SEQ ID NO 24
<211> LENGTH: 499
<212> TYPE: PRT
<213> ORGANISM: Artificial sequence
<220> FEATURE:
<223> OTHER INFORMATION: Recombinant F protein

<400> SEQUENCE: 24

Met Lys Ala Phe Ser Val Thr Cys Leu Ser Phe Ala Val Phe Ser Ser
1               5                   10                  15

Ser Ile Cys Val Asn Ile Asn Ile Leu Gln Gln Ile Gly Tyr Ile Lys
                20                  25                  30

Gln Gln Val Arg Gln Leu Ser Tyr Tyr Ser Gln Ser Ser Ser Ser Tyr
            35                  40                  45

Ile Val Val Lys Leu Leu Pro Asn Ile Gln Pro Thr Asp Asp Ser Cys
        50                  55                  60

Glu Phe Lys Ser Val Thr Gln Tyr Asn Lys Thr Leu Ser Asn Leu Leu
65                  70                  75                  80

Leu Pro Ile Ala Glu Asn Ile Asn Asn Ile Ala Ser Pro Ser Pro Gly
                85                  90                  95

Ser Arg Arg His Gly Gly Gly Ala Gly Ile Ala Ile Gly Ile Ala Ala
            100                 105                 110

Leu Gly Val Ala Thr Ala Ala Gln Val Thr Ala Ala Val Ser Leu Val
            115                 120                 125

Gln Ala Gln Thr Asn Ala Arg Ala Ile Ala Ala Met Lys Asn Ser Ile
        130                 135                 140

Gln Ala Thr Asn Arg Ala Val Phe Glu Val Lys Glu Gly Thr Gln Gln
145                 150                 155                 160

Leu Ala Ile Ala Val Gln Ala Ile Gln Asp His Ile Asn Thr Ile Met
                165                 170                 175

Asn Thr Gln Leu Asn Asn Met Ser Cys Gln Ile Leu Asp Asn Gln Leu
                180                 185                 190

Ala Thr Ser Leu Gly Leu Tyr Leu Thr Glu Leu Thr Thr Val Phe Gln
            195                 200                 205

Pro Gln Leu Thr Asn Pro Ala Leu Ser Pro Ile Ser Cys Gln Ala Leu
        210                 215                 220

Arg Ser Leu Leu Gly Ser Met Thr Pro Ala Val Val Gln Ala Thr Leu
225                 230                 235                 240

Ser Thr Ser Ile Ser Ala Ala Glu Ile Leu Ser Ala Gly Leu Cys Glu
                245                 250                 255

Gly Gln Ile Ile Ser Val Leu Leu Asp Glu Met Gln Met Ile Val Lys
            260                 265                 270

Ile Asn Ile Pro Thr Ile Val Thr Gln Ser Asn Ala Leu Val Ile Asp
        275                 280                 285

Phe Tyr Ser Ile Ser Ser Phe Ile Asn Asn Gln Glu Ser Ile Ile Gln
    290                 295                 300

Leu Pro Asp Arg Ile Leu Glu Ile Gly Asn Glu Gln Trp Ser Tyr Pro
305                 310                 315                 320

Ala Lys Asn Cys Lys Leu Thr Arg His His Ile Phe Cys Gln Tyr Asn
                325                 330                 335

Glu Ala Glu Arg Leu Ser Leu Glu Ser Lys Leu Cys Leu Ala Gly Asn
            340                 345                 350

Ile Ser Ala Cys Val Phe Ser Pro Ile Ala Gly Ser Tyr Met Arg Arg
        355                 360                 365

Phe Val Ala Leu Asp Gly Thr Ile Val Ala Asn Cys Arg Ser Leu Thr
```

-continued

```
              370             375             380
Cys Leu Cys Lys Ser Pro Ser Tyr Pro Ile Tyr Gln Pro Asp His His
385             390             395             400

Ala Val Thr Thr Ile Asp Leu Thr Ala Cys Gln Thr Leu Ser Leu Asp
                405             410             415

Gly Leu Asp Phe Ser Ile Val Ser Leu Ser Asn Ile Thr Tyr Ala Glu
                420             425             430

Asn Leu Thr Ile Ser Leu Ser Gln Thr Ile Asn Thr Gln Pro Ile Asp
                435             440             445

Ile Ser Thr Glu Leu Ser Lys Val Asn Ala Ser Leu Gln Asn Ala Val
        450             455             460

Lys Tyr Ile Lys Glu Ile Glu Asp Lys Ile Glu Glu Ile Leu Ser Lys
465             470             475             480

Ile Tyr His Ile Glu Asn Glu Ile Ala Arg Ile Lys Lys Leu Ile Gly
                485             490             495

Glu Ala Pro
```

<210> SEQ ID NO 25
<211> LENGTH: 499
<212> TYPE: PRT
<213> ORGANISM: Artificial sequence
<220> FEATURE:
<223> OTHER INFORMATION: Recombinant F protein

<400> SEQUENCE: 25

```
Met Lys Ala Phe Ser Val Thr Cys Leu Ser Phe Ala Val Phe Ser Ser
1               5               10              15

Ser Ile Cys Val Asn Ile Asn Ile Leu Gln Gln Ile Gly Tyr Ile Lys
                20              25              30

Gln Gln Val Arg Gln Leu Ser Tyr Tyr Ser Gln Ser Ser Ser Ser Tyr
                35              40              45

Ile Val Val Lys Leu Leu Pro Asn Ile Gln Pro Thr Asp Asp Ser Cys
        50              55              60

Glu Phe Lys Ser Val Thr Gln Tyr Asn Lys Thr Leu Ser Asn Leu Leu
65              70              75              80

Leu Pro Ile Ala Glu Asn Ile Asn Asn Ile Ala Ser Pro Ser Pro Gly
                85              90              95

Ser Arg Arg His Gly Gly Gly Ala Gly Ile Ala Ile Gly Ile Ala Ala
                100             105             110

Leu Gly Val Ala Thr Ala Ala Gln Val Thr Ala Ala Val Ser Leu Val
                115             120             125

Gln Ala Gln Thr Asn Ala Arg Ala Ile Ala Ala Met Lys Asn Ser Ile
        130             135             140

Gln Ala Thr Asn Arg Ala Val Phe Glu Val Lys Glu Gly Thr Gln Gln
145             150             155             160

Leu Ala Ile Ala Val Gln Ala Ile Gln Asp His Ile Asn Thr Ile Met
                165             170             175

Asn Thr Gln Leu Asn Asn Met Pro Cys Gln Ile Leu Asp Asn Gln Leu
                180             185             190

Ala Thr Ser Leu Gly Leu Tyr Leu Thr Glu Leu Thr Thr Val Phe Gln
                195             200             205

Pro Gln Leu Thr Asn Pro Ala Leu Ser Pro Ile Ser Ile Gln Ala Leu
        210             215             220

Arg Ser Leu Leu Gly Ser Met Thr Pro Ala Val Val Gln Ala Thr Leu
225             230             235             240
```

-continued

```
Ser Thr Ser Ile Ser Ala Ala Glu Ile Leu Ser Ala Gly Leu Met Glu
             245                 250                 255

Gly Gln Ile Ile Ser Val Leu Leu Asp Glu Met Gln Met Ile Val Lys
             260                 265                 270

Ile Asn Ile Pro Thr Ile Val Thr Gln Ser Asn Ala Leu Val Ile Asp
             275                 280                 285

Phe Tyr Ser Ile Ser Ser Phe Ile Asn Asn Gln Glu Ser Ile Ile Gln
        290                 295                 300

Leu Pro Asp Arg Ile Leu Glu Ile Gly Asn Glu Gln Trp Ser Tyr Pro
305                 310                 315                 320

Ala Lys Asn Cys Lys Leu Thr Arg His His Ile Phe Cys Gln Tyr Asn
                 325                 330                 335

Glu Ala Glu Arg Leu Ser Leu Glu Ser Lys Leu Cys Leu Ala Gly Asn
             340                 345                 350

Ile Ser Ala Cys Val Phe Ser Pro Ile Ala Gly Ser Tyr Met Arg Arg
             355                 360                 365

Phe Val Ala Leu Asp Gly Thr Ile Val Ala Asn Cys Arg Ser Leu Thr
        370                 375                 380

Cys Leu Cys Lys Ser Pro Ser Tyr Pro Ile Tyr Gln Pro Asp His His
385                 390                 395                 400

Ala Val Thr Thr Ile Asp Leu Thr Ala Cys Gln Thr Leu Ser Leu Asp
             405                 410                 415

Gly Leu Asp Phe Ser Ile Val Ser Leu Ser Asn Ile Thr Tyr Ala Glu
             420                 425                 430

Asn Leu Thr Ile Ser Leu Ser Gln Thr Ile Asn Thr Gln Pro Ile Asp
             435                 440                 445

Ile Ser Thr Glu Leu Ser Lys Val Asn Ala Ser Leu Gln Asn Ala Val
        450                 455                 460

Lys Tyr Ile Lys Glu Ile Glu Asp Lys Ile Glu Glu Ile Leu Ser Lys
465                 470                 475                 480

Ile Tyr His Ile Glu Asn Glu Ile Ala Arg Ile Lys Lys Leu Ile Gly
        485                 490                 495

Glu Ala Pro
```

<210> SEQ ID NO 26
<211> LENGTH: 506
<212> TYPE: PRT
<213> ORGANISM: Artificial sequence
<220> FEATURE:
<223> OTHER INFORMATION: Recombinant F protein

<400> SEQUENCE: 26

```
Met Lys Ala Phe Ser Val Thr Cys Leu Ser Phe Ala Val Phe Ser Ser
1               5                   10                  15

Ser Ile Cys Val Asn Ile Asn Ile Leu Gln Gln Ile Gly Tyr Ile Lys
             20                  25                  30

Gln Gln Val Arg Gln Leu Ser Tyr Tyr Ser Gln Ser Ser Ser Ser Tyr
             35                  40                  45

Val Val Val Lys Leu Leu Pro Asn Ile Gln Pro Thr Asp Asn Ser Cys
        50                  55                  60

Glu Phe Lys Ser Val Thr Gln Tyr Asn Lys Thr Leu Ser Asn Leu Leu
65                  70                  75                  80

Leu Pro Ile Ala Glu Asn Ile Asn Asn Ile Ala Ser Pro Ser Pro Gly
                 85                  90                  95
```

-continued

```
Ser Arg Arg His Gly Gly Gly Ala Gly Ile Ala Ile Gly Ile Ala Ala
            100                 105                 110

Leu Gly Val Ala Thr Ala Ala Gln Val Thr Ala Ala Val Ser Leu Val
            115                 120                 125

Gln Ala Gln Thr Asn Ala Arg Ala Ile Ala Ala Met Lys Asn Ser Ile
        130                 135                 140

Gln Ala Thr Asn Arg Ala Val Phe Glu Val Lys Glu Gly Thr Gln Gln
145                 150                 155                 160

Leu Ala Ile Ala Val Gln Ala Ile Gln Asp His Ile Asn Thr Ile Met
                165                 170                 175

Asn Thr Gln Leu Asn Asn Met Ser Cys Gln Ile Leu Asp Asn Gln Leu
            180                 185                 190

Ala Thr Ser Leu Gly Leu Tyr Leu Thr Glu Leu Thr Thr Cys Phe Gln
            195                 200                 205

Pro Gln Leu Ile Asn Pro Ala Leu Ser Pro Ile Ser Ile Gln Cys Leu
        210                 215                 220

Arg Ser Leu Leu Gly Ser Met Thr Pro Ala Val Val Gln Ala Thr Leu
225                 230                 235                 240

Ser Thr Ser Ile Ser Ala Ala Glu Ile Leu Ser Ala Gly Leu Met Glu
                245                 250                 255

Gly Gln Ile Val Ser Val Leu Leu Asp Glu Met Gln Met Ile Val Lys
            260                 265                 270

Ile Asn Val Pro Thr Ile Val Thr Gln Ser Asn Ala Leu Val Ile Asp
            275                 280                 285

Phe Tyr Ser Ile Ser Ser Phe Ile Asn Asn Gln Glu Ser Ile Ile Gln
        290                 295                 300

Leu Pro Asp Arg Ile Leu Glu Ile Gly Asn Glu Gln Trp Arg Tyr Pro
305                 310                 315                 320

Ala Lys Asn Cys Lys Ser Thr Arg His His Ile Phe Cys Gln Tyr Asn
                325                 330                 335

Glu Ala Glu Arg Leu Ser Leu Glu Thr Lys Leu Cys Leu Ala Gly Asn
            340                 345                 350

Ile Ser Ala Cys Val Phe Ser Pro Ile Ala Gly Ser Tyr Met Arg Arg
            355                 360                 365

Phe Val Ala Leu Asp Gly Thr Ile Val Ala Asn Cys Arg Ser Leu Thr
        370                 375                 380

Cys Leu Cys Lys Ser Pro Ser Tyr Pro Ile Tyr Gln Pro Asp His His
385                 390                 395                 400

Ala Val Thr Thr Ile Asp Leu Thr Ser Cys Gln Thr Leu Ser Leu Asp
                405                 410                 415

Gly Leu Asp Phe Ser Ile Val Ser Leu Ser Asn Ile Thr Tyr Ala Glu
            420                 425                 430

Asn Leu Thr Ile Ser Leu Ser Gln Thr Ile Asn Thr Gln Pro Ile Asp
            435                 440                 445

Ile Ser Thr Glu Leu Ser Lys Val Asn Ala Ser Leu Gln Asn Ala Val
        450                 455                 460

Lys Tyr Ile Lys Glu Ser Asn His Gln Leu Gln Ser Ile Glu Asp Lys
465                 470                 475                 480

Ile Glu Glu Ile Leu Ser Lys Ile Tyr His Ile Glu Asn Glu Ile Ala
                485                 490                 495

Arg Ile Lys Lys Leu Ile Gly Glu Ala Pro
            500                 505
```

<210> SEQ ID NO 27
<211> LENGTH: 966
<212> TYPE: PRT
<213> ORGANISM: Artificial sequence
<220> FEATURE:
<223> OTHER INFORMATION: Recombinant F protein

<400> SEQUENCE: 27

Met Lys Ala Phe Ser Val Thr Cys Leu Ser Phe Ala Val Phe Ser Ser
1               5                   10                  15

Ser Ile Cys Val Asn Ile Asn Ile Leu Gln Gln Ile Gly Tyr Ile Lys
                20                  25                  30

Gln Gln Val Arg Gln Leu Ser Tyr Tyr Ser Gln Ser Ser Ser Ser Tyr
            35                  40                  45

Ile Val Val Lys Leu Leu Pro Asn Ile Gln Pro Thr Asp Asp Ser Cys
        50                  55                  60

Glu Phe Lys Ser Val Thr Gln Tyr Asn Lys Thr Leu Ser Asn Leu Leu
65                  70                  75                  80

Leu Pro Ile Ala Glu Asn Ile Asn Asn Ile Ala Ser Pro Ser Pro Gly
                85                  90                  95

Ser Arg Arg His Gly Gly Gly Ala Gly Ile Ala Ile Gly Ile Ala Ala
            100                 105                 110

Leu Gly Val Ala Thr Ala Ala Gln Val Thr Ala Ala Val Ser Leu Val
            115                 120                 125

Gln Ala Gln Thr Asn Ala Arg Ala Ile Ala Ala Met Lys Asn Ser Ile
        130                 135                 140

Gln Ala Thr Asn Arg Ala Val Phe Glu Val Lys Glu Gly Thr Gln Gln
145                 150                 155                 160

Leu Ala Ile Ala Val Gln Ala Ile Gln Asp His Ile Asn Thr Ile Met
                165                 170                 175

Asn Thr Gln Leu Asn Asn Met Ser Cys Gln Ile Leu Asp Asn Gln Leu
                180                 185                 190

Ala Thr Ser Leu Gly Leu Tyr Leu Thr Glu Leu Thr Thr Cys Phe Gln
            195                 200                 205

Pro Gln Leu Thr Asn Pro Ala Leu Ser Pro Ile Ser Ile Gln Cys Leu
        210                 215                 220

Arg Ser Leu Leu Gly Ser Met Thr Pro Ala Val Val Gln Ala Thr Leu
225                 230                 235                 240

Ser Thr Ser Ile Ser Ala Ala Glu Ile Leu Ser Ala Gly Leu Met Glu
                245                 250                 255

Gly Gln Ile Ile Ser Val Leu Leu Asp Glu Met Gln Met Ile Val Lys
            260                 265                 270

Ile Asn Ile Pro Thr Ile Val Thr Gln Ser Asn Ala Leu Val Ile Asp
            275                 280                 285

Phe Tyr Ser Ile Ser Ser Phe Ile Asn Asn Gln Glu Ser Ile Ile Gln
        290                 295                 300

Leu Pro Asp Arg Ile Leu Glu Ile Gly Asn Glu Gln Trp Ser Tyr Pro
305                 310                 315                 320

Ala Lys Asn Cys Lys Leu Thr Arg His His Ile Phe Cys Gln Tyr Asn
                325                 330                 335

Glu Ala Glu Arg Leu Ser Leu Glu Ser Lys Leu Cys Leu Ala Gly Asn
                340                 345                 350

Ile Ser Ala Cys Val Phe Ser Pro Ile Ala Gly Ser Tyr Met Arg Arg
            355                 360                 365

Phe Val Ala Leu Asp Gly Thr Ile Val Ala Asn Cys Arg Ser Leu Thr

-continued

```
        370             375             380

Cys Leu Cys Lys Ser Pro Ser Tyr Pro Ile Tyr Gln Pro Asp His His
385             390             395             400

Ala Val Thr Thr Ile Asp Leu Thr Ala Cys Gln Thr Leu Ser Leu Asp
                405             410             415

Gly Leu Asp Phe Ser Ile Val Ser Leu Ser Asn Ile Thr Tyr Ala Glu
            420             425             430

Asn Leu Thr Ile Ser Leu Ser Gln Thr Ile Asn Thr Gln Pro Ile Asp
            435             440             445

Ile Ser Thr Glu Leu Ser Lys Val Asn Ala Ser Leu Gln Asn Ala Val
    450             455             460

Lys Tyr Ile Lys Glu Ser Asn His Gln Leu Gln Ser Ile Glu Asp Lys
465             470             475             480

Ile Glu Glu Ile Leu Ser Lys Ile Tyr His Ile Glu Asn Glu Ile Ala
            485             490             495

Arg Ile Lys Lys Leu Ile Gly Glu Ala Pro Gly Ser Gly Gly Gly Gly
            500             505             510

Gly Gly Asn Ile Pro Leu Val Asn Asp Leu Arg Phe Ile Asn Gly Ile
            515             520             525

Asn Lys Phe Ile Ile Glu Asp Tyr Ala Thr His Asp Phe Ser Ile Gly
            530             535             540

His Pro Leu Asn Met Pro Ser Phe Ile Pro Thr Ala Thr Ser Pro Asn
545             550             555             560

Gly Cys Thr Arg Ile Pro Ser Phe Ser Leu Gly Lys Thr His Trp Cys
            565             570             575

Tyr Thr His Asn Val Ile Asn Ala Asn Cys Lys Asp His Thr Ser Ser
            580             585             590

Asn Gln Tyr Val Ser Met Gly Ile Leu Val Gln Thr Ala Ser Gly Tyr
            595             600             605

Pro Met Phe Lys Thr Leu Lys Ile Gln Tyr Leu Ser Asp Gly Leu Asn
    610             615             620

Arg Lys Ser Cys Ser Ile Ala Thr Val Pro Asp Gly Cys Ala Met Tyr
625             630             635             640

Cys Tyr Val Ser Thr Gln Leu Glu Thr Asp Asp Tyr Ala Gly Ser Ser
            645             650             655

Pro Pro Thr Gln Lys Leu Thr Leu Leu Phe Tyr Asn Asp Thr Val Thr
            660             665             670

Glu Arg Thr Ile Ser Pro Ser Gly Leu Glu Gly Asn Trp Ala Thr Leu
            675             680             685

Val Pro Gly Val Gly Ser Gly Ile Tyr Phe Glu Asn Lys Leu Ile Phe
    690             695             700

Pro Ala Tyr Gly Gly Val Leu Pro Asn Ser Thr Leu Gly Val Lys Ser
705             710             715             720

Ala Arg Glu Phe Phe Arg Pro Val Asn Pro Tyr Asn Pro Cys Ser Gly
            725             730             735

Pro Gln Gln Asp Leu Asp Gln Arg Ala Leu Arg Ser Tyr Phe Pro Ser
            740             745             750

Tyr Phe Ser Asn Arg Arg Ile Gln Ser Ala Phe Leu Val Cys Ala Trp
            755             760             765

Asn Gln Ile Leu Val Thr Asn Cys Glu Leu Val Val Pro Ser Ser Asn
    770             775             780

Gln Thr Met Met Gly Ala Glu Gly Arg Val Leu Leu Ile Asn Asn Arg
785             790             795             800
```

Leu Leu Tyr Tyr Gln Arg Ser Thr Ser Trp Trp Pro Tyr Glu Leu Leu
                805                     810                     815

Tyr Glu Ile Ser Phe Thr Phe Thr Asn Ser Gly Pro Ser Ser Val Asn
                820                     825                 830

Met Ser Trp Ile Pro Ile Tyr Ser Phe Thr Arg Pro Gly Ser Gly Asn
            835                 840                 845

Cys Ser Gly Glu Asn Val Cys Pro Thr Ala Cys Val Ser Gly Val Tyr
        850                 855                 860

Leu Asp Pro Trp Pro Leu Thr Pro Tyr Ser His Gln Ser Gly Ile Asn
865                 870                 875                     880

Arg Asn Phe Tyr Phe Thr Gly Ala Leu Leu Asn Ser Ser Thr Thr Arg
                885                 890                     895

Val Asn Pro Thr Leu Tyr Val Ser Ala Leu Asn Asn Leu Lys Val Leu
            900                 905                 910

Ala Pro Tyr Gly Thr Gln Gly Leu Phe Ala Ser Tyr Thr Thr Thr Thr
            915                 920                 925

Cys Phe Gln Asp Thr Gly Asp Ala Ser Val Tyr Cys Val Tyr Ile Met
        930                 935                 940

Glu Leu Ala Ser Asn Ile Val Gly Glu Phe Gln Ile Leu Pro Val Leu
945                 950                 955                     960

Thr Arg Leu Thr Ile Thr
                965

<210> SEQ ID NO 28
<211> LENGTH: 981
<212> TYPE: PRT
<213> ORGANISM: Artificial sequence
<220> FEATURE:
<223> OTHER INFORMATION: Recombinant F protein

<400> SEQUENCE: 28

Met Lys Ala Phe Ser Val Thr Cys Leu Ser Phe Ala Val Phe Ser Ser
1               5                   10                  15

Ser Ile Cys Val Asn Ile Asn Ile Leu Gln Gln Ile Gly Tyr Ile Lys
            20                  25                  30

Gln Gln Val Arg Gln Leu Ser Tyr Tyr Ser Gln Ser Ser Ser Ser Tyr
            35                  40                  45

Ile Val Val Lys Leu Leu Pro Asn Ile Gln Pro Thr Asp Asp Ser Cys
        50                  55                  60

Glu Phe Lys Ser Val Thr Gln Tyr Asn Lys Thr Leu Ser Asn Leu Leu
65                  70                  75                  80

Leu Pro Ile Ala Glu Asn Ile Asn Asn Ile Ala Ser Pro Ser Pro Gly
                85                  90                  95

Ser Arg Arg His Gly Gly Gly Ala Gly Ile Ala Ile Gly Ile Ala Ala
            100                 105                 110

Leu Gly Val Ala Thr Ala Ala Gln Val Thr Ala Ala Val Ser Leu Val
            115                 120                 125

Gln Ala Gln Thr Asn Ala Arg Ala Ile Ala Ala Met Lys Asn Ser Ile
        130                 135                 140

Gln Ala Thr Asn Arg Ala Val Phe Glu Val Lys Glu Gly Thr Gln Gln
145                 150                 155                 160

Leu Ala Ile Ala Val Gln Ala Ile Gln Asp His Ile Asn Thr Ile Met
                165                 170                 175

Asn Thr Gln Leu Asn Asn Met Ser Cys Gln Ile Leu Asp Asn Gln Leu
            180                 185                 190

-continued

```
Ala Thr Ser Leu Gly Leu Tyr Leu Thr Glu Leu Thr Thr Cys Phe Gln
        195                 200                 205

Pro Gln Leu Thr Asn Pro Ala Leu Ser Pro Ile Ser Ile Gln Cys Leu
        210                 215                 220

Arg Ser Leu Leu Gly Ser Met Thr Pro Ala Val Val Gln Ala Thr Leu
225                 230                 235                 240

Ser Thr Ser Ile Ser Ala Ala Glu Ile Leu Ser Ala Gly Leu Met Glu
                245                 250                 255

Gly Gln Ile Ile Ser Val Leu Leu Asp Glu Met Gln Met Ile Val Lys
                260                 265                 270

Ile Asn Ile Pro Thr Ile Val Thr Gln Ser Asn Ala Leu Val Ile Asp
        275                 280                 285

Phe Tyr Ser Ile Ser Ser Phe Ile Asn Asn Gln Glu Ser Ile Ile Gln
        290                 295                 300

Leu Pro Asp Arg Ile Leu Glu Ile Gly Asn Glu Gln Trp Ser Tyr Pro
305                 310                 315                 320

Ala Lys Asn Cys Lys Leu Thr Arg His His Ile Phe Cys Gln Tyr Asn
                325                 330                 335

Glu Ala Glu Arg Leu Ser Leu Glu Ser Lys Leu Cys Leu Ala Gly Asn
                340                 345                 350

Ile Ser Ala Cys Val Phe Ser Pro Ile Ala Gly Ser Tyr Met Arg Arg
                355                 360                 365

Phe Val Ala Leu Asp Gly Thr Ile Val Ala Asn Cys Arg Ser Leu Thr
        370                 375                 380

Cys Leu Cys Lys Ser Pro Ser Tyr Pro Ile Tyr Gln Pro Asp His His
385                 390                 395                 400

Ala Val Thr Thr Ile Asp Leu Thr Ala Cys Gln Thr Leu Ser Leu Asp
                405                 410                 415

Gly Leu Asp Phe Ser Ile Val Ser Leu Ser Asn Ile Thr Tyr Ala Glu
                420                 425                 430

Asn Leu Thr Ile Ser Leu Ser Gln Thr Ile Asn Thr Gln Pro Ile Asp
        435                 440                 445

Ile Ser Thr Glu Leu Ser Lys Val Asn Ala Ser Leu Gln Asn Ala Val
        450                 455                 460

Lys Tyr Ile Lys Glu Ser Asn His Gln Leu Gln Ser Ile Glu Asp Lys
465                 470                 475                 480

Ile Glu Glu Ile Leu Ser Lys Ile Tyr His Ile Glu Asn Glu Ile Ala
                485                 490                 495

Arg Ile Lys Lys Leu Ile Gly Glu Ala Pro Gly Ser Gly Tyr Ile Pro
                500                 505                 510

Glu Ala Pro Arg Asp Gly Gln Ala Tyr Val Arg Lys Asp Gly Glu Trp
                515                 520                 525

Val Leu Leu Ser Thr Phe Leu Gly Ser Gly Gly Gly Gly Gly Gly Phe
        530                 535                 540

Leu Ala Val Ser Lys Gly Asn Cys Ser Gly Pro Thr Thr Ile Arg Gly
545                 550                 555                 560

Gln Phe Ser Asn Met Ser Leu Ser Leu Leu Asp Leu Tyr Leu Gly Arg
                565                 570                 575

Gly Tyr Asn Val Ser Ser Ile Val Thr Met Thr Ser Gln Gly Met Tyr
                580                 585                 590

Gly Gly Thr Tyr Leu Val Glu Lys Pro Asn Leu Ser Ser Lys Arg Ser
        595                 600                 605
```

```
Glu Leu Ser Gln Leu Ser Met Tyr Arg Val Phe Glu Val Gly Val Ile
    610             615                 620

Arg Asn Pro Gly Leu Gly Ala Pro Val Phe His Met Thr Asn Tyr Leu
625             630                 635                 640

Glu Gln Pro Val Ser Asn Asp Leu Ser Asn Cys Met Val Ala Leu Gly
            645                 650                 655

Glu Leu Lys Leu Ala Ala Leu Cys His Gly Glu Asp Ser Ile Thr Ile
            660                 665                 670

Pro Tyr Gln Gly Ser Gly Lys Gly Val Ser Phe Gln Leu Val Lys Leu
        675                 680                 685

Gly Val Trp Lys Ser Pro Ala Asp Met Gln Ser Trp Val Pro Leu Ser
    690                 695                 700

Thr Asp Asp Pro Val Ile Asp Arg Leu Tyr Leu Ser Ser His Arg Gly
705                 710                 715                 720

Val Ile Ala Asp Asn Gln Ala Lys Trp Ala Val Pro Thr Thr Arg Thr
                725                 730                 735

Asp Asp Lys Leu Arg Met Glu Thr Cys Phe Gln Gln Ala Cys Lys Gly
            740                 745                 750

Lys Ile Gln Thr Leu Cys Glu Asn Pro Glu Trp Ala Pro Leu Lys Asp
        755                 760                 765

Asn Arg Ile Pro Ser Tyr Gly Val Leu Ser Val Asp Leu Ser Leu Thr
    770                 775                 780

Val Glu Leu Lys Ile Lys Ile Ala Ser Gly Phe Gly Pro Leu Ile Thr
785                 790                 795                 800

His Gly Ser Gly Met Asp Leu Tyr Lys Ser Asn His Asn Asn Val Tyr
                805                 810                 815

Trp Leu Thr Ile Pro Pro Met Lys Asn Leu Ala Leu Gly Val Ile Asn
            820                 825                 830

Thr Leu Glu Trp Ile Pro Arg Phe Lys Val Ser Pro Tyr Leu Phe Thr
            835                 840                 845

Val Pro Ile Lys Glu Ala Gly Glu Asp Cys His Ala Pro Thr Tyr Leu
    850                 855                 860

Pro Ala Glu Val Asp Gly Asp Val Lys Leu Ser Ser Asn Leu Val Ile
865                 870                 875                 880

Leu Pro Gly Gln Asp Leu Gln Tyr Val Leu Ala Thr Tyr Asp Thr Ser
            885                 890                 895

Arg Val Glu His Ala Val Val Tyr Tyr Val Tyr Ser Pro Gly Arg Ser
            900                 905                 910

Phe Ser Tyr Phe Tyr Pro Phe Arg Leu Pro Ile Lys Gly Val Pro Ile
        915                 920                 925

Glu Leu Gln Val Glu Cys Phe Thr Trp Asp Gln Lys Leu Trp Cys Arg
    930                 935                 940

His Phe Cys Val Leu Ala Asp Ser Glu Ser Gly Gly His Ile Thr His
945                 950                 955                 960

Ser Gly Met Val Gly Met Gly Val Ser Cys Thr Val Thr Arg Glu Asp
                965                 970                 975

Gly Thr Asn Arg Arg
            980
```

<210> SEQ ID NO 29
<211> LENGTH: 1006
<212> TYPE: PRT
<213> ORGANISM: Artificial sequence
<220> FEATURE:
<223> OTHER INFORMATION: Recombinant F protein -continued

<400> SEQUENCE: 29

```
Met Lys Ala Phe Ser Val Thr Cys Leu Ser Phe Ala Val Phe Ser Ser
1               5                   10                  15

Ser Ile Cys Val Asn Ile Asn Ile Leu Gln Gln Ile Gly Tyr Ile Lys
                20                  25                  30

Gln Gln Val Arg Gln Leu Ser Tyr Tyr Ser Gln Ser Ser Ser Ser Tyr
            35                  40                  45

Ile Val Val Lys Leu Leu Pro Asn Ile Gln Pro Thr Asp Asp Ser Cys
        50                  55                  60

Glu Phe Lys Ser Val Thr Gln Tyr Asn Lys Thr Leu Ser Asn Leu Leu
65                  70                  75                  80

Leu Pro Ile Ala Glu Asn Ile Asn Asn Ile Ala Ser Pro Ser Pro Gly
                85                  90                  95

Ser Arg Arg His Gly Gly Gly Ala Gly Ile Ala Ile Gly Ile Ala Ala
            100                 105                 110

Leu Gly Val Ala Thr Ala Ala Gln Val Thr Ala Ala Val Ser Leu Val
            115                 120                 125

Gln Ala Gln Thr Asn Ala Arg Ala Ile Ala Ala Met Lys Asn Ser Ile
        130                 135                 140

Gln Ala Thr Asn Arg Ala Val Phe Glu Val Lys Glu Gly Thr Gln Gln
145                 150                 155                 160

Leu Ala Ile Ala Val Gln Ala Ile Gln Asp His Ile Asn Thr Ile Met
                165                 170                 175

Asn Thr Gln Leu Asn Asn Met Ser Cys Gln Ile Leu Asp Asn Gln Leu
            180                 185                 190

Ala Thr Ser Leu Gly Leu Tyr Leu Thr Glu Leu Thr Thr Cys Phe Gln
            195                 200                 205

Pro Gln Leu Thr Asn Pro Ala Leu Ser Pro Ile Ser Ile Gln Cys Leu
        210                 215                 220

Arg Ser Leu Leu Gly Ser Met Thr Pro Ala Val Val Gln Ala Thr Leu
225                 230                 235                 240

Ser Thr Ser Ile Ser Ala Ala Glu Ile Leu Ser Ala Gly Leu Met Glu
                245                 250                 255

Gly Gln Ile Ile Ser Val Leu Leu Asp Glu Met Gln Met Ile Val Lys
            260                 265                 270

Ile Asn Ile Pro Thr Ile Val Thr Gln Ser Asn Ala Leu Val Ile Asp
        275                 280                 285

Phe Tyr Ser Ile Ser Ser Phe Ile Asn Asn Gln Glu Ser Ile Ile Gln
        290                 295                 300

Leu Pro Asp Arg Ile Leu Glu Ile Gly Asn Glu Gln Trp Ser Tyr Pro
305                 310                 315                 320

Ala Lys Asn Cys Lys Leu Thr Arg His His Ile Phe Cys Gln Tyr Asn
                325                 330                 335

Glu Ala Glu Arg Leu Ser Leu Glu Ser Lys Leu Cys Leu Ala Gly Asn
            340                 345                 350

Ile Ser Ala Cys Val Phe Ser Pro Ile Ala Gly Ser Tyr Met Arg Arg
            355                 360                 365

Phe Val Ala Leu Asp Gly Thr Ile Val Ala Asn Cys Arg Ser Leu Thr
        370                 375                 380

Cys Leu Cys Lys Ser Pro Ser Tyr Pro Ile Tyr Gln Pro Asp His His
385                 390                 395                 400

Ala Val Thr Thr Ile Asp Leu Thr Ala Cys Gln Thr Leu Ser Leu Asp
```

```
                    405                 410                 415

Gly Leu Asp Phe Ser Ile Val Ser Leu Ser Asn Ile Thr Tyr Ala Glu
                420                 425                 430

Asn Leu Thr Ile Ser Leu Ser Gln Thr Ile Asn Thr Gln Pro Ile Asp
                435                 440                 445

Ile Ser Thr Glu Leu Ser Lys Val Asn Ala Ser Leu Gln Asn Ala Val
        450                 455                 460

Lys Tyr Ile Lys Glu Ser Asn His Gln Leu Gln Ser Ile Glu Asp Lys
465                 470                 475                 480

Ile Glu Glu Ile Leu Ser Lys Ile Tyr His Ile Glu Asn Glu Ile Ala
                485                 490                 495

Arg Ile Lys Lys Leu Ile Gly Glu Ala Pro Gly Ser Gly Tyr Ile Pro
                500                 505                 510

Glu Ala Pro Arg Asp Gly Gln Ala Tyr Val Arg Lys Asp Gly Glu Trp
                515                 520                 525

Val Leu Leu Ser Thr Phe Leu Gly Ser Gly Gly Gly Gly Gly Gly Ala
        530                 535                 540

Asp Val Ala Ala Glu Glu Leu Met Asn Ala Leu Val Asn Ser Thr Leu
545                 550                 555                 560

Leu Glu Ala Arg Ala Thr Asn Gln Phe Leu Ala Val Ser Lys Gly Asn
                565                 570                 575

Cys Ser Gly Pro Thr Thr Ile Arg Gly Gln Phe Ser Asn Met Ser Leu
                580                 585                 590

Ser Leu Leu Asp Leu Tyr Leu Ser Arg Gly Tyr Asn Val Ser Ser Ile
                595                 600                 605

Val Thr Met Thr Ser Gln Gly Met Tyr Gly Gly Thr Tyr Leu Val Gly
        610                 615                 620

Lys Pro Asn Leu Ser Ser Lys Gly Ser Glu Leu Ser Gln Leu Ser Met
625                 630                 635                 640

His Arg Val Phe Glu Val Gly Val Ile Arg Asn Pro Gly Leu Gly Ala
                645                 650                 655

Pro Val Phe His Met Thr Asn Tyr Phe Glu Gln Pro Val Ser Asn Asp
                660                 665                 670

Phe Ser Asn Cys Met Val Ala Leu Gly Glu Leu Lys Phe Ala Ala Leu
                675                 680                 685

Cys His Arg Glu Asp Ser Ile Thr Ile Pro Tyr Gln Gly Ser Gly Lys
        690                 695                 700

Gly Val Ser Phe Gln Leu Val Lys Leu Gly Val Trp Lys Ser Pro Thr
705                 710                 715                 720

Asp Met Arg Ser Trp Val Pro Leu Ser Thr Asp Asp Pro Val Ile Asp
                725                 730                 735

Arg Leu Tyr Leu Ser Ser His Arg Gly Val Ile Ala Asp Asn Gln Ala
                740                 745                 750

Lys Trp Ala Val Pro Thr Thr Arg Thr Asp Asp Lys Leu Arg Met Glu
                755                 760                 765

Thr Cys Phe Gln Gln Ala Cys Lys Gly Lys Asn Gln Ala Leu Cys Glu
        770                 775                 780

Asn Pro Glu Trp Ala Pro Leu Lys Asp Asn Arg Ile Pro Ser Tyr Gly
785                 790                 795                 800

Val Leu Ser Val Asn Leu Ser Leu Thr Val Glu Leu Lys Ile Lys Ile
                805                 810                 815

Ala Ser Gly Phe Gly Pro Leu Ile Thr His Gly Ser Gly Met Asp Leu
                820                 825                 830
```

```
Tyr Lys Thr Asn His Asn Asn Val Tyr Trp Leu Thr Ile Pro Pro Met
    835                 840                 845

Lys Asn Leu Ala Leu Gly Val Ile Asn Thr Leu Glu Trp Ile Pro Arg
    850                 855                 860

Phe Lys Val Ser Pro Asn Leu Phe Thr Val Pro Ile Lys Glu Ala Gly
865                 870                 875                 880

Glu Asp Cys His Ala Pro Thr Tyr Leu Pro Ala Glu Val Asp Gly Asp
                885                 890                 895

Val Lys Leu Ser Ser Asn Leu Val Ile Leu Pro Gly Gln Asp Leu Gln
                900                 905                 910

Tyr Val Leu Ala Thr Tyr Asp Thr Ser Arg Val Glu His Ala Val Val
                915                 920                 925

Tyr Tyr Val Tyr Ser Pro Ser Arg Ser Phe Ser Tyr Phe Tyr Pro Phe
    930                 935                 940

Arg Leu Pro Ile Lys Gly Val Pro Ile Glu Leu Gln Val Glu Cys Phe
945                 950                 955                 960

Thr Trp Asp Lys Lys Leu Trp Cys Arg His Phe Cys Val Leu Ala Asp
                965                 970                 975

Ser Glu Ser Gly Gly His Ile Thr His Ser Gly Met Val Gly Met Gly
                980                 985                 990

Val Ser Cys Thr Val Thr Arg Glu  Asp Gly Thr Asn Arg  Arg
        995                 1000                1005
```

<210> SEQ ID NO 30
<211> LENGTH: 452
<212> TYPE: PRT
<213> ORGANISM: Mumps virus

<400> SEQUENCE: 30

```
Asn Ile Pro Leu Val Asn Asp Leu Arg Phe Ile Asn Gly Ile Asn Lys
1               5                   10                  15

Phe Ile Ile Glu Asp Tyr Ala Thr His Asp Phe Ser Ile Gly His Pro
                20                  25                  30

Leu Asn Met Pro Ser Phe Ile Pro Thr Ala Thr Ser Pro Asn Gly Cys
        35                  40                  45

Thr Arg Ile Pro Ser Phe Ser Leu Gly Lys Thr His Trp Cys Tyr Thr
    50                  55                  60

His Asn Val Ile Asn Ala Asn Cys Lys Asp His Thr Ser Ser Asn Gln
65                  70                  75                  80

Tyr Val Ser Met Gly Ile Leu Val Gln Thr Ala Ser Gly Tyr Pro Met
                85                  90                  95

Phe Lys Thr Leu Lys Ile Gln Tyr Leu Ser Asp Gly Leu Asn Arg Lys
                100                 105                 110

Ser Cys Ser Ile Ala Thr Val Pro Asp Gly Cys Ala Met Tyr Cys Tyr
        115                 120                 125

Val Ser Thr Gln Leu Glu Thr Asp Asp Tyr Ala Gly Ser Ser Pro Pro
    130                 135                 140

Thr Gln Lys Leu Thr Leu Leu Phe Tyr Asn Asp Thr Val Thr Glu Arg
145                 150                 155                 160

Thr Ile Ser Pro Ser Gly Leu Glu Gly Asn Trp Ala Thr Leu Val Pro
                165                 170                 175

Gly Val Gly Ser Gly Ile Tyr Phe Glu Asn Lys Leu Ile Phe Pro Ala
                180                 185                 190

Tyr Gly Gly Val Leu Pro Asn Ser Thr Leu Gly Val Lys Ser Ala Arg
```

```
              195                200                205

Glu Phe Phe Arg Pro Val Asn Pro Tyr Asn Pro Cys Ser Gly Pro Gln
    210                215                220

Gln Asp Leu Asp Gln Arg Ala Leu Arg Ser Tyr Phe Pro Ser Tyr Phe
225                230                235                240

Ser Asn Arg Arg Ile Gln Ser Ala Phe Leu Val Cys Ala Trp Asn Gln
                245                250                255

Ile Leu Val Thr Asn Cys Glu Leu Val Val Pro Ser Ser Asn Gln Thr
                260                265                270

Met Met Gly Ala Glu Gly Arg Val Leu Leu Ile Asn Asn Arg Leu Leu
                275                280                285

Tyr Tyr Gln Arg Ser Thr Ser Trp Trp Pro Tyr Glu Leu Leu Tyr Glu
    290                295                300

Ile Ser Phe Thr Phe Thr Asn Ser Gly Pro Ser Ser Val Asn Met Ser
305                310                315                320

Trp Ile Pro Ile Tyr Ser Phe Thr Arg Pro Gly Ser Gly Asn Cys Ser
                325                330                335

Gly Glu Asn Val Cys Pro Thr Ala Cys Val Ser Gly Val Tyr Leu Asp
                340                345                350

Pro Trp Pro Leu Thr Pro Tyr Ser His Gln Ser Gly Ile Asn Arg Asn
                355                360                365

Phe Tyr Phe Thr Gly Ala Leu Leu Asn Ser Ser Thr Thr Arg Val Asn
    370                375                380

Pro Thr Leu Tyr Val Ser Ala Leu Asn Asn Leu Lys Val Leu Ala Pro
385                390                395                400

Tyr Gly Thr Gln Gly Leu Phe Ala Ser Tyr Thr Thr Thr Thr Cys Phe
                405                410                415

Gln Asp Thr Gly Asp Ala Ser Val Tyr Cys Val Tyr Ile Met Glu Leu
                420                425                430

Ala Ser Asn Ile Val Gly Glu Phe Gln Ile Leu Pro Val Leu Thr Arg
                435                440                445

Leu Thr Ile Thr
    450

<210> SEQ ID NO 31
<211> LENGTH: 438
<212> TYPE: PRT
<213> ORGANISM: Measles virus

<400> SEQUENCE: 31

Phe Leu Ala Val Ser Lys Gly Asn Cys Ser Gly Pro Thr Thr Ile Arg
1               5                  10                 15

Gly Gln Phe Ser Asn Met Ser Leu Ser Leu Leu Asp Leu Tyr Leu Gly
                20                 25                 30

Arg Gly Tyr Asn Val Ser Ser Ile Val Thr Met Thr Ser Gln Gly Met
            35                 40                 45

Tyr Gly Gly Thr Tyr Leu Val Glu Lys Pro Asn Leu Ser Ser Lys Arg
    50                 55                 60

Ser Glu Leu Ser Gln Leu Ser Met Tyr Arg Val Phe Glu Val Gly Val
65                 70                 75                 80

Ile Arg Asn Pro Gly Leu Gly Ala Pro Val Phe His Met Thr Asn Tyr
                85                 90                 95

Leu Glu Gln Pro Val Ser Asn Asp Leu Ser Asn Cys Met Val Ala Leu
                100                105                110
```

-continued

```
Gly Glu Leu Lys Leu Ala Ala Leu Cys His Gly Glu Asp Ser Ile Thr
        115                 120                 125

Ile Pro Tyr Gln Gly Ser Gly Lys Gly Val Ser Phe Gln Leu Val Lys
        130                 135                 140

Leu Gly Val Trp Lys Ser Pro Ala Asp Met Gln Ser Trp Val Pro Leu
145                 150                 155                 160

Ser Thr Asp Asp Pro Val Ile Asp Arg Leu Tyr Leu Ser Ser His Arg
                165                 170                 175

Gly Val Ile Ala Asp Asn Gln Ala Lys Trp Ala Val Pro Thr Thr Arg
                180                 185                 190

Thr Asp Asp Lys Leu Arg Met Glu Thr Cys Phe Gln Gln Ala Cys Lys
                195                 200                 205

Gly Lys Ile Gln Thr Leu Cys Glu Asn Pro Glu Trp Ala Pro Leu Lys
        210                 215                 220

Asp Asn Arg Ile Pro Ser Tyr Gly Val Leu Ser Val Asp Leu Ser Leu
225                 230                 235                 240

Thr Val Glu Leu Lys Ile Lys Ile Ala Ser Gly Phe Gly Pro Leu Ile
                245                 250                 255

Thr His Gly Ser Gly Met Asp Leu Tyr Lys Ser Asn His Asn Asn Val
                260                 265                 270

Tyr Trp Leu Thr Ile Pro Pro Met Lys Asn Leu Ala Leu Gly Val Ile
        275                 280                 285

Asn Thr Leu Glu Trp Ile Pro Arg Phe Lys Val Ser Pro Tyr Leu Phe
        290                 295                 300

Thr Val Pro Ile Lys Glu Ala Gly Glu Asp Cys His Ala Pro Thr Tyr
305                 310                 315                 320

Leu Pro Ala Glu Val Asp Gly Asp Val Lys Leu Ser Ser Asn Leu Val
                325                 330                 335

Ile Leu Pro Gly Gln Asp Leu Gln Tyr Val Leu Ala Thr Tyr Asp Thr
                340                 345                 350

Ser Arg Val Glu His Ala Val Val Tyr Tyr Val Tyr Ser Pro Gly Arg
        355                 360                 365

Ser Phe Ser Tyr Phe Tyr Pro Phe Arg Leu Pro Ile Lys Gly Val Pro
        370                 375                 380

Ile Glu Leu Gln Val Glu Cys Phe Thr Trp Asp Gln Lys Leu Trp Cys
385                 390                 395                 400

Arg His Phe Cys Val Leu Ala Asp Ser Glu Ser Gly Gly His Ile Thr
                405                 410                 415

His Ser Gly Met Val Gly Met Gly Val Ser Cys Thr Val Thr Arg Glu
                420                 425                 430

Asp Gly Thr Asn Arg Arg
        435
```

<210> SEQ ID NO 32
<211> LENGTH: 463
<212> TYPE: PRT
<213> ORGANISM: Measles virus

<400> SEQUENCE: 32

```
Ala Asp Val Ala Ala Glu Glu Leu Met Asn Ala Leu Val Asn Ser Thr
1               5                   10                  15

Leu Leu Glu Ala Arg Ala Thr Asn Gln Phe Leu Ala Val Ser Lys Gly
                20                  25                  30

Asn Cys Ser Gly Pro Thr Thr Ile Arg Gly Gln Phe Ser Asn Met Ser
        35                  40                  45
```

```
Leu Ser Leu Leu Asp Leu Tyr Leu Ser Arg Gly Tyr Asn Val Ser Ser
    50                  55                  60

Ile Val Thr Met Thr Ser Gln Gly Met Tyr Gly Gly Thr Tyr Leu Val
65                  70                  75                  80

Gly Lys Pro Asn Leu Ser Ser Lys Gly Ser Glu Leu Ser Gln Leu Ser
                85                  90                  95

Met His Arg Val Phe Glu Val Gly Val Ile Arg Asn Pro Gly Leu Gly
            100                 105                 110

Ala Pro Val Phe His Met Thr Asn Tyr Phe Glu Gln Pro Val Ser Asn
            115                 120                 125

Asp Phe Ser Asn Cys Met Val Ala Leu Gly Glu Leu Lys Phe Ala Ala
    130                 135                 140

Leu Cys His Arg Glu Asp Ser Ile Thr Ile Pro Tyr Gln Gly Ser Gly
145                 150                 155                 160

Lys Gly Val Ser Phe Gln Leu Val Lys Leu Gly Val Trp Lys Ser Pro
                165                 170                 175

Thr Asp Met Arg Ser Trp Val Pro Leu Ser Thr Asp Asp Pro Val Ile
            180                 185                 190

Asp Arg Leu Tyr Leu Ser Ser His Arg Gly Val Ile Ala Asp Asn Gln
            195                 200                 205

Ala Lys Trp Ala Val Pro Thr Thr Arg Thr Asp Asp Lys Leu Arg Met
    210                 215                 220

Glu Thr Cys Phe Gln Gln Ala Cys Lys Gly Lys Asn Gln Ala Leu Cys
225                 230                 235                 240

Glu Asn Pro Glu Trp Ala Pro Leu Lys Asp Asn Arg Ile Pro Ser Tyr
            245                 250                 255

Gly Val Leu Ser Val Asn Leu Ser Leu Thr Val Glu Leu Lys Ile Lys
            260                 265                 270

Ile Ala Ser Gly Phe Gly Pro Leu Ile Thr His Gly Ser Gly Met Asp
    275                 280                 285

Leu Tyr Lys Thr Asn His Asn Asn Val Tyr Trp Leu Thr Ile Pro Pro
    290                 295                 300

Met Lys Asn Leu Ala Leu Gly Val Ile Asn Thr Leu Glu Trp Ile Pro
305                 310                 315                 320

Arg Phe Lys Val Ser Pro Asn Leu Phe Thr Val Pro Ile Lys Glu Ala
            325                 330                 335

Gly Glu Asp Cys His Ala Pro Thr Tyr Leu Pro Ala Glu Val Asp Gly
            340                 345                 350

Asp Val Lys Leu Ser Ser Asn Leu Val Ile Leu Pro Gly Gln Asp Leu
            355                 360                 365

Gln Tyr Val Leu Ala Thr Tyr Asp Thr Ser Arg Val Glu His Ala Val
    370                 375                 380

Val Tyr Tyr Val Tyr Ser Pro Ser Arg Ser Phe Ser Tyr Phe Tyr Pro
385                 390                 395                 400

Phe Arg Leu Pro Ile Lys Gly Val Pro Ile Glu Leu Gln Val Glu Cys
                405                 410                 415

Phe Thr Trp Asp Lys Lys Leu Trp Cys Arg His Phe Cys Val Leu Ala
            420                 425                 430

Asp Ser Glu Ser Gly Gly His Ile Thr His Ser Gly Met Val Gly Met
            435                 440                 445

Gly Val Ser Cys Thr Val Thr Arg Glu Asp Gly Thr Asn Arg Arg
    450                 455                 460
```

<210> SEQ ID NO 33
<211> LENGTH: 30
<212> TYPE: PRT
<213> ORGANISM: Artificial sequence
<220> FEATURE:
<223> OTHER INFORMATION: GCN4 trimerization domain

<400> SEQUENCE: 33

Ile Glu Asp Lys Ile Glu Glu Ile Leu Ser Lys Ile Tyr His Ile Glu
1               5                   10                  15

Asn Glu Ile Ala Arg Ile Lys Lys Leu Ile Gly Glu Ala Pro
            20                  25                  30

<210> SEQ ID NO 34
<211> LENGTH: 27
<212> TYPE: PRT
<213> ORGANISM: Artificial sequence
<220> FEATURE:
<223> OTHER INFORMATION: T4 Fibritin Trimerization domain

<400> SEQUENCE: 34

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Leu
            20                  25

<210> SEQ ID NO 35
<211> LENGTH: 59
<212> TYPE: PRT
<213> ORGANISM: Artificial sequence
<220> FEATURE:
<223> OTHER INFORMATION: GCN4/T4 Fibritin trimerization domain

<400> SEQUENCE: 35

Ile Glu Asp Lys Ile Glu Glu Ile Leu Ser Lys Ile Tyr His Ile Glu
1               5                   10                  15

Asn Glu Ile Ala Arg Ile Lys Lys Leu Ile Gly Glu Ala Pro Gly Ser
            20                  25                  30

Gly Tyr Ile Pro Glu Ala Pro Arg Asp Gly Gln Ala Tyr Val Arg Lys
        35                  40                  45

Asp Gly Glu Trp Val Leu Leu Ser Thr Phe Leu
    50                  55

<210> SEQ ID NO 36
<211> LENGTH: 550
<212> TYPE: PRT
<213> ORGANISM: Measles virus

<400> SEQUENCE: 36

Met Gly Leu Lys Val Asn Val Ser Ala Ile Phe Met Ala Val Leu Leu
1               5                   10                  15

Thr Leu Gln Thr Pro Thr Gly Gln Ile His Trp Gly Asn Leu Ser Lys
            20                  25                  30

Ile Gly Val Val Gly Ile Gly Ser Ala Ser Tyr Lys Val Met Thr Arg
        35                  40                  45

Ser Ser His Gln Ser Leu Val Ile Lys Leu Met Pro Asn Ile Thr Leu
    50                  55                  60

Leu Asn Asn Cys Thr Arg Val Glu Ile Ala Glu Tyr Arg Arg Leu Leu
65                  70                  75                  80

Arg Thr Val Leu Glu Pro Ile Arg Asp Ala Leu Asn Ala Met Thr Gln
                85                  90                  95

-continued

```
Asn Ile Arg Pro Val Gln Ser Val Ala Ser Ser Arg Arg His Lys Arg
            100                 105                 110

Phe Ala Gly Val Val Leu Ala Gly Ala Ala Leu Gly Val Ala Thr Ala
            115                 120                 125

Ala Gln Ile Thr Ala Gly Ile Ala Leu His Gln Ser Met Leu Asn Ser
    130                 135                 140

Gln Ala Ile Asp Asn Leu Arg Ala Ser Leu Glu Thr Thr Asn Gln Ala
145                 150                 155                 160

Ile Glu Ala Ile Arg Gln Ala Gly Gln Glu Met Ile Leu Ala Val Gln
                165                 170                 175

Gly Val Gln Asp Tyr Ile Asn Asn Glu Leu Ile Pro Ser Met Asn Gln
                180                 185                 190

Leu Ser Cys Asp Leu Ile Gly Gln Lys Leu Gly Leu Lys Leu Leu Arg
            195                 200                 205

Tyr Tyr Thr Glu Ile Leu Ser Leu Phe Gly Pro Ser Leu Arg Asp Pro
    210                 215                 220

Ile Ser Ala Glu Ile Ser Ile Gln Ala Leu Ser Tyr Ala Leu Gly Gly
225                 230                 235                 240

Asp Ile Asn Lys Val Leu Glu Lys Leu Gly Tyr Ser Gly Gly Asp Leu
                245                 250                 255

Leu Gly Ile Leu Glu Ser Arg Gly Ile Lys Ala Arg Ile Thr His Val
            260                 265                 270

Asp Thr Glu Ser Tyr Leu Ile Val Leu Ser Ile Ala Tyr Pro Thr Leu
            275                 280                 285

Ser Glu Ile Lys Gly Val Ile Val His Arg Leu Glu Gly Val Ser Tyr
    290                 295                 300

Asn Ile Gly Ser Gln Glu Trp Tyr Thr Thr Val Pro Lys Tyr Val Ala
305                 310                 315                 320

Thr Gln Gly Tyr Leu Ile Ser Asn Phe Asp Glu Ser Ser Cys Thr Phe
                325                 330                 335

Met Pro Glu Gly Thr Val Cys Ser Gln Asn Ala Leu Tyr Pro Met Ser
            340                 345                 350

Pro Leu Leu Gln Glu Cys Leu Arg Gly Ser Thr Lys Ser Cys Ala Arg
            355                 360                 365

Thr Leu Val Ser Gly Ser Phe Gly Asn Arg Phe Ile Leu Ser Gln Gly
    370                 375                 380

Asn Leu Ile Ala Asn Cys Ala Ser Ile Leu Cys Lys Cys Tyr Thr Thr
385                 390                 395                 400

Gly Thr Ile Ile Asn Gln Asp Pro Asp Lys Ile Leu Thr Tyr Ile Ala
                405                 410                 415

Ala Asp His Cys Pro Val Val Glu Val Asn Gly Val Thr Ile Gln Val
            420                 425                 430

Gly Ser Arg Arg Tyr Pro Asp Ala Val Tyr Leu His Arg Ile Asp Leu
            435                 440                 445

Gly Pro Pro Ile Leu Leu Glu Arg Leu Asp Val Gly Thr Asn Leu Gly
    450                 455                 460

Asn Ala Ile Ala Lys Leu Glu Asp Ala Lys Glu Leu Leu Glu Ser Ser
465                 470                 475                 480

Asp Gln Ile Leu Arg Ser Met Lys Gly Leu Ser Ser Thr Cys Ile Val
                485                 490                 495

Tyr Ile Leu Ile Ala Val Cys Leu Gly Gly Leu Ile Gly Ile Pro Ala
            500                 505                 510
```

-continued

```
Leu Ile Cys Cys Cys Arg Gly Arg Cys Asn Lys Lys Gly Glu Gln Val
        515             520             525

Gly Met Ser Arg Pro Gly Leu Lys Pro Asp Leu Thr Gly Thr Ser Lys
        530             535             540

Ser Tyr Val Arg Ser Leu
545             550

<210> SEQ ID NO 37
<211> LENGTH: 513
<212> TYPE: PRT
<213> ORGANISM: Artificial sequence
<220> FEATURE:
<223> OTHER INFORMATION: Recombinant F protein

<400> SEQUENCE: 37

Met Tyr Ser Met Gln Leu Ala Ser Cys Val Thr Leu Thr Leu Val Leu
1               5               10              15

Leu Val Asn Ser Gln Ile His Trp Gly Asn Leu Ser Lys Ile Gly Val
        20              25              30

Val Gly Ile Gly Ser Ala Ser Tyr Lys Val Met Thr Arg Ser Ser His
        35              40              45

Gln Ser Leu Val Ile Lys Leu Met Pro Asn Ile Thr Leu Leu Asn Asn
        50              55              60

Cys Thr Arg Val Glu Ile Ala Glu Tyr Arg Arg Leu Leu Arg Thr Val
65              70              75              80

Leu Glu Pro Ile Arg Asp Cys Leu Asn Ala Val Thr Gln Asn Ile Arg
                85              90              95

Pro Val Gln Ser Val Ala Ser Ser Arg Arg His Gly Gly Gly Ala Gly
        100             105             110

Val Val Leu Ala Gly Ala Ala Leu Gly Val Ala Thr Ala Ala Gln Ile
        115             120             125

Thr Ala Gly Ile Ala Leu His Gln Ser Met Leu Asn Ser Gln Ala Ile
        130             135             140

Asp Asn Leu Arg Ala Ser Leu Glu Thr Thr Asn Gln Ala Ile Glu Ala
145             150             155             160

Ile Arg Gln Ala Gly Gln Glu Met Ile Leu Ala Val Gln Gly Val Gln
                165             170             175

Asp Tyr Ile Asn Asn Glu Leu Ile Pro Ser Met Asn Gln Leu Ser Cys
        180             185             190

Asp Leu Ile Gly Gln Lys Leu Gly Leu Lys Leu Leu Arg Tyr Tyr Thr
        195             200             205

Glu Ile Leu Ser Leu Phe Gly Pro Ser Leu Arg Asp Pro Cys Ser Ala
        210             215             220

Glu Ile Ser Ile Gln Ala Leu Ser Tyr Ala Leu Gly Gly Asp Ile Asn
225             230             235             240

Lys Val Leu Glu Lys Leu Gly Tyr Ser Gly Gly Asp Leu Leu Gly Ile
                245             250             255

Leu Glu Ser Arg Gly Ile Lys Ala Arg Ile Thr His Val Asp Thr Glu
        260             265             270

Ser Tyr Phe Ile Val Leu Ser Ile Ala Tyr Pro Thr Leu Ser Glu Ile
        275             280             285

Lys Gly Val Ile Val His Arg Leu Glu Gly Val Ser Tyr Asn Ile Gly
        290             295             300

Ser Gln Glu Trp Tyr Thr Thr Val Pro Lys Tyr Val Ala Thr Gln Gly
305             310             315             320
```

-continued

```
Tyr Leu Ile Ser Asn Phe Asp Glu Ser Ser Cys Thr Phe Met Pro Glu
                325                 330                 335

Gly Thr Val Cys Ser Gln Asn Ala Leu Tyr Pro Met Ser Pro Leu Leu
                340                 345                 350

Gln Glu Cys Leu Arg Gly Ser Thr Lys Ser Cys Ala Arg Thr Leu Val
                355                 360                 365

Ser Gly Ser Phe Gly Asn Arg Phe Ile Leu Ser Gln Gly Asn Leu Ile
                370                 375                 380

Ala Asn Cys Ala Ser Ile Leu Cys Lys Cys Tyr Thr Thr Gly Thr Ile
385                 390                 395                 400

Ile Asn Gln Asp Pro Asp Lys Ile Leu Thr Tyr Ile Ala Ala Asp His
                405                 410                 415

Cys Pro Val Val Glu Val Asn Gly Val Thr Ile Gln Val Gly Ser Arg
                420                 425                 430

Arg Tyr Pro Asp Ala Val Tyr Leu His Arg Ile Asp Leu Gly Pro Pro
                435                 440                 445

Ile Ser Leu Glu Arg Leu Asp Val Gly Thr Asn Leu Gly Asn Ala Ile
                450                 455                 460

Ala Lys Leu Glu Asp Ala Lys Glu Leu Leu Glu Ser Ser Asp Gln Ile
465                 470                 475                 480

Leu Ser Ala Ile Glu Asp Lys Ile Glu Glu Ile Leu Ser Lys Ile Tyr
                485                 490                 495

His Ile Glu Asn Glu Ile Ala Arg Ile Lys Lys Leu Ile Gly Glu Ala
                500                 505                 510

Pro
```

```
<210> SEQ ID NO 38
<211> LENGTH: 513
<212> TYPE: PRT
<213> ORGANISM: Artificial sequence
<220> FEATURE:
<223> OTHER INFORMATION: Recombinant F protein
```

<400> SEQUENCE: 38

```
Met Tyr Ser Met Gln Leu Ala Ser Cys Val Thr Leu Thr Leu Val Leu
1               5                   10                  15

Leu Val Asn Ser Gln Ile His Trp Gly Asn Leu Ser Lys Ile Gly Val
                20                  25                  30

Val Gly Ile Gly Ser Ala Ser Tyr Lys Val Met Thr Arg Ser Ser His
                35                  40                  45

Gln Ser Leu Val Ile Lys Leu Met Pro Asn Ile Thr Leu Leu Asn Asn
                50                  55                  60

Cys Thr Arg Val Glu Ile Ala Glu Tyr Arg Arg Leu Leu Arg Thr Val
65                  70                  75                  80

Leu Glu Pro Ile Arg Asp Ala Leu Asn Ala Val Thr Gln Asn Ile Arg
                85                  90                  95

Pro Val Gln Ser Val Ala Ser Ser Arg Arg His Gly Gly Gly Ala Gly
                100                 105                 110

Val Val Leu Ala Gly Ala Ala Leu Gly Val Ala Thr Ala Ala Gln Ile
                115                 120                 125

Thr Ala Gly Ile Ala Leu His Gln Ser Met Leu Asn Ser Gln Ala Ile
                130                 135                 140

Asp Asn Leu Arg Ala Ser Leu Glu Thr Thr Asn Gln Ala Ile Glu Ala
145                 150                 155                 160

Ile Cys Gln Ala Gly Gln Glu Cys Ile Leu Ala Val Gln Gly Val Gln
```

-continued

```
                165                  170                  175

Asp Tyr Ile Asn Asn Glu Leu Ile Pro Ser Met Asn Gln Leu Ser Cys
            180                  185                  190

Asp Leu Ile Gly Gln Lys Leu Gly Leu Lys Leu Leu Arg Tyr Tyr Thr
            195                  200                  205

Glu Ile Leu Ser Leu Phe Gly Pro Ser Leu Arg Asp Pro Ile Ser Ala
        210                  215                  220

Glu Ile Ser Ile Gln Ala Leu Ser Tyr Ala Leu Gly Gly Asp Ile Asn
225                  230                  235                  240

Lys Val Leu Glu Lys Leu Gly Tyr Ser Gly Gly Asp Leu Leu Gly Ile
                245                  250                  255

Leu Glu Ser Arg Gly Ile Lys Ala Arg Ile Thr His Val Asp Thr Glu
                260                  265                  270

Ser Tyr Phe Ile Val Leu Ser Ile Ala Tyr Pro Thr Leu Ser Glu Ile
                275                  280                  285

Lys Gly Val Ile Val His Arg Leu Glu Gly Val Ser Tyr Asn Ile Gly
        290                  295                  300

Ser Gln Glu Trp Tyr Thr Thr Val Pro Lys Tyr Val Ala Thr Gln Gly
305                  310                  315                  320

Tyr Leu Ile Ser Asn Phe Asp Glu Ser Ser Cys Thr Phe Met Pro Glu
                325                  330                  335

Gly Thr Val Cys Ser Gln Asn Ala Leu Tyr Pro Met Ser Pro Leu Leu
            340                  345                  350

Gln Glu Cys Leu Arg Gly Ser Thr Lys Ser Cys Ala Arg Thr Leu Val
            355                  360                  365

Ser Gly Ser Phe Gly Asn Arg Phe Ile Leu Ser Gln Gly Asn Leu Ile
        370                  375                  380

Ala Asn Cys Ala Ser Ile Leu Cys Lys Cys Tyr Thr Thr Gly Thr Ile
385                  390                  395                  400

Ile Asn Gln Asp Pro Asp Lys Ile Leu Thr Tyr Ile Ala Ala Asp His
                405                  410                  415

Cys Pro Val Val Glu Val Asn Gly Val Thr Ile Gln Val Gly Ser Arg
            420                  425                  430

Arg Tyr Pro Asp Ala Val Tyr Leu His Arg Ile Asp Leu Gly Pro Pro
            435                  440                  445

Ile Ser Leu Glu Arg Leu Asp Val Gly Thr Asn Leu Gly Asn Ala Ile
        450                  455                  460

Ala Lys Leu Glu Asp Ala Lys Glu Leu Leu Glu Ser Ser Asp Gln Ile
465                  470                  475                  480

Leu Ser Ala Ile Glu Asp Lys Ile Glu Glu Ile Leu Ser Lys Ile Tyr
                485                  490                  495

His Ile Glu Asn Glu Ile Ala Arg Ile Lys Lys Leu Ile Gly Glu Ala
            500                  505                  510

Pro
```

```
<210> SEQ ID NO 39
<211> LENGTH: 513
<212> TYPE: PRT
<213> ORGANISM: Artificial sequence
<220> FEATURE:
<223> OTHER INFORMATION: Recombinant F protein

<400> SEQUENCE: 39

Met Tyr Ser Met Gln Leu Ala Ser Cys Val Thr Leu Thr Leu Val Leu
1               5                   10                  15
```

-continued

```
Leu Val Asn Ser Gln Ile His Trp Gly Asn Leu Ser Lys Ile Gly Val
              20                  25                  30

Val Gly Ile Gly Ser Ala Ser Tyr Lys Val Met Thr Arg Ser Ser His
              35                  40                  45

Gln Ser Leu Val Ile Lys Leu Met Pro Asn Ile Thr Leu Leu Asn Asn
        50                  55                  60

Cys Thr Arg Val Glu Ile Ala Glu Tyr Arg Arg Leu Leu Arg Thr Val
65                  70                  75                  80

Leu Glu Pro Ile Arg Asp Ala Leu Asn Ala Val Thr Gln Asn Ile Arg
                  85                  90                  95

Pro Val Gln Ser Val Ala Ser Ser Arg Arg His Gly Gly Gly Ala Gly
             100                 105                 110

Val Val Leu Ala Gly Ala Ala Leu Gly Val Ala Thr Ala Ala Gln Ile
             115                 120                 125

Thr Ala Gly Ile Ala Leu His Gln Ser Met Leu Asn Ser Gln Ala Ile
        130                 135                 140

Asp Asn Leu Arg Ala Ser Leu Glu Thr Thr Asn Gln Ala Ile Glu Ala
145                 150                 155                 160

Ile Arg Gln Ala Gly Gln Glu Met Ile Cys Ala Val Gln Gly Val Gln
                 165                 170                 175

Asp Tyr Ile Asn Asn Glu Leu Ile Pro Ser Met Asn Gln Leu Ser Cys
             180                 185                 190

Asp Leu Ile Gly Gln Lys Leu Gly Leu Lys Leu Leu Arg Tyr Tyr Thr
        195                 200                 205

Glu Ile Leu Ser Leu Phe Gly Pro Ser Leu Arg Asp Pro Ile Ser Ala
        210                 215                 220

Glu Ile Ser Ile Gln Ala Leu Ser Tyr Ala Leu Gly Gly Asp Ile Asn
225                 230                 235                 240

Lys Cys Leu Glu Lys Leu Gly Tyr Ser Gly Gly Asp Leu Leu Gly Ile
             245                 250                 255

Leu Glu Ser Arg Gly Ile Lys Ala Arg Ile Thr His Val Asp Thr Glu
             260                 265                 270

Ser Tyr Phe Ile Val Leu Ser Ile Ala Tyr Pro Thr Leu Ser Glu Ile
             275                 280                 285

Lys Gly Val Ile Val His Arg Leu Glu Gly Val Ser Tyr Asn Ile Gly
        290                 295                 300

Ser Gln Glu Trp Tyr Thr Thr Val Pro Lys Tyr Val Ala Thr Gln Gly
305                 310                 315                 320

Tyr Leu Ile Ser Asn Phe Asp Glu Ser Ser Cys Thr Phe Met Pro Glu
             325                 330                 335

Gly Thr Val Cys Ser Gln Asn Ala Leu Tyr Pro Met Ser Pro Leu Leu
             340                 345                 350

Gln Glu Cys Leu Arg Gly Ser Thr Lys Ser Cys Ala Arg Thr Leu Val
             355                 360                 365

Ser Gly Ser Phe Gly Asn Arg Phe Ile Leu Ser Gln Gly Asn Leu Ile
        370                 375                 380

Ala Asn Cys Ala Ser Ile Leu Cys Lys Cys Tyr Thr Thr Gly Thr Ile
385                 390                 395                 400

Ile Asn Gln Asp Pro Asp Lys Ile Leu Thr Tyr Ile Ala Ala Asp His
                 405                 410                 415

Cys Pro Val Val Glu Val Asn Gly Val Thr Ile Gln Val Gly Ser Arg
             420                 425                 430
```

-continued

```
Arg Tyr Pro Asp Ala Val Tyr Leu His Arg Ile Asp Leu Gly Pro Pro
        435             440             445

Ile Ser Leu Glu Arg Leu Asp Val Gly Thr Asn Leu Gly Asn Ala Ile
    450             455             460

Ala Lys Leu Glu Asp Ala Lys Glu Leu Leu Glu Ser Ser Asp Gln Ile
465             470             475             480

Leu Ser Ala Ile Glu Asp Lys Ile Glu Glu Ile Leu Ser Lys Ile Tyr
                485             490             495

His Ile Glu Asn Glu Ile Ala Arg Ile Lys Lys Leu Ile Gly Glu Ala
            500             505             510

Pro

<210> SEQ ID NO 40
<211> LENGTH: 513
<212> TYPE: PRT
<213> ORGANISM: Artificial sequence
<220> FEATURE:
<223> OTHER INFORMATION: Recombinant F protein

<400> SEQUENCE: 40

Met Tyr Ser Met Gln Leu Ala Ser Cys Val Thr Leu Thr Leu Val Leu
1               5               10              15

Leu Val Asn Ser Gln Ile His Trp Gly Asn Leu Ser Lys Ile Gly Val
            20              25              30

Val Gly Ile Gly Ser Ala Ser Tyr Lys Val Met Thr Arg Ser Ser His
        35              40              45

Gln Ser Leu Val Ile Lys Leu Met Pro Asn Ile Thr Leu Leu Asn Asn
    50              55              60

Cys Thr Arg Val Glu Ile Ala Glu Tyr Arg Arg Leu Leu Arg Thr Val
65              70              75              80

Leu Glu Pro Ile Arg Asp Ala Leu Asn Ala Val Thr Gln Asn Ile Arg
                85              90              95

Pro Val Gln Ser Val Ala Ser Ser Arg Arg His Gly Gly Gly Ala Gly
            100             105             110

Val Val Leu Ala Gly Ala Ala Leu Gly Val Ala Thr Ala Ala Gln Ile
        115             120             125

Thr Ala Gly Ile Ala Leu His Gln Ser Met Leu Asn Ser Gln Ala Ile
    130             135             140

Asp Asn Leu Arg Ala Ser Leu Glu Thr Thr Asn Gln Ala Ile Glu Ala
145             150             155             160

Ile Arg Gln Ala Gly Gln Glu Met Ile Leu Ala Cys Gln Gly Val Gln
                165             170             175

Asp Tyr Ile Asn Asn Glu Leu Ile Pro Ser Met Asn Gln Leu Ser Cys
            180             185             190

Asp Leu Ile Gly Gln Lys Leu Gly Leu Lys Leu Leu Arg Tyr Tyr Thr
        195             200             205

Glu Ile Leu Ser Leu Phe Gly Pro Ser Leu Arg Asp Pro Ile Ser Ala
    210             215             220

Glu Ile Ser Ile Gln Ala Leu Ser Tyr Ala Leu Gly Gly Cys Ile Asn
225             230             235             240

Lys Val Leu Glu Lys Leu Gly Tyr Ser Gly Gly Asp Leu Leu Gly Ile
                245             250             255

Leu Glu Ser Arg Gly Ile Lys Ala Arg Ile Thr His Val Asp Thr Glu
            260             265             270

Ser Tyr Phe Ile Val Leu Ser Ile Ala Tyr Pro Thr Leu Ser Glu Ile
```

```
                    275                 280                 285
Lys Gly Val Ile Val His Arg Leu Glu Gly Val Ser Tyr Asn Ile Gly
    290                 295                 300
Ser Gln Glu Trp Tyr Thr Thr Val Pro Lys Tyr Val Ala Thr Gln Gly
305                 310                 315                 320
Tyr Leu Ile Ser Asn Phe Asp Glu Ser Ser Cys Thr Phe Met Pro Glu
                    325                 330                 335
Gly Thr Val Cys Ser Gln Asn Ala Leu Tyr Pro Met Ser Pro Leu Leu
                340                 345                 350
Gln Glu Cys Leu Arg Gly Ser Thr Lys Ser Cys Ala Arg Thr Leu Val
                355                 360                 365
Ser Gly Ser Phe Gly Asn Arg Phe Ile Leu Ser Gln Gly Asn Leu Ile
    370                 375                 380
Ala Asn Cys Ala Ser Ile Leu Cys Lys Cys Tyr Thr Thr Gly Thr Ile
385                 390                 395                 400
Ile Asn Gln Asp Pro Asp Lys Ile Leu Thr Tyr Ile Ala Ala Asp His
                    405                 410                 415
Cys Pro Val Val Glu Val Asn Gly Val Thr Ile Gln Val Gly Ser Arg
                420                 425                 430
Arg Tyr Pro Asp Ala Val Tyr Leu His Arg Ile Asp Leu Gly Pro Pro
                435                 440                 445
Ile Ser Leu Glu Arg Leu Asp Val Gly Thr Asn Leu Gly Asn Ala Ile
    450                 455                 460
Ala Lys Leu Glu Asp Ala Lys Glu Leu Leu Glu Ser Ser Asp Gln Ile
465                 470                 475                 480
Leu Ser Ala Ile Glu Asp Lys Ile Glu Glu Ile Leu Ser Lys Ile Tyr
                    485                 490                 495
His Ile Glu Asn Glu Ile Ala Arg Ile Lys Lys Leu Ile Gly Glu Ala
                500                 505                 510
Pro

<210> SEQ ID NO 41
<211> LENGTH: 513
<212> TYPE: PRT
<213> ORGANISM: Artificial sequence
<220> FEATURE:
<223> OTHER INFORMATION: Recombinant F protein

<400> SEQUENCE: 41

Met Tyr Ser Met Gln Leu Ala Ser Cys Val Thr Leu Thr Leu Val Leu
1               5                   10                  15
Leu Val Asn Ser Gln Ile His Trp Gly Asn Leu Ser Lys Ile Gly Val
                20                  25                  30
Val Gly Ile Gly Ser Ala Ser Tyr Lys Val Met Thr Arg Ser Ser His
            35                  40                  45
Gln Ser Leu Val Ile Lys Leu Met Pro Asn Ile Thr Leu Leu Asn Asn
    50                  55                  60
Cys Thr Arg Val Glu Ile Ala Glu Tyr Arg Arg Leu Leu Arg Thr Val
65                  70                  75                  80
Leu Glu Pro Ile Arg Asp Ala Leu Asn Ala Val Thr Gln Asn Ile Arg
                85                  90                  95
Pro Val Gln Ser Val Ala Ser Ser Arg Arg His Gly Gly Gly Ala Gly
            100                 105                 110
Val Val Leu Ala Gly Ala Ala Leu Gly Val Ala Thr Ala Ala Gln Ile
        115                 120                 125
```

-continued

```
Thr Ala Gly Ile Ala Leu His Gln Ser Met Leu Asn Ser Gln Ala Ile
    130                 135                 140

Asp Asn Leu Arg Ala Ser Leu Glu Thr Thr Asn Gln Ala Ile Glu Ala
145                 150                 155                 160

Ile Arg Gln Ala Gly Gln Glu Met Ile Leu Ala Val Gln Gly Val Gln
                165                 170                 175

Asp Tyr Ile Asn Asn Glu Leu Ile Pro Ser Met Asn Gln Leu Ser Cys
            180                 185                 190

Asp Leu Ile Gly Gln Lys Leu Gly Leu Lys Leu Leu Arg Tyr Tyr Thr
        195                 200                 205

Glu Ile Leu Ser Cys Phe Gly Pro Ser Leu Arg Asp Pro Ile Ser Ala
    210                 215                 220

Glu Ile Ser Ile Gln Cys Leu Ser Tyr Ala Leu Gly Gly Asp Ile Asn
225                 230                 235                 240

Lys Val Leu Glu Lys Leu Gly Tyr Ser Gly Gly Asp Leu Leu Gly Ile
                245                 250                 255

Leu Glu Ser Arg Gly Ile Lys Ala Arg Ile Thr His Val Asp Thr Glu
                260                 265                 270

Ser Tyr Phe Ile Val Leu Ser Ile Ala Tyr Pro Thr Leu Ser Glu Ile
            275                 280                 285

Lys Gly Val Ile Val His Arg Leu Glu Gly Val Ser Tyr Asn Ile Gly
    290                 295                 300

Ser Gln Glu Trp Tyr Thr Thr Val Pro Lys Tyr Val Ala Thr Gln Gly
305                 310                 315                 320

Tyr Leu Ile Ser Asn Phe Asp Glu Ser Ser Cys Thr Phe Met Pro Glu
                325                 330                 335

Gly Thr Val Cys Ser Gln Asn Ala Leu Tyr Pro Met Ser Pro Leu Leu
            340                 345                 350

Gln Glu Cys Leu Arg Gly Ser Thr Lys Ser Cys Ala Arg Thr Leu Val
        355                 360                 365

Ser Gly Ser Phe Gly Asn Arg Phe Ile Leu Ser Gln Gly Asn Leu Ile
    370                 375                 380

Ala Asn Cys Ala Ser Ile Leu Cys Lys Cys Tyr Thr Thr Gly Thr Ile
385                 390                 395                 400

Ile Asn Gln Asp Pro Asp Lys Ile Leu Thr Tyr Ile Ala Ala Asp His
                405                 410                 415

Cys Pro Val Val Glu Val Asn Gly Val Thr Ile Gln Val Gly Ser Arg
            420                 425                 430

Arg Tyr Pro Asp Ala Val Tyr Leu His Arg Ile Asp Leu Gly Pro Pro
        435                 440                 445

Ile Ser Leu Glu Arg Leu Asp Val Gly Thr Asn Leu Gly Asn Ala Ile
    450                 455                 460

Ala Lys Leu Glu Asp Ala Lys Glu Leu Leu Glu Ser Ser Asp Gln Ile
465                 470                 475                 480

Leu Ser Ala Ile Glu Asp Lys Ile Glu Glu Ile Leu Ser Lys Ile Tyr
                485                 490                 495

His Ile Glu Asn Glu Ile Ala Arg Ile Lys Lys Leu Ile Gly Glu Ala
            500                 505                 510

Pro
```

<210> SEQ ID NO 42
<211> LENGTH: 513
<212> TYPE: PRT

```
<213> ORGANISM: Artificial sequence
<220> FEATURE:
<223> OTHER INFORMATION: Recombinant F protein

<400> SEQUENCE: 42

Met Tyr Ser Met Gln Leu Ala Ser Cys Val Thr Leu Thr Leu Val Leu
1               5                   10                  15

Leu Val Asn Ser Gln Ile His Trp Gly Asn Leu Ser Lys Ile Gly Val
                20                  25                  30

Val Gly Ile Gly Ser Ala Ser Tyr Lys Val Met Thr Arg Ser Ser His
            35                  40                  45

Gln Ser Leu Val Ile Lys Leu Met Pro Asn Ile Thr Leu Leu Asn Asn
        50                  55                  60

Cys Thr Arg Val Glu Ile Ala Glu Tyr Arg Arg Leu Leu Arg Thr Val
65                  70                  75                  80

Leu Glu Pro Ile Arg Asp Ala Leu Asn Ala Val Thr Gln Asn Ile Arg
                85                  90                  95

Pro Val Gln Ser Val Ala Ser Ser Arg Arg His Gly Gly Gly Ala Gly
            100                 105                 110

Val Val Leu Ala Gly Ala Ala Leu Gly Val Ala Thr Ala Ala Gln Ile
        115                 120                 125

Thr Ala Gly Ile Ala Leu His Gln Ser Met Leu Asn Ser Gln Ala Ile
    130                 135                 140

Asp Asn Leu Arg Ala Ser Leu Glu Thr Thr Asn Gln Ala Ile Glu Ala
145                 150                 155                 160

Ile Arg Gln Ala Gly Gln Glu Met Ile Leu Ala Val Gln Gly Val Gln
                165                 170                 175

Asp Tyr Ile Asn Asn Glu Leu Ile Pro Ser Met Asn Gln Leu Ser Cys
            180                 185                 190

Asp Leu Ile Gly Gln Lys Leu Gly Leu Lys Leu Leu Arg Tyr Tyr Thr
        195                 200                 205

Glu Ile Leu Ser Leu Phe Gly Cys Ser Leu Arg Asp Cys Ile Ser Ala
    210                 215                 220

Glu Ile Ser Ile Gln Ala Leu Ser Tyr Ala Leu Gly Gly Asp Ile Asn
225                 230                 235                 240

Lys Val Leu Glu Lys Leu Gly Tyr Ser Gly Gly Asp Leu Leu Gly Ile
                245                 250                 255

Leu Glu Ser Arg Gly Ile Lys Ala Arg Ile Thr His Val Asp Thr Glu
            260                 265                 270

Ser Tyr Phe Ile Val Leu Ser Ile Ala Tyr Pro Thr Leu Ser Glu Ile
        275                 280                 285

Lys Gly Val Ile Val His Arg Leu Glu Gly Val Ser Tyr Asn Ile Gly
    290                 295                 300

Ser Gln Glu Trp Tyr Thr Thr Val Pro Lys Tyr Val Ala Thr Gln Gly
305                 310                 315                 320

Tyr Leu Ile Ser Asn Phe Asp Glu Ser Ser Cys Thr Phe Met Pro Glu
                325                 330                 335

Gly Thr Val Cys Ser Gln Asn Ala Leu Tyr Pro Met Ser Pro Leu Leu
            340                 345                 350

Gln Glu Cys Leu Arg Gly Ser Thr Lys Ser Cys Ala Arg Thr Leu Val
        355                 360                 365

Ser Gly Ser Phe Gly Asn Arg Phe Ile Leu Ser Gln Gly Asn Leu Ile
    370                 375                 380

Ala Asn Cys Ala Ser Ile Leu Cys Lys Cys Tyr Thr Thr Gly Thr Ile
```

-continued
_____

```
385                 390                 395                 400

Ile Asn Gln Asp Pro Asp Lys Ile Leu Thr Tyr Ile Ala Ala Asp His
            405                 410                 415

Cys Pro Val Val Glu Val Asn Gly Val Thr Ile Gln Val Gly Ser Arg
            420                 425                 430

Arg Tyr Pro Asp Ala Val Tyr Leu His Arg Ile Asp Leu Gly Pro Pro
            435                 440                 445

Ile Ser Leu Glu Arg Leu Asp Val Gly Thr Asn Leu Gly Asn Ala Ile
    450                 455                 460

Ala Lys Leu Glu Asp Ala Lys Glu Leu Leu Glu Ser Ser Asp Gln Ile
465                 470                 475                 480

Leu Ser Ala Ile Glu Asp Lys Ile Glu Glu Ile Leu Ser Lys Ile Tyr
                485                 490                 495

His Ile Glu Asn Glu Ile Ala Arg Ile Lys Lys Leu Ile Gly Glu Ala
            500                 505                 510

Pro
```

```
<210> SEQ ID NO 43
<211> LENGTH: 513
<212> TYPE: PRT
<213> ORGANISM: Artificial sequence
<220> FEATURE:
<223> OTHER INFORMATION: Recombinant F protein

<400> SEQUENCE: 43

Met Tyr Ser Met Gln Leu Ala Ser Cys Val Thr Leu Thr Leu Val Leu
1               5                   10                  15

Leu Val Asn Ser Gln Ile His Trp Gly Asn Leu Ser Lys Ile Gly Val
            20                  25                  30

Val Gly Ile Gly Ser Ala Ser Tyr Lys Val Met Thr Arg Ser Ser His
        35                  40                  45

Gln Ser Leu Val Ile Lys Leu Met Pro Asn Ile Thr Leu Leu Asn Asn
    50                  55                  60

Cys Thr Arg Val Glu Ile Ala Glu Tyr Arg Arg Leu Leu Arg Thr Val
65                  70                  75                  80

Leu Glu Pro Ile Arg Asp Ala Leu Asn Ala Val Thr Gln Asn Ile Arg
                85                  90                  95

Pro Val Gln Ser Val Ala Ser Ser Arg Arg His Gly Gly Gly Ala Gly
            100                 105                 110

Val Val Leu Ala Gly Ala Ala Leu Gly Val Ala Thr Ala Ala Gln Ile
        115                 120                 125

Thr Ala Gly Ile Ala Leu His Gln Ser Met Leu Asn Ser Gln Ala Ile
    130                 135                 140

Asp Asn Leu Arg Ala Ser Leu Glu Thr Thr Asn Gln Ala Ile Glu Ala
145                 150                 155                 160

Ile Arg Gln Ala Gly Gln Glu Met Ile Leu Ala Val Gln Gly Val Gln
                165                 170                 175

Asp Tyr Ile Asn Asn Glu Leu Ile Pro Ser Met Asn Gln Leu Pro Cys
            180                 185                 190

Asp Leu Ile Gly Gln Lys Leu Gly Leu Lys Leu Leu Arg Tyr Tyr Thr
            195                 200                 205

Glu Ile Leu Ser Leu Phe Gly Pro Ser Leu Arg Asp Pro Ile Ser Ala
    210                 215                 220

Glu Ile Ser Ile Gln Ala Leu Ser Tyr Ala Leu Gly Gly Asp Ile Asn
225                 230                 235                 240
```

Lys Val Leu Glu Lys Leu Gly Tyr Ser Gly Gly Asp Leu Leu Gly Ile
                245                 250                 255

Leu Glu Ser Arg Gly Ile Lys Ala Arg Ile Thr His Val Asp Thr Glu
            260                 265                 270

Ser Tyr Phe Ile Val Leu Ser Ile Ala Tyr Pro Thr Leu Ser Glu Ile
        275                 280                 285

Lys Gly Val Ile Val His Arg Leu Glu Gly Val Ser Tyr Asn Ile Gly
    290                 295                 300

Ser Gln Glu Trp Tyr Thr Thr Val Pro Lys Tyr Val Ala Thr Gln Gly
305                 310                 315                 320

Tyr Leu Ile Ser Asn Phe Asp Glu Ser Ser Cys Thr Phe Met Pro Glu
                325                 330                 335

Gly Thr Val Cys Ser Gln Asn Ala Leu Tyr Pro Met Ser Pro Leu Leu
            340                 345                 350

Gln Glu Cys Leu Arg Gly Ser Thr Lys Ser Cys Ala Arg Thr Leu Val
            355                 360                 365

Ser Gly Ser Phe Gly Asn Arg Phe Ile Leu Ser Gln Gly Asn Leu Ile
    370                 375                 380

Ala Asn Cys Ala Ser Ile Leu Cys Lys Cys Tyr Thr Thr Gly Thr Ile
385                 390                 395                 400

Ile Asn Gln Asp Pro Asp Lys Ile Leu Thr Tyr Ile Ala Ala Asp His
                405                 410                 415

Cys Pro Val Val Glu Val Asn Gly Val Thr Ile Gln Val Gly Ser Arg
            420                 425                 430

Arg Tyr Pro Asp Ala Val Tyr Leu His Arg Ile Asp Leu Gly Pro Pro
            435                 440                 445

Ile Ser Leu Glu Arg Leu Asp Val Gly Thr Asn Leu Gly Asn Ala Ile
    450                 455                 460

Ala Lys Leu Glu Asp Ala Lys Glu Leu Leu Glu Ser Ser Asp Gln Ile
465                 470                 475                 480

Leu Ser Ala Ile Glu Asp Lys Ile Glu Glu Ile Leu Ser Lys Ile Tyr
                485                 490                 495

His Ile Glu Asn Glu Ile Ala Arg Ile Lys Lys Leu Ile Gly Glu Ala
                500                 505                 510

Pro

<210> SEQ ID NO 44
<211> LENGTH: 24
<212> TYPE: PRT
<213> ORGANISM: Artificial sequence
<220> FEATURE:
<223> OTHER INFORMATION: transmembrane domain

<400> SEQUENCE: 44

Gly Ala Ile Ile Val Ala Ala Leu Val Leu Ser Ile Leu Ser Ile Ile
1               5                   10                  15

Ile Ser Leu Leu Phe Cys Cys Trp
            20

<210> SEQ ID NO 45
<211> LENGTH: 163
<212> TYPE: PRT
<213> ORGANISM: Artificial sequence
<220> FEATURE:
<223> OTHER INFORMATION: Ferritin subunit

<400> SEQUENCE: 45

Asp Ile Ile Lys Leu Leu Asn Glu Gln Val Asn Lys Glu Met Gln Ser
1               5                   10                  15

Ser Asn Leu Tyr Met Ser Met Ser Ser Trp Cys Tyr Thr His Ser Leu
                20                  25                  30

Asp Gly Ala Gly Leu Phe Leu Phe Asp His Ala Ala Glu Glu Tyr Glu
            35                  40                  45

His Ala Lys Lys Leu Ile Ile Phe Leu Asn Glu Asn Asn Val Pro Val
        50                  55                  60

Gln Leu Thr Ser Ile Ser Ala Pro Glu His Lys Phe Glu Gly Leu Thr
65                  70                  75                  80

Gln Ile Phe Gln Lys Ala Tyr Glu His Glu Gln His Ile Ser Glu Ser
                85                  90                  95

Ile Asn Asn Ile Val Asp His Ala Ile Lys Ser Lys Asp His Ala Thr
                100                 105                 110

Phe Asn Phe Leu Gln Trp Tyr Val Ala Glu Gln His Glu Glu Glu Val
            115                 120                 125

Leu Phe Lys Asp Ile Leu Asp Lys Ile Glu Leu Ile Gly Asn Glu Asn
        130                 135                 140

His Gly Leu Tyr Leu Ala Asp Gln Tyr Val Lys Gly Ile Ala Lys Ser
145                 150                 155                 160

Arg Lys Ser

<210> SEQ ID NO 46
<211> LENGTH: 154
<212> TYPE: PRT
<213> ORGANISM: Artificial sequence
<220> FEATURE:
<223> OTHER INFORMATION: lumazine synthase subunit

<400> SEQUENCE: 46

Met Gln Ile Tyr Glu Gly Lys Leu Thr Ala Glu Gly Leu Arg Phe Gly
1               5                   10                  15

Ile Val Ala Ser Arg Phe Asn His Ala Leu Val Asp Arg Leu Val Glu
                20                  25                  30

Gly Ala Ile Asp Cys Ile Val Arg His Gly Gly Arg Glu Glu Asp Ile
            35                  40                  45

Thr Leu Val Arg Val Pro Gly Ser Trp Glu Ile Pro Val Ala Ala Gly
        50                  55                  60

Glu Leu Ala Arg Lys Glu Asp Ile Asp Ala Val Ile Ala Ile Gly Val
65                  70                  75                  80

Leu Ile Arg Gly Ala Thr Pro His Phe Asp Tyr Ile Ala Ser Glu Val
                85                  90                  95

Ser Lys Gly Leu Ala Asp Leu Ser Leu Glu Leu Arg Lys Pro Ile Thr
                100                 105                 110

Phe Gly Val Ile Thr Ala Asp Thr Leu Glu Gln Ala Ile Glu Arg Ala
            115                 120                 125

Gly Thr Lys His Gly Asn Lys Gly Trp Glu Ala Ala Leu Ser Ala Ile
        130                 135                 140

Glu Met Ala Asn Leu Phe Lys Ser Leu Arg
145                 150

<210> SEQ ID NO 47
<211> LENGTH: 265
<212> TYPE: PRT
<213> ORGANISM: Artificial sequence
<220> FEATURE:

-continued

<223> OTHER INFORMATION: encapsulin subunit

<400> SEQUENCE: 47

Met Glu Phe Leu Lys Arg Ser Phe Ala Pro Leu Thr Glu Lys Gln Trp
1               5                   10                  15

Gln Glu Ile Asp Asn Arg Ala Arg Glu Ile Phe Lys Thr Gln Leu Tyr
                20                  25                  30

Gly Arg Lys Phe Val Asp Val Glu Gly Pro Tyr Gly Trp Glu Tyr Ala
            35                  40                  45

Ala His Pro Leu Gly Glu Val Glu Val Leu Ser Asp Glu Asn Glu Val
        50                  55                  60

Val Lys Trp Gly Leu Arg Lys Ser Leu Pro Leu Ile Glu Leu Arg Ala
65                  70                  75                  80

Thr Phe Thr Leu Asp Leu Trp Glu Leu Asp Asn Leu Glu Arg Gly Lys
                85                  90                  95

Pro Asn Val Asp Leu Ser Ser Leu Glu Glu Thr Val Arg Lys Val Ala
                100                 105                 110

Glu Phe Glu Asp Glu Val Ile Phe Arg Gly Cys Glu Lys Ser Gly Val
        115                 120                 125

Lys Gly Leu Leu Ser Phe Glu Glu Arg Lys Ile Glu Cys Gly Ser Thr
    130                 135                 140

Pro Lys Asp Leu Leu Glu Ala Ile Val Arg Ala Leu Ser Ile Phe Ser
145                 150                 155                 160

Lys Asp Gly Ile Glu Gly Pro Tyr Thr Leu Val Ile Asn Thr Asp Arg
                165                 170                 175

Trp Ile Asn Phe Leu Lys Glu Glu Ala Gly His Tyr Pro Leu Glu Lys
                180                 185                 190

Arg Val Glu Glu Cys Leu Arg Gly Gly Lys Ile Ile Thr Thr Pro Arg
        195                 200                 205

Ile Glu Asp Ala Leu Val Val Ser Glu Arg Gly Gly Asp Phe Lys Leu
    210                 215                 220

Ile Leu Gly Gln Asp Leu Ser Ile Gly Tyr Glu Asp Arg Glu Lys Asp
225                 230                 235                 240

Ala Val Arg Leu Phe Ile Thr Glu Thr Phe Thr Phe Gln Val Val Asn
                245                 250                 255

Pro Glu Ala Leu Ile Leu Leu Lys Phe
            260                 265

<210> SEQ ID NO 48
<211> LENGTH: 265
<212> TYPE: PRT
<213> ORGANISM: Artificial sequence
<220> FEATURE:
<223> OTHER INFORMATION: Sulfur Oxygenase Reductase (SOR) subunit

<400> SEQUENCE: 48

Met Glu Phe Leu Lys Arg Ser Phe Ala Pro Leu Thr Glu Lys Gln Trp
1               5                   10                  15

Gln Glu Ile Asp Asn Arg Ala Arg Glu Ile Phe Lys Thr Gln Leu Tyr
                20                  25                  30

Gly Arg Lys Phe Val Asp Val Glu Gly Pro Tyr Gly Trp Glu Tyr Ala
            35                  40                  45

Ala His Pro Leu Gly Glu Val Glu Val Leu Ser Asp Glu Asn Glu Val
        50                  55                  60

Val Lys Trp Gly Leu Arg Lys Ser Leu Pro Leu Ile Glu Leu Arg Ala
65                  70                  75                  80

-continued

```
Thr Phe Thr Leu Asp Leu Trp Glu Leu Asp Asn Leu Glu Arg Gly Lys
            85              90              95

Pro Asn Val Asp Leu Ser Ser Leu Glu Glu Thr Val Arg Lys Val Ala
            100             105             110

Glu Phe Glu Asp Glu Val Ile Phe Arg Gly Cys Glu Lys Ser Gly Val
            115             120             125

Lys Gly Leu Leu Ser Phe Glu Glu Arg Lys Ile Glu Cys Gly Ser Thr
        130             135             140

Pro Lys Asp Leu Leu Glu Ala Ile Val Arg Ala Leu Ser Ile Phe Ser
145             150             155             160

Lys Asp Gly Ile Glu Gly Pro Tyr Thr Leu Val Ile Asn Thr Asp Arg
                165             170             175

Trp Ile Asn Phe Leu Lys Glu Glu Ala Gly His Tyr Pro Leu Glu Lys
                180             185             190

Arg Val Glu Glu Cys Leu Arg Gly Gly Lys Ile Ile Thr Thr Pro Arg
                195             200             205

Ile Glu Asp Ala Leu Val Val Ser Glu Arg Gly Gly Asp Phe Lys Leu
        210             215             220

Ile Leu Gly Gln Asp Leu Ser Ile Gly Tyr Glu Asp Arg Glu Lys Asp
225             230             235             240

Ala Val Arg Leu Phe Ile Thr Glu Thr Phe Thr Phe Gln Val Val Asn
            245             250             255

Pro Glu Ala Leu Ile Leu Leu Lys Phe
            260             265
```

<210> SEQ ID NO 49
<211> LENGTH: 617
<212> TYPE: PRT
<213> ORGANISM: Measles virus

<400> SEQUENCE: 49

```
Met Ser Pro Gln Arg Asp Arg Ile Asn Ala Phe Tyr Lys Asp Asn Pro
1               5               10              15

His Pro Lys Gly Ser Arg Ile Val Ile Asn Arg Glu His Leu Met Ile
            20              25              30

Asp Arg Pro Tyr Val Leu Leu Ala Val Leu Phe Val Met Phe Leu Ser
        35              40              45

Leu Ile Gly Leu Leu Ala Ile Ala Gly Ile Arg Leu His Arg Ala Ala
        50              55              60

Ile Tyr Thr Ala Glu Ile His Lys Ser Leu Ser Thr Asn Leu Asp Val
65              70              75              80

Thr Asn Ser Ile Glu His Gln Val Lys Asp Val Leu Thr Pro Leu Phe
            85              90              95

Lys Ile Ile Gly Asp Glu Val Gly Leu Arg Thr Pro Gln Arg Phe Thr
            100             105             110

Asp Leu Val Lys Phe Ile Ser Asp Lys Ile Lys Phe Leu Asn Pro Asp
        115             120             125

Arg Glu Tyr Asp Phe Arg Asp Leu Thr Trp Cys Ile Asn Pro Pro Glu
        130             135             140

Arg Ile Lys Leu Asp Tyr Asp Gln Tyr Cys Ala Asp Val Ala Ala Glu
145             150             155             160

Glu Leu Met Asn Ala Leu Val Asn Ser Thr Leu Leu Glu Thr Arg Thr
            165             170             175

Thr Asn Gln Phe Leu Ala Val Ser Lys Gly Asn Cys Ser Gly Pro Thr
```

-continued

```
                 180                    185                    190

Thr Ile Arg Gly Gln Phe Ser Asn Met Ser Leu Ser Leu Leu Asp Leu
             195                    200                    205

Tyr Leu Gly Arg Gly Tyr Asn Val Ser Ser Ile Val Thr Met Thr Ser
             210                    215                    220

Gln Gly Met Tyr Gly Gly Thr Tyr Leu Val Glu Lys Pro Asn Leu Ser
    225                    230                    235                    240

Ser Lys Arg Ser Glu Leu Ser Gln Leu Ser Met Tyr Arg Val Phe Glu
                     245                    250                    255

Val Gly Val Ile Arg Asn Pro Gly Leu Gly Ala Pro Val Phe His Met
                     260                    265                    270

Thr Asn Tyr Leu Glu Gln Pro Val Ser Asn Asp Leu Ser Asn Cys Met
                     275                    280                    285

Val Ala Leu Gly Glu Leu Lys Leu Ala Ala Leu Cys His Gly Glu Asp
             290                    295                    300

Ser Ile Thr Ile Pro Tyr Gln Gly Ser Gly Lys Gly Val Ser Phe Gln
    305                    310                    315                    320

Leu Val Lys Leu Gly Val Trp Lys Ser Pro Thr Asp Met Gln Ser Trp
                     325                    330                    335

Val Pro Leu Ser Thr Asp Asp Pro Val Ile Asp Arg Leu Tyr Leu Ser
                     340                    345                    350

Ser His Arg Gly Val Ile Ala Asp Asn Gln Ala Lys Trp Ala Val Pro
             355                    360                    365

Thr Thr Arg Thr Asp Asp Lys Leu Arg Met Glu Thr Cys Phe Gln Gln
             370                    375                    380

Ala Cys Lys Gly Lys Ile Gln Ala Leu Cys Glu Asn Pro Glu Trp Ala
    385                    390                    395                    400

Pro Leu Lys Asp Asn Arg Ile Pro Ser Tyr Gly Val Leu Ser Val Asp
                     405                    410                    415

Leu Ser Leu Thr Val Glu Leu Lys Ile Lys Ile Ala Ser Gly Phe Gly
                     420                    425                    430

Pro Leu Ile Thr His Gly Ser Gly Met Asp Leu Tyr Lys Ser Asn His
             435                    440                    445

Asn Asn Val Tyr Trp Leu Thr Ile Pro Pro Met Lys Asn Leu Ala Leu
             450                    455                    460

Gly Val Ile Asn Thr Leu Glu Trp Ile Pro Arg Phe Lys Val Ser Pro
    465                    470                    475                    480

Tyr Leu Phe Thr Val Pro Ile Lys Glu Ala Gly Glu Asp Cys His Ala
                     485                    490                    495

Pro Thr Tyr Leu Pro Ala Glu Val Asp Gly Asp Val Lys Leu Ser Ser
                     500                    505                    510

Asn Leu Val Ile Leu Pro Gly Gln Asp Leu Gln Tyr Val Leu Ala Thr
             515                    520                    525

Tyr Asp Thr Ser Arg Val Glu His Ala Val Val Tyr Tyr Val Tyr Ser
             530                    535                    540

Pro Ser Arg Ser Phe Ser Tyr Phe Tyr Pro Phe Arg Leu Pro Ile Lys
    545                    550                    555                    560

Gly Val Pro Ile Glu Leu Gln Val Glu Cys Phe Thr Trp Asp Gln Lys
                     565                    570                    575

Leu Trp Cys Arg His Phe Cys Val Leu Ala Asp Ser Glu Ser Gly Gly
                     580                    585                    590

His Ile Thr His Ser Gly Met Val Gly Met Gly Val Ser Cys Thr Val
             595                    600                    605
```

-continued

Thr Arg Glu Asp Gly Thr Asn Arg Arg
    610             615

<210> SEQ ID NO 50
<211> LENGTH: 582
<212> TYPE: PRT
<213> ORGANISM: Mumps virus

<400> SEQUENCE: 50

Met Glu Pro Ser Lys Phe Phe Thr Ile Ser Asp Ser Ala Thr Phe Ala
1               5                   10                  15

Pro Gly Pro Val Ser Asn Ala Ala Asp Lys Lys Thr Phe Arg Thr Cys
            20                  25                  30

Phe Arg Ile Leu Val Leu Ser Val Gln Ala Val Thr Leu Ile Leu Val
        35                  40                  45

Ile Val Thr Leu Gly Glu Leu Val Arg Met Ile Asn Asp Gln Gly Leu
    50                  55                  60

Ser Asn Gln Leu Ser Ser Ile Thr Asp Lys Ile Arg Glu Ser Ala Thr
65                  70                  75                  80

Met Ile Ala Ser Ala Val Gly Val Met Asn Gln Val Ile His Gly Val
                85                  90                  95

Thr Val Ser Leu Pro Leu Gln Ile Glu Gly Asn Gln Asn Gln Leu Leu
            100                 105                 110

Ala Thr Leu Ala Thr Ile Cys Ala Ser Gln Lys Gln Val Ser Asn Cys
            115                 120                 125

Ser Thr Asn Ile Pro Leu Val Asn Asp Leu Arg Phe Ile Asn Gly Ile
    130                 135                 140

Asn Lys Phe Ile Ile Glu Asp Tyr Ala Thr His Asp Phe Ser Ile Gly
145                 150                 155                 160

His Pro Leu Asn Met Pro Ser Phe Ile Pro Thr Ala Thr Ser Pro Asn
                165                 170                 175

Gly Cys Thr Arg Ile Pro Ser Phe Ser Leu Gly Lys Thr His Trp Cys
            180                 185                 190

Tyr Thr His Asn Val Ile Asn Ala Asn Cys Lys Asp His Thr Ser Ser
            195                 200                 205

Asn Gln Tyr Val Ser Met Gly Ile Leu Val Gln Thr Ala Ser Gly Tyr
    210                 215                 220

Pro Met Phe Lys Thr Leu Lys Ile Gln Tyr Leu Ser Asp Gly Leu Asn
225                 230                 235                 240

Arg Lys Ser Cys Ser Ile Ala Thr Val Pro Asp Gly Cys Ala Met Tyr
                245                 250                 255

Cys Tyr Val Ser Thr Gln Leu Glu Thr Asp Asp Tyr Ala Gly Ser Ser
            260                 265                 270

Pro Pro Thr Gln Lys Leu Thr Leu Leu Phe Tyr Asn Asp Thr Val Thr
            275                 280                 285

Glu Arg Thr Ile Ser Pro Ser Gly Leu Glu Gly Asn Trp Ala Thr Leu
    290                 295                 300

Val Pro Gly Val Gly Ser Gly Ile Tyr Phe Glu Asn Lys Leu Ile Phe
305                 310                 315                 320

Pro Ala Tyr Gly Gly Val Leu Pro Asn Ser Thr Leu Gly Val Lys Ser
                325                 330                 335

Ala Arg Glu Phe Phe Arg Pro Val Asn Pro Tyr Asn Pro Cys Ser Gly
            340                 345                 350

Pro Gln Gln Asp Leu Asp Gln Arg Ala Leu Arg Ser Tyr Phe Pro Ser

```
                355                 360                 365

Tyr Phe Ser Asn Arg Arg Ile Gln Ser Ala Phe Leu Val Cys Ala Trp
        370                 375                 380

Asn Gln Ile Leu Val Thr Asn Cys Glu Leu Val Val Pro Ser Ser Asn
385                 390                 395                 400

Gln Thr Met Met Gly Ala Glu Gly Arg Val Leu Leu Ile Asn Asn Arg
                405                 410                 415

Leu Leu Tyr Tyr Gln Arg Ser Thr Ser Trp Trp Pro Tyr Glu Leu Leu
                420                 425                 430

Tyr Glu Ile Ser Phe Thr Phe Thr Asn Ser Gly Pro Ser Ser Val Asn
                435                 440                 445

Met Ser Trp Ile Pro Ile Tyr Ser Phe Thr Arg Pro Gly Ser Gly Asn
        450                 455                 460

Cys Ser Gly Glu Asn Val Cys Pro Thr Ala Cys Val Ser Gly Val Tyr
465                 470                 475                 480

Leu Asp Pro Trp Pro Leu Thr Pro Tyr Ser His Gln Ser Gly Ile Asn
                485                 490                 495

Arg Asn Phe Tyr Phe Thr Gly Ala Leu Leu Asn Ser Ser Thr Thr Arg
                500                 505                 510

Val Asn Pro Thr Leu Tyr Val Ser Ala Leu Asn Asn Leu Lys Val Leu
        515                 520                 525

Ala Pro Tyr Gly Thr Gln Gly Leu Phe Ala Ser Tyr Thr Thr Thr Thr
        530                 535                 540

Cys Phe Gln Asp Thr Gly Asp Ala Ser Val Tyr Cys Val Tyr Ile Met
545                 550                 555                 560

Glu Leu Ala Ser Asn Ile Val Gly Glu Phe Gln Ile Leu Pro Val Leu
                565                 570                 575

Thr Arg Leu Thr Ile Thr
            580

<210> SEQ ID NO 51
<211> LENGTH: 506
<212> TYPE: PRT
<213> ORGANISM: Artificial sequence
<220> FEATURE:
<223> OTHER INFORMATION: Recombinant F protein

<400> SEQUENCE: 51

Met Lys Val Ser Leu Val Thr Cys Leu Gly Phe Ala Val Phe Ser Phe
1               5                   10                  15

Ser Ile Cys Val Asn Ile Asn Ile Leu Gln Gln Ile Gly Tyr Ile Lys
                20                  25                  30

Gln Gln Val Arg Gln Leu Ser Tyr Tyr Ser Gln Ser Ser Ser Ser Tyr
            35                  40                  45

Ile Val Val Lys Leu Leu Pro Asn Ile Gln Pro Thr Asp Asn Ser Cys
        50                  55                  60

Glu Phe Lys Ser Val Thr Gln Tyr Asn Lys Thr Leu Ser Asn Leu Leu
65                  70                  75                  80

Leu Pro Ile Ala Glu Asn Ile Asn Asn Ile Ala Ser Pro Ser Pro Gly
                85                  90                  95

Ser Arg Arg His Gly Gly Gly Ala Gly Ile Ala Ile Gly Ile Ala Ala
            100                 105                 110

Leu Gly Val Ala Thr Ala Ala Gln Val Thr Ala Ala Val Ser Leu Val
        115                 120                 125

Gln Ala Gln Thr Asn Ala Arg Ala Ile Ala Ala Met Lys Asn Ser Ile
```

-continued

```
        130                135                140

Gln Ala Thr Asn Arg Ala Val Phe Glu Val Lys Glu Gly Thr Gln Gln
145                150                155                160

Leu Ala Ile Ala Val Gln Ala Ile Gln Asn His Ile Asn Thr Ile Met
                165                170                175

Asn Thr Gln Leu Asn Asn Met Ser Cys Gln Ile Leu Asp Asn Gln Leu
                180                185                190

Ala Thr Ser Leu Gly Leu Tyr Leu Thr Glu Leu Thr Thr Cys Phe Gln
                195                200                205

Pro Gln Leu Ile Asn Pro Ala Leu Ser Pro Ile Ser Ile Gln Cys Leu
        210                215                220

Arg Ser Leu Leu Gly Ser Met Thr Pro Ala Val Val Gln Ala Thr Leu
225                230                235                240

Ser Thr Ser Ile Ser Ala Ala Glu Ile Leu Ser Ala Gly Leu Met Glu
                245                250                255

Gly Gln Ile Val Ser Val Leu Leu Asp Glu Met Gln Met Ile Val Lys
                260                265                270

Ile Asn Ile Pro Thr Ile Val Thr Gln Ser Asn Ala Leu Val Ile Asp
        275                280                285

Phe Tyr Ser Ile Ser Ser Phe Ile Asn Gly Gln Glu Ser Ile Ile Gln
        290                295                300

Leu Pro Asp Arg Ile Leu Glu Ile Gly Asn Glu Gln Trp Ser Tyr Pro
305                310                315                320

Ala Lys Asn Cys Lys Leu Thr Arg His Asn Ile Phe Cys Gln Tyr Asn
                325                330                335

Glu Ala Glu Arg Leu Ser Leu Glu Ser Lys Leu Cys Leu Ala Gly Asn
                340                345                350

Ile Ser Ala Cys Val Phe Ser Pro Ile Ala Gly Ser Tyr Met Arg Arg
                355                360                365

Phe Val Ala Leu Asp Gly Thr Ile Val Ala Asn Cys Arg Ser Leu Thr
        370                375                380

Cys Leu Cys Lys Ser Pro Ser Tyr Pro Ile Tyr Gln Pro Asp His His
385                390                395                400

Ala Val Thr Thr Ile Asp Leu Thr Ala Cys Gln Thr Leu Ser Leu Asp
                405                410                415

Gly Leu Asp Phe Ser Ile Val Ser Leu Ser Asn Ile Thr Tyr Ala Glu
                420                425                430

Asn Leu Thr Ile Ser Leu Ser Gln Thr Ile Asn Thr Gln Pro Ile Asp
                435                440                445

Ile Ser Thr Glu Leu Ile Lys Val Asn Ala Ser Leu Gln Asn Ala Val
        450                455                460

Lys Tyr Ile Lys Glu Ser Asn His Gln Leu Gln Ser Ile Glu Asp Lys
465                470                475                480

Ile Glu Glu Ile Leu Ser Lys Ile Tyr His Ile Glu Asn Glu Ile Ala
                485                490                495

Arg Ile Lys Lys Leu Ile Gly Glu Ala Pro
                500                505
```

<210> SEQ ID NO 52
<211> LENGTH: 516
<212> TYPE: PRT
<213> ORGANISM: Artificial sequence
<220> FEATURE:
<223> OTHER INFORMATION: Recombinant F protein

```
<400> SEQUENCE: 52

Met Lys Ala Phe Ser Val Thr Cys Leu Ser Phe Ala Val Phe Ser Ser
1               5                   10                  15

Ser Ile Cys Val Asn Ile Asn Ile Leu Gln Gln Ile Gly Tyr Ile Lys
            20                  25                  30

Gln Gln Val Arg Gln Leu Ser Tyr Tyr Ser Gln Ser Ser Ser Ser Tyr
            35                  40                  45

Ile Val Val Lys Leu Leu Pro Asn Ile Gln Pro Thr Asp Asp Ser Cys
    50                  55                  60

Glu Phe Lys Ser Val Thr Gln Tyr Asn Lys Thr Leu Ser Asn Leu Leu
65                  70                  75                  80

Leu Pro Ile Ala Glu Asn Ile Asn Asn Ile Ala Ser Pro Ser Pro Gly
                85                  90                  95

Ser Arg Arg His Gly Gly Gly Ala Gly Ile Ala Ile Gly Ile Ala Ala
            100                 105                 110

Leu Gly Val Ala Thr Ala Ala Gln Val Thr Ala Ala Val Ser Leu Val
            115                 120                 125

Gln Ala Gln Thr Asn Ala Arg Ala Ile Ala Ala Met Lys Asn Ser Ile
    130                 135                 140

Gln Ala Thr Asn Arg Ala Val Phe Glu Val Cys Glu Gly Thr Gln Gln
145                 150                 155                 160

Cys Ala Ile Ala Val Gln Ala Ile Gln Asp His Ile Asn Thr Ile Met
            165                 170                 175

Asn Thr Gln Leu Asn Asn Met Ser Cys Gln Ile Leu Asp Asn Gln Leu
            180                 185                 190

Ala Thr Ser Leu Gly Leu Tyr Leu Thr Glu Leu Thr Thr Val Phe Gln
            195                 200                 205

Pro Gln Leu Thr Asn Pro Ala Leu Ser Pro Ile Ser Ile Gln Ala Leu
    210                 215                 220

Arg Ser Leu Leu Gly Ser Met Thr Pro Ala Val Val Gln Ala Thr Leu
225                 230                 235                 240

Ser Thr Ser Ile Ser Ala Ala Glu Ile Leu Ser Ala Gly Leu Met Glu
            245                 250                 255

Gly Gln Ile Ile Ser Val Leu Leu Asp Glu Met Gln Met Ile Val Lys
            260                 265                 270

Ile Asn Ile Pro Thr Ile Val Thr Gln Ser Asn Ala Leu Val Ile Asp
            275                 280                 285

Phe Tyr Ser Ile Ser Ser Phe Ile Asn Asn Gln Glu Ser Ile Ile Gln
    290                 295                 300

Leu Pro Asp Arg Ile Leu Glu Ile Gly Asn Glu Gln Trp Ser Tyr Pro
305                 310                 315                 320

Ala Lys Asn Cys Lys Leu Thr Arg His His Ile Phe Cys Gln Tyr Asn
            325                 330                 335

Glu Ala Glu Arg Leu Ser Leu Glu Ser Lys Leu Cys Leu Ala Gly Asn
            340                 345                 350

Ile Ser Ala Cys Val Phe Ser Pro Ile Ala Gly Ser Tyr Met Arg Arg
            355                 360                 365

Phe Val Ala Leu Asp Gly Thr Ile Val Ala Asn Cys Arg Ser Leu Thr
    370                 375                 380

Cys Leu Cys Lys Ser Pro Ser Tyr Pro Ile Tyr Gln Pro Asp His His
385                 390                 395                 400

Ala Val Thr Thr Ile Asp Leu Thr Ala Cys Gln Thr Leu Ser Leu Asp
            405                 410                 415
```

```
Gly Leu Asp Phe Ser Ile Val Ser Leu Ser Asn Ile Thr Tyr Ala Glu
              420                     425                     430

Asn Leu Thr Ile Ser Leu Ser Gln Thr Ile Asn Thr Gln Pro Ile Asp
              435                     440                     445

Ile Ser Thr Glu Leu Ser Lys Val Asn Ala Ser Leu Gln Asn Ala Val
              450                     455                     460

Lys Tyr Ile Lys Glu Ser Asn His Gln Leu Gln Ser Val Ser Val Asn
465                     470                     475                     480

Ser Lys Ile Gly Ala Ile Ile Glu Asp Lys Ile Glu Glu Ile Leu Ser
                        485                     490                     495

Lys Ile Tyr His Ile Glu Asn Glu Ile Ala Arg Ile Lys Lys Leu Ile
              500                     505                     510

Gly Glu Ala Pro
              515
```

```
<210> SEQ ID NO 53
<211> LENGTH: 513
<212> TYPE: PRT
<213> ORGANISM: Artificial sequence
<220> FEATURE:
<223> OTHER INFORMATION: Recombinant F protein

<400> SEQUENCE: 53
```

```
Met Tyr Ser Met Gln Leu Ala Ser Cys Val Thr Leu Thr Leu Val Leu
1                       5                       10                      15

Leu Val Asn Ser Gln Ile His Trp Gly Asn Leu Ser Lys Ile Gly Val
              20                      25                      30

Val Gly Ile Gly Ser Ala Ser Tyr Lys Val Met Thr Cys Ser Ser His
              35                      40                      45

Gln Ser Leu Val Ile Lys Leu Met Pro Asn Ile Thr Leu Leu Asn Asn
              50                      55                      60

Cys Thr Arg Val Glu Ile Ala Glu Tyr Arg Arg Leu Leu Arg Thr Val
65                      70                      75                      80

Leu Glu Pro Ile Arg Asp Ala Leu Asn Ala Val Thr Gln Asn Ile Arg
                        85                      90                      95

Pro Val Gln Ser Val Ala Ser Ser Arg Arg His Gly Gly Gly Ala Gly
              100                     105                     110

Val Val Leu Ala Gly Ala Ala Leu Gly Val Ala Thr Ala Ala Gln Ile
              115                     120                     125

Thr Ala Gly Ile Ala Leu His Gln Ser Met Leu Asn Ser Gln Ala Ile
              130                     135                     140

Asp Asn Leu Arg Ala Ser Leu Glu Thr Thr Asn Gln Ala Ile Glu Ala
145                     150                     155                     160

Ile Arg Gln Ala Gly Gln Glu Met Ile Leu Ala Val Gln Gly Val Gln
                        165                     170                     175

Asp Tyr Ile Asn Asn Glu Leu Ile Pro Ser Met Asn Gln Leu Ser Cys
              180                     185                     190

Asp Leu Ile Gly Gln Lys Leu Gly Leu Lys Leu Leu Arg Tyr Tyr Thr
              195                     200                     205

Glu Ile Leu Ser Leu Phe Gly Pro Ser Leu Arg Asp Pro Ile Ser Ala
              210                     215                     220

Glu Ile Ser Ile Gln Ala Leu Ser Tyr Ala Leu Gly Gly Asp Ile Asn
225                     230                     235                     240

Lys Val Leu Glu Lys Leu Gly Tyr Ser Gly Gly Asp Leu Leu Gly Ile
                        245                     250                     255
```

-continued

```
Leu Glu Ser Arg Gly Ile Lys Ala Arg Ile Thr His Val Asp Thr Glu
            260                 265                 270

Ser Tyr Phe Ile Val Leu Ser Ile Cys Tyr Pro Thr Leu Ser Glu Ile
            275                 280                 285

Lys Gly Val Ile Val His Arg Leu Glu Gly Val Ser Tyr Asn Ile Gly
            290                 295                 300

Ser Gln Glu Trp Tyr Thr Thr Val Pro Lys Tyr Val Ala Thr Gln Gly
305                 310                 315                 320

Tyr Leu Ile Ser Asn Phe Asp Glu Ser Ser Cys Thr Phe Met Pro Glu
                325                 330                 335

Gly Thr Val Cys Ser Gln Asn Ala Leu Tyr Pro Met Ser Pro Leu Leu
                340                 345                 350

Gln Glu Cys Leu Arg Gly Ser Thr Lys Ser Cys Ala Arg Thr Leu Val
            355                 360                 365

Ser Gly Ser Phe Gly Asn Arg Phe Ile Leu Ser Gln Gly Asn Leu Ile
            370                 375                 380

Ala Asn Cys Ala Ser Ile Leu Cys Lys Cys Tyr Thr Thr Gly Thr Ile
385                 390                 395                 400

Ile Asn Gln Asp Pro Asp Lys Ile Leu Thr Tyr Ile Ala Ala Asp His
                405                 410                 415

Cys Pro Val Val Glu Val Asn Gly Val Thr Ile Gln Val Gly Ser Arg
                420                 425                 430

Arg Tyr Pro Asp Ala Val Tyr Leu His Arg Ile Asp Leu Gly Pro Pro
            435                 440                 445

Ile Ser Leu Glu Arg Leu Asp Val Gly Thr Asn Leu Gly Asn Ala Ile
            450                 455                 460

Ala Lys Leu Glu Asp Ala Lys Glu Leu Leu Glu Ser Ser Asp Gln Ile
465                 470                 475                 480

Leu Ser Ala Ile Glu Asp Lys Ile Glu Glu Ile Leu Ser Lys Ile Tyr
                485                 490                 495

His Ile Glu Asn Glu Ile Ala Arg Ile Lys Lys Leu Ile Gly Glu Ala
                500                 505                 510

Pro
```

<210> SEQ ID NO 54
<211> LENGTH: 513
<212> TYPE: PRT
<213> ORGANISM: Artificial sequence
<220> FEATURE:
<223> OTHER INFORMATION: Recombinant F protein

<400> SEQUENCE: 54

```
Met Tyr Ser Met Gln Leu Ala Ser Cys Val Thr Leu Thr Leu Val Leu
1               5                   10                  15

Leu Val Asn Ser Gln Ile His Trp Gly Asn Leu Ser Lys Ile Gly Val
                20                  25                  30

Val Gly Ile Gly Ser Ala Ser Tyr Lys Val Met Thr Arg Ser Ser His
            35                  40                  45

Gln Ser Leu Val Ile Lys Leu Met Pro Asn Ile Thr Leu Leu Asn Asn
        50                  55                  60

Cys Thr Arg Val Glu Ile Ala Glu Tyr Arg Arg Leu Leu Arg Thr Val
65                  70                  75                  80

Leu Glu Pro Ile Arg Asp Ala Leu Asn Ala Val Thr Gln Asn Ile Arg
                85                  90                  95
```

-continued

```
Pro Val Gln Ser Val Ala Ser Ser Arg Arg His Gly Gly Gly Ala Gly
        100                 105                 110

Val Val Leu Ala Gly Ala Ala Leu Gly Val Ala Thr Ala Ala Gln Ile
        115                 120                 125

Thr Ala Gly Ile Ala Leu His Gln Ser Cys Leu Asn Ser Gln Ala Ile
        130                 135                 140

Asp Asn Leu Arg Ala Ser Leu Glu Thr Thr Asn Gln Ala Ile Glu Ala
145                 150                 155                 160

Ile Arg Gln Ala Gly Gln Glu Met Ile Leu Ala Val Gln Gly Val Gln
                165                 170                 175

Asp Tyr Ile Asn Asn Glu Leu Ile Pro Ser Met Asn Gln Leu Ser Cys
                180                 185                 190

Asp Leu Ile Gly Gln Lys Leu Gly Leu Lys Leu Leu Arg Tyr Tyr Thr
        195                 200                 205

Glu Ile Leu Ser Leu Phe Gly Pro Ser Leu Arg Asp Pro Ile Ser Ala
        210                 215                 220

Glu Ile Ser Ile Gln Ala Leu Ser Tyr Ala Leu Gly Gly Asp Ile Asn
225                 230                 235                 240

Lys Val Leu Glu Lys Leu Gly Tyr Ser Gly Gly Asp Leu Leu Gly Ile
                245                 250                 255

Leu Glu Ser Arg Gly Ile Lys Ala Arg Ile Cys His Val Asp Thr Glu
                260                 265                 270

Ser Tyr Phe Ile Val Leu Ser Ile Ala Tyr Pro Thr Leu Ser Glu Ile
        275                 280                 285

Lys Gly Val Ile Val His Arg Leu Glu Gly Val Ser Tyr Asn Ile Gly
        290                 295                 300

Ser Gln Glu Trp Tyr Thr Thr Val Pro Lys Tyr Val Ala Thr Gln Gly
305                 310                 315                 320

Tyr Leu Ile Ser Asn Phe Asp Glu Ser Ser Cys Thr Phe Met Pro Glu
                325                 330                 335

Gly Thr Val Cys Ser Gln Asn Ala Leu Tyr Pro Met Ser Pro Leu Leu
                340                 345                 350

Gln Glu Cys Leu Arg Gly Ser Thr Lys Ser Cys Ala Arg Thr Leu Val
        355                 360                 365

Ser Gly Ser Phe Gly Asn Arg Phe Ile Leu Ser Gln Gly Asn Leu Ile
        370                 375                 380

Ala Asn Cys Ala Ser Ile Leu Cys Lys Cys Tyr Thr Thr Gly Thr Ile
385                 390                 395                 400

Ile Asn Gln Asp Pro Asp Lys Ile Leu Thr Tyr Ile Ala Ala Asp His
                405                 410                 415

Cys Pro Val Val Glu Val Asn Gly Val Thr Ile Gln Val Gly Ser Arg
        420                 425                 430

Arg Tyr Pro Asp Ala Val Tyr Leu His Arg Ile Asp Leu Gly Pro Pro
        435                 440                 445

Ile Ser Leu Glu Arg Leu Asp Val Gly Thr Asn Leu Gly Asn Ala Ile
        450                 455                 460

Ala Lys Leu Glu Asp Ala Lys Glu Leu Leu Glu Ser Ser Asp Gln Ile
465                 470                 475                 480

Leu Ser Ala Ile Glu Asp Lys Ile Glu Glu Ile Leu Ser Lys Ile Tyr
                485                 490                 495

His Ile Glu Asn Glu Ile Ala Arg Ile Lys Lys Leu Ile Gly Glu Ala
                500                 505                 510

Pro
```

```
<210> SEQ ID NO 55
<211> LENGTH: 513
<212> TYPE: PRT
<213> ORGANISM: Artificial sequence
<220> FEATURE:
<223> OTHER INFORMATION: Recombinant F protein

<400> SEQUENCE: 55

Met Tyr Ser Met Gln Leu Ala Ser Cys Val Thr Leu Thr Leu Val Leu
1               5                   10                  15

Leu Val Asn Ser Gln Ile His Trp Gly Asn Leu Ser Lys Ile Gly Val
                20                  25                  30

Val Gly Ile Gly Ser Ala Ser Tyr Lys Val Met Thr Arg Ser Ser His
            35                  40                  45

Gln Ser Leu Val Ile Lys Leu Met Pro Asn Ile Thr Leu Leu Asn Asn
        50                  55                  60

Cys Thr Arg Val Glu Ile Ala Glu Tyr Arg Arg Leu Leu Arg Thr Val
65                  70                  75                  80

Leu Glu Pro Ile Arg Asp Ala Leu Asn Ala Val Thr Gln Asn Ile Arg
                85                  90                  95

Pro Val Gln Ser Val Ala Ser Ser Arg Arg His Gly Gly Gly Ala Gly
                100                 105                 110

Val Val Leu Ala Gly Ala Ala Leu Gly Val Ala Thr Ala Ala Gln Ile
            115                 120                 125

Thr Ala Gly Ile Ala Leu His Gln Ser Met Leu Asn Ser Gln Ala Ile
        130                 135                 140

Asp Asn Leu Arg Ala Ser Leu Glu Thr Thr Asn Gln Ala Ile Glu Ala
145                 150                 155                 160

Ile Arg Gln Ala Gly Gln Glu Met Ile Leu Ala Val Gln Gly Val Gln
                165                 170                 175

Asp Tyr Ile Asn Asn Glu Leu Ile Pro Ser Met Asn Gln Leu Ser Cys
                180                 185                 190

Asp Leu Ile Gly Gln Lys Leu Gly Leu Lys Leu Leu Arg Tyr Tyr Thr
            195                 200                 205

Cys Ile Leu Ser Leu Phe Gly Pro Ser Leu Arg Asp Pro Ile Ser Ala
        210                 215                 220

Glu Ile Ser Ile Gln Ala Leu Ser Cys Ala Leu Gly Gly Asp Ile Asn
225                 230                 235                 240

Lys Val Leu Glu Lys Leu Gly Tyr Ser Gly Gly Asp Leu Leu Gly Ile
                245                 250                 255

Leu Glu Ser Arg Gly Ile Lys Ala Arg Ile Thr His Val Asp Thr Glu
                260                 265                 270

Ser Tyr Phe Ile Val Leu Ser Ile Ala Tyr Pro Thr Leu Ser Glu Ile
            275                 280                 285

Lys Gly Val Ile Val His Arg Leu Glu Gly Val Ser Tyr Asn Ile Gly
        290                 295                 300

Ser Gln Glu Trp Tyr Thr Thr Val Pro Lys Tyr Val Ala Thr Gln Gly
305                 310                 315                 320

Tyr Leu Ile Ser Asn Phe Asp Glu Ser Ser Cys Thr Phe Met Pro Glu
                325                 330                 335

Gly Thr Val Cys Ser Gln Asn Ala Leu Tyr Pro Met Ser Pro Leu Leu
            340                 345                 350

Gln Glu Cys Leu Arg Gly Ser Thr Lys Ser Cys Ala Arg Thr Leu Val
        355                 360                 365
```

```
Ser Gly Ser Phe Gly Asn Arg Phe Ile Leu Ser Gln Gly Asn Leu Ile
    370             375             380

Ala Asn Cys Ala Ser Ile Leu Cys Lys Cys Tyr Thr Thr Gly Thr Ile
385             390             395             400

Ile Asn Gln Asp Pro Asp Lys Ile Leu Thr Tyr Ile Ala Ala Asp His
            405             410             415

Cys Pro Val Val Glu Val Asn Gly Val Thr Ile Gln Val Gly Ser Arg
        420             425             430

Arg Tyr Pro Asp Ala Val Tyr Leu His Arg Ile Asp Leu Gly Pro Pro
        435             440             445

Ile Ser Leu Glu Arg Leu Asp Val Gly Thr Asn Leu Gly Asn Ala Ile
    450             455             460

Ala Lys Leu Glu Asp Ala Lys Glu Leu Leu Glu Ser Ser Asp Gln Ile
465             470             475             480

Leu Ser Ala Ile Glu Asp Lys Ile Glu Glu Ile Leu Ser Lys Ile Tyr
            485             490             495

His Ile Glu Asn Glu Ile Ala Arg Ile Lys Lys Leu Ile Gly Glu Ala
            500             505             510

Pro
```

```
<210> SEQ ID NO 56
<211> LENGTH: 959
<212> TYPE: PRT
<213> ORGANISM: Artificial sequence
<220> FEATURE:
<223> OTHER INFORMATION: Recombinant F protein

<400> SEQUENCE: 56
```

```
Met Tyr Ser Met Gln Leu Ala Ser Cys Val Thr Leu Thr Leu Val Leu
1               5               10              15

Leu Val Asn Ser Gln Ile His Trp Gly Asn Leu Ser Lys Ile Gly Val
            20              25              30

Val Gly Ile Gly Ser Ala Ser Tyr Lys Val Met Thr Arg Ser Ser His
        35              40              45

Gln Ser Leu Val Ile Lys Leu Met Pro Asn Ile Thr Leu Leu Asn Asn
    50              55              60

Cys Thr Arg Val Glu Ile Ala Glu Tyr Arg Arg Leu Leu Arg Thr Val
65              70              75              80

Leu Glu Pro Ile Arg Asp Ala Leu Asn Ala Val Thr Gln Asn Ile Arg
            85              90              95

Pro Val Gln Ser Val Ala Ser Ser Arg Arg His Gly Gly Gly Ala Gly
            100             105             110

Val Val Leu Ala Gly Ala Ala Leu Gly Val Ala Thr Ala Ala Gln Ile
        115             120             125

Thr Ala Gly Ile Ala Leu His Gln Ser Met Leu Asn Ser Gln Ala Ile
    130             135             140

Asp Asn Leu Arg Ala Ser Leu Glu Thr Thr Asn Gln Ala Ile Glu Ala
145             150             155             160

Ile Cys Gln Ala Gly Gln Glu Cys Ile Leu Ala Val Gln Gly Val Gln
            165             170             175

Asp Tyr Ile Asn Asn Glu Leu Ile Pro Ser Met Asn Gln Leu Ser Cys
            180             185             190

Asp Leu Ile Gly Gln Lys Leu Gly Leu Lys Leu Leu Arg Tyr Tyr Thr
            195             200             205
```

-continued

```
Glu Ile Leu Ser Leu Phe Gly Pro Ser Leu Arg Asp Pro Ile Ser Ala
    210                 215                 220

Glu Ile Ser Ile Gln Ala Leu Ser Tyr Ala Leu Gly Gly Asp Ile Asn
225                 230                 235                 240

Lys Val Leu Glu Lys Leu Gly Tyr Ser Gly Gly Asp Leu Leu Gly Ile
                245                 250                 255

Leu Glu Ser Arg Gly Ile Lys Ala Arg Ile Thr His Val Asp Thr Glu
                260                 265                 270

Ser Tyr Phe Ile Val Leu Ser Ile Ala Tyr Pro Thr Leu Ser Glu Ile
            275                 280                 285

Lys Gly Val Ile Val His Arg Leu Glu Gly Val Ser Tyr Asn Ile Gly
    290                 295                 300

Ser Gln Glu Trp Tyr Thr Thr Val Pro Lys Tyr Val Ala Thr Gln Gly
305                 310                 315                 320

Tyr Leu Ile Ser Asn Phe Asp Glu Ser Ser Cys Thr Phe Met Pro Glu
                325                 330                 335

Gly Thr Val Cys Ser Gln Asn Ala Leu Tyr Pro Met Ser Pro Leu Leu
                340                 345                 350

Gln Glu Cys Leu Arg Gly Ser Thr Lys Ser Cys Ala Arg Thr Leu Val
            355                 360                 365

Ser Gly Ser Phe Gly Asn Arg Phe Ile Leu Ser Gln Gly Asn Leu Ile
    370                 375                 380

Ala Asn Cys Ala Ser Ile Leu Cys Lys Cys Tyr Thr Thr Gly Thr Ile
385                 390                 395                 400

Ile Asn Gln Asp Pro Asp Lys Ile Leu Thr Tyr Ile Ala Ala Asp His
                405                 410                 415

Cys Pro Val Val Glu Val Asn Gly Val Thr Ile Gln Val Gly Ser Arg
                420                 425                 430

Arg Tyr Pro Asp Ala Val Tyr Leu His Arg Ile Asp Leu Gly Pro Pro
            435                 440                 445

Ile Ser Leu Glu Arg Leu Asp Val Gly Thr Asn Leu Gly Asn Ala Ile
    450                 455                 460

Ala Lys Leu Glu Asp Ala Lys Glu Leu Leu Glu Ser Ser Asp Gln Ile
465                 470                 475                 480

Leu Ser Ala Ile Glu Asp Lys Ile Glu Glu Ile Leu Ser Lys Ile Tyr
                485                 490                 495

His Ile Glu Asn Glu Ile Ala Arg Ile Lys Lys Leu Ile Gly Glu Ala
                500                 505                 510

Pro Gly Ser Gly Gly Gly Gly Gly Phe Leu Ala Val Ser Lys Gly
            515                 520                 525

Asn Cys Ser Gly Pro Thr Thr Ile Arg Gly Gln Phe Ser Asn Met Ser
    530                 535                 540

Leu Ser Leu Leu Asp Leu Tyr Leu Gly Arg Gly Tyr Asn Val Ser Ser
545                 550                 555                 560

Ile Val Thr Met Thr Ser Gln Gly Met Tyr Gly Gly Thr Tyr Leu Val
                565                 570                 575

Glu Lys Pro Asn Leu Ser Ser Lys Arg Ser Glu Leu Ser Gln Leu Ser
                580                 585                 590

Met Tyr Arg Val Phe Glu Val Gly Val Ile Arg Asn Pro Gly Leu Gly
            595                 600                 605

Ala Pro Val Phe His Met Thr Asn Tyr Leu Glu Gln Pro Val Ser Asn
    610                 615                 620

Asp Leu Ser Asn Cys Met Val Ala Leu Gly Glu Leu Lys Leu Ala Ala
```

-continued

```
625                 630                 635                 640

Leu Cys His Gly Glu Asp Ser Ile Thr Ile Pro Tyr Gln Gly Ser Gly
            645                 650                 655

Lys Gly Val Ser Phe Gln Leu Val Lys Leu Gly Val Trp Lys Ser Pro
            660                 665                 670

Ala Asp Met Gln Ser Trp Val Pro Leu Ser Thr Asp Pro Val Ile
            675                 680                 685

Asp Arg Leu Tyr Leu Ser Ser His Arg Gly Val Ile Ala Asp Asn Gln
            690                 695                 700

Ala Lys Trp Ala Val Pro Thr Thr Arg Thr Asp Asp Lys Leu Arg Met
705                 710                 715                 720

Glu Thr Cys Phe Gln Gln Ala Cys Lys Gly Lys Ile Gln Thr Leu Cys
            725                 730                 735

Glu Asn Pro Glu Trp Ala Pro Leu Lys Asp Asn Arg Ile Pro Ser Tyr
            740                 745                 750

Gly Val Leu Ser Val Asp Leu Ser Leu Thr Val Glu Leu Lys Ile Lys
            755                 760                 765

Ile Ala Ser Gly Phe Gly Pro Leu Ile Thr His Gly Ser Gly Met Asp
            770                 775                 780

Leu Tyr Lys Ser Asn His Asn Asn Val Tyr Trp Leu Thr Ile Pro Pro
785                 790                 795                 800

Met Lys Asn Leu Ala Leu Gly Val Ile Asn Thr Leu Glu Trp Ile Pro
            805                 810                 815

Arg Phe Lys Val Ser Pro Tyr Leu Phe Thr Val Pro Ile Lys Glu Ala
            820                 825                 830

Gly Glu Asp Cys His Ala Pro Thr Tyr Leu Pro Ala Glu Val Asp Gly
            835                 840                 845

Asp Val Lys Leu Ser Ser Asn Leu Val Ile Leu Pro Gly Gln Asp Leu
            850                 855                 860

Gln Tyr Val Leu Ala Thr Tyr Asp Thr Ser Arg Val Glu His Ala Val
865                 870                 875                 880

Val Tyr Tyr Val Tyr Ser Pro Gly Arg Ser Phe Ser Tyr Phe Tyr Pro
            885                 890                 895

Phe Arg Leu Pro Ile Lys Gly Val Pro Ile Glu Leu Gln Val Glu Cys
            900                 905                 910

Phe Thr Trp Asp Gln Lys Leu Trp Cys Arg His Phe Cys Val Leu Ala
            915                 920                 925

Asp Ser Glu Ser Gly Gly His Ile Thr His Ser Gly Met Val Gly Met
            930                 935                 940

Gly Val Ser Cys Thr Val Thr Arg Glu Asp Gly Thr Asn Arg Arg
945                 950                 955
```

<210> SEQ ID NO 57
<211> LENGTH: 973
<212> TYPE: PRT
<213> ORGANISM: Artificial sequence
<220> FEATURE:
<223> OTHER INFORMATION: Recombinant F protein

<400> SEQUENCE: 57

```
Met Tyr Ser Met Gln Leu Ala Ser Cys Val Thr Leu Thr Leu Val Leu
1                   5                   10                  15

Leu Val Asn Ser Gln Ile His Trp Gly Asn Leu Ser Lys Ile Gly Val
            20                  25                  30

Val Gly Ile Gly Ser Ala Ser Tyr Lys Val Met Thr Arg Ser Ser His
```

-continued

```
         35                40                45
Gln Ser Leu Val Ile Lys Leu Met Pro Asn Ile Thr Leu Leu Asn Asn
    50                55                60
Cys Thr Arg Val Glu Ile Ala Glu Tyr Arg Arg Leu Leu Arg Thr Val
65                70                75                80
Leu Glu Pro Ile Arg Asp Ala Leu Asn Ala Val Thr Gln Asn Ile Arg
                85                90                95
Pro Val Gln Ser Val Ala Ser Ser Arg Arg His Gly Gly Gly Ala Gly
            100               105               110
Val Val Leu Ala Gly Ala Ala Leu Gly Val Ala Thr Ala Ala Gln Ile
        115               120               125
Thr Ala Gly Ile Ala Leu His Gln Ser Met Leu Asn Ser Gln Ala Ile
    130               135               140
Asp Asn Leu Arg Ala Ser Leu Glu Thr Thr Asn Gln Ala Ile Glu Ala
145               150               155               160
Ile Cys Gln Ala Gly Gln Glu Cys Ile Leu Ala Val Gln Gly Val Gln
            165               170               175
Asp Tyr Ile Asn Asn Glu Leu Ile Pro Ser Met Asn Gln Leu Ser Cys
            180               185               190
Asp Leu Ile Gly Gln Lys Leu Gly Leu Lys Leu Leu Arg Tyr Tyr Thr
        195               200               205
Glu Ile Leu Ser Leu Phe Gly Pro Ser Leu Arg Asp Pro Ile Ser Ala
    210               215               220
Glu Ile Ser Ile Gln Ala Leu Ser Tyr Ala Leu Gly Gly Asp Ile Asn
225               230               235               240
Lys Val Leu Glu Lys Leu Gly Tyr Ser Gly Gly Asp Leu Leu Gly Ile
            245               250               255
Leu Glu Ser Arg Gly Ile Lys Ala Arg Ile Thr His Val Asp Thr Glu
        260               265               270
Ser Tyr Phe Ile Val Leu Ser Ile Ala Tyr Pro Thr Leu Ser Glu Ile
        275               280               285
Lys Gly Val Ile Val His Arg Leu Glu Gly Val Ser Tyr Asn Ile Gly
    290               295               300
Ser Gln Glu Trp Tyr Thr Thr Val Pro Lys Tyr Val Ala Thr Gln Gly
305               310               315               320
Tyr Leu Ile Ser Asn Phe Asp Glu Ser Ser Cys Thr Phe Met Pro Glu
            325               330               335
Gly Thr Val Cys Ser Gln Asn Ala Leu Tyr Pro Met Ser Pro Leu Leu
            340               345               350
Gln Glu Cys Leu Arg Gly Ser Thr Lys Ser Cys Ala Arg Thr Leu Val
        355               360               365
Ser Gly Ser Phe Gly Asn Arg Phe Ile Leu Ser Gln Gly Asn Leu Ile
    370               375               380
Ala Asn Cys Ala Ser Ile Leu Cys Lys Cys Tyr Thr Thr Gly Thr Ile
385               390               395               400
Ile Asn Gln Asp Pro Asp Lys Ile Leu Thr Tyr Ile Ala Ala Asp His
            405               410               415
Cys Pro Val Val Glu Val Asn Gly Val Thr Ile Gln Val Gly Ser Arg
            420               425               430
Arg Tyr Pro Asp Ala Val Tyr Leu His Arg Ile Asp Leu Gly Pro Pro
        435               440               445
Ile Ser Leu Glu Arg Leu Asp Val Gly Thr Asn Leu Gly Asn Ala Ile
    450               455               460
```

```
Ala Lys Leu Glu Asp Ala Lys Glu Leu Leu Glu Ser Ser Asp Gln Ile
465                 470                 475                 480

Leu Ser Ala Ile Glu Asp Lys Ile Glu Glu Ile Leu Ser Lys Ile Tyr
                485                 490                 495

His Ile Glu Asn Glu Ile Ala Arg Ile Lys Lys Leu Ile Gly Glu Ala
                500                 505                 510

Pro Gly Ser Gly Gly Gly Gly Gly Asn Ile Pro Leu Val Asn Asp
                515                 520                 525

Leu Arg Phe Ile Asn Gly Ile Asn Lys Phe Ile Ile Glu Asp Tyr Ala
                530                 535                 540

Thr His Asp Phe Ser Ile Gly His Pro Leu Asn Met Pro Ser Phe Ile
545                 550                 555                 560

Pro Thr Ala Thr Ser Pro Asn Gly Cys Thr Arg Ile Pro Ser Phe Ser
                565                 570                 575

Leu Gly Lys Thr His Trp Cys Tyr Thr His Asn Val Ile Asn Ala Asn
                580                 585                 590

Cys Lys Asp His Thr Ser Ser Asn Gln Tyr Val Ser Met Gly Ile Leu
                595                 600                 605

Val Gln Thr Ala Ser Gly Tyr Pro Met Phe Lys Thr Leu Lys Ile Gln
                610                 615                 620

Tyr Leu Ser Asp Gly Leu Asn Arg Lys Ser Cys Ser Ile Ala Thr Val
625                 630                 635                 640

Pro Asp Gly Cys Ala Met Tyr Cys Tyr Val Ser Thr Gln Leu Glu Thr
                645                 650                 655

Asp Asp Tyr Ala Gly Ser Ser Pro Pro Thr Gln Lys Leu Thr Leu Leu
                660                 665                 670

Phe Tyr Asn Asp Thr Val Thr Glu Arg Thr Ile Ser Pro Ser Gly Leu
                675                 680                 685

Glu Gly Asn Trp Ala Thr Leu Val Pro Gly Val Gly Ser Gly Ile Tyr
                690                 695                 700

Phe Glu Asn Lys Leu Ile Phe Pro Ala Tyr Gly Gly Val Leu Pro Asn
705                 710                 715                 720

Ser Thr Leu Gly Val Lys Ser Ala Arg Glu Phe Phe Arg Pro Val Asn
                725                 730                 735

Pro Tyr Asn Pro Cys Ser Gly Pro Gln Gln Asp Leu Asp Gln Arg Ala
                740                 745                 750

Leu Arg Ser Tyr Phe Pro Ser Tyr Phe Ser Asn Arg Arg Ile Gln Ser
                755                 760                 765

Ala Phe Leu Val Cys Ala Trp Asn Gln Ile Leu Val Thr Asn Cys Glu
                770                 775                 780

Leu Val Val Pro Ser Ser Asn Gln Thr Met Met Gly Ala Glu Gly Arg
785                 790                 795                 800

Val Leu Leu Ile Asn Asn Arg Leu Leu Tyr Tyr Gln Arg Ser Thr Ser
                805                 810                 815

Trp Trp Pro Tyr Glu Leu Leu Tyr Glu Ile Ser Phe Thr Phe Thr Asn
                820                 825                 830

Ser Gly Pro Ser Ser Val Asn Met Ser Trp Ile Pro Ile Tyr Ser Phe
                835                 840                 845

Thr Arg Pro Gly Ser Gly Asn Cys Ser Gly Glu Asn Val Cys Pro Thr
                850                 855                 860

Ala Cys Val Ser Gly Val Tyr Leu Asp Pro Trp Pro Leu Thr Pro Tyr
865                 870                 875                 880
```

```
Ser His Gln Ser Gly Ile Asn Arg Asn Phe Tyr Phe Thr Gly Ala Leu
            885                 890                 895

Leu Asn Ser Ser Thr Thr Arg Val Asn Pro Thr Leu Tyr Val Ser Ala
            900                 905                 910

Leu Asn Asn Leu Lys Val Leu Ala Pro Tyr Gly Thr Gln Gly Leu Phe
            915                 920                 925

Ala Ser Tyr Thr Thr Thr Thr Cys Phe Gln Asp Thr Gly Asp Ala Ser
    930                 935                 940

Val Tyr Cys Val Tyr Ile Met Glu Leu Ala Ser Asn Ile Val Gly Glu
945                 950                 955                 960

Phe Gln Ile Leu Pro Val Leu Thr Arg Leu Thr Ile Thr
                965                 970
```

<210> SEQ ID NO 58
<211> LENGTH: 510
<212> TYPE: PRT
<213> ORGANISM: Artificial sequence
<220> FEATURE:
<223> OTHER INFORMATION: Recombinant HN protein

<400> SEQUENCE: 58

```
Met Tyr Ser Met Gln Leu Ala Ser Cys Val Thr Leu Thr Leu Val Leu
1               5                   10                  15

Leu Val Asn Ser Gln Gly Ser Gly Tyr Ile Pro Glu Ala Pro Arg Asp
            20                  25                  30

Gly Gln Ala Tyr Val Arg Lys Asp Gly Glu Trp Val Leu Leu Ser Thr
        35                  40                  45

Phe Leu Gly Ser Gly Gly Gly Gly Gly Asn Ile Pro Leu Val Asn
    50                  55                  60

Asp Leu Arg Phe Ile Asn Gly Ile Asn Lys Phe Ile Ile Glu Asp Tyr
65                  70                  75                  80

Ala Thr His Asp Phe Ser Ile Gly His Pro Leu Asn Met Pro Ser Phe
            85                  90                  95

Ile Pro Thr Ala Thr Ser Pro Asn Gly Cys Thr Arg Ile Pro Ser Phe
            100                 105                 110

Ser Leu Gly Lys Thr His Trp Cys Tyr Thr His Asn Val Ile Asn Ala
            115                 120                 125

Asn Cys Lys Asp His Thr Ser Ser Asn Gln Tyr Val Ser Met Gly Ile
        130                 135                 140

Leu Val Gln Thr Ala Ser Gly Tyr Pro Met Phe Lys Thr Leu Lys Ile
145                 150                 155                 160

Gln Tyr Leu Ser Asp Gly Leu Asn Arg Lys Ser Cys Ser Ile Ala Thr
                165                 170                 175

Val Pro Asp Gly Cys Ala Met Tyr Cys Tyr Val Ser Thr Gln Leu Glu
            180                 185                 190

Thr Asp Asp Tyr Ala Gly Ser Ser Pro Pro Thr Gln Lys Leu Thr Leu
            195                 200                 205

Leu Phe Tyr Asn Asp Thr Val Thr Glu Arg Thr Ile Ser Pro Ser Gly
        210                 215                 220

Leu Glu Gly Asn Trp Ala Thr Leu Val Pro Gly Val Gly Ser Gly Ile
225                 230                 235                 240

Tyr Phe Glu Asn Lys Leu Ile Phe Pro Ala Tyr Gly Gly Val Leu Pro
                245                 250                 255

Asn Ser Thr Leu Gly Val Lys Ser Ala Arg Glu Phe Phe Arg Pro Val
            260                 265                 270
```

```
Asn Pro Tyr Asn Pro Cys Ser Gly Pro Gln Gln Asp Leu Asp Gln Arg
        275             280             285

Ala Leu Arg Ser Tyr Phe Pro Ser Tyr Phe Ser Asn Arg Arg Ile Gln
    290             295             300

Ser Ala Phe Leu Val Cys Ala Trp Asn Gln Ile Leu Val Thr Asn Cys
305             310             315             320

Glu Leu Val Val Pro Ser Ser Asn Gln Thr Met Met Gly Ala Glu Gly
            325             330             335

Arg Val Leu Leu Ile Asn Asn Arg Leu Leu Tyr Tyr Gln Arg Ser Thr
        340             345             350

Ser Trp Trp Pro Tyr Glu Leu Leu Tyr Glu Ile Ser Phe Thr Phe Thr
        355             360             365

Asn Ser Gly Pro Ser Ser Val Asn Met Ser Trp Ile Pro Ile Tyr Ser
    370             375             380

Phe Thr Arg Pro Gly Ser Gly Asn Cys Ser Gly Glu Asn Val Cys Pro
385             390             395             400

Thr Ala Cys Val Ser Gly Val Tyr Leu Asp Pro Trp Pro Leu Thr Pro
            405             410             415

Tyr Ser His Gln Ser Gly Ile Asn Arg Asn Phe Tyr Phe Thr Gly Ala
        420             425             430

Leu Leu Asn Ser Ser Thr Thr Arg Val Asn Pro Thr Leu Tyr Val Ser
        435             440             445

Ala Leu Asn Asn Leu Lys Val Leu Ala Pro Tyr Gly Thr Gln Gly Leu
    450             455             460

Phe Ala Ser Tyr Thr Thr Thr Thr Cys Phe Gln Asp Thr Gly Asp Ala
465             470             475             480

Ser Val Tyr Cys Val Tyr Ile Met Glu Leu Ala Ser Asn Ile Val Gly
            485             490             495

Glu Phe Gln Ile Leu Pro Val Leu Thr Arg Leu Thr Ile Thr
            500             505             510
```

<210> SEQ ID NO 59
<211> LENGTH: 496
<212> TYPE: PRT
<213> ORGANISM: Artificial sequence
<220> FEATURE:
<223> OTHER INFORMATION: Recombinant H protein

<400> SEQUENCE: 59

```
Met Tyr Ser Met Gln Leu Ala Ser Cys Val Thr Leu Thr Leu Val Leu
1               5               10              15

Leu Val Asn Ser Gln Gly Ser Gly Tyr Ile Pro Glu Ala Pro Arg Asp
                20              25              30

Gly Gln Ala Tyr Val Arg Lys Asp Gly Glu Trp Val Leu Leu Ser Thr
        35              40              45

Phe Leu Gly Ser Gly Gly Gly Gly Gly Phe Leu Ala Val Ser Lys
    50              55              60

Gly Asn Cys Ser Gly Pro Thr Thr Ile Arg Gly Gln Phe Ser Asn Met
65              70              75              80

Ser Leu Ser Leu Leu Asp Leu Tyr Leu Gly Arg Gly Tyr Asn Val Ser
            85              90              95

Ser Ile Val Thr Met Thr Ser Gln Gly Met Tyr Gly Gly Thr Tyr Leu
            100             105             110

Val Glu Lys Pro Asn Leu Ser Ser Lys Arg Ser Glu Leu Ser Gln Leu
        115             120             125
```

Ser Met Tyr Arg Val Phe Glu Val Gly Val Ile Arg Asn Pro Gly Leu
    130                 135                 140

Gly Ala Pro Val Phe His Met Thr Asn Tyr Leu Glu Gln Pro Val Ser
145                 150                 155                 160

Asn Asp Leu Ser Asn Cys Met Val Ala Leu Gly Glu Leu Lys Leu Ala
                165                 170                 175

Ala Leu Cys His Gly Glu Asp Ser Ile Thr Ile Pro Tyr Gln Gly Ser
            180                 185                 190

Gly Lys Gly Val Ser Phe Gln Leu Val Lys Leu Gly Val Trp Lys Ser
            195                 200                 205

Pro Ala Asp Met Gln Ser Trp Val Pro Leu Ser Thr Asp Asp Pro Val
    210                 215                 220

Ile Asp Arg Leu Tyr Leu Ser Ser His Arg Gly Val Ile Ala Asp Asn
225                 230                 235                 240

Gln Ala Lys Trp Ala Val Pro Thr Thr Arg Thr Asp Asp Lys Leu Arg
                245                 250                 255

Met Glu Thr Cys Phe Gln Gln Ala Cys Lys Gly Lys Ile Gln Thr Leu
            260                 265                 270

Cys Glu Asn Pro Glu Trp Ala Pro Leu Lys Asp Asn Arg Ile Pro Ser
            275                 280                 285

Tyr Gly Val Leu Ser Val Asp Leu Ser Leu Thr Val Glu Leu Lys Ile
    290                 295                 300

Lys Ile Ala Ser Gly Phe Gly Pro Leu Ile Thr His Gly Ser Gly Met
305                 310                 315                 320

Asp Leu Tyr Lys Ser Asn His Asn Asn Val Tyr Trp Leu Thr Ile Pro
                325                 330                 335

Pro Met Lys Asn Leu Ala Leu Gly Val Ile Asn Thr Leu Glu Trp Ile
            340                 345                 350

Pro Arg Phe Lys Val Ser Pro Tyr Leu Phe Thr Val Pro Ile Lys Glu
            355                 360                 365

Ala Gly Glu Asp Cys His Ala Pro Thr Tyr Leu Pro Ala Glu Val Asp
    370                 375                 380

Gly Asp Val Lys Leu Ser Ser Asn Leu Val Ile Leu Pro Gly Gln Asp
385                 390                 395                 400

Leu Gln Tyr Val Leu Ala Thr Tyr Asp Thr Ser Arg Val Glu His Ala
                405                 410                 415

Val Val Tyr Tyr Val Tyr Ser Pro Gly Arg Ser Phe Ser Tyr Phe Tyr
            420                 425                 430

Pro Phe Arg Leu Pro Ile Lys Gly Val Pro Ile Glu Leu Gln Val Glu
            435                 440                 445

Cys Phe Thr Trp Asp Gln Lys Leu Trp Cys Arg His Phe Cys Val Leu
    450                 455                 460

Ala Asp Ser Glu Ser Gly Gly His Ile Thr His Ser Gly Met Val Gly
465                 470                 475                 480

Met Gly Val Ser Cys Thr Val Thr Arg Glu Asp Gly Thr Asn Arg Arg
                485                 490                 495

<210> SEQ ID NO 60
<211> LENGTH: 459
<212> TYPE: PRT
<213> ORGANISM: Artificial sequence
<220> FEATURE:
<223> OTHER INFORMATION: Recombinant H protein

<400> SEQUENCE: 60

```
Met Tyr Ser Met Gln Leu Ala Ser Cys Val Thr Leu Thr Leu Val Leu
1                5                10               15

Leu Val Asn Ser Gln Phe Leu Ala Val Ser Lys Gly Asn Cys Ser Gly
            20               25               30

Pro Thr Thr Ile Arg Gly Gln Phe Ser Asn Met Ser Leu Ser Leu Leu
        35               40               45

Asp Leu Tyr Leu Gly Arg Gly Tyr Asn Val Ser Ser Ile Val Thr Met
    50               55               60

Thr Ser Gln Gly Met Tyr Gly Gly Thr Tyr Leu Val Glu Lys Pro Asn
65               70               75               80

Leu Ser Ser Lys Arg Ser Glu Leu Ser Gln Leu Ser Met Tyr Arg Val
            85               90               95

Phe Glu Val Gly Val Ile Arg Asn Pro Gly Leu Gly Ala Pro Val Phe
            100              105              110

His Met Thr Asn Tyr Leu Glu Gln Pro Val Ser Asn Asp Leu Ser Asn
        115              120              125

Cys Met Val Ala Leu Gly Glu Leu Lys Leu Ala Ala Leu Cys His Gly
    130              135              140

Glu Asp Ser Ile Thr Ile Pro Tyr Gln Gly Ser Gly Lys Gly Val Ser
145              150              155              160

Phe Gln Leu Val Lys Leu Gly Val Trp Lys Ser Pro Ala Asp Met Gln
            165              170              175

Ser Trp Val Pro Leu Ser Thr Asp Asp Pro Val Ile Asp Arg Leu Tyr
            180              185              190

Leu Ser Ser His Arg Gly Val Ile Ala Asp Asn Gln Ala Lys Trp Ala
            195              200              205

Val Pro Thr Thr Arg Thr Asp Asp Lys Leu Arg Met Glu Thr Cys Phe
    210              215              220

Gln Gln Ala Cys Lys Gly Lys Ile Gln Thr Leu Cys Glu Asn Pro Glu
225              230              235              240

Trp Ala Pro Leu Lys Asp Asn Arg Ile Pro Ser Tyr Gly Val Leu Ser
            245              250              255

Val Asp Leu Ser Leu Thr Val Glu Leu Lys Ile Lys Ile Ala Ser Gly
            260              265              270

Phe Gly Pro Leu Ile Thr His Gly Ser Gly Met Asp Leu Tyr Lys Ser
    275              280              285

Asn His Asn Asn Val Tyr Trp Leu Thr Ile Pro Pro Met Lys Asn Leu
    290              295              300

Ala Leu Gly Val Ile Asn Thr Leu Glu Trp Ile Pro Arg Phe Lys Val
305              310              315              320

Ser Pro Tyr Leu Phe Thr Val Pro Ile Lys Glu Ala Gly Glu Asp Cys
            325              330              335

His Ala Pro Thr Tyr Leu Pro Ala Glu Val Asp Gly Asp Val Lys Leu
        340              345              350

Ser Ser Asn Leu Val Ile Leu Pro Gly Gln Asp Leu Gln Tyr Val Leu
        355              360              365

Ala Thr Tyr Asp Thr Ser Arg Val Glu His Ala Val Val Tyr Tyr Val
    370              375              380

Tyr Ser Pro Gly Arg Ser Phe Ser Tyr Phe Tyr Pro Phe Arg Leu Pro
385              390              395              400

Ile Lys Gly Val Pro Ile Glu Leu Gln Val Glu Cys Phe Thr Trp Asp
            405              410              415

Gln Lys Leu Trp Cys Arg His Phe Cys Val Leu Ala Asp Ser Glu Ser
```

-continued

```
                420             425             430
Gly Gly His Ile Thr His Ser Gly Met Val Gly Met Gly Val Ser Cys
        435             440             445

Thr Val Thr Arg Glu Asp Gly Thr Asn Arg Arg
    450             455

<210> SEQ ID NO 61
<211> LENGTH: 497
<212> TYPE: PRT
<213> ORGANISM: Artificial sequence
<220> FEATURE:
<223> OTHER INFORMATION: Recombinant F protein

<400> SEQUENCE: 61

Met Tyr Ser Met Gln Leu Ala Ser Cys Val Thr Leu Thr Leu Val Leu
1               5                   10                  15

Leu Val Asn Ser Gln Ile His Trp Gly Asn Leu Ser Lys Ile Gly Val
            20                  25                  30

Val Gly Ile Gly Ser Ala Ser Tyr Lys Val Met Thr Arg Ser Ser His
        35                  40                  45

Gln Ser Leu Val Ile Lys Leu Met Pro Asn Ile Thr Leu Leu Asn Asn
    50                  55                  60

Cys Thr Arg Val Glu Ile Ala Glu Tyr Arg Arg Leu Leu Arg Thr Val
65                  70                  75                  80

Leu Glu Pro Ile Arg Asp Ala Leu Asn Ala Val Thr Gln Asn Ile Arg
                85                  90                  95

Pro Val Gln Ser Val Ala Ser Ser Gly Ser Gly Gly Ser Ala Gln
            100                 105                 110

Ile Thr Ala Gly Ile Ala Leu His Gln Ser Met Leu Asn Ser Gln Ala
            115                 120                 125

Ile Asp Asn Leu Arg Ala Ser Leu Glu Thr Thr Asn Gln Ala Ile Glu
    130                 135                 140

Ala Ile Arg Gln Ala Gly Gln Glu Met Ile Leu Ala Val Gln Gly Val
145                 150                 155                 160

Gln Asp Tyr Ile Asn Asn Glu Leu Ile Pro Ser Met Asn Gln Leu Ser
                165                 170                 175

Cys Asp Leu Ile Gly Gln Lys Leu Gly Leu Lys Leu Leu Arg Tyr Tyr
            180                 185                 190

Thr Glu Ile Leu Ser Leu Phe Gly Pro Ser Leu Arg Asp Pro Ile Ser
            195                 200                 205

Ala Glu Ile Ser Ile Gln Ala Leu Ser Tyr Ala Leu Gly Gly Asp Ile
    210                 215                 220

Asn Lys Val Leu Glu Lys Leu Gly Tyr Ser Gly Gly Asp Leu Leu Gly
225                 230                 235                 240

Ile Leu Glu Ser Arg Gly Ile Lys Ala Arg Ile Thr His Val Asp Thr
                245                 250                 255

Glu Ser Tyr Phe Ile Val Leu Ser Ile Ala Tyr Pro Thr Leu Ser Glu
                260                 265                 270

Ile Lys Gly Val Ile Val His Arg Leu Glu Gly Val Ser Tyr Asn Ile
            275                 280                 285

Gly Ser Gln Glu Trp Tyr Thr Thr Val Pro Lys Tyr Val Ala Thr Gln
    290                 295                 300

Gly Tyr Leu Ile Ser Asn Phe Asp Glu Ser Ser Cys Thr Phe Met Pro
305                 310                 315                 320

Glu Gly Thr Val Cys Ser Gln Asn Ala Leu Tyr Pro Met Ser Pro Leu
```

```
                     325                 330                 335

Leu Gln Glu Cys Leu Arg Gly Ser Thr Lys Ser Cys Ala Arg Thr Leu
             340                 345                 350

Val Ser Gly Ser Phe Gly Asn Arg Phe Ile Leu Ser Gln Gly Asn Leu
             355                 360                 365

Ile Ala Asn Cys Ala Ser Ile Leu Cys Lys Cys Tyr Thr Thr Gly Thr
             370                 375                 380

Ile Ile Asn Gln Asp Pro Asp Lys Ile Leu Thr Tyr Ile Ala Ala Asp
385                 390                 395                 400

His Cys Pro Val Val Glu Val Asn Gly Val Thr Ile Gln Val Gly Ser
                 405                 410                 415

Arg Arg Tyr Pro Asp Ala Val Tyr Leu His Arg Ile Asp Leu Gly Pro
             420                 425                 430

Pro Ile Ser Leu Glu Arg Leu Asp Val Gly Thr Asn Leu Gly Asn Ala
             435                 440                 445

Ile Ala Lys Leu Glu Asp Ala Lys Glu Leu Leu Glu Ser Ser Asp Gln
     450                 455                 460

Ile Leu Ser Ala Ile Gly Gly Tyr Ile Pro Glu Ala Pro Arg Asp Gly
465                 470                 475                 480

Gln Ala Tyr Val Arg Lys Asp Gly Glu Trp Val Leu Leu Ser Thr Phe
                 485                 490                 495

Leu
```

<210> SEQ ID NO 62
<211> LENGTH: 513
<212> TYPE: PRT
<213> ORGANISM: Artificial sequence
<220> FEATURE:
<223> OTHER INFORMATION: Recombinant F protein

<400> SEQUENCE: 62

```
Met Tyr Ser Met Gln Leu Ala Ser Cys Val Thr Leu Thr Leu Val Leu
1               5                   10                  15

Leu Val Asn Ser Gln Ile His Trp Gly Asn Leu Ser Lys Ile Gly Val
             20                  25                  30

Val Gly Ile Gly Ser Ala Ser Tyr Lys Val Met Thr Arg Ser Ser His
             35                  40                  45

Gln Ser Leu Val Ile Lys Leu Met Pro Asn Ile Thr Leu Leu Asn Asn
     50                  55                  60

Cys Thr Arg Val Glu Ile Ala Glu Tyr Arg Arg Leu Leu Arg Thr Val
65                  70                  75                  80

Leu Glu Pro Ile Arg Asp Ala Leu Asn Ala Val Thr Gln Asn Ile Arg
                 85                  90                  95

Pro Val Gln Cys Val Ala Ser Ser Arg Arg His Gly Gly Gly Ala Gly
             100                 105                 110

Val Cys Leu Ala Gly Ala Ala Leu Gly Val Ala Thr Ala Ala Gln Ile
             115                 120                 125

Thr Ala Gly Ile Ala Leu His Gln Ser Met Leu Asn Ser Gln Ala Ile
     130                 135                 140

Asp Asn Leu Arg Ala Ser Leu Glu Thr Thr Asn Gln Ala Ile Glu Ala
145                 150                 155                 160

Ile Arg Gln Ala Gly Gln Glu Met Ile Leu Ala Val Gln Gly Val Gln
                 165                 170                 175

Asp Tyr Ile Asn Asn Glu Leu Ile Pro Ser Met Asn Gln Leu Ser Cys
             180                 185                 190
```

```
Asp Leu Ile Gly Gln Lys Leu Gly Leu Lys Leu Leu Arg Tyr Tyr Thr
        195                 200                 205

Glu Ile Leu Ser Leu Phe Gly Pro Ser Leu Arg Asp Pro Ile Ser Ala
        210                 215                 220

Glu Ile Ser Ile Gln Ala Leu Ser Tyr Ala Leu Gly Gly Asp Ile Asn
225                 230                 235                 240

Lys Val Leu Glu Lys Leu Gly Tyr Ser Gly Gly Asp Leu Leu Gly Ile
                245                 250                 255

Leu Glu Ser Arg Gly Ile Lys Ala Arg Ile Thr His Val Asp Thr Glu
                260                 265                 270

Ser Tyr Phe Ile Val Leu Ser Ile Ala Tyr Pro Thr Leu Ser Glu Ile
                275                 280                 285

Lys Gly Val Ile Val His Arg Leu Glu Gly Val Ser Tyr Asn Ile Gly
        290                 295                 300

Ser Gln Glu Trp Tyr Thr Thr Val Pro Lys Tyr Val Ala Thr Gln Gly
305                 310                 315                 320

Tyr Leu Ile Ser Asn Phe Asp Glu Ser Ser Cys Thr Phe Met Pro Glu
                325                 330                 335

Gly Thr Val Cys Ser Gln Asn Ala Leu Tyr Pro Met Ser Pro Leu Leu
                340                 345                 350

Gln Glu Cys Leu Arg Gly Ser Thr Lys Ser Cys Ala Arg Thr Leu Val
                355                 360                 365

Ser Gly Ser Phe Gly Asn Arg Phe Ile Leu Ser Gln Gly Asn Leu Ile
        370                 375                 380

Ala Asn Cys Ala Ser Ile Leu Cys Lys Cys Tyr Thr Thr Gly Thr Ile
385                 390                 395                 400

Ile Asn Gln Asp Pro Asp Lys Ile Leu Thr Tyr Ile Ala Ala Asp His
                405                 410                 415

Cys Pro Val Val Glu Val Asn Gly Val Thr Ile Gln Val Gly Ser Arg
                420                 425                 430

Arg Tyr Pro Asp Ala Val Tyr Leu His Arg Ile Asp Leu Gly Pro Pro
                435                 440                 445

Ile Ser Leu Glu Arg Leu Asp Val Gly Thr Asn Leu Gly Asn Ala Ile
        450                 455                 460

Ala Lys Leu Glu Asp Ala Lys Glu Leu Leu Glu Ser Ser Asp Gln Ile
465                 470                 475                 480

Leu Ser Ala Ile Glu Asp Lys Ile Glu Glu Ile Leu Ser Lys Ile Tyr
                485                 490                 495

His Ile Glu Asn Glu Ile Ala Arg Ile Lys Lys Leu Ile Gly Glu Ala
        500                 505                 510

Pro
```

<210> SEQ ID NO 63
<211> LENGTH: 513
<212> TYPE: PRT
<213> ORGANISM: Artificial sequence
<220> FEATURE:
<223> OTHER INFORMATION: Recombinant F protein

<400> SEQUENCE: 63

```
Met Tyr Ser Met Gln Leu Ala Ser Cys Val Thr Leu Thr Leu Val Leu
1               5                   10                  15

Leu Val Asn Ser Gln Ile His Trp Gly Asn Leu Ser Lys Ile Gly Val
        20                  25                  30
```

-continued

```
Val Gly Ile Gly Ser Ala Ser Tyr Lys Val Met Thr Arg Ser Ser His
        35              40                  45

Gln Ser Leu Val Ile Lys Leu Met Pro Asn Ile Thr Leu Leu Asn Asn
    50              55                  60

Cys Thr Arg Val Glu Ile Ala Glu Tyr Arg Arg Leu Leu Arg Thr Val
65              70                  75                  80

Leu Glu Pro Ile Arg Asp Ala Leu Asn Ala Val Thr Gln Asn Ile Arg
                85                  90                  95

Pro Val Gln Ser Val Ala Ser Ser Arg Arg His Gly Gly Gly Ala Gly
            100                 105                 110

Val Val Leu Ala Gly Ala Ala Leu Gly Val Ala Thr Ala Ala Gln Ile
            115                 120                 125

Thr Ala Gly Ile Ala Leu His Gln Ser Met Leu Asn Ser Gln Ala Ile
    130                 135                 140

Asp Asn Leu Arg Ala Ser Leu Glu Thr Thr Asn Gln Ala Ile Glu Ala
145                 150                 155                 160

Ile Arg Gln Ala Gly Gln Glu Met Ile Leu Ala Phe Gln Gly Val Gln
                165                 170                 175

Asp Tyr Ile Asn Asn Glu Leu Ile Pro Ser Met Asn Gln Leu Ser Cys
            180                 185                 190

Asp Leu Ile Gly Gln Lys Leu Gly Leu Lys Leu Leu Arg Tyr Tyr Thr
            195                 200                 205

Glu Ile Leu Ser Leu Phe Gly Pro Ser Leu Arg Asp Pro Ile Ser Ala
    210                 215                 220

Glu Ile Ser Ile Gln Ala Leu Ser Tyr Ala Leu Gly Gly Asp Ile Asn
225                 230                 235                 240

Lys Val Leu Glu Lys Leu Gly Tyr Ser Gly Gly Asp Leu Leu Gly Ile
                245                 250                 255

Leu Glu Ser Arg Gly Ile Lys Ala Arg Ile Thr His Val Asp Thr Glu
            260                 265                 270

Ser Tyr Phe Ile Val Leu Ser Ile Ala Tyr Pro Thr Leu Ser Glu Ile
            275                 280                 285

Lys Gly Val Ile Val His Arg Leu Glu Gly Val Ser Tyr Asn Ile Gly
    290                 295                 300

Ser Gln Glu Trp Tyr Thr Thr Val Pro Lys Tyr Val Ala Thr Gln Gly
305                 310                 315                 320

Tyr Leu Ile Ser Asn Phe Asp Glu Ser Ser Cys Thr Phe Met Pro Glu
                325                 330                 335

Gly Thr Val Cys Ser Gln Asn Ala Leu Tyr Pro Met Ser Pro Leu Leu
            340                 345                 350

Gln Glu Cys Leu Arg Gly Ser Thr Lys Ser Cys Ala Arg Thr Leu Val
            355                 360                 365

Ser Gly Ser Phe Gly Asn Arg Phe Ile Leu Ser Gln Gly Asn Leu Ile
    370                 375                 380

Ala Asn Cys Ala Ser Ile Leu Cys Lys Cys Tyr Thr Thr Gly Thr Ile
385                 390                 395                 400

Ile Asn Gln Asp Pro Asp Lys Ile Leu Thr Tyr Ile Ala Ala Asp His
                405                 410                 415

Cys Pro Val Val Glu Val Asn Gly Val Thr Ile Gln Val Gly Ser Arg
            420                 425                 430

Arg Tyr Pro Asp Ala Val Tyr Leu His Arg Ile Asp Leu Gly Pro Pro
            435                 440                 445

Ile Ser Leu Glu Arg Leu Asp Val Gly Thr Asn Leu Gly Asn Ala Ile
```

-continued

```
              450                 455                 460

Ala Lys Leu Glu Asp Ala Lys Glu Leu Leu Glu Ser Ser Asp Gln Ile
465                 470                 475                 480

Leu Ser Ala Ile Glu Asp Lys Ile Glu Glu Ile Leu Ser Lys Ile Tyr
                485                 490                 495

His Ile Glu Asn Glu Ile Ala Arg Ile Lys Lys Leu Ile Gly Glu Ala
                500                 505                 510

Pro

<210> SEQ ID NO 64
<211> LENGTH: 513
<212> TYPE: PRT
<213> ORGANISM: Artificial sequence
<220> FEATURE:
<223> OTHER INFORMATION: Recombinant F protein

<400> SEQUENCE: 64

Met Tyr Ser Met Gln Leu Ala Ser Cys Val Thr Leu Thr Leu Val Leu
1               5                   10                  15

Leu Val Asn Ser Gln Ile His Trp Gly Asn Leu Ser Lys Ile Gly Val
                20                  25                  30

Val Gly Ile Gly Ser Ala Ser Tyr Lys Val Met Thr Arg Ser Ser His
            35                  40                  45

Gln Ser Leu Val Ile Lys Leu Met Pro Asn Ile Thr Leu Leu Asn Asn
        50                  55                  60

Cys Thr Arg Val Glu Ile Ala Glu Tyr Arg Arg Leu Leu Arg Thr Val
65                  70                  75                  80

Leu Glu Pro Ile Arg Asp Ala Leu Asn Ala Val Thr Gln Asn Ile Arg
                85                  90                  95

Pro Val Gln Cys Val Ala Ser Ser Arg Arg His Gly Gly Gly Ala Gly
                100                 105                 110

Val Cys Leu Ala Gly Ala Ala Leu Gly Val Ala Thr Ala Ala Gln Ile
            115                 120                 125

Thr Ala Gly Ile Ala Leu His Gln Ser Met Leu Asn Ser Gln Ala Ile
        130                 135                 140

Asp Asn Leu Arg Ala Ser Leu Glu Thr Thr Asn Gln Ala Ile Glu Ala
145                 150                 155                 160

Ile Arg Gln Ala Gly Gln Glu Met Ile Leu Ala Phe Gln Gly Val Gln
                165                 170                 175

Asp Tyr Ile Asn Asn Glu Leu Ile Pro Ser Met Asn Gln Leu Pro Cys
            180                 185                 190

Asp Leu Ile Gly Gln Lys Leu Gly Leu Lys Leu Leu Arg Tyr Tyr Thr
        195                 200                 205

Glu Ile Leu Ser Leu Phe Gly Pro Ser Leu Arg Asp Pro Ile Ser Ala
        210                 215                 220

Glu Ile Ser Ile Gln Ala Leu Ser Tyr Ala Leu Gly Gly Asp Ile Asn
225                 230                 235                 240

Lys Val Leu Glu Lys Leu Gly Tyr Ser Gly Gly Asp Leu Leu Gly Ile
                245                 250                 255

Leu Glu Ser Arg Gly Ile Lys Ala Arg Ile Thr His Val Asp Thr Glu
            260                 265                 270

Ser Tyr Phe Ile Val Leu Ser Ile Ala Tyr Pro Thr Leu Ser Glu Ile
        275                 280                 285

Lys Gly Val Ile Val His Arg Leu Glu Gly Val Ser Tyr Asn Ile Gly
    290                 295                 300
```

Ser Gln Glu Trp Tyr Thr Thr Val Pro Lys Tyr Val Ala Thr Gln Gly
305                 310                 315                 320

Tyr Leu Ile Ser Asn Phe Asp Glu Ser Ser Cys Thr Phe Met Pro Glu
                325                 330                 335

Gly Thr Val Cys Ser Gln Asn Ala Leu Tyr Pro Met Ser Pro Leu Leu
            340                 345                 350

Gln Glu Cys Leu Arg Gly Ser Thr Lys Ser Cys Ala Arg Thr Leu Val
            355                 360                 365

Ser Gly Ser Phe Gly Asn Arg Phe Ile Leu Ser Gln Gly Asn Leu Ile
    370                 375                 380

Ala Asn Cys Ala Ser Ile Leu Cys Lys Cys Tyr Thr Thr Gly Thr Ile
385                 390                 395                 400

Ile Asn Gln Asp Pro Asp Lys Ile Leu Thr Tyr Ile Ala Ala Asp His
                405                 410                 415

Cys Pro Val Val Glu Val Asn Gly Val Thr Ile Gln Val Gly Ser Arg
            420                 425                 430

Arg Tyr Pro Asp Ala Val Tyr Leu His Arg Ile Asp Leu Gly Pro Pro
            435                 440                 445

Ile Ser Leu Glu Arg Leu Asp Val Gly Thr Asn Leu Gly Asn Ala Ile
    450                 455                 460

Ala Lys Leu Glu Asp Ala Lys Glu Leu Leu Glu Ser Ser Asp Gln Ile
465                 470                 475                 480

Leu Ser Ala Ile Glu Asp Lys Ile Glu Glu Ile Leu Ser Lys Ile Tyr
                485                 490                 495

His Ile Glu Asn Glu Ile Ala Arg Ile Lys Lys Leu Ile Gly Glu Ala
            500                 505                 510

Pro

<210> SEQ ID NO 65
<211> LENGTH: 513
<212> TYPE: PRT
<213> ORGANISM: Artificial sequence
<220> FEATURE:
<223> OTHER INFORMATION: Recombinant F protein

<400> SEQUENCE: 65

Met Tyr Ser Met Gln Leu Ala Ser Cys Val Thr Leu Thr Leu Val Leu
1               5                   10                  15

Leu Val Asn Ser Gln Ile His Trp Gly Asn Leu Ser Lys Ile Gly Val
                20                  25                  30

Val Gly Ile Gly Ser Ala Ser Tyr Lys Val Met Thr Arg Ser Ser His
            35                  40                  45

Gln Ser Leu Val Ile Lys Leu Met Pro Asn Ile Thr Leu Leu Asn Asn
    50                  55                  60

Cys Thr Arg Val Glu Ile Ala Glu Tyr Arg Arg Leu Leu Arg Thr Val
65                  70                  75                  80

Leu Glu Pro Ile Arg Asp Ala Leu Asn Ala Val Thr Gln Asn Ile Arg
                85                  90                  95

Pro Val Gln Cys Val Ala Ser Ser Arg Arg His Gly Gly Gly Ala Gly
            100                 105                 110

Val Cys Leu Ala Gly Ala Ala Leu Gly Val Ala Thr Ala Ala Gln Ile
            115                 120                 125

Thr Ala Gly Ile Ala Leu His Gln Ser Met Leu Asn Ser Gln Ala Ile
    130                 135                 140

Asp Asn Leu Arg Ala Ser Leu Glu Thr Thr Asn Gln Ala Ile Glu Ala
145                 150                 155                 160

Ile Cys Gln Ala Gly Gln Glu Cys Ile Leu Ala Phe Gln Gly Val Gln
                165                 170                 175

Asp Tyr Ile Asn Asn Glu Leu Ile Pro Ser Met Asn Gln Leu Pro Cys
                180                 185                 190

Asp Leu Ile Gly Gln Lys Leu Gly Leu Lys Leu Leu Arg Tyr Tyr Thr
                195                 200                 205

Glu Ile Leu Ser Leu Phe Gly Pro Ser Leu Arg Asp Pro Ile Ser Ala
        210                 215                 220

Glu Ile Ser Ile Gln Ala Leu Ser Tyr Ala Leu Gly Gly Asp Ile Asn
225                 230                 235                 240

Lys Val Leu Glu Lys Leu Gly Tyr Ser Gly Gly Asp Leu Leu Gly Ile
                245                 250                 255

Leu Glu Ser Arg Gly Ile Lys Ala Arg Ile Thr His Val Asp Thr Glu
                260                 265                 270

Ser Tyr Phe Ile Val Leu Ser Ile Ala Tyr Pro Thr Leu Ser Glu Ile
                275                 280                 285

Lys Gly Val Ile Val His Arg Leu Glu Gly Val Ser Tyr Asn Ile Gly
        290                 295                 300

Ser Gln Glu Trp Tyr Thr Thr Val Pro Lys Tyr Val Ala Thr Gln Gly
305                 310                 315                 320

Tyr Leu Ile Ser Asn Phe Asp Glu Ser Ser Cys Thr Phe Met Pro Glu
                325                 330                 335

Gly Thr Val Cys Ser Gln Asn Ala Leu Tyr Pro Met Ser Pro Leu Leu
                340                 345                 350

Gln Glu Cys Leu Arg Gly Ser Thr Lys Ser Cys Ala Arg Thr Leu Val
                355                 360                 365

Ser Gly Ser Phe Gly Asn Arg Phe Ile Leu Ser Gln Gly Asn Leu Ile
        370                 375                 380

Ala Asn Cys Ala Ser Ile Leu Cys Lys Cys Tyr Thr Thr Gly Thr Ile
385                 390                 395                 400

Ile Asn Gln Asp Pro Asp Lys Ile Leu Thr Tyr Ile Ala Ala Asp His
                405                 410                 415

Cys Pro Val Val Glu Val Asn Gly Val Thr Ile Gln Val Gly Ser Arg
                420                 425                 430

Arg Tyr Pro Asp Ala Val Tyr Leu His Arg Ile Asp Leu Gly Pro Pro
                435                 440                 445

Ile Ser Leu Glu Arg Leu Asp Val Gly Thr Asn Leu Gly Asn Ala Ile
        450                 455                 460

Ala Lys Leu Glu Asp Ala Lys Glu Leu Leu Glu Ser Ser Asp Gln Ile
465                 470                 475                 480

Leu Ser Ala Ile Glu Asp Lys Ile Glu Glu Ile Leu Ser Lys Ile Tyr
                485                 490                 495

His Ile Glu Asn Glu Ile Ala Arg Ile Lys Lys Leu Ile Gly Glu Ala
        500                 505                 510

Pro

<210> SEQ ID NO 66
<211> LENGTH: 513
<212> TYPE: PRT
<213> ORGANISM: Artificial sequence
<220> FEATURE:
<223> OTHER INFORMATION: Recombinant F protein

```
<400> SEQUENCE: 66

Met Tyr Ser Met Gln Leu Ala Ser Cys Val Thr Leu Thr Leu Val Leu
1               5                   10                  15

Leu Val Asn Ser Gln Ile His Trp Gly Asn Leu Ser Lys Ile Gly Val
                20                  25                  30

Val Gly Ile Gly Ser Ala Ser Tyr Lys Val Met Thr Arg Ser Ser His
            35                  40                  45

Gln Ser Leu Val Ile Lys Leu Met Pro Asn Ile Thr Leu Leu Asn Asn
    50                  55                  60

Cys Thr Arg Val Glu Ile Ala Glu Tyr Arg Arg Leu Leu Arg Thr Val
65                  70                  75                  80

Leu Glu Pro Ile Arg Asp Ala Leu Asn Ala Val Thr Gln Asn Ile Cys
                85                  90                  95

Pro Val Gln Ser Val Ala Ser Ser Arg Arg His Gly Gly Gly Ala Gly
                100                 105                 110

Val Cys Leu Ala Gly Ala Ala Leu Gly Val Ala Thr Ala Ala Gln Ile
            115                 120                 125

Thr Ala Gly Ile Ala Leu His Gln Ser Met Leu Asn Ser Gln Ala Ile
    130                 135                 140

Asp Asn Leu Arg Ala Ser Leu Glu Thr Thr Asn Gln Ala Ile Glu Ala
145                 150                 155                 160

Ile Arg Gln Ala Gly Gln Glu Met Ile Leu Ala Val Gln Gly Val Gln
                165                 170                 175

Asp Tyr Ile Asn Asn Glu Leu Ile Pro Ser Met Asn Gln Leu Ser Cys
                180                 185                 190

Asp Leu Ile Gly Gln Lys Leu Gly Leu Lys Leu Leu Arg Tyr Tyr Thr
            195                 200                 205

Glu Ile Leu Ser Leu Phe Gly Pro Ser Leu Arg Asp Pro Ile Ser Ala
    210                 215                 220

Glu Ile Ser Ile Gln Ala Leu Ser Tyr Ala Leu Gly Gly Asp Ile Asn
225                 230                 235                 240

Lys Val Leu Glu Lys Leu Gly Tyr Ser Gly Gly Asp Leu Leu Gly Ile
                245                 250                 255

Leu Glu Ser Arg Gly Ile Lys Ala Arg Ile Thr His Val Asp Thr Glu
            260                 265                 270

Ser Tyr Phe Ile Val Leu Ser Ile Ala Tyr Pro Thr Leu Ser Glu Ile
        275                 280                 285

Lys Gly Val Ile Val His Arg Leu Glu Gly Val Ser Tyr Asn Ile Gly
    290                 295                 300

Ser Gln Glu Trp Tyr Thr Thr Val Pro Lys Tyr Val Ala Thr Gln Gly
305                 310                 315                 320

Tyr Leu Ile Ser Asn Phe Asp Glu Ser Ser Cys Thr Phe Met Pro Glu
                325                 330                 335

Gly Thr Val Cys Ser Gln Asn Ala Leu Tyr Pro Met Ser Pro Leu Leu
            340                 345                 350

Gln Glu Cys Leu Arg Gly Ser Thr Lys Ser Cys Ala Arg Thr Leu Val
        355                 360                 365

Ser Gly Ser Phe Gly Asn Arg Phe Ile Leu Ser Gln Gly Asn Leu Ile
    370                 375                 380

Ala Asn Cys Ala Ser Ile Leu Cys Lys Cys Tyr Thr Thr Gly Thr Ile
385                 390                 395                 400

Ile Asn Gln Asp Pro Asp Lys Ile Leu Thr Tyr Ile Ala Ala Asp His
                405                 410                 415
```

-continued

```
Cys Pro Val Val Glu Val Asn Gly Val Thr Ile Gln Val Gly Ser Arg
            420             425             430

Arg Tyr Pro Asp Ala Val Tyr Leu His Arg Ile Asp Leu Gly Pro Pro
            435             440             445

Ile Ser Leu Glu Arg Leu Asp Val Gly Thr Asn Leu Gly Asn Ala Ile
    450             455             460

Ala Lys Leu Glu Asp Ala Lys Glu Leu Leu Glu Ser Ser Asp Gln Ile
465             470             475             480

Leu Ser Ala Ile Glu Asp Lys Ile Glu Glu Ile Leu Ser Lys Ile Tyr
                485             490             495

His Ile Glu Asn Glu Ile Ala Arg Ile Lys Lys Leu Ile Gly Glu Ala
            500             505             510

Pro

<210> SEQ ID NO 67
<211> LENGTH: 513
<212> TYPE: PRT
<213> ORGANISM: Artificial sequence
<220> FEATURE:
<223> OTHER INFORMATION: Recombinant F protein

<400> SEQUENCE: 67

Met Tyr Ser Met Gln Leu Ala Ser Cys Val Thr Leu Thr Leu Val Leu
1               5               10              15

Leu Val Asn Ser Gln Ile His Trp Gly Asn Leu Ser Lys Ile Gly Val
                20              25              30

Val Gly Ile Gly Ser Ala Ser Tyr Lys Val Met Thr Arg Ser Ser His
            35              40              45

Gln Ser Leu Val Ile Lys Leu Met Pro Asn Ile Thr Leu Leu Asn Asn
    50              55              60

Cys Thr Arg Val Glu Ile Ala Glu Tyr Arg Arg Leu Leu Arg Thr Val
65              70              75              80

Leu Glu Pro Ile Arg Asp Ala Leu Asn Ala Val Thr Gln Asn Ile Cys
                85              90              95

Pro Val Gln Ser Val Ala Ser Ser Arg Arg His Gly Gly Gly Ala Gly
            100             105             110

Val Cys Leu Ala Gly Ala Ala Leu Gly Val Ala Thr Ala Ala Gln Ile
            115             120             125

Thr Ala Gly Ile Ala Leu His Gln Ser Met Leu Asn Ser Gln Ala Ile
    130             135             140

Asp Asn Leu Arg Ala Ser Leu Glu Thr Thr Asn Gln Ala Ile Glu Ala
145             150             155             160

Ile Arg Gln Ala Gly Gln Glu Met Ile Leu Ala Phe Gln Gly Val Gln
                165             170             175

Asp Tyr Ile Asn Asn Glu Leu Ile Pro Ser Met Asn Gln Leu Pro Cys
                180             185             190

Asp Leu Ile Gly Gln Lys Leu Gly Leu Lys Leu Leu Arg Tyr Tyr Thr
                195             200             205

Glu Ile Leu Ser Leu Phe Gly Pro Ser Leu Arg Asp Pro Ile Ser Ala
    210             215             220

Glu Ile Ser Ile Gln Ala Leu Ser Tyr Ala Leu Gly Gly Asp Ile Asn
225             230             235             240

Lys Val Leu Glu Lys Leu Gly Tyr Ser Gly Gly Asp Leu Leu Gly Ile
                245             250             255
```

-continued

```
Leu Glu Ser Arg Gly Ile Lys Ala Arg Ile Thr His Val Asp Thr Glu
            260             265             270

Ser Tyr Phe Ile Val Leu Ser Ile Ala Tyr Pro Thr Leu Ser Glu Ile
        275             280             285

Lys Gly Val Ile Val His Arg Leu Glu Gly Val Ser Tyr Asn Ile Gly
        290             295             300

Ser Gln Glu Trp Tyr Thr Thr Val Pro Lys Tyr Val Ala Thr Gln Gly
305             310             315             320

Tyr Leu Ile Ser Asn Phe Asp Glu Ser Ser Cys Thr Phe Met Pro Glu
            325             330             335

Gly Thr Val Cys Ser Gln Asn Ala Leu Tyr Pro Met Ser Pro Leu Leu
            340             345             350

Gln Glu Cys Leu Arg Gly Ser Thr Lys Ser Cys Ala Arg Thr Leu Val
            355             360             365

Ser Gly Ser Phe Gly Asn Arg Phe Ile Leu Ser Gln Gly Asn Leu Ile
        370             375             380

Ala Asn Cys Ala Ser Ile Leu Cys Lys Cys Tyr Thr Thr Gly Thr Ile
385             390             395             400

Ile Asn Gln Asp Pro Asp Lys Ile Leu Thr Tyr Ile Ala Ala Asp His
                405             410             415

Cys Pro Val Val Glu Val Asn Gly Val Thr Ile Gln Val Gly Ser Arg
            420             425             430

Arg Tyr Pro Asp Ala Val Tyr Leu His Arg Ile Asp Leu Gly Pro Pro
            435             440             445

Ile Ser Leu Glu Arg Leu Asp Val Gly Thr Asn Leu Gly Asn Ala Ile
        450             455             460

Ala Lys Leu Glu Asp Ala Lys Glu Leu Leu Glu Ser Ser Asp Gln Ile
465             470             475             480

Leu Ser Ala Ile Glu Asp Lys Ile Glu Glu Ile Leu Ser Lys Ile Tyr
                485             490             495

His Ile Glu Asn Glu Ile Ala Arg Ile Lys Lys Leu Ile Gly Glu Ala
            500             505             510

Pro
```

```
<210> SEQ ID NO 68
<211> LENGTH: 513
<212> TYPE: PRT
<213> ORGANISM: Artificial sequence
<220> FEATURE:
<223> OTHER INFORMATION: Recombinant F protein

<400> SEQUENCE: 68
```

```
Met Tyr Ser Met Gln Leu Ala Ser Cys Val Thr Leu Thr Leu Val Leu
1               5               10              15

Leu Val Asn Ser Gln Ile His Trp Gly Asn Leu Ser Lys Ile Gly Val
            20              25              30

Val Gly Ile Gly Ser Ala Ser Tyr Lys Val Met Thr Arg Ser Ser His
        35              40              45

Gln Ser Leu Val Ile Lys Leu Met Pro Asn Ile Thr Leu Leu Asn Asn
    50              55              60

Cys Thr Arg Val Glu Ile Ala Glu Tyr Arg Arg Leu Leu Arg Thr Val
65              70              75              80

Leu Glu Pro Ile Arg Asp Ala Leu Asn Ala Val Thr Gln Asn Ile Cys
                85              90              95

Pro Val Gln Ser Val Ala Ser Ser Arg Arg His Gly Gly Gly Ala Gly
```

-continued

```
              100                 105                 110

Val Cys Leu Ala Gly Ala Ala Leu Gly Val Ala Thr Ala Ala Gln Ile
        115                 120                 125

Thr Ala Gly Ile Ala Leu His Gln Ser Met Leu Asn Ser Gln Ala Ile
    130                 135                 140

Asp Asn Leu Arg Ala Ser Leu Glu Thr Thr Asn Gln Ala Ile Glu Ala
145                 150                 155                 160

Ile Cys Gln Ala Gly Gln Glu Cys Ile Leu Ala Phe Gln Gly Val Gln
                165                 170                 175

Asp Tyr Ile Asn Asn Glu Leu Ile Pro Ser Met Asn Gln Leu Pro Cys
            180                 185                 190

Asp Leu Ile Gly Gln Lys Leu Gly Leu Lys Leu Leu Arg Tyr Tyr Thr
        195                 200                 205

Glu Ile Leu Ser Leu Phe Gly Pro Ser Leu Arg Asp Pro Ile Ser Ala
    210                 215                 220

Glu Ile Ser Ile Gln Ala Leu Ser Tyr Ala Leu Gly Gly Asp Ile Asn
225                 230                 235                 240

Lys Val Leu Glu Lys Leu Gly Tyr Ser Gly Gly Asp Leu Leu Gly Ile
                245                 250                 255

Leu Glu Ser Arg Gly Ile Lys Ala Arg Ile Thr His Val Asp Thr Glu
            260                 265                 270

Ser Tyr Phe Ile Val Leu Ser Ile Ala Tyr Pro Thr Leu Ser Glu Ile
        275                 280                 285

Lys Gly Val Ile Val His Arg Leu Glu Gly Val Ser Tyr Asn Ile Gly
    290                 295                 300

Ser Gln Glu Trp Tyr Thr Thr Val Pro Lys Tyr Val Ala Thr Gln Gly
305                 310                 315                 320

Tyr Leu Ile Ser Asn Phe Asp Glu Ser Ser Cys Thr Phe Met Pro Glu
                325                 330                 335

Gly Thr Val Cys Ser Gln Asn Ala Leu Tyr Pro Met Ser Pro Leu Leu
            340                 345                 350

Gln Glu Cys Leu Arg Gly Ser Thr Lys Ser Cys Ala Arg Thr Leu Val
        355                 360                 365

Ser Gly Ser Phe Gly Asn Arg Phe Ile Leu Ser Gln Gly Asn Leu Ile
    370                 375                 380

Ala Asn Cys Ala Ser Ile Leu Cys Lys Cys Tyr Thr Thr Gly Thr Ile
385                 390                 395                 400

Ile Asn Gln Asp Pro Asp Lys Ile Leu Thr Tyr Ile Ala Ala Asp His
                405                 410                 415

Cys Pro Val Val Glu Val Asn Gly Val Thr Ile Gln Val Gly Ser Arg
            420                 425                 430

Arg Tyr Pro Asp Ala Val Tyr Leu His Arg Ile Asp Leu Gly Pro Pro
        435                 440                 445

Ile Ser Leu Glu Arg Leu Asp Val Gly Thr Asn Leu Gly Asn Ala Ile
    450                 455                 460

Ala Lys Leu Glu Asp Ala Lys Glu Leu Leu Glu Ser Ser Asp Gln Ile
465                 470                 475                 480

Leu Ser Ala Ile Glu Asp Lys Ile Glu Glu Ile Leu Ser Lys Ile Tyr
                485                 490                 495

His Ile Glu Asn Glu Ile Ala Arg Ile Lys Lys Leu Ile Gly Glu Ala
            500                 505                 510

Pro
```

<210> SEQ ID NO 69
<211> LENGTH: 520
<212> TYPE: PRT
<213> ORGANISM: Artificial sequence
<220> FEATURE:
<223> OTHER INFORMATION: Recombinant F protein

<400> SEQUENCE: 69

Met Tyr Ser Met Gln Leu Ala Ser Cys Val Thr Leu Thr Leu Val Leu
1               5                   10                  15

Leu Val Asn Ser Gln Ile His Trp Gly Asn Leu Ser Lys Ile Gly Val
            20                  25                  30

Val Gly Ile Gly Ser Ala Ser Tyr Lys Val Met Thr Arg Ser Ser His
        35                  40                  45

Gln Ser Leu Val Ile Lys Leu Met Pro Asn Ile Thr Leu Leu Asn Asn
    50                  55                  60

Cys Thr Arg Val Glu Ile Ala Glu Tyr Arg Arg Leu Leu Arg Thr Val
65                  70                  75                  80

Leu Glu Pro Ile Arg Asp Ala Leu Asn Ala Val Thr Gln Asn Ile Cys
                85                  90                  95

Pro Val Gln Ser Val Ala Ser Ser Arg Arg His Gly Gly Gly Ala Gly
            100                 105                 110

Val Cys Leu Ala Gly Ala Ala Leu Gly Val Ala Thr Ala Ala Gln Ile
        115                 120                 125

Thr Ala Gly Ile Ala Leu His Gln Ser Met Leu Asn Ser Gln Ala Ile
    130                 135                 140

Asp Asn Leu Arg Ala Ser Leu Glu Thr Thr Asn Gln Ala Ile Glu Ala
145                 150                 155                 160

Ile Arg Gln Ala Gly Gln Glu Met Ile Leu Ala Val Gln Gly Val Gln
                165                 170                 175

Asp Tyr Ile Asn Asn Glu Leu Ile Pro Ser Met Asn Gln Leu Ser Cys
            180                 185                 190

Asp Leu Ile Gly Gln Lys Leu Gly Leu Lys Leu Leu Arg Tyr Tyr Thr
        195                 200                 205

Glu Ile Leu Ser Leu Phe Gly Pro Ser Leu Arg Asp Pro Ile Ser Ala
    210                 215                 220

Glu Ile Ser Ile Gln Ala Leu Ser Tyr Ala Leu Gly Gly Asp Ile Asn
225                 230                 235                 240

Lys Val Leu Glu Lys Leu Gly Tyr Ser Gly Gly Asp Leu Leu Gly Ile
                245                 250                 255

Leu Glu Ser Arg Gly Ile Lys Ala Arg Ile Thr His Val Asp Thr Glu
            260                 265                 270

Ser Tyr Phe Ile Val Leu Ser Ile Ala Tyr Pro Thr Leu Ser Glu Ile
        275                 280                 285

Lys Gly Val Ile Val His Arg Leu Glu Gly Val Ser Tyr Asn Ile Gly
    290                 295                 300

Ser Gln Glu Trp Tyr Thr Thr Val Pro Lys Tyr Val Ala Thr Gln Gly
305                 310                 315                 320

Tyr Leu Ile Ser Asn Phe Asp Glu Ser Ser Cys Thr Phe Met Pro Glu
                325                 330                 335

Gly Thr Val Cys Ser Gln Asn Ala Leu Tyr Pro Met Ser Pro Leu Leu
            340                 345                 350

Gln Glu Cys Leu Arg Gly Ser Thr Lys Ser Cys Ala Arg Thr Leu Val
        355                 360                 365

```
Ser Gly Ser Phe Gly Asn Arg Phe Ile Leu Ser Gln Gly Asn Leu Ile
    370             375             380

Ala Asn Cys Ala Ser Ile Leu Cys Lys Cys Tyr Thr Thr Gly Thr Ile
385             390             395             400

Ile Asn Gln Asp Pro Asp Lys Ile Leu Thr Tyr Ile Ala Ala Asp His
            405             410             415

Cys Pro Val Val Glu Val Asn Gly Val Thr Ile Gln Val Gly Ser Arg
            420             425             430

Arg Tyr Pro Asp Ala Val Tyr Leu His Arg Ile Asp Leu Gly Pro Pro
            435             440             445

Ile Ser Leu Glu Arg Leu Asp Val Gly Thr Asn Leu Gly Asn Ala Ile
    450             455             460

Ala Lys Leu Glu Asp Ala Lys Glu Leu Leu Glu Ser Ser Asp Gln Ile
465             470             475             480

Leu Arg Ser Met Lys Gly Leu Ser Ser Ala Ile Glu Asp Lys Ile Glu
            485             490             495

Glu Ile Leu Ser Lys Ile Tyr His Ile Glu Asn Glu Ile Ala Arg Ile
            500             505             510

Lys Lys Leu Ile Gly Glu Ala Pro
        515             520
```

<210> SEQ ID NO 70
<211> LENGTH: 520
<212> TYPE: PRT
<213> ORGANISM: Artificial sequence
<220> FEATURE:
<223> OTHER INFORMATION: Recombinant F protein

<400> SEQUENCE: 70

```
Met Tyr Ser Met Gln Leu Ala Ser Cys Val Thr Leu Thr Leu Val Leu
1               5               10              15

Leu Val Asn Ser Gln Ile His Trp Gly Asn Leu Ser Lys Ile Gly Val
            20              25              30

Val Gly Ile Gly Ser Ala Ser Tyr Lys Val Met Thr Arg Ser Ser His
            35              40              45

Gln Ser Leu Val Ile Lys Leu Met Pro Asn Ile Thr Leu Leu Asn Asn
    50              55              60

Cys Thr Arg Val Glu Ile Ala Glu Tyr Arg Arg Leu Leu Arg Thr Val
65              70              75              80

Leu Glu Pro Ile Arg Asp Ala Leu Asn Ala Val Thr Gln Asn Ile Cys
            85              90              95

Pro Val Gln Ser Val Ala Ser Ser Arg Arg His Gly Gly Gly Ala Gly
            100             105             110

Val Cys Leu Ala Gly Ala Ala Leu Gly Val Ala Thr Ala Ala Gln Ile
            115             120             125

Thr Ala Gly Ile Ala Leu His Gln Ser Met Leu Asn Ser Gln Ala Ile
    130             135             140

Asp Asn Leu Arg Ala Ser Leu Glu Thr Thr Asn Gln Ala Ile Glu Ala
145             150             155             160

Ile Arg Gln Ala Gly Gln Glu Met Ile Leu Ala Phe Gln Gly Val Gln
            165             170             175

Asp Tyr Ile Asn Asn Glu Leu Ile Pro Ser Met Asn Gln Leu Pro Cys
            180             185             190

Asp Leu Ile Gly Gln Lys Leu Gly Leu Lys Leu Leu Arg Tyr Tyr Thr
            195             200             205
```

```
Glu Ile Leu Ser Leu Phe Gly Pro Ser Leu Arg Asp Pro Ile Ser Ala
    210             215             220

Glu Ile Ser Ile Gln Ala Leu Ser Tyr Ala Leu Gly Gly Asp Ile Asn
225             230             235             240

Lys Val Leu Glu Lys Leu Gly Tyr Ser Gly Gly Asp Leu Leu Gly Ile
            245             250             255

Leu Glu Ser Arg Gly Ile Lys Ala Arg Ile Thr His Val Asp Thr Glu
            260             265             270

Ser Tyr Phe Ile Val Leu Ser Ile Ala Tyr Pro Thr Leu Ser Glu Ile
        275             280             285

Lys Gly Val Ile Val His Arg Leu Glu Gly Val Ser Tyr Asn Ile Gly
    290             295             300

Ser Gln Glu Trp Tyr Thr Thr Val Pro Lys Tyr Val Ala Thr Gln Gly
305             310             315             320

Tyr Leu Ile Ser Asn Phe Asp Glu Ser Ser Cys Thr Phe Met Pro Glu
            325             330             335

Gly Thr Val Cys Ser Gln Asn Ala Leu Tyr Pro Met Ser Pro Leu Leu
            340             345             350

Gln Glu Cys Leu Arg Gly Ser Thr Lys Ser Cys Ala Arg Thr Leu Val
        355             360             365

Ser Gly Ser Phe Gly Asn Arg Phe Ile Leu Ser Gln Gly Asn Leu Ile
    370             375             380

Ala Asn Cys Ala Ser Ile Leu Cys Lys Cys Tyr Thr Thr Gly Thr Ile
385             390             395             400

Ile Asn Gln Asp Pro Asp Lys Ile Leu Thr Tyr Ile Ala Ala Asp His
            405             410             415

Cys Pro Val Val Glu Val Asn Gly Val Thr Ile Gln Val Gly Ser Arg
            420             425             430

Arg Tyr Pro Asp Ala Val Tyr Leu His Arg Ile Asp Leu Gly Pro Pro
        435             440             445

Ile Ser Leu Glu Arg Leu Asp Val Gly Thr Asn Leu Gly Asn Ala Ile
    450             455             460

Ala Lys Leu Glu Asp Ala Lys Glu Leu Leu Glu Ser Ser Asp Gln Ile
465             470             475             480

Leu Arg Ser Met Lys Gly Leu Ser Ser Ala Ile Glu Asp Lys Ile Glu
            485             490             495

Glu Ile Leu Ser Lys Ile Tyr His Ile Glu Asn Glu Ile Ala Arg Ile
            500             505             510

Lys Lys Leu Ile Gly Glu Ala Pro
        515             520
```

<210> SEQ ID NO 71
<211> LENGTH: 520
<212> TYPE: PRT
<213> ORGANISM: Artificial sequence
<220> FEATURE:
<223> OTHER INFORMATION: Recombinant F protein

<400> SEQUENCE: 71

```
Met Tyr Ser Met Gln Leu Ala Ser Cys Val Thr Leu Thr Leu Val Leu
1               5               10              15

Leu Val Asn Ser Gln Ile His Trp Gly Asn Leu Ser Lys Ile Gly Val
            20              25              30

Val Gly Ile Gly Ser Ala Ser Tyr Lys Val Met Thr Arg Ser Ser His
        35              40              45
```

-continued

```
Gln Ser Leu Val Ile Lys Leu Met Pro Asn Ile Thr Leu Leu Asn Asn
    50              55              60

Cys Thr Arg Val Glu Ile Ala Glu Tyr Arg Arg Leu Leu Arg Thr Val
65              70              75              80

Leu Glu Pro Ile Arg Asp Ala Leu Asn Ala Val Thr Gln Asn Ile Cys
                85              90              95

Pro Val Gln Ser Val Ala Ser Ser Arg Arg His Gly Gly Gly Ala Gly
                100             105             110

Val Cys Leu Ala Gly Ala Ala Leu Gly Val Ala Thr Ala Ala Gln Ile
        115             120             125

Thr Ala Gly Ile Ala Leu His Gln Ser Met Leu Asn Ser Gln Ala Ile
    130             135             140

Asp Asn Leu Arg Ala Ser Leu Glu Thr Thr Asn Gln Ala Ile Glu Ala
145             150             155             160

Ile Cys Gln Ala Gly Gln Glu Cys Ile Leu Ala Phe Gln Gly Val Gln
                165             170             175

Asp Tyr Ile Asn Asn Glu Leu Ile Pro Ser Met Asn Gln Leu Pro Cys
                180             185             190

Asp Leu Ile Gly Gln Lys Leu Gly Leu Lys Leu Leu Arg Tyr Tyr Thr
        195             200             205

Glu Ile Leu Ser Leu Phe Gly Pro Ser Leu Arg Asp Pro Ile Ser Ala
    210             215             220

Glu Ile Ser Ile Gln Ala Leu Ser Tyr Ala Leu Gly Gly Asp Ile Asn
225             230             235             240

Lys Val Leu Glu Lys Leu Gly Tyr Ser Gly Gly Asp Leu Leu Gly Ile
                245             250             255

Leu Glu Ser Arg Gly Ile Lys Ala Arg Ile Thr His Val Asp Thr Glu
                260             265             270

Ser Tyr Phe Ile Val Leu Ser Ile Ala Tyr Pro Thr Leu Ser Glu Ile
                275             280             285

Lys Gly Val Ile Val His Arg Leu Glu Gly Val Ser Tyr Asn Ile Gly
    290             295             300

Ser Gln Glu Trp Tyr Thr Thr Val Pro Lys Tyr Val Ala Thr Gln Gly
305             310             315             320

Tyr Leu Ile Ser Asn Phe Asp Glu Ser Ser Cys Thr Phe Met Pro Glu
                325             330             335

Gly Thr Val Cys Ser Gln Asn Ala Leu Tyr Pro Met Ser Pro Leu Leu
                340             345             350

Gln Glu Cys Leu Arg Gly Ser Thr Lys Ser Cys Ala Arg Thr Leu Val
        355             360             365

Ser Gly Ser Phe Gly Asn Arg Phe Ile Leu Ser Gln Gly Asn Leu Ile
    370             375             380

Ala Asn Cys Ala Ser Ile Leu Cys Lys Cys Tyr Thr Thr Gly Thr Ile
385             390             395             400

Ile Asn Gln Asp Pro Asp Lys Ile Leu Thr Tyr Ile Ala Ala Asp His
                405             410             415

Cys Pro Val Val Glu Val Asn Gly Val Thr Ile Gln Val Gly Ser Arg
        420             425             430

Arg Tyr Pro Asp Ala Val Tyr Leu His Arg Ile Asp Leu Gly Pro Pro
        435             440             445

Ile Ser Leu Glu Arg Leu Asp Val Gly Thr Asn Leu Gly Asn Ala Ile
    450             455             460

Ala Lys Leu Glu Asp Ala Lys Glu Leu Leu Glu Ser Ser Asp Gln Ile
```

-continued

```
465                470                475                480
Leu Arg Ser Met Lys Gly Leu Ser Ser Ala Ile Glu Asp Lys Ile Glu
               485                490                495

Glu Ile Leu Ser Lys Ile Tyr His Ile Glu Asn Glu Ile Ala Arg Ile
               500                505                510

Lys Lys Leu Ile Gly Glu Ala Pro
           515                520

<210> SEQ ID NO 72
<211> LENGTH: 513
<212> TYPE: PRT
<213> ORGANISM: Artificial sequence
<220> FEATURE:
<223> OTHER INFORMATION: Recombinant F protein

<400> SEQUENCE: 72

Met Tyr Ser Met Gln Leu Ala Ser Cys Val Thr Leu Thr Leu Val Leu
1               5                10                15

Leu Val Asn Ser Gln Ile His Trp Gly Asn Leu Ser Lys Ile Gly Val
               20                25                30

Val Gly Ile Gly Ser Ala Ser Tyr Lys Val Met Thr Arg Ser Ser His
           35                40                45

Gln Ser Leu Val Ile Lys Leu Met Pro Asn Ile Thr Leu Leu Asn Asn
       50                55                60

Cys Thr Arg Val Glu Ile Ala Glu Tyr Arg Arg Leu Leu Arg Thr Val
65                70                75                80

Leu Glu Pro Ile Arg Asp Ala Leu Asn Ala Val Thr Gln Asn Ile Arg
               85                90                95

Cys Val Gln Ser Val Ala Ser Ser Arg Arg His Gly Gly Gly Ala Gly
               100                105                110

Val Cys Leu Ala Gly Ala Ala Leu Gly Val Ala Thr Ala Ala Gln Ile
           115                120                125

Thr Ala Gly Ile Ala Leu His Gln Ser Met Leu Asn Ser Gln Ala Ile
       130                135                140

Asp Asn Leu Arg Ala Ser Leu Glu Thr Thr Asn Gln Ala Ile Glu Ala
145                150                155                160

Ile Cys Gln Ala Gly Gln Glu Cys Ile Leu Ala Phe Gln Gly Val Gln
               165                170                175

Asp Tyr Ile Asn Asn Glu Leu Ile Pro Ser Met Asn Gln Leu Pro Cys
           180                185                190

Asp Leu Ile Gly Gln Lys Leu Gly Leu Lys Leu Leu Arg Tyr Tyr Thr
           195                200                205

Glu Ile Leu Ser Leu Phe Gly Pro Ser Leu Arg Asp Pro Ile Ser Ala
       210                215                220

Glu Ile Ser Ile Gln Ala Leu Ser Tyr Ala Leu Gly Gly Asp Ile Asn
225                230                235                240

Lys Val Leu Glu Lys Leu Gly Tyr Ser Gly Gly Asp Leu Leu Gly Ile
               245                250                255

Leu Glu Ser Arg Gly Ile Lys Ala Arg Ile Thr His Val Asp Thr Glu
           260                265                270

Ser Tyr Phe Ile Val Leu Ser Ile Ala Tyr Pro Thr Leu Ser Glu Ile
           275                280                285

Lys Gly Val Ile Val His Arg Leu Glu Gly Val Ser Tyr Asn Ile Gly
       290                295                300

Ser Gln Glu Trp Tyr Thr Thr Val Pro Lys Tyr Val Ala Thr Gln Gly
```

```
305             310             315             320

Tyr Leu Ile Ser Asn Phe Asp Glu Ser Ser Cys Thr Phe Met Pro Glu
            325             330             335

Gly Thr Val Cys Ser Gln Asn Ala Leu Tyr Pro Met Ser Pro Leu Leu
            340             345             350

Gln Glu Cys Leu Arg Gly Ser Thr Lys Ser Cys Ala Arg Thr Leu Val
            355             360             365

Ser Gly Ser Phe Gly Asn Arg Phe Ile Leu Ser Gln Gly Asn Leu Ile
            370             375             380

Ala Asn Cys Ala Ser Ile Leu Cys Lys Cys Tyr Thr Thr Gly Thr Ile
385             390             395             400

Ile Asn Gln Asp Pro Asp Lys Ile Leu Thr Tyr Ile Ala Ala Asp His
            405             410             415

Cys Pro Val Val Glu Val Asn Gly Val Thr Ile Gln Val Gly Ser Arg
            420             425             430

Arg Tyr Pro Asp Ala Val Tyr Leu His Arg Ile Asp Leu Gly Pro Pro
            435             440             445

Ile Ser Leu Glu Arg Leu Asp Val Gly Thr Asn Leu Gly Asn Ala Ile
            450             455             460

Ala Lys Leu Glu Asp Ala Lys Glu Leu Leu Glu Ser Ser Asp Gln Ile
465             470             475             480

Leu Ser Ala Ile Glu Asp Lys Ile Glu Glu Ile Leu Ser Lys Ile Tyr
            485             490             495

His Ile Glu Asn Glu Ile Ala Arg Ile Lys Lys Leu Ile Gly Glu Ala
            500             505             510

Pro
```

```
<210> SEQ ID NO 73
<211> LENGTH: 513
<212> TYPE: PRT
<213> ORGANISM: Artificial sequence
<220> FEATURE:
<223> OTHER INFORMATION: Recombinant F protein

<400> SEQUENCE: 73
```

```
Met Tyr Ser Met Gln Leu Ala Ser Cys Val Thr Leu Thr Leu Val Leu
1               5               10              15

Leu Val Asn Ser Gln Ile His Trp Gly Asn Leu Ser Lys Ile Gly Val
            20              25              30

Val Gly Ile Gly Ser Ala Ser Tyr Lys Val Met Thr Arg Ser Ser His
            35              40              45

Gln Ser Leu Val Ile Lys Leu Met Pro Asn Ile Thr Leu Leu Asn Asn
            50              55              60

Cys Thr Arg Val Glu Ile Ala Glu Tyr Arg Arg Leu Leu Arg Thr Val
65              70              75              80

Leu Glu Pro Ile Arg Asp Ala Leu Asn Ala Val Thr Gln Asn Ile Arg
            85              90              95

Pro Cys Gln Ser Val Ala Ser Ser Arg Arg His Gly Gly Gly Ala Gly
            100             105             110

Val Cys Leu Ala Gly Ala Ala Leu Gly Val Ala Thr Ala Ala Gln Ile
            115             120             125

Thr Ala Gly Ile Ala Leu His Gln Ser Met Leu Asn Ser Gln Ala Ile
            130             135             140

Asp Asn Leu Arg Ala Ser Leu Glu Thr Thr Asn Gln Ala Ile Glu Ala
145             150             155             160
```

Ile Cys Gln Ala Gly Gln Glu Cys Ile Leu Ala Phe Gln Gly Val Gln
                165                     170                     175

Asp Tyr Ile Asn Asn Glu Leu Ile Pro Ser Met Asn Gln Leu Pro Cys
                180                     185                     190

Asp Leu Ile Gly Gln Lys Leu Gly Leu Lys Leu Leu Arg Tyr Tyr Thr
                195                     200                     205

Glu Ile Leu Ser Leu Phe Gly Pro Ser Leu Arg Asp Pro Ile Ser Ala
        210                     215                     220

Glu Ile Ser Ile Gln Ala Leu Ser Tyr Ala Leu Gly Gly Asp Ile Asn
225                     230                     235                     240

Lys Val Leu Glu Lys Leu Gly Tyr Ser Gly Gly Asp Leu Leu Gly Ile
                245                     250                     255

Leu Glu Ser Arg Gly Ile Lys Ala Arg Ile Thr His Val Asp Thr Glu
                260                     265                     270

Ser Tyr Phe Ile Val Leu Ser Ile Ala Tyr Pro Thr Leu Ser Glu Ile
                275                     280                     285

Lys Gly Val Ile Val His Arg Leu Glu Gly Val Ser Tyr Asn Ile Gly
        290                     295                     300

Ser Gln Glu Trp Tyr Thr Thr Val Pro Lys Tyr Val Ala Thr Gln Gly
305                     310                     315                     320

Tyr Leu Ile Ser Asn Phe Asp Glu Ser Ser Cys Thr Phe Met Pro Glu
                325                     330                     335

Gly Thr Val Cys Ser Gln Asn Ala Leu Tyr Pro Met Ser Pro Leu Leu
                340                     345                     350

Gln Glu Cys Leu Arg Gly Ser Thr Lys Ser Cys Ala Arg Thr Leu Val
                355                     360                     365

Ser Gly Ser Phe Gly Asn Arg Phe Ile Leu Ser Gln Gly Asn Leu Ile
        370                     375                     380

Ala Asn Cys Ala Ser Ile Leu Cys Lys Cys Tyr Thr Thr Gly Thr Ile
385                     390                     395                     400

Ile Asn Gln Asp Pro Asp Lys Ile Leu Thr Tyr Ile Ala Ala Asp His
                405                     410                     415

Cys Pro Val Val Glu Val Asn Gly Val Thr Ile Gln Val Gly Ser Arg
                420                     425                     430

Arg Tyr Pro Asp Ala Val Tyr Leu His Arg Ile Asp Leu Gly Pro Pro
                435                     440                     445

Ile Ser Leu Glu Arg Leu Asp Val Gly Thr Asn Leu Gly Asn Ala Ile
        450                     455                     460

Ala Lys Leu Glu Asp Ala Lys Glu Leu Leu Glu Ser Ser Asp Gln Ile
465                     470                     475                     480

Leu Ser Ala Ile Glu Asp Lys Ile Glu Glu Ile Leu Ser Lys Ile Tyr
                485                     490                     495

His Ile Glu Asn Glu Ile Ala Arg Ile Lys Lys Leu Ile Gly Glu Ala
                500                     505                     510

Pro

<210> SEQ ID NO 74
<211> LENGTH: 513
<212> TYPE: PRT
<213> ORGANISM: Artificial sequence
<220> FEATURE:
<223> OTHER INFORMATION: Recombinant F protein

<400> SEQUENCE: 74

-continued

```
Met Tyr Ser Met Gln Leu Ala Ser Cys Val Thr Leu Thr Leu Val Leu
1               5                   10                  15

Leu Val Asn Ser Gln Ile His Trp Gly Asn Leu Ser Lys Ile Gly Val
            20                  25                  30

Val Gly Ile Gly Ser Ala Ser Tyr Lys Val Met Thr Arg Ser Ser His
        35                  40                  45

Gln Ser Leu Val Ile Lys Leu Met Pro Asn Ile Thr Leu Leu Asn Asn
    50                  55                  60

Cys Thr Arg Val Glu Ile Ala Glu Tyr Arg Arg Leu Leu Arg Thr Val
65                  70                  75                  80

Leu Glu Pro Ile Arg Asp Ala Leu Asn Ala Val Thr Gln Asn Ile Arg
                85                  90                  95

Pro Val Cys Ser Val Ala Ser Ser Arg Arg His Gly Gly Gly Ala Gly
            100                 105                 110

Val Cys Leu Ala Gly Ala Ala Leu Gly Val Ala Thr Ala Ala Gln Ile
        115                 120                 125

Thr Ala Gly Ile Ala Leu His Gln Ser Met Leu Asn Ser Gln Ala Ile
        130                 135                 140

Asp Asn Leu Arg Ala Ser Leu Glu Thr Thr Asn Gln Ala Ile Glu Ala
145                 150                 155                 160

Ile Cys Gln Ala Gly Gln Glu Cys Ile Leu Ala Phe Gln Gly Val Gln
                165                 170                 175

Asp Tyr Ile Asn Asn Glu Leu Ile Pro Ser Met Asn Gln Leu Pro Cys
                180                 185                 190

Asp Leu Ile Gly Gln Lys Leu Gly Leu Lys Leu Leu Arg Tyr Tyr Thr
                195                 200                 205

Glu Ile Leu Ser Leu Phe Gly Pro Ser Leu Arg Asp Pro Ile Ser Ala
    210                 215                 220

Glu Ile Ser Ile Gln Ala Leu Ser Tyr Ala Leu Gly Gly Asp Ile Asn
225                 230                 235                 240

Lys Val Leu Glu Lys Leu Gly Tyr Ser Gly Gly Asp Leu Leu Gly Ile
                245                 250                 255

Leu Glu Ser Arg Gly Ile Lys Ala Arg Ile Thr His Val Asp Thr Glu
                260                 265                 270

Ser Tyr Phe Ile Val Leu Ser Ile Ala Tyr Pro Thr Leu Ser Glu Ile
        275                 280                 285

Lys Gly Val Ile Val His Arg Leu Glu Gly Val Ser Tyr Asn Ile Gly
    290                 295                 300

Ser Gln Glu Trp Tyr Thr Thr Val Pro Lys Tyr Val Ala Thr Gln Gly
305                 310                 315                 320

Tyr Leu Ile Ser Asn Phe Asp Glu Ser Ser Cys Thr Phe Met Pro Glu
                325                 330                 335

Gly Thr Val Cys Ser Gln Asn Ala Leu Tyr Pro Met Ser Pro Leu Leu
            340                 345                 350

Gln Glu Cys Leu Arg Gly Ser Thr Lys Ser Cys Ala Arg Thr Leu Val
        355                 360                 365

Ser Gly Ser Phe Gly Asn Arg Phe Ile Leu Ser Gln Gly Asn Leu Ile
    370                 375                 380

Ala Asn Cys Ala Ser Ile Leu Cys Lys Cys Tyr Thr Thr Gly Thr Ile
385                 390                 395                 400

Ile Asn Gln Asp Pro Asp Lys Ile Leu Thr Tyr Ile Ala Ala Asp His
                405                 410                 415

Cys Pro Val Val Glu Val Asn Gly Val Thr Ile Gln Val Gly Ser Arg
```

-continued

```
                420                 425                 430

Arg Tyr Pro Asp Ala Val Tyr Leu His Arg Ile Asp Leu Gly Pro Pro
        435                 440                 445

Ile Ser Leu Glu Arg Leu Asp Val Gly Thr Asn Leu Gly Asn Ala Ile
    450                 455                 460

Ala Lys Leu Glu Asp Ala Lys Glu Leu Leu Glu Ser Ser Asp Gln Ile
465                 470                 475                 480

Leu Ser Ala Ile Glu Asp Lys Ile Glu Glu Ile Leu Ser Lys Ile Tyr
                485                 490                 495

His Ile Glu Asn Glu Ile Ala Arg Ile Lys Lys Leu Ile Gly Glu Ala
                500                 505                 510

Pro

<210> SEQ ID NO 75
<211> LENGTH: 513
<212> TYPE: PRT
<213> ORGANISM: Artificial sequence
<220> FEATURE:
<223> OTHER INFORMATION: Recombinant F protein

<400> SEQUENCE: 75

Met Tyr Ser Met Gln Leu Ala Ser Cys Val Thr Leu Thr Leu Val Leu
1               5                   10                  15

Leu Val Asn Ser Gln Ile His Trp Gly Asn Leu Ser Lys Ile Gly Val
                20                  25                  30

Val Gly Ile Gly Ser Ala Ser Tyr Lys Val Met Thr Arg Ser Ser His
        35                  40                  45

Gln Ser Leu Val Ile Lys Leu Met Pro Asn Ile Thr Leu Leu Asn Asn
    50                  55                  60

Cys Thr Arg Val Glu Ile Ala Glu Tyr Arg Arg Leu Leu Arg Thr Val
65                  70                  75                  80

Leu Glu Pro Ile Arg Asp Ala Leu Asn Ala Val Thr Gln Asn Ile Arg
                85                  90                  95

Pro Val Gln Ser Val Ala Ser Ser Arg Arg His Gly Gly Gly Ala Gly
                100                 105                 110

Val Val Leu Ala Gly Ala Ala Leu Gly Val Ala Thr Ala Ala Gln Ile
        115                 120                 125

Thr Ala Gly Ile Ala Leu His Gln Ser Cys Leu Asn Ser Gln Ala Ile
    130                 135                 140

Asp Asn Leu Arg Ala Ser Leu Glu Thr Thr Asn Gln Ala Ile Glu Ala
145                 150                 155                 160

Ile Cys Gln Ala Gly Gln Glu Cys Ile Leu Ala Val Gln Gly Val Gln
                165                 170                 175

Asp Tyr Ile Asn Asn Glu Leu Ile Pro Ser Met Asn Gln Leu Ser Cys
                180                 185                 190

Asp Leu Ile Gly Gln Lys Leu Gly Leu Lys Leu Leu Arg Tyr Tyr Thr
        195                 200                 205

Glu Ile Leu Ser Leu Phe Gly Pro Ser Leu Arg Asp Pro Ile Ser Ala
    210                 215                 220

Glu Ile Ser Ile Gln Ala Leu Ser Tyr Ala Leu Gly Gly Asp Ile Asn
225                 230                 235                 240

Lys Val Leu Glu Lys Leu Gly Tyr Ser Gly Gly Asp Leu Leu Gly Ile
                245                 250                 255

Leu Glu Ser Arg Gly Ile Lys Ala Arg Ile Cys His Val Asp Thr Glu
        260                 265                 270
```

-continued

```
Ser Tyr Phe Ile Val Leu Ser Ile Ala Tyr Pro Thr Leu Ser Glu Ile
        275                 280                 285

Lys Gly Val Ile Val His Arg Leu Glu Gly Val Ser Tyr Asn Ile Gly
        290                 295                 300

Ser Gln Glu Trp Tyr Thr Thr Val Pro Lys Tyr Val Ala Thr Gln Gly
305                 310                 315                 320

Tyr Leu Ile Ser Asn Phe Asp Glu Ser Ser Cys Thr Phe Met Pro Glu
                325                 330                 335

Gly Thr Val Cys Ser Gln Asn Ala Leu Tyr Pro Met Ser Pro Leu Leu
                340                 345                 350

Gln Glu Cys Leu Arg Gly Ser Thr Lys Ser Cys Ala Arg Thr Leu Val
        355                 360                 365

Ser Gly Ser Phe Gly Asn Arg Phe Ile Leu Ser Gln Gly Asn Leu Ile
        370                 375                 380

Ala Asn Cys Ala Ser Ile Leu Cys Lys Cys Tyr Thr Thr Gly Thr Ile
385                 390                 395                 400

Ile Asn Gln Asp Pro Asp Lys Ile Leu Thr Tyr Ile Ala Ala Asp His
                405                 410                 415

Cys Pro Val Val Glu Val Asn Gly Val Thr Ile Gln Val Gly Ser Arg
                420                 425                 430

Arg Tyr Pro Asp Ala Val Tyr Leu His Arg Ile Asp Leu Gly Pro Pro
        435                 440                 445

Ile Ser Leu Glu Arg Leu Asp Val Gly Thr Asn Leu Gly Asn Ala Ile
        450                 455                 460

Ala Lys Leu Glu Asp Ala Lys Glu Leu Leu Glu Ser Ser Asp Gln Ile
465                 470                 475                 480

Leu Ser Ala Ile Glu Asp Lys Ile Glu Glu Ile Leu Ser Lys Ile Tyr
                485                 490                 495

His Ile Glu Asn Glu Ile Ala Arg Ile Lys Lys Leu Ile Gly Glu Ala
                500                 505                 510

Pro
```

```
<210> SEQ ID NO 76
<211> LENGTH: 513
<212> TYPE: PRT
<213> ORGANISM: Artificial sequence
<220> FEATURE:
<223> OTHER INFORMATION: Recombinant F protein

<400> SEQUENCE: 76
```

```
Met Tyr Ser Met Gln Leu Ala Ser Cys Val Thr Leu Thr Leu Val Leu
1                   5                   10                  15

Leu Val Asn Ser Gln Ile His Trp Gly Asn Leu Ser Lys Ile Gly Val
                20                  25                  30

Val Gly Ile Gly Ser Ala Ser Tyr Lys Val Met Thr Arg Ser Ser His
        35                  40                  45

Gln Ser Leu Val Ile Lys Leu Met Pro Asn Ile Thr Leu Leu Asn Asn
        50                  55                  60

Cys Thr Arg Val Glu Ile Ala Glu Tyr Arg Arg Leu Leu Arg Thr Val
65                  70                  75                  80

Leu Glu Pro Ile Arg Asp Ala Leu Asn Ala Val Thr Gln Asn Ile Arg
                85                  90                  95

Pro Val Gln Ser Val Ala Ser Ser Arg Arg His Gly Gly Gly Ala Gly
                100                 105                 110
```

```
Val Val Leu Ala Gly Ala Ala Leu Gly Val Ala Thr Ala Ala Gln Ile
        115                 120                 125

Thr Ala Gly Ile Ala Leu His Gln Ser Met Leu Asn Ser Gln Ala Ile
        130                 135                 140

Asp Asn Leu Arg Ala Ser Leu Glu Thr Thr Asn Gln Ala Ile Glu Ala
145                 150                 155                 160

Ile Cys Gln Ala Gly Gln Glu Cys Ile Leu Ala Val Gln Gly Val Gln
                165                 170                 175

Asp Tyr Ile Asn Asn Glu Leu Ile Pro Ser Met Asn Gln Leu Ser Cys
        180                 185                 190

Asp Leu Ile Gly Gln Lys Leu Gly Leu Lys Leu Leu Arg Tyr Tyr Thr
        195                 200                 205

Cys Ile Leu Ser Leu Phe Gly Pro Ser Leu Arg Asp Pro Ile Ser Ala
        210                 215                 220

Glu Ile Ser Ile Gln Ala Leu Ser Cys Ala Leu Gly Gly Asp Ile Asn
225                 230                 235                 240

Lys Val Leu Glu Lys Leu Gly Tyr Ser Gly Gly Asp Leu Leu Gly Ile
                245                 250                 255

Leu Glu Ser Arg Gly Ile Lys Ala Arg Ile Thr His Val Asp Thr Glu
        260                 265                 270

Ser Tyr Phe Ile Val Leu Ser Ile Ala Tyr Pro Thr Leu Ser Glu Ile
        275                 280                 285

Lys Gly Val Ile Val His Arg Leu Glu Gly Val Ser Tyr Asn Ile Gly
        290                 295                 300

Ser Gln Glu Trp Tyr Thr Thr Val Pro Lys Tyr Val Ala Thr Gln Gly
305                 310                 315                 320

Tyr Leu Ile Ser Asn Phe Asp Glu Ser Ser Cys Thr Phe Met Pro Glu
                325                 330                 335

Gly Thr Val Cys Ser Gln Asn Ala Leu Tyr Pro Met Ser Pro Leu Leu
                340                 345                 350

Gln Glu Cys Leu Arg Gly Ser Thr Lys Ser Cys Ala Arg Thr Leu Val
        355                 360                 365

Ser Gly Ser Phe Gly Asn Arg Phe Ile Leu Ser Gln Gly Asn Leu Ile
        370                 375                 380

Ala Asn Cys Ala Ser Ile Leu Cys Lys Cys Tyr Thr Thr Gly Thr Ile
385                 390                 395                 400

Ile Asn Gln Asp Pro Asp Lys Ile Leu Thr Tyr Ile Ala Ala Asp His
                405                 410                 415

Cys Pro Val Val Glu Val Asn Gly Val Thr Ile Gln Val Gly Ser Arg
                420                 425                 430

Arg Tyr Pro Asp Ala Val Tyr Leu His Arg Ile Asp Leu Gly Pro Pro
        435                 440                 445

Ile Ser Leu Glu Arg Leu Asp Val Gly Thr Asn Leu Gly Asn Ala Ile
        450                 455                 460

Ala Lys Leu Glu Asp Ala Lys Glu Leu Leu Glu Ser Ser Asp Gln Ile
465                 470                 475                 480

Leu Ser Ala Ile Glu Asp Lys Ile Glu Glu Ile Leu Ser Lys Ile Tyr
                485                 490                 495

His Ile Glu Asn Glu Ile Ala Arg Ile Lys Lys Leu Ile Gly Glu Ala
        500                 505                 510

Pro
```

<210> SEQ ID NO 77

```
<211> LENGTH: 513
<212> TYPE: PRT
<213> ORGANISM: Artificial sequence
<220> FEATURE:
<223> OTHER INFORMATION: Recombinant F protein

<400> SEQUENCE: 77

Met Tyr Ser Met Gln Leu Ala Ser Cys Val Thr Leu Thr Leu Val Leu
1               5                   10                  15

Leu Val Asn Ser Gln Ile His Trp Gly Asn Leu Ser Lys Ile Gly Val
            20                  25                  30

Val Gly Ile Gly Ser Ala Ser Tyr Lys Val Met Thr Cys Ser Ser His
        35                  40                  45

Gln Ser Leu Val Ile Lys Leu Met Pro Asn Ile Thr Leu Leu Asn Asn
    50                  55                  60

Cys Thr Arg Val Glu Ile Ala Glu Tyr Arg Arg Leu Leu Arg Thr Val
65                  70                  75                  80

Leu Glu Pro Ile Arg Asp Ala Leu Asn Ala Val Thr Gln Asn Ile Arg
                85                  90                  95

Pro Val Gln Ser Val Ala Ser Ser Arg Arg His Gly Gly Gly Ala Gly
            100                 105                 110

Val Val Leu Ala Gly Ala Ala Leu Gly Val Ala Thr Ala Ala Gln Ile
        115                 120                 125

Thr Ala Gly Ile Ala Leu His Gln Ser Met Leu Asn Ser Gln Ala Ile
    130                 135                 140

Asp Asn Leu Arg Ala Ser Leu Glu Thr Thr Asn Gln Ala Ile Glu Ala
145                 150                 155                 160

Ile Cys Gln Ala Gly Gln Glu Cys Ile Leu Ala Val Gln Gly Val Gln
                165                 170                 175

Asp Tyr Ile Asn Asn Glu Leu Ile Pro Ser Met Asn Gln Leu Ser Cys
            180                 185                 190

Asp Leu Ile Gly Gln Lys Leu Gly Leu Lys Leu Leu Arg Tyr Tyr Thr
            195                 200                 205

Glu Ile Leu Ser Leu Phe Gly Pro Ser Leu Arg Asp Pro Ile Ser Ala
    210                 215                 220

Glu Ile Ser Ile Gln Ala Leu Ser Tyr Ala Leu Gly Gly Asp Ile Asn
225                 230                 235                 240

Lys Val Leu Glu Lys Leu Gly Tyr Ser Gly Gly Asp Leu Leu Gly Ile
                245                 250                 255

Leu Glu Ser Arg Gly Ile Lys Ala Arg Ile Thr His Val Asp Thr Glu
            260                 265                 270

Ser Tyr Phe Ile Val Leu Ser Ile Cys Tyr Pro Thr Leu Ser Glu Ile
        275                 280                 285

Lys Gly Val Ile Val His Arg Leu Glu Gly Val Ser Tyr Asn Ile Gly
    290                 295                 300

Ser Gln Glu Trp Tyr Thr Thr Val Pro Lys Tyr Val Ala Thr Gln Gly
305                 310                 315                 320

Tyr Leu Ile Ser Asn Phe Asp Glu Ser Ser Cys Thr Phe Met Pro Glu
                325                 330                 335

Gly Thr Val Cys Ser Gln Asn Ala Leu Tyr Pro Met Ser Pro Leu Leu
            340                 345                 350

Gln Glu Cys Leu Arg Gly Ser Thr Lys Ser Cys Ala Arg Thr Leu Val
            355                 360                 365

Ser Gly Ser Phe Gly Asn Arg Phe Ile Leu Ser Gln Gly Asn Leu Ile
    370                 375                 380
```

-continued

```
Ala Asn Cys Ala Ser Ile Leu Cys Lys Cys Tyr Thr Thr Gly Thr Ile
385                 390             395                 400

Ile Asn Gln Asp Pro Asp Lys Ile Leu Thr Tyr Ile Ala Ala Asp His
                405             410             415

Cys Pro Val Val Glu Val Asn Gly Val Thr Ile Gln Val Gly Ser Arg
            420             425             430

Arg Tyr Pro Asp Ala Val Tyr Leu His Arg Ile Asp Leu Gly Pro Pro
            435             440             445

Ile Ser Leu Glu Arg Leu Asp Val Gly Thr Asn Leu Gly Asn Ala Ile
        450             455             460

Ala Lys Leu Glu Asp Ala Lys Glu Leu Leu Glu Ser Ser Asp Gln Ile
465                 470             475                 480

Leu Ser Ala Ile Glu Asp Lys Ile Glu Glu Ile Leu Ser Lys Ile Tyr
                485             490             495

His Ile Glu Asn Glu Ile Ala Arg Ile Lys Lys Leu Ile Gly Glu Ala
                500             505             510

Pro
```

<210> SEQ ID NO 78
<211> LENGTH: 513
<212> TYPE: PRT
<213> ORGANISM: Artificial sequence
<220> FEATURE:
<223> OTHER INFORMATION: Recombinant F protein

<400> SEQUENCE: 78

```
Met Tyr Ser Met Gln Leu Ala Ser Cys Val Thr Leu Thr Leu Val Leu
1               5                   10                  15

Leu Val Asn Ser Gln Ile His Trp Gly Asn Leu Ser Lys Ile Gly Val
                20                  25                  30

Val Gly Ile Gly Ser Ala Ser Tyr Lys Val Met Thr Arg Ser Ser His
            35                  40                  45

Gln Ser Leu Val Ile Lys Leu Met Pro Asn Ile Thr Leu Leu Asn Asn
        50                  55                  60

Cys Thr Arg Val Glu Ile Ala Glu Tyr Arg Arg Leu Leu Arg Thr Val
65                  70                  75                  80

Leu Glu Pro Ile Arg Asp Ala Leu Asn Ala Val Thr Gln Asn Ile Cys
                85                  90                  95

Pro Val Gln Ser Val Ala Ser Ser Arg Arg His Lys Arg Phe Ala Gly
            100                 105                 110

Val Cys Leu Ala Gly Ala Ala Leu Gly Val Ala Thr Ala Ala Gln Ile
            115                 120                 125

Thr Ala Gly Ile Ala Leu His Gln Ser Met Leu Asn Ser Gln Ala Ile
        130                 135                 140

Asp Asn Leu Arg Ala Ser Leu Glu Thr Thr Asn Gln Ala Ile Glu Ala
145                 150                 155                 160

Ile Arg Gln Ala Gly Gln Glu Met Ile Leu Ala Val Gln Gly Val Gln
                165                 170                 175

Asp Tyr Ile Asn Asn Glu Leu Ile Pro Ser Met Asn Gln Leu Ser Cys
            180                 185                 190

Asp Leu Ile Gly Gln Lys Leu Gly Leu Lys Leu Leu Arg Tyr Tyr Thr
            195                 200                 205

Glu Ile Leu Ser Leu Phe Gly Pro Ser Leu Arg Asp Pro Ile Ser Ala
        210                 215                 220
```

```
Glu Ile Ser Ile Gln Ala Leu Ser Tyr Ala Leu Gly Gly Asp Ile Asn
225                 230                 235                 240

Lys Val Leu Glu Lys Leu Gly Tyr Ser Gly Gly Asp Leu Leu Gly Ile
                245                 250                 255

Leu Glu Ser Arg Gly Ile Lys Ala Arg Ile Thr His Val Asp Thr Glu
                260                 265                 270

Ser Tyr Phe Ile Val Leu Ser Ile Ala Tyr Pro Thr Leu Ser Glu Ile
                275                 280                 285

Lys Gly Val Ile Val His Arg Leu Glu Gly Val Ser Tyr Asn Ile Gly
                290                 295                 300

Ser Gln Glu Trp Tyr Thr Thr Val Pro Lys Tyr Val Ala Thr Gln Gly
305                 310                 315                 320

Tyr Leu Ile Ser Asn Phe Asp Glu Ser Ser Cys Thr Phe Met Pro Glu
                325                 330                 335

Gly Thr Val Cys Ser Gln Asn Ala Leu Tyr Pro Met Ser Pro Leu Leu
                340                 345                 350

Gln Glu Cys Leu Arg Gly Ser Thr Lys Ser Cys Ala Arg Thr Leu Val
                355                 360                 365

Ser Gly Ser Phe Gly Asn Arg Phe Ile Leu Ser Gln Gly Asn Leu Ile
                370                 375                 380

Ala Asn Cys Ala Ser Ile Leu Cys Lys Cys Tyr Thr Thr Gly Thr Ile
385                 390                 395                 400

Ile Asn Gln Asp Pro Asp Lys Ile Leu Thr Tyr Ile Ala Ala Asp His
                405                 410                 415

Cys Pro Val Val Glu Val Asn Gly Val Thr Ile Gln Val Gly Ser Arg
                420                 425                 430

Arg Tyr Pro Asp Ala Val Tyr Leu His Arg Ile Asp Leu Gly Pro Pro
                435                 440                 445

Ile Ser Leu Glu Arg Leu Asp Val Gly Thr Asn Leu Gly Asn Ala Ile
                450                 455                 460

Ala Lys Leu Glu Asp Ala Lys Glu Leu Leu Glu Ser Ser Asp Gln Ile
465                 470                 475                 480

Leu Ser Ala Ile Glu Asp Lys Ile Glu Glu Ile Leu Ser Lys Ile Tyr
                485                 490                 495

His Ile Glu Asn Glu Ile Ala Arg Ile Lys Lys Leu Ile Gly Glu Ala
                500                 505                 510

Pro
```

```
<210> SEQ ID NO 79
<211> LENGTH: 513
<212> TYPE: PRT
<213> ORGANISM: Artificial sequence
<220> FEATURE:
<223> OTHER INFORMATION: Recombinant F protein

<400> SEQUENCE: 79
```

```
Met Tyr Ser Met Gln Leu Ala Ser Cys Val Thr Leu Thr Leu Val Leu
1                   5                   10                  15

Leu Val Asn Ser Gln Ile His Trp Gly Asn Leu Ser Lys Ile Gly Val
                20                  25                  30

Val Gly Ile Gly Ser Ala Ser Tyr Lys Val Met Thr Arg Ser Ser His
                35                  40                  45

Gln Ser Leu Val Ile Lys Leu Met Pro Asn Ile Thr Leu Leu Asn Asn
        50                  55                  60

Cys Thr Arg Val Glu Ile Ala Glu Tyr Arg Arg Leu Leu Arg Thr Val
```

-continued

```
65                  70                  75                  80

Leu Glu Pro Ile Arg Asp Ala Leu Asn Ala Val Thr Gln Asn Ile Cys
                85                  90                  95

Pro Val Gln Ser Val Ala Ser Ser Arg Arg His Lys Arg Phe Ala Gly
                100                 105                 110

Val Cys Leu Ala Gly Ala Ala Leu Gly Val Ala Thr Ala Ala Gln Ile
                115                 120                 125

Thr Ala Gly Ile Ala Leu His Gln Ser Met Leu Asn Ser Gln Ala Ile
                130                 135                 140

Asp Asn Leu Arg Ala Ser Leu Glu Thr Thr Asn Gln Ala Ile Glu Ala
145                 150                 155                 160

Ile Arg Gln Ala Gly Gln Glu Met Ile Leu Ala Phe Gln Gly Val Gln
                165                 170                 175

Asp Tyr Ile Asn Asn Glu Leu Ile Pro Ser Met Asn Gln Leu Pro Cys
                180                 185                 190

Asp Leu Ile Gly Gln Lys Leu Gly Leu Lys Leu Leu Arg Tyr Tyr Thr
                195                 200                 205

Glu Ile Leu Ser Leu Phe Gly Pro Ser Leu Arg Asp Pro Ile Ser Ala
    210                 215                 220

Glu Ile Ser Ile Gln Ala Leu Ser Tyr Ala Leu Gly Gly Asp Ile Asn
225                 230                 235                 240

Lys Val Leu Glu Lys Leu Gly Tyr Ser Gly Gly Asp Leu Leu Gly Ile
                245                 250                 255

Leu Glu Ser Arg Gly Ile Lys Ala Arg Ile Thr His Val Asp Thr Glu
                260                 265                 270

Ser Tyr Phe Ile Val Leu Ser Ile Ala Tyr Pro Thr Leu Ser Glu Ile
                275                 280                 285

Lys Gly Val Ile Val His Arg Leu Glu Gly Val Ser Tyr Asn Ile Gly
    290                 295                 300

Ser Gln Glu Trp Tyr Thr Thr Val Pro Lys Tyr Val Ala Thr Gln Gly
305                 310                 315                 320

Tyr Leu Ile Ser Asn Phe Asp Glu Ser Ser Cys Thr Phe Met Pro Glu
                325                 330                 335

Gly Thr Val Cys Ser Gln Asn Ala Leu Tyr Pro Met Ser Pro Leu Leu
                340                 345                 350

Gln Glu Cys Leu Arg Gly Ser Thr Lys Ser Cys Ala Arg Thr Leu Val
    355                 360                 365

Ser Gly Ser Phe Gly Asn Arg Phe Ile Leu Ser Gln Gly Asn Leu Ile
    370                 375                 380

Ala Asn Cys Ala Ser Ile Leu Cys Lys Cys Tyr Thr Thr Gly Thr Ile
385                 390                 395                 400

Ile Asn Gln Asp Pro Asp Lys Ile Leu Thr Tyr Ile Ala Ala Asp His
                405                 410                 415

Cys Pro Val Val Glu Val Asn Gly Val Thr Ile Gln Val Gly Ser Arg
                420                 425                 430

Arg Tyr Pro Asp Ala Val Tyr Leu His Arg Ile Asp Leu Gly Pro Pro
    435                 440                 445

Ile Ser Leu Glu Arg Leu Asp Val Gly Thr Asn Leu Gly Asn Ala Ile
    450                 455                 460

Ala Lys Leu Glu Asp Ala Lys Glu Leu Leu Glu Ser Ser Asp Gln Ile
465                 470                 475                 480

Leu Ser Ala Ile Glu Asp Lys Ile Glu Glu Ile Leu Ser Lys Ile Tyr
                485                 490                 495
```

-continued

```
His Ile Glu Asn Glu Ile Ala Arg Ile Lys Lys Leu Ile Gly Glu Ala
            500                 505                 510

Pro

<210> SEQ ID NO 80
<211> LENGTH: 513
<212> TYPE: PRT
<213> ORGANISM: Artificial sequence
<220> FEATURE:
<223> OTHER INFORMATION: Recombinant F protein

<400> SEQUENCE: 80

Met Tyr Ser Met Gln Leu Ala Ser Cys Val Thr Leu Thr Leu Val Leu
1               5                   10                  15

Leu Val Asn Ser Gln Ile His Trp Gly Asn Leu Ser Lys Ile Gly Val
            20                  25                  30

Val Gly Ile Gly Ser Ala Ser Tyr Lys Val Met Thr Arg Ser Ser His
        35                  40                  45

Gln Ser Leu Val Ile Lys Leu Met Pro Asn Ile Thr Leu Leu Asn Asn
    50                  55                  60

Cys Thr Arg Val Glu Ile Ala Glu Tyr Arg Arg Leu Leu Arg Thr Val
65                  70                  75                  80

Leu Glu Pro Ile Arg Asp Ala Leu Asn Ala Val Thr Gln Asn Ile Cys
            85                  90                  95

Pro Val Gln Ser Val Ala Ser Ser Arg Arg His Lys Arg Phe Ala Gly
            100                 105                 110

Val Cys Leu Ala Gly Ala Ala Leu Gly Val Ala Thr Ala Ala Gln Ile
            115                 120                 125

Thr Ala Gly Ile Ala Leu His Gln Ser Met Leu Asn Ser Gln Ala Ile
        130                 135                 140

Asp Asn Leu Arg Ala Ser Leu Glu Thr Thr Asn Gln Ala Ile Glu Ala
145                 150                 155                 160

Ile Cys Gln Ala Gly Gln Glu Cys Ile Leu Ala Phe Gln Gly Val Gln
                165                 170                 175

Asp Tyr Ile Asn Asn Glu Leu Ile Pro Ser Met Asn Gln Leu Pro Cys
            180                 185                 190

Asp Leu Ile Gly Gln Lys Leu Gly Leu Lys Leu Leu Arg Tyr Tyr Thr
            195                 200                 205

Glu Ile Leu Ser Leu Phe Gly Pro Ser Leu Arg Asp Pro Ile Ser Ala
        210                 215                 220

Glu Ile Ser Ile Gln Ala Leu Ser Tyr Ala Leu Gly Gly Asp Ile Asn
225                 230                 235                 240

Lys Val Leu Glu Lys Leu Gly Tyr Ser Gly Gly Asp Leu Leu Gly Ile
                245                 250                 255

Leu Glu Ser Arg Gly Ile Lys Ala Arg Ile Thr His Val Asp Thr Glu
            260                 265                 270

Ser Tyr Phe Ile Val Leu Ser Ile Ala Tyr Pro Thr Leu Ser Glu Ile
            275                 280                 285

Lys Gly Val Ile Val His Arg Leu Glu Gly Val Ser Tyr Asn Ile Gly
    290                 295                 300

Ser Gln Glu Trp Tyr Thr Thr Val Pro Lys Tyr Val Ala Thr Gln Gly
305                 310                 315                 320

Tyr Leu Ile Ser Asn Phe Asp Glu Ser Ser Cys Thr Phe Met Pro Glu
                325                 330                 335
```

-continued

```
Gly Thr Val Cys Ser Gln Asn Ala Leu Tyr Pro Met Ser Pro Leu Leu
            340                 345                 350

Gln Glu Cys Leu Arg Gly Ser Thr Lys Ser Cys Ala Arg Thr Leu Val
            355                 360                 365

Ser Gly Ser Phe Gly Asn Arg Phe Ile Leu Ser Gln Gly Asn Leu Ile
        370                 375                 380

Ala Asn Cys Ala Ser Ile Leu Cys Lys Cys Tyr Thr Thr Gly Thr Ile
385                 390                 395                 400

Ile Asn Gln Asp Pro Asp Lys Ile Leu Thr Tyr Ile Ala Ala Asp His
                405                 410                 415

Cys Pro Val Val Glu Val Asn Gly Val Thr Ile Gln Val Gly Ser Arg
            420                 425                 430

Arg Tyr Pro Asp Ala Val Tyr Leu His Arg Ile Asp Leu Gly Pro Pro
            435                 440                 445

Ile Ser Leu Glu Arg Leu Asp Val Gly Thr Asn Leu Gly Asn Ala Ile
        450                 455                 460

Ala Lys Leu Glu Asp Ala Lys Glu Leu Leu Glu Ser Ser Asp Gln Ile
465                 470                 475                 480

Leu Ser Ala Ile Glu Asp Lys Ile Glu Glu Ile Leu Ser Lys Ile Tyr
                485                 490                 495

His Ile Glu Asn Glu Ile Ala Arg Ile Lys Lys Leu Ile Gly Glu Ala
            500                 505                 510

Pro
```

<210> SEQ ID NO 81
<211> LENGTH: 988
<212> TYPE: PRT
<213> ORGANISM: Artificial sequence
<220> FEATURE:
<223> OTHER INFORMATION: Recombinant F protein

<400> SEQUENCE: 81

```
Met Tyr Ser Met Gln Leu Ala Ser Cys Val Thr Leu Thr Leu Val Leu
1               5                   10                  15

Leu Val Asn Ser Gln Ile His Trp Gly Asn Leu Ser Lys Ile Gly Val
            20                  25                  30

Val Gly Ile Gly Ser Ala Ser Tyr Lys Val Met Thr Arg Ser Ser His
        35                  40                  45

Gln Ser Leu Val Ile Lys Leu Met Pro Asn Ile Thr Leu Leu Asn Asn
    50                  55                  60

Cys Thr Arg Val Glu Ile Ala Glu Tyr Arg Arg Leu Leu Arg Thr Val
65                  70                  75                  80

Leu Glu Pro Ile Arg Asp Ala Leu Asn Ala Val Thr Gln Asn Ile Arg
                85                  90                  95

Pro Val Gln Ser Val Ala Ser Ser Arg Arg His Gly Gly Gly Ala Gly
            100                 105                 110

Val Val Leu Ala Gly Ala Ala Leu Gly Val Ala Thr Ala Ala Gln Ile
            115                 120                 125

Thr Ala Gly Ile Ala Leu His Gln Ser Met Leu Asn Ser Gln Ala Ile
        130                 135                 140

Asp Asn Leu Arg Ala Ser Leu Glu Thr Thr Asn Gln Ala Ile Glu Ala
145                 150                 155                 160

Ile Cys Gln Ala Gly Gln Glu Cys Ile Leu Ala Val Gln Gly Val Gln
                165                 170                 175

Asp Tyr Ile Asn Asn Glu Leu Ile Pro Ser Met Asn Gln Leu Ser Cys
```

-continued

```
                180              185              190

Asp Leu Ile Gly Gln Lys Leu Gly Leu Lys Leu Leu Arg Tyr Tyr Thr
            195              200              205

Glu Ile Leu Ser Leu Phe Gly Pro Ser Leu Arg Asp Pro Ile Ser Ala
        210              215              220

Glu Ile Ser Ile Gln Ala Leu Ser Tyr Ala Leu Gly Gly Asp Ile Asn
225              230              235              240

Lys Val Leu Glu Lys Leu Gly Tyr Ser Gly Gly Asp Leu Leu Gly Ile
            245              250              255

Leu Glu Ser Arg Gly Ile Lys Ala Arg Ile Thr His Val Asp Thr Glu
            260              265              270

Ser Tyr Phe Ile Val Leu Ser Ile Ala Tyr Pro Thr Leu Ser Glu Ile
            275              280              285

Lys Gly Val Ile Val His Arg Leu Glu Gly Val Ser Tyr Asn Ile Gly
        290              295              300

Ser Gln Glu Trp Tyr Thr Thr Val Pro Lys Tyr Val Ala Thr Gln Gly
305              310              315              320

Tyr Leu Ile Ser Asn Phe Asp Glu Ser Ser Cys Thr Phe Met Pro Glu
            325              330              335

Gly Thr Val Cys Ser Gln Asn Ala Leu Tyr Pro Met Ser Pro Leu Leu
            340              345              350

Gln Glu Cys Leu Arg Gly Ser Thr Lys Ser Cys Ala Arg Thr Leu Val
            355              360              365

Ser Gly Ser Phe Gly Asn Arg Phe Ile Leu Ser Gln Gly Asn Leu Ile
        370              375              380

Ala Asn Cys Ala Ser Ile Leu Cys Lys Cys Tyr Thr Thr Gly Thr Ile
385              390              395              400

Ile Asn Gln Asp Pro Asp Lys Ile Leu Thr Tyr Ile Ala Ala Asp His
            405              410              415

Cys Pro Val Val Glu Val Asn Gly Val Thr Ile Gln Val Gly Ser Arg
            420              425              430

Arg Tyr Pro Asp Ala Val Tyr Leu His Arg Ile Asp Leu Gly Pro Pro
            435              440              445

Ile Ser Leu Glu Arg Leu Asp Val Gly Thr Asn Leu Gly Asn Ala Ile
        450              455              460

Ala Lys Leu Glu Asp Ala Lys Glu Leu Leu Glu Ser Ser Asp Gln Ile
465              470              475              480

Leu Ser Ala Ile Glu Asp Lys Ile Glu Glu Ile Leu Ser Lys Ile Tyr
            485              490              495

His Ile Glu Asn Glu Ile Ala Arg Ile Lys Lys Leu Ile Gly Glu Ala
            500              505              510

Pro Gly Ser Gly Tyr Ile Pro Glu Ala Pro Arg Asp Gly Gln Ala Tyr
            515              520              525

Val Arg Lys Asp Gly Glu Trp Val Leu Leu Ser Thr Phe Leu Gly Ser
        530              535              540

Gly Gly Gly Gly Gly Gly Phe Leu Ala Val Ser Lys Gly Asn Cys Ser
545              550              555              560

Gly Pro Thr Thr Ile Arg Gly Gln Phe Ser Asn Met Ser Leu Ser Leu
            565              570              575

Leu Asp Leu Tyr Leu Gly Arg Gly Tyr Asn Val Ser Ser Ile Val Thr
            580              585              590

Met Thr Ser Gln Gly Met Tyr Gly Gly Thr Tyr Leu Val Glu Lys Pro
            595              600              605
```

```
Asn Leu Ser Ser Lys Arg Ser Glu Leu Ser Gln Leu Ser Met Tyr Arg
    610             615             620

Val Phe Glu Val Gly Val Ile Arg Asn Pro Gly Leu Gly Ala Pro Val
625             630             635             640

Phe His Met Thr Asn Tyr Leu Glu Gln Pro Val Ser Asn Asp Leu Ser
                645             650             655

Asn Cys Met Val Ala Leu Gly Glu Leu Lys Leu Ala Ala Leu Cys His
                660             665             670

Gly Glu Asp Ser Ile Thr Ile Pro Tyr Gln Gly Ser Gly Lys Gly Val
                675             680             685

Ser Phe Gln Leu Val Lys Leu Gly Val Trp Lys Ser Pro Ala Asp Met
    690             695             700

Gln Ser Trp Val Pro Leu Ser Thr Asp Asp Pro Val Ile Asp Arg Leu
705             710             715             720

Tyr Leu Ser Ser His Arg Gly Val Ile Ala Asp Asn Gln Ala Lys Trp
                725             730             735

Ala Val Pro Thr Thr Arg Thr Asp Asp Lys Leu Arg Met Glu Thr Cys
                740             745             750

Phe Gln Gln Ala Cys Lys Gly Lys Ile Gln Thr Leu Cys Glu Asn Pro
                755             760             765

Glu Trp Ala Pro Leu Lys Asp Asn Arg Ile Pro Ser Tyr Gly Val Leu
    770             775             780

Ser Val Asp Leu Ser Leu Thr Val Glu Leu Lys Ile Lys Ile Ala Ser
785             790             795             800

Gly Phe Gly Pro Leu Ile Thr His Gly Ser Gly Met Asp Leu Tyr Lys
                805             810             815

Ser Asn His Asn Asn Val Tyr Trp Leu Thr Ile Pro Pro Met Lys Asn
                820             825             830

Leu Ala Leu Gly Val Ile Asn Thr Leu Glu Trp Ile Pro Arg Phe Lys
                835             840             845

Val Ser Pro Tyr Leu Phe Thr Val Pro Ile Lys Glu Ala Gly Glu Asp
    850             855             860

Cys His Ala Pro Thr Tyr Leu Pro Ala Glu Val Asp Gly Asp Val Lys
865             870             875             880

Leu Ser Ser Asn Leu Val Ile Leu Pro Gly Gln Asp Leu Gln Tyr Val
                885             890             895

Leu Ala Thr Tyr Asp Thr Ser Arg Val Glu His Ala Val Val Tyr Tyr
                900             905             910

Val Tyr Ser Pro Gly Arg Ser Phe Ser Tyr Phe Tyr Pro Phe Arg Leu
    915             920             925

Pro Ile Lys Gly Val Pro Ile Glu Leu Gln Val Glu Cys Phe Thr Trp
    930             935             940

Asp Gln Lys Leu Trp Cys Arg His Phe Cys Val Leu Ala Asp Ser Glu
945             950             955             960

Ser Gly Gly His Ile Thr His Ser Gly Met Val Gly Met Gly Val Ser
                965             970             975

Cys Thr Val Thr Arg Glu Asp Gly Thr Asn Arg Arg
                980             985
```

<210> SEQ ID NO 82
<211> LENGTH: 950
<212> TYPE: PRT
<213> ORGANISM: Artificial sequence
<220> FEATURE:

-continued

<223> OTHER INFORMATION: Recombinant HN/H protein

<400> SEQUENCE: 82

```
Met Tyr Ser Met Gln Leu Ala Ser Cys Val Thr Leu Thr Leu Val Leu
1               5                   10                  15

Leu Val Asn Ser Gln Asn Ile Pro Leu Val Asn Asp Leu Arg Phe Ile
            20                  25                  30

Asn Gly Ile Asn Lys Phe Ile Ile Glu Asp Tyr Ala Thr His Asp Phe
        35                  40                  45

Ser Ile Gly His Pro Leu Asn Met Pro Ser Phe Ile Pro Thr Ala Thr
    50                  55                  60

Ser Pro Asn Gly Cys Thr Arg Ile Pro Ser Phe Ser Leu Gly Lys Thr
65                  70                  75                  80

His Trp Cys Tyr Thr His Asn Val Ile Asn Ala Asn Cys Lys Asp His
                85                  90                  95

Thr Ser Ser Asn Gln Tyr Val Ser Met Gly Ile Leu Val Gln Thr Ala
            100                 105                 110

Ser Gly Tyr Pro Met Phe Lys Thr Leu Lys Ile Gln Tyr Leu Ser Asp
        115                 120                 125

Gly Leu Asn Arg Lys Ser Cys Ser Ile Ala Thr Val Pro Asp Gly Cys
    130                 135                 140

Ala Met Tyr Cys Tyr Val Ser Thr Gln Leu Glu Thr Asp Asp Tyr Ala
145                 150                 155                 160

Gly Ser Ser Pro Pro Thr Gln Lys Leu Thr Leu Leu Phe Tyr Asn Asp
                165                 170                 175

Thr Val Thr Glu Arg Thr Ile Ser Pro Ser Gly Leu Glu Gly Asn Trp
            180                 185                 190

Ala Thr Leu Val Pro Gly Val Gly Ser Gly Ile Tyr Phe Glu Asn Lys
        195                 200                 205

Leu Ile Phe Pro Ala Tyr Gly Gly Val Leu Pro Asn Ser Thr Leu Gly
    210                 215                 220

Val Lys Ser Ala Arg Glu Phe Phe Arg Pro Val Asn Pro Tyr Asn Pro
225                 230                 235                 240

Cys Ser Gly Pro Gln Gln Asp Leu Asp Gln Arg Ala Leu Arg Ser Tyr
                245                 250                 255

Phe Pro Ser Tyr Phe Ser Asn Arg Arg Ile Gln Ser Ala Phe Leu Val
            260                 265                 270

Cys Ala Trp Asn Gln Ile Leu Val Thr Asn Cys Glu Leu Val Val Pro
        275                 280                 285

Ser Ser Asn Gln Thr Met Met Gly Ala Glu Gly Arg Val Leu Leu Ile
    290                 295                 300

Asn Asn Arg Leu Leu Tyr Tyr Gln Arg Ser Thr Ser Trp Trp Pro Tyr
305                 310                 315                 320

Glu Leu Leu Tyr Glu Ile Ser Phe Thr Phe Thr Asn Ser Gly Pro Ser
                325                 330                 335

Ser Val Asn Met Ser Trp Ile Pro Ile Tyr Ser Phe Thr Arg Pro Gly
            340                 345                 350

Ser Gly Asn Cys Ser Gly Glu Asn Val Cys Pro Thr Ala Cys Val Ser
        355                 360                 365

Gly Val Tyr Leu Asp Pro Trp Pro Leu Thr Pro Tyr Ser His Gln Ser
    370                 375                 380

Gly Ile Asn Arg Asn Phe Tyr Phe Thr Gly Ala Leu Leu Asn Ser Ser
385                 390                 395                 400
```

-continued

```
Thr Thr Arg Val Asn Pro Thr Leu Tyr Val Ser Ala Leu Asn Asn Leu
                405                 410                 415

Lys Val Leu Ala Pro Tyr Gly Thr Gln Gly Leu Phe Ala Ser Tyr Thr
            420                 425                 430

Thr Thr Thr Cys Phe Gln Asp Thr Gly Asp Ala Ser Val Tyr Cys Val
            435                 440                 445

Tyr Ile Met Glu Leu Ala Ser Asn Ile Val Gly Glu Phe Gln Ile Leu
        450                 455                 460

Pro Val Leu Thr Arg Leu Thr Ile Thr Gly Gly Ser Gly Tyr Ile
465                 470                 475                 480

Pro Glu Ala Pro Arg Asp Gly Gln Ala Tyr Val Arg Lys Asp Gly Glu
                485                 490                 495

Trp Val Leu Leu Ser Thr Phe Leu Gly Ser Gly Gly Gly Gly Gly
            500                 505                 510

Phe Leu Ala Val Ser Lys Gly Asn Cys Ser Gly Pro Thr Thr Ile Arg
            515                 520                 525

Gly Gln Phe Ser Asn Met Ser Leu Ser Leu Leu Asp Leu Tyr Leu Gly
        530                 535                 540

Arg Gly Tyr Asn Val Ser Ser Ile Val Thr Met Thr Ser Gln Gly Met
545                 550                 555                 560

Tyr Gly Gly Thr Tyr Leu Val Glu Lys Pro Asn Leu Ser Ser Lys Arg
                565                 570                 575

Ser Glu Leu Ser Gln Leu Ser Met Tyr Arg Val Phe Glu Val Gly Val
            580                 585                 590

Ile Arg Asn Pro Gly Leu Gly Ala Pro Val Phe His Met Thr Asn Tyr
        595                 600                 605

Leu Glu Gln Pro Val Ser Asn Asp Leu Ser Asn Cys Met Val Ala Leu
        610                 615                 620

Gly Glu Leu Lys Leu Ala Ala Leu Cys His Gly Glu Asp Ser Ile Thr
625                 630                 635                 640

Ile Pro Tyr Gln Gly Ser Gly Lys Gly Val Ser Phe Gln Leu Val Lys
                645                 650                 655

Leu Gly Val Trp Lys Ser Pro Thr Asp Met Gln Ser Trp Val Pro Leu
            660                 665                 670

Ser Thr Asp Asp Pro Val Ile Asp Arg Leu Tyr Leu Ser Ser His Arg
            675                 680                 685

Gly Val Ile Ala Asp Asn Gln Ala Lys Trp Ala Val Pro Thr Thr Arg
        690                 695                 700

Thr Asp Asp Lys Leu Arg Met Glu Thr Cys Phe Gln Gln Ala Cys Lys
705                 710                 715                 720

Gly Lys Ile Gln Ala Leu Cys Glu Asn Pro Glu Trp Ala Pro Leu Lys
            725                 730                 735

Asp Asn Arg Ile Pro Ser Tyr Gly Val Leu Ser Val Asp Leu Ser Leu
            740                 745                 750

Thr Val Glu Leu Lys Ile Lys Ile Ala Ser Gly Phe Gly Pro Leu Ile
            755                 760                 765

Thr His Gly Ser Gly Met Asp Leu Tyr Lys Ser Asn His Asn Asn Val
        770                 775                 780

Tyr Trp Leu Thr Ile Pro Pro Met Lys Asn Leu Ala Leu Gly Val Ile
785                 790                 795                 800

Asn Thr Leu Glu Trp Ile Pro Arg Phe Lys Val Ser Pro Tyr Leu Phe
                805                 810                 815

Asn Val Pro Ile Lys Glu Ala Gly Glu Asp Cys His Ala Pro Thr Tyr
```

```
                   820              825              830
Leu Pro Ala Glu Val Asp Gly Asp Val Lys Leu Ser Ser Asn Leu Val
        835              840              845

Ile Leu Pro Gly Gln Asp Leu Gln Tyr Val Leu Ala Thr Tyr Asp Thr
        850              855              860

Ser Arg Val Glu His Ala Val Val Tyr Tyr Val Tyr Ser Pro Ser Arg
865              870              875              880

Ser Phe Ser Tyr Phe Tyr Pro Phe Arg Leu Pro Ile Lys Gly Val Pro
                885              890              895

Ile Glu Leu Gln Val Glu Cys Phe Thr Trp Asp Gln Lys Leu Trp Cys
        900              905              910

Arg His Phe Cys Val Leu Ala Asp Ser Glu Ser Gly Gly His Ile Thr
        915              920              925

His Ser Gly Met Glu Gly Met Gly Val Ser Cys Thr Val Thr Arg Glu
930              935              940

Asp Gly Thr Asn Arg Arg
945              950
```

<210> SEQ ID NO 83
<211> LENGTH: 985
<212> TYPE: PRT
<213> ORGANISM: Artificial sequence
<220> FEATURE:
<223> OTHER INFORMATION: Recombinant HN/H protein

<400> SEQUENCE: 83

```
Met Tyr Ser Met Gln Leu Ala Ser Cys Val Thr Leu Thr Leu Val Leu
1               5               10              15

Leu Val Asn Ser Gln Asn Ile Pro Leu Val Asn Asp Leu Arg Phe Ile
                20              25              30

Asn Gly Ile Asn Lys Phe Ile Ile Glu Asp Tyr Ala Thr His Asp Phe
        35              40              45

Ser Ile Gly His Pro Leu Asn Met Pro Ser Phe Ile Pro Thr Ala Thr
        50              55              60

Ser Pro Asn Gly Cys Thr Arg Ile Pro Ser Phe Ser Leu Gly Lys Thr
65              70              75              80

His Trp Cys Tyr Thr His Asn Val Ile Asn Ala Asn Cys Lys Asp His
                85              90              95

Thr Ser Ser Asn Gln Tyr Val Ser Met Gly Ile Leu Val Gln Thr Ala
        100             105             110

Ser Gly Tyr Pro Met Phe Lys Thr Leu Lys Ile Gln Tyr Leu Ser Asp
        115             120             125

Gly Leu Asn Arg Lys Ser Cys Ser Ile Ala Thr Val Pro Asp Gly Cys
        130             135             140

Ala Met Tyr Cys Tyr Val Ser Thr Gln Leu Glu Thr Asp Asp Tyr Ala
145             150             155             160

Gly Ser Ser Pro Pro Thr Gln Lys Leu Thr Leu Leu Phe Tyr Asn Asp
                165             170             175

Thr Val Thr Glu Arg Thr Ile Ser Pro Ser Gly Leu Glu Gly Asn Trp
                180             185             190

Ala Thr Leu Val Pro Gly Val Gly Ser Gly Ile Tyr Phe Glu Asn Lys
        195             200             205

Leu Ile Phe Pro Ala Tyr Gly Gly Val Leu Pro Asn Ser Thr Leu Gly
        210             215             220

Val Lys Ser Ala Arg Glu Phe Phe Arg Pro Val Asn Pro Tyr Asn Pro
```

-continued

```
225                  230                  235                  240

Cys Ser Gly Pro Gln Gln Asp Leu Asp Gln Arg Ala Leu Arg Ser Tyr
            245                  250                  255

Phe Pro Ser Tyr Phe Ser Asn Arg Arg Ile Gln Ser Ala Phe Leu Val
            260                  265                  270

Cys Ala Trp Asn Gln Ile Leu Val Thr Asn Cys Glu Leu Val Val Pro
            275                  280                  285

Ser Ser Asn Gln Thr Met Met Gly Ala Glu Gly Arg Val Leu Leu Ile
            290                  295                  300

Asn Asn Arg Leu Leu Tyr Tyr Gln Arg Ser Thr Ser Trp Trp Pro Tyr
305                  310                  315                  320

Glu Leu Leu Tyr Glu Ile Ser Phe Thr Phe Thr Asn Ser Gly Pro Ser
            325                  330                  335

Ser Val Asn Met Ser Trp Ile Pro Ile Tyr Ser Phe Thr Arg Pro Gly
            340                  345                  350

Ser Gly Asn Cys Ser Gly Glu Asn Val Cys Pro Thr Ala Cys Val Ser
            355                  360                  365

Gly Val Tyr Leu Asp Pro Trp Pro Leu Thr Pro Tyr Ser His Gln Ser
            370                  375                  380

Gly Ile Asn Arg Asn Phe Tyr Phe Thr Gly Ala Leu Leu Asn Ser Ser
385                  390                  395                  400

Thr Thr Arg Val Asn Pro Thr Leu Tyr Val Ser Ala Leu Asn Asn Leu
            405                  410                  415

Lys Val Leu Ala Pro Tyr Gly Thr Gln Gly Leu Phe Ala Ser Tyr Thr
            420                  425                  430

Thr Thr Thr Cys Phe Gln Asp Thr Gly Asp Ala Ser Val Tyr Cys Val
            435                  440                  445

Tyr Ile Met Glu Leu Ala Ser Asn Ile Val Gly Glu Phe Gln Ile Leu
            450                  455                  460

Pro Val Leu Thr Arg Leu Thr Ile Thr Gly Gly Lys Leu Met Lys Gln
465                  470                  475                  480

Ile Glu Asp Lys Ile Glu Glu Ile Leu Ser Lys Ile Tyr His Ile Glu
            485                  490                  495

Asn Glu Ile Ala Arg Ile Lys Lys Leu Ile Gly Glu Ala Pro Gly Ser
            500                  505                  510

Gly Tyr Ile Pro Glu Ala Pro Arg Asp Gly Gln Ala Tyr Val Arg Lys
            515                  520                  525

Asp Gly Glu Trp Val Leu Leu Ser Thr Phe Leu Gly Ser Gly Gly Gly
            530                  535                  540

Gly Gly Gly Phe Leu Ala Val Ser Lys Gly Asn Cys Ser Gly Pro Thr
545                  550                  555                  560

Thr Ile Arg Gly Gln Phe Ser Asn Met Ser Leu Ser Leu Leu Asp Leu
            565                  570                  575

Tyr Leu Gly Arg Gly Tyr Asn Val Ser Ser Ile Val Thr Met Thr Ser
            580                  585                  590

Gln Gly Met Tyr Gly Gly Thr Tyr Leu Val Glu Lys Pro Asn Leu Ser
            595                  600                  605

Ser Lys Arg Ser Glu Leu Ser Gln Leu Ser Met Tyr Arg Val Phe Glu
            610                  615                  620

Val Gly Val Ile Arg Asn Pro Gly Leu Gly Ala Pro Val Phe His Met
625                  630                  635                  640

Thr Asn Tyr Leu Glu Gln Pro Val Ser Asn Asp Leu Ser Asn Cys Met
            645                  650                  655
```

-continued

```
Val Ala Leu Gly Glu Leu Lys Leu Ala Ala Leu Cys His Gly Glu Asp
            660                 665                 670

Ser Ile Thr Ile Pro Tyr Gln Gly Ser Gly Lys Gly Val Ser Phe Gln
            675                 680                 685

Leu Val Lys Leu Gly Val Trp Lys Ser Pro Thr Asp Met Gln Ser Trp
            690                 695                 700

Val Pro Leu Ser Thr Asp Asp Pro Val Ile Asp Arg Leu Tyr Leu Ser
705                 710                 715                 720

Ser His Arg Gly Val Ile Ala Asp Asn Gln Ala Lys Trp Ala Val Pro
                    725                 730                 735

Thr Thr Arg Thr Asp Asp Lys Leu Arg Met Glu Thr Cys Phe Gln Gln
            740                 745                 750

Ala Cys Lys Gly Lys Ile Gln Ala Leu Cys Glu Asn Pro Glu Trp Ala
            755                 760                 765

Pro Leu Lys Asp Asn Arg Ile Pro Ser Tyr Gly Val Leu Ser Val Asp
            770                 775                 780

Leu Ser Leu Thr Val Glu Leu Lys Ile Lys Ile Ala Ser Gly Phe Gly
785                 790                 795                 800

Pro Leu Ile Thr His Gly Ser Gly Met Asp Leu Tyr Lys Ser Asn His
                    805                 810                 815

Asn Asn Val Tyr Trp Leu Thr Ile Pro Pro Met Lys Asn Leu Ala Leu
                    820                 825                 830

Gly Val Ile Asn Thr Leu Glu Trp Ile Pro Arg Phe Lys Val Ser Pro
                    835                 840                 845

Tyr Leu Phe Asn Val Pro Ile Lys Glu Ala Gly Glu Asp Cys His Ala
            850                 855                 860

Pro Thr Tyr Leu Pro Ala Glu Val Asp Gly Asp Val Lys Leu Ser Ser
865                 870                 875                 880

Asn Leu Val Ile Leu Pro Gly Gln Asp Leu Gln Tyr Val Leu Ala Thr
                    885                 890                 895

Tyr Asp Thr Ser Arg Val Glu His Ala Val Val Tyr Tyr Val Tyr Ser
                    900                 905                 910

Pro Ser Arg Ser Phe Ser Tyr Phe Tyr Pro Phe Arg Leu Pro Ile Lys
            915                 920                 925

Gly Val Pro Ile Glu Leu Gln Val Glu Cys Phe Thr Trp Asp Gln Lys
            930                 935                 940

Leu Trp Cys Arg His Phe Cys Val Leu Ala Asp Ser Glu Ser Gly Gly
945                 950                 955                 960

His Ile Thr His Ser Gly Met Glu Gly Met Gly Val Ser Cys Thr Val
                    965                 970                 975

Thr Arg Glu Asp Gly Thr Asn Arg Arg
            980                 985

<210> SEQ ID NO 84
<211> LENGTH: 948
<212> TYPE: PRT
<213> ORGANISM: Artificial sequence
<220> FEATURE:
<223> OTHER INFORMATION: Recombinant HN/H protein

<400> SEQUENCE: 84

Met Tyr Ser Met Gln Leu Ala Ser Cys Val Thr Leu Thr Leu Val Leu
1               5                   10                  15

Leu Val Asn Ser Gln Phe Leu Ala Val Ser Lys Gly Asn Cys Ser Gly
            20                  25                  30
```

-continued

```
Pro Thr Thr Ile Arg Gly Gln Phe Ser Asn Met Ser Leu Ser Leu Leu
        35              40              45

Asp Leu Tyr Leu Gly Arg Gly Tyr Asn Val Ser Ser Ile Val Thr Met
    50              55              60

Thr Ser Gln Gly Met Tyr Gly Gly Thr Tyr Leu Val Glu Lys Pro Asn
65              70              75              80

Leu Ser Ser Lys Arg Ser Glu Leu Ser Gln Leu Ser Met Tyr Arg Val
            85              90              95

Phe Glu Val Gly Val Ile Arg Asn Pro Gly Leu Gly Ala Pro Val Phe
            100             105             110

His Met Thr Asn Tyr Leu Glu Gln Pro Val Ser Asn Asp Leu Ser Asn
        115             120             125

Cys Met Val Ala Leu Gly Glu Leu Lys Leu Ala Ala Leu Cys His Gly
    130             135             140

Glu Asp Ser Ile Thr Ile Pro Tyr Gln Gly Ser Gly Lys Gly Val Ser
145             150             155             160

Phe Gln Leu Val Lys Leu Gly Val Trp Lys Ser Pro Thr Asp Met Gln
            165             170             175

Ser Trp Val Pro Leu Ser Thr Asp Asp Pro Val Ile Asp Arg Leu Tyr
            180             185             190

Leu Ser Ser His Arg Gly Val Ile Ala Asp Asn Gln Ala Lys Trp Ala
        195             200             205

Val Pro Thr Thr Arg Thr Asp Asp Lys Leu Arg Met Glu Thr Cys Phe
    210             215             220

Gln Gln Ala Cys Lys Gly Lys Ile Gln Ala Leu Cys Glu Asn Pro Glu
225             230             235             240

Trp Ala Pro Leu Lys Asp Asn Arg Ile Pro Ser Tyr Gly Val Leu Ser
            245             250             255

Val Asp Leu Ser Leu Thr Val Glu Leu Lys Ile Lys Ile Ala Ser Gly
            260             265             270

Phe Gly Pro Leu Ile Thr His Gly Ser Gly Met Asp Leu Tyr Lys Ser
        275             280             285

Asn His Asn Asn Val Tyr Trp Leu Thr Ile Pro Pro Met Lys Asn Leu
    290             295             300

Ala Leu Gly Val Ile Asn Thr Leu Glu Trp Ile Pro Arg Phe Lys Val
305             310             315             320

Ser Pro Tyr Leu Phe Asn Val Pro Ile Lys Glu Ala Gly Glu Asp Cys
            325             330             335

His Ala Pro Thr Tyr Leu Pro Ala Glu Val Asp Gly Asp Val Lys Leu
            340             345             350

Ser Ser Asn Leu Val Ile Leu Pro Gly Gln Asp Leu Gln Tyr Val Leu
        355             360             365

Ala Thr Tyr Asp Thr Ser Arg Val Glu His Ala Val Val Tyr Tyr Val
    370             375             380

Tyr Ser Pro Ser Arg Ser Phe Ser Tyr Phe Tyr Pro Phe Arg Leu Pro
385             390             395             400

Ile Lys Gly Val Pro Ile Glu Leu Gln Val Glu Cys Phe Thr Trp Asp
            405             410             415

Gln Lys Leu Trp Cys Arg His Phe Cys Val Leu Ala Asp Ser Glu Ser
            420             425             430

Gly Gly His Ile Thr His Ser Gly Met Glu Gly Met Gly Val Ser Cys
        435             440             445
```

-continued

```
Thr Val Thr Arg Glu Asp Gly Thr Asn Arg Arg Gly Ser Gly Tyr Ile
450             455             460

Pro Glu Ala Pro Arg Asp Gly Gln Ala Tyr Val Arg Lys Asp Gly Glu
465             470             475             480

Trp Val Leu Leu Ser Thr Phe Leu Gly Ser Gly Gly Gly Gly Gly Gly
                485             490             495

Asn Ile Pro Leu Val Asn Asp Leu Arg Phe Ile Asn Gly Ile Asn Lys
            500             505             510

Phe Ile Ile Glu Asp Tyr Ala Thr His Asp Phe Ser Ile Gly His Pro
            515             520             525

Leu Asn Met Pro Ser Phe Ile Pro Thr Ala Thr Ser Pro Asn Gly Cys
530             535             540

Thr Arg Ile Pro Ser Phe Ser Leu Gly Lys Thr His Trp Cys Tyr Thr
545             550             555             560

His Asn Val Ile Asn Ala Asn Cys Lys Asp His Thr Ser Ser Asn Gln
            565             570             575

Tyr Val Ser Met Gly Ile Leu Val Gln Thr Ala Ser Gly Tyr Pro Met
            580             585             590

Phe Lys Thr Leu Lys Ile Gln Tyr Leu Ser Asp Gly Leu Asn Arg Lys
            595             600             605

Ser Cys Ser Ile Ala Thr Val Pro Asp Gly Cys Ala Met Tyr Cys Tyr
    610             615             620

Val Ser Thr Gln Leu Glu Thr Asp Asp Tyr Ala Gly Ser Ser Pro Pro
625             630             635             640

Thr Gln Lys Leu Thr Leu Leu Phe Tyr Asn Asp Thr Val Thr Glu Arg
            645             650             655

Thr Ile Ser Pro Ser Gly Leu Glu Gly Asn Trp Ala Thr Leu Val Pro
            660             665             670

Gly Val Gly Ser Gly Ile Tyr Phe Glu Asn Lys Leu Ile Phe Pro Ala
            675             680             685

Tyr Gly Gly Val Leu Pro Asn Ser Thr Leu Gly Val Lys Ser Ala Arg
    690             695             700

Glu Phe Phe Arg Pro Val Asn Pro Tyr Asn Pro Cys Ser Gly Pro Gln
705             710             715             720

Gln Asp Leu Asp Gln Arg Ala Leu Arg Ser Tyr Phe Pro Ser Tyr Phe
            725             730             735

Ser Asn Arg Arg Ile Gln Ser Ala Phe Leu Val Cys Ala Trp Asn Gln
            740             745             750

Ile Leu Val Thr Asn Cys Glu Leu Val Val Pro Ser Ser Asn Gln Thr
            755             760             765

Met Met Gly Ala Glu Gly Arg Val Leu Leu Ile Asn Asn Arg Leu Leu
    770             775             780

Tyr Tyr Gln Arg Ser Thr Ser Trp Trp Pro Tyr Glu Leu Leu Tyr Glu
785             790             795             800

Ile Ser Phe Thr Phe Thr Asn Ser Gly Pro Ser Ser Val Asn Met Ser
            805             810             815

Trp Ile Pro Ile Tyr Ser Phe Thr Arg Pro Gly Ser Gly Asn Cys Ser
            820             825             830

Gly Glu Asn Val Cys Pro Thr Ala Cys Val Ser Gly Val Tyr Leu Asp
            835             840             845

Pro Trp Pro Leu Thr Pro Tyr Ser His Gln Ser Gly Ile Asn Arg Asn
850             855             860

Phe Tyr Phe Thr Gly Ala Leu Leu Asn Ser Ser Thr Thr Arg Val Asn
```

-continued

```
865            870            875            880

Pro Thr Leu Tyr Val Ser Ala Leu Asn Asn Leu Lys Val Leu Ala Pro
                885                890                895

Tyr Gly Thr Gln Gly Leu Phe Ala Ser Tyr Thr Thr Thr Thr Cys Phe
                900                905            910

Gln Asp Thr Gly Asp Ala Ser Val Tyr Cys Val Tyr Ile Met Glu Leu
                915                920            925

Ala Ser Asn Ile Val Gly Glu Phe Gln Ile Leu Pro Val Leu Thr Arg
        930                935                940

Leu Thr Ile Thr
945

<210> SEQ ID NO 85
<211> LENGTH: 981
<212> TYPE: PRT
<213> ORGANISM: Artificial sequence
<220> FEATURE:
<223> OTHER INFORMATION: Recombinant HN/H protein

<400> SEQUENCE: 85

Met Tyr Ser Met Gln Leu Ala Ser Cys Val Thr Leu Thr Leu Val Leu
1                5                10                15

Leu Val Asn Ser Gln Phe Leu Ala Val Ser Lys Gly Asn Cys Ser Gly
                20                25                30

Pro Thr Thr Ile Arg Gly Gln Phe Ser Asn Met Ser Leu Ser Leu Leu
                35                40                45

Asp Leu Tyr Leu Gly Arg Gly Tyr Asn Val Ser Ser Ile Val Thr Met
        50                55                60

Thr Ser Gln Gly Met Tyr Gly Gly Thr Tyr Leu Val Glu Lys Pro Asn
65                70                75                80

Leu Ser Ser Lys Arg Ser Glu Leu Ser Gln Leu Ser Met Tyr Arg Val
                85                90                95

Phe Glu Val Gly Val Ile Arg Asn Pro Gly Leu Gly Ala Pro Val Phe
                100                105                110

His Met Thr Asn Tyr Leu Glu Gln Pro Val Ser Asn Asp Leu Ser Asn
                115                120                125

Cys Met Val Ala Leu Gly Glu Leu Lys Leu Ala Ala Leu Cys His Gly
        130                135                140

Glu Asp Ser Ile Thr Ile Pro Tyr Gln Gly Ser Gly Lys Gly Val Ser
145                150                155                160

Phe Gln Leu Val Lys Leu Gly Val Trp Lys Ser Pro Thr Asp Met Gln
                165                170                175

Ser Trp Val Pro Leu Ser Thr Asp Asp Pro Val Ile Asp Arg Leu Tyr
                180                185                190

Leu Ser Ser His Arg Gly Val Ile Ala Asp Asn Gln Ala Lys Trp Ala
                195                200                205

Val Pro Thr Thr Arg Thr Asp Asp Lys Leu Arg Met Glu Thr Cys Phe
        210                215                220

Gln Gln Ala Cys Lys Gly Lys Ile Gln Ala Leu Cys Glu Asn Pro Glu
225                230                235                240

Trp Ala Pro Leu Lys Asp Asn Arg Ile Pro Ser Tyr Gly Val Leu Ser
                245                250                255

Val Asp Leu Ser Leu Thr Val Glu Leu Lys Ile Lys Ile Ala Ser Gly
                260                265                270

Phe Gly Pro Leu Ile Thr His Gly Ser Gly Met Asp Leu Tyr Lys Ser
```

-continued

<pre>
                275                    280                    285

Asn His Asn Asn Val Tyr Trp Leu Thr Ile Pro Pro Met Lys Asn Leu
    290                    295                    300

Ala Leu Gly Val Ile Asn Thr Leu Glu Trp Ile Pro Arg Phe Lys Val
305                    310                    315                    320

Ser Pro Tyr Leu Phe Asn Val Pro Ile Lys Glu Ala Gly Glu Asp Cys
                325                    330                    335

His Ala Pro Thr Tyr Leu Pro Ala Glu Val Asp Gly Asp Val Lys Leu
                340                    345                    350

Ser Ser Asn Leu Val Ile Leu Pro Gly Gln Asp Leu Gln Tyr Val Leu
                355                    360                    365

Ala Thr Tyr Asp Thr Ser Arg Val Glu His Ala Val Val Tyr Tyr Val
    370                    375                    380

Tyr Ser Pro Ser Arg Ser Phe Ser Tyr Phe Tyr Pro Phe Arg Leu Pro
385                    390                    395                    400

Ile Lys Gly Val Pro Ile Glu Leu Gln Val Glu Cys Phe Thr Trp Asp
                405                    410                    415

Gln Lys Leu Trp Cys Arg His Phe Cys Val Leu Ala Asp Ser Glu Ser
                420                    425                    430

Gly Gly His Ile Thr His Ser Gly Met Glu Gly Met Gly Val Ser Cys
                435                    440                    445

Thr Val Thr Arg Glu Asp Gly Thr Asn Arg Arg Met Lys Gln Ile Glu
    450                    455                    460

Asp Lys Ile Glu Glu Ile Leu Ser Lys Ile Tyr His Ile Glu Asn Glu
465                    470                    475                    480

Ile Ala Arg Ile Lys Lys Leu Ile Gly Glu Ala Pro Gly Ser Gly Tyr
                485                    490                    495

Ile Pro Glu Ala Pro Arg Asp Gly Gln Ala Tyr Val Arg Lys Asp Gly
                500                    505                    510

Glu Trp Val Leu Leu Ser Thr Phe Leu Gly Ser Gly Gly Gly Gly Gly
                515                    520                    525

Gly Asn Ile Pro Leu Val Asn Asp Leu Arg Phe Ile Asn Gly Ile Asn
    530                    535                    540

Lys Phe Ile Ile Glu Asp Tyr Ala Thr His Asp Phe Ser Ile Gly His
545                    550                    555                    560

Pro Leu Asn Met Pro Ser Phe Ile Pro Thr Ala Thr Ser Pro Asn Gly
                565                    570                    575

Cys Thr Arg Ile Pro Ser Phe Ser Leu Gly Lys Thr His Trp Cys Tyr
                580                    585                    590

Thr His Asn Val Ile Asn Ala Asn Cys Lys Asp His Thr Ser Ser Asn
    595                    600                    605

Gln Tyr Val Ser Met Gly Ile Leu Val Gln Thr Ala Ser Gly Tyr Pro
    610                    615                    620

Met Phe Lys Thr Leu Lys Ile Gln Tyr Leu Ser Asp Gly Leu Asn Arg
625                    630                    635                    640

Lys Ser Cys Ser Ile Ala Thr Val Pro Asp Gly Cys Ala Met Tyr Cys
                645                    650                    655

Tyr Val Ser Thr Gln Leu Glu Thr Asp Asp Tyr Ala Gly Ser Ser Pro
                660                    665                    670

Pro Thr Gln Lys Leu Thr Leu Leu Phe Tyr Asn Asp Thr Val Thr Glu
                675                    680                    685

Arg Thr Ile Ser Pro Ser Gly Leu Glu Gly Asn Trp Ala Thr Leu Val
    690                    695                    700
</pre>

```
Pro Gly Val Gly Ser Gly Ile Tyr Phe Glu Asn Lys Leu Ile Phe Pro
705                     710                 715                 720

Ala Tyr Gly Gly Val Leu Pro Asn Ser Thr Leu Gly Val Lys Ser Ala
                        725                 730                 735

Arg Glu Phe Phe Arg Pro Val Asn Pro Tyr Asn Pro Cys Ser Gly Pro
            740                 745                 750

Gln Gln Asp Leu Asp Gln Arg Ala Leu Arg Ser Tyr Phe Pro Ser Tyr
            755                 760                 765

Phe Ser Asn Arg Arg Ile Gln Ser Ala Phe Leu Val Cys Ala Trp Asn
        770                 775                 780

Gln Ile Leu Val Thr Asn Cys Glu Leu Val Val Pro Ser Ser Asn Gln
785                     790                 795                 800

Thr Met Met Gly Ala Glu Gly Arg Val Leu Leu Ile Asn Asn Arg Leu
                    805                 810                 815

Leu Tyr Tyr Gln Arg Ser Thr Ser Trp Trp Pro Tyr Glu Leu Leu Tyr
            820                 825                 830

Glu Ile Ser Phe Thr Phe Thr Asn Ser Gly Pro Ser Ser Val Asn Met
            835                 840                 845

Ser Trp Ile Pro Ile Tyr Ser Phe Thr Arg Pro Gly Ser Gly Asn Cys
        850                 855                 860

Ser Gly Glu Asn Val Cys Pro Thr Ala Cys Val Ser Gly Val Tyr Leu
865                     870                 875                 880

Asp Pro Trp Pro Leu Thr Pro Tyr Ser His Gln Ser Gly Ile Asn Arg
                    885                 890                 895

Asn Phe Tyr Phe Thr Gly Ala Leu Leu Asn Ser Ser Thr Thr Arg Val
            900                 905                 910

Asn Pro Thr Leu Tyr Val Ser Ala Leu Asn Asn Leu Lys Val Leu Ala
            915                 920                 925

Pro Tyr Gly Thr Gln Gly Leu Phe Ala Ser Tyr Thr Thr Thr Thr Cys
        930                 935                 940

Phe Gln Asp Thr Gly Asp Ala Ser Val Tyr Cys Val Tyr Ile Met Glu
945                     950                 955                 960

Leu Ala Ser Asn Ile Val Gly Glu Phe Gln Ile Leu Pro Val Leu Thr
                    965                 970                 975

Arg Leu Thr Ile Thr
                980
```

```
<210> SEQ ID NO 86
<211> LENGTH: 580
<212> TYPE: PRT
<213> ORGANISM: Artificial sequence
<220> FEATURE:
<223> OTHER INFORMATION: Recombinant H protein

<400> SEQUENCE: 86

Met Tyr Ser Met Gln Leu Ala Ser Cys Val Thr Leu Thr Leu Val Leu
1               5                   10                  15

Leu Val Asn Ser Gln Arg Leu His Arg Ala Ala Ile Tyr Thr Ala Glu
                20                  25                  30

Ile His Lys Ser Leu Ser Thr Asn Leu Asp Val Thr Asn Ser Ile Glu
            35                  40                  45

His Gln Val Lys Asp Val Leu Thr Pro Leu Phe Lys Ile Ile Gly Asp
        50                  55                  60

Glu Val Gly Leu Arg Thr Pro Gln Arg Phe Thr Asp Leu Val Lys Phe
65                  70                  75                  80
```

-continued

```
Ile Ser Asp Lys Ile Lys Phe Leu Asn Pro Asp Arg Glu Tyr Asp Phe
            85              90              95

Arg Asp Leu Thr Trp Cys Ile Asn Pro Pro Glu Arg Ile Lys Leu Asp
            100             105             110

Tyr Asp Gln Tyr Cys Ala Asp Val Ala Ala Glu Glu Leu Met Asn Ala
            115             120             125

Leu Val Asn Ser Thr Leu Leu Glu Thr Arg Thr Thr Asn Gln Phe Leu
        130             135             140

Ala Val Ser Lys Gly Asn Cys Ser Gly Pro Thr Thr Ile Arg Gly Gln
145             150             155             160

Phe Ser Asn Met Ser Leu Ser Leu Leu Asp Leu Tyr Leu Gly Arg Gly
                165             170             175

Tyr Asn Val Ser Ser Ile Val Thr Met Thr Ser Gln Gly Met Tyr Gly
            180             185             190

Gly Thr Tyr Leu Val Glu Lys Pro Asn Leu Ser Ser Lys Arg Ser Glu
            195             200             205

Leu Ser Gln Leu Ser Met Tyr Arg Val Phe Glu Val Gly Val Ile Arg
        210             215             220

Asn Pro Gly Leu Gly Ala Pro Val Phe His Met Thr Asn Tyr Leu Glu
225             230             235             240

Gln Pro Val Ser Asn Asp Leu Ser Asn Cys Met Val Ala Leu Gly Glu
                245             250             255

Leu Lys Leu Ala Ala Leu Cys His Gly Glu Asp Ser Ile Thr Ile Pro
            260             265             270

Tyr Gln Gly Ser Gly Lys Gly Val Ser Phe Gln Leu Val Lys Leu Gly
            275             280             285

Val Trp Lys Ser Pro Thr Asp Met Gln Ser Trp Val Pro Leu Ser Thr
        290             295             300

Asp Asp Pro Val Ile Asp Arg Leu Tyr Leu Ser Ser His Arg Gly Val
305             310             315             320

Ile Ala Asp Asn Gln Ala Lys Trp Ala Val Pro Thr Thr Arg Thr Asp
                325             330             335

Asp Lys Leu Arg Met Glu Thr Cys Phe Gln Gln Ala Cys Lys Gly Lys
            340             345             350

Ile Gln Ala Leu Cys Glu Asn Pro Glu Trp Ala Pro Leu Lys Asp Asn
            355             360             365

Arg Ile Pro Ser Tyr Gly Val Leu Ser Val Asp Leu Ser Leu Thr Val
        370             375             380

Glu Leu Lys Ile Lys Ile Ala Ser Gly Phe Gly Pro Leu Ile Thr His
385             390             395             400

Gly Ser Gly Met Asp Leu Tyr Lys Ser Asn His Asn Asn Val Tyr Trp
                405             410             415

Leu Thr Ile Pro Pro Met Lys Asn Leu Ala Leu Gly Val Ile Asn Thr
            420             425             430

Leu Glu Trp Ile Pro Arg Phe Lys Val Ser Pro Tyr Leu Phe Asn Val
            435             440             445

Pro Ile Lys Glu Ala Gly Glu Asp Cys His Ala Pro Thr Tyr Leu Pro
        450             455             460

Ala Glu Val Asp Gly Asp Val Lys Leu Ser Ser Asn Leu Val Ile Leu
465             470             475             480

Pro Gly Gln Asp Leu Gln Tyr Val Leu Ala Thr Tyr Asp Thr Ser Arg
                485             490             495
```

-continued

```
Val Glu His Ala Val Val Tyr Tyr Val Tyr Ser Pro Ser Arg Ser Phe
        500             505             510

Ser Tyr Phe Tyr Pro Phe Arg Leu Pro Ile Lys Gly Val Pro Ile Glu
        515             520             525

Leu Gln Val Glu Cys Phe Thr Trp Asp Gln Lys Leu Trp Cys Arg His
        530             535             540

Phe Cys Val Leu Ala Asp Ser Glu Ser Gly Gly His Ile Thr His Ser
545             550             555             560

Gly Met Glu Gly Met Gly Val Ser Cys Thr Val Thr Arg Glu Asp Gly
                565             570             575

Thr Asn Arg Arg
                580
```

```
<210> SEQ ID NO 87
<211> LENGTH: 577
<212> TYPE: PRT
<213> ORGANISM: Artificial sequence
<220> FEATURE:
<223> OTHER INFORMATION: Recombinant H protein

<400> SEQUENCE: 87
```

```
Met Tyr Ser Met Gln Leu Ala Ser Cys Val Thr Leu Thr Leu Val Leu
1               5               10              15

Leu Val Asn Ser Gln Arg Ala Ala Ile Tyr Thr Ala Glu Ile His Lys
                20              25              30

Ser Leu Ser Thr Asn Leu Asp Val Thr Asn Ser Ile Glu His Gln Val
        35              40              45

Lys Asp Val Leu Thr Pro Leu Phe Lys Ile Ile Gly Asp Glu Val Gly
        50              55              60

Leu Arg Thr Pro Gln Arg Phe Thr Asp Leu Val Lys Phe Ile Ser Asp
65              70              75              80

Lys Ile Lys Phe Leu Asn Pro Asp Arg Glu Tyr Asp Phe Arg Asp Leu
                85              90              95

Thr Trp Cys Ile Asn Pro Pro Glu Arg Ile Lys Leu Asp Tyr Asp Gln
                100             105             110

Tyr Cys Ala Asp Val Ala Ala Glu Glu Leu Met Asn Ala Leu Val Asn
        115             120             125

Ser Thr Leu Leu Glu Thr Arg Thr Thr Asn Gln Phe Leu Ala Val Ser
        130             135             140

Lys Gly Asn Cys Ser Gly Pro Thr Thr Ile Arg Gly Gln Phe Ser Asn
145             150             155             160

Met Ser Leu Ser Leu Leu Asp Leu Tyr Leu Gly Arg Gly Tyr Asn Val
                165             170             175

Ser Ser Ile Val Thr Met Thr Ser Gln Gly Met Tyr Gly Gly Thr Tyr
                180             185             190

Leu Val Glu Lys Pro Asn Leu Ser Ser Lys Arg Ser Glu Leu Ser Gln
        195             200             205

Leu Ser Met Tyr Arg Val Phe Glu Val Gly Val Ile Arg Asn Pro Gly
        210             215             220

Leu Gly Ala Pro Val Phe His Met Thr Asn Tyr Leu Glu Gln Pro Val
225             230             235             240

Ser Asn Asp Leu Ser Asn Cys Met Val Ala Leu Gly Glu Leu Lys Leu
                245             250             255

Ala Ala Leu Cys His Gly Glu Asp Ser Ile Thr Ile Pro Tyr Gln Gly
        260             265             270
```

-continued

```
Ser Gly Lys Gly Val Ser Phe Gln Leu Val Lys Leu Gly Val Trp Lys
        275                 280                 285

Ser Pro Thr Asp Met Gln Ser Trp Val Pro Leu Ser Thr Asp Asp Pro
        290                 295                 300

Val Ile Asp Arg Leu Tyr Leu Ser Ser His Arg Gly Val Ile Ala Asp
305                 310                 315                 320

Asn Gln Ala Lys Trp Ala Val Pro Thr Thr Arg Thr Asp Asp Lys Leu
                325                 330                 335

Arg Met Glu Thr Cys Phe Gln Gln Ala Cys Lys Gly Lys Ile Gln Ala
        340                 345                 350

Leu Cys Glu Asn Pro Glu Trp Ala Pro Leu Lys Asp Asn Arg Ile Pro
        355                 360                 365

Ser Tyr Gly Val Leu Ser Val Asp Leu Ser Leu Thr Val Glu Leu Lys
        370                 375                 380

Ile Lys Ile Ala Ser Gly Phe Gly Pro Leu Ile Thr His Gly Ser Gly
385                 390                 395                 400

Met Asp Leu Tyr Lys Ser Asn His Asn Asn Val Tyr Trp Leu Thr Ile
                405                 410                 415

Pro Pro Met Lys Asn Leu Ala Leu Gly Val Ile Asn Thr Leu Glu Trp
                420                 425                 430

Ile Pro Arg Phe Lys Val Ser Pro Tyr Leu Phe Asn Val Pro Ile Lys
        435                 440                 445

Glu Ala Gly Glu Asp Cys His Ala Pro Thr Tyr Leu Pro Ala Glu Val
        450                 455                 460

Asp Gly Asp Val Lys Leu Ser Ser Asn Leu Val Ile Leu Pro Gly Gln
465                 470                 475                 480

Asp Leu Gln Tyr Val Leu Ala Thr Tyr Asp Thr Ser Arg Val Glu His
                485                 490                 495

Ala Val Val Tyr Tyr Val Tyr Ser Pro Ser Arg Ser Phe Ser Tyr Phe
                500                 505                 510

Tyr Pro Phe Arg Leu Pro Ile Lys Gly Val Pro Ile Glu Leu Gln Val
        515                 520                 525

Glu Cys Phe Thr Trp Asp Gln Lys Leu Trp Cys Arg His Phe Cys Val
        530                 535                 540

Leu Ala Asp Ser Glu Ser Gly Gly His Ile Thr His Ser Gly Met Glu
545                 550                 555                 560

Gly Met Gly Val Ser Cys Thr Val Thr Arg Glu Asp Gly Thr Asn Arg
                565                 570                 575

Arg
```

```
<210> SEQ ID NO 88
<211> LENGTH: 579
<212> TYPE: PRT
<213> ORGANISM: Artificial sequence
<220> FEATURE:
<223> OTHER INFORMATION: Recombinant H protein

<400> SEQUENCE: 88

Met Tyr Ser Met Gln Leu Ala Ser Cys Val Thr Leu Thr Leu Val Leu
1                   5                   10                  15

Leu Val Asn Ser Gln Leu His Arg Ala Ala Ile Tyr Thr Ala Glu Ile
                20                  25                  30

His Lys Ser Leu Ser Thr Asn Leu Asp Val Thr Asn Ser Ile Glu His
        35                  40                  45

Gln Val Lys Asp Val Leu Thr Pro Leu Phe Lys Ile Ile Gly Asp Glu
```

-continued

```
          50                55                60

Val Gly Leu Arg Thr Pro Gln Arg Phe Thr Asp Leu Val Lys Phe Ile
65                  70                75                80

Ser Asp Lys Ile Lys Phe Leu Asn Pro Asp Arg Glu Tyr Asp Phe Arg
                85                90                95

Asp Leu Thr Trp Cys Ile Asn Pro Pro Glu Arg Ile Lys Leu Asp Tyr
              100               105               110

Asp Gln Tyr Cys Ala Asp Val Ala Ala Glu Glu Leu Met Asn Ala Leu
          115               120               125

Val Asn Ser Thr Leu Leu Glu Thr Arg Thr Thr Asn Gln Phe Leu Ala
      130               135               140

Val Ser Lys Gly Asn Cys Ser Gly Pro Thr Thr Ile Arg Gly Gln Phe
145               150               155               160

Ser Asn Met Ser Leu Ser Leu Leu Asp Leu Tyr Leu Gly Arg Gly Tyr
              165               170               175

Asn Val Ser Ser Ile Val Thr Met Thr Ser Gln Gly Met Tyr Gly Gly
              180               185               190

Thr Tyr Leu Val Glu Lys Pro Asn Leu Ser Ser Lys Arg Ser Glu Leu
          195               200               205

Ser Gln Leu Ser Met Tyr Arg Val Phe Glu Val Gly Val Ile Arg Asn
      210               215               220

Pro Gly Leu Gly Ala Pro Val Phe His Met Thr Asn Tyr Leu Glu Gln
225               230               235               240

Pro Val Ser Asn Asp Leu Ser Asn Cys Met Val Ala Leu Gly Glu Leu
              245               250               255

Lys Leu Ala Ala Leu Cys His Gly Glu Asp Ser Ile Thr Ile Pro Tyr
              260               265               270

Gln Gly Ser Gly Lys Gly Val Ser Phe Gln Leu Val Lys Leu Gly Val
              275               280               285

Trp Lys Ser Pro Thr Asp Met Gln Ser Trp Val Pro Leu Ser Thr Asp
      290               295               300

Asp Pro Val Ile Asp Arg Leu Tyr Leu Ser Ser His Arg Gly Val Ile
305               310               315               320

Ala Asp Asn Gln Ala Lys Trp Ala Val Pro Thr Thr Arg Thr Asp Asp
              325               330               335

Lys Leu Arg Met Glu Thr Cys Phe Gln Gln Ala Cys Lys Gly Lys Ile
              340               345               350

Gln Ala Leu Cys Glu Asn Pro Glu Trp Ala Pro Leu Lys Asp Asn Arg
          355               360               365

Ile Pro Ser Tyr Gly Val Leu Ser Val Asp Leu Ser Leu Thr Val Glu
      370               375               380

Leu Lys Ile Lys Ile Ala Ser Gly Phe Gly Pro Leu Ile Thr His Gly
385               390               395               400

Ser Gly Met Asp Leu Tyr Lys Ser Asn His Asn Asn Val Tyr Trp Leu
              405               410               415

Thr Ile Pro Pro Met Lys Asn Leu Ala Leu Gly Val Ile Asn Thr Leu
              420               425               430

Glu Trp Ile Pro Arg Phe Lys Val Ser Pro Tyr Leu Phe Asn Val Pro
              435               440               445

Ile Lys Glu Ala Gly Glu Asp Cys His Ala Pro Thr Tyr Leu Pro Ala
      450               455               460

Glu Val Asp Gly Asp Val Lys Leu Ser Ser Asn Leu Val Ile Leu Pro
465               470               475               480
```

-continued

```
Gly Gln Asp Leu Gln Tyr Val Leu Ala Thr Tyr Asp Thr Ser Arg Val
                485                 490                 495

Glu His Ala Val Val Tyr Tyr Val Tyr Ser Pro Ser Arg Ser Phe Ser
                500                 505                 510

Tyr Phe Tyr Pro Phe Arg Leu Pro Ile Lys Gly Val Pro Ile Glu Leu
                515             520                 525

Gln Val Glu Cys Phe Thr Trp Asp Gln Lys Leu Trp Cys Arg His Phe
        530                 535             540

Cys Val Leu Ala Asp Ser Glu Ser Gly Gly His Ile Thr His Ser Gly
545                 550                 555                 560

Met Glu Gly Met Gly Val Ser Cys Thr Val Thr Arg Glu Asp Gly Thr
                565                 570                 575

Asn Arg Arg
```

```
<210> SEQ ID NO 89
<211> LENGTH: 572
<212> TYPE: PRT
<213> ORGANISM: Artificial sequence
<220> FEATURE:
<223> OTHER INFORMATION: Recombinant H protein

<400> SEQUENCE: 89
```

```
Met Tyr Ser Met Gln Leu Ala Ser Cys Val Thr Leu Thr Leu Val Leu
1               5                   10                  15

Leu Val Asn Ser Gln Thr Ala Glu Ile His Lys Ser Leu Ser Thr Asn
                20                  25                  30

Leu Asp Val Thr Asn Ser Ile Glu His Gln Val Lys Asp Val Leu Thr
                35                  40                  45

Pro Leu Phe Lys Ile Ile Gly Asp Glu Val Gly Leu Arg Thr Pro Gln
        50                  55                  60

Arg Phe Thr Asp Leu Val Lys Phe Ile Ser Asp Lys Ile Lys Phe Leu
65                  70                  75                  80

Asn Pro Asp Arg Glu Tyr Asp Phe Arg Asp Leu Thr Trp Cys Ile Asn
                85                  90                  95

Pro Pro Glu Arg Ile Lys Leu Asp Tyr Asp Gln Tyr Cys Ala Asp Val
                100                 105                 110

Ala Ala Glu Glu Leu Met Asn Ala Leu Val Asn Ser Thr Leu Leu Glu
                115                 120                 125

Thr Arg Thr Thr Asn Gln Phe Leu Ala Val Ser Lys Gly Asn Cys Ser
        130                 135                 140

Gly Pro Thr Thr Ile Arg Gly Gln Phe Ser Asn Met Ser Leu Ser Leu
145                 150                 155                 160

Leu Asp Leu Tyr Leu Gly Arg Gly Tyr Asn Val Ser Ser Ile Val Thr
                165                 170                 175

Met Thr Ser Gln Gly Met Tyr Gly Gly Thr Tyr Leu Val Glu Lys Pro
                180                 185                 190

Asn Leu Ser Ser Lys Arg Ser Glu Leu Ser Gln Leu Ser Met Tyr Arg
                195                 200                 205

Val Phe Glu Val Gly Val Ile Arg Asn Pro Gly Leu Gly Ala Pro Val
        210                 215                 220

Phe His Met Thr Asn Tyr Leu Glu Gln Pro Val Ser Asn Asp Leu Ser
225                 230                 235                 240

Asn Cys Met Val Ala Leu Gly Glu Leu Lys Leu Ala Ala Leu Cys His
                245                 250                 255
```

```
Gly Glu Asp Ser Ile Thr Ile Pro Tyr Gln Gly Ser Gly Lys Gly Val
            260                 265                 270

Ser Phe Gln Leu Val Lys Leu Gly Val Trp Lys Ser Pro Thr Asp Met
            275                 280                 285

Gln Ser Trp Val Pro Leu Ser Thr Asp Asp Pro Val Ile Asp Arg Leu
            290                 295                 300

Tyr Leu Ser Ser His Arg Gly Val Ile Ala Asp Asn Gln Ala Lys Trp
305                 310                 315                 320

Ala Val Pro Thr Thr Arg Thr Asp Asp Lys Leu Arg Met Glu Thr Cys
                325                 330                 335

Phe Gln Gln Ala Cys Lys Gly Lys Ile Gln Ala Leu Cys Glu Asn Pro
            340                 345                 350

Glu Trp Ala Pro Leu Lys Asp Asn Arg Ile Pro Ser Tyr Gly Val Leu
            355                 360                 365

Ser Val Asp Leu Ser Leu Thr Val Glu Leu Lys Ile Lys Ile Ala Ser
            370                 375                 380

Gly Phe Gly Pro Leu Ile Thr His Gly Ser Gly Met Asp Leu Tyr Lys
385                 390                 395                 400

Ser Asn His Asn Asn Val Tyr Trp Leu Thr Ile Pro Pro Met Lys Asn
                405                 410                 415

Leu Ala Leu Gly Val Ile Asn Thr Leu Glu Trp Ile Pro Arg Phe Lys
            420                 425                 430

Val Ser Pro Tyr Leu Phe Asn Val Pro Ile Lys Glu Ala Gly Glu Asp
            435                 440                 445

Cys His Ala Pro Thr Tyr Leu Pro Ala Glu Val Asp Gly Asp Val Lys
            450                 455                 460

Leu Ser Ser Asn Leu Val Ile Leu Pro Gly Gln Asp Leu Gln Tyr Val
465                 470                 475                 480

Leu Ala Thr Tyr Asp Thr Ser Arg Val Glu His Ala Val Val Tyr Tyr
                485                 490                 495

Val Tyr Ser Pro Ser Arg Ser Phe Ser Tyr Phe Tyr Pro Phe Arg Leu
            500                 505                 510

Pro Ile Lys Gly Val Pro Ile Glu Leu Gln Val Glu Cys Phe Thr Trp
            515                 520                 525

Asp Gln Lys Leu Trp Cys Arg His Phe Cys Val Leu Ala Asp Ser Glu
            530                 535                 540

Ser Gly Gly His Ile Thr His Ser Gly Met Glu Gly Met Gly Val Ser
545                 550                 555                 560

Cys Thr Val Thr Arg Glu Asp Gly Thr Asn Arg Arg
                565                 570
```

<210> SEQ ID NO 90
<211> LENGTH: 550
<212> TYPE: PRT
<213> ORGANISM: Artificial sequence
<220> FEATURE:
<223> OTHER INFORMATION: Recombinant HN protein

<400> SEQUENCE: 90

```
Met Tyr Ser Met Gln Leu Ala Ser Cys Val Thr Leu Thr Leu Val Leu
1               5                   10                  15

Leu Val Asn Ser Gln Glu Leu Val Arg Met Ile Asn Asp Gln Gly Leu
            20                  25                  30

Ser Asn Gln Leu Ser Ser Ile Thr Asp Lys Ile Arg Glu Ser Ala Thr
            35                  40                  45
```

-continued

```
Met Ile Ala Ser Ala Val Gly Val Met Asn Gln Val Ile His Gly Val
    50                  55                  60

Thr Val Ser Leu Pro Leu Gln Ile Glu Gly Asn Gln Asn Gln Leu Leu
65                  70                  75                  80

Ala Thr Leu Ala Thr Ile Cys Thr Ser Gln Lys Gln Val Ser Asn Cys
                85                  90                  95

Ser Thr Asn Ile Pro Leu Val Asn Asp Leu Arg Phe Ile Asn Gly Ile
                100                 105                 110

Asn Lys Phe Ile Ile Glu Asp Tyr Ala Thr His Asp Phe Ser Ile Gly
            115                 120                 125

His Pro Leu Asn Met Pro Ser Phe Ile Pro Thr Ala Thr Ser Pro Asn
    130                 135                 140

Gly Cys Thr Arg Ile Pro Ser Phe Ser Leu Gly Lys Thr His Trp Cys
145                 150                 155                 160

Tyr Thr His Asn Val Ile Asn Ala Asn Cys Lys Asp His Thr Ser Ser
                165                 170                 175

Asn Gln Tyr Val Ser Met Gly Ile Leu Val Gln Thr Ala Ser Gly Tyr
            180                 185                 190

Pro Met Phe Lys Thr Leu Lys Ile Gln Tyr Leu Ser Asp Gly Leu Asn
    195                 200                 205

Arg Lys Ser Cys Ser Ile Ala Thr Val Pro Asp Gly Cys Ala Met Tyr
    210                 215                 220

Cys Tyr Val Ser Thr Gln Leu Glu Thr Asp Asp Tyr Ala Gly Ser Ser
225                 230                 235                 240

Pro Pro Thr Gln Lys Leu Thr Leu Leu Phe Tyr Asn Asp Thr Val Thr
                245                 250                 255

Glu Arg Thr Ile Ser Pro Ser Gly Leu Glu Gly Asn Trp Ala Thr Leu
            260                 265                 270

Val Pro Gly Val Gly Ser Gly Ile Tyr Phe Glu Asn Lys Leu Ile Phe
    275                 280                 285

Pro Ala Tyr Gly Gly Val Leu Pro Asn Ser Thr Leu Gly Val Lys Ser
    290                 295                 300

Ala Arg Glu Phe Phe Arg Pro Val Asn Pro Tyr Asn Pro Cys Ser Gly
305                 310                 315                 320

Pro Gln Gln Asp Leu Asp Gln Arg Ala Leu Arg Ser Tyr Phe Pro Ser
                325                 330                 335

Tyr Phe Ser Asn Arg Arg Ile Gln Ser Ala Phe Leu Val Cys Ala Trp
            340                 345                 350

Asn Gln Ile Leu Val Thr Asn Cys Glu Leu Val Val Pro Ser Ser Asn
            355                 360                 365

Gln Thr Met Met Gly Ala Glu Gly Arg Val Leu Leu Ile Asn Asn Arg
    370                 375                 380

Leu Leu Tyr Tyr Gln Arg Ser Thr Ser Trp Trp Pro Tyr Glu Leu Leu
385                 390                 395                 400

Tyr Glu Ile Ser Phe Thr Phe Thr Asn Ser Gly Pro Ser Ser Val Asn
                405                 410                 415

Met Ser Trp Ile Pro Ile Tyr Ser Phe Thr Arg Pro Gly Ser Gly Asn
            420                 425                 430

Cys Ser Gly Glu Asn Val Cys Pro Thr Ala Cys Val Ser Gly Val Tyr
            435                 440                 445

Leu Asp Pro Trp Pro Leu Thr Pro Tyr Ser His Gln Ser Gly Ile Asn
    450                 455                 460

Arg Asn Phe Tyr Phe Thr Gly Ala Leu Leu Asn Ser Ser Thr Thr Arg
```

```
465               470               475               480

Val Asn Pro Thr Leu Tyr Val Ser Ala Leu Asn Asn Leu Lys Val Leu
                485               490               495

Ala Pro Tyr Gly Thr Gln Gly Leu Phe Ala Ser Tyr Thr Thr Thr Thr
                500               505               510

Cys Phe Gln Asp Thr Gly Asp Ala Ser Val Tyr Cys Val Tyr Ile Met
                515               520               525

Glu Leu Ala Ser Asn Ile Val Gly Glu Phe Gln Ile Leu Pro Val Leu
                530               535               540

Thr Arg Leu Thr Ile Thr
545               550

<210> SEQ ID NO 91
<211> LENGTH: 543
<212> TYPE: PRT
<213> ORGANISM: Artificial sequence
<220> FEATURE:
<223> OTHER INFORMATION: Recombinant HN protein

<400> SEQUENCE: 91

Met Tyr Ser Met Gln Leu Ala Ser Cys Val Thr Leu Thr Leu Val Leu
1               5               10               15

Leu Val Asn Ser Gln Asp Gln Gly Leu Ser Asn Gln Leu Ser Ser Ile
                20               25               30

Thr Asp Lys Ile Arg Glu Ser Ala Thr Met Ile Ala Ser Ala Val Gly
                35               40               45

Val Met Asn Gln Val Ile His Gly Val Thr Val Ser Leu Pro Leu Gln
                50               55               60

Ile Glu Gly Asn Gln Asn Gln Leu Leu Ala Thr Leu Ala Thr Ile Cys
65               70               75               80

Thr Ser Gln Lys Gln Val Ser Asn Cys Ser Thr Asn Ile Pro Leu Val
                85               90               95

Asn Asp Leu Arg Phe Ile Asn Gly Ile Asn Lys Phe Ile Ile Glu Asp
                100               105               110

Tyr Ala Thr His Asp Phe Ser Ile Gly His Pro Leu Asn Met Pro Ser
                115               120               125

Phe Ile Pro Thr Ala Thr Ser Pro Asn Gly Cys Thr Arg Ile Pro Ser
                130               135               140

Phe Ser Leu Gly Lys Thr His Trp Cys Tyr Thr His Asn Val Ile Asn
145               150               155               160

Ala Asn Cys Lys Asp His Thr Ser Ser Asn Gln Tyr Val Ser Met Gly
                165               170               175

Ile Leu Val Gln Thr Ala Ser Gly Tyr Pro Met Phe Lys Thr Leu Lys
                180               185               190

Ile Gln Tyr Leu Ser Asp Gly Leu Asn Arg Lys Ser Cys Ser Ile Ala
                195               200               205

Thr Val Pro Asp Gly Cys Ala Met Tyr Cys Tyr Val Ser Thr Gln Leu
                210               215               220

Glu Thr Asp Asp Tyr Ala Gly Ser Ser Pro Pro Thr Gln Lys Leu Thr
225               230               235               240

Leu Leu Phe Tyr Asn Asp Thr Val Thr Glu Arg Thr Ile Ser Pro Ser
                245               250               255

Gly Leu Glu Gly Asn Trp Ala Thr Leu Val Pro Gly Val Gly Ser Gly
                260               265               270

Ile Tyr Phe Glu Asn Lys Leu Ile Phe Pro Ala Tyr Gly Gly Val Leu
```

-continued

```
              275                    280                    285
Pro Asn Ser Thr Leu Gly Val Lys Ser Ala Arg Glu Phe Phe Arg Pro
    290                    295                    300

Val Asn Pro Tyr Asn Pro Cys Ser Gly Pro Gln Gln Asp Leu Asp Gln
305                    310                    315                    320

Arg Ala Leu Arg Ser Tyr Phe Pro Ser Tyr Phe Ser Asn Arg Arg Ile
                    325                    330                    335

Gln Ser Ala Phe Leu Val Cys Ala Trp Asn Gln Ile Leu Val Thr Asn
                    340                    345                    350

Cys Glu Leu Val Val Pro Ser Ser Asn Gln Thr Met Met Gly Ala Glu
                    355                    360                    365

Gly Arg Val Leu Leu Ile Asn Asn Arg Leu Leu Tyr Tyr Gln Arg Ser
                    370                    375                    380

Thr Ser Trp Trp Pro Tyr Glu Leu Leu Tyr Glu Ile Ser Phe Thr Phe
385                    390                    395                    400

Thr Asn Ser Gly Pro Ser Ser Val Asn Met Ser Trp Ile Pro Ile Tyr
                    405                    410                    415

Ser Phe Thr Arg Pro Gly Ser Gly Asn Cys Ser Gly Glu Asn Val Cys
                    420                    425                    430

Pro Thr Ala Cys Val Ser Gly Val Tyr Leu Asp Pro Trp Pro Leu Thr
                    435                    440                    445

Pro Tyr Ser His Gln Ser Gly Ile Asn Arg Asn Phe Tyr Phe Thr Gly
    450                    455                    460

Ala Leu Leu Asn Ser Ser Thr Thr Arg Val Asn Pro Thr Leu Tyr Val
465                    470                    475                    480

Ser Ala Leu Asn Asn Leu Lys Val Leu Ala Pro Tyr Gly Thr Gln Gly
                    485                    490                    495

Leu Phe Ala Ser Tyr Thr Thr Thr Thr Cys Phe Gln Asp Thr Gly Asp
                    500                    505                    510

Ala Ser Val Tyr Cys Val Tyr Ile Met Glu Leu Ala Ser Asn Ile Val
                    515                    520                    525

Gly Glu Phe Gln Ile Leu Pro Val Leu Thr Arg Leu Thr Ile Thr
    530                    535                    540
```

```
<210> SEQ ID NO 92
<211> LENGTH: 541
<212> TYPE: PRT
<213> ORGANISM: Artificial sequence
<220> FEATURE:
<223> OTHER INFORMATION: Recombinant HN protein

<400> SEQUENCE: 92

Met Tyr Ser Met Gln Leu Ala Ser Cys Val Thr Leu Thr Leu Val Leu
1                    5                     10                    15

Leu Val Asn Ser Gln Gly Leu Ser Asn Gln Leu Ser Ser Ile Thr Asp
                    20                    25                    30

Lys Ile Arg Glu Ser Ala Thr Met Ile Ala Ser Ala Val Gly Val Met
             35                    40                    45

Asn Gln Val Ile His Gly Val Thr Val Ser Leu Pro Leu Gln Ile Glu
    50                    55                    60

Gly Asn Gln Asn Gln Leu Leu Ala Thr Leu Ala Thr Ile Cys Thr Ser
65                    70                    75                    80

Gln Lys Gln Val Ser Asn Cys Ser Thr Asn Ile Pro Leu Val Asn Asp
                    85                    90                    95

Leu Arg Phe Ile Asn Gly Ile Asn Lys Phe Ile Ile Glu Asp Tyr Ala
```

-continued

```
              100              105              110

Thr His Asp Phe Ser Ile Gly His Pro Leu Asn Met Pro Ser Phe Ile
        115              120              125

Pro Thr Ala Thr Ser Pro Asn Gly Cys Thr Arg Ile Pro Ser Phe Ser
        130              135              140

Leu Gly Lys Thr His Trp Cys Tyr Thr His Asn Val Ile Asn Ala Asn
145              150              155              160

Cys Lys Asp His Thr Ser Ser Asn Gln Tyr Val Ser Met Gly Ile Leu
              165              170              175

Val Gln Thr Ala Ser Gly Tyr Pro Met Phe Lys Thr Leu Lys Ile Gln
        180              185              190

Tyr Leu Ser Asp Gly Leu Asn Arg Lys Ser Cys Ser Ile Ala Thr Val
        195              200              205

Pro Asp Gly Cys Ala Met Tyr Cys Tyr Val Ser Thr Gln Leu Glu Thr
        210              215              220

Asp Asp Tyr Ala Gly Ser Ser Pro Pro Thr Gln Lys Leu Thr Leu Leu
225              230              235              240

Phe Tyr Asn Asp Thr Val Thr Glu Arg Thr Ile Ser Pro Ser Gly Leu
              245              250              255

Glu Gly Asn Trp Ala Thr Leu Val Pro Gly Val Gly Ser Gly Ile Tyr
              260              265              270

Phe Glu Asn Lys Leu Ile Phe Pro Ala Tyr Gly Gly Val Leu Pro Asn
        275              280              285

Ser Thr Leu Gly Val Lys Ser Ala Arg Glu Phe Phe Arg Pro Val Asn
        290              295              300

Pro Tyr Asn Pro Cys Ser Gly Pro Gln Gln Asp Leu Asp Gln Arg Ala
305              310              315              320

Leu Arg Ser Tyr Phe Pro Ser Tyr Phe Ser Asn Arg Arg Ile Gln Ser
              325              330              335

Ala Phe Leu Val Cys Ala Trp Asn Gln Ile Leu Val Thr Asn Cys Glu
              340              345              350

Leu Val Val Pro Ser Ser Asn Gln Thr Met Met Gly Ala Glu Gly Arg
        355              360              365

Val Leu Leu Ile Asn Asn Arg Leu Leu Tyr Tyr Gln Arg Ser Thr Ser
        370              375              380

Trp Trp Pro Tyr Glu Leu Leu Tyr Glu Ile Ser Phe Thr Phe Thr Asn
385              390              395              400

Ser Gly Pro Ser Ser Val Asn Met Ser Trp Ile Pro Ile Tyr Ser Phe
              405              410              415

Thr Arg Pro Gly Ser Gly Asn Cys Ser Gly Glu Asn Val Cys Pro Thr
              420              425              430

Ala Cys Val Ser Gly Val Tyr Leu Asp Pro Trp Pro Leu Thr Pro Tyr
              435              440              445

Ser His Gln Ser Gly Ile Asn Arg Asn Phe Tyr Phe Thr Gly Ala Leu
        450              455              460

Leu Asn Ser Ser Thr Thr Arg Val Asn Pro Thr Leu Tyr Val Ser Ala
465              470              475              480

Leu Asn Asn Leu Lys Val Leu Ala Pro Tyr Gly Thr Gln Gly Leu Phe
              485              490              495

Ala Ser Tyr Thr Thr Thr Thr Cys Phe Gln Asp Thr Gly Asp Ala Ser
              500              505              510

Val Tyr Cys Val Tyr Ile Met Glu Leu Ala Ser Asn Ile Val Gly Glu
              515              520              525
```

-continued

```
Phe Gln Ile Leu Pro Val Leu Thr Arg Leu Thr Ile Thr
    530             535             540

<210> SEQ ID NO 93
<211> LENGTH: 549
<212> TYPE: PRT
<213> ORGANISM: Artificial sequence
<220> FEATURE:
<223> OTHER INFORMATION: Recombinant HN protein

<400> SEQUENCE: 93

Met Tyr Ser Met Gln Leu Ala Ser Cys Val Thr Leu Thr Leu Val Leu
1               5                   10                  15

Leu Val Asn Ser Gln Leu Val Arg Met Ile Asn Asp Gln Gly Leu Ser
            20                  25                  30

Asn Gln Leu Ser Ser Ile Thr Asp Lys Ile Arg Glu Ser Ala Thr Met
        35                  40                  45

Ile Ala Ser Ala Val Gly Val Met Asn Gln Val Ile His Gly Val Thr
    50                  55                  60

Val Ser Leu Pro Leu Gln Ile Glu Gly Asn Gln Asn Gln Leu Leu Ala
65                  70                  75                  80

Thr Leu Ala Thr Ile Cys Thr Ser Gln Lys Gln Val Ser Asn Cys Ser
                85                  90                  95

Thr Asn Ile Pro Leu Val Asn Asp Leu Arg Phe Ile Asn Gly Ile Asn
            100                 105                 110

Lys Phe Ile Ile Glu Asp Tyr Ala Thr His Asp Phe Ser Ile Gly His
        115                 120                 125

Pro Leu Asn Met Pro Ser Phe Ile Pro Thr Ala Thr Ser Pro Asn Gly
    130                 135                 140

Cys Thr Arg Ile Pro Ser Phe Ser Leu Gly Lys Thr His Trp Cys Tyr
145                 150                 155                 160

Thr His Asn Val Ile Asn Ala Asn Cys Lys Asp His Thr Ser Ser Asn
                165                 170                 175

Gln Tyr Val Ser Met Gly Ile Leu Val Gln Thr Ala Ser Gly Tyr Pro
            180                 185                 190

Met Phe Lys Thr Leu Lys Ile Gln Tyr Leu Ser Asp Gly Leu Asn Arg
        195                 200                 205

Lys Ser Cys Ser Ile Ala Thr Val Pro Asp Gly Cys Ala Met Tyr Cys
    210                 215                 220

Tyr Val Ser Thr Gln Leu Glu Thr Asp Asp Tyr Ala Gly Ser Ser Pro
225                 230                 235                 240

Pro Thr Gln Lys Leu Thr Leu Leu Phe Tyr Asn Asp Thr Val Thr Glu
                245                 250                 255

Arg Thr Ile Ser Pro Ser Gly Leu Glu Gly Asn Trp Ala Thr Leu Val
            260                 265                 270

Pro Gly Val Gly Ser Gly Ile Tyr Phe Glu Asn Lys Leu Ile Phe Pro
        275                 280                 285

Ala Tyr Gly Gly Val Leu Pro Asn Ser Thr Leu Gly Val Lys Ser Ala
    290                 295                 300

Arg Glu Phe Phe Arg Pro Val Asn Pro Tyr Asn Pro Cys Ser Gly Pro
305                 310                 315                 320

Gln Gln Asp Leu Asp Gln Arg Ala Leu Arg Ser Tyr Phe Pro Ser Tyr
                325                 330                 335

Phe Ser Asn Arg Arg Ile Gln Ser Ala Phe Leu Val Cys Ala Trp Asn
            340                 345                 350
```

-continued

```
Gln Ile Leu Val Thr Asn Cys Glu Leu Val Val Pro Ser Ser Asn Gln
        355                 360                 365

Thr Met Met Gly Ala Glu Gly Arg Val Leu Leu Ile Asn Asn Arg Leu
        370                 375                 380

Leu Tyr Tyr Gln Arg Ser Thr Ser Trp Trp Pro Tyr Glu Leu Leu Tyr
385                 390                 395                 400

Glu Ile Ser Phe Thr Phe Thr Asn Ser Gly Pro Ser Ser Val Asn Met
                405                 410                 415

Ser Trp Ile Pro Ile Tyr Ser Phe Thr Arg Pro Gly Ser Gly Asn Cys
                420                 425                 430

Ser Gly Glu Asn Val Cys Pro Thr Ala Cys Val Ser Gly Val Tyr Leu
        435                 440                 445

Asp Pro Trp Pro Leu Thr Pro Tyr Ser His Gln Ser Gly Ile Asn Arg
        450                 455                 460

Asn Phe Tyr Phe Thr Gly Ala Leu Leu Asn Ser Ser Thr Thr Arg Val
465                 470                 475                 480

Asn Pro Thr Leu Tyr Val Ser Ala Leu Asn Asn Leu Lys Val Leu Ala
                485                 490                 495

Pro Tyr Gly Thr Gln Gly Leu Phe Ala Ser Tyr Thr Thr Thr Thr Cys
                500                 505                 510

Phe Gln Asp Thr Gly Asp Ala Ser Val Tyr Cys Val Tyr Ile Met Glu
        515                 520                 525

Leu Ala Ser Asn Ile Val Gly Glu Phe Gln Ile Leu Pro Val Leu Thr
        530                 535                 540

Arg Leu Thr Ile Thr
545

<210> SEQ ID NO 94
<211> LENGTH: 1653
<212> TYPE: DNA
<213> ORGANISM: Measles virus

<400> SEQUENCE: 94
atgggtctca aggtgaacgt ctctgccata ttcatggcag tactgttaac tctccaaaca      60
cccaccggtc aaatccattg gggcaatctc tctaagatag gggtggtagg aataggaagt     120
gcaagctaca aagttatgac tcgttccagc catcaatcat tagtcataaa attaatgccc     180
aatataactc tcctcaataa ctgcacgagg gtagagattg cagaatacag gagactactg     240
agaacagttt tggaaccaat tagagatgca cttaatgcaa tgacccagaa tataagaccg     300
gttcagagtg tagcttcaag taggagacac aagagatttg cgggagtagt cctggcaggt     360
gcggccctag gcgttgccac agctgctcag ataacagccg gcattgcact tcaccagtcc     420
atgctgaact ctcaagccat cgacaatctg agagcgagcc tggaaactac taatcaggca     480
attgaggcaa tcagacaagc agggcaggag atgatattgg ctgttcaggg tgtccaagac     540
tacatcaata tgagctgat accgtctatg aaccaactat cttgtgattt aatcggccag     600
aagctcgggc tcaaattgct cagatactat acagaaatcc tgtcattatt tggccccagc     660
ttacgggacc ccatatctgc ggagatatct atccaggctt tgagctatgc gcttggagga     720
gacatcaata aggtgttaga aaagctcgga tacagtggag gtgatttact gggcatctta     780
gagagcagag aataaaggc ccggataact cacgtcgaca cagagtccta cttaattgtc     840
ctcagtatag cctatccgac gctgtccgag attaaggggg tgattgtcca ccggctagag     900
ggggtctcgt acaacatagg ctctcaagag tggtatacca ctgtgcccaa gtatgttgca     960
```

-continued

```
acccaagggt accttatctc gaattttgat gagtcatcgt gtactttcat gccagagggg      1020
actgtgtgca gccaaaatgc cttgtacccg atgagtcctc tgctccaaga atgcctccgg      1080
gggtccacca agtcctgtgc tcgtacactc gtatccgggt cttttgggaa ccggttcatt      1140
ttatcacaag ggaacctaat agccaattgt gcatcaatcc tttgcaagtg ttacacaaca      1200
ggaacgatca ttaatcaaga ccctgacaag atcctaacat acattgctgc cgatcactgc      1260
ccggtagtcg aggtgaacgg cgtgaccatc caagtcggga gcaggaggta tccagacgct      1320
gtgtacttgc acagaattga cctcggtcct cccatattat tggagaggtt ggacgtaggg      1380
acaaatctgg ggaatgcaat tgctaagttg gaggatgcca aggaattgtt ggagtcatcg      1440
gaccagatat tgaggagtat gaaaggttta tcgagcactt gcatagtcta catcctgatt      1500
gcagtgtgtc ttggagggtt gatagggatc cccgctttaa tatgttgctg caggggggcgt      1560 tgtaacaaaa agggagaaca agttggtatg tcaagaccag gcctaaagcc tgatcttacg      1620
ggaacatcaa aatcctatgt aaggtcgctc tga      1653
```

<210> SEQ ID NO 95
<211> LENGTH: 1617
<212> TYPE: DNA
<213> ORGANISM: Mumps virus

<400> SEQUENCE: 95

```
atgaaggcct tttcagttac ttgcttgggc tttgcagtct tttcgtcttc tatatgtgtg        60
aatatcaaca tcttgcagca aattggatat atcaagcaac aagtcaggca actaagctat       120
tactcacaaa gttctagctc ctacatagtg gtcaagcttt taccgaatat ccaacccact       180
gataacagct gtgaatttaa gagtgtaact caatacaata agaccttgag taacttgctt       240
cttcccattg cagaaaacat aaacaatatt gcatcgccct cacctgggtc aagacgtcat       300
aaaaggtttg ctggcattgc cattggcatt gctgcgctcg tgttgcgac cgcagcacag       360 gtaactgccg ctgtctcatt agttcaagca cagacaaatg cacgtgcaat agcggcgatg       420
aaaaattcaa tacaggcaac taatcgggca atcttcgaag tgaaggaagg cacccaacag       480
ttagctatag cggtacaagc aatacaagac cacatcaata ctattatgaa cacccaattg       540
aacaatatgt cttgtcagat ccttgataac cagcttgcaa cctacctagg attatacct        600 acagaattaa caacagtgtt tcagccacaa ttaattaatc cggcattgtc accgattagt       660
atacaagcct tgaggtcttt gcttggaagt atgacgcctg cagtggttca agcaacatta       720
tctacgtcaa tttctgctgc tgaaatacta agtgccggtc taatggaggg tcagattgtt       780
tctgttctgc tagatgagat gcagatgata gtcaagataa atattccaac cattgtcaca       840
caatcaaatg cattggtgat tgacttctac tcaatttcga gctttattaa taatcaagaa       900
tccataattc aattgccaga caggatccta gagatcggga tgaacaatg gagctatcca        960 gctaaaaatt gtaagttgac aagacaccac atattctgcc aatacaatga ggcagagagg      1020
ctgagcctag aatcaaaact atgccttgca ggtaatataa gtgcctgtgt gttctcaccc      1080
atagcaggga gttatatgag gcgatttgta gcactggatg gaacaattgt tgcaaactgt      1140
cgaagtctaa cgtgtctatg caagagtcca tcttatccta taccaacc tgaccatcat        1200 gcagtcacga ccattgatct aaccacatgt caaacattgt ccctagacgg attggacttc      1260
agcattgtct ctctaagcaa catcacttac gctgagaacc ttaccatttc attgtctcaa      1320
acaatcaata ctcaacccat tgacatatca actgaactga gtaaagttaa tgcatccctc      1380
```

-continued

```
caaaatgccg ttaagtacat aaaggagagc aaccatcaac tccaatctgt gagtgtaaat    1440
tccaaaattg gagctataat tgtagcagcc ttagttttga gcatcctgtc aattatcatt    1500
tcgctattgt tttgctgctg ggcttacatt gcaactaaag aaatcagaag aatcaacttc    1560
aaaacaaatc atatcaacac aatatcgagt agtgtcgatg atctcatcag gtactaa      1617

<210> SEQ ID NO 96
<211> LENGTH: 1854
<212> TYPE: DNA
<213> ORGANISM: Measles virus

<400> SEQUENCE: 96
atgtcaccac aacgagaccg gataaatgcc ttctacaaag ataacccca tcccaaggga      60 agtaggatag tcattaacag agaacatctt atgattgata gaccttatgt tttgctggct     120
gttctgtttg tcatgtttct gagcttgatc gggttgctag ccattgcagg cattagactt     180
catcgggcag ccatctacac cgcagagatc cataaaagcc tcagcaccaa tctagatgta     240
actaactcaa tcgagcatca ggtcaaggac gtgctgacac cactcttcaa aatcatcggt     300
gatgaagtgg gcctgaggac acctcagaga ttcactgacc tagtgaaatt catctctgac     360
aagattaaat tccttaatcc ggatagggag tacgacttca gagatctcac ttggtgtatc     420
aacccgccag agagaatcaa attggattat gatcaatact gtgcagatgt ggctgctgaa     480
gagctcatga atgcattggt gaactcaact ctactggaga ccagaacaac caatcagttc     540
ctagctgtct caaagggaaa ctgctcaggg cccactacaa tcagaggtca attctcaaac     600
atgtcgctgt ccctgttaga cttgtattta ggtcgaggtt acaatgtgtc atctatagtc     660
actatgacat cccagggaat gtatggggga acttacctag tggaaaagcc taatctgagc     720
agcaaaaggt cagagttgtc acaactgagc atgtaccgag tgtttgaagt aggtgttatc     780
agaaatccgg gtttgggggc tccggtgttc catatgacaa actatcttga gcaaccagtc     840
agtaatgatc tcagcaactg tatggtggct ttggggagc tcaaactcgc agccctttgt      900
cacggggaag attctatcac aattccctat cagggatcag ggaaaggtgt cagcttccag     960
ctcgtcaagc taggtgtctg gaaatcccca accgacatgc aatcctgggt cccccttatca   1020 acggatgatc cagtgataga caggctttac ctctcatctc acagaggtgt tatcgctgac    1080
aatcaagcaa aatgggctgt cccgacaaca cgaacagatg acaagttgcg aatggagaca    1140
tgcttccaac aggcgtgtaa gggtaaaatc caagcactct gcgagaatcc cgagtgggca    1200
ccattgaagg ataacaggat tccttcatac ggggtcttgt ctgttgatct gagtctgaca    1260
gttgagctta aaatcaaaat tgcttcggga ttcgggccat tgatcacaca cggttcaggg    1320
atggacctat acaaatccaa ccacaacaat gtgtattggc tgactatccc gccaatgaag    1380
aacctagcct taggtgtaat caacacattg gagtggatac cgagattcaa ggttagtccc    1440
tacctcttca ctgtcccaat taaggaagca ggcgaagact gccatgcccc aacataccta    1500
cctgcggagg tggatggtga tgtcaaactc agttccaatc tggtgattct acctggtcaa    1560
gatctccaat atgttttggc aacctacgat acttccaggg ttgaacatgc tgtggtttat    1620
tacgtttaca gcccaagccg ctcattttct tacttttatc ctttttaggtt gcctataaag    1680 ggggtcccca tcgaattaca agtggaatgc ttcacatggg accaaaaact ctggtgccgt    1740
cacttctgtg tgcttgcgga ctcagaatct ggtggacata tcactcactc tgggatggtg   1800
ggcatgggag tcagctgcac agtcacccgg gaagatggaa ccaatcgcag atag          1854
```

-continued

```
<210> SEQ ID NO 97
<211> LENGTH: 1749
<212> TYPE: DNA
<213> ORGANISM: Mumps virus

<400> SEQUENCE: 97
atggagccct cgaaattctt cacaatatcg gacagtgcca cctttgcacc tgggcctgtc      60
agcaatgcgg ctgacaagaa gacattccga acctgcttcc gaatactggt actatctgta     120
caagctgtca ccctcatatt ggttattgtc actttaggtg agcttgtaag gatgatcaat     180
gatcaaggct tgagcaatca gttgtcttca attacagaca agataagaga gtcagctact     240
atgattgcat ctgctgtggg agtaatgaat caagttattc atggagtaac ggtatcctta     300
cccctacaaa ttgagggaaa ccaaaatcaa ttgttagcca cacttgccac aatctgcgcc     360
agccaaaaac aagtctcaaa ctgctctaca aacatccct tagtcaatga cctcaggttt      420
ataaatggga tcaataaatt tattattgaa gattacgcaa ctcatgattt ctctatcggc     480
catccactca atatgcccag ctttatccca actgcaactt cacccaatgg ttgcacaaga     540
attccatcct tttctttagg taagacacac tggtgctaca cacataatgt aattaatgcc     600
aactgcaagg accatacttc gtctaaccaa tatgtgtcca tggggattct cgttcagacc     660
gcgtcagggt atcctatgtt caaaacctta aaaatccaat atctcagtga tggcctgaat     720
cggaaaagct gctcaattgc aacagtccct gatgggtgcg cgatgtactg ttatgtctct     780
actcaacttg aaaccgacga ctatgcgggg tccagtccac ccacccaaaa acttaccctg     840
ttattctata tgacaccgt cacagaaagg acaatatctc catctggtct tgaagggaat     900
tgggctactt tggtgccagg agtggggagt gggatatatt ttgagaataa gttgatcttc     960
cctgcatatg ggggtgtctt gcccaatagt acactcgggg ttaaatcagc aagagaattt    1020
tttcggcctg ttaatccata taatccatgt tcaggaccac aacaagattt agatcagcgt    1080
gctttgaggt catacttccc aagttacttc tctaatcgaa gaatacagag tgcatttctt    1140
gtctgtgcct ggaatcagat cctagttaca aattgtgagc tagttgtccc ctcaagcaat    1200
cagacaatga tgggtgcaga agggagagtt ttattgatca ataatcgact attatattat    1260
cagagaagta ccagctggtg gccgtatgaa ctcctctacg agatatcatt cacatttaca    1320
aactctggtc catcatctgt aaatatgtcc tggataccta tatattcatt cactcgtcct    1380
ggttcaggca attgcagtgg tgaaaatgtg tgcccgactg cttgtgtgtc aggggtttat    1440
cttgatccct ggccattaac tccatatagc caccaatcag gtattaacag aaatttctat    1500
ttcacaggtg cactattaaa ttcaagtaca actagagtaa atcctaccct ttatgtctct    1560
gcccttaata atcttaaagt actagcccca tatggtactc aaggactgtt tgcctcgtac    1620
accacaacca cctgctttca agataccggt gatgctagtg tgtattgtgt ttatattatg    1680
gagctagcat caaatattgt tggagaattc caaattctac ctgtgctaac tagattgact    1740
atcacttga                                                            1749

<210> SEQ ID NO 98
<211> LENGTH: 476
<212> TYPE: PRT
<213> ORGANISM: Mumps virus

<400> SEQUENCE: 98

Met Lys Ala Tyr Pro Val Ile Cys Leu Gly Phe Ala Val Phe Ser Ser
1               5                   10                  15

Ser Ile Cys Val Asn Ile Asn Ile Leu Gln Gln Ile Gly Tyr Ile Lys
```

-continued

```
              20                  25                  30

Gln Gln Val Arg Gln Leu Ser Tyr Tyr Ser Gln Ser Ser Ser Ser Tyr
              35                  40                  45

Val Val Val Lys Leu Leu Pro Asn Ile Gln Pro Thr Asp Asn Ser Cys
      50                  55                  60

Glu Phe Lys Ser Val Thr Gln Tyr Asn Lys Thr Leu Ser Asn Leu Leu
65                  70                  75                  80

Leu Pro Ile Ala Glu Asn Ile Asn Asn Ile Ala Ser Pro Ser Pro Gly
                  85                  90                  95

Ser Arg Arg His Lys Arg Phe Ala Gly Ile Ala Ile Gly Ile Ala Ala
              100                 105                 110

Leu Gly Val Ala Thr Ala Ala Gln Val Thr Ala Ala Val Ser Leu Val
              115                 120                 125

Gln Ala Gln Thr Asn Ala Arg Ala Ile Ala Ala Met Lys Asn Ser Ile
      130                 135                 140

Gln Ala Thr Asn Arg Ala Ile Phe Glu Val Lys Glu Gly Thr Gln Gln
145                 150                 155                 160

Leu Ala Ile Ala Val Gln Ala Ile Gln Asp His Ile Asn Thr Ile Met
              165                 170                 175

Asn Thr Gln Leu Asn Asn Met Ser Cys Gln Ile Leu Asp Asn Gln Leu
              180                 185                 190

Ala Thr Tyr Leu Gly Leu Tyr Leu Thr Glu Leu Thr Thr Val Phe Gln
              195                 200                 205

Pro Gln Leu Ile Asn Pro Ala Leu Ser Pro Ile Ser Ile Gln Ala Leu
      210                 215                 220

Arg Ser Leu Leu Gly Ser Met Thr Pro Ala Val Val Gln Ala Thr Leu
225                 230                 235                 240

Ser Thr Ser Ile Ser Ala Ala Glu Ile Leu Ser Ala Gly Leu Met Glu
              245                 250                 255

Gly Gln Ile Val Ser Val Leu Leu Asp Glu Met Gln Met Ile Val Lys
              260                 265                 270

Ile Asn Ile Pro Thr Ile Val Thr Gln Ser Asn Ala Leu Val Ile Asp
              275                 280                 285

Phe Tyr Ser Ile Ser Ser Phe Ile Asn Asn Gln Glu Ser Ile Ile Gln
      290                 295                 300

Leu Pro Asp Arg Ile Leu Glu Ile Gly Asn Glu Gln Trp Ser Tyr Pro
305                 310                 315                 320

Ala Lys Asn Cys Lys Ser Thr Arg His His Ile Phe Cys Gln Tyr Asn
              325                 330                 335

Glu Ala Glu Arg Leu Ser Leu Glu Thr Lys Leu Cys Leu Ala Gly Asn
              340                 345                 350

Ile Ser Ala Cys Val Phe Ser Pro Ile Ala Gly Ser Tyr Met Arg Arg
              355                 360                 365

Phe Val Ala Leu Asp Gly Thr Ile Val Ala Asn Cys Arg Ser Leu Thr
      370                 375                 380

Cys Leu Cys Lys Ser Pro Ser Tyr Pro Ile Tyr Gln Pro Asp His His
385                 390                 395                 400

Ala Val Thr Thr Ile Asp Leu Thr Ser Cys Gln Thr Leu Ser Leu Asp
              405                 410                 415

Gly Leu Asp Phe Ser Ile Val Ser Leu Ser Asn Ile Thr Tyr Ala Glu
              420                 425                 430

Asn Leu Thr Ile Ser Leu Ser Gln Thr Ile Asn Thr Gln Pro Ile Asp
              435                 440                 445
```

-continued

Ile Ser Thr Glu Leu Ser Lys Val Asn Ala Ser Leu Gln Asn Ala Val
    450                 455                 460

Lys Tyr Ile Lys Glu Ser Asn His Gln Leu Gln Ser
465                 470                 475

<210> SEQ ID NO 99
<211> LENGTH: 55
<212> TYPE: PRT
<213> ORGANISM: Artificial sequence
<220> FEATURE:
<223> OTHER INFORMATION: transmembrane domain and cytoplasmic tail

<400> SEQUENCE: 99

Gly Ala Ile Ile Val Ala Ala Leu Val Leu Ser Ile Leu Ser Ile Ile
1               5                   10                  15

Ile Ser Leu Leu Phe Cys Cys Trp Ala Tyr Ile Ala Thr Lys Glu Ile
                20                  25                  30

Arg Arg Ile Asn Phe Lys Thr Asn His Ile Asn Thr Ile Ser Ser Ser
        35                  40                  45

Val Asp Asp Leu Ile Arg Tyr
    50                  55

<210> SEQ ID NO 100
<211> LENGTH: 17
<212> TYPE: PRT
<213> ORGANISM: Artificial sequence
<220> FEATURE:
<223> OTHER INFORMATION: transmembrane domain

<400> SEQUENCE: 100

Cys Ile Val Tyr Ile Leu Ile Ala Val Cys Leu Gly Gly Leu Ile Gly
1               5                   10                  15

Ile

<210> SEQ ID NO 101
<211> LENGTH: 57
<212> TYPE: PRT
<213> ORGANISM: Artificial sequence
<220> FEATURE:
<223> OTHER INFORMATION: transmembrane domain and cytoplasmic tail

<400> SEQUENCE: 101

Cys Ile Val Tyr Ile Leu Ile Ala Val Cys Leu Gly Gly Leu Ile Gly
1               5                   10                  15

Ile Pro Ala Leu Ile Cys Cys Cys Arg Gly Arg Cys Asn Lys Lys Gly
                20                  25                  30

Glu Gln Val Gly Met Ser Arg Pro Gly Leu Lys Pro Asp Leu Thr Gly
        35                  40                  45

Thr Ser Lys Ser Tyr Val Arg Ser Leu
    50                  55

<210> SEQ ID NO 102
<211> LENGTH: 476
<212> TYPE: PRT
<213> ORGANISM: Mumps virus

<400> SEQUENCE: 102

Met Lys Ala Phe Leu Val Thr Cys Leu Gly Phe Ala Val Phe Ser Ser
1               5                   10                  15

Ser Ile Cys Val Asn Ile Asn Ile Leu Gln Gln Ile Gly Tyr Ile Lys
                20                  25                  30

-continued

```
Gln Gln Val Arg Gln Leu Ser Tyr Tyr Ser Gln Ser Ser Ser Tyr
        35              40              45

Ile Val Val Lys Leu Leu Pro Asn Ile Gln Pro Thr Asp Asn Ser Cys
        50              55              60

Glu Phe Lys Ser Val Thr Gln Tyr Asn Lys Thr Leu Ser Asn Leu Leu
65              70              75              80

Leu Pro Ile Ala Glu Asn Ile Asn Asn Ile Ala Ser Pro Ser Pro Gly
                85              90              95

Ser Arg Arg His Lys Arg Phe Ala Gly Ile Ala Ile Gly Ile Ala Ala
                100             105             110

Leu Gly Val Ala Thr Ala Ala Gln Val Thr Ala Ala Val Ser Leu Val
                115             120             125

Gln Ala Gln Thr Asn Ala Arg Ala Ile Ala Ala Met Lys Asn Ser Ile
        130             135             140

Gln Ala Thr Asn Arg Ala Ile Phe Glu Val Lys Glu Gly Thr Gln Gln
145             150             155             160

Leu Ala Ile Ala Val Gln Ala Ile Gln Asp His Ile Asn Thr Ile Met
                165             170             175

Asn Thr Gln Leu Asn Asn Met Ser Cys Gln Ile Leu Asp Asn Gln Leu
                180             185             190

Ala Thr Tyr Leu Gly Leu Tyr Leu Thr Glu Leu Thr Thr Val Phe Gln
                195             200             205

Pro Gln Leu Ile Asn Pro Ala Leu Ser Pro Ile Ser Ile Gln Ala Leu
        210             215             220

Arg Ser Leu Leu Gly Ser Met Thr Pro Ala Val Val Gln Ala Thr Leu
225             230             235             240

Ser Thr Ser Ile Ser Ala Ala Glu Ile Leu Ser Ala Gly Leu Met Glu
                245             250             255

Gly Gln Ile Val Ser Val Leu Leu Asp Glu Met Gln Met Ile Val Lys
                260             265             270

Ile Asn Ile Pro Thr Ile Val Thr Gln Ser Asn Ala Leu Val Ile Asp
        275             280             285

Phe Tyr Ser Ile Ser Ser Phe Ile Asn Asn Gln Glu Ser Ile Ile Gln
        290             295             300

Leu Pro Asp Arg Ile Leu Glu Ile Gly Asn Glu Gln Trp Ser Tyr Pro
305             310             315             320

Ala Lys Asn Cys Lys Leu Thr Arg His His Ile Phe Cys Gln Tyr Asn
                325             330             335

Glu Ala Glu Arg Leu Ser Leu Glu Ser Lys Leu Cys Leu Ala Gly Asn
                340             345             350

Ile Ser Ala Cys Val Phe Ser Pro Ile Ala Gly Ser Tyr Met Arg Arg
                355             360             365

Phe Val Ala Leu Asp Gly Thr Ile Val Ala Asn Cys Arg Ser Leu Thr
        370             375             380

Cys Leu Cys Lys Ser Pro Ser Tyr Pro Ile Tyr Gln Pro Asp His His
385             390             395             400

Ala Val Thr Thr Ile Asp Leu Thr Thr Cys Gln Thr Leu Ser Leu Asp
                405             410             415

Gly Leu Asp Phe Ser Ile Val Ser Leu Ser Asn Ile Thr Tyr Ala Glu
                420             425             430

Asn Leu Thr Ile Ser Leu Ser Gln Thr Ile Asn Thr Gln Pro Ile Asp
        435             440             445
```

-continued

```
Ile Ser Thr Glu Leu Ser Lys Val Asn Ala Ser Leu Gln Asn Ala Val
    450             455             460

Lys Tyr Ile Lys Glu Ser Asn His Gln Leu Gln Ser
465             470             475

<210> SEQ ID NO 103
<211> LENGTH: 476
<212> TYPE: PRT
<213> ORGANISM: Mumps virus

<400> SEQUENCE: 103

Met Lys Ala Phe Ser Val Thr Cys Leu Ser Phe Ala Val Phe Ser Ser
1               5               10              15

Ser Ile Cys Val Asn Ile Asn Ile Leu Gln Gln Ile Gly Tyr Ile Lys
                20              25              30

Gln Gln Val Arg Gln Leu Ser Tyr Tyr Ser Gln Ser Ser Ser Ser Tyr
            35              40              45

Ile Val Val Lys Leu Leu Pro Asn Ile Gln Pro Thr Glu Asn Ser Cys
    50              55              60

Glu Phe Lys Ser Ile Thr Gln Tyr Asn Lys Thr Leu Ser Asn Leu Leu
65              70              75              80

Leu Pro Ile Ala Glu Asn Ile Asn Asn Ile Ala Ser Pro Ser Pro Gly
                85              90              95

Ser Arg Arg His Lys Arg Phe Ala Gly Ile Ala Ile Gly Ile Ala Ala
            100             105             110

Leu Gly Val Ala Thr Ala Ala Gln Val Thr Ala Ala Val Ser Leu Val
            115             120             125

Gln Ala Gln Thr Asn Ala Arg Ala Ile Ala Ala Met Lys Asn Ser Ile
    130             135             140

Gln Ala Thr Asn Arg Ala Ile Phe Glu Val Lys Glu Gly Thr Gln Gln
145             150             155             160

Leu Ala Ile Ala Val Gln Ala Leu Gln Asp His Ile Asn Thr Ile Met
                165             170             175

Asn Thr Gln Leu Asn Asn Met Ser Cys Gln Ile Leu Asp Asn Gln Leu
            180             185             190

Ala Thr Tyr Leu Gly Leu Tyr Leu Thr Glu Leu Thr Thr Val Phe Gln
            195             200             205

Pro Gln Leu Ile Asn Pro Ala Leu Ser Pro Ile Ser Ile Gln Ala Leu
    210             215             220

Arg Ser Leu Leu Gly Ser Met Thr Pro Ala Val Val Gln Ala Thr Leu
225             230             235             240

Ser Thr Ser Ile Ser Ala Ala Glu Ile Leu Ser Ala Gly Leu Met Glu
                245             250             255

Gly Gln Ile Val Ser Val Leu Leu Asp Glu Met Gln Met Ile Val Lys
            260             265             270

Ile Asn Ile Pro Thr Ile Val Thr Gln Ser Asn Ala Leu Val Ile Asp
            275             280             285

Phe Tyr Ser Ile Ser Ser Phe Ile Asn Asn Gln Glu Ser Ile Ile Gln
    290             295             300

Leu Pro Asp Arg Ile Leu Glu Ile Gly Asn Glu Gln Trp Ser Tyr Pro
305             310             315             320

Ala Lys Asn Cys Lys Leu Thr Arg His His Ile Phe Cys Gln Tyr Asn
                325             330             335

Glu Ala Glu Arg Leu Ser Leu Glu Ser Lys Leu Cys Leu Ala Gly Asn
            340             345             350
```

-continued

```
Ile Ser Ala Cys Val Phe Ser Pro Ile Ala Gly Ser Tyr Met Arg Arg
        355                 360                 365

Phe Val Ala Leu Asp Gly Thr Ile Val Ala Asn Cys Arg Ser Leu Thr
    370                 375                 380

Cys Leu Cys Lys Ser Pro Ser Tyr Pro Ile Tyr Gln Pro Asp His His
385                 390                 395                 400

Ala Val Thr Thr Ile Asp Leu Thr Thr Cys Gln Thr Leu Ser Leu Asp
                405                 410                 415

Gly Leu Asp Phe Ser Ile Val Ser Leu Ser Asn Ile Thr Tyr Ala Glu
            420                 425                 430

Asn Leu Thr Ile Ser Leu Ser Gln Thr Ile Asn Thr Gln Pro Ile Asp
            435                 440                 445

Ile Ser Thr Glu Leu Ser Lys Val Asn Ala Ser Leu Gln Asn Ala Val
    450                 455                 460

Lys Tyr Ile Lys Glu Ser Asn His Gln Leu Gln Ser
465                 470                 475
```

<210> SEQ ID NO 104
<211> LENGTH: 476
<212> TYPE: PRT
<213> ORGANISM: Mumps virus

<400> SEQUENCE: 104

```
Met Lys Ala Phe Leu Val Ile Cys Leu Gly Phe Ala Val Phe Ser Ser
1               5                   10                  15

Ser Ile Cys Val Asn Ile Asn Ile Leu Gln Gln Val Gly Tyr Ile Lys
                20                  25                  30

Gln Gln Val Arg Gln Leu Ser Tyr Tyr Ser Gln Ser Ser Ser Ser Tyr
            35                  40                  45

Ile Val Val Lys Leu Leu Pro Asn Ile Gln Pro Thr Asp Asn Ser Cys
    50                  55                  60

Glu Phe Lys Ser Val Thr Gln Tyr Asn Lys Thr Leu Gly Asn Leu Leu
65                  70                  75                  80

Leu Pro Ile Ala Glu Asn Ile Asn Asn Ile Ala Ser Pro Ser Pro Gly
                85                  90                  95

Ser Arg Arg His Lys Arg Phe Ala Gly Ile Ala Ile Gly Ile Ala Ala
            100                 105                 110

Leu Gly Val Ala Thr Ala Ala Gln Val Thr Ala Ala Val Ser Leu Val
            115                 120                 125

Gln Ala Gln Thr Asn Ala Arg Ala Ile Ala Ala Met Lys Asn Ser Ile
    130                 135                 140

Gln Ala Thr Asn Arg Ala Ile Phe Glu Val Lys Glu Gly Thr Gln Gln
145                 150                 155                 160

Leu Ala Ile Ala Val Gln Ala Ile Gln Asp His Ile Asn Thr Ile Met
            165                 170                 175

Asn Thr Gln Leu Ser Asn Met Ser Cys Gln Ile Leu Asp Asn Gln Leu
            180                 185                 190

Ala Thr Tyr Leu Gly Leu Tyr Leu Thr Glu Leu Thr Thr Val Phe Gln
            195                 200                 205

Pro Gln Leu Ile Asn Pro Ala Leu Ser Pro Ile Ser Ile Gln Ala Leu
    210                 215                 220

Arg Ser Leu Leu Gly Ser Met Thr Pro Ala Val Val Gln Ala Thr Leu
225                 230                 235                 240

Ser Thr Ser Ile Ser Ala Ala Glu Ile Leu Ser Ala Gly Leu Met Glu
```

-continued

```
                    245                 250                 255

Gly Gln Ile Val Ser Val Leu Leu Asp Glu Met Gln Met Ile Val Lys
                    260                 265                 270

Ile Asn Ile Pro Thr Ile Val Thr Gln Ser Asn Ala Leu Val Ile Asp
                    275                 280                 285

Phe Tyr Ser Ile Ser Ser Phe Ile Asn Asn Gln Glu Ser Ile Ile Gln
                    290                 295                 300

Leu Pro Asp Arg Ile Leu Glu Ile Gly Asn Glu Gln Trp Ser Tyr Pro
305                 310                 315                 320

Ala Lys Asn Cys Lys Leu Thr Arg His Asn Ile Phe Cys Gln Tyr Asn
                    325                 330                 335

Glu Ala Glu Arg Leu Ser Leu Glu Ser Lys Leu Cys Leu Ala Gly Asn
                    340                 345                 350

Ile Ser Ala Cys Val Phe Ser Pro Ile Ala Gly Ser Tyr Met Arg Arg
                    355                 360                 365

Phe Val Ala Leu Asp Gly Thr Ile Val Ala Asn Cys Arg Ser Leu Thr
                    370                 375                 380

Cys Leu Cys Lys Ser Pro Ser Tyr Pro Ile Tyr Gln Pro Asp His His
385                 390                 395                 400

Ala Val Thr Thr Ile Asp Leu Thr Thr Cys Gln Thr Leu Ser Leu Asp
                    405                 410                 415

Gly Leu Asp Phe Ser Ile Val Ser Leu Ser Asn Ile Thr Tyr Ala Glu
                    420                 425                 430

Asn Leu Thr Ile Ser Leu Ser Gln Thr Ile Asn Thr Gln Pro Ile Asp
                    435                 440                 445

Ile Ser Thr Glu Leu Ser Lys Val Asn Ala Ser Leu Gln Asn Ala Val
    450                 455                 460

Lys Tyr Ile Lys Glu Ser Asn Gln Gln Leu Gln Ser
465                 470                 475

<210> SEQ ID NO 105
<211> LENGTH: 476
<212> TYPE: PRT
<213> ORGANISM: Mumps virus

<400> SEQUENCE: 105

Met Lys Ala Ser Leu Val Thr Cys Leu Gly Phe Ala Val Phe Ser Ser
1               5                   10                  15

Ser Ile Cys Val Asn Ile Asn Ile Leu Gln Gln Ile Gly Tyr Ile Lys
                20                  25                  30

Gln Gln Val Arg Gln Leu Ser Tyr Tyr Ser Gln Ser Ser Ser Ser Tyr
                35                  40                  45

Ile Val Val Lys Leu Leu Pro Asn Ile Gln Pro Thr Asp Asn Ser Cys
    50                  55                  60

Glu Phe Lys Ser Val Thr Gln Tyr Asn Lys Thr Leu Ser Asn Leu Leu
65                  70                  75                  80

Leu Pro Ile Ala Glu Asn Ile Asn Asn Ile Ala Ser Pro Ser Pro Gly
                85                  90                  95

Ser Arg Arg His Lys Arg Phe Ala Gly Ile Ala Ile Gly Ile Ala Ala
                100                 105                 110

Leu Gly Val Ala Thr Ala Ala Gln Val Thr Ala Ala Val Ser Leu Val
                115                 120                 125

Gln Ala Gln Thr Asn Ala Arg Ala Ile Ala Ala Met Lys Asn Ser Ile
    130                 135                 140
```

```
Gln Ala Thr Asn Arg Ala Ile Phe Glu Val Lys Glu Gly Thr Gln Gln
145                 150                 155                 160

Leu Ala Ile Ala Val Gln Ala Ile Gln Asn His Ile Asn Thr Ile Met
                165                 170                 175

Asn Thr Gln Leu Asn Asn Met Ser Cys Gln Ile Leu Asp Asn Gln Leu
                180                 185                 190

Ala Thr Tyr Leu Gly Leu Tyr Leu Thr Glu Leu Thr Thr Val Phe Gln
                195                 200                 205

Pro Gln Leu Ile Asn Pro Ala Leu Ser Pro Ile Ser Ile Gln Ala Leu
        210                 215                 220

Arg Ser Leu Leu Gly Ser Met Thr Pro Ala Val Val Gln Ala Thr Leu
225                 230                 235                 240

Ser Thr Ser Ile Ser Ala Ala Glu Ile Leu Ser Ala Gly Leu Met Glu
                245                 250                 255

Gly Gln Ile Val Ser Val Leu Leu Asp Glu Met Gln Met Ile Val Lys
                260                 265                 270

Ile Asn Ile Pro Thr Ile Val Thr Gln Ser Asn Ala Leu Val Ile Asp
                275                 280                 285

Phe Tyr Ser Ile Ser Ser Phe Ile Asn Asn Gln Glu Ser Ile Ile Gln
        290                 295                 300

Leu Pro Asp Arg Ile Leu Glu Ile Gly Asn Glu Gln Trp Ser Tyr Pro
305                 310                 315                 320

Ala Lys Asn Cys Lys Leu Thr Arg His Asn Ile Phe Cys Gln Tyr Asn
                325                 330                 335

Glu Ala Glu Arg Leu Ser Leu Glu Ser Lys Leu Cys Leu Ala Gly Asn
                340                 345                 350

Ile Ser Ala Cys Val Phe Ser Pro Ile Ala Gly Ser Tyr Met Arg Arg
                355                 360                 365

Phe Val Ala Leu Asp Gly Thr Ile Val Ala Asn Cys Arg Ser Leu Thr
        370                 375                 380

Cys Leu Cys Lys Ser Pro Ser Tyr Pro Ile Tyr Gln Pro Asp His His
385                 390                 395                 400

Ala Val Thr Thr Ile Asp Leu Thr Thr Cys Gln Met Leu Ser Leu Asp
                405                 410                 415

Gly Leu Asp Phe Ser Ile Val Ser Leu Ser Asn Ile Thr Tyr Ala Glu
                420                 425                 430

Asn Leu Thr Ile Ser Leu Ser Gln Thr Ile Asn Thr Gln Pro Ile Asp
        435                 440                 445

Ile Ser Thr Glu Leu Ile Lys Val Asn Ala Ser Leu Gln Asn Ala Val
        450                 455                 460

Lys Tyr Ile Lys Glu Ser Asn His Gln Leu Gln Ser
465                 470                 475

<210> SEQ ID NO 106
<211> LENGTH: 476
<212> TYPE: PRT
<213> ORGANISM: Mumps virus

<400> SEQUENCE: 106

Met Lys Ala Phe Ser Val Thr Cys Leu Gly Phe Ala Val Phe Ser Ser
1               5                   10                  15

Ser Ile Cys Val Asn Ile Asn Ile Leu Gln Gln Ile Gly Tyr Ile Lys
                20                  25                  30

Gln Gln Val Arg Gln Leu Ser Tyr Tyr Ser Gln Ser Ser Ser Ser Tyr
        35                  40                  45
```

-continued

```
Ile Val Val Lys Leu Leu Pro Asn Ile Gln Pro Pro Asp Asp Ser Cys
    50              55              60

Glu Phe Lys Ser Val Ile Ser Tyr Asn Lys Thr Leu Ser Asn Leu Leu
65              70              75              80

Leu Pro Ile Ala Glu Asn Ile Asn Asn Ile Ala Ser Pro Ser Pro Gly
                85              90              95

Ser Arg Arg His Lys Arg Phe Ala Gly Ile Ala Ile Gly Ile Ala Ala
            100             105             110

Leu Gly Val Ala Thr Ala Ala Gln Val Thr Ala Ala Val Ser Leu Val
            115             120             125

Gln Ala Gln Thr Asn Ala Arg Ala Ile Ala Ala Met Lys Asn Ser Ile
    130             135             140

Gln Ala Thr Asn Arg Ala Ile Phe Glu Val Lys Glu Gly Thr Gln Gln
145             150             155             160

Leu Ala Ile Ala Val Gln Ala Ile Gln Asp His Ile Asn Thr Ile Met
            165             170             175

Asn Thr Gln Leu Asn Asn Met Ser Cys Gln Ile Leu Asp Asn Gln Leu
            180             185             190

Ala Thr Tyr Leu Gly Leu Tyr Leu Thr Glu Leu Thr Thr Val Phe Gln
            195             200             205

Pro Gln Leu Ile Asn Pro Ala Leu Ser Pro Ile Ser Ile Gln Ala Leu
    210             215             220

Arg Ser Leu Leu Gly Ser Met Thr Pro Ala Val Val Gln Ala Ala Leu
225             230             235             240

Ser Thr Ser Ile Ser Ala Ala Glu Ile Leu Ser Ala Gly Leu Met Glu
            245             250             255

Gly Gln Ile Val Ser Val Leu Leu Asp Glu Met Gln Met Ile Val Lys
            260             265             270

Ile Asn Ile Pro Thr Ile Val Thr Gln Ser Asn Ala Leu Val Ile Asp
    275             280             285

Phe Tyr Ser Ile Ser Ser Phe Ile Asn Asn Gln Glu Ser Ile Ile Gln
    290             295             300

Leu Pro Asp Arg Ile Leu Glu Ile Gly Asn Glu Gln Trp Ser Tyr Pro
305             310             315             320

Ala Lys Asn Cys Lys Leu Thr Arg His His Ile Phe Cys Gln Tyr Asn
            325             330             335

Glu Ala Glu Arg Leu Ser Leu Glu Ser Lys Leu Cys Leu Ala Gly Asn
            340             345             350

Ile Ser Ala Cys Val Phe Ser Pro Ile Ala Gly Ser Tyr Met Arg Arg
            355             360             365

Phe Val Ala Leu Asp Gly Thr Ile Val Ala Asn Cys Arg Ser Leu Thr
    370             375             380

Cys Leu Cys Lys Ser Pro Ser Tyr Pro Ile Tyr Gln Pro Asp His His
385             390             395             400

Ala Val Thr Thr Val Asp Leu Thr Thr Cys Gln Thr Leu Ser Leu Asp
            405             410             415

Gly Leu Asp Phe Ser Ile Val Ser Leu Ser Asn Ile Thr Tyr Ala Glu
            420             425             430
```

-continued

```
Asn Leu Thr Ile Ser Leu Ser Gln Thr Ile Asn Thr Gln Pro Ile Asp
        435             440             445

Ile Ser Thr Glu Leu Ser Lys Val Asn Ala Ser Leu Gln Asn Ala Val
    450             455             460

Lys Tyr Ile Lys Glu Ser Asn His Gln Leu Gln Ser
465             470             475
```

MUMPS AND MEASLES VIRUS IMMUNOGENS AND THEIR USE

CROSS-REFERENCE TO RELATED APPLICATIONS

This is the U.S. National Stage of International Application No. PCT/US2020/064619, filed Dec. 11, 2020, which was published in English under PCT Article 21 (2), which in turn claims the benefit of the earlier filing date of U.S. Provisional Application No. 62/946,902, filed Dec. 11, 2019. The provisional application is incorporated herein by reference in its entirety.

FIELD

This disclosure relates to polypeptides, polynucleotides, compositions, and methods of their use, for elicitation and detection of an immune response to mumps virus (MuV) and measles virus (MeV).

BACKGROUND

MeV and MuV are highly contagious paramyxoviruses that can be transmitted by respiratory droplets from or direct contact with an infected person. The resulting diseases can lead to serious complications or death among children. The existing vaccines for MeV and MuV are live attenuated virus, which are administered in two subcutaneous doses at 1 year of age and as early as one month later. Two doses of a combination measles, mumps and rubella vaccine are 97% effective against measles and 88% effective against mumps. A single dose of a combination measles, mumps and rubella vaccine is 93% effective against measles and 78% effective against mumps.

Despite the effectiveness of the current licensed vaccines against MeV and MuV, incidences of both have increased in recent years. Contributing factors include reduced vaccination rates due to vaccine hesitancy and circulation of divergent strains against which the licensed MMR vaccine offers limited protection.

In the case of MuV, recent studies have shown that immunity wanes significantly after the second MMR vaccination which normally occurs in childhood. Additionally, there has been a drifting of genotypes in the current circulating MuV strains away from the Jeryl-Lynn strain in the standard Mumps vaccine. In response to recent recurring MuV disease outbreaks in the U.S. and Europe, the Advisory Committee on Immunization Practices is advising a third MMR vaccination to boost protection. However, existing immunity neutralizes a third MMR vaccination limiting its effectiveness.

SUMMARY

Disclosed herein are recombinant MuV F ectodomain trimers and recombinant MeV F ectodomain trimers comprising protomers comprising one or more modifications (such as amino acid substitutions) for stabilization in a prefusion conformation. Further provided are embodiments of the recombinant MuV F ectodomain trimers and recombinant MeV F ectodomain trimers linked to MuV HN ectodomain or a MeV H ectodomain. Chimeric proteins are provided, that include combinations of MuV F ectodomain trimer and MeV H ectodomain, or MeV F ectodomain trimer and MuV HN ectodomain. Embodiments of such proteins are demonstrated to produce a superior immune response in animal models, and can be used, for example, to elicit or boost an immune response to MeV and/or MuV in a subject.

In some embodiments, the immunogen comprises a recombinant MuV F ectodomain trimer stabilized in a prefusion conformation by one or more amino acid substitutions in protomers of the trimer, the amino acid substitutions comprising cysteine substitutions that form a non-natural disulfide bond to stabilize the MuV F ectodomain trimer in the prefusion conformation. In some embodiments, the recombinant MuV F ectodomain trimer is stabilized in the prefusion conformation by a non-natural disulfide bond between the cysteine substitutions in protomers of the trimer at MuV F positions 206 and 223. In some embodiments, the protomers of the trimer further comprise a mutation to remove a F1/F2 furin cleavage site of the MuV F ectodomain. In some embodiments, the protomers of the recombinant MuV F ectodomain trimer are fused C-terminally to a trimerization domain, such as a GCN4 trimerization domain. In additional embodiments, the protomers of the recombinant MuV F ectodomain trimer are linked to a heterologous protein, such as a MuV HN ectodomain or a MeV H ectodomain.

In some embodiments, the immunogen comprises a recombinant MeV F ectodomain trimer stabilized in a prefusion conformation by one or more amino acid substitutions in protomers of the trimer, the amino acid substitutions comprising cysteine substitutions that form a non-natural disulfide bond to stabilize the MeV F ectodomain trimer in the prefusion conformation. In some embodiments, the recombinant MeV F ectodomain trimer is stabilized in the prefusion conformation by a non-natural disulfide bond between the cysteine substitutions in protomers of the trimer at MeV F positions 165 and 171. In some embodiments, the protomers of the trimer further comprise a mutation to remove a F1/F2 furin cleavage site of the MeV F ectodomain. In some embodiments, the protomers of the recombinant MeV F ectodomain trimer are fused C-terminally to a trimerization domain, such as a GCN4 trimerization domain. In additional embodiments, the protomers of the recombinant MeV F ectodomain trimer are linked to a heterologous protein, such as a MuV HN ectodomain or a MeV H ectodomain.

In some embodiments, an immunogen is provided that comprises a trimer of fusion proteins, each fusion protein comprising, in an N- to C-terminal direction: a trimerization domain and one or more MuV HN ectodomains or MeV H ectodomain.

In some embodiments, the immunogen comprises a dimer of a MeV H ectodomain head.

Nucleic acid molecules encoding the disclosed proteins are also provided, as are vectors including the nucleic acid molecules, and methods of their production.

Immunogenic compositions including a disclosed immunogen that are suitable for administration to a subject are also provided, and may also be contained in a unit dosage form. The immunogen may also contain a carrier to facilitate presentation to the immune system.

Methods of inducing an immune response in a subject are disclosed, as are methods of inhibiting or preventing a MuV or MeV infection in a subject, by administering to the subject an effective amount of a disclosed immunogen, nucleic acid molecule, or vector.

The foregoing and other features and advantages of this disclosure will become more apparent from the following detailed description of several embodiments which proceeds with reference to the accompanying figures.

BRIEF DESCRIPTION OF THE FIGURES

FIGS. 1A-1E. Structure-based design of a disulfide sta-bilized prefusion mumps F trimer. (FIG. 1A) Structure-based design of prefusion mumps F glycoprotein trimer by systematic screening of disulfides and GCN4 attachment positions, showing both yield and percentage of prefusion relative to postfusion F conformation as determined by negative-stain EM. (FIG. 1B) Homogenous prefusion F trimers were observed at high yield with combination of V206C/A223C with 476-GCN4, upper panel and postfusion is shown in the lower panel. (FIG. 1C) S200 gel filtration analysis shows monodispersal of prefusion F (PreF), glyco-sylated and deglycosylated, HN and prefusion F-HN. (FIG. 1D) Crystal structure to 2.16 Å resolution of prefusion mumps F trimer (SEQ ID NO: 11) with protomers shown, where residues that undergo >5 Å conformational change to transition to the postfusion conformation shown in black. GCN4 trimerization (TD) motif is shown in dotted line, connected to F residue 476. Zoom insets highlight mutated residues to stabilize the trimeric prefusion F structure. (FIG. 1E) A single protomer of the prefusion mumps trimer showing the D1-3 subregions and the locations of the six N-linked glycans per protomer.

FIGS. 2A-2H. Structural comparison of mumps and PIV5 prefusion Fs and analysis of mumps F and HN genotypic variation. (FIG. 2A) Structural superimposition of mumps prefusion F trimer and the related paramyxovirus PIV5 prefusion F trimer showing similar overall topology (RMSD=1.68 Å), yet share 49% sequence identity. (FIG. 2B) The apical loops of the mumps preF associate in a 'closed cap' assembly, whereas in PIV5, these loops are splayed apart (top panel) and the residues that stabilize the mumps preF apex are T178, T179 and N181 (lower panel). (FIG. 2C) The mumps F glycoprotein is glycosylated with 6 glycans per protomer totaling 18 per trimer with 6 glycans in the conformationally mobile region (black) and 12 gly-cans in the less conformationally variable region, providing substantial glycan shielding to the trimer. (FIG. 2D) Phylo-genetic analysis of fusion glycoproteins from mumps geno-types A-J. (FIG. 2E) Phylogenetic analysis of hemaggluti-nin-neuraminidase glycoproteins from mumps genotypes A-J. (FIGS. 2F and 2G) Sequence alignment of Jeryl Lynn vaccine strain (genotype A, SEQ ID NO: 98) with fusion glycoproteins from mumps genotypes C (SEQ ID NO: 102), D (SEQ ID NO: 103), F (SEQ ID NO: 104), G (SEQ ID NO: 105), and H (SEQ ID NO: 106). (FIG. 2H) Structural mapping of mumps genotype variations on prefusion F (left panels) and HN (right panels), showing A-J genotype varia-tion (top panels) and genotype G versus A (Jeryl Lynn (JL)) (lower panels), showing residue differences and glycan differences.

(FIG. 3A) Immunization in CB6F1/J mice was performed 3 times at 10 µg/dose with Poly(I:C) adjuvant at times 0, 3 and 10 weeks with blood sampling at 2, 5, 12 and 16 weeks. (FIG. 3B) Negative-stain characterization of mumps F and preF-HN proteins confirming the conformational and molecular iden-tity of the immunogens and mumps neutralization titers for postfusion F (left), prefusion F (center), and prefusion F-HN (right) immunogens elicited after 1, 2 or 3 immunizations in mice (shown in arrows), and PRN titers for genotype G virus, Jeryl Lynn genotype A virus, and genotype H virus.

FIGS. 4A-4E. Design of prefusion mumps F-HN immu-nogen, analysis of sera for specificity and durability of neutralization titers for three diverse mumps genotype viruses. (FIG. 4A) Negative-stain characterization of mumps preF-HN fusion protein, showing positions of preF head, GCN4 trimerization domain and three HN head-groups. (FIG. 4B) Binding titers for immunized mice using the mumps prefusion F probe and (FIG. 4C) HN probe using Octet Bioinferometry. (FIG. 4D) Durability analysis of mice immunized with three doses of 10 µg prefusion F protein with Poly(I:C) with monthly serum sampling and PRNT analyses for six months against genotype G virus, Jeryl Lynn virus, and genotype H virus. (FIG. 4E) Durability analysis of mice immunized with three doses of 10 µg prefusion F-HN protein with Poly(I:C) with monthly serum sampling and PRNT analyses for six months against genotype G virus, Jeryl Lynn virus and genotype H virus.

Figure 5A:
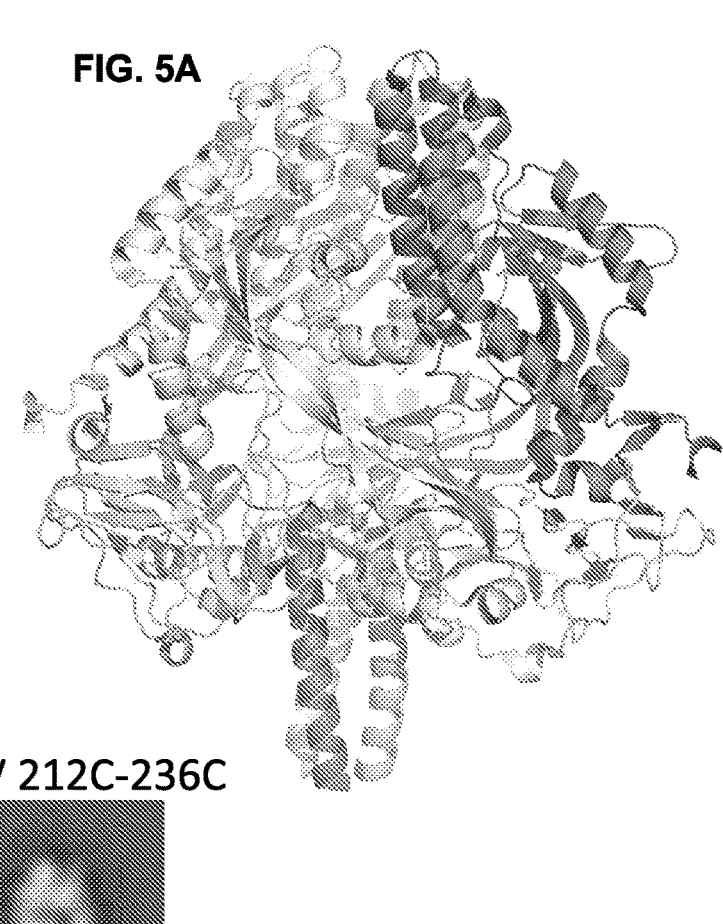
Figure 5B:
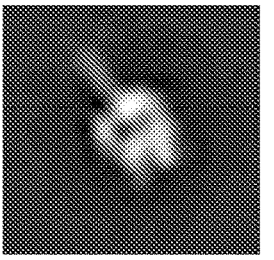
Figure 5B:
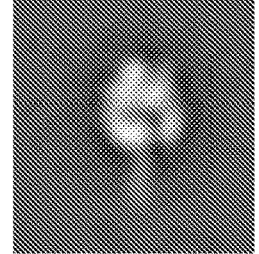
Figure 5B:
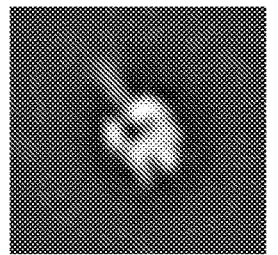
Figure 5B:
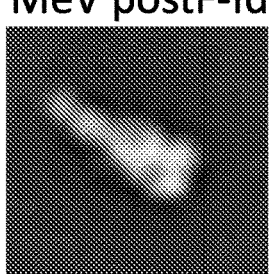
Figure 5B:
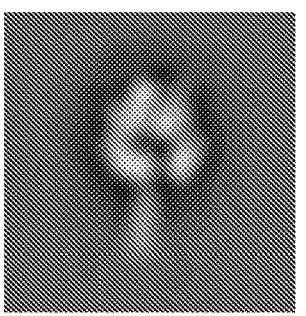
Figure 5C:
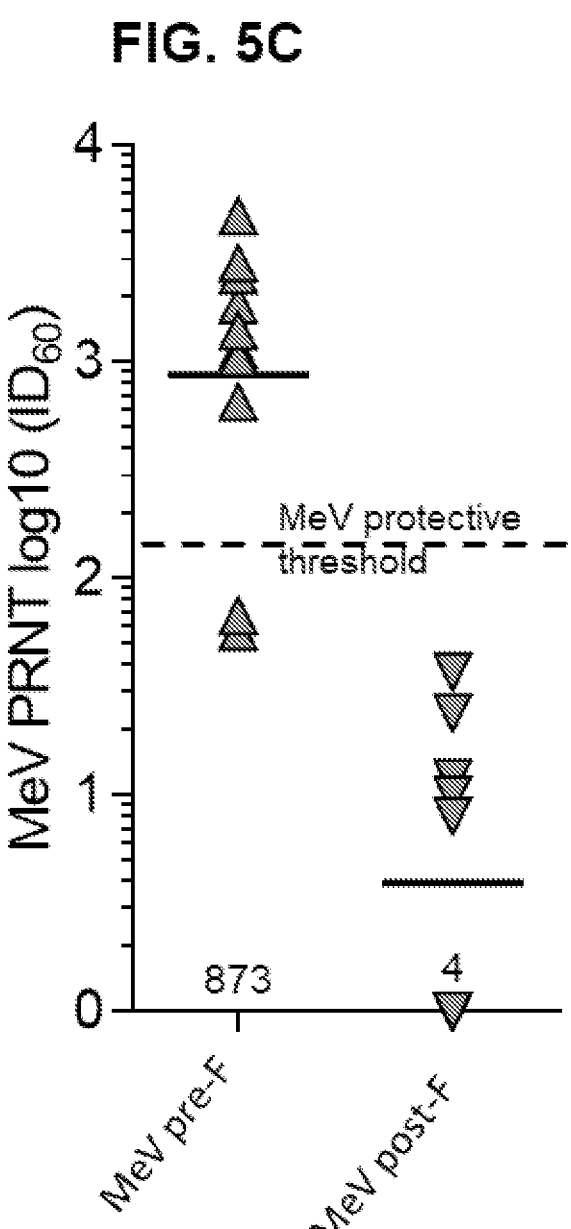

FIGS. 5A-5C. Structure-Based Design of prefusion Measles F. (FIG. 5A) Structure-based design of prefusion-stabilized measles F glycoprotein mutations that stabilize the prefusion conformation. (FIG. 5B) Negative stain EM analy-sis of measles F variants including the indicated non-native disulfide bond and a C-terminal GCN4 trimerization domain, and (FIG. 5C) Immunogenicity of prefusion (MeV F R165C/M171C-486-GCN4, SEQ ID NO: 38) and postfu-sion (native MeV F sequence with –486-GCN4) measles F glycoproteins.

Figure 6A:
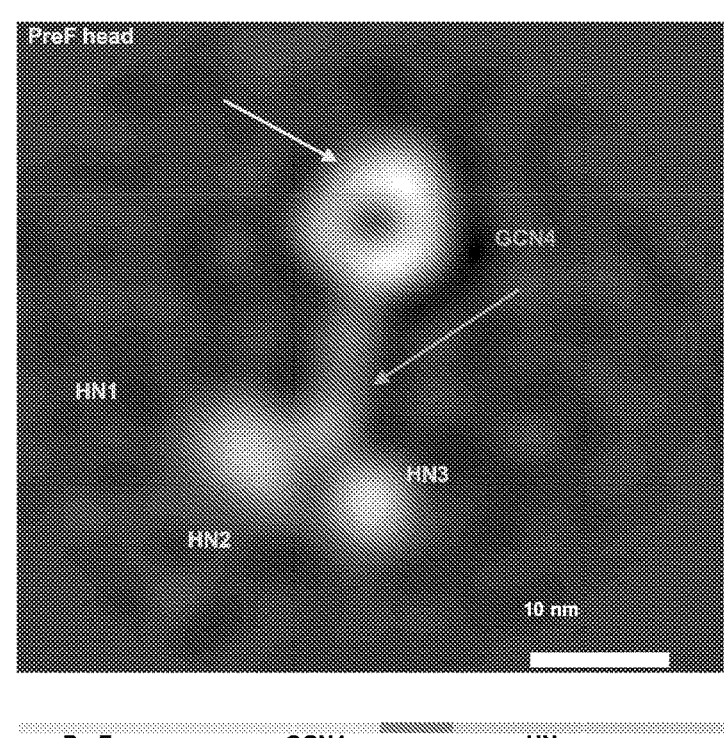
Figure 6B:
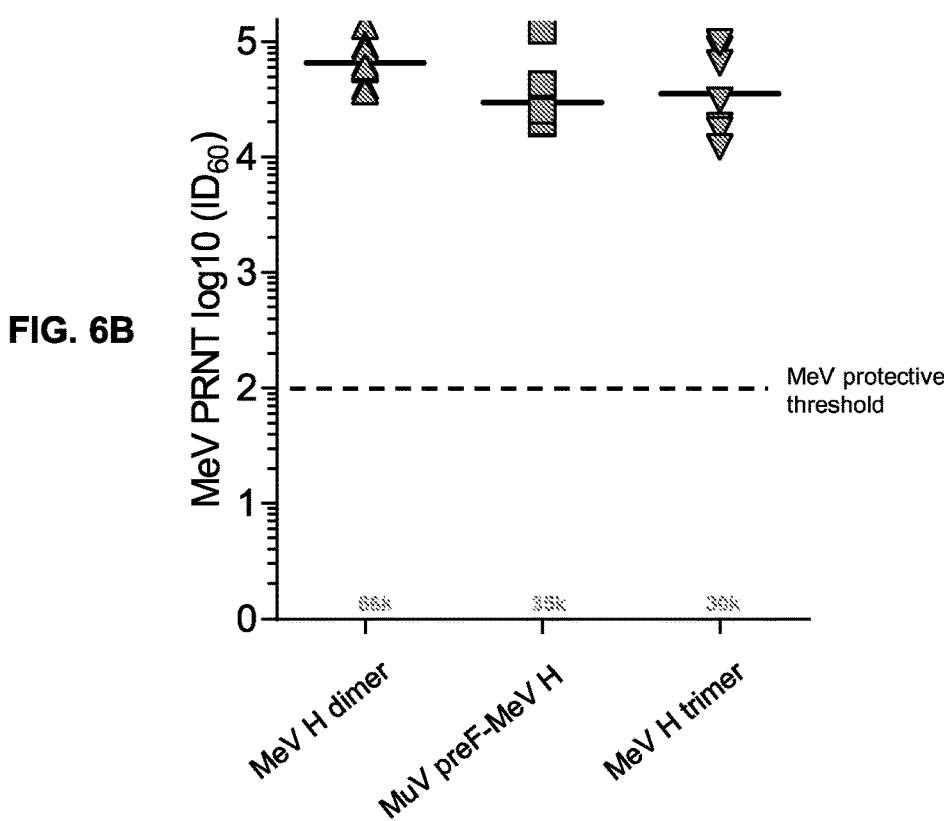
Figure 6C:
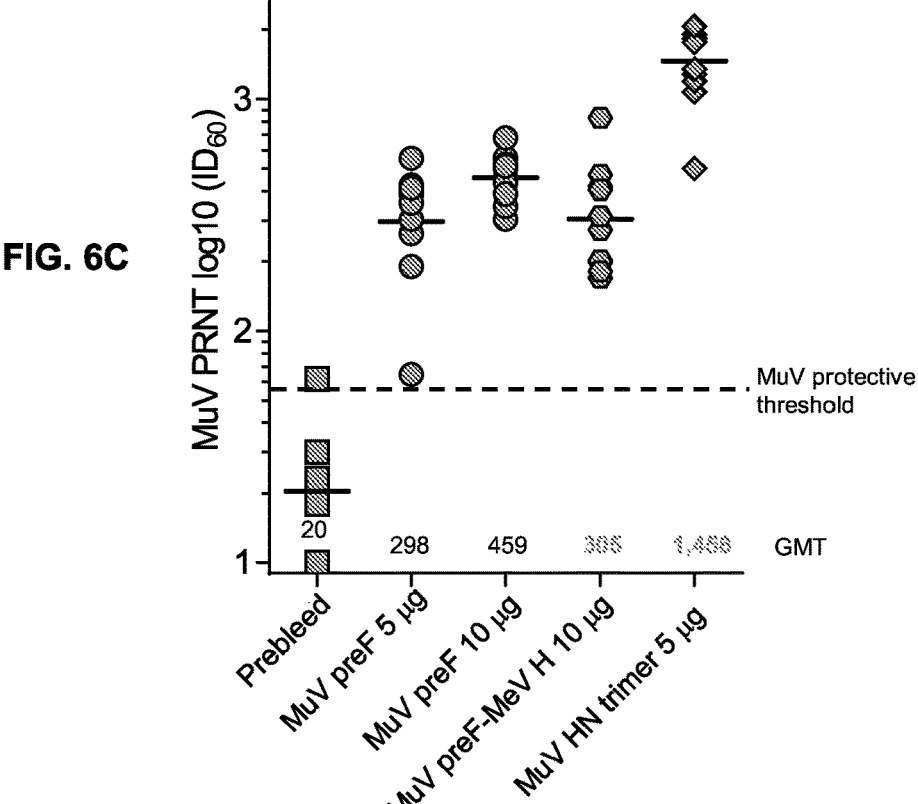

FIGS. 6A-6C. Design of mumps pre-F-measles H chime-ric immunogen. (FIG. 6A) Negative-stain characterization of measles H dimer (upper left), measles H trimer (upper middle), mumps HN trimer (upper right), and mumps pre-F with measles H (MuV F 206C/223C-476+GCN4/Fd+MeV-H, SEQ ID NO: 28) (lower). (FIG. 6B) Measles plaque reduction neutralization titer assays (PRNT). (FIG. 6C) Mumps (genotype G) PRNT assays.

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence.txt" (~456 kb), which was created on Jun. 2, 2022, which is incorporated by reference herein.

Structural Coordinates

The atomic coordinates of the crystal structure of MuV F ectodomain trimer stabilized in a prefusion conformation are recited in Table 1 of U.S. Provisional Application No. 62/946,902, filed Dec. 11, 2019, which is incorporated by reference herein in its entirety, and which is submitted therein as an ASCII text file in the form of the file named "Table_1.txt" (~555 KB), which was created on Dec. 9, 2019.

DETAILED DESCRIPTION

I. Summary of Terms

Unless otherwise noted, technical terms are used accord-ing to conventional usage. Definitions of common terms in molecular biology may be found in Benjamin Lewin, Genes X, published by Jones & Bartlett Publishers, 2009; and Meyers et al. (eds.), *The Encyclopedia of Cell Biology and Molecular Medicine*, published by Wiley-VCH in 16 volumes, 2008; and other similar references. As used herein, the singular forms "a," "an," and "the," refer to both the singular as well as plural, unless the context indicates otherwise. For example, the term "an antigen" includes single or plural antigens and can be considered equivalent to the phrase "at least one antigen." As used herein, the term "comprises" means "includes." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting. To facilitate review of the various embodiments, the following explanations of terms are provided:

Adjuvant: A vehicle used to enhance antigenicity. In some embodiments, an adjuvant includes a suspension of minerals (alum, aluminum hydroxide, or phosphate) on which antigen is adsorbed; or water-in-oil emulsion, for example, in which antigen solution is emulsified in mineral oil (Freund incomplete adjuvant), sometimes with the inclusion of killed mycobacteria (Freund's complete adjuvant) to further enhance antigenicity (inhibits degradation of antigen and/or causes influx of macrophages). In some embodiments, the adjuvant used in a disclosed immunogenic composition is a combination of lecithin and carbomer homopolymer (such as the ADJUPLEX™ adjuvant available from Advanced BioAdjuvants, LLC, see also Wegmann, Clin Vaccine Immunol, 22(9): 1004-1012, 2015). Additional adjuvants for use in the disclosed immunogenic compositions include the QS21 purified plant extract, Matrix M, AS01, MF59, and ALFQ adjuvants. Immunostimulatory oligonucleotides (such as those including a CpG motif) can also be used as adjuvants. Adjuvants include biological molecules (a "biological adjuvant"), such as costimulatory molecules. Exemplary adjuvants include IL-2, RANTES, GM-CSF, TNF-α, IFN-γ, G-CSF, LFA-3, CD72, B7-1, B7-2, OX-40L, 4-1BBL, immune stimulating complex (ISCOM) matrix, and toll-like receptor (TLR) agonists, such as TLR-9 agonists, Poly I:C, or PolyICLC. (See, e.g., Singh (ed.) Vaccine Adjuvants and Delivery Systems. Wiley-Interscience, 2007).

Administration: The introduction of a composition into a subject by a chosen route. Administration can be local or systemic. For example, if the chosen route is intranasal, the composition (such as a composition including a disclosed recombinant MuV F ectodomain trimer or recombinant MeV F ectodomain trimer) is administered by introducing the composition into the nasal passages of the subject. Exemplary routes of administration include, but are not limited to, oral, injection (such as subcutaneous, intramuscular, intradermal, intraperitoneal, and intravenous), sublingual, rectal, transdermal (for example, topical), intranasal, vaginal, and inhalation routes.

Amino acid substitution: The replacement of an amino acid in a polypeptide with one or more different amino acids. In the context of a protein sequence, an amino acid substitution is also referred to as a mutation.

Antibody: An immunoglobulin, antigen-binding fragment, or derivative thereof, that specifically binds and recognizes an analyte (antigen) such as MuV or MeV F protein, an antigenic fragment thereof, or a dimer or multimer of the antigen. The term "antibody" is used herein in the broadest sense and encompasses various antibody structures, including but not limited to monoclonal antibodies, polyclonal antibodies, multispecific antibodies (e.g., bispecific antibodies), and antibody fragments, so long as they exhibit the desired antigen-binding activity. Non-limiting examples of antibodies include, for example, intact immunoglobulins and variants and fragments thereof that retain binding affinity for the antigen. Examples of antibody fragments include but are not limited to Fv, Fab, Fab', Fab'-SH, F(ab')₂; diabodies; linear antibodies; single-chain antibody molecules (e.g. scFv); and multispecific antibodies formed from antibody fragments. Antibody fragments include antigen binding fragments either produced by the modification of whole antibodies or those synthesized de novo using recombinant DNA methodologies (see, e.g., Kontermann and Dubel (Ed), Antibody Engineering, Vols. 1-2, $2^{nd}$ Ed., Springer Press, 2010).

Carrier: An immunogenic molecule to which an antigen can be linked. When linked to a carrier, the antigen may become more immunogenic. Carriers are chosen to increase the immunogenicity of the antigen and/or to elicit antibodies against the carrier which are diagnostically, analytically, and/or therapeutically beneficial. Useful carriers include polymeric carriers, which can be natural (for example, proteins from bacteria or viruses), semi-synthetic or synthetic materials containing one or more functional groups to which a reactant moiety can be attached.

Conservative variants: "Conservative" amino acid substitutions are those substitutions that do not substantially affect or decrease a function of a protein, such as the ability of the protein to induce an immune response when administered to a subject. The term conservative variation also includes the use of a substituted amino acid in place of an unsubstituted parent amino acid. Furthermore, individual substitutions, deletions or additions which alter, add or delete a single amino acid or a small percentage of amino acids (for instance less than 5%, in some embodiments less than 1%) in an encoded sequence are conservative variations where the alterations result in the substitution of an amino acid with a chemically similar amino acid.

The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Non-conservative substitutions are those that reduce an activity or function of the recombinant MuV or MeV F ectodomain trimer, such as the ability to induce an immune response when administered to a subject. For instance, if an amino acid residue is essential for a function of the protein, even an otherwise conservative substitution may disrupt that activity. Thus, a conservative substitution does not alter the basic function of a protein of interest.

Control: A reference standard. In some embodiments, the control is a negative control sample obtained from a healthy patient. In other embodiments, the control is a positive control sample obtained from a patient diagnosed with MuV or MeV infection. In still other embodiments, the control is a historical control or standard reference value or range of values (such as a previously tested control sample, such as a group of MuV or MeV patients with known prognosis or outcome, or group of samples that represent baseline or normal values).

A difference between a test sample and a control can be an increase or conversely a decrease. The difference can be a qualitative difference or a quantitative difference, for example a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater than 500%.

Degenerate variant: In the context of the present disclosure, a "degenerate variant" refers to a polynucleotide encoding a polypeptide that includes a sequence that is degenerate as a result of the genetic code. There are 20 natural amino acids, most of which are specified by more than one codon. Therefore, all degenerate nucleotide sequences encoding a peptide are included as long as the amino acid sequence of the peptide encoded by the nucleotide sequence is unchanged.

Effective amount: An amount of agent, such as an immunogen, that is sufficient to elicit a desired response, such as an immune response in a subject. It is understood that to obtain a protective immune response against an antigen of interest can require multiple administrations of a disclosed immunogen, and/or administration of a disclosed immunogen as the "prime" in a prime boost protocol wherein the boost immunogen can be different from the prime immunogen. Accordingly, an effective amount of a disclosed immunogen can be the amount of the immunogen sufficient to elicit a priming immune response in a subject that can be subsequently boosted with the same or a different immunogen to elicit a protective immune response.

In one example, a desired response is to inhibit or reduce or prevent MuV infection. The MuV infection does not need to be completely eliminated or reduced or prevented for the method to be effective. For example, administration of an effective amount of the agent can decrease the MuV infection (for example, as measured by infection of cells, or by number or percentage of subjects infected by MuV) by a desired amount, for example by at least 50%, at least 60%, at least 70%, at least 80%, at least 90%, at least 95%, at least 98%, or even at least 100% (elimination or prevention of detectable MuV infection), as compared to a suitable control.

In one example, a desired response is to inhibit or reduce or prevent MeV infection. The MeV infection does not need to be completely eliminated or reduced or prevented for the method to be effective. For example, administration of an effective amount of the agent can decrease the MeV infection (for example, as measured by infection of cells, or by number or percentage of subjects infected by MeV) by a desired amount, for example by at least 50%, at least 60%, at least 70%, at least 80%, at least 90%, at least 95%, at least 98%, or even at least 100% (elimination or prevention of detectable MeV infection), as compared to a suitable control.

In one example, a desired response is to inhibit or reduce or prevent both MuV and MeV infection. The MuV and MeV infections do not need to be completely eliminated or reduced or prevented for the method to be effective. For example, administration of an effective amount of the agent can decrease the MuV and MeV infections (for example, as measured by infection of cells, or by number or percentage of subjects infected by MuV and/or MeV) by a desired amount, for example by at least 50%, at least 60%, at least 70%, at least 80%, at least 90%, at least 95%, at least 98%, or even at least 100% (elimination or prevention of detectable MuV and/or MeV infection), as compared to a suitable control.

Expression: Transcription or translation of a nucleic acid sequence. For example, a gene is expressed when its DNA is transcribed into an RNA or RNA fragment, which in some examples is processed to become mRNA. A gene may also be expressed when its mRNA is translated into an amino acid sequence, such as a protein or a protein fragment. In a particular example, a heterologous gene is expressed when it is transcribed into an RNA. In another example, a heterologous gene is expressed when its RNA is translated into an amino acid sequence. The term "expression" is used herein to denote either transcription or translation. Regulation of expression can include controls on transcription, translation, RNA transport and processing, degradation of intermediary molecules such as mRNA, or through activation, inactivation, compartmentalization or degradation of specific protein molecules after they are produced.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see for example, Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (such as metallothionein promoter) or from mammalian viruses (such as the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

Expression vector: A vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

GCN4 trimerization domain: A trimerization domain from the GCN4 protein that comprises a leucine zipper amino acid sequence that naturally forms a trimeric structure. Embodiments of the GCN4 trimerization domain is described, for example, Harbury et al. (1993 *Science* 262: 1401-1407). In some examples, a GCN4 trimerization domain can be included in the amino acid sequence of a disclosed recombinant protein so that the recombinant protein will trimerize. A non-limiting example of a GCN4 trimerization domain sequence for use with the disclosed embodiments is provided as (SEQ ID NO: 33)
IEDKIEEILSKIYHIENEIARIKKLIGEAP.

Heterologous: Originating from a different genetic source.

Host cells: Cells in which a vector can be propagated and its nucleic acid expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies.

Immunogen: A compound, composition, or substance (for example, a recombinant MuV or MeV F ectodomain trimer) that can elicit an immune response in an animal, including compositions that are injected or absorbed into an animal. Administration of an immunogen to a subject can lead to protective immunity against a pathogen of interest.

Immunogenic composition: A composition comprising a disclosed immunogen that induces a measurable CTL response against MuV or MeV, or induces a measurable B cell response (such as production of antibodies) against the MuV or MeV, when administered to a subject. It further refers to isolated nucleic acid molecules and vectors encoding a protomer of a disclosed recombinant MuV or MeV F ectodomain trimer that can be used to express the protomer (and thus be used to elicit an immune response against recombinant MuV or MeV F ectodomain trimer). For in vivo use, the immunogenic composition will typically include the recombinant MuV or MeV F ectodomain trimer or a nucleic acid molecule encoding a protomer of the recombinant MuV or MeV F ectodomain trimer in a pharmaceutically acceptable carrier and may also include other agents, such as an adjuvant.

Inhibiting or treating a disease: Inhibiting the full development of a disease or condition, for example, in a subject who is at risk for a disease such as MuV infection or MeV infection. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. Inhibiting a disease can include preventing or reducing the risk of the disease, such as preventing or reducing the risk of viral infection. The beneficial effect can be evidenced, for example, by a delayed onset of clinical symptoms of the disease in a susceptible subject, a reduction in severity of some or all clinical symptoms of the disease, a slower progression of the disease, a reduction in the viral load, an improvement in the overall health or well-being of the subject, or by other parameters that are specific to the particular disease. A "prophylactic" treatment is a treatment administered to a subject who does not exhibit signs of a disease or exhibits only early signs for the purpose of decreasing the risk of developing pathology.

Isolated: An "isolated" biological component has been substantially separated or purified away from other biological components, such as other biological components in which the component naturally occurs, such as other chromosomal and extrachromosomal DNA, RNA, and proteins. Proteins, peptides, nucleic acids, and viruses that have been "isolated" include those purified by standard purification methods. Isolated does not require absolute purity, and can include protein, peptide, nucleic acid, or virus molecules that are at least 50% isolated, such as at least 75%, 80%, 90%, 95%, 98%, 99%, or even 99.9% isolated.

Linker and Linked: A bi-functional molecule that can be used to link two molecules into one contiguous molecule. Non-limiting examples of peptide linkers include glycine-serine peptide linkers. Unless context indicates otherwise, reference to "linking" a first polypeptide and a second polypeptide, or to two polypeptides "linked" together, or to a first polypeptide having a "linkage" to a second polypeptide, refers to covalent linkage by peptide bond (for example via a peptide linker) such that the first and second polypeptides form a contiguous polypeptide chain. If a peptide linker is involved, the covalent linkage of the first and second polypeptides can be to the N- and C-termini of the peptide linker. Typically, such linkage is accomplished using molecular biology techniques to genetically manipulate DNA encoding the first polypeptide linked to the second polypeptide by the peptide linker.

Native protein, sequence, or disulfide bond: A polypeptide, sequence or disulfide bond that has not been modified, for example, by selective mutation. For example, selective mutation to focus the antigenicity of the antigen to a target epitope, or to introduce a disulfide bond into a protein that does not occur in the native protein. Native protein or native sequence are also referred to as wild-type protein or wild-type sequence. A non-native disulfide bond is a disulfide bond that is not present in a native protein, for example, a disulfide bond that forms in a protein due to introduction of one or more cysteine residues into the protein by genetic engineering.

Measles: An infectious disease caused by measles virus. Symptoms usually develop 10-12 days after exposure to an infected person and last 7-10 days. Initial symptoms typically include fever, cough, runny nose, and inflamed eyes. Small white spots known as Koplik's spots may form inside the mouth two or three days after the start of symptoms. A red, flat rash which usually starts on the face and then spreads to the rest of the body typically begins three to five days after the start of symptoms. Common complications include diarrhea, middle ear infection, and pneumonia. These occur in part due to measles-induced immunosuppression. Less commonly seizures, blindness, or inflammation of the brain may occur.

Measles virus: A non-segmented, negative-stranded RNA virus of the family Paramyxoviridae, genus Morbillivirus that causes measles disease. Measles virus genomic RNA contains 6 linked transcription units that encode open reading frames for eight proteins: the nucleoprotein (N), phosphoprotein (P), C protein, V protein, matrix (M) protein, fusion (F) protein, hemagglutinin (H) protein, and the large (L) protein. There are at least 7 known genotypes of MeV, designated as genotypes A, B, C, D, F, G, and H, that are currently circulating globally.

MeV fusion (F) protein: An envelope glycoprotein of MeV that facilitates fusion of viral and cellular membranes. In nature, the F protein from MeV is initially synthesized as a single polypeptide precursor approximately 550 amino acids in length, designated $F_0$. $F_0$ includes an N-terminal signal peptide that directs localization to the endoplasmic reticulum, where the signal peptide is proteolytically cleaved. The remaining $F_0$ residues oligomerize to form a trimer and may be proteolytically processed by a cellular protease to generate two disulfide-linked fragments, $F_1$ and $F_2$. In MeV F the cleavage site is located approximately between residues 113/114. The smaller of these fragments, $F_2$, originates from the N-terminal portion of the $F_0$ precursor (approximately residues 24-113). The larger of these fragments, $F_1$, includes the C-terminal portion of the $F_0$ precursor (approximately residues 114-550) including an extracellular/luminal region (approximately residues 110-486), and a transmembrane and cytosolic regions (approximately residues 487-550). The extracellular portion of the MeV F protein is the MeV F ectodomain, which includes the $F_2$ protein and the $F_1$ ectodomain.

The MeV F protein exhibits remarkable sequence conservation within MeV strains. In view of this conservation, the person of ordinary skill in the art can easily compare amino acid positions of different MeV F proteins. Unless context indicates otherwise, the numbering of MeV F amino acids is made with reference to SEQ ID NO: 36 (NCBI Reference Sequence P35973.1, which is incorporated by reference herein):

```
mglkvnvsaifmavlltlqtptgQIHWGNLSKIGVVGIGSASYKVMTRS

SHQSLVIKLMPNITLLNNCTRVEIAEYRRLLRTVLEPIRDALNAMTQNI

RPVQSVASSRRHKRFAGVVLAGAALGVATAAQITAGIALHQSMLNSQAI

DNLRASLETTNQAIEAIRQAGQEMILAVQGVQDYINNELIPSMNQLSCD

LIGQKLGLKLLRYYTEILSLFGPSLRDPISAEISIQALSYALGGDINKV

LEKLGYSGGDLLGILESRGIKARITHVDTESYLIVLSIAYPTLSEIKGV

IVHRLEGVSYNIGSQEWYTTVPKYVATQGYLISNFDESSCTFMPEGTVC

SQNALYPMSPLLQECLRGSTKSCARTLVSGSFGNRFILSQGNLIANCAS

ILCKCYTTGTIINQDPDKILTYIAADHCPVVEVNGVTIQVGSRRYPDAV

YLHRIDLGPPILLERLDVGTNLGNAIAKLEDAKELLESSDQILRSMKGL

SSTCIVYILIAVCLGGLIGIPALICCCRGRCNKKGEQVGMSRPGLKPDL

TGTSKSYVRSL
```

Three MeV F protomers oligomerize in the mature F protein, which adopts a metastable prefusion conformation that is triggered to undergo a conformational change to a postfusion conformation upon contact with a target cell membrane. This conformational change exposes a hydrophobic sequence, known as the fusion peptide, which is located at the N-terminus of the $F_1$ ectodomain, and which associates with the host cell membrane and promotes fusion of the membrane of the virus, or an infected cell, with the target cell membrane.

An MeV F ectodomain trimer "stabilized in a prefusion conformation" comprises one or more amino acid substitutions, deletions, or insertions compared to a corresponding native MeV F sequence that provide for increased retention of the prefusion conformation compared to MeV F ectodomain trimers formed from a corresponding native MeV F sequence. The "stabilization" of the prefusion conformation can be, for example, energetic stabilization (for example, reducing the energy of the prefusion conformation relative to the postfusion open conformation) and/or kinetic stabilization (for example, reducing the rate of transition from the prefusion conformation to the postfusion conformation). Additionally, stabilization of the MeV F ectodomain trimer in the prefusion conformation can include an increase in resistance to denaturation compared to a corresponding native MeV F sequence. Methods of determining if a MeV F ectodomain trimer is in the prefusion conformation are provided herein, and include (but are not limited to) negative stain electron microscopy and antibody binding assays using a prefusion conformation specific antibody. The term "pre-F" with reference to a MeV F protein describes a molecule that is a trimeric class I fusion protein stabilized in the prefusion conformation by one or more amino acid substitutions.

MeV F prefusion specific antibody: An antibody that specifically binds to the MeV F protein in a prefusion conformation, but does not specifically bind to the MeV F protein in a postfusion conformation.

MeV hemagglutinin (H) protein: An MeV envelope glycoprotein that is a type II membrane protein and facilitates attachment of MeV to host cell membranes. The full-length H protein has an N-terminal cytoplasmic tail and transmembrane domain (CT and TM, approximately amino acids 1-58), and an ectodomain (approximately amino acids 59-617) including stalk (approximately amino acids 59-179) and head (approximately amino acids 180-617) regions. An exemplary MeV H protein sequence is provided herein as SEQ ID NO: 49 (NCBI Reference Sequence AAA56644.1, which is incorporated by reference herein):

```
Mspqrdrinafykdnphpkgsrivinrehlmidrpyvllavlfvmflsl igllaiagirihraaiytaeihkslstnldvtnsiehqvkdvltplfki igdevglrtpqrftdivkfisdkikfinpdreydfrdltwcinpperik ldydqycadvaaeelmnalvnstlletrttnqFLAVSKGNCSGPTTIRG

QFSNMSLSLLDLYLGRGYNVSSIVTMTSQGMYGGTYLVEKPNLSSKRSE

LSQLSMYRVFEVGVIRNPGLGAPVFHMTNYLEQPVSNDLSNCMVALGEL

KLAALCHGEDSITIPYQGSGKGVSFQLVKLGVWKSPTDMQSWVPLSTDD

PVIDRLYLSSHRGVIADNQAKWAVPTTRTDDKLRMETCFQQACKGKIQA

LCENPEWAPLKDNRIPSYGVLSVDLSLTVELKIKIASGFGPLITHGSGM

DLYKSNHNNVYWLTIPPMKNLALGVINTLEWIPRFKVSPYLFTVPIKEA

GEDCHAPTYLPAEVDGDVKLSSNLVILPGQDLQYVLATYDTSRVEHAVV

YYVYSPSRSFSYFYPFRLPIKGVPIELQVECFTWDQKLWCRHFCVLADS

ESGGHITHSGMVGMGVSCTVTREDGTNRR
```

As used herein, MeV H residue positioning is made with reference to the sequence of the set forth as SEQ ID NO: 49.

Mumps: An infectious disease caused by mumps virus. Mumps is characterized by inflammation of the salivary glands, typically the parotid glands. Severe complications of mumps virus infection can occur, such as meningitis, encephalitis, pancreatitis, oophoritis (in females), orchitis (in males) and hearing loss.

Mumps virus (MuV): A non-segmented, negative-stranded RNA virus of the family Paramyxoviridae, subfamily Paramyxovirinae, genus *Rubulavirus* that causes mumps disease. Mumps virus genomic RNA contains 7 tandemly linked transcription units that encode open reading frames for the nucleoprotein (N), phosphoprotein (P), V protein, I protein, matrix (M) protein, fusion (F) protein, small hydrophobic (SH) protein, hemagglutinin-neuraminidase (HN) protein, and the large (L) protein. A schematic of the mumps virus genome is shown in FIG. 6. Due to RNA editing by insertion of guanine nucleotides, the P gene (also referred to as the "V/P/I gene") results in three mRNA transcripts corresponding to the V, P and I proteins. Specifically, faithful transcription of the P gene produces the V protein, insertion of two guanine nucleotides produces an mRNA encoding the P protein, and insertion of four guanine residues results in an mRNA encoding the I protein. The SH gene is the most variable gene amongst different genotypes of MuV and is therefore generally used as the basis for genotyping. There are 12 known genotypes of MuV, designated as genotypes A, B, C, D, F, G, H, I, J, K, L and N, that are currently circulating globally. Most current MuV vaccines are based on genotype A (Jeryl Lynn), genotype B (Urabe-AM9) or undetermined genotype (Leningrad-Zagreb) viruses.

MuV fusion (F) protein: An envelope glycoprotein of MuV that facilitates fusion of viral and cellular membranes. In nature, the F protein from MuV is initially synthesized as a single polypeptide precursor approximately 538 amino acids in length, designated $F_0$. $F_0$ includes an N-terminal signal peptide that directs localization to the endoplasmic reticulum, where the signal peptide is proteolytically cleaved. The remaining $F_0$ residues oligomerize to form a trimer and may be proteolytically processed by a cellular protease to generate two disulfide-linked fragments, $F_1$ and $F_2$. In MuV F the cleavage site is located approximately between residues 103/104. The smaller of these fragments, $F_2$, originates from the N-terminal portion of the $F_0$ precursor (approximately residues 20-103). The larger of these fragments, $F_1$, includes the C-terminal portion of the $F_0$ precursor (approximately residues 104-538) including an extracellular/luminal region (approximately residues 110-483), and a transmembrane and cytosolic regions (approximately residues 484-538). The extracellular portion of the MuV F protein is the MuV F ectodomain, which includes the $F_2$ protein and the $F_1$ ectodomain.

The MuV F protein exhibits remarkable sequence conservation within MuV strains. In view of this conservation, the person of ordinary skill in the art can easily compare amino acid positions of different MuV F proteins. Unless context indicates otherwise, the numbering of MuV F amino acids is made with reference to SEQ ID NO: 1 (NCBI Reference Sequence P09458.1, which is incorporated by reference herein):

mkafsvtclgfavfsssicVNINILQQIGYIKQQVRQLSYYSQSSSSYIV

VKLLPNIQPTDNSCEFKSVTQYNKTLSNLLLPIAENINNIASPSPGSRRH

KRFAGIAIGIAALGVATAAQVTAAVSLVQAQTNARAIAAMKNSIQATNRA

14

-continued

IFEVKEGTQQLAIAVQAIQDHINTIMNTQLNNMSCQILDNQLATYLGLYL

TELTTVFQPQLINPALSPISIQALRSLLGSMTPAVVQATLSTSISAAEIL

SAGLMEGQIVSVLLDEMQMIVKINIPTIVTQSNALVIDFYSISSFINNQE

SIIQLPDRILEIGNEQWSYPAKNCKLTRHHIFCQYNEAERLSLESKLCLA

GNISACVFSPIAGSYMRRFVALDGTIVANCRSLTCLCKSPSYPIYQPDHH

AVTTIDLTTCQTLSLDGLDFSIVSLSNITYAENLTISLSQTINTQPIDIS

TELSKVNASLQNAVKYIKESNHQLQSVSVNSKIGAIIVAALVLSILSIII

SLLFCCWAYIATKEIRRINFKTNHINTISSSVDDLIRY

Three MuV F protomers oligomerize in the mature F protein, which adopts a metastable prefusion conformation that is triggered to undergo a conformational change to a postfusion conformation upon contact with a target cell membrane. This conformational change exposes a hydrophobic sequence, known as the fusion peptide, which is located at the N-terminus of the $F_1$ ectodomain, and which associates with the host cell membrane and promotes fusion of the membrane of the virus, or an infected cell, with the target cell membrane.

An MuV F ectodomain trimer "stabilized in a prefusion conformation" comprises one or more amino acid substitutions, deletions, or insertions compared to a corresponding native MuV F sequence that provide for increased retention of the prefusion conformation compared to MuV F ectodomain trimers formed from a corresponding native MuV F sequence. The "stabilization" of the prefusion conformation can be, for example, energetic stabilization (for example, reducing the energy of the prefusion conformation relative to the postfusion open conformation) and/or kinetic stabilization (for example, reducing the rate of transition from the prefusion conformation to the postfusion conformation). Additionally, stabilization of the MuV F ectodomain trimer in the prefusion conformation can include an increase in resistance to denaturation compared to a corresponding native MuV F sequence. Methods of determining if a MuV F ectodomain trimer is in the prefusion conformation are provided herein, and include (but are not limited to) negative stain electron microscopy and antibody binding assays using a prefusion conformation specific antibody. The term "pre-F" with reference to a MuV F protein describes a molecule that is a trimeric class I fusion protein stabilized in the prefusion conformation by one or more amino acid substitutions.

MuV hemagglutinin-neuraminidase (HN) protein: An MuV envelope glycoprotein that is a type II membrane protein and facilitates attachment of MuV to host cell membranes. The full-length MuV HN protein has an N-terminal cytoplasmic tail and transmembrane domain (CT and TM, approximately amino acids 1-53), and an ectodomain (approximately amino acids 54-582) including stalk (approximately amino acids 54-130) and head regions (approximately amino acids 131-582). An exemplary MuV HN protein sequence is provided herein as SEQ ID NO: 50 (NCBI Reference Sequence AQT03695.1, which is incorporated by reference herein):

mepskfftisdsatfapgpvsnaadkktfrtcfrilvlsvqavtlilviv tlgelvrmindqglsnqlssitdkiresatmiasavgvmnqvihgvtvsl

```
-continued
plqiegnqnqllatlaticasqkqvsncstNIPLVNDLRFINGINKFIIE

DYATHDFSIGHPLNMPSFIPTATSPNGCTRIPSFSLGKTHWCYTHNVINA

NCKDHTSSNQYVSMGILVQTASGYPMFKTLKIQYLSDGLNRKSCSIATVP

DGCAMYCYVSTQLETDDYAGSSPPTQKLTLLFYNDTVTERTISPSGLEGN

WATLVPGVGSGIYFENKLIEPAYGGVLPNSTLGVKSAREFFRPVNPYNPC

SGPQQDLDQRALRSYFPSYFSNRRIQSAFLVCAWNQILVTNCELVVPSSN

QTMMGAEGRVLLINNRLLYYQRSTSWWPYELLYEISFTFTNSGPSSVNMS

WIPIYSFTRPGSGNCSGENVCPTACVSGVYLDPWPLTPYSHQSGINRNFY

FTGALLNSSTTRVNPTLYVSALNNLKVLAPYGTQGLFASYTTTTCFQDTG

DASVYCVYIMELASNIVGEFQILPVLTRLTIT
```

As used herein, MuV HN residue positioning is made with reference to the sequence of the set forth as SEQ ID NO: 50.

MuV F prefusion specific antibody: An antibody that specifically binds to the MuV F protein in a prefusion conformation, but does not specifically bind to the MuV F protein in a postfusion conformation.

Nucleic acid molecule: A polymeric form of nucleotides, which may include both sense and anti-sense strands of RNA, cDNA, genomic DNA, and synthetic forms and mixed polymers of the above. A nucleotide refers to a ribonucleotide, deoxynucleotide or a modified form of either type of nucleotide. The term "nucleic acid molecule" as used herein is synonymous with "nucleic acid" and "polynucle-otide." A nucleic acid molecule is usually at least 10 bases in length, unless otherwise specified. The term includes single- and double-stranded forms of DNA. A polynucle-otide may include either or both naturally occurring and modified nucleotides linked together by naturally occurring and/or non-naturally occurring nucleotide linkages. "cDNA" refers to a DNA that is complementary or identical to an mRNA, in either single stranded or double stranded form. "Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom.

Operably linked A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the cod-ing sequence. Generally, operably linked nucleic acid sequences are contiguous and, where necessary to join two protein-coding regions, in the same reading frame.

Pharmaceutically acceptable carriers: The pharmaceuti-cally acceptable carriers of use are conventional. *Reming-ton's Pharmaceutical Sciences*, by E. W. Martin, Mack Publishing Co., Easton, PA, 19th Edition, 1995, describes compositions and formulations suitable for pharmaceutical delivery of the disclosed immunogens.

In general, the nature of the carrier will depend on the particular mode of administration being employed. For instance, parenteral formulations usually comprise inject-able fluids that include pharmaceutically and physiologi-cally acceptable fluids such as water, physiological saline, balanced salt solutions, aqueous dextrose, glycerol or the like as a vehicle. For solid compositions (e.g., powder, pill, tablet, or capsule forms), conventional non-toxic solid car-riers can include, for example, pharmaceutical grades of mannitol, lactose, starch, or magnesium stearate. In addition to biologically neutral carriers, pharmaceutical composi-tions (such as immunogenic compositions) to be adminis-tered can contain minor amounts of non-toxic auxiliary substances, such as wetting or emulsifying agents, preser-vatives, and pH buffering agents and the like, for example sodium acetate or sorbitan monolaurate. In particular embodiments, suitable for administration to a subject the carrier may be sterile, and/or suspended or otherwise con-tained in a unit dosage form containing one or more mea-sured doses of the composition suitable to induce the desired immune response. It may also be accompanied by medica-tions for its use for treatment purposes. The unit dosage form may be, for example, in a sealed vial that contains sterile contents or a syringe for injection into a subject, or lyo-philized for subsequent solubilization and administration or in a solid or controlled release dosage.

Polypeptide: Any chain of amino acids, regardless of length or post-translational modification (e.g., glycosylation or phosphorylation). "Polypeptide" applies to amino acid polymers including naturally occurring amino acid polymers and non-naturally occurring amino acid polymer as well as in which one or more amino acid residue is a non-natural amino acid, for example, an artificial chemical mimetic of a corresponding naturally occurring amino acid. A "residue" refers to an amino acid or amino acid mimetic incorporated in a polypeptide by an amide bond or amide bond mimetic. A polypeptide has an amino terminal (N-terminal) end and a carboxy terminal (C-terminal) end. "Polypeptide" is used interchangeably with peptide or protein, and is used herein to refer to a polymer of amino acid residues.

Prime-boost vaccination: An immunotherapy including administration of a first immunogenic composition (the primer vaccine) followed by administration of a second immunogenic composition (the booster vaccine) to a subject to induce an immune response. The primer vaccine and/or the booster vaccine include a vector (such as a viral vector, RNA, or DNA vector) expressing the antigen to which the immune response is directed. The booster vaccine is admin-istered to the subject after the primer vaccine; a suitable time interval between administration of the primer vaccine and the booster vaccine, and examples of such timeframes are disclosed herein. In some embodiments, the primer vaccine, the booster vaccine, or both primer vaccine and the booster vaccine additionally include an adjuvant. In one non-limit-ing example, the primer vaccine is a DNA-based vaccine (or other vaccine based on gene delivery), and the booster vaccine is a protein subunit or protein nanoparticle based vaccine.

Protein nanoparticle: A self-assembling, multi-subunit, protein-based polyhedron shaped structure. The subunits are each composed of proteins or polypeptides (for example a glycosylated polypeptide), and, optionally of single or mul-tiple features of the following: nucleic acids, prosthetic groups, organic and inorganic compounds. Non-limiting examples of protein nanoparticles include ferritin nanopar-ticles (see, e.g., Zhang, Y. *Int. J. Mol. Sci.*, 12:5406-5421, 2011, incorporated by reference herein), encapsulin nan-oparticles (see, e.g., Sutter et al., Nature Struct. and Mol. Biol., 15:939-947, 2008, incorporated by reference herein), Sulfur Oxygenase Reductase (SOR) nanoparticles (see, e.g., Urich et al., Science, 311:996-1000, 2006, incorporated by reference herein), lumazine synthase nanoparticles (see, e.g., Zhang et al., *J. Mol. Biol.*, 306: 1099-1114, 2001) or pyruvate dehydrogenase nanoparticles (see, e.g., Izard et al., PNAS 96: 1240-1245, 1999, incorporated by reference herein). Ferritin, encapsulin, SOR, lumazine synthase, and pyruvate dehydrogenase are monomeric proteins that self-assemble into a globular protein complexes that in some cases consists of 24, 60, 24, 60, and 60 protein subunits, respectively. In some examples, ferritin, encapsulin, SOR, lumazine synthase, or pyruvate dehydrogenase monomers are linked to a recombinant MuV or MeV F ectodomain and self-assemble into a protein nanoparticle presenting the recombinant MuV or MeV F ectodomain trimer on its surface, which can be administered to a subject to stimulate an immune response to the antigen.

Recombinant: A recombinant nucleic acid molecule is one that has a sequence that is not naturally occurring, for example, includes one or more nucleic acid substitutions, deletions or insertions, and/or has a sequence that is made by an artificial combination of two otherwise separated segments of sequence. This artificial combination can be accomplished by chemical synthesis or, more commonly, by the artificial manipulation of isolated segments of nucleic acids, for example, by genetic engineering techniques.

A recombinant virus is one that includes a genome that includes a recombinant nucleic acid molecule.

A recombinant protein is one that has a sequence that is not naturally occurring or has a sequence that is made by an artificial combination of two otherwise separated segments of sequence. In several embodiments, a recombinant protein is encoded by a heterologous (for example, recombinant) nucleic acid that has been introduced into a host cell, such as a bacterial or eukaryotic cell, or into the genome of a recombinant virus.

Sequence identity: The similarity between amino acid sequences is expressed in terms of the similarity between the sequences, otherwise referred to as sequence identity. Sequence identity is frequently measured in terms of percentage identity; the higher the percentage, the more similar the two sequences are. Homologs, orthologs, or variants of a polypeptide will possess a relatively high degree of sequence identity when aligned using standard methods.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. In the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

Variants of a polypeptide are typically characterized by possession of at least about 75%, for example, at least about 80%, 85%, 90%, 91%, 92%, 93%, 94%, 95%, 96%, 97%, 98% or 99% sequence identity counted over the full length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet.

As used herein, reference to "at least 90% identity" (or similar language) refers to "at least 90%, at least 91%, at least 92%, at least 93%, at least 94%, at least 95%, at least 96%, at least 97%, at least 98%, at least 99%, or even 100% identity" to a specified reference sequence.

Signal Peptide: A short amino acid sequence (e.g., approximately 18-25 amino acids in length) that directs newly synthesized secretory or membrane proteins to and through membranes (for example, the endoplasmic reticulum membrane). Signal peptides are typically located at the N-terminus of a polypeptide and are removed by signal peptidases after the polypeptide has crossed the membrane. Signal peptide sequences typically contain three common structural features: an N-terminal polar basic region (n-region), a hydrophobic core, and a hydrophilic c-region). An exemplary signal peptide sequence is set forth as MKAFSVTCLSFAVFSSSIC (residues 1-19 of SEQ ID NO: 2).

Specifically bind: When referring to the formation of an antibody:antigen protein complex, or a protein:protein complex, refers to a binding reaction which determines the presence of a target protein, peptide, or polysaccharide (for example, a glycoprotein), in the presence of a heterogeneous population of proteins and other biologics. Thus, under designated conditions, a particular antibody or protein binds preferentially to a particular target protein, peptide or polysaccharide (such as an antigen present on the surface of a pathogen, for example, an antigenic site at the membrane distal apex of the prefusion conformation of the MuV F or MeV F ectodomain timer) and does not bind in a significant amount to other proteins or polysaccharides present in the sample or subject or to alternative conformations of the same protein (for example, the postfusion conformation of the MuV or MeV F proteins). Specific binding can be determined by methods known in the art. A first protein or antibody specifically binds to a target protein when the interaction has a $K_D$ of less than $10^{-6}$ Molar, such as less than $10^{-7}$ Molar, less than $10^{-8}$ Molar, less than $10^{-9}$, or even less than $10^{-10}$ Molar.

Soluble protein: A protein capable of dissolving in aqueous liquid at room temperature and remaining dissolved. The solubility of a protein may change depending on the concentration of the protein in the water-based liquid, the buffering condition of the liquid, the concentration of other solutes in the liquid, for example salt and protein concentrations, and the heat of the liquid. In several embodiments, a soluble protein is one that dissolves to a concentration of at least 0.5 mg/ml in phosphate buffered saline (pH 7.4) at room temperature and remains dissolved for at least 48 hours.

Subject: Living multi-cellular vertebrate organisms, a category that includes human and non-human mammals. In an example, a subject is a human. In a particular example, the subject is a newborn infant. In an additional example, a subject is selected that is in need of inhibiting of a MuV or MeV infection. For example, the subject is either uninfected and at risk of MuV or MeV infection or is infected in need of treatment.

T4 fibritin trimerization domain: Also referred to as a "foldon" domain, the T4 fibritin trimerization domain comprises an amino acid sequence that naturally forms a trimeric structure. In some examples, a T4 fibritin trimerization domain can be included in the amino acid sequence of a disclosed recombinant protein so that the antigen will form a trimer. In one example, a T4 fibritin trimerization domain comprises the amino acid sequence set forth as GYIPEAPRDGQAYVRKDGEWVLLSTFL (SEQ ID NO: 34). Several embodiments include a T4 fibritin trimerization domain that can be cleaved from a purified protein, for example by incorporation of a thrombin cleave site adjacent to the T4 fibritin trimerization domain that can be used for cleavage purposes.

Transmembrane domain: An amino acid sequence that inserts into a lipid bilayer, such as the lipid bilayer of a cell or virus or virus-like particle. A transmembrane domain can be used to anchor an antigen to a membrane. In some examples a transmembrane domain is a MuV F transmembrane domain. In other examples a transmembrane domain is a MeV F transmembrane domain.

Under conditions sufficient for: A phrase that is used to describe any environment that permits a desired activity.

Vaccine: A preparation of immunogenic material capable of stimulating an immune response, administered for the prevention, amelioration, or treatment of infectious or other types of disease. The immunogenic material may include attenuated or killed microorganisms (such as bacteria or viruses), or antigenic proteins, peptides, or DNA derived from them. A vaccine may include a disclosed immunogen (such as a recombinant MuV or MeV F ectodomain trimer or nucleic acid molecule encoding same), a virus, a cell or one or more cellular constituents. Vaccines may elicit both prophylactic (preventative or protective) and therapeutic responses. Methods of administration vary according to the vaccine, but may include inoculation, ingestion, inhalation or other forms of administration. Vaccines may be administered with an adjuvant to boost the immune response. In one specific, non-limiting example, a vaccine prevents and/ or reduces the severity of the symptoms associated with MuV infection and/or decreases the viral load compared to a control. In another specific, non-limiting example, a vaccine prevents and/or reduces the severity of the symptoms associated with MeV infection and/or decreases the viral load compared to a control.

Vector: An entity containing a DNA or RNA molecule bearing a promoter(s) that is operationally linked to the coding sequence of an antigen(s) of interest and can express the coding sequence. Non-limiting examples include a naked or packaged (lipid and/or protein) DNA, a naked or packaged RNA, a subcomponent of a virus or bacterium or other microorganism that may be replication-incompetent, or a virus or bacterium or other microorganism that may be replication-competent. A vector is sometimes referred to as a construct. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant nucleic acid vectors having at least some nucleic acid sequences derived from one or more viruses.

Virus-like particle (VLP): A non-replicating, viral shell, derived from any of several viruses. VLPs are generally composed of one or more viral proteins, such as, but not limited to, those proteins referred to as capsid, coat, shell, surface and/or envelope proteins, or particle-forming polypeptides derived from these proteins. VLPs can form spontaneously upon recombinant expression of the protein in an appropriate expression system. Methods for producing particular VLPs are known in the art. The presence of VLPs following recombinant expression of viral proteins can be detected using conventional techniques known in the art, such as by electron microscopy, biophysical characterization, and the like. Further, VLPs can be isolated by known techniques, e.g., density gradient centrifugation and identified by characteristic density banding. See, for example, Baker et al. (1991) *Biophys. J.* 60:1445-1456; and Hagensee et al. (1994) *J. Virol.* 68:4503-4505; Vincente, *J Invertebr Pathol.,* 2011; Schneider-Ohrum and Ross, *Curr. Top. Microbiol. Immunol.,* 354: 53073, 2012).

II. Immunogens

A. Recombinant MuV F Ectodomain Trimers

Recombinant MuV F ectodomain trimers are disclosed herein that are modified from a native form (e.g., by introduction of one or more amino acid substitutions) to be stabilized in a prefusion conformation. As described in the Examples, embodiments of the disclosed MuV F ectodomain trimers have been selected through multiple rounds of structure based design for optimized solubility, stability, expression, and immunogenicity. The recombinant MuV F ectodomain trimers are useful to induce an immune response in a vertebrate animal (such humans) to MuV. Exemplary embodiments are shown to produce a superior immune response in an animal model compared to corresponding MuV F ectodomain trimers that are not stabilized in the prefusion conformation.

In some embodiments, the immunogen comprises a recombinant MuV F ectodomain trimer comprising protomers comprising one or more amino acid substitutions or deletions that stabilize the MuV F ectodomain trimer in the prefusion conformation.

In some embodiments, the immunogen comprises a recombinant MuV F ectodomain trimer stabilized in a prefusion conformation by one or more amino acid substitutions in protomers of the trimer, the amino acid substitutions comprising cysteine substitutions that form a non-natural disulfide bond to stabilize the MuV F ectodomain trimer in the prefusion conformation. A non-natural disulfide bond is one that does not occur in a native MuV F protein, and is introduced by protein engineering (e.g., by including one or more substituted cysteine residues that form the non-natural disulfide bond). For example, in some embodiments, any of the disclosed recombinant MuV F proteins can be stabilized in a prefusion conformation by any one of 1, 2, 3, 4, 5, 6, 7, 8, 9, or 10 non-natural disulfide bonds.

The cysteine residues that form the disulfide bond can be introduced into a native MuV F sequence by one or more amino acid substitutions. For example, in some embodiments, a single amino acid substitution introduces a cysteine that forms a disulfide bond with a cysteine residue present in the native MuV F sequence. Alternately, two cysteine residues can be introduced into a native MuV F sequence to form the disulfide bond. The location of the cysteine (or cysteines) of the non-natural disulfide bond can be determined by the person of ordinary skill in the art using the disclosed structure of the MuV F ectodomain trimer in a prefusion conformation.

The amino acid positions of the cysteines are typically within a sufficiently close distance for formation of a disulfide bond in the prefusion conformation of the MuV F protein trimer. Methods of using three-dimensional structure data (for example, as provided in Table 1) to determine if two residues are within a sufficiently close distance to one another for disulfide bond formation are known (see, e.g., Peterson et al., *Protein engineering,* 12:535-548, 1999 and Dombkowski, *Bioinformatics,* 19:1852-1853, 3002 (disclosing DISULFIDE BY DESIGN™), each of which is incorporated by reference herein). Residues can be selected manually, based on the three dimensional structure of the MuV F trimer in a prefusion conformation provided herein, or a software, such as DISULFIDEBYDESIGN™, can be used. Without being bound by theory, ideal distances for formation of a disulfide bond are generally considered to be about ~5.6 Å for Cα-Cα distance, ~2.02 Å for Sγ-Sγ distance, and 3.5-4.25 Å for Cβ-Cβ distance (using the optimal rotomer). The person of ordinary skill in the art will appreciate that variations from these distances are included when selecting residues in a three dimensional structure that can be substituted for cysteines for introduction of a disulfide bond. For example, in some embodiments the selected residues have a Cα-Cα distance of less than 7.0 Å and/or a Cβ-Cβ distance of less than 4.7 Å. In some embodiments the selected residues have a Cα-Cα distance of from 2.0-8.0 Å and/or a Cβ-Cβ distance of from 2.0-6.0 Å.

In some embodiments, the protomers of the recombinant MuV F ectodomain trimer comprise cysteine substitutions at MuV F positions 86 and 215 (such as N86C and A215C substitutions) that form a non-natural intra-protomer disulfide bond for stabilization in the prefusion conformation.

In some embodiments, the protomers of the recombinant MuV F ectodomain trimer comprise cysteine substitutions at MuV F positions 155 and 161 (such as K155C and L161C substitutions) that form a non-natural intra-protomer disulfide bond for stabilization in the prefusion conformation.

In some embodiments, the protomers of the recombinant MuV F ectodomain trimer comprise cysteine substitutions at MuV F positions 165 and 231 (such as V165C and M231C substitutions) that form a non-natural intra-protomer disulfide bond for stabilization in the prefusion conformation.

In some embodiments, the protomers of the recombinant MuV F ectodomain trimer comprise cysteine substitutions at MuV F positions 206 and 223 (such as V206C and A223C substitutions) that form a non-natural intra-protomer disulfide bond for stabilization in the prefusion conformation.

In some embodiments, the protomers of the recombinant MuV F ectodomain trimer comprise cysteine substitutions at MuV F positions 209 and 214 (such as P209C and P214C substitutions) that form a non-natural intra-protomer disulfide bond for stabilization in the prefusion conformation.

In some embodiments, the protomers of the recombinant MuV F ectodomain trimer comprise cysteine substitutions at MuV F positions 221 and 255 (such as I221C and M255C substitutions) that form a non-natural intra-protomer disulfide bond for stabilization in the prefusion conformation.

Any of the above recombinant MuV F proteins can further comprise modification to eliminate the protease cleavage site between the F1 and F2 polypeptides to generate a "single chain" recombinant F protein. For example, any of the above recombinant MuV proteins can comprise deletion of MuV F positions 101-103 with positions 100 and 104 fused by a peptide linker. This modification removes the F2/F1 furin cleavage site and also removed the first residue of the fusion peptide (which is hydrophobic). Any suitable peptide linker may be used that fuses the F2 and F1 ectodomain and allows folding of the F ectodomain into the prefusion conformation. In some embodiments, the peptide linker is a glycine, serine, or glycine-serine peptide linker. In some embodiments, the peptide linker is a Gly-Gly-Gly linker.

In a non-limiting example, a recombinant MuV F ectodomain trimer is provided that includes protomers with V206C and A223C substitutions to form a non-natural disulfide bond and a deletion of MuV F positions 101-103 with positions 100 and 104 fused by a Gly-Gly-Gly peptide linker.

In several embodiments, the protomers of the recombinant MuV F ectodomain can comprise one or more additional amino acid substitutions, for example, to increase stabilization of the prefusion conformation, or for other purposes, such as to increase solubility or to reduce and unwanted immune response.

The above-listed non-native disulfide bonds stabilize the membrane-distal portion of the MuV F ectodomain in its prefusion conformation. Any of these mutations can be combined with modifications to the membrane proximal portion (such as the stem) of the MuV F ectodomain, for example, to increase trimerization of the ectodomain.

In several embodiments, the N-terminal position of the recombinant $F_2$ polypeptide in the protomer can be one of MuV F positions 20-30 (such as position 20), and the C-terminal position of the $F_1$ ectodomain can be from the stem region of the ectodomain, such as one of MuV F positions 469-483 (such as position 476).

In a non-limiting example, a recombinant MuV F ectodomain trimer is provided that includes protomers including MuV positions 20-476 with V206C and A223C substitutions to form a non-natural disulfide bond and a deletion of MuV F positions 101-103 with positions 100 and 104 fused by a Gly-Gly-Gly peptide linker.

Non-limiting examples of protomers of a MuV F ectodomain trimer including amino acid substitutions for stabilization in the prefusion conformation are provided herein. In some embodiments, the protomers of the MuV F ectodomain trimer comprise an amino acid sequence at least 90% identical to residues 20-483 of any one of SEQ ID NOs: 3-8, residues 20-476 of any one of SEQ ID NOs: 11-16, 26, or 51, or residues 20-469 of any one of SEQ ID NOs: 19-24; wherein the protomers comprise the one or more amino acid substitutions that stabilize the MuV F ectodomain trimer in the prefusion conformation. In some embodiments, the protomers of the MuV F ectodomain trimer comprise residues 20-483 of any one of SEQ ID NOs: 3-8, residues 20-476 of any one of SEQ ID NOs: 11-16, 26, or 51, or residues 20-469 of any one of SEQ ID NOs: 19-4.

In several embodiments, the recombinant MuV F ectodomain trimer is a soluble protein complex, for example, for use as a recombinant subunit vaccine. In several such embodiments, the protomers of the recombinant MuV F ectodomain trimer can each comprise a C-terminal linkage to a trimerization domain, such as a GCN4 trimerization domain or a T4 fibritin trimerization domain, or both. The trimerization domain promotes trimerization and stabilization of the membrane proximal aspect of the recombinant MuV F ectodomain trimer. For example, a C-terminal residue of the protomers of the recombinant MuV F ectodomain trimer (such as a residue of the stem region of the trimer) can be directly linked to the trimerization domain, or indirectly linked to the trimerization domain via a peptide linker Exemplary linkers include glycine and glycine-serine linkers. Non-limiting examples of exogenous multimerization domains that promote stable trimers of soluble recombinant proteins include: the GCN4 leucine zipper, a T4 fibritin trimerization domain, the trimerization motif from the lung surfactant protein (Hoppe et al. 1994 *FEBS Lett* 344:191-195) or collagen (McAlinden et al. 2003 *J Biol Chem* 278:42200-42207), any of which can be linked to the C-terminus of the protomers of a recombinant MuV F ectodomain to promote trimerization, as long as the recombinant MuV F ectodomain trimer retains the prefusion conformation. In some examples, the protomers of the recombinant MuV F ectodomain trimer can be linked to a MuV trimerization domain, for example, each protomer in the trimer can include a C-terminal linkage to the GCN4 trimerization domain, such as a linkage to any one of MuV F positions 469-483, such as MuV F position 469, MuV F position 476, or MuV F position 483. In specific examples, the GCN4 trimerization domain comprises or consists of the amino acid sequence IEDKIEEILSKIYHIENEIARIK-KLIGEAP (SEQ ID NO: 33). In specific examples, the T4 fibritin trimerization domain comprises or consists of the amino acid sequence GYIPEAPRDGQAY-VRKDGEWVLLSTFL (SEQ ID NO: 34). In specific examples, the GCN4 trimerization domain fused to the fibritin trimerization domain comprises or consists of the amino acid sequence IEDKIEEILSKIYHIENEIARIK-KLIGEAPGSGYIPEAPRDGQAYVRKDGEWVLLSTFL (SEQ ID NO: 35).

In a non-limiting example, a recombinant MuV F ectodomain trimer is provided that includes protomers including MuV positions 20-476 with V206C and A223C substitutions to form a non-natural disulfide bond, a deletion of MuV F positions 101-103 with positions 100 and 104 fused by a Gly-Gly-Gly peptide linker, and a GCN4 trimerization domain linked to the C-terminus of the protomers in the ectodomain.

Non-limiting examples of protomers of a MuV F ectodomain trimer including amino acid substitutions for stabilization in the prefusion conformation as well as a C-terminal linkage to a trimerization domain are provided herein. In some embodiments, the protomers of the MuV F ectodomain trimer comprise an amino acid sequence at least 90% identical to residues 20-513 of any one of SEQ ID NOs: 3-8, residues 20-506 of any one of SEQ ID NOs: 11-16, 26, or 51, or residues 20-499 of any one of SEQ ID NOs: 19-24; and wherein the protomers comprise the one or more amino acid substitutions that stabilize the MuV F ectodomain trimer in the prefusion conformation. In some embodiments, the protomers of the MuV F ectodomain trimer comprise residues 20-513 of any one of SEQ ID NOs: 3-8, residues 20-506 of any one of SEQ ID NOs: 11-16, 26, or 51, or residues 20-499 of any one of SEQ ID NOs: 19-24.

In some embodiments, the recombinant MuV F ectodomain trimer can be a membrane anchored protein complex, for example, for use in an attenuated virus or virus like particle vaccine. Membrane anchoring can be accomplished, for example, by C-terminal linkage of the protomers of the recombinant MuV F ectodomain trimer to a transmembrane domain and optionally a cytoplasmic tail, such as a MuV F transmembrane domain and cytoplasmic tail. In some embodiments, one or more peptide linkers (such as a gly-ser linker, for example, a 10 amino acid glycine-serine peptide linker can be used to link the protomers of the recombinant MuV F ectodomain trimer to the transmembrane domain. A non-limiting example of a transmembrane domain for use with the disclosed embodiments includes a MuV F transmembrane domain, such as GAIIVAALVLSILSIIISLL-FCCW (SEQ ID NO: 44). A non-limiting example of a transmembrane domain and cytoplasmic tail for use with the disclosed embodiments includes a MuV F transmembrane domain and cytoplasmic tail, such as

24

```
                                 (SEQ ID NO: 99)
GAIIVAALVLSILSIIISLLFCCWAYIATKEIRRINFKTNHINTISSSVD

DLIRY
```

Native MuV F proteins from different MuV strains, as well as nucleic acid sequences encoding such proteins and methods, are known and can be altered using the description provided herein to generate a recombinant MuV F ectodomain trimer.

The recombinant MuV F ectodomain trimer can be derivatized or linked to another molecule (such as another peptide or protein). In general, the recombinant MuV F ectodomain is derivatized such that the binding to neutralizing antibodies to a trimer of the recombinant MuV F protein is not affected adversely by the derivatization or labeling. For example, the recombinant MuV F ectodomain can be functionally linked (by chemical coupling, genetic fusion, non-covalent association or otherwise) to one or more other molecular entities, such as a carrier protein, an antibody, a heterologous protein, or a detection tag.

In some embodiments, the recombinant MuV F ectodomain trimers are fused to one or more MuV HN ectodomains, such as the ectodomain head of the MuV HN sequence set forth as:

```
MuV HN ectodomain head (genotype G,
Arkansas16, GenBank ARM65482.1
                                 (SEQ ID NO: 30)
NIPLVNDLRFINGINKFIIEDYATHDFSIGHPLNMPSFIPTATSPNGCTR

IPSFSLGKTHWCYTHNVINANCKDHTSSNQYVSMGILVQTASGYPMFKTL

KIQYLSDGLNRKSCSIATVPDGCAMYCYVSTQLETDDYAGSSPPTQKLTL

LFYNDTVTERTISPSGLEGNWATLVPGVGSGIYFENKLIFPAYGGVLPNS

TLGVKSAREFFRPVNPYNPCSGPQQDLDQRALRSYFPSYFSNRRIQSAFL

VCAWNQILVTNCELVVPSSNQTMMGAEGRVLLINNRLLYYQRSTSWWPYE

LLYEISFTFTNSGPSSVNMSWIPIYSFTRPGSGNCSGENVCPTACVSGVY

LDPWPLTPYSHQSGINRNFYFTGALLNSSTTRVNPTLYVSALNNLKVLAP

YGTQGLFASYTTTTCFQDTGDASVYCVYIMELASNIVGEFQILPVLTRLT

IT
```

In some embodiments, the recombinant MuV F ectodomain trimers are fused to one or more MuV HN ectodomains, such as the ectodomain stalk and head of any one of MuV HN positions 54-130 to MuV HN position 582 (such as MuV HN positions 54-63 to MuV HN position 582, for example, positions 54-582, 61-582, 63-582, or 55-582). In some embodiments, the recombinant MuV F ectodomain trimers are fused to one or more MuV HN ectodomains, such as the ectodomain stalk and head of the sequence set forth as residues 22-550 of SEQ ID NO: 90, residues 22-543 of SEQ ID NO: 91, residues 22-541 of SEQ ID NO: 92, or residues 22-549 of SEQ ID NO: 93.

For example, the protomers of the recombinant MuV F ectodomain trimer are each fused to a MuV HN ectodomain. The fusion can be direct or via a peptide linker. In some embodiments, the MuV HN ectodomain can be fused, directly or indirectly via a peptide linker, to the C-terminus of the protomers of the MuV F ectodomain trimer. In some such embodiments, the MuV HN ectodomain can be fused, directly or indirectly via a peptide linker, to the C-terminus of a trimerization domain (such as a GCN4 or T4 fibritin trimerization domain) fused to the C-terminus of the protomers of the MuV F ectodomain trimer. In some such embodiments, the protomers of the MuV F ectodomain trimer linked to the trimerization domain and the MuV HN ectodomain comprise an amino acid sequence set forth as residues 20-966 of SEQ ID NO: 27, or an amino acid sequence at least 90% identical to residues 20-966 of SEQ ID NO: 27.

In some embodiments, the recombinant MuV F ectodomain trimers are fused to one or more MeV H ectodomains, such as the ectodomain head of the H sequence set forth as:

```
MeV H ectodomain head
                                (SEQ ID NO: 31)
FLAVSKGNCSGPTTIRGQFSNMSLSLLDLYLGRGYNVSSIVTMTSQGMYG

GTYLVEKPNLSSKRSELSQLSMYRVFEVGVIRNPGLGAPVFHMTNYLEQP

VSNDLSNCMVALGELKLAALCHGEDSITIPYQGSGKGVSFQLVKLGVWKS

PADMQSWVPLSTDDPVIDRLYLSSHRGVIADNQAKWAVPTTRTDDKLRME

TCFQQACKGKIQTLCENPEWAPLKDNRIPSYGVLSVDLSLTVELKIKIAS

GFGPLITHGSGMDLYKSNHNNVYWLTIPPMKNLALGVINTLEWIPRFKVS

PYLFTVPIKEAGEDCHAPTYLPAEVDGDVKLSSNLVILPGQDLQYVLATY

DTSRVEHAVVYYVYSPGRSFSYFYPFRLPIKGVPIELQVECFTWDQKLWC

RHFCVLADSESGGHITHSGMVGMGVSCTVTREDGTNRR

MeV H ectodomain head
                                (SEQ ID NO: 32)
ADVAAEELMNALVNSTLLEARATNQFLAVSKGNCSGPTTIRGQFSNMSLS

LLDLYLSRGYNVSSIVTMTSQGMYGGTYLVGKPNLSSKGSELSQLSMHRV

FEVGVIRNPGLGAPVFHMTNYFEQPVSNDFSNCMVALGELKFAALCHRED

SITIPYQGSGKGVSFQLVKLGVWKSPTDMRSWVPLSTDDPVIDRLYLSSH

RGVIADNQAKWAVPTTRTDDKLRMETCFQQACKGKNQALCENPEWAPLKD

NRIPSYGVLSVNLSLTVELKIKIASGFGPLITHGSGMDLYKTNHNNVYWL

TIPPMKNLALGVINTLEWIPRFKVSPNLFTVPIKEAGEDCHAPTYLPAEV
```

```
DGDVKLSSNLVILPGQDLQYVLATYDTSRVEHAVVYYVYSPSRSFSYFYP

FRLPIKGVPIELQVECFTWDKKLWCRHFCVLADSESGGHITHSGMVGMGV

SCTVTREDGTNRR
```

In some embodiments, the recombinant MuV F ectodomain trimers are fused to one or more MeV H ectodomains, such as the ectodomain stalk and head of any one of MeV H positions 59-179 to MeV H position 617 (such as any one of MeV H positions 59-67 to MeV H position 617, for example positions 59-617, 62-617, 60-617, or 67-617). In some embodiments, the recombinant MuV F ectodomain trimers are fused to one or more MeV H ectodomains, such as the ectodomain stalk and head of the sequence set forth as residues 22-580 of SEQ ID NO: 86, residues 22-577 of SEQ ID NO: 87, residues 22-579 of SEQ ID NO: 88, or residues 22-572 of SEQ ID NO: 89.

For example, the protomers of the recombinant MuV F ectodomain trimer stabilized in the prefusion conformation are each fused to a MeV H ectodomain. The fusion can be direct or via a peptide linker. In some embodiments, the MeV H ectodomain can be fused, directly or indirectly via a peptide linker, to the C-terminus of the protomers of the prefusion MuV F ectodomain trimer. In some such embodiments, the MeV H ectodomain can be fused, directly or indirectly via a peptide linker, to the C-terminus of a trimerization domain (such as a GCN4 or T4 fibritin trimerization domain) fused to the C-terminus of the protomers of the MuV F ectodomain trimer. In some such embodiments, the protomers of the MuV F ectodomain trimer linked to the trimerization domain and the MeV H ectodomain comprise an amino acid sequence set forth as residues 21-981 of SEQ ID NO: 28 or residues 20-1006 of SEQ ID NO: 29, or an amino acid sequence at least 90% identical to residues 21-981 of SEQ ID NO: 28 or residues 20-1006 of SEQ ID NO: 29.

Non-limiting examples of sequences containing a MuV F ectodomain with amino acid substitutions for stabilization in a prefusion conformation are provided as follows:

```
MuV F V206C/A223C-GGG-483-GCN4
                                                    (SEQ ID NO: 3)
mkafsvtclsfavfsssicvninilqqiqyikqqvrqlsyysqssssyivvkllpniqptddscefksvtqynktlsnll lpiaeninniaspspgsrrhGGGagiaigiaalgvataaqvtaavslvqaqtnaraiaamknsiqatnravfevkegtqq laiavqaiqdhintimntqlnnmscqildnqlatslglyltelttCfqpqltnpalspisiqClrsllgsmtpavvqatl stsisaaeilsaglmegqiisvlldemqmivkiniptivtqsnalvidfysissfinnqesiiqlpdrileigneqwsyp aknckltrhhifcqyneaerlslesklclagnisacvfspiagsymrrfvaldgtivancrsltclckspsypiyqpdhh avttidltacqtlsldgldfsivsisnityaenltislsqtintqpidistelskvnaslqnavkyikesnhqlqsvsvn ski  IEDKIEEILSKIYHIENEIARIKKLIGEAP MuV F N86C/A215C-GGG-483-GCN4
                                                    (SEQ ID NO: 4)
mkafsvtclsfavfsssicvninilqqigyikqqvrqlsyysqssssyivvkllpniqptddscefksvtqynktlsnll lpiaeCinniaspspgsrrhGGGagiaigiaalgvataaqvtaavslvqaqtnaraiaamknsiqatnravfevkegtqq laiavqaiqdhintimntqlnnmscqildnqlatslglyltelttvfqpqltnpClspisiqalrsllgsmtpavvqatl stsisaaeilsaglmegqiisvlldemqmivkiniptivtqsnalvidfysissfinnqesiiqlpdrileigneqwsyp aknckltrhhifcqyneaerlslesklclagnisacvfspiagsymrrfvaldgtivancrsltclckspsypiyqpdhh avttidltacqtlsldgldfsivsisnityaenltislsqtintqpidistelskvnaslqnavkyikesnhqlqsvsvn ski  IEDKIEEILSKIYHIENEIARIKKLIGEAP
```

-continued

MuV F P209C/P214C-GGG-483-GCN4

(SEQ ID NO: 5)

mkafsvtclsfavfsssicvninilqqigyikqqvrqlsyysqssssyivvkllpniqptddscefksvtqynktlsnll lpiaeninniaspspgsrrhGGGagiaigiaalgvataaqvtaavslvqaqtnaraiaamknsiqatnravfevkegtqq laiavqaiqdhintimntqlnnmscqildnqlatslglyltelttvfqCqltnCalspisiqalrsllgsmtpavvqatl stsisaaeilsaglmegqiisvlldemqmivkiniptivtqsnalvidfysissfinnqesiiqlpdrileigneqwsyp akncklktrhhifcqyneaerlslesklclagnisacvfspiagsymrrfvaldgtivancrsltclckspsypiyqpdhh avttidltacqtlsldgldfsivsisnityaenltislsqtintqpidistelskvnaslqnavkyikesnhqlqsvsvn ski  IEDKIEEILSKIYHIENEIARIKKLIGEAP MuV F K155C/L161C-GGG-483-GCN4

(SEQ ID NO: 6)

mkafsvtclsfavfsssicvninilqqigyikqqvrqlsyysqssssyivvkllpniqptddscefksvtqynktlsnll lpiaeninniaspspgsrrhGGGagiaigiaalgvataaqvtaavslvqaqtnaraiaamknsiqatnravfevCegtqq Caiavqaiqdhintimntqlnnmscqildnqlatslglyltelttvfqpqltnpalspisiqalrsllgsmtpavvqatl stsisaaeilsaglmegqiisvlldemqmivkiniptivtqsnalvidfysissfinnqesiiqlpdrileigneqwsyp akncklktrhhifcqyneaerlslesklclagnisacvfspiagsymrrfvaldgtivancrsltclckspsypiyqpdhh avttidltacqtlsldgldfsivsisnityaenltislsqtintqpidistelskvnaslqnavkyikesnhqlqsvsvn ski  IEDKIEEILSKIYHIENEIARIKKLIGEAP MuV F V165C/M231C-GGG-483-GCN4

(SEQ ID NO: 7)

mkafsvtclsfavfsssicvninilqqigyikqqvrqlsyysqssssyivvkllpniqptddscefksvtqynktlsnll lpiaeninniaspspgsrrhGGGagiaigiaalgvataaqvtaavslvqaqtnaraiaamknsiqatnravfevkegtqq laiaCqaiqdhintimntqlnnmscqildnqlatslglyltelttvfqpqltnpalspisiqalrsllgsCtpavvqatl stsisaaeilsaglmegqiisvlldemqmivkiniptivtqsnalvidfysissfinnqesiiqlpdrileigneqwsyp akncklktrhhifcqyneaerlslesklclagnisacvfspiagsymrrfvaldgtivancrsltclckspsypiyqpdhh avttidltacqtlsldgldfsivsisnityaenltislsqtintqpidistelskvnaslqnavkyikesnhqlqsvsvn ski  IEDKIEEILSKIYHIENEIARIKKLIGEAP MuV F I221C/M255C-GGG-483-GCN4

(SEQ ID NO: 8)

mkafsvtclsfavfsssicvninilqqigyikqqvrqlsyysqssssyivvkllpniqptddscefksvtqynktlsnll lpiaeninniaspspgsrrhGGGagiaigiaalgvataaqvtaavslvqaqtnaraiaamknsiqatnravfevkegtqq laiavqaiqdhintimntqlnnmscqildnqlatslglyltelttvfqpqltnpalspisCqalrsllgsmtpavvqatl stsisaaeilsaglCegqiisvlldemqmivkiniptivtqsnalvidfysissfinnqesiiqlpdrileigneqwsyp akncklktrhhifcqyneaerlslesklclagnisacvfspiagsymrrfvaldgtivancrsltclckspsypiyqpdhh avttidltacqtlsldgldfsivsisnityaenltislsqtintqpidistelskvnaslqnavkyikesnhqlqsvsvn ski  IEDKIEEILSKIYHIENEIARIKKLIGEAP MuV F V206C/A223C-GGG-476-GCN4

(SEQ ID NO: 11)

mkafsvtclsfavfsssicvninilqqiqyikqqvrqlsyysqssssyivvkllpniqptddscefksvtqynktlsnll lpiaeninniaspspgsrrhGGGagiaigiaalgvataaqvtaavslvqaqtnaraiaamknsiqatnravfevkegtqq laiavqaiqdhintimntqlnnmscqildnqlatslglyltelttCfqpqltnpalspisiqClrsllgsmtpavvqatl stsisaaeilsaglmegqiisvlldemqmivkiniptivtqsnalvidfysissfinnqesiiqlpdrileigneqwsyp akncklktrhhifcqyneaerlslesklclagnisacvfspiagsymrrfvaldgtivancrsltclckspsypiyqpdhh avttidltacqtlsldgldfsivsisnityaenltislsqtintqpidistelskvnaslqnavkyikesnhqlqs

IEDKIEEILSKIYHIENEIARIKKLIGEAP

MuV F N86C/A215C-GGG-476-GCN4

(SEQ ID NO: 12)

<u>mkafsvtclsfavfsssic</u>vninilqqiqyikqqvrqlsyysqssssyivvkllpniqptddscefksvtqynktlsnll lpiae<u>C</u>inniaspspgsrrhGGGagiaigiaalgvataaqvtaavslvqaqtnaraiaamknsiqatnravfevkegtqq laiavqaiqdhintimntqlnnmscqildnqlatslglyltelttvfqpqltnp<u>C</u>lspisiqalrsllgsmtpavvqatl stsisaaeilsaglmegqiisvlldemqmivkiniptivtqsnalvidfysissfinnqesiiqlpdrileigneqwsyp aknckltrhhifcqyneaerlslesklclagnisacvfspiagsymrrfvaldgtivancrsltclckspsypiyqpdhh avttidltacqtlsldgldf sivslsnityaenltislsqtintqpidistelskvnaslqnavkyikesnhqlqs

IEDKIEEILSKIYHIENEIARIKKLIGEAP

MuV F P209C/P214C-GGG-476-GCN4

(SEQ ID NO: 13)

mkafsvtclsfavfsssicvninilqqiqyikqqvrqlsyysqssssyivvkllpniqptddscefksvtqynktlsnll lpiaeninniaspspgsrrhGGGagiaigiaalgvataaqvtaavslvqaqtnaraiaamknsiqatnravfevkegtqq laiavqaiqdhintimntqlnnmscqildnqlatslglyltelttvfq<u>C</u>qltn<u>C</u>alspisiqalrsllgsmtpavvqatl stsisaaeilsaglmegqiisvlldemqmivkiniptivtqsnalvidfysissfinnqesiiqlpdrileigneqwsyp aknckltrhhifcqyneaerlslesklclagnisacvfspiagsymrrfvaldgtivancrsltclckspsypiyqpdhh avttidltacqtlsldgldfsivsisnityaenltislsqtintqpidistelskvnaslqnavkyikesnhqlqs

IEDKIEEILSKIYHIENEIARIKKLIGEAP

MuV F K155C/L161C-GGG-476-GCN4

(SEQ ID NO: 14)

<u>mkafsvtclsfavfsssic</u>vninilqqiqyikqqvrqlsyysqssssyivvkllpniqptddscefksvtqynktlsnll lpiaeninniaspspgsrrhGGGagiaigiaalgvataaqvtaavslvqaqtnaraiaamknsiqatnravfev<u>C</u>egtqq <u>C</u>aiavqaiqdhintimntqlnnmscqildnqlatslglyltelttvfqpqltnpalspisiqalrsllgsmtpavvqatl stsisaaeilsaglmegqiisvlldemqmivkiniptivtqsnalvidfysissfinnqesiiqlpdrileigneqwsyp aknckltrhhifcqyneaerlslesklclagnisacvfspiagsymrrfvaldgtivancrsltclckspsypiyqpdhh avttidltacqtlsldgldfsivsisnityaenltislsqtintqpidistelskvnaslqnavkyikesnhqlqs

IEDKIEEILSKIYHIENEIARIKKLIGEAP

MuV F V165C/M231C-GGG-476-GCN4

(SEQ ID NO: 15)

<u>mkafsvtclsfavfsssic</u>vninilqqiqyikqqvrqlsyysqssssyivvkllpniqptddscefksvtqynktlsnll lpiaeninniaspspgsrrhGGGagiaigiaalgvataaqvtaavslvqaqtnaraiaamknsiqatnravfevkegtqq laia<u>C</u>qaiqdhintimntqlnnmscqildnqlatslglyltelttvfqpqltnpalspisiqalrsllgs<u>C</u>tpavvqatl stsisaaeilsaglmegqiisvlldemqmivkiniptivtqsnalvidfysissfinnqesiiqlpdrileigneqwsyp aknckltrhhifcqyneaerlslesklclagnisacvfspiagsymrrfvaldgtivancrsltclckspsypiyqpdhh avttidltacqtlsldgldfsivsisnityaenltislsqtintqpidistelskvnaslqnavkyikesnhqlqs

IEDKIEEILSKIYHIENEIARIKKLIGEAP

MuV F I221C/M255C-GGG-476-GCN4

(SEQ ID NO: 16)

<u>mkafsvtclsfavfsssic</u>vninilqqigyikqqvrqlsyysqssssyivvkllpniqptddscefksvtqynktlsnll lpiaeninniaspspgsrrhGGGagiaigiaalgvataaqvtaavslvqaqtnaraiaamknsiqatnravfevkegtqq laiavqaiqdhintimntqlnnmscqildnqlatslglyltelttvfqpqltnpalspis<u>C</u>qalrsllgsmtpavvqatl stsisaaeilsagl<u>C</u>egqiisvlldemqmivkiniptivtqsnalvidfysissfinnqesiiqlpdrileigneqwsyp aknckltrhhifcqyneaerlslesklclagnisacvfspiagsymrrfvaldgtivancrsltclckspsypiyqpdhh avttidltacqtlsldgldfsivsisnityaenltislsqtintqpidistelskvnaslqnavkyikesnhqlqs

IEDKIEEILSKIYHIENEIARIKKLIGEAP

-continued

MuV F V206C/A223C-GGG-469-GCN4

(SEQ ID NO: 19)

mkafsvtclsfavfsssic vninilqqigyikqqvrqlsyysqssssyivvkllpniqptddscefksvtqynktlsnll lpiaeninniaspspgsrrhGGGagiaigiaalgvataaqvtaavslvqaqtnaraiaamknsiqatnravfevkegtqq laiavqaiqdhintimntqlnnmscqildnqlatslglyltelttCfqpqltnpalspisiqClrsllgsmtpavvqatl stsisaaeilsaglmegqiisvlldemqmivkiniptivtqsnalvidfysissfinnqesiiqlpdrileigneqwsyp akncklt rhhifcqyneaerlslesklclagnisacvfspiagsymrrfvaldgtivancrsltclckspsypiyqpdhh avttidltacqtlsldgldfsivsisnityaenltislsqtintqpidistelskvnaslqnavkyike

IEDKIEEILSKIYHIENEIARIKKLIGEAP

MuV F N86C/A215C-GGG-469-GCN4

(SEQ ID NO: 20)

mkafsvtclsfavfsssic vninilqqigyikqqvrqlsyysqssssyivvkllpniqptddscefksvtqynktlsnll lpiaeCinniaspspgsrrhGGGagiaigiaalgvataaqvtaavslvqaqtnaraiaamknsiqatnravfevkegtqq laiavqaiqdhintimntqlnnmscqildnqlatslglyltelttvfqpqltnpClspisiqalrsllgsmtpavvqatl stsisaaeilsaglmegqiisvlldemqmivkiniptivtqsnalvidfysissfinnqesiiqlpdrileigneqwsyp akncklt rhhifcqyneaerlslesklclagnisacvfspiagsymrrfvaldgtivancrsltclckspsypiyqpdhh avttidltacqtlsldgldfsivsisnityaenltislsqtintqpidistelskvnaslqnavkyike

IEDKIEEILSKIYHIENEIARIKKLIGEAP

MuV F P209C/P214C-GGG-469-GCN4

(SEQ ID NO: 21)

mkafsvtclsfavfsssic vninilqqigyikqqvrqlsyysqssssyivvkllpniqptddscefksvtqynktlsnll lpiaeninniaspspgsrrhGGGagiaigiaalgvataaqvtaavslvqaqtnaraiaamknsiqatnravfevkegtqq laiavqaiqdhintimntqlnnmscqildnqlatslglyltelttvfqCqltnCalspisiqalrsllgsmtpavvqatl stsisaaeilsaglmegqiisvlldemqmivkiniptivtqsnalvidfysissfinnqesiiqlpdrileigneqwsyp akncklt rhhifcqyneaerlslesklclagnisacvfspiagsymrrfvaldgtivancrsltclckspsypiyqpdhh avttidltacqtlsldgldfsivsisnityaenltislsqtintqpidistelskvnaslqnavkyike

IEDKIEEILSKIYHIENEIARIKKLIGEAP

MuV F K155C/L161C-GGG-469-GCN4

(SEQ ID NO: 22)

mkafsvtclsfavfsssic vninilqqigyikqqvrqlsyysqssssyivvkllpniqptddscefksvtqynktlsnll lpiaeninniaspspgsrrhGGGagiaigiaalgvataaqvtaavslvqaqtnaraiaamknsiqatnravfevCegtqq CaiavqaiqdhintimntqlnnmscqildnqlatslglyItelttvfqpqltnpalspisiqalrsllgsmtpavvqatl stsisaaeilsaglmegqiisvlldemqmivkiniptivtqsnalvidfysissfinnqesiiqlpdrileigneqwsyp akncklt rhhifcqyneaerlslesklclagnisacvfspiagsymrrfvaldgtivancrsltclckspsypiyqpdhh avttidltacqtlsldgldfsivsisnityaenltislsqtintqpidistelskvnaslqnavkyike

IEDKIEEILSKIYHIENEIARIKKLIGEAP

MuV F V165C/M231C-GGG-469-GCN4

(SEQ ID NO: 23)

mkafsvtclsfavfsssic vninilqqigyikqqvrqlsyysqssssyivvkllpniqptddscefksvtqynktlsnll lpiaeninniaspspgsrrhGGGagiaigiaalgvataaqvtaavslvqaqtnaraiaamknsiqatnravfevkegtqq laiaCqaiqdhintimntqlnnmscqildnqlatslglyltelttvfqpqltnpalspisiqalrsiIgsCtpavvqatl stsisaaeilsaglmegqiisvlldemqmivkiniptivtqsnalvidfysissfinnqesiiqlpdrileigneqwsyp akncklt rhhifcqyneaerlslesklclagnisacvfspiagsymrrfvaldgtivancrsltclckspsypiyqpdhh avttidltacqtlsldgldfsivsisnityaenltislsqtintqpidistelskvnaslqnavkyike

IEDKIEEILSKIYHIENEIARIKKLIGEAP

-continued

MuV F I221C/M255C-GGG-469-GCN4

(SEQ ID NO: 24)

mkafsvtclsfavfsssicvninilqqiqyikqqvrqlsyysqssssyivvkllpniqptddscefksvtqynktlsnll lpiaeninniaspspgsrrhGGGagiaigiaalgvataaqvtaavslvqaqtnaraiaamknsiqatnravfevkegtqq laiavqaiqdhintimntqlnnmscqildnqlatslglyltelttvfqpqltnpalspisCqalrsllgsmtpavvqatl stsisaaeilsaglCegqiisvlldemqmivkiniptivtqsnalvidfysissfinnqesiiqlpdrileigneqwsyp akncklfrhhifcqyneaerlsleskllcagnisacvfspiagsymrrfvaldgtivancrsltclckspsypiyqpdhh avttidltacqtlsldgldfsivsisnityaenltislsqtintqpidistelskvnaslqnavkyike

IEDKIEEILSKIYHIENEIARIKKLIGEAP

MuV-JL F 206C/A223C-GGG-476-GCN4

(SEQ ID NO: 26)

mkafsvtclsfavfsssicvninilqqiqyikqqvrqlsyysqssssyVvvkllpniqptdNscefksvtqynktlsnll lpiaeninniaspspgsrrhGGGagiaigiaalgvataaqvtaavslvqaqtnaraiaamknsiqatnravfevkegtqq laiavqaiqdhintimntqlnnmscqildnqlatslglyltelttCfqpqlInpalspisiqClrsllgsmtpavvqatl stsisaaeilsaglmegqiVsvlldemqmivkinVptivtqsnalvidfysissfinnqesiiqlpdrileigneqwRyp aknckStrhhifcqyneaerisleTklclagnisacvfspiagsymrrfvaldgtivancrsltclckspsypiyqpdhh avttidltScqtlsldgldfsivsisnityaenltislsqtintqpidistelskvnaslqnavkyikesnhqlqs

IEDKIEEILSKIYHIENEIARIKKLIGEAP

MuV-IL17 F 206C/A223C-GGG-476-GCN4

(SEQ ID NO: 51)

mkvslvtclgfavfsfsicvninilqqiqyikqqvrqlsyysqssssyivvkllpniqptdnscefksvtqynktlsnll lpiaeninniaspspgsrrhGGGagiaigiaalgvataaqvtaavslvqaqtnaraiaamknsiqatnravfevkegtqq laiavqaiqnhintimntqlnnmscqildnqlatslglylteLTTCfqpqlinpalspisiqCLRSllgsmtpavvqatl stsisaaeilsaglmegqivsvlldemqmivkiniptivtqsnalvidfysissfingqesiiqlpdrileigneqwsyp akncklfrhhifcqyneaerlsleskllcagnisacvfspiagsymrrfvaldgtivancrsltclckspsypiyqpdhh avttidltacqtlsldgldfsivsisnityaenltisisqtintqpidistelikvnaslqnavkyikesnhqlqs

IEDKIEEILSKIYHIENEIARIKKLIGEAP

The above sequences include an N-terminal signal peptide, a MuV F ectodomain, and a GCN4 trimerization domain. It will be appreciated that an alternative trimerization domain can be used, such as a T4 Fibritin trimerization domain. Additionally, many of the above sequence include a GGG linker to remove the native furin cleavage site separating the F1 and F2 subunits. Alternate glycine linkers can also be used, such as GSG, GGS, or SGG. Additionally, in any of the sequences, the native furin cleavage site can be included instead of the GGG linker. It will be appreciated that the N-terminal signal peptide is removed during cellular processing and is not present in the purified protein. Additionally, the MuV F ectodomain of any of the above sequences can be included in a full-length MuV F protein to provide a membrane anchored version of the prefusion MuV F protein, for example for mRNA immunization.

Non-limiting examples of sequences containing a MuV F ectodomain with amino acid substitutions for stabilization in a prefusion conformation linked to a MuV HN ectodomain or a MeV H ectodomain are provided as follows:

MuV F 206C/223C-GGG-476 + GCN4 + MuV HN_G (SEQ ID NO: 27)

Mkafsvtclsfavfsssicvninilqqiqyikqqvrqlsyysqssssyiv vkllpniqptddscefksvtqynktlsnllllpiaeninniaspspgsrrh -continued GGGagiaigiaalgvataaqvtaavslvqaqtnaraiaamknsiqatnra vfevkegtqqlaiavqaiqdhintimntqlnnmscqildnqlatslglyl telttCfqpqltnpalspisiqClrsllgsmtpavvqatlstsisaaeil saglmegqiisvlldemqmivkiniptivtqsnalvidfysissfinnqe siiqlpdrileigneqwsypakncklfrhhifcqyneaerlsleskllcla gnisacvfspiagsymrrfvaldgtivancrsltclckspsypiyqpdhh avttidltacqtlsldgldfsivsisnityaenltislsqtintqpidis telskvnaslqnavkyikesnhqlqsIEDKIEEILSKIYHIENEIARIKK LIGEAP GSGGGGGGNiplvndlrfinginkfiiedyathdfsighpinm psfiptatspngctripsfsigkthwcythnvinanckdhtssnqyvsmg ilvqtasgypmfktikiqylsdglnrkscsiatvpdgcamycyvstqlet ddyagsspptqkltllfyndtvtertispsglegnwativpgvgsgiyfe nklifpayggvlpnstigvksareffrpvnpynpcsgpqqdldqralrsy -continued fpsyfsnrriqsaflvcawnqilvtncelvvpssnqtmmgaegrvllinn rllyyqrstswwpyellyeisftftnsgpssvnmswipiysftrpgsgnc sgenvcptacvsgvyldpwpltpyshqsginrnfyftgallnssttrvnp tlyvsalnnlkvlapygtqglfasyttttcfqdtgdasvycvyimelasn ivgefqilpvltrltit MuV F 206C/223C-GGG-476 + GCN4/Fd + MeV_H
(SEQ ID NO: 28)
Mkafsvtclsfavfsssicvninilqqiqyikqqvrqlsyysqssssyiv vkllpniqptddscefksvtqynktlsnlllpiaeninniaspspgsrrh GGGagiaigiaalgvataaqvtaavslvqaqtnaraiaamknsiqatnra vfevkegtqqlaiavqaiqdhintimntqlnnmscqildnqlatslglyl telttCfqpqltnpalspisiqClrsllgsmtpavvqatlstsisaaeil saglmegqiisvlldemqmivkiniptivtqsnalvidfysissfinnqe siiqlpdrileigneqwsypaknckltrhhifcqyneaerlslesklcla gnisacvfspiagsymrrfvaldgtivancrsltclckspsypiyqpdhh avttidltacqtlsldgldfsivsisnityaenltislsqtintqpidis telskvnaslqnavkyikesnhqlqsIEDKIEEILSKIYHIENEIARIKK LIGEAP  GS  GYIPEAPRDGQAYVRKDGEWVLLSTFL  GSGGGGGgF lavskgncsgpttirgqfsnmsislldlylgrgynvssivtmtsqgmygg tylvekpnlsskrselsqlsmyrvfevgvirnpglgapvfhmtnyleqpv sndlsncmvalgelklaalchgedsitipyqgsgkgvsfqlvklgvwksp admqswvplstddpvidrlyisshrgviadnqakwavpttrtddklrmet cfqqackgkiqticenpewaplkdnripsygvlsvdlsltvelkikiasg fgplithgsgmdlyksnhnnvywltippmknlalgvintlewiprfkvsp ylftvpikeagedchaptyipaevdgdvklssnlvilpgqdlqyvlatyd tsrvehavvyyvyspgrsfsfyfypfrlpikgvpielqvecftwdqklwcr hfcvladsesgghithsgmvgmgvsctvtredgtnrr MuV F 206C/223C-GGG-476 + GCN4/Fd + MeV_H
(SEQ ID NO: 29)
Mkafsvtclsfavfsssicvninilqqigyikqqvrqlsyysqssssyiv vkllpniqptddscefksvtqynktlsnlllpiaeninniaspspgsrrh GGGagiaigiaalgvataaqvtaavslvqaqtnaraiaamknsiqatnra vfevkegtqqlaiavqaiqdhintimntqlnnmscqildnqlatslglyl telttCfqpqltnpalspisiqClrsllgsmtpavvqatlstsisaaeil saglmegqiisvlldemqmivkiniptivtqsnalvidfysissfinnqe siiqlpdrileigneqwsypaknckltrhhifcqyneaerlslesklcla gnisacvfspiagsymrrfvaldgtivancrsltclckspsypiyqpdhh avttidltacqtlsldgldfsivsisnityaenltislsqtintqpidis telskvnaslqnavkyikesnhqlqsIEDKIEEILSKIYHIENEIARIKK LIGEAP  GS  GYIPEAPRDGQAYVRKDGEWVLLSTFL  GSGGGGGgA dvaaeelmnalvnstllearatnqflavskgncsgpttirgqfsnmslsl ldlylsrgynvssivtmtsqgmyggtylvgkpnlsskgselsqlsmhrvf evgvirnpglgapvfhmtnyfeqpvsndfsncmvalgelkfaalchreds -continued itipyqgsgkgvsfqlvklgvwksptdmrswvplstddpvidrlyisshr gviadnqakwavpttrtddklrmetcfqqackgknqalcenpewaplkdn ripsygvlsvnlsitvelkikiasgfgplithgsgmdlyktnhnnvywlt ippmknlalgvintlewiprfkvspniftvpikeagedchaptyIpaevd gdvkissnlvilpgqdlqyvlatydtsrvehawyyvyspsrsfsyfypfr ipikgvpielqvecftwdkklwcrhfcvladsesgghithsgmvgmgvsc tvtredgtnrr The above sequences include an N-terminal signal peptide and a MuV F ectodomain in combination with various other elements, including a GCN4 trimerization domain, a T4-fibritin trimerization domain, peptide cleavage sites (e.g., thrombin), a HIS tag, a Strep tag, as well as various linker residues between segments. Purified forms of these proteins typically lack the N-terminal signal peptide and C-terminal residues removed by peptide cleavage.

B. Recombinant MeV F Ectodomain Trimers

Recombinant MeV F ectodomain trimers are disclosed herein that are modified from a native form (e.g., by introduction of one or more amino acid substitutions) to be stabilized in a prefusion conformation. As described in the Examples, embodiments of the disclosed MeV F ectodomain trimers have been selected through multiple rounds of structure based design for optimized solubility, stability, expression, and immunogenicity. The recombinant MeV F ectodomain trimers are useful to induce an immune response in a vertebrate animal (such humans) to MeV. Exemplary embodiments are shown to produce a superior immune response in an animal model compared to corresponding MeV F ectodomain trimers that are not stabilized in the prefusion conformation.

In some embodiments, the immunogen comprises a recombinant MeV F ectodomain trimer comprising protomers comprising one or more amino acid substitutions or deletions that stabilize the MeV F ectodomain trimer in the prefusion conformation.

In some embodiments, the protomers of the recombinant MeV F ectodomain trimer comprise cysteine substitutions at MeV F positions 48 and 284 (such as R48C and A284C substitutions) that form a non-natural intra-protomer disulfide bond for stabilization in the prefusion conformation.

In some embodiments, the protomers of the recombinant MeV F ectodomain trimer comprise cysteine substitutions at MeV F positions 90 and 225 (such as A90C and I225C substitutions) that form a non-natural intra-protomer disulfide bond for stabilization in the prefusion conformation.

In some embodiments, the protomers of the recombinant MeV F ectodomain trimer comprise cysteine substitutions at MeV F positions 141 and 270 (such as M141C and T270C substitutions) that form a non-natural intra-protomer disulfide bond for stabilization in the prefusion conformation.

In some embodiments, the protomers of the recombinant MeV F ectodomain trimer comprise cysteine substitutions at MeV F positions 165 and 171 (such as R165C and M171C substitutions) that form a non-natural intra-protomer disulfide bond for stabilization in the prefusion conformation.

In some embodiments, the protomers of the recombinant MeV F ectodomain trimer comprise cysteine substitutions at MeV F positions 173 and 245 (such as L173C and V245C substitutions) that form a non-natural intra-protomer disulfide bond for stabilization in the prefusion conformation.

In some embodiments, the protomers of the recombinant MeV F ectodomain trimer comprise cysteine substitutions at MeV F positions 175 and 241 (such as V175C and D241C substitutions) that form a non-natural intra-protomer disulfide bond for stabilization in the prefusion conformation.

In some embodiments, the protomers of the recombinant MeV F ectodomain trimer comprise cysteine substitutions at MeV F positions 212 and 236 (such as E212C and Y236C substitutions) that form a non-natural intra-protomer disulfide bond for stabilization in the prefusion conformation.

In some embodiments, the protomers of the recombinant MeV F ectodomain trimer comprise cysteine substitutions at MeV F positions 216 and 233 (such as L216C and A233C substitutions) that form a non-natural intra-protomer disulfide bond for stabilization in the prefusion conformation.

In some embodiments, the protomers of the recombinant MeV F ectodomain trimer comprise cysteine substitutions at MeV F positions 219 and 224 (such as P219C and P224C substitutions) that form a non-natural intra-protomer disulfide bond for stabilization in the prefusion conformation. In some embodiments, the protomers of the recombinant MeV F ectodomain trimer comprise cysteine substitutions at MeV F positions 99 and 117 (such as R99C and V117C substitutions) that form a non-natural intra-protomer disulfide bond for stabilization in the prefusion conformation.

In some embodiments, the protomers of the recombinant MeV F ectodomain trimer comprise cysteine substitutions at MeV F positions 100 and 117 (such as P100C and V117C substitutions) that form a non-natural intra-protomer disulfide bond for stabilization in the prefusion conformation.

In some embodiments, the protomers of the recombinant MeV F ectodomain trimer comprise cysteine substitutions at MeV F positions 101 and 117 (such as V101C and V117C substitutions) that form a non-natural intra-protomer disulfide bond for stabilization in the prefusion conformation.

In some embodiments, the protomers of the recombinant MeV F ectodomain trimer comprise cysteine substitutions at MeV F positions 102 and 117 (such as Q102C and V117C substitutions) that form a non-natural intra-protomer disulfide bond for stabilization in the prefusion conformation.

In some embodiments, the protomers of the recombinant MeV F ectodomain trimer comprise cysteine substitutions at MeV F positions 103 and 117 (such as S103C and V117C substitutions) that form a non-natural intra-protomer disulfide bond for stabilization in the prefusion conformation.

In some embodiments, the protomers of the recombinant MeV F ectodomain trimer comprise cysteine substitutions at MeV F positions 165 and 171 (such as R165C and M171C substitutions) and positions 141 and 270 (such as M141C and T270C substitutions) that form a non-natural intra-protomer disulfide bond for stabilization in the prefusion conformation.

In some embodiments, the protomers of the recombinant MeV F ectodomain trimer comprise cysteine substitutions at MeV F positions 165 and 171 (such as R165C and M171C substitutions) and positions 212 and 236 (such as E212C and Y236C substitutions) that form a non-natural intra-protomer disulfide bond for stabilization in the prefusion conformation.

In some embodiments, the protomers of the recombinant MeV F ectodomain trimer comprise cysteine substitutions at MeV F positions 165 and 171 (such as R165C and M171C substitutions) and positions 48 and 284 (such as R48C and A284C substitutions) that form a non-natural intra-protomer disulfide bond for stabilization in the prefusion conformation.

In some embodiments, the protomers of the recombinant MeV F ectodomain trimer comprise a phenylalanine at MeV F position 175 (such as a V175F substitution) for stabilization in the prefusion conformation. The phenylalanine substitution can be combined with any of the disclosed cysteine substitutions or the proline substitution at MeV F position 194 to stabilize the recombinant MeV F ectodomain trimer in the prefusion conformation.

In some embodiments, the protomers of the recombinant MeV F ectodomain trimer comprise a proline substitution at MeV F position 194 (such as a S194P substitution) for stabilization in the prefusion conformation. The proline substitution can be combined with any of the disclosed cysteine substitutions to stabilize the recombinant MeV F ectodomain trimer in the prefusion conformation.

Any of the above recombinant MeV F proteins can further comprise modification to eliminate the protease cleavage site between the F1 and F2 polypeptides to generate a "single chain" recombinant F protein. For example, any of the above recombinant MeV F proteins can comprise deletion of MeV F positions 111-113 with positions 110 and 114 fused by a peptide linker. This modification removes the F2/F1 furin cleavage site and also removed the first residue of the fusion peptide (which is hydrophobic). Any suitable peptide linker may be used that fuses the F2 and F1 ectodomain and allows folding of the F ectodomain into the prefusion conformation. In some embodiments, the peptide linker is a glycine, serine, or glycine-serine peptide linker. In some embodiments, the peptide linker is a Gly-Gly-Gly linker.

In a non-limiting example, a recombinant MeV F ectodomain trimer is provided that includes protomers with R165C and M171C substitutions to form a non-natural disulfide bond and a deletion of MeV F positions 111-113 with positions 110 and 114 fused by a Gly-Gly-Gly peptide linker.

In several embodiments, the protomers of the recombinant MeV F ectodomain can comprise one or more additional amino acid substitutions, for example, to increase stabilization of the prefusion conformation, or for other purposes, such as to increase solubility or to reduce and unwanted immune response.

The above-listed non-native disulfide bonds stabilize the membrane-distal portion of the MeV F ectodomain in its prefusion conformation. Any of these mutations can be combined with modifications to the membrane proximal portion (such as the stem) of the MeV F ectodomain, for example, to increase trimerization of the ectodomain.

In several embodiments, the N-terminal position of the recombinant F2 polypeptide in the protomer can be one of MeV F positions 24-34 (such as position 24), and the C-terminal position of the F1 ectodomain can be from the stem region of the ectodomain, such as one of MeV F positions 472-486 (such as position 486).

In a non-limiting example, a recombinant MeV F ectodomain trimer is provided that includes protomers including MeV positions 24-486 with R165C and M171C substitutions to form a non-natural disulfide bond and a deletion of MeV F positions 111-113 with positions 110 and 114 fused by a Gly-Gly-Gly peptide linker.

Non-limiting examples of protomers of a MeV F ectodomain trimer including amino acid substitutions for stabilization in the prefusion conformation are provided herein. In some embodiments, the protomers of the MeV F ectodomain trimer comprise an amino acid sequence at least 90% identical to residues 21-483 of any one of SEQ ID NOs: 37-43 or 53-55; wherein the protomers comprise the one or more amino acid substitutions that stabilize the MeV F ectodomain trimer in the prefusion conformation. In some embodiments, the protomers of the MeV F ectodomain trimer comprise residues 21-483 of any one of SEQ ID NOs: 37-43 or 53-55.

In several embodiments, the recombinant MeV F ectodomain trimer is a soluble protein complex, for example, for use as a recombinant subunit vaccine. In several such embodiments, the protomers of the recombinant MeV F ectodomain trimer can each comprise a C-terminal linkage to a trimerization domain, such as a GCN4 trimerization domain or a T4 fibritin trimerization domain, or both. The trimerization domain promotes trimerization and stabilization of the membrane proximal aspect of the recombinant MeV F ectodomain trimer. For example, a C-terminal residue of the protomers of the recombinant MeV F ectodomain trimer (such as a residue of the stem region of the trimer) can be directly linked to the trimerization domain, or indirectly linked to the trimerization domain via a peptide linker Exemplary linkers include glycine and glycine-serine linkers. Non-limiting examples of exogenous multimerization domains that promote stable trimers of soluble recombinant proteins include: the GCN4 leucine zipper, a T4 fibritin trimerization domain, the trimerization motif from the lung surfactant protein (Hoppe et al. 1994 *FEBS Lett* 344:191-195) or collagen (McAlinden et al. 2003 *J Biol Chem* 278:42200-42207), any of which can be linked to the C-terminus of the protomers of a recombinant MeV F ectodomain to promote trimerization, as long as the recombinant MeV F ectodomain trimer retains the prefusion conformation. In some examples, the protomers of the recombinant MeV F ectodomain trimer can be linked to a MeV trimerization domain, for example, each protomer in the trimer can include a C-terminal linkage to the GCN4 trimerization domain, such as a linkage to any one of MeV F positions 472-486, such as MeV F position 486. In specific examples, the GCN4 trimerization domain comprises or consists of the amino acid sequence IEDKIEEILSKIYHIE-NEIARIKKLIGEAP (SEQ ID NO: 33). In specific examples, the T4 fibritin trimerization domain comprises or consists of the amino acid sequence GYIPEAPRDGQAY-VRKDGEWVLLSTFL (SEQ ID NO: 34). In specific examples, the GCN4 trimerization domain fused to the fibritin trimerization domain comprises or consists of the amino acid sequence

```
                                    (SEQ ID NO: 35)
IEDKIEEILSKIYHIENEIARIKKLIGEAPGSGYIPEAPRDGQAYVRKDG

EWVLLSTFL
```

In a non-limiting example, a recombinant MeV F ectodomain trimer is provided that includes protomers including MeV positions 24-486 with R165C and M171C substitutions to form a non-natural disulfide bond and a deletion of MeV F positions 111-113 with positions 110 and 114 fused by a Gly-Gly-Gly peptide linker, and a GCN4 trimerization domain linked to the C-terminus of the protomers in the ectodomain.

Non-limiting examples of protomers of a MeV F ectodomain trimer including amino acid substitutions for stabilization in the prefusion conformation as well as a C-terminal linkage to a trimerization domain are provided herein. In some embodiments, the protomers of the MeV F ectodomain trimer comprise an amino acid sequence at least 90% identical to residues 21-513 of any one of SEQ ID NOs: 37-43 or 53-55; wherein the protomers comprise the one or more amino acid substitutions that stabilize the MeV F ectodomain trimer in the prefusion conformation. In some embodiments, the protomers of the MeV F ectodomain trimer comprise residues 21-513 of any one of SEQ ID NOs: 37-43 or 53-55.

In some embodiments, the recombinant MeV F ectodomain trimer can be a membrane anchored protein complex, for example, for use in an attenuated virus or virus like particle vaccine. Membrane anchoring can be accomplished, for example, by C-terminal linkage of the protomers of the recombinant MeV F ectodomain trimer to a transmembrane domain and optionally a cytoplasmic tail, such as a MeV F transmembrane domain and cytoplasmic tail. In some embodiments, one or more peptide linkers (such as a gly-ser linker, for example, a 10 amino acid glycine-serine peptide linker can be used to link the protomers of the recombinant MeV F ectodomain trimer to the transmembrane domain. A non-limiting example of a transmembrane domain for use with the disclosed embodiments includes a MeV F transmembrane domain, such as CIVYILIAVCLGGLIGI (SEQ ID NO: 100). A non-limiting example of a transmembrane domain for use with the disclosed embodiments includes a MeV F transmembrane domain, such as

```
                                    (SEQ ID NO: 101)
CIVYILIAVCLGGLIGIPALICCCRGRCNKKGEQVGMSRPGLKPDLTGTS

KSYVRSL
```

Native MeV F proteins from different MeV strains, as well as nucleic acid sequences encoding such proteins and methods, are known and can be altered using the description provided herein to generate a recombinant MeV F ectodomain trimer.

The recombinant MeV F ectodomain trimer can be derivatized or linked to another molecule (such as another peptide or protein). In general, the recombinant MeV F ectodomain is derivatized such that the binding to cross-neutralizing antibodies to a trimer of the recombinant MeV F protein is not affected adversely by the derivatization or labeling. For example, the recombinant MeV F ectodomain can be functionally linked (by chemical coupling, genetic fusion, non-covalent association or otherwise) to one or more other molecular entities, such as a carrier protein, an antibody, a heterologous protein, or a detection tag.

In some embodiments, the recombinant MeV F ectodomain trimers are fused to one or more MuV HN ectodomains, such as the ectodomain of the MuV HN sequence set forth as:

```
MuV HN ectodomain head
                                    (SEQ ID NO: 30)
NIPLVNDLRFINGINKFIIEDYATHDFSIGHPLNMPSFIPTATSPNGCTR

IPSFSLGKTHWCYTHNVINANCKDHTSSNQYVSMGILVQTASGYPMFKTL

KIQYLSDGLNRKSCSIATVPDGCAMYCYVSTQLETDDYAGSSPPTQKLTL

LFYNDTVTERTISPSGLEGNWATLVPGVGSGIYFENKLIFPAYGGVLPNS

TLGVKSAREFFRPVNPYNPCSGPQQDLDQRALRSYFPSYFSNRRIQSAFL

VCAWNQILVTNCELVVPSSNQTMMGAEGRVLLINNRLLYYQRSTSWWPYE

LLYEISFTFTNSGPSSVNMSWIPIYSFTRPGSGNCSGENVCPTACVSGVY
```

-continued

LDPWPLTPYSHQSGINRNFYFTGALLNSSTTRVNPTLYVSALNNLKVLAP

YGTQGLFASYTTTTCFQDTGDASVYCVYIMELASNIVGEFQILPVLTRLT

IT

For example, the protomers of the recombinant MeV F ectodomain trimer are each fused to a MuV HN ectodomain. The fusion can be direct or via a peptide linker. In some embodiments, the MuV HN ectodomain can be fused, directly or indirectly via a peptide linker, to the C-terminus of the protomers of the MeV F ectodomain trimer. In some such embodiments, the MuV HN ectodomain can be fused, directly or indirectly via a peptide linker, to the C-terminus of a trimerization domain (such as a GCN4 or T4 fibritin trimerization domain) fused to the C-terminus of the protomers of the MeV F ectodomain trimer. In some such embodiments, the protomers of the MeV F ectodomain trimer linked to the trimerization domain and the MuV HN ectodomain comprise an amino acid sequence set forth as residues 20-966 of SEQ ID NO: 27, or an amino acid sequence at least 90% identical to residues 20-966 of SEQ ID NO: 27.

In some embodiments, the recombinant MeV F ectodomain trimers are fused to one or more MeV H ectodomains, such as the ectodomain of the H sequence set forth as:

MeV H ectodomain (SEQ ID NO: 31)

FLAVSKGNCSGPTTIRGQFSNMSLSLLDLYLGRGYNVSSIVTMTSQGMYG

GTYLVEKPNLSSKRSELSQLSMYRVFEVGVIRNPGLGAPVFHMTNYLEQP

VSNDLSNCMVALGELKLAALCHGEDSITIPYQGSGKGVSFQLVKLGVWKS

PADMQSWVPLSTDDPVIDRLYLSSHRGVIADNQAKWAVPTTRTDDKLRME

TCFQQACKGKIQTLCENPEWAPLKDNRIPSYGVLSVDLSLTVELKIKIAS

GFGPLITHGSGMDLYKSNHNNVYWLTIPPMKNLALGVINTLEWIPRFKVS

PYLFTVPIKEAGEDCHAPTYLPAEVDGDVKLSSNLVILPGQDLQYVLATY

DTSRVEHAVVYVVYSPGRSFSYFYPFRLPIKGVPIELQVECFTWDQKLWC

RHFCVLADSESGGHITHSGMVGMGVSCTVTREDGTNRR

MeV H ectodomain (SEQ ID NO: 32)

ADVAAEELMNALVNSTLLEARATNQFLAVSKGNCSGPTTIRGQFSNMSLS

LLDLYLSRGYNVSSIVTMTSQGMYGGTYLVGKPNLSSKGSELSQLSMHRV

FEVGVIRNPGLGAPVFHMTNYFEQPVSNDFSNCMVALGELKFAALCHRED

SITIPYQGSGKGVSFQLVKLGVWKSPTDMRSWVPLSTDDPVIDRLYLSSH

RGVIADNQAKWAVPTTRTDDKLRMETCFQQACKGKNQALCENPEWAPLKD

NRIPSYGVLSVNLSLTVELKIKIASGFGPLITHGSGMDLYKTNHNNVYWL

TIPPMKNLALGVINTLEWIPRFKVSPNLFTVPIKEAGEDCHAPTYLPAEV

DGDVKLSSNLVILPGQDLQYVLATYDTSRVEHAVVYYVYSPSRSFSYFYP

FRLPIKGVPIELQVECFTWDKKLWCRHFCVLADSESGGHITHSGMVGMGV

SCTVTREDGTNRR

For example, the protomers of the recombinant MeV F ectodomain trimer are each fused to a MeV H ectodomain. The fusion can be direct or via a peptide linker. In some embodiments, the MeV H ectodomain can be fused, directly or indirectly via a peptide linker, to the C-terminus of the protomers of the MeV F ectodomain trimer. In some such embodiments, the MeV H ectodomain can be fused, directly or indirectly via a peptide linker, to the C-terminus of a trimerization domain (such as a GCN4 or T4 fibritin trimerization domain) fused to the C-terminus of the protomers of the MeV F ectodomain trimer. In some such embodiments, the protomers of the MeV F ectodomain trimer linked to the trimerization domain and the MeV H ectodomain comprise an amino acid sequence set forth as residues 21-959 of SEQ ID NO: 56 or 21-973 of SEQ ID NO 57 or an amino acid sequence at least 90% identical thereto.

Non-limiting examples of sequences containing a MeV F ectodomain with amino acid substitutions for stabilization in a prefusion conformation are provided as follows:

MeV F R48C/A284C-GGG-486-GCN4

(SEQ ID NO: 53)

mysmqlascvtltlvllvnsqihwgnlskigvvgigsasykvmtCsshqslviklmpnitllnnctrveiaeyrrllrtv lepirdalnavtqnirpvqsvassrrhGGGagvvlagaalgvataaqitagialhqsmlnsqaidnlraslettnqaiea irqagqemilavqgvqdyinnelipsmnqlscdligqklglkllryytellsifgpslrdpisaeisiqalsyalggdin kvleklgysggdllgilesrgikarithvdtesyfivlsiCyptlseikgvivhrlegvsynigsqewyttvpkyvatqg ylisnfdessctfmpegtvcsqnalypmspllqeclrgstkscartlvsgsfgnrfiisqgnllaneaslickcyttgti inqdpdkiltyiaadhcpvvevngvtiqvgsrrypdavylhridlgppislerIdvgtnlgnaiakledakellessdqi lsa IEDKIEEILSKIYHIENEIARIKKLIGEAP MeV F A90C/I225C-GGG-486-GCN4

(SEQ ID NO: 37)

mysmqlascvtltlvllvnsqihwgnlskigvvgigsasykvmtrsshqslviklmpnitllnnctrveiaeyrrllrtv lepirdClnavtqnirpvqsvassrrhGGGagvvlagaalgvataaqitagialhqsmlnsqaidnlraslettnqaiea irqagqemilavqgvqdyinnelipsmnqlscdligqklglkllryytellsifgpslrdpCsaeisiqalsyalggdin kvleklqysqqdllqilesrgikarithvdtesyfivlsiayptlseikqvivhrleqvsynigsqewyttvpkyvatqq -continued ylisnfdessctfmpegtvcsqnalypmspllqeclrgstkscartlvsgsfgnrfilsqgnliancasilckcyttgti inqdpdkiltyiaadhcpvvevngvtiqvgsrrypdavylhridlgppislerldvgtnlgnaiakledakellessdqi lsaIEDKIEEILSKIYHIENEIARIKKLIGEAP MeV F M141C/T270C-GGG-486-GCN4

(SEQ ID NO: 54)

<u>mysmql</u>ascvtltlvllvnsqihwqnlskigvvgiqsasykvmtrsshqslviklmpnitllnnctrveiaeyrrllrtv lepirdalnavtqnirpvqsvassrrhGGGagvvlagaalgvataaqitagialhqs<u>C</u>lnsqaidnlraslettnqaiea irqagqemilavqgvqdyinnelipsmnqlscdlligqklglkllryytellsifgpslrdpisaeisiqalsyalggdin kvleklgysggdllgilesrgikari<u>C</u>hvdtesyfivlsiayptlseikgvivhrlegvsynigsqewyttvpkyvatqg ylisnfdesscttfmpegtvcsqnalypmspllqeclrgstkscartlvsgsfgnrfilsqgnliancasilckcyttgti inqdpdkiltyiaadhcpvvevngvtiqvgsrrypdavylhridlgppislerldvgtnlgnaiakledakellessdqi lsa IEDKIEEILSKIYHIENEIARIKKLIGEAP MeV F R165C/M171C-GGG-486-GCN4

(SEQ ID NO: 38)

<u>mysmql</u>ascvtltlvllvnsqihwqnlskigvvgigsasykvmtrsshqslviklmpnitllnnctrveiaeyrrllrtv lepirdalnavtqnirpvqsvassrrhGGGagvvlagaaIgvataaqitagiaihqsmlnsqaidnlraslettnqaiea i<u>C</u>qagqe<u>C</u>ilavqgvqdyinnelipsmnqlscdlligqklglkllryyteilsifgpslrdpisaeisiqalsyalggdin kvleklgysggdllgilesrgikarithvdtesyfivlsiayptlseikgvivhrlegvsynigsqewyttvpkyvatqg ylisnfdesscttfmpegtvcsqnalypmspllqeclrgstkscartlvsgsfgnrfilsqgnliancasilckcyttgti inqdpdkiltyiaadhcpvvevngvtiqvgsrrypdavylhridlgppislerldvgtnlgnaiakledakellessdqi lsa IEDKIEEILSKIYHIENEIARIKKLIGEAP MeV F L173C/V245C-GGG-486-GCN4

(SEQ ID NO: 39)

<u>mysmql</u>ascvtltlvllvnsqihwqnlskigvvgigsasykvmtrsshqslviklmpnitllnnctrveiaeyrrllrtv lepirdalnavtqnirpvqsvassrrhGGGagvvlagaaigvataaqitagiaihqsmlnsqaidnlraslettnqaiea irqagqemi<u>C</u>avqgvqdyinnelipsmnqlscdlligqklglkllryyteilsifgpslrdpisaeisiqalsyalggdin k<u>C</u>leklqysqqdllqilesrqikarithvdtesyfivlsiayptlseikgvivhrlegvsynigsqewyttvpkyvatqg ylisnfdesscttfmpegtvcsqnalypmspllqeclrgstkscartlvsgsfgnrfilsqgnliancasilckcyttgti inqdpdkiltyiaadhcpvvevngvtiqvgsrrypdavylhridlgppislerldvgtnlgnaiakledakellessdqi lsa IEDKIEEILSKIYHIENEIARIKKLIGEAP MeV F V175C/D241C-GGG-486-GCN4

(SEQ ID NO: 40)

<u>mysmql</u>ascvtltlvllvnsqihwqnlskigvvgigsasykvmtrsshqslviklmpnitllnnctrveiaeyrrllrtv lepirdalnavtqnirpvqsvassrrhGGGagvvlagaaigvataaqitagiaihqsmlnsqaidnlraslettnqaiea irqagqemila<u>C</u>qgvqdyinnelipsmnqlscdlligqklglkllryyteilslfgpslrdpisaeisiqalsyalgg<u>C</u>in kvleklgysggdllgilesrgikarithvdtesyfivlsiayptlseikgvivhrlegvsynigsqewyttvpkyvatqg ylisnfdesscttfmpegtvcsqnalypmspllqeclrgstkscartlvsgsfgnrfilsqgnliancasilckcyttgti inqdpdkiltyiaadhcpvvevngvtiqvgsrrypdavylhridlgppislerldvgtnlgnaiakledakellessdqi lsa IEDKIEEILSKIYHIENEIARIKKLIGEAP MeV F E212C/Y236C-GGG-486-GCN4

(SEQ ID NO: 55)

<u>mysmql</u>ascvtltlvllvnsqihwqnlskigvvgigsasykvmtrsshqslviklmpnitllnnctrveiaeyrrllrtv lepirdalnavtqnirpvqsvassrrhGGGagvvlagaaigvataaqitagiaihqsmlnsqaidnlraslettnqaiea irqagqemilavqgvqdyinnelipsmnqlscdlligqklglkllryyt<u>C</u>ilslfgpslrdpisaeisiqals<u>C</u>algggdin kvleklgysggdllgilesrgikarithvdtesyfivlsiayptlseikgvivhrlegvsynigsqewyttvpkyvatqg ylisnfdessctfmpegtvcsqnalypmspllqeclrgstkscartlvsgsfgnrfilsqgnliancasilckcyttgti inqdpdkiltyiaadhcpvvevngvtiqvgsrrypdavylhridlgppislerldvgtnlgnaiakledakellessdqi lsa IEDKIEEILSKIYHIENEIARIKKLIGEAP MeV F L216C/A233C-GGG-486-GCN4

(SEQ ID NO: 41)

<u>mysmqlascvtltlvllvns</u>qihwgnlskigvvgigsasykvmtrsshqslviklmpnitllnnctrveiaeyrrllrtv lepirdalnavtqnirpvqsvassrrhGGGagvvlagaaigvataaqitagiaihqsmlnsqaidnlraslettnqaiea irqagqemilavqgvqdyinnelipsmnqlscdligqklglkllrryyteils<u>C</u>fgpslrdpisaeisiq<u>C</u>lsyalggdin kvleklgysggdllgilesrgikarithvdtesyfivlsiayptlseikgvivhrlegvsynigsqewyttvpkyvatqg ylisnfdessctfmpegtvcsqnalypmspllqeclrgstkscartlvsgsfgnrfilsqgnliancasilckcyttgti inqdpdkiltyiaadhcpvvevngvtiqvgsrrypdavylhridlgppislerldvgtnlgnaiakledakellessdqi lsa IEDKIEEILSKIYHIENEIARIKKLIGEAP MeV F P219C/P224C-GGG-486-GCN4

(SEQ ID NO: 42)

<u>mysmqlascvtltlvllvns</u>qihwgnlskigvvgigsasykvmtrsshqslviklmpnitllnnctrveiaeyrrllrtv lepirdalnavtqnirpvqsvassrrhGGGagvvlagaaigvataaqitagiaihqsmlnsqaidnlraslettnqaiea irqagqemilavqgvqdyinnelipsmnqlscdligqklglkllrryyteilslfg<u>C</u>slrd<u>C</u>isaeisiqalsyalggdin kvleklgysggdllgilesrgikarithvdtesyfivlsiayptlseikgvivhrlegvsynigsqewyttvpkyvatqg ylisnfdessctfmpegtvcsqnalypmspllqeclrgstkscartlvsgsfgnrfilsqgnliancasilckcyttgti inqdpdkiltyiaadhcpvvevngvtiqvgsrrypdavylhridlgppislerIdvgtnlgnaiakledakellessdqi lsa IEDKIEEILSKIYHIENEIARIKKLIGEAP MeV F S194P-GGG-486-GCN4

(SEQ ID NO: 43)

<u>mysmqlascvtltlvllvns</u>qihwgnlskigvvgigsasykvmtrsshqslviklmpnitllnnctrveiaeyrrllrtv lepirdalnavtqnirpvqsvassrrhGGGagvvlagaalgvataaqitagialhqsmlnsqaidnlraslettnqaiea irqagqemilavqgvqdyinnelipsmnql<u>P</u>cdligqklglkllrryyteilslfgpslrdpisaeisiqalsyalggdin kvleklgysggdllgilesrgikarithvdtesyfivlsiayptlseikgvivhrlegvsynigsqewyttvpkyvatqg ylisnfdessctfmpegtvcsqnalypmspllqeclrgstkscartlvsgsfgnrfilsqgnliancasilckcyttgti inqdpdkiltyiaadhcpvvevngvtiqvgsrrypdavylhridlgppislerIdvgtnlgnaiakledakellessdqi lsa IEDKIEEILSKIYHIENEIARIKKLIGEAP MeV F S103C/V117C-GGG-486-GCN4

(SEQ ID NO: 62)

<u>mysmqlascvtltlvllvns</u>qihwqnlskigvvgiqsasykvmtrsshqslviklmpnitllnnctrveiaeyrrllrtv lepirdalnavtqnirpvq<u>C</u>vassrrhGGGagv<u>C</u>lagaaIgvataaqitagiaIhqsmlnsqaidnlraslettnqaIea irqagqemilavqgvqdyinnelipsmnqlscdligqklglkllrryytellsifgpslrdpisaeisiqalsyalggdin kvleklgysggdllgilesrgikarithvdtesyfivlsiayptlseikgvivhrlegvsynigsqewyttvpkyvatqg ylisnfdessctfmpegtvcsqnalypmspllqeclrgstkscartlvsgsfgnrfilsqgnliancasilckcyttgti inqdpdkiltyiaadhcpvvevngvtiqvgsrrypdavylhridlgppislerIdvgtnlgnaiakledakellessdqi lsa IEDKIEEILSKIYHIENEIARIKKLIGEAP MeV F V175F-GGG-486-GCN4

(SEQ ID NO: 63)

<u>mysmqlascvtltlvllvns</u>qihwgnlskigvvgigsasykvmtrsshqslviklmpnitllnnctrveiaeyrrllrtv lepirdalnavtqnirpvqsvassrrhGGGagvvlagaaigvataaqitagiaihqsmlnsqaidnlraslettnqalea irqagqemila<u>F</u>qgvqdyinnelipsmnqlscdligqklglkllrryytellsifgpslrdpisaeisiqalsyalggdin -continued kvleklgysggdllgilesrgikarithvdtesyfivlsiayptlseikgvivhrlegvsynigsqewyttvpkyvatqg ylisnfdessctfmpegtvcsqnalypmspllqeclrgstkscartlvsgsfgnrfilsqgnliancasilckcyttgti inqdpdkiltyiaadhcpvvevngvtiqvgsrrypdavylhridlgppislerldvgtnlgnaiakledakellessdqi lsa IEDKIEEILSKIYHIENEIARIKKLIGEAP MeV F S103C/V117C, V175F, S194P-GGG-486-GCN4
                                                                (SEQ ID NO: 64)
mysmqlascvtitlvllvnsqihwgnlskigvvgigsasykvmtrsshqslviklmpnitllnnctrveiaeyrrllrtv lepirdalnavtqnirpvqCvassrrhGGGagvClagaaigvataaqitagiaihqsmlnsqaidnlraslettnqaiea irqagqemilaFqgvqdyinnelipsmnqlPcdligqklglkllrryytellsifgpslrdpisaeisiqalsyalggdin kvleklgysggdllgilesrgikarithvdtesyfivlsiayptlseikgvivhrlegvsynigsqewyttvpkyvatqg ylisnfdessctfmpegtvcsqnalypmspllqeclrgstkscartlvsgsfgnrfilsqgnliancasilckcyttgti inqdpdkiltyiaadhcpvvevngvtiqvgsrrypdavylhridlgppislerldvgtnlgnaiakledakellessdqi lsa IEDKIEEILSKIYHIENEIARIKKLIGEAP MeV F S103C/V117C, R165C/M171C, S194P-GGG-486-GCN4
                                                                (SEQ ID NO: 65)
mysmqlascvtltlvllvnsqihwgnlskigvvgigsasykvmtrsshqslviklmpnitllnnctrveiaeyrrllrtv lepirdalnavtqnirpvqCvassrrhGGGagvClagaaIgvataaqitagiaIhqsmlnsqaidnlraslettnqalea iCqagqeCilaFqgvqdyinnelipsmnqlPcdligqklglkllrryytellsifgpslrdpisaeisiqalsyalggdin kvleklgysggdllgilesrgikarithvdtesyfivlsiayptlseikgvivhrlegvsynigsqewyttvpkyvatqg ylisnfdessctfmpegtvcsqnalypmspllqeclrgstkscartlvsgsfgnrfilsqgnliancasilckcyttgti inqdpdkiltyiaadhcpvvevngvtiqvgsrrypdavylhridlgppislerldvgtnlgnaiakledakellessdqi lsa IEDKIEEILSKIYHIENEIARIKKLIGEAP MeV F R99C/V117C-GGG-486-GCN4
                                                                (SEQ ID NO: 66)
mysmqlascvtitlvllvnsqihwgnlskigvvgiqsasykvmtrsshqslviklmpnitllnnctrveiaeyrrllrtv lepirdalnavtqniCpvqsvassrrhGGGagvClagaaIgvataaqitagiaihqsmlnsqaidnlraslettnqalea irqagqemilavqgvqdyinnelipsmnqlscdligqklglkllrryvtellsifgpslrdpisaeisiqalsyalggdin kvleklgysggdllgilesrgikarithvdtesyfivlsiayptlseikgvivhrlegvsynigsqewyttvpkyvatqg ylisnfdessctfmpegtvcsqnalypmspllqeclrgstkscartlvsgsfgnrfilsqgnliancasilckcyttgti inqdpdkiltyiaadhcpvvevngvtiqvgsrrypdavylhridlgppislerldvgtnlgnaiakledakellessdqi lsa IEDKIEEILSKIYHIENEIARIKKLIGEAP MeV F R99C/V117C, V175F, S194P-GGG-486-GCN4
                                                                (SEQ ID NO: 67)
mysmqlascvtltlvllvnsqihwgnlskigvvgigsasykvmtrsshqslviklmpnitllnnctrveiaeyrrllrtv lepirdalnavtqniCpvqsvassrrhGGGagvClagaaigvataaqitagiaihqsminsqaidnlraslettnqaiea irqagqemilaFqgvqdyinnelipsmnqlPcdligqklglkllrryyteilsifgpslrdpisaeisiqalsyalggdin kvleklgysggdllgilesrgikarithvdtesyfivlsiayptlseikgvivhrlegvsynigsqewyttvpkyvatqg ylisnfdessctfmpegtvcsqnalypmspllqeclrgstkscartlvsgsfgnrfilsqgnliancasilckcyttgti inqdpdkiltyiaadhcpvvevngvtiqvgsrrypdavylhridlgppisleridvgtnlgnaiakledakellessdqi lsa IEDKIEEILSKIYHIENEIARIKKLIGEAP MeV F R99C/VH7C, R165C/M171C, S194P-GGG-486-GCN4
                                                                (SEQ ID NO: 68)
mysmqlascvtitlvllvnsqihwgnlskigvvgigsasykvmtrsshqslviklmpnitllnnctrveiaeyrrllrtv lepirdalnavtqniCpvqsvassrrhGGGagvClagaaIgvataaqitagiaihqsminsqaidnlraslettnqaiea iCqagqeCilaFqgvqdyinnelipsmnqlPcdligqklglkllrryytellsifgpslrdpisaeisiqalsyalggdin kvleklgysggdllgilesrgikarithvdtesyfivlsiayptlseikgvivhrlegvsynigsqewyttvpkyvatqg ylisnfdessctfmpegtvcsqnalypmspllqeclrgstkscartlvsgsfgnrfilsqgnliancasilckcyttgti inqdpdkiltyiaadhcpvvevngvtiqvgsrrypdavylhridlgppisleridvgtnlgnaiakledakellessdqi lsa IEDKIEEILSKIYHIENEIARIKKLIGEAP MeV F R99C/V117C-GGG-493-GCN4

(SEQ ID NO: 69)

mysmqlascvtltlvllvnsqihwgnlskigvvgigsasykvmtrsshqslviklmpnitllnnctrveiaeyrrllrtv lepirdalnavtqniCpvqsvassrrhGGGagvClagaaigvataaqitagiaihqsminsqaidnlraslettnqaiea irqagqemilavqgvqdvinnelipsmnqlscdligqklglkllrvvteilsifgpslrdpisaeisiqalsyalggdin kvleklgysggdllgilesrgikarithvdtesyfivlsiayptlseikgvivhrlegvsynigsqewyttvpkyvatqg ylisnfdessctfmpegtvcsqnalypmspllqeclrgstkscartlvsgsfgnrfilsqgnliancasilckcyttgti inqdpdkiltyiaadhcpvvevngvtiqvgsrrypdavylhridlgppisleridvgtnlgnaiakledakellessdqi l rsmkglssa IEDKIEEILSKIYHIENEIARIKKLIGEAP MeV F R99C/V117C, V175F, S194P-GGG-493-GCN4

(SEQ ID NO: 70)

mysmqlascvtltlvllvnsqihwgnlskigvvgigsasykvmtrsshqslviklmpnitllnnctrveiaeyrrllrtv lepirdalnavtqniCpvqsvassrrhGGGagvClagaaIgvataaqitagiaihqsminsqaidnlraslettnqaiea irqagqemilaFqgvqdyinnelipsmnqlPcdligqklglkllryyteilsifgpslrdpisaeisiqalsyalggdin kvleklgysggdllgilesrgikarithvdtesyfivlsiayptlseikgvivhrlegvsynigsqewyttvpkyvatqg ylisnfdessctfmpegtvcsqnalypmspllqeclrgstkscartlvsgsfgnrfilsqgnliancasilckcyttgti inqdpdkiltyiaadhcpvvevngvtiqvgsrrypdavylhridlgppisleridvgtnlgnaiakledakellessdqi l rsmkglssa IEDKIEEILSKIYHIENEIARIKKLIGEAP MeV F R99C/V117C, R165C/M171C, S194P-GGG-493-GCN4

(SEQ ID NO: 71)

mysmqlascvtltlvllvnsqihwgnlskigvvgigsasykvmtrsshqslviklmpnitllnnctrveiaeyrrllrtv lepirdalnavtqniCpvqsvassrrhGGGagvClagaaIgvataaqitagiaihqsminsqaidnlraslettnqaiea iCqagqeCilaFqgvqdyinnelipsmnqlPcdligqklglkllryyteilsifgpslrdpisaeisiqalsyalggdin kvleklgysggdllgilesrgikarithvdtesyfivlsiayptlseikgvivhrlegvsynigsqewyttvpkyvatqg ylisnfdessctfmpegtvcsqnalypmspllqeclrgstkscartlvsgsfgnrfilsqgnliancasilckcyttgti inqdpdkiltyiaadhcpvvevngvtiqvgsrrypdavylhridlgppisleridvgtnlgnaiakledakellessdqi l rsmkglssa IEDKIEEILSKIYHIENEIARIKKLIGEAP MeV F P100C/V117C, R165C/M171C, S194P-GGG-486-GCN4

(SEQ ID NO: 72)

mysmqlascvtltlvllvnsqihwgnlskigvvgigsasykvmtrsshqslviklmpnitllnnctrveiaeyrrllrtv lepirdaInavtqnirCvqsvassrrhGGGagvClagaaigvataaqitagiaihqsminsqaidnlraslettnqaiea iCqagqeCilaFqgvqdyinnelipsmnqlPcdligqklglkllryyteilsifgpslrdpisaeisiqalsyalggdin kvleklgysggdllgilesrgikarithvdtesyfivlsiayptlseikgvivhrlegvsynigsqewyttvpkyvatqg ylisnfdessctfmpegtvcsqnalypmspllqeclrgstkscartlvsgsfgnrfilsqgnliancasilckcyttgti inqdpdkiltyiaadhcpvvevngvtiqvgsrrypdavylhridlgppisleridvgtnlgnaiakledakellessdqi lsa IEDKIEEILSKIYHIENEIARIKKLIGEAP MeV F V101C/V117C, R165C/M171C, S194P-GGG-486-GCN4

(SEQ ID NO: 73)

mysmqlascvtltlvllvnsqihwgnlskigvvgigsasykvmtrsshqslviklmpnitllnnctrveiaeyrrllrtv lepirdaInavtqnirpCqsvassrrhGGGagvClagaaigvataaqitagiaihqsminsqaidnlraslettnqaiea iCqagqeCilaFqgvqdyinnelipsmnqlPcdligqklglkllryyteilsifgpslrdpisaeisiqalsyalggdin kvleklgysggdllgilesrgikarithvdtesyfivlsiayptlseikgvivhrlegvsynigsqewyttvpkyvatqg -continued ylisnfdessctfmpegtvcsqnalypmspllqeclrgstkscartlvsgsfgnrfilsqgnliancasilckcyttgti inqdpdkiltyiaadhcpvvevngvtiqvgsrrypdavylhridlgppisleridvgtnlgnaiakledakellessdqi lsa IEDKIEEILSKIYHIENEIARIKKLIGEAP MeV F Q102C/V117C, R165C/M171C, S194P-GGG-486-GCN4

(SEQ ID NO: 74)

mysmqlascvtltlvllvnsqihwqnlskigvvgiqsasykvmtrsshqslviklmpnitllnnctrveiaeyrrllrtv lepirdalnavtqnirpvCsvassrrhGGGagvClagaaigvataaqitagiaihqsmlnsqaidnlraslettnqaiea iCqagqeCilaFqgvqdyinnelipsmnqlPcdligqklglkllryyteilsifgpslrdpisaeisiqalsyalggdin kvleklgysggdllgilesrgikarithvdtesyfivlsiayptlseikgvivhrlegvsynigsqewyttvpkyvatqg ylisnfdessctfmpegtvcsqnalypmspllqeclrgstkscartlvsgsfgnrfilsqgnliancasilckcyttgti inqdpdkiltyiaadhcpvvevngvtiqvgsrrypdavylhridlgppislerIdvgtnlgnaiakledakellessdqi lsa IEDKIEEILSKIYHIENEIARIKKLIGEAP MeV F R165C/M171C, M1 41C/T270C-GGG-486-GCN4

(SEQ ID NO: 75)

mysmqlascvtitlvllvnsqihwqnlskigvvgigsasykvmtrsshqslviklmpnitllnnctrveiaeyrrllrtv lepirdalnavtqnirpvqsvassrrhGGGagvvlagaaigvataaqitagiaihqsClnsqaidnlraslettnqaiea iCqagqeCilavqgvqdyinnelipsmnqlscdligqklglkllryyteilsifgpslrdpisaeisiqalsyalggdin kvleklgysggdllgilesrgikarichvdtesyfivlsiayptlseikgvivhrlegvsynigsqewyttvpkyvatqg ylisnfdessctfmpegtvcsqnalypmspllqeclrgstkscartlvsgsfgnrfilsqgnliancasilckcyttgti inqdpdkiltyiaadhcpvvevngvtiqvgsrrypdavylhridlgppisleridvgtnlgnaiakledakellessdqi lsa IEDKIEEILSKIYHIENEIARIKKLIGEAP MeV F R165C/M171C, E212C/Y236C-GGG-486-GCN4

(SEQ ID NO: 76)

mysmqlascvtltlvllvnsqihwqnlskigvvgigsasykvmtrsshqslviklmpnitllnnctrveiaeyrrllrtv lepirdalnavtqnirpvqsvassrrhGGGagvvlagaaigvataaqitagiaihqsmlnsqaidnlraslettnqaiea iCqagqeCilavqgvqdyinnelipsmnqlscdligqklglkllryytCilslfgpslrdpisaeisiqalsCalggdin kvleklgysggdllgilesrgikarithvdtesyfivlsiayptlseikgvivhrlegvsynigsqewyttvpkyvatqg ylisnfdessctfmpegtvcsqnalypmspllqeclrgstkscartlvsgsfgnrfilsqgnliancasilckcyttgti inqdpdkiltyiaadhcpvvevngvtiqvgsrrypdavylhridlgppisleridvgtnlgnaiakledakellessdqi lsa IEDKIEEILSKIYHIENEIARIKKLIGEAP MeV F R165C/M171C, R48C/A284C -GGG-486-GCN4

(SEQ ID NO: 77)

mysmqlascvtltlvllvnsqihwqnlskigvvgigsasykvmtCsshqslviklmpnitllnnctrveiaeyrrllrtv lepirdalnavtqnirpvqsvassrrhGGGagvvlagaaigvataaqitagiaihqsmlnsqaidnlraslettnqaiea iCqagqeCilavqgvqdyinnelipsmnqlscdligqklglkllryyteilsifgpslrdpisaeisiqalsyalggdin kvleklgysggdllgilesrgikarithvdtesyfivisiCyptIseikgvivhrlegvsynigsqewyttvpkyvatqg ylisnfdessctfmpegtvcsqnalypmspllqeclrgstkscartlvsgsfgnrfilsqgnliancasilckcyttgti inqdpdkiltyiaadhcpvvevngvtiqvgsrrypdavylhridlgppisleridvgtnlgnaiakledakellessdqi lsa IEDKIEEILSKIYHIENEIARIKKLIGEAP MeV F R99C/V117C, native furin-486-GCN4

(SEQ ID NO: 78)

mysmqlascvtltlvllvnsqihwqnlskigvvgigsasykvmtrsshqslviklmpnitllnnctrveiaeyrrllrtv lepirdaInavtqniCpvqsvassrrhkrfagvClagaaigvataaqitagiaihqsmlnsqaidnlraslettnqaiea irqagqemilavqgvqdyinnelipsmnqlscdligqklglkllryyteilsifgpslrdpisaeisiqalsyalggdin kvleklgysggdllgilesrgikarithvdtesyfivlsiayptlseikgvivhrlegvsynigsqewyttvpkyvatqg -continued ylisnfdessctfmpegtvcsqnalypmspllqeclrgstkscartlvsgsfgnrfilsqgnliancasilckcyttgti inqdpdkiltyiaadhcpvvevngvtiqvgsrrypdavylhridlgppisleridvgtnlgnaiakledakellessdqi lsa IEDKIEEILSKIYHIENEIARIKKLIGEAP MeV F R99C/V117C, V175F, S194P, native furin-486-GCN4
                                                                                (SEQ ID NO: 79)
mysmqlascvtltlvllvnsqihwgnlskigvvgigsasykvmtrsshqslviklmpnitllnnctrveiaeyrrllrtv lepirdaInavtqniCpvqsvassrrhkrfagvClagaaigvataaqitagiaihqsmlnsqaidnlraslettnqaiea irqagqemilaFqgvqdyinnelipsmnqlPcdligqklglkllryyteilsifgpslrdpisaeisiqalsyalggdin kvleklgysggdllgilesrgikarithvdtesyfivlsiayptlseikgvivhrlegvsynigsqewyttvpkyvatqg ylisnfdessctfmpegtvcsqnalypmspllqeclrgstkscartlvsgsfgnrfilsqgnliancasilckcyttgti inqdpdkiltyiaadhcpvvevngvtiqvgsrrypdavylhridlgppisleridvgtnlgnaiakledakellessdqi lsa IEDKIEEILSKIYHIENEIARIKKLIGEAP MeV F R99C/V117C, R165C/M171C, S194P, native furin-486-GCN4
                                                                                (SEQ ID NO: 80)
mysmqlascvtltlvllvnsqihwgnlskigvvgigsasykvmtrsshqslviklmpnitllnnctrveiaeyrrllrtv lepirdaInavtqniCpvqsvassrrhkrfagvClagaaigvataaqitagiaihqsmlnsqaidnlraslettnqaiea iCqagqeCilaFqgvqdyinnelipsmnqlPcdligqklglkllryyteilsifgpslrdpisaeisiqalsyalggdin kvleklgysggdllgilesrgikarithvdtesyfivlsiayptlseikgvivhrlegvsynigsqewyttvpkyvatqg ylisnfdessctfmpegtvcsqnalypmspllqeclrgstkscartlvsgsfgnrfilsqgnliancasilckcyttgti inqdpdkiltyiaadhcpvvevngvtiqvgsrrypdavylhridlgppisleridvgtnlgnaiakledakellessdqi lsa IEDKIEEILSKIYHIENEIARIKKLIGEAP The above sequences include an N-terminal signal peptide, a MeV F ectodomain, and a GCN4 trimerization domain. It will be appreciated that an alternative trimerization domain can be used, such as a T4 Fibritin trimerization domain. Additionally, many of the above sequence include a GGG linker to remove the native furin cleavage site separating the F1 and F2 subunits. Alternate glycine linkers can also be used, such as GSG, GGS, or SGG. Additionally, in any of the sequences, the native furin cleavage site can be included instead of the GGG linker. It will be appreciated that the N-terminal signal peptide is removed during cellular processing and is not present in the purified protein. Additionally, the MeV F ectodomain of any of the above sequences can be included in a full-length MeV F protein to provide a membrane anchored version of the prefusion MeV F protein, for example for mRNA immunization.

Non-limiting examples of sequences containing a MeV F ectodomain with amino acid substitutions for stabilization in a prefusion conformation linked to a MuV HN ectodomain or a MeV H ectodomain are provided as follows:

MeV F R165C/M171C-GGG-486-GCN4 + MeV_H
                                                (SEQ ID NO: 56)
mysmqlascvtltlvllvnsqihwgnlskigvvgigsasykvmtrsshqs lviklmpnitllnnctrveiaeyrrllrtvlepirdalnavtqnirpvqs vassrrhGGGagvvlagaalgvataaqitagialhqsmlnsqaidnlras lettnqaieaiCqagqeCilavqgvqdyinnelipsmnqlscdligqklg lkllryyteilslfgpslrdpisaeisiqalsyalggdinkvleklgysg gdllgilesrgikarithvdtesyfivlsiayptlseikgvivhrlegvs -continued ynigsqewyttvpkyvatqgylisnfdessctfmpegtvcsqnalypmsp llqeclrgstkscartlvsgsfgnrfilsqgnliancasilckcyttgti inqdpdkiltyiaadhcpvvevngvtiqvgsrrypdavylhridlgppis leridvgtnlgnaiakledakellessdqilsa IEDKIEEILSKIYHI ENEIARIKKLIGEAP GSGGGGGGflavskgncsgpttirgqfsnmsis lldlylgrgynvssivtmtsqgmyggtyivekpnlsskrselsqlsmyrv fevgvirnpglgapvfhmtnyleqpvsndlsncmvalgelklaalchged sitipyqgsgkgvsfqlvklgvwkspadmqswvplstddpvidrlyissh rgviadnqakwavpttrtddklrmetcfqqackgkiqticenpewaplkd nripsygvlsvdlsltvelkikiasgfgplithgsgmdlyksnhnnvywl tippmknlalgvintlewiprfkvspylftvpikeagedchaptyipaev dgdvklssnlvilpgqdlqyvlatydtsrvehavvyvvyspgrsfsyfyp fripikgvpielqvecftwdqklwcrhfcvladsesgghithsgmvgmgv sctvtredgtnrr MeV F R165C/M171C-GGG-486-GCN4 + MuV HN
                                                (SEQ ID NO: 57)
mysmqlascvtltlvllvnsqihwgnlskiqvvqiqsasykvmtrsshqs lviklmpnitllnnctrveiaeyrrHrtvlepirdalnavtqnirpvqsv assrrhGGGagvvlagaalgvataaqitagiaihqsmlnsqaidnlrasl ettnqaieaiCqagqeCilavqgvqdyinnelipsmnqlscdligqklgl kllryyteilsifgpslrdpisaeisiqalsyalggdinkvleklgysgg -continued

```
dllgilesrgikarithvdtesyfivlsiayptlseikgvivhrlegvsy nigsqewyttvpkyvatqgylisnfdessctfmpegtvcsqnalypmspl lqeclrgstkscartlvsgsfgnrfilsqgnliancasilckcyttgtii nqdpdkiltyiaadhcpvvevngvtiqvgsrrypdavylhridlgppisl eridvgtnlgnaiakledakellessdqilsa  IEDKIEEILSKIYHIE NEIARIKKLIGEAPG  sggggggniplvndlrfinginkfHedyathdf sighplnmpsfiptatspngctripsfslgkthwcythnvinanckdhts snqyvsmqilvqtasgypmfktikiqylsdglnrkscsiatvpdgcamyc yvstqletddyagsspptqkltllfyndtvtertispsglegnwativpg vgsgiyfenklifpayggvlpnstigvksareffrpvnpynpcsgpqqdl dqralrsyfpsyfsnrriqsaflvcawnqilvtncelvvpssnqtmmgae grvllinnrllyyqrstswwpyellyeisftftnsgpssvnmswipiysf trpgsgncsgenvcptacvsgvyldpwpltpyshqsginrnfyftgalln ssttrvnptlyvsalnnlkvlapygtqglfasyttttcfqdtgdasvycv yimelasnivgefqilpvltritit MeV F R165C/M171C-GGG-486-GCN4/Fd + MeV_H
                            (SEQ ID NO: 81)
mysmqlascvtltlvllvnsqihwgnlskigvvgigsasykvmtrsshqs lviklmpnitllnnctrveiaeyrrllrtvlepirdalnavtqnirpvqs vassrrhGGGagvvlagaaigvataaqitagiaihqsmlnsqaidnlras lettnqaieaiCqagqeCilavqgvqdyinnelipsmnqlscdligqklg lkllryyteilsifgpslrdpisaeisiqalsyalggdinkvleklgysg gdllgilesrgikarithvdtesyfivlsiayptlseikgvivhrlegvs ynigsqewyttvpkyvatqgylisnfdessctfmpegtvcsqnalypmsp llqeclrgstkscartlvsgsfgnrfilsqgnliancasilckcyttgti inqdpdkiltyiaadhcpvvevngvtiqvgsrrypdavylhridlgppis leridvgtnlgnaiakledakellessdqilsa  IEDKIEEILSKIYHIE

NEIARIKKLIGEAP GS GYIPEAPRDGQAYVRKDGEWVLLSTFL GSGG

GGGg  flavskgncsgpttirgqfsnmslslldlylgrgynvssivtmts qgmyggtylvekpnlsskrselsqlsmyrvfevgvirnpglgapvfhmtn yleqpvsndlsncmvalgelklaalchgedsitipyqgsgkgvsfqlvkl gvwkspadmqswvplstddpvidrlylsshrgviadnqakwavpttrtdd klrmetcfqqackgkiqticenpewaplkdnripsygvlsvdlsitvelk ikiasgfgplithgsgmdlyksnhnnvywltippmknlalgvintlewip rfkvspyiftvpikeagedchaptylpaevdgdvklssnlvilpgqdlqy vlatydtsrvehavvyyvyspgrsfsyfypfripikgvpielqvecftwd qklwcrhfcvladsesgghithsgmvgmgvsctvtredgtnrr
```

The above sequences include an N-terminal signal pep-
tide, a MeV F ectodomain, a trimerization domain (GCN4
and/or T4Fibritin), and a MeV H ectodomain head or a MuV
HN ectodomain head region. The MeV F ectodomain
sequence includes a GGG linker to remove the native furin
cleavage site separating the F1 and F2 subunits. Alternate
glycine linkers can also be used, such as GSG, GGS, or
SGG. Additionally, in any of the sequences, the native furin cleavage site can be included instead of the GGG linker. It
will be appreciated that the N-terminal signal peptide is
removed during cellular processing and is not present in the
purified protein.

C. MuV HN and MuV H Multimers

In some embodiments, an immunogen is provided that
comprises a multimer of the MuV HN ectodomain and/or the
MeV H ectodomain. The H or HN ectodomain can include
the ectodomain head or the ectodomain stalk and head.

In some embodiments, the immunogen comprises a trimer
of fusion proteins, each fusion protein comprising one or
more MuV HN ectodomains or MeV H ectodomains and a
trimerization domain (such as a GCN4 trimerization
domain, a T4 fibritin trimerization domain, or a GCN4
trimerization domain fused to a T4 fibritin trimerization
domain).

In some embodiments, the fusion protein comprises, in an
N- to C-terminal direction, a trimerization domain (such as
a GCN4 trimerization domain, a T4 fibritin trimerization
domain, or a GCN4 trimerization domain fused to a T4
fibritin trimerization domain) and one or more (such as one,
two, or three) MuV HN ectodomains or Mev H ectodomains.
The trimerization domains interact to form the trimer. In
some embodiments, a fragment of the ectodomain is
included, for example the head region of the MuV HN
ectodomain or the head region of the MeV H ectodomain
can be fused to the trimerization domain, optionally by a
peptide linker. In some embodiment, the fusion proteins in
the trimer comprise or consist of an amino acid sequence set
forth as residues 24-510 of SEQ ID NO: 58 or residues
24-496 of SEQ ID NO: 59, or a sequence at least 90%
identical to any one of residues 25-510 of SEQ ID NO: 58
or residues 25-496 of SEQ ID NO: 59.

In some embodiments, the fusion protein comprises, in an
N- to C-terminal direction, one or more (such as one, two,
or three) MuV HN ectodomains or Mev H ectodomains, a
trimerization domain (such as a GCN4 trimerization
domain, a T4 fibritin trimerization domain, or a GCN4
trimerization domain fused to a T4 fibritin trimerization
domain), and one or more (such as one, two, or three) MuV
HN ectodomains or Mev H ectodomains. The trimerization
domains interact to form the trimer. In some embodiments,
a fragment of the ectodomain is included, for example the
head region of the MuV HN ectodomain or the head region
of the MeV H ectodomain can be fused to the trimerization
domain, optionally by a peptide linker. In some embodi-
ment, the fusion proteins in the trimer comprise or consist of
an amino acid sequence set forth as residues 22-950 of SEQ
ID NO: 82, residues 25-985 of SEQ ID NO: 83, residues
22-948 of SEQ ID NO: 84, or residues 22-981 of SEQ ID
NO: 85, or a sequence at least 90% identical to any one of
residues 22-950 of SEQ ID NO: 82, residues 25-985 of SEQ
ID NO: 83, residues 22-948 of SEQ ID NO: 84, or residues
22-981 of SEQ ID NO: 85.

In some embodiments, the multimer is a dimer of MeV H
ectodomain head regions. The MeV H ectodomain head
region can be expressed in mammalian cells and spontane-
ously forms a dimer in physiological solution. This dimer
can then be purified and used as an immunogen. In some
embodiments, the subunits of the dimer comprise or consist
of an amino acid sequence set forth as residues 22-459 of
SEQ ID NO: 60 or a sequence at least 90% identical to
residues 22-459 of SEQ ID NO: 60.

In some embodiments, the multimer is a dimer of MeV H
ectodomain stalk and head regions. The MeV H ectodomain
stalk and head region can be expressed in mammalian cells
and spontaneously form a dimer in physiological solution.

This dimer can then be purified and used as an immunogen. In some embodiments, the subunits of the dimer comprise or consist of an amino acid sequence of any one of MeV H positions 59-197 to MeV H position 617 (such as any one of MeV H positions 59-67 to MeV H position 617, for example positions 59-617, 62-617, 60-617, or 67-617). In some embodiments, the subunits of the dimer comprise or consist of an amino acid sequence set forth as residues 22-580 of SEQ ID NO: 86, residues 22-577 of SEQ ID NO: 87, residues 22-579 of SEQ ID NO: 88, or residues 22-572 of SEQ ID NO: 89, or a sequence at least 90% identical to residues 22-580 of SEQ ID NO: 86, residues 22-577 of SEQ ID NO: 87, residues 22-579 of SEQ ID NO: 88, or residues 22-572 of SEQ ID NO: 89.

In some embodiments, the multimer is a dimer of MuV HN ectodomain head regions. In some embodiments, the subunits of the dimer comprise or consist of an amino acid sequence set forth as SEQ ID NO: 30 or a sequence at least 90% identical to SEQ ID NO: 30.

In some embodiments, the multimer is a dimer of MuV H ectodomain stalk and head regions. In some embodiments, the subunits of the dimer comprise or consist of an amino acid sequence of any one of MuV H positions 54-130 to MuV HN position 582 (such as any one of MuV H positions 54-63 to MuV HN position 582, for example positions 54-582, 61-582, 63-582, or 55-582). In some embodiments, the subunits of the dimer comprise or consist of an amino acid sequence set forth as residues 22-550 of SEQ ID NO: 90, residues 22-543 of SEQ ID NO: 91, residues 22-541 of SEQ ID NO: 92, or residues 22-549 of SEQ ID NO: 93, or a sequence at least 90% identical to residues 22-550 of SEQ ID NO: 90, residues 22-543 of SEQ ID NO: 91, residues 22-541 of SEQ ID NO: 92, or residues 22-549 of SEQ ID NO: 93.

D. Additional Description

The protomers in the recombinant MuV or MeV F ectodomain trimer can comprise modifications of the native MuV F or MeV F sequence in addition to those noted above, such as amino acid substitutions, deletions or insertions, glycosylation and/or covalent linkage to unrelated proteins (e.g., a protein tag), as long as the recombinant MuV or MeV F ectodomain trimer remains stabilized in the prefusion conformation and retains immunogenicity. Further, in embodiments including a heterologous MuV HN ectodomain or a MeV H ectodomain, or a multimer of a MuV HN ectodomain or a MeV H ectodomain, the HN or H ectodomain can include modifications of the native HN or H sequence, such as amino acid substitutions, deletions or insertions, glycosylation and/or covalent linkage to unrelated proteins (e.g., a protein tag), as long as the HN or H ectodomain retains immunogenicity. These variations in sequence can be naturally occurring variations or they can be engineered through the use of genetic engineering technique known to those skilled in the art. Examples of such techniques are found in see, e.g., Sambrook et al. (Molecular Cloning: A Laboratory Manual, $4^{th}$ ed., Cold Spring Harbor, New York, 2012) and Ausubel et al. (In Current Protocols in Molecular Biology, John Wiley & Sons, New York, through supplement 104, 2013, both of which are incorporated herein by reference in their entirety.

In some embodiments, the protomers in the recombinant MuV F ectodomain trimer or comprise one or more amino acid substitutions compared to a corresponding native MuV F sequence. For example, in some embodiments, the $F_2$ polypeptide, $F_1$ ectodomain, or both, can include up to 20 (such as up to 1, 2, 3, 4, 5, 6, 7, 8, 9, 10, 11, 12, 13, 14, 15, 16, 17, 18, or 19) amino acid substitutions (such as conservative amino acid substitutions) compared to a native MuV F sequence.

In some embodiments, the protomers in the recombinant MeV F ectodomain trimer or comprise one or more amino acid substitutions compared to a corresponding native MeV F sequence. For example, in some embodiments, the $F_2$ polypeptide, $F_1$ ectodomain, or both, can include up to 20 (such as up to 1, 2, 3, 4, 5, 6, 7, 8, 9, 10, 11, 12, 13, 14, 15, 16, 17, 18, or 19) amino acid substitutions (such as conservative amino acid substitutions) compared to a native MeV F sequence.

In some embodiments, the MuV HN ectodomain comprises one or more amino acid substitutions compared to a corresponding native MuV HN ectodomain sequence. For example, in some embodiments, the MuV HN ectodomain includes up to 20 (such as up to 1, 2, 3, 4, 5, 6, 7, 8, 9, 10, 11, 12, 13, 14, 15, 16, 17, 18, or 19) amino acid substitutions (such as conservative amino acid substitutions) compared to a native MuV HN ectodomain sequence.

In some embodiments, the MeV H ectodomain comprises one or more amino acid substitutions compared to a corresponding native MeV H ectodomain sequence. For example, in some embodiments, the MeV H ectodomain includes up to 20 (such as up to 1, 2, 3, 4, 5, 6, 7, 8, 9, 10, 11, 12, 13, 14, 15, 16, 17, 18, or 19) amino acid substitutions (such as conservative amino acid substitutions) compared to a native MeV H ectodomain sequence.

The simplest modifications involve the substitution of one or more amino acids for amino acids having similar biochemical properties, such as conservative amino acid substitutions. Such substitutions are likely to have minimal impact on the activity of the resultant protein.

In some embodiments, protomers in the recombinant MeV F ectodomain trimer or the MuV F ectodomain trimer can be joined at either end to other unrelated sequences (for example non-MuV F or MeV F protein sequences, non-viral envelope, or non-viral protein sequences)

In several embodiments, the recombinant MuV F ectodomain trimer or MeV F ectodomain trimer, or fusions of these protomers with heterologous proteins such as MuV HN ectodomain or MeV H ectodomain is soluble in aqueous solution. In some embodiments, the recombinant MuV F ectodomain trimer MeV F ectodomain trimer, or corresponding fusions with heterologous proteins such as MuV HN ectodomain or MeV H ectodomain dissolves to a concentration of at least 0.5 mg/ml (such as at least 1.0 mg/ml, 1.5 mg/ml, 2.0 mg/ml, 3.0 mg/ml, 4.0 mg/ml or at least 5.0 mg/ml) in aqueous solution (such as phosphate buffered saline (pH 7.4) or 350 mM NaCl (pH 7.0)) at room temperature (e.g., 20-22 degrees Celsius) and remain dissolved for at least 12 hours (such as at least 24 hours, at least 48 hours, at least one week, at least two weeks, at least one month, or more time). In one embodiment, the phosphate buffered saline includes NaCl (137 mM), KCl (2.7 mM), $Na_2HPO_4$ (10 mM), $KH_2PO_4$ (1.8 mM) at pH 7.4. In some embodiments, the phosphate buffered saline further includes $CaCl_2$) (1 mM) and $MgCl_2$ (0.5 mM). The person of skill in the art is familiar with methods of determining if a protein remains in solution over time. For example, the concentration of the protein dissolved in an aqueous solution can be tested over time using standard methods.

In some embodiments, the immunogen is provided as a homogenous population of soluble trimers that are substantially in the prefusion conformation with limited to no MuV F ectodomain trimer and/or MeV F ectodomain trimer in a postfusion conformation. The conformation of the MeV F ectodomain trimer or the MuV F ectodomain trimer can be detected, for example, by negative stain electron microscopy and/or specific binding by appropriate pre- or post-fusion specific antibody. In some embodiments, at least about 95% of the recombinant MuV F ectodomain trimer or MeV F ectodomain trimer (such as at least about 95%, 96%, 97%, 98%, 99% or 99.9% of the MuV or MeV F proteins) in the homogeneous population are stabilized in the prefusion conformation.

In some embodiments, the recombinant MuV F ectodomain trimer or MeV F ectodomain trimer retains specific binding for a prefusion specific antibody following incubation at 50° C. for one hour in phosphate buffered saline. In some embodiments, the recombinant MuV F ectodomain trimer or MeV F ectodomain trimer retains specific binding for a prefusion specific antibody following incubation at 4° C. for six months in phosphate buffered saline.

In certain embodiments, an immunogen provided herein may be further modified to contain additional nonproteinaceous moieties that are known in the art and readily available. The moieties suitable for derivatization of the immunogen include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the immunogen to be improved or altered, whether the immunogen derivative will be used in a therapy under defined conditions, etc.

Some of the sequences including recombinant MuV F ectodomain trimer, or MeV F ectodomain trimer, or MuV HN ectodomain or MeV H ectodomain provided herein include the sequence of protease cleavage sites (such as thrombin sites), protein tags (such as a His tag, a Strep Tag II, a Avi tag, etc.), and signal peptides; such sequences can be removed from an isolated immunogen including a recombinant MuV F ectodomain trimer, or MeV F ectodomain trimer, or MuV HN ectodomain or MeV H ectodomain for therapeutic use.

E. Protein Nanoparticles

In some embodiments, a protein nanoparticle is provided that includes one or more of the disclosed recombinant MuV F ectodomain trimers or recombinant MeV F ectodomain trimers, or MuV HN, or MeV H multimers, or chimera thereof.

In some embodiments, the protein nanoparticle comprises the MeV F ectodomain trimer or MuV F ectodomain trimer displayed on a two-component self-assembling nanoparticle platform as described in Marcandalli et al. "Induction of potent neutralizing antibody responses by a designed protein nanoparticle vaccine for respiratory syncytial virus," Cell, 176(6):1420-1431, 2019, which is incorporated by reference herein.

In additional non-limiting example of nanoparticles include ferritin nanoparticles, encapsulin nanoparticles, Sulfur Oxygenase Reductase (SOR) nanoparticles, and lumazine synthase nanoparticles, which are comprised of an assembly of monomeric subunits including ferritin proteins, encapsulin proteins, SOR proteins, and lumazine synthase, respectively. To construct such protein nanoparticles a protomer of the recombinant MuV F ectodomain trimer or recombinant MeV F ectodomain trimer, or a subunit of a MuV HN or MeV H multimer, is linked to a subunit of the protein nanoparticle (such as a ferritin protein, an encapsulin protein, a SOR protein, or a lumazine synthase protein) and expressed in cells under appropriate conditions. The fusion protein self-assembles into a nanoparticle any can be purified.

In some embodiments, a protomer of a disclosed recombinant MuV F ectodomain trimer or recombinant MeV F ectodomain trimer, or a subunit of a MuV HN or MeV H multimer, can be linked to a ferritin subunit to construct a ferritin nanoparticle. Ferritin nanoparticles and their use for immunization purposes (e.g., for immunization against influenza antigens) have been disclosed in the art (see, e.g., Kanekiyo et al., Nature, 499:102-106, 2013, incorporated by reference herein in its entirety). The globular form of the ferritin nanoparticle is made up of monomeric subunits, which are polypeptides having a molecule weight of approximately 17-20 kDa. Following production, these monomeric subunit proteins self-assemble into the globular ferritin protein. Thus, the globular form of ferritin comprises 24 monomeric, subunit proteins, and has a capsid-like structure having 432 symmetry. Methods of constructing ferritin nanoparticles are further described herein (see, e.g., Zhang, *Int. J. Mol. Sci.,* 12:5406-5421, 2011, which is incorporated herein by reference in its entirety). An example of the amino acid sequence of one such monomeric ferritin subunit is represented by:

```
                                        (SEQ ID NO: 45)
DIIKLLNEQVNKEMQSSNLYMSMSSWCYTHSLDGAGLFLFDHAAEEYEHA

KKLIIFLNENNVPVQLTSISAPEHKFEGLTQIFQKAYEHEQHISESINNI

VDHAIKSKDHATFNFLQWYVAEQHEEEVLFKDILDKIELIGNENHGLYLA

DQYVKGIAKSRKS
```

In specific examples, the ferritin polypeptide is *E. coli* ferritin, *Helicobacter pylori* ferritin, human light chain ferritin, bullfrog ferritin or a hybrid thereof, such as *E. coli*-human hybrid ferritin, *E. coli*-bullfrog hybrid ferritin, or human-bullfrog hybrid ferritin. Exemplary amino acid sequences of ferritin polypeptides and nucleic acid sequences encoding ferritin polypeptides for use to make a ferritin nanoparticle including a recombinant MuV or MeV F ectodomain trimer can be found in GENBANK®, for example at accession numbers ZP_03085328, ZP_06990637, EJB64322.1, AAA35832, NP_000137 AAA49532, AAA49525, AAA49524 and AAA49523, which are specifically incorporated by reference herein in their entirety as available Apr. 10, 2015. In some embodiments, a protomer of a recombinant MuV or MeV F ectodomain trimer can be linked to a ferritin subunit including an amino acid sequence at least 80% (such as at least 85%, at least 90%, at least 95%, or at least 97%) identical to amino acid sequence set forth as SEQ ID NO: 45.

In some embodiments, a protomer of a disclosed recombinant MuV F ectodomain trimer or recombinant MuV or MeV F ectodomain trimer, or a subunit of a MuV HN or MeV H multimer, can be linked to a lumazine synthase subunit to construct a lumazine synthase nanoparticle. The globular form of lumazine synthase nanoparticle is made up of monomeric subunits; an example of the sequence of one such lumazine synthase subunit is provides as the amino acid sequence set forth as:

```
                              (SEQ ID NO: 46)
MQIYEGKLTAEGLRFGIVASRFNHALVDRLVEGAIDCIVRHGGREEDITL

VRVPGSWEIPVAAGELARKEDIDAVIAIGVLIRGATPHFDYIASEVSKGL

ADLSLELRKPITFGVITADTLEQAIERAGTKHGNKGWEAALSAIEMANLF

KSLR.
```

In some embodiments, a protomer of a disclosed recombinant MuV F ectodomain trimer or recombinant MeV F ectodomain trimer, or a subunit of a MuV HN or MeV H multimer, can be linked to a lumazine synthase subunit including an amino acid sequence at least 80% (such as at least 85%, at least 90%, at least 95%, or at least 97%) identical to amino acid sequence set forth as SEQ ID NO: 46.

In some embodiments, a protomer of a disclosed recombinant MuV F ectodomain trimer or recombinant MeV F ectodomain trimer, or a subunit of a MuV HN or MeV H multimer, can be linked to an encapsulin nanoparticle subunit to construct an encapsulin nanoparticle. The globular form of the encapsulin nanoparticle is made up of monomeric subunits; an example of the sequence of one such encapsulin subunit is provides as the amino acid sequence set forth as

```
                              (SEQ ID NO: 47)
MEFLKRSFAPLTEKQWQEIDNRAREIFKTQLYGRKFVDVEGPYGWEYAAH

PLGEVEVLSDENEVVKWGLRKSLPLIELRATFTLDLWELDNLERGKPNVD

LSSLEETVRKVAEFEDEVIFRGCEKSGVKGLLSFEERKIECGSTPKDLLE

AIVRALSIFSKDGIEGPYTLVINTDRWINFLKEEAGHYPLEKRVEECLRG

GKIITTPRIEDALVVSERGGDFKLILGQDLSIGYEDREKDAVRLFITETF

TFQVVNPEALILLKE.
```

In some embodiments, a protomer of a disclosed recombinant MuV F ectodomain trimer or recombinant MeV F ectodomain trimer, or a subunit of a MuV HN or MeV H multimer, can be linked to an encapsulin subunit including an amino acid sequence at least 80% (such as at least 85%, at least 90%, at least 95%, or at least 97%) identical to amino acid sequence set forth as SEQ ID NO: 47.

Encapsulin proteins are a conserved family of bacterial proteins also known as linocin-like proteins that form large protein assemblies that function as a minimal compartment to package enzymes. The encapsulin assembly is made up of monomeric subunits, which are polypeptides having a molecule weight of approximately 30 kDa. Following production, the monomeric subunits self-assemble into the globular encapsulin assembly including 60, or in some cases, 180 monomeric subunits. Methods of constructing encapsulin nanoparticles are further described (see, for example, Sutter et al., Nature Struct. and Mol. Biol., 15:939-947, 2008, which is incorporated by reference herein in its entirety). In specific examples, the encapsulin polypeptide is bacterial encapsulin, such as *Thermotoga maritime* or *Pyrococcus furiosus* or *Rhodococcus erythropolis* or *Myxococcus xanthus* encapsulin.

In some embodiments, a protomer of a disclosed recombinant MuV F ectodomain trimer or recombinant MeV F ectodomain trimer, or a subunit of a MuV HN or MeV H multimer, can be linked to a Sulfur Oxygenase Reductase (SOR) subunit to construct a recombinant SOR nanoparticle. In some embodiments, the SOR subunit can include the amino acid sequence set forth as

```
                              (SEQ ID NO: 48)
MEFLKRSFAPLTEKQWQEIDNRAREIFKTQLYGRKFVDVEGPYGWEYAAH

PLGEVEVLSDENEVVKWGLRKSLPLIELRATFTLDLWELDNLERGKPNVD

LSSLEETVRKVAEFEDEVIFRGCEKSGVKGLLSFEERKIECGSTPKDLLE

AIVRALSIFSKDGIEGPYTLVINTDRWINFLKEEAGHYPLEKRVEECLRG

GKIITTPRIEDALVVSERGGDFKLILGQDLSIGYEDREKDAVRLFITETF

TFQVVNPEALILLKE.
```

In some embodiments, a protomer of a disclosed recombinant MuV F ectodomain trimer or recombinant MeV F ectodomain trimer, or a subunit of a MuV HN or MeV H multimer, can be linked to a SOR subunit including an amino acid sequence at least 80% (such as at least 85%, at least 90%, at least 95%, or at least 97%) identical to amino acid sequence set forth as SEQ ID NO: 48.

SOR proteins are microbial proteins (for example from the thermoacidophilic archaeon *Acidianus ambivalens* that form 24 subunit protein assemblies. Methods of constructing SOR nanoparticles are described in Urich et al., Science, 311:996-1000, 2006, which is incorporated by reference herein in its entirety. An example of an amino acid sequence of a SOR protein for use to make SOR nanoparticles is set forth in Urich et al., Science, 311:996-1000, 2006, which is incorporated by reference herein in its entirety.

For production purposes, the recombinant MuV F ectodomain or recombinant MeV F ectodomain, or the subunit of the MuV HN or MeV H multimer, linked to the nanoparticle subunit can include an N-terminal signal peptide that is cleaved during cellular processing. For example, the recombinant MuV F ectodomain protomer, or the recombinant MeV F ectodomain protomer, linked to the protein nanoparticle subunit can include a signal peptide at its N-terminus including, for example, a native MuV or MeV F signal peptide.

The protein nanoparticles can be expressed in appropriate cells (e.g., HEK 293 Freestyle cells) and fusion proteins are secreted from the cells self-assembled into nanoparticles. The nanoparticles can be purified using known techniques, for example by a few different chromatography procedures, e.g. Mono Q (anion exchange) followed by size exclusion (SUPEROSE® 6) chromatography.

The fusion proteins need not comprise the full-length sequence of a monomeric subunit polypeptide of a ferritin, encapsulin, SOR, or lumazine synthase protein. Portions, or regions, of the monomeric subunit polypeptide can be utilized so long as the portion comprises amino acid sequences that direct self-assembly of monomeric subunits into the globular form of the protein.

II. Polynucleotides and Expression

Also provided are polynucleotides encoding any of the disclosed immunogens. For example, a polynucleotide encoding a protomer of a MuV F ectodomain trimer stabilized in the prefusion conformation, a protomer of a MeV F ectodomain trimer stabilized in the prefusion conformation, a chimera of one of these protomers linked to a MuV HN or MeV H ectodomain, or a subunit of a self-assembling protein nanoparticle containing a recombinant MuV or MeV F ectodomain. These polynucleotides include DNA, cDNA and RNA sequences, including vectors including the DNA, cDNA and RNA sequences, such as a DNA or RNA vector used for immunization. The genetic code can be used to construct a variety of functionally equivalent nucleic acids, such as nucleic acids which differ in sequence but which encode the same protein sequence, or encode a conjugate or fusion protein including the nucleic acid sequence.

An exemplary nucleic acid sequence encoding full-length MeV F protein is provided as SEQ ID NO: 94:

atgggtctcaaggtgaacgtctctgccatattcatggcagtactgttaactctccaaacacccaccggtcaaatccattg gggcaatctctctaagatagggggtggtaggaataggaagtgcaagctacaaagttatgactcgttccagccatcaatcat tagtcataaaattaatgcccaatataactctcctcaataactgcacgagggtagagattgcagaatacaggagactactg agaacagttttggaaccaattagagatgcacttaatgcaatgacccagaatataagaccggttcagagtgtagcttcaag taggagacacaagagatttgcgggagtagtcctggcaggtgcggccctaggcgttgccacagctgctcagataacagccg gcattgcacttcaccagtccatgctgaactctcaagccatcgacaatctgagagcgagcctggaaactactaatcaggca attgaggcaatcagacaagcagggcaggagatgatattggctgttcagggtgtccaagactacatcaataatgagctgat accgtctatgaaccaactatcttgtgatttaatcggccagaagctcgggctcaaattgctcagatactatacagaaatcc tgtcattatttggccccagcttacgggaccccatatctgcggagatatctatccaggctttgagctatgcgcttggagga gacatcaataaggtgttagaaaagctcggatacagtggaggtgatttactgggcatcttagagagcagaggaataaaggc ccggataactcacgtcgacacagagtcctacttaattgtcctcagtatagcctatccgacgctgtccgagattaaggggg tgattgtccaccggctagagggggctctcgtacaacataggctctcaagagtggtataccactgtgcccaagtatgttgca acccaagggtaccttatctcgaattttgatgagtcatcgtgtactttcatgccagaggggactgtgtgcagccaaaatgc cttgtaccgatgagtcctctgctccaagaatgcctccgggggtccaccaagtcctgtgctcgtacactcgtatccgggt cttttgggaaccggttcattttatcacaagggaacctaatagccaattgtgcatcaatcctttgcaagtgttacacaaca ggaacgatcattaatcaagaccctgacaagatcctaacatacattgctgccgatcactgcccggtagtcgaggtgaacgg cgtgaccatccaagtcgggagcaggaggtatccagacgctgtgtacttgcacagaattgacctcggtcctcccatattat tggagaggttggacgtagggacaaatctggggaatgcaattgctaagttggaggatgccaaggaattgttggagtcatcg gaccagatattgaggagtatgaaaggtttatcgagcacttgcatagtctacatcctgattgcagtgtgtcttggagggtt gatagggatccccgctttaatatgttgctgcaggggggcgttgtaacaaaaagggagaacaagttggtatgtcaagaccag gcctaaagcctgatcttacgggaacatcaaaatcctatgtaaggtcgctctga An exemplary nucleic acid sequence encoding full-length MuV F protein is provided as SEQ ID NO: 95:

atgaaggccttttcagttacttgcttgggctttgcagtcttttcgtcttctatatgtgtgaatatcaacatcttgcagca aattggatatatcaagcaacaagtcaggcaactaagctattactcacaaagttctagctcctacatagtggtcaagctt taccgaatatccaacccactgataacagctgtgaatttaagagtgtaactcaatacaataagaccttgagtaacttgctt cttcccattgcagaaaacataaacaatattgcatcgccctcacctgggtcaagacgtcataaaaggtttgctggcattgc cattggcattgctgcgctcggtgttgcgaccgcagcacaggtaactgccgctgtctcattagttcaagcacagacaaatg cacgtgcaatagcggcgatgaaaaattcaatacaggcaactaatcgggcaatcttcgaagtgaaggaaggcacccaacag ttagctatagcggtacaagcaatacaagaccacatcaatactattatgaacacccaattgaacaatatgtcttgtcagat ccttgataaccagcttgcaacctacctaggattatacctaacagaattaacaacagtgtttcagccacaattaattaatc cggcattgtcaccgattagtatacaagccttgaggtctttgcttggaagtatgacgcctgcagtggttcaagcaacatta tctacgtcaatttctgctgctgaaatactaagtgccggtctaatggagggtcagattgtttctgttctgctagatgagat gcagatgatagtcaagataaatattccaaccattgtcacacaatcaaatgcattggtgattgacttctactcaatttcga gctttattaataatcaagaatccataattcaattgccagacaggatcctagagatcgggaatgaacaatggagctatcca gctaaaaattgtaagttgacaagacaccacatattctgccaatacaatgaggcagagaggctgagcctagaatcaaaact -continued atgccttgcaggtaatataagtgcctgtgtgttctcacccatagcagggagttatatgaggcgatttgtagcactggatg gaacaattgttgcaaactgtcgaagtctaacgtgtctatgcaagagtccatcttatcctatataccaacctgaccatcat gcagtcacgaccattgatctaaccacatgtcaaacattgtccctagacggattggacttcagcattgtctctctaagcaa catcacttacgctgagaaccttaccatttcattgtctcaaacaatcaatactcaacccattgacatatcaactgaactga gtaaagttaatgcatccctccaaaatgccgttaagtacataaaggagagcaaccatcaactccaatctgtgagtgtaaat tccaaaattggagctataattgtagcagccttagttttgagcatcctgtcaattatcatttcgctattgtttttgctgctg ggcttacattgcaactaaagaaatcagaagaatcaacttcaaaacaaatcatatcaacacaatatcgagtagtgtcgatg atctcatcaggtactaa An exemplary nucleic acid sequence encoding full-length MeV H protein is provided
as SEQ ID NO: 96:
atgtcaccacaacgagaccggataaatgccttctacaaagataaccccatcccaagggaagtaggatagtcattaacag agaacatcttatgattgatagaccttatgttttgctggctgttctgtttgtcatgtttctgagcttgatcgggttgctag ccattgcaggcattagacttcatcgggcagccatctacaccgcagagatccataaaagcctcagcaccaatctagatgta actaactcaatcgagcatcaggtcaaggacgtgctgacaccactcttcaaaatcatcggtgatgaagtgggcctgaggac acctcagagattcactgacctagtgaaattcatctctgacaagattaaattccttaatccggatagggagtacgacttca gagatctcacttggtgtatcaacccgccagagagaatcaaattggattatgatcaatactgtgcagatgtggctgctgaa gagctcatgaatgcattggtgaactcaactctactggagaccagaacaaccaatcagttcctagctgtctcaaaggggaaa ctgctcagggcccactacaatcagaggtcaattctcaaacatgtcgctgtccctgttagacttgtatttaggtcgaggtt acaatgtgtcatctatagtcactatgacatcccagggaatgtatgggggaacttacctagtggaaaagcctaatctgagc agcaaaaggtcagagttgtcacaactgagcatgtaccgagtgtttgaagtaggtgttatcagaaatccgggtttgggggc tccggtgttccatatgacaaactatcttgagcaaccagtcagtaatgatctcagcaactgtatggtggctttggggggagc tcaaactcgcagcccttgtcacggggaagattctatcacaattccctatcagggatcagggaaaggtgtcagcttccag ctcgtcaagctaggtgtctggaaatccccaaccgacatgcaatcctgggtcccttatcaacggatgatccagtgataga caggcttacctctcatctcacagaggtgttatcgctgacaatcaagcaaaatgggctgtcccgacaacacgaacagatg acaagttgcgaatggagacatgcttccaacaggcgtgtaagggtaaatccaagcactctgcgagaatcccgagtgggca ccattgaaggataacaggattccttcatacggggtcttgtctgttgatctgagtctgacagttgagcttaaaatcaaaat tgcttcgggattcgggccattgatcacacacggttcagggatggacctatacaaatccaaccacaacaatgtgtattggc tgactatcccgccaatgaagaacctagccttaggtgtaatcaacacattggagtggataccgagattcaaggttagtccc tacctcttcactgtcccaattaaggaagcaggcgaagactgccatgccccaacatacctacctgcggaggtggatggtga tgtcaaactcagttccaatctggtgattctacctggtcaagatctccaatatgtttttggcaacctacgtacttccaggg ttgaacatgctgtggtttattacgtttacagcccaagccgctcattttcttacttttatccttttaggttgcctataaag ggggtccccatcgaattacaagtggaatgcttcacatgggaccaaaaactctggtgccgtcacttctgtgtgcttgcgga ctcagaatctggtggacatatcactcactctgggatggtgggcatgggagtcagctgcacagtcacccgggaagatggaa ccaatcgcagatag An exemplary nucleic acid sequence encoding full-length MuV HN protein is pro-
vided
as SEQ ID NO: 97:
atggagccctcgaaattcttcacaatatcggacagtgccacctttgcacctgggcctgtcagcaatgcggctgacaagaa gacattccgaacctgcttccgaatactggtactatctgtacaagctgtcaccctcatattggttattgtcactttaggtg agcttgtaaggatgatcaatgatcaaggcttgagcaatcagttgtcttcaattacagacaagataagagagtcagctact atgattgcatctgctgtgggagtaatgaatcaagttattcatggagtaacggtatccttacccctacaaattgagggaaa ccaaaatcaattgttagccacacttgccacaatctgcgccagccaaaaacaagtctcaaactgctctacaaacatcccct tagtcaatgacctcaggtttataaatgggatcaataaaatttattattgaagattacgcaactcatgatttctctatcggc -continued

```
catccactcaatatgcccagctttatcccaactgcaacttcacccaatggttgcacaagaattccatccttttctttagg taagacacactggtgctacacacataatgtaattaatgccaactgcaaggaccatacttcgtctaaccaatatgtgtcca tggggattctcgttcagaccgcgtcagggtatcctatgttcaaaaccttaaaaatccaatatctcagtgatggcctgaat cggaaaagctgctcaattgcaacagtccctgatgggtgcgcgatgtactgttatgtctctactcaacttgaaaccgacga ctatgcggggtccagtccacccacccaaaaacttaccctgttattctataatgacaccgtcacagaaaggacaatatctc catctggtcttgaagggaattgggctactttggtgccaggagtggggagtgggatatattttgagaataagttgatcttc cctgcatatgggggtgtcttgcccaatagtacactcggggttaaatcagcaagagaattttttcggcctgttaatccata taatccatgttcaggaccacaacaagatttagatcagcgtgctttgaggtcatacttcccaagttacttctctaatcgaa gaatacagagtgcatttcttgtctgtgcctggaatcagatcctagttacaaattgtgagctagttgtccctcaagcaat cagacaatgatgggtgcagaagggagagtttttattgatcaataatcgactattatattatcagagaagtaccagctggtg gccgtatgaactcctctacgagatatcattcacatttacaaactctggtccatcatctgtaaatatgtcctggataccta tatattcattcactcgtcctggttcaggcaattgcagtggtgaaaatgtgtgcccgactgcttgtgtgtcaggggtttat cttgatccctggccattaactccatatagccaccaatcaggtattaacagaaatttctatttcacaggtgcactattaaa ttcaagtacaactagagtaaatcctacccctttatgtctctgcccttaataatcttaaagtactagccccatatggtactc aaggactgtttgcctcgtacaccacaaccacctgctttcaagataccggtgatgctagtgtgtattgtgtttatattatg gagctagcatcaaatattgttggagaattccaaattctacctgtgctaactagattgactatcacttga
```

These exemplary nucleic acid sequences (or a corresponding RNA sequence) can be modified to encode any of the immunogens provided herein.

In several embodiments, the nucleic acid molecule encodes a precursor of a protomer of the MuV or MeV F ectodomain trimer or a promoter of the MeV F ectodomain trimer or a chimera of such a protomer with a MuV HN or MeV H ectodomain, or a subunit of a MuV HN or MeV H multimer, that, when expressed in an appropriate cell, is processed into a protomer of the F ectodomain trimer, or subunit of a MuV HN or MeV H multimer, that can self-assemble into the corresponding trimer or multimer. For example, the nucleic acid molecule can encode a protomer of the MuV or MeV F ectodomain trimer or a promoter of the MeV F ectodomain trimer including a N-terminal signal sequence for entry into the cellular secretory system that is proteolytically cleaved in the during processing of the recombinant F ectodomain in the cell.

In some embodiments, the nucleic acid molecule encodes a $F_0$ polypeptide that, when expressed in an appropriate cell, is processed into a protomer of the MuV or MeV F ectodomain trimer or a promoter of the MeV F ectodomain trimer including a $F_2$ polypeptide linked to a $F_1$ ectodomain, wherein the recombinant $F_2$-$F_1$ ectodomain protomer includes any of the prefusion-stabilizing modifications described herein, and optionally can be linked to a trimerization domain, such as a GCN4 trimerization domain and/or a T4 fibritin trimerization domain.

In some embodiments, the nucleic acid molecule encodes a full-length $F_0$ polypeptide that, when expressed in an appropriate cell, is processed into a protomer of the MuV or MeV F ectodomain trimer or a promoter of the MuV or MeV F ectodomain trimer including an $F_2$ polypeptide linked to a $F_1$ polypeptide including the $F_1$ transmembrane and cytosolic tail, wherein the recombinant $F_2$-$F_1$ ectodomain protomer includes any of the prefusion-stabilizing modifications described herein.

Exemplary nucleic acids can be prepared by cloning techniques. Examples of appropriate cloning and sequencing techniques, and instructions sufficient to direct persons of skill through many cloning exercises are known (see, e.g., Sambrook et al. (Molecular Cloning: A Laboratory Manual, $4^{th}$ ed, Cold Spring Harbor, New York, 2012) and Ausubel et al. (In Current Protocols in Molecular Biology, John Wiley & Sons, New York, through supplement 104, 2013).

Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

The polynucleotides encoding a protomer of the MuV or MeV F ectodomain trimer, or a subunit of a MuV HN or MeV H multimer, can include a recombinant DNA which is incorporated into a vector (such as an expression vector) into an autonomously replicating plasmid or virus or into the genomic DNA of a prokaryote or eukaryote, or which exists as a separate molecule (such as a cDNA) independent of other sequences. The nucleotides can be ribonucleotides, deoxyribonucleotides, or modified forms of either nucleotide. The term includes single and double forms of DNA.

Polynucleotide sequences encoding a protomer of the MuV or MeV F ectodomain trimer or a promoter of the MeV F ectodomain trimer or a chimera of such a protomer with a MuV HN or MeV H ectodomain, or a subunit of a MuV HN or MeV H multimer, can be operatively linked to expression control sequences. An expression control sequence operatively linked to a coding sequence is ligated such that expression of the coding sequence is achieved under conditions compatible with the expression control sequences. The expression control sequences include, but are not limited to, appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

DNA sequences encoding the protomer of the MuV or MeV F ectodomain trimer or a promoter of the MeV F ectodomain trimer or a chimera of such a protomer with a MuV HN or MeV H ectodomain, or a subunit of a MuV HN or MeV H multimer, can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

Hosts can include microbial, yeast, insect and mammalian organisms. Methods of expressing DNA sequences having eukaryotic or viral sequences in prokaryotes are well known in the art. Non-limiting examples of suitable host cells include bacteria, archea, insect, fungi (for example, yeast), plant, and animal cells (for example, mammalian cells, such as human). Exemplary cells of use include *Escherichia coli, Bacillus subtilis, Saccharomyces cerevisiae, Salmonella typhimurium,* SF9 cells, C129 cells, 293 cells, *Neurospora,* and immortalized mammalian myeloid and lymphoid cell lines. Techniques for the propagation of mammalian cells in culture are well-known (see, e.g., Helgason and Miller (Eds.), 2012, Basic Cell Culture Protocols (Methods in Molecular Biology), 4th Ed., Humana Press). Examples of commonly used mammalian host cell lines are VERO and HeLa cells, CHO cells, and WI38, BHK, and COS cell lines, although cell lines may be used, such as cells designed to provide higher expression, desirable glycosylation patterns, or other features. In some embodiments, the host cells include HEK293 cells or derivatives thereof, such as GnTI$^{-/-}$ cells (ATCC® No. CRL-3022), or HEK-293F cells.

Transformation of a host cell with recombinant DNA can be carried out by conventional techniques. In some embodiments where the host is prokaryotic, such as, but not limited to, *E. coli,* competent cells which are capable of DNA uptake can be prepared from cells harvested after exponential growth phase and subsequently treated by the CaCl$_2$) method. Alternatively, MgCl$_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or viral vectors can be used. Eukaryotic cells can also be co-transformed with polynucleotide sequences encoding a disclosed antigen, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, Viral Expression Vectors, Springer press, Muzyczka ed., 2011). Appropriate expression systems such as plasmids and vectors of use in producing proteins in cells including higher eukaryotic cells such as the COS, CHO, HeLa and myeloma cell lines.

In one non-limiting example, a disclosed immunogen is expressed using the pVRC8400 vector (described in Barouch et al., *J. Virol.,* 79, 8828-8834, 2005, which is incorporated by reference herein).

Modifications can be made to a nucleic acid encoding a disclosed immunogen without diminishing its biological activity. Some modifications can be made to facilitate the cloning, expression, or incorporation of the targeting molecule into a fusion protein. Exemplary modifications include termination codons, a methionine added at the amino terminus to provide an initiation, site, additional amino acids placed on either terminus to create conveniently located restriction sites, or additional amino acids (such as poly His) to aid in purification steps.

In some embodiments, the nucleic acid encoding the protomer of the MuV or MeV F ectodomain trimer or the promoter of the MeV F ectodomain trimer or a chimera of such a protomer with a MuV HN or MeV H ectodomain, or a subunit of a MuV HN or MeV H multimer, can be expressed in cells under conditions where the protomers self-assemble into trimers which are secreted from the cells into the cell media, for example as described for RSV F proteins (see, e.g., PCT Pub. WO2014160463, McLellan et al., *Science,* 340:1113-1117, 2013; McLellan et al., *Science,* 342:592-598, 2013, each of which is incorporated by reference herein in its entirety). In such embodiments, the protomer contains a leader sequence (signal peptide) that causes the protein to enter the secretory system, and the signal peptide is cleaved and the protomers form a trimer, before being secreted in the cell media. The medium can be centrifuged and recombinant MuV or MeV F ectodomain trimer or recombinant MuV or MeV F ectodomain trimer or a chimera thereof with a MuV HN or MeV H ectodomain purified from the supernatant.

III. Viral Vectors

A nucleic acid molecule encoding a disclosed immunogen can be included in a viral vector, for example, for expression of the immunogen in a host cell, or for immunization of a subject as disclosed herein. In some embodiments, the viral vectors are administered to a subject as part of a prime-boost vaccination. Typically such viral vectors include a nucleic acid molecule encoding an immunogen that contains a transmembrane domain. In several embodiments, the viral vectors are included in a vaccine, such as a primer vaccine or a booster vaccine for use in a prime-boost vaccination.

In some examples, the viral vector can be replication-competent. For example, the viral vector can have a mutation (e.g., insertion of nucleic acid encoding the protomer) in the viral genome that attenuates, but does not completely block viral replication in host cells.

In several embodiments, the viral vector can be delivered via the respiratory tract. For example, a hPIV vector, such as bovine parainfluenza virus (BPIV) vector (e.g., a BPIV1, BPIV2, or BPIV3 vector) or human hPIV vector (e.g., a hPIV3 vector), a metapneumovirus (MPV) vector, a Sendia virus vector, a New Castle Disease Virus (NCDV (vector), a mumps virus vector, a measles virus vector, or another paramyxovirus or pneumovirus vector is used to express a disclosed antigen.

Additional viral vectors are also available for expression of the disclosed antigens, including polyoma, i.e., SV40 (Madzak et al., 1992, *J. Gen. Virol.,* 73:15331536), adenovirus (Berkner, 1992, *Cur. Top. Microbiol. Immunol.,* 158: 39-6; Berliner et al., 1988, *Bio Techniques,* 6:616-629; Gorziglia et al., 1992, *J. Virol.,* 66:4407-4412; Quantin et al., 1992, *Proc. Natl. Acad. Sci. USA,* 89:2581-2584; Rosenfeld et al., 1992, *Cell,* 68:143-155; Wilkinson et al., 1992, *Nucl. Acids Res.,* 20:2233-2239; Stratford-Perricaudet et al., 1990, *Hum. Gene Ther.,* 1:241-256), vaccinia virus (Mackett et al., 1992, *Biotechnology,* 24:495-499), adeno-associated virus (Muzyczka, 1992, *Curr. Top. Microbiol. Immunol.,* 158:91-

123; On et al., 1990, *Gene,* 89:279-282), herpes viruses including HSV and EBV and CMV (Margolskee, 1992, *Curr. Top. Microbiol. Immunol.,* 158:67-90; Johnson et al., 1992, *J. Virol.,* 66:29522965; Fink et al., 1992, *Hum. Gene Ther.* 3:11-19; Breakfield et al., 1987, *Mol. Neurobiol.,* 1:337-371; Fresse et al., 1990, *Biochem. Pharmacol.,* 40:2189-2199), Sindbis viruses (H. Herweijer et al., 1995, *Human Gene Therapy* 6:1161-1167; U.S. Pat. Nos. 5,091, 309 and 5,2217,879), alphaviruses (S. Schlesinger, 1993, *Trends Biotechnol.* 11:18-22; I. Frolov et al., 1996, *Proc. Natl. Acad. Sci. USA* 93:11371-11377) and retroviruses of avian (Brandyopadhyay et al., 1984, *Mol. Cell Biol.,* 4:749-754; Petropouplos et al., 1992, *J. Virol.,* 66:3391-3397), murine (Miller, 1992, *Curr. Top. Microbiol. Immunol.,* 158: 1-24; Miller et al., 1985, *Mol. Cell Biol.,* 5:431-437; Sorge et al., 1984, *Mol. Cell Biol.,* 4:1730-1737; Mann et al., 1985, *J. Virol.,* 54:401-407), and human origin (Page et al., 1990, *J. Virol.,* 64:5370-5276; Buchschalcher et al., 1992, *J. Virol.,* 66:2731-2739). Baculovirus (*Autographa californica* multinuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif.).

IV. Virus-Like Particles

In some embodiments, a virus-like particle (VLP) is provided that includes a disclosed immunogen. Typically such VLPs include an immunogen containing a transmembrane domain, for example, a recombinant MuV F ectodomain trimer with protomers containing a MuV F transmembrane domain and cytosolic tail, or a recombinant MeV F ectodomain trimer with protomers containing a MeV F transmembrane domain and cytosolic tail. VLPs lack the viral components that are required for virus replication and thus represent a highly attenuated, replication-incompetent form of a virus. However, the VLP can display a polypeptide (e.g., a recombinant MuV or MeV F ectodomain trimer) that is analogous to that expressed on infectious virus particles and can eliciting an immune response to MuV or MeV when administered to a subject. Exemplary virus like particles and methods of their production, as well as viral proteins from several viruses that are known to form VLPs, including human papillomavirus, HIV (Kang et al., Biol. Chem. 380: 353-64 (1999)), Semliki-Forest virus (Notka et al., Biol. Chem. 380: 341-52 (1999)), human polyomavirus (Goldmann et al., J. Virol. 73: 4465-9 (1999)), rotavirus (Jiang et al., Vaccine 17: 1005-13 (1999)), parvovirus (Casal, Biotechnology and Applied Biochemistry, Vol 29, Part 2, pp 141-150 (1999)), canine parvovirus (Hurtado et al., J. Virol. 70: 5422-9 (1996)), hepatitis E virus (Li et al., J. Virol. 71: 7207-13 (1997)), and Newcastle disease virus. The formation of such VLPs can be detected by any suitable technique. Examples of suitable techniques for detection of VLPs in a medium include, e.g., electron microscopy techniques, dynamic light scattering (DLS), selective chromatographic separation (e.g., ion exchange, hydrophobic interaction, and/or size exclusion chromatographic separation of the VLPs) and density gradient centrifugation.

V. Immunogenic Compositions

Immunogenic compositions comprising a disclosed immunogen (e.g., recombinant MuV F ectodomain trimer, a recombinant MeV F ectodomain trimer, or corresponding fusions with MuV HN ectodomain or MeV H ectodomain, or a MuV HN or MeV H multimer) and a pharmaceutically acceptable carrier are also provided. Such compositions can be administered to subjects by a variety of administration modes, for example, intramuscular, subcutaneous, intravenous, intra-arterial, intra-articular, intraperitoneal, or parenteral routes. In several embodiments, a pharmaceutical composition including one or more of the disclosed immunogens are immunogenic compositions. Actual methods for preparing administrable compositions are described in more detail in such publications as *Remingtons Pharmaceutical Sciences,* 19$^{th}$ Ed., Mack Publishing Company, Easton, Pa., 1995.

Thus, an immunogen described herein can be formulated with pharmaceutically acceptable carriers to help retain biological activity while also promoting increased stability during storage within an acceptable temperature range. Potential carriers include, but are not limited to, physiologically balanced culture medium, phosphate buffer saline solution, water, emulsions (e.g., oil/water or water/oil emulsions), various types of wetting agents, cryoprotective additives or stabilizers such as proteins, peptides or hydrolysates (e.g., albumin, gelatin), sugars (e.g., sucrose, lactose, sorbitol), amino acids (e.g., sodium glutamate), or other protective agents. The resulting aqueous solutions may be packaged for use as is or lyophilized Lyophilized preparations are combined with a sterile solution prior to administration for either single or multiple dosing.

Formulated compositions, especially liquid formulations, may contain a bacteriostat to prevent or minimize degradation during storage, including but not limited to effective concentrations (usually 1% w/v) of benzyl alcohol, phenol, m-cresol, chlorobutanol, methylparaben, and/or propylparaben. A bacteriostat may be contraindicated for some patients; therefore, a lyophilized formulation may be reconstituted in a solution either containing or not containing such a component.

The immunogenic compositions of the disclosure can contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate.

The immunogenic composition may optionally include an adjuvant to enhance an immune response of the host. Adjuvants, such as aluminum hydroxide (e.g., ALHYDRO-GEL®, available from Brenntag Biosector, Copenhagen, Denmark and Amphogel®, Wyeth Laboratories, Madison, NJ), Freund's adjuvant, MPL™ (3-O-deacylated monophosphoryl lipid A; Corixa, Hamilton, IN) and IL-12 (Genetics Institute, Cambridge, MA), TLR agonists (such as TLR-9 agonists, for example cytidine-phospho-guanosine oligodeoxynucleotide (CpG-ODN)1018), among many other suitable adjuvants well known in the art, can be included in the compositions. Suitable adjuvants are, for example, toll-like receptor agonists, alum, AlPO4, alhydrogel, Lipid-A and derivatives or variants thereof, oil-emulsions, saponins, neutral liposomes, liposomes containing the vaccine and cytokines, non-ionic block copolymers, and chemokines. Non-ionic block polymers containing polyoxyethylene (POE) and polyxylpropylene (POP), such as POE-POP-POE block copolymers, MPL™ (3-O-deacylated monophosphoryl lipid A; Corixa, Hamilton, IN) and IL-12 (Genetics Institute, Cambridge, MA), may be used as an adjuvant (Newman et al., 1998, *Critical Reviews in Therapeutic Drug Carrier Systems* 15:89-142). These adjuvants have the advantage in that they help to stimulate the immune system in a non-specific way, thus enhancing the immune response to a pharmaceutical product.

In some instances, the adjuvant formulation is a mineral salt, such as a calcium or aluminum (alum) salt, for example calcium phosphate, aluminum phosphate or aluminum hydroxide. In some embodiments, the disclosed immunogen comprises one or more phosphoserine modifications and is used with a Alum adjuvant. In some embodiments, the adjuvant includes an oil and water emulsion, e.g., an oil-in-water emulsion (such as MF59 (Novartis) or AS03 (GlaxoSmithKline). One example of an oil-in-water emulsion comprises a metabolisable oil, such as squalene, a tocol such as a tocopherol, e.g., alpha-tocopherol, and a surfactant, such as sorbitan trioleate (Span 85) or polyoxyethylene sorbitan monooleate (Tween 80), in an aqueous carrier.

In some instances, it may be desirable to combine a disclosed immunogen with other pharmaceutical products (e.g., vaccines) which induce protective responses to other agents. For example, a composition including a recombinant MuV F ectodomain trimer, a recombinant MeV F ectodomain trimer, or corresponding fusions with MuV HN ectodomain or MeV H ectodomain as described herein can be can be administered simultaneously (typically separately) or sequentially with other vaccines recommended by the Advisory Committee on Immunization Practices (ACIP; cdc.gov/vaccines/acip/index.html) for the targeted age group (e.g., infants from approximately one to six months of age). As such, a disclosed immunogen described herein may be administered simultaneously or sequentially with vaccines against, for example, hepatitis B (HepB), diphtheria, tetanus and pertussis (DTaP), pneumococcal bacteria (PCV), *Haemophilus influenzae* type b (Hib), polio, influenza and rotavirus.

In some embodiments, the composition can be provided as a sterile composition. The immunogenic composition typically contains an effective amount of a disclosed immunogen and can be prepared by conventional techniques. Typically, the amount of immunogen in each dose of the immunogenic composition is selected as an amount which induces an immune response without significant, adverse side effects. In some embodiments, the composition can be provided in unit dosage form for use to induce an immune response in a subject, for example, to inhibit MuV and/or MeV infection in the subject. A unit dosage form contains a suitable single preselected dosage for administration to a subject, or suitable marked or measured multiples of two or more preselected unit dosages, and/or a metering mechanism for administering the unit dose or multiples thereof.

VI. Methods of Inducing an Immune Response

The disclosed immunogens (e.g., recombinant MuV F ectodomain trimer, a recombinant MeV F ectodomain trimer, or corresponding fusions with MuV HN ectodomain or MeV H ectodomain, MuV HN or MeV H multimer, a nucleic acid molecule (such as an RNA molecule) encoding a disclosed immunogen, or a protein nanoparticle or virus like particle comprising the immunogen) can be administered to a subject to induce an immune response to MuV and/or MeV in the subject. In a particular example, the subject is a human. The immune response can be a protective immune response, for example a response that inhibits subsequent infection with MuV and/or MeV. Elicitation of the immune response can also be used to treat or inhibit MuV and/or MeV infection and illnesses associated therewith.

A subject can be selected for treatment that has, or is at risk for developing MuV or MeV infection, for example because of exposure or the possibility of exposure to MuV or MeV. Following administration of a disclosed immunogen, the subject can be monitored for the MuV and/or MeV infection or symptoms associated therewith, or both.

Typical subjects intended for treatment with the therapeutics and methods of the present disclosure include humans. In some embodiments, the subject is a human subject that is seronegative for MuV and/or MeV specific antibodies. In some embodiments, the subject is a human subject that is seropositive for MuV and/or MeV specific antibodies, and the immunogen is administered to boost the immune response to MeV and/or MuV in the subject. To identify subjects for treatment according to the methods of the disclosure, accepted screening methods are employed to determine risk factors associated with a targeted or suspected disease or condition, or to determine the status of an existing disease or condition in a subject. These screening methods include, for example, conventional work-ups to determine environmental, familial, occupational, and other such risk factors that may be associated with the targeted or suspected disease or condition, as well as diagnostic methods, such as various ELISA and other immunoassay methods to detect and/or characterize MuV and/or MeV infection. These and other routine methods allow the clinician to select patients in need of therapy using the methods and immunogenic compositions of the disclosure. In accordance with these methods and principles, a composition can be administered according to the teachings herein, or other conventional methods, as an independent prophylaxis or treatment program, or as a follow-up, adjunct or coordinate treatment regimen to other treatments.

The administration of a disclosed immunogen can be for prophylactic or therapeutic purpose. When provided prophylactically, the immunogen can be provided in advance of any symptom, for example in advance of infection. The prophylactic administration serves to prevent or ameliorate any subsequent infection. In some embodiments, the methods can involve selecting a subject at risk for contracting MuV and/or MeV infection, and administering a therapeutically effective amount of a disclosed immunogen to the subject. The immunogen can be provided prior to the anticipated exposure to MuV and/or MeV so as to attenuate the anticipated severity, duration or extent of an infection and/or associated disease symptoms, after exposure or suspected exposure to the virus, or after the actual initiation of an infection. Populations that benefit from prophylactic use of the disclosed immunogen (for example, as a boost immunization) include children entering school (e.g., 5 years old) and adolescents entering high school or college or military (e.g., 15-18 years old). Transplant recipients may also need to be revaccinated or immunocompromised children like HIV+ would benefit from a protein vaccine as opposed to a live-attenuated virus that may not be safe including pregnant women.

When provided therapeutically, the disclosed immunogens are provided at or after the onset of a symptom of MuV and/or MeV infection, or after diagnosis of MuV and/or MeV infection. Treatment of MuV by inhibiting MuV replication or infection can include delaying and/or reducing signs or symptoms of MuV infection in a subject. Treatment of MeV by inhibiting MeV replication or infection can include delaying and/or reducing signs or symptoms of MeV infection in a subject. In some examples, treatment using the methods disclosed herein prolongs the time of survival of the subject.

In some embodiments, administration of a disclosed immunogen to a subject can elicit the production of an immune response that is protective against or reduces symptoms of disease when the subject is subsequently infected or re-infected with a wild-type MuV and/or MeV. While the naturally circulating virus may still be capable of causing infection there can be a reduced possibility of serious or life-threatening symptoms as a result of the vaccination and a possible boosting of resistance by subsequent infection by wild-type virus. Following vaccination, there are detectable levels of host engendered serum and secretory antibodies which are capable of neutralizing homologous (of the same subgroup) wild-type virus in vitro and in vivo. In many instances the host antibodies will also neutralize wild-type virus of a different, non-vaccine subgroup.

The immunogens described herein, and immunogenic compositions thereof, are provided to a subject in an amount effective to induce or enhance an immune response against MuV and/or MeV in the subject, preferably a human. The actual dosage of disclosed immunogen will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the composition for eliciting the desired activity or biological response in the subject. Dosage regimens can be adjusted to provide an optimum prophylactic or therapeutic response.

An immunogenic composition including one or more of the disclosed immunogens can be used in coordinate (or prime-boost) vaccination protocols or combinatorial formulations. In certain embodiments, novel combinatorial immunogenic compositions and coordinate immunization protocols employ separate immunogens or formulations, each directed toward eliciting an anti-viral immune response, such as an immune response to MuV F protein and/or MeV F protein. Separate immunogenic compositions that elicit the anti-viral immune response can be combined in a polyvalent immunogenic composition administered to a subject in a single immunization step, or they can be administered separately (in monovalent immunogenic compositions) in a coordinate (or prime-boost) immunization protocol.

There can be several boosts, and each boost can be a different disclosed immunogen. In some examples that the boost may be the same immunogen as another boost, or the prime. The prime and boost can be administered as a single dose or multiple doses, for example two doses, three doses, four doses, five doses, six doses or more can be administered to a subject over days, weeks or months. Multiple boosts can also be given, such one to five (e.g., 1, 2, 3, 4 or 5 boosts), or more. Different dosages can be used in a series of sequential immunizations. For example a relatively large dose in a primary immunization and then a boost with relatively smaller doses.

In some embodiments, the boost can be administered about two, about three to eight, or about four, weeks following the prime, or about several months after the prime. In some embodiments, the boost can be administered about 5, about 6, about 7, about 8, about 10, about 12, about 18, about 24, months after the prime, or more or less time after the prime. Periodic additional boosts can also be used at appropriate time points to enhance the subject's "immune memory." The adequacy of the vaccination parameters chosen, e.g., formulation, dose, regimen and the like, can be determined by taking aliquots of serum from the subject and assaying antibody titers during the course of the immunization program. In addition, the clinical condition of the subject can be monitored for the desired effect, e.g., inhibition of MuV and/or MeV infection or improvement in disease state (e.g., reduction in viral load). If such monitoring indicates that vaccination is sub-optimal, the subject can be boosted with an additional dose of immunogenic composition, and the vaccination parameters can be modified in a fashion expected to potentiate the immune response.

In some embodiments, the prime-boost method can include DNA-primer and protein-boost vaccination protocol to a subject. The method can include two or more administrations of the nucleic acid molecule or the protein.

For protein therapeutics, typically, each human dose will comprise 1-1000 µg of protein, such as from about 1 µg to about 100 µg, for example, from about 1 µg to about 50 µg, such as about 1 µg, about 2 µg, about 5 µg, about 10 µg, about 15 µg, about 20 µg, about 25 µg, about 30 µg, about 40 µg, or about 50 µg.

The amount utilized in an immunogenic composition is selected based on the subject population (e.g., infant or elderly). An optimal amount for a particular composition can be ascertained by standard studies involving observation of antibody titers and other responses in subjects. It is understood that an effective amount of a disclosed immunogen, such as a recombinant MuV or MeV F ectodomain trimer or recombinant MeV F ectodomain trimer or a chimera thereof with a MuV HN or MeV H ectodomain, viral vector, or nucleic acid molecule in a immunogenic composition, can include an amount that is ineffective at eliciting an immune response by administration of a single dose, but that is effective upon administration of multiple dosages, for example in a prime-boost administration protocol.

Upon administration of a disclosed immunogen the immune system of the subject typically responds to the immunogenic composition by producing antibodies specific for viral protein. Such a response signifies that an immunologically effective dose was delivered to the subject.

For each particular subject, specific dosage regimens can be evaluated and adjusted over time according to the individual need and professional judgment of the person administering or supervising the administration of the immunogenic composition. The dosage and number of doses will depend on the setting, for example, in an adult or anyone primed by prior MuV and/or MeV infection or immunization, a single dose may be a sufficient booster. In naïve subjects, in some examples, at least two doses would be given, for example, at least three doses. In some embodiments, an annual boost is given, for example, along with an annual influenza vaccination.

In some embodiments, the antibody response of a subject will be determined in the context of evaluating effective dosages/immunization protocols. In most instances it will be sufficient to assess the antibody titer in serum or plasma obtained from the subject. Decisions as to whether to administer booster inoculations and/or to change the amount of the therapeutic agent administered to the individual can be at least partially based on the antibody titer level. The antibody titer level can be based on, for example, an immunobinding assay which measures the concentration of antibodies in the serum which bind to an antigen including, for example, a MuV F protein and/or a MeV F protein.

Determination of effective dosages is typically based on animal model studies followed up by human clinical trials and is guided by administration protocols that significantly reduce the occurrence or severity of targeted disease symptoms or conditions in the subject, or that induce a desired response in the subject (such as a neutralizing immune response). Suitable models in this regard include, for example, murine, rat, porcine, feline, ferret, non-human primate, and other accepted animal model subjects known in the art. Alternatively, effective dosages can be determined using in vitro models (for example, immunologic and histopathologic assays). Using such models, only ordinary calculations and adjustments are required to determine an appropriate concentration and dose to administer an effective amount of the composition (for example, amounts that are effective to elicit a desired immune response or alleviate one or more symptoms of a targeted disease). In alternative embodiments, an effective amount or effective dose of the composition may simply inhibit or enhance one or more selected biological activities correlated with a disease or condition, as set forth herein, for either therapeutic or diagnostic purposes.

Administration of an immunogenic composition that elicits an immune response to reduce or prevent an infection, can, but does not necessarily completely, eliminate such an infection, so long as the infection is measurably diminished. For example, administration of an effective amount of the agent can decrease the MuV or MeV infection (for example, as measured by infection of cells, or by number or percentage of subjects infected by MuV or MeV by a desired amount, for example by at least 10%, at least 20%, at least 50%, at least 60%, at least 70%, at least 80%, at least 90%, at least 95%, at least 98%, or even at least 100% (elimination or prevention of detectable MuV or MeV infection, as compared to a suitable control, also referred to as sterilizing immunity).

In some embodiments, administration of an effective amount of one or more of the disclosed immunogens to a subject induces a neutralizing immune response in the subject. To assess neutralization activity, following immunization of a subject, serum can be collected from the subject at appropriate time points, frozen, and stored for neutralization testing. Methods to assay for neutralization activity include, but are not limited to, plaque reduction neutralization titer (PRNT) assays, microneutralization assays, flow cytometry-based assays, single-cycle infection assays. In some embodiments, the serum neutralization activity can be assayed using a panel of MuV and/or MeV pseudoviruses.

One approach to administration of nucleic acids is direct immunization with plasmid DNA, such as with a mammalian expression plasmid. Immunization by nucleic acid constructs is well known in the art and taught, for example, in U.S. Pat. No. 5,643,578 (which describes methods of immunizing vertebrates by introducing DNA encoding a desired antigen to elicit a cell-mediated or a humoral response), and U.S. Pat. Nos. 5,593,972 and 5,817,637 (which describe operably linking a nucleic acid sequence encoding an antigen to regulatory sequences enabling expression). U.S. Pat. No. 5,880,103 describes several methods of delivery of nucleic acids encoding immunogenic peptides or other antigens to an organism. The methods include liposomal delivery of the nucleic acids (or of the synthetic peptides themselves), and immune-stimulating constructs, or ISCOMS™, negatively charged cage-like structures of 30-40 nm in size formed spontaneously on mixing cholesterol and Quil A™ (saponin). Protective immunity has been generated in a variety of experimental models of infection, including toxoplasmosis and Epstein-Barr virus-induced tumors, using ISCOMS™ as the delivery vehicle for antigens (Mowat and Donachie, *Immunol. Today* 12:383, 1991). Doses of antigen as low as 1 μg encapsulated in ISCOMS™ have been found to produce Class I mediated CTL responses (Takahashi et al., *Nature* 344:873, 1990).

In some embodiments, a plasmid DNA vaccine is used to express a disclosed immunogen in a subject. For example, a nucleic acid molecule encoding a disclosed immunogen can be administered to a subject to elicit an immune response to the F protein of MuV or MeV. In some embodiments, the nucleic acid molecule can be included on a plasmid vector for DNA immunization, such as the pVRC8400 vector (described in Barouch et al., J. Virol, 79, 8828-8834, 2005, which is incorporated by reference herein).

In another approach to using nucleic acids for immunization, a disclosed immunogen can be expressed by attenuated viral hosts (such as an attenuated MuV or MeV vector) or vectors or bacterial vectors. Recombinant vaccinia virus, adeno-associated virus (AAV), herpesvirus, retrovirus, cytogmeglovirus, paramyxovirus, pneumovirus, or other viral vectors can be used to express the peptide or protein, thereby eliciting a CTL response. For example, vaccinia vectors and methods useful in immunization protocols are described in U.S. Pat. No. 4,722,848. BCG (*Bacillus* Calmette Guerin) provides another vector for expression of the peptides (see Stover, *Nature* 351:456-460, 1991).

In another example, a disclosed immunogen can be administered to a subject using RNA immunization, such as with a lipid-encapsulated mRNA immunization platform (see, e.g., Roth et al., "A Modified mRNA Vaccine Targeting Immunodominant NS Epitopes Protects Against Dengue Virus Infection in HLA Class I Transgenic Mice," Frot Immunol., Jun. 21, 2019, Vol. 10, Article 1424; Jagger et al., J Infect Dis, "Protective Efficacy of Nucleic Acid Vaccines Against Transmission of Zika Virus During Pregnancy in Mice," jiz338, Jul. 1, 2019; Feldman et al., "mRNA vaccines against H10N8 and H7N9 influenza viruses of pandemic potential are immunogenic and well tolerated in healthy adults in phase 1 randomized clinical trials," Vaccine, 37(25), 3326-3334, 2019; and Hasset et al., "Optimization of Lipid Nanoparticles for Intramuscular Administration of mRNA Vaccines," Mol Ther Nucleic Acids, 15: 1-11, 2019.

In one embodiment, a nucleic acid encoding a protomer of a disclosed MuV F or MeV F ectodomain trimer is introduced directly into cells. For example, the nucleic acid can be loaded onto gold microspheres by standard methods and introduced into the skin by a device such as Bio-Rad's HELIOS™ Gene Gun. The nucleic acids can be "naked," consisting of plasmids under control of a strong promoter. Typically, the DNA is injected into muscle, although it can also be injected directly into other sites. Dosages for injection are usually around 0.5 μg/kg to about 50 mg/kg, and typically are about 0.005 mg/kg to about 5 mg/kg (see, e.g., U.S. Pat. No. 5,589,466).

In another embodiment, an mRNA-based immunization protocol can be used to deliver a nucleic acid encoding a disclosed immunogen directly into cells. In some embodiments, nucleic acid-based vaccines based on mRNA may provide a potent alternative to the previously mentioned approaches. mRNA vaccines preclude safety concerns about DNA integration into the host genome and can be directly translated in the host cell cytoplasm. Moreover, the simple cell-free, in vitro synthesis of RNA avoids the manufacturing complications associated with viral vectors. Two exemplary forms of RNA-based vaccination that can be used to deliver a nucleic acid encoding a disclosed immunogen include conventional non-amplifying mRNA immunization (see, e.g., Petsch et al., "Protective efficacy of in vitro synthesized, specific mRNA vaccines against influenza A virus infection," Nature biotechnology, 30(12):1210-6, 2012) and self-amplifying mRNA immunization (see, e.g., Geall et al., "Nonviral delivery of self-amplifying RNA vaccines," PNAS, 109(36): 14604-14609, 2012; Magini et al., "Self-Amplifying mRNA Vaccines Expressing Multiple Conserved Influenza Antigens Confer Protection against Homologous and Heterosubtypic Viral Challenge," PLoS One, 11(8):e0161193, 2016; and Brito et al., "Self-amplifying mRNA vaccines," Adv Genet., 89:179-233, 2015).

In some embodiments, a lipid nanoparticle including mRNA encoding a disclosed immunogen is used in the method of eliciting an immune response, for example, as described in WO2017070626, US2019/0192646, and for the mRNA-1273 vaccine described in Jackson et al. "An mRNA vaccine against SARS-CoV2—preliminary report," N. Engl. J. Med., 383(20):1920-1931, 2020, each of which is incorporated by reference herein. As described in WO2017070626, the mRNA encoding the immunogen can be formulated in lipid nanoparticles with 50 mol % ionizable lipid, 10 mol % DSPC, 38.5 mol % cholesterol, and 1.5 mol % (PEG2000 DMG). Further, the mRNA encoding the immunogen can be a modified mRNA with 1-methylpseudouridine in place of uridine and a 7mG(5')ppp(5') N1mpNp cap (enzymatic), as well as a 5'UTR, a 3'UTR, and a polyA tail.

EXAMPLES

The following examples are provided to illustrate particular features of certain embodiments, but the scope of the claims should not be limited to those features exemplified.

Example 1

MuV F Proteins Stabilized in a Prefusion Conformation and Fusions Thereof with MuV HN Ectodomain This example illustrates embodiments of a MuV F ectodomain trimer stabilized in a prefusion conformation by one or more amino acid substitutions. Further provided are MuV F ectodomain trimers linked to a MuV HN ectodomain. The prefusion-stabilized MuV F ectodomain trimers and corresponding fusions with MuV HN ectodomain are useful, for example, for inducing a neutralizing immune response to MuV in a subject.

Before the introduction of mumps-containing vaccines in the late 1960s, mumps caused widespread morbidity characterized by fever, parotitis and less commonly, orchiditis, meningitis, encephalitis and deafness. The combination measles, mumps and rubella vaccine (MMR) dramatically reduced the incidence of mumps throughout the world. Two doses of MMR vaccine are approximately 88% effective for the prevention of mumps disease however since 2006, there has been a resurgence in the number of cases of mumps disease in the world among highly-vaccinated populations, with >30,000 affected individuals in the U.S. Contributing factors may include waning immunity, poorly effective antibody responses, and antigenic differences between the Jeryl Lynn strain used in the MMR vaccine and circulating wildtype strains. The predominant mumps genotype characterizing outbreaks in the USA and Europe in recent years has been genotype G.

As described herein, structure-based design was used to engineer a MuV F glycoprotein stabilized in the prefusion conformation. A crystal structure of mumps fusion glycoprotein at 2.16 Å resolution reveals the basis for prefusion conformational stabilization. Potent cross-mumps genotype plaque reduction neutralizing titers (PRNT) were elicited in mice from the mumps prefusion-stabilized F glycoprotein or a chimeric fusion glycoprotein of prefusion-stabilized mumps F trimer linked to genotype G mumps hemagglutinin neuraminidase (HN). The prefusion F-HN mumps chimera could elicit the highest PRNT to genotypes A, G and H mumps viruses, greater than 100-fold the reported human protective titer. Additionally, monoclonal antibodies to mumps prefusion F and HN were isolated from immunized mice, which were capable of neutralizing genotype G mumps virus with a spectrum of potencies. Structural and binding analyses of these prefusion F-specific antibodies revealed binding to four discrete neutralizing antigenic sites. The engineered immunogens are vaccine candidates for mumps either as novel or as booster vaccines.

Results

Disulfide Bond and Membrane-Proximal Coiled Coil Stabilization Robustly Stabilize and Allow Production of a Soluble Prefusion Mumps F Trimer.

When produced in cells, the MuV F ectodomain linked to a C-terminal GCN4 trimerization domain forms trimers that spontaneously transition to the prefusion conformation. Unstabilized recombinant MuV F-GCN4 is so unstable, 100% of molecules have transitioned to the postfusion conformation at the point of evaluation (EM). Also protein expression is substantially reduced without stabilization. Accordingly, structure-based vaccine design was used to identify mutations for the stabilization of the MuV F ectodomain in a prefusion conformation and also to eliminate the F1/F2 cleavage site to produce a "single chain" MuV F protein with increased expression.

The crystal structures of the simian prefusion parainfluenza virus 5 (PIV5) F glycoprotein (PDB IDs 4GIP, 4WSG) (Welch, B. D. et al. *Proc Natl Acad Sci USA* 109, 16672-16677, 2012) were used to construct a homology model for the prefusion mumps F protein, consisting of three intertwined monomers forming a quaternary assembly of DI, DII, DIII and HRB domains.

Multiple stabilization strategies were employed to "lock" the MuV F ectodomain in the prefusion conformation, including introduction of disulfide bonds and proline substitutions. The selection of residues to mutate to cysteines in MuV F were based on homology design from the PIV5 prefusion F structure (PDB 4WSG), based on residues that would be predicted to undergo conformational change in transitioning from prefusion to postfusion conformation. The residue pairs Cbeta atoms were identified to be within 5 angstrom and orientated such that the formation of a disulfide bond might be possible. In total, approximately 60 different mutants were designed, expressed, purified, assessed for expression level, and assessed for prefusion conformation by negative stain EM.

The mutations were introduced into a MuV F ectodomain (based on C-terminal truncations at MuV F position 469, 476, or 483, and linked to a C-terminal GCN4 trimerization domain, and the resulting mutants were screened as noted above. The ectodomain also included a mutation to remove the F1/F2 furin cleavage site. The prefusion stabilizing mutations assessed included: cysteine substitutions at one or more of MuV F positions 86 and 215, 155 and 161, 163 and 235, 165 and 231, 206 and 223, 209 and 214, 221 and 255 that form a non-natural disulfide bond; and a proline substitution at MuV F position 184. Relevant sequences are shown below. In FIG. 1A, a summary of the initial successful prefusion-stabilizing mutations are reported.

The expression and purification of the single chain and prefusion-stabilized MuV F proteins showed a substantial increase in expression level compared to the unmodified MuV F.

As illustrated in FIGS. 1A and B, negative stain EM can be used to distinguish MuV F ectodomain trimers that are in the prefusion conformation from those that are in the postfusion conformation.

By creating a matrix of disulfide substitutions and C-terminal coiled-coil-GCN4 attachment positions, the level of protein expression and the proportion of protein adopting the prefusion or postfusion trimer conformation was evaluated using negative-stain EM (FIG. 1A). It was observed that while five combinations of disulfide bonds and GCN4 attachment positions gave rise to 100% prefusion trimers, one such combination gave rise to high-yield protein expression (V206C-A223C with 476-GCN4) at about 4.8 mg/L from Expi293 cells. The negative stain EM 2D average of this design (FIG. 1B, top inset) contrasts with the postfusion mumps F glycoprotein trimer (FIG. 1B, lower inset) and was consistent with prior observations for parainfluenza virus F protein conformations.

Figures 2D, 2E:
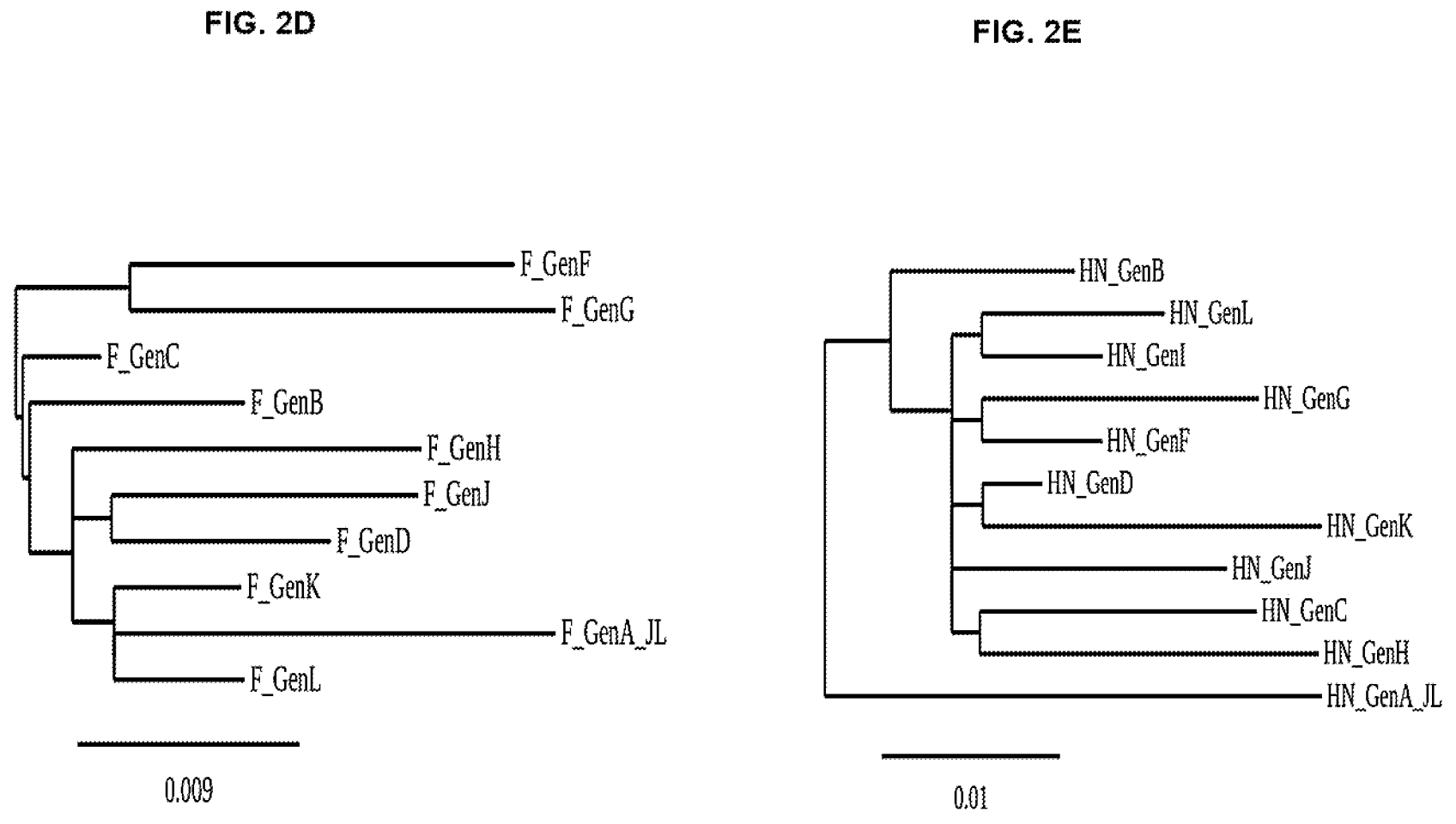
Figure 1C:
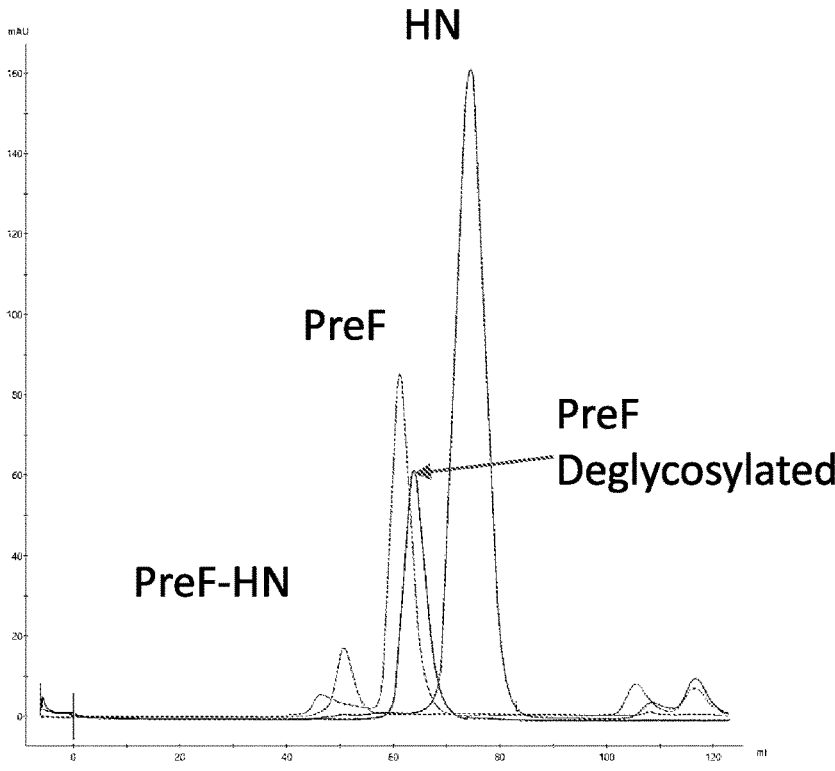
Figure 1D:
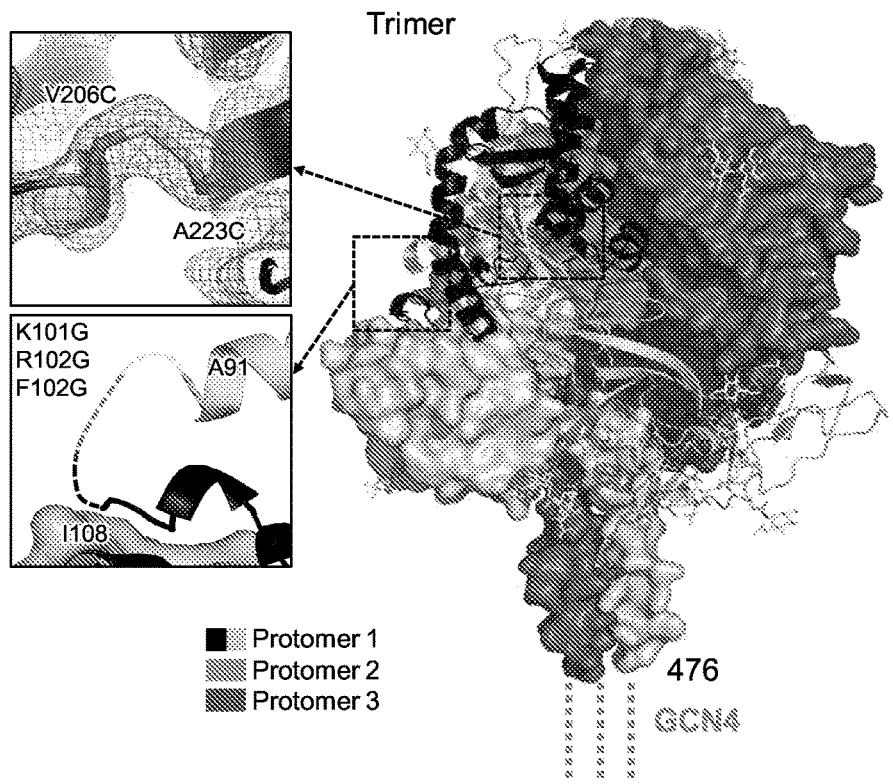
Figure 1E:
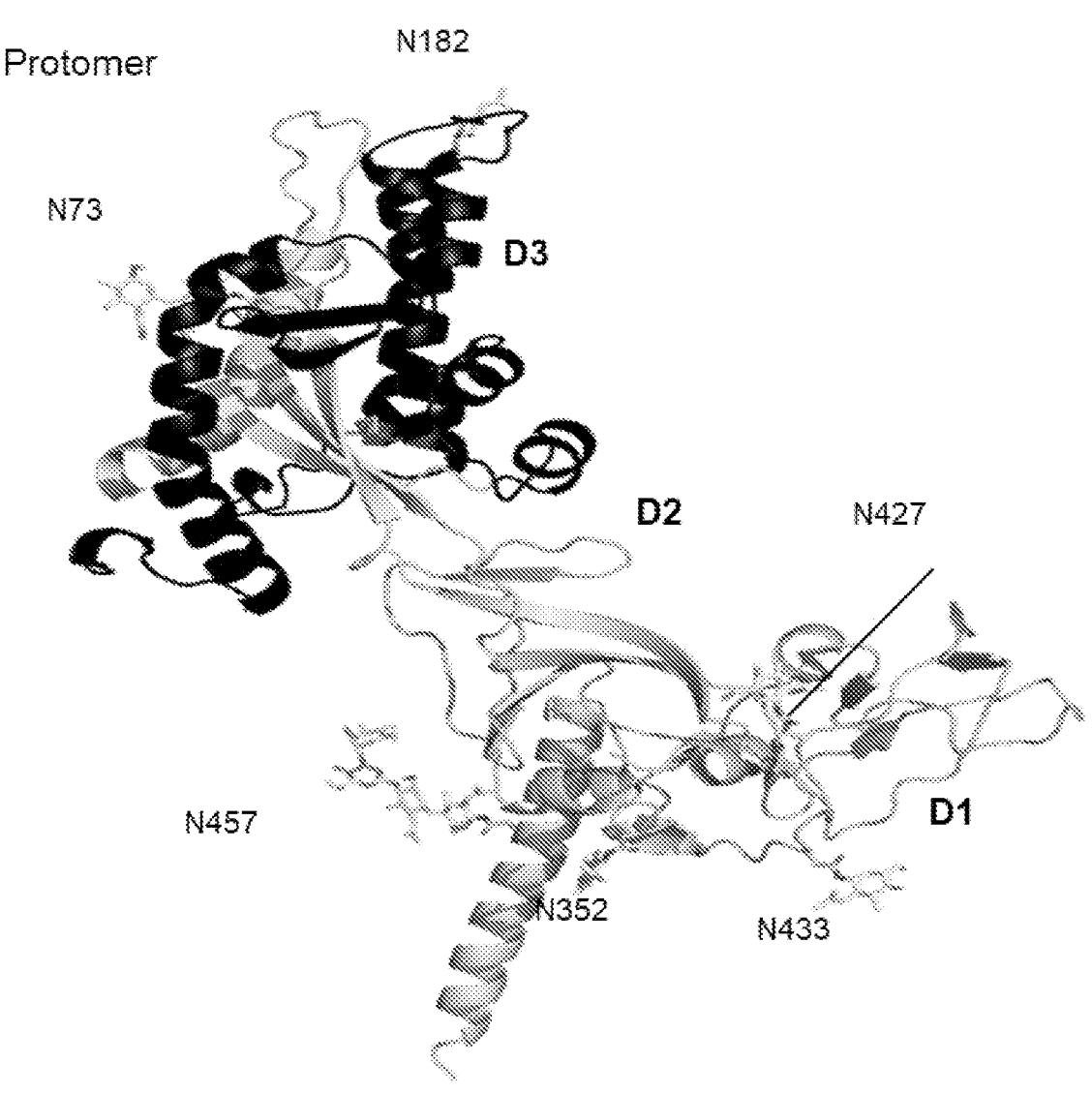
Figure 2F:
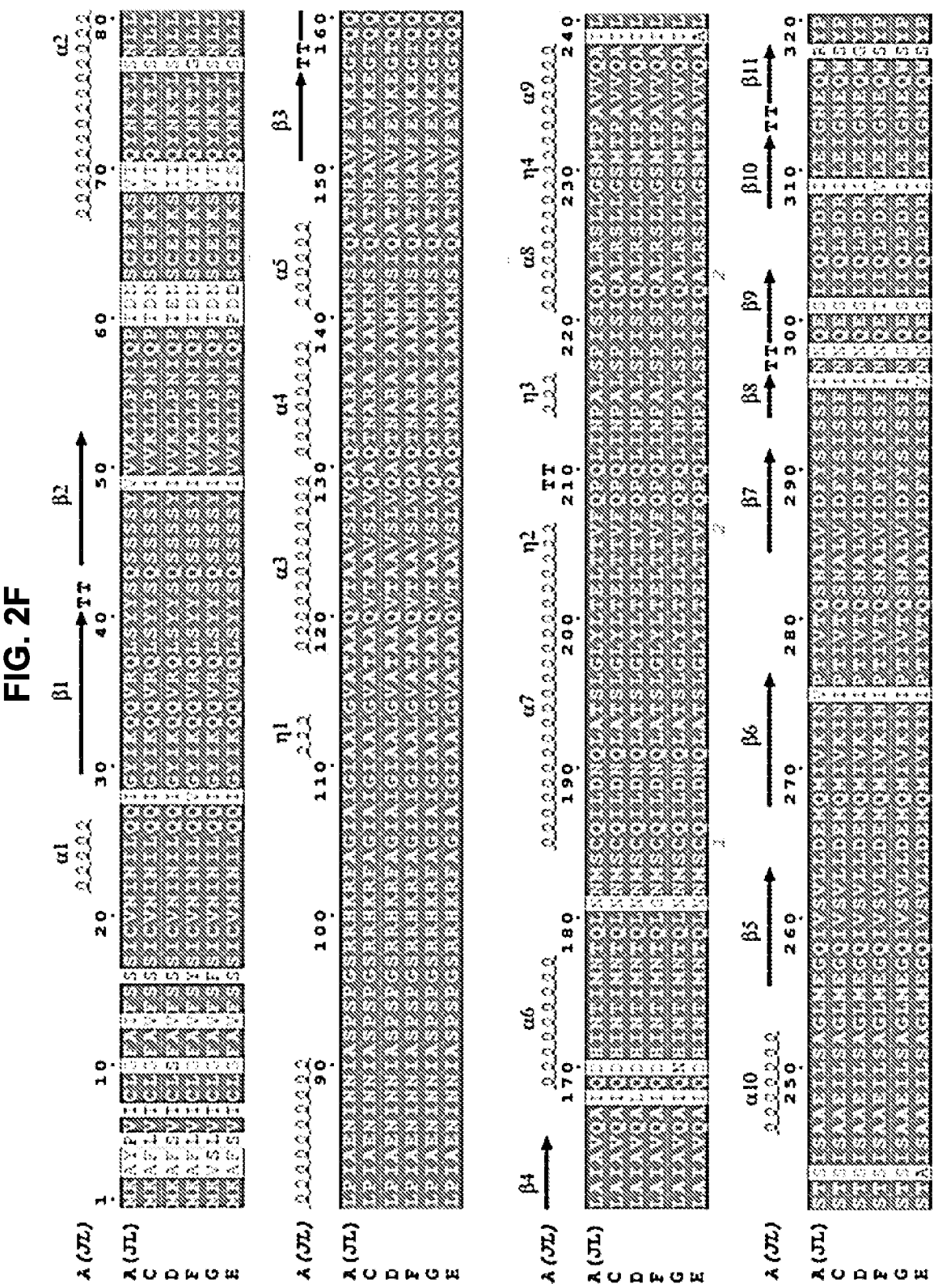
Figure 2G:
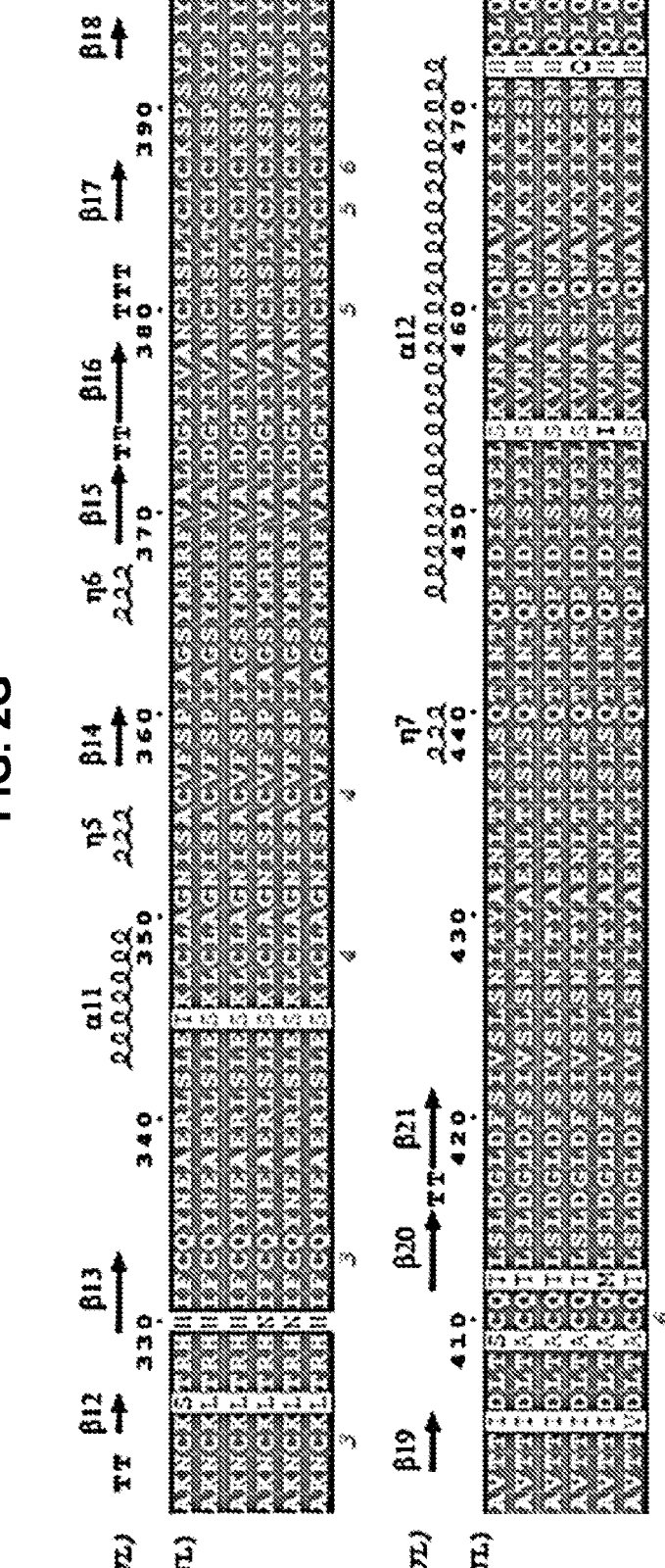
Figure 2H:
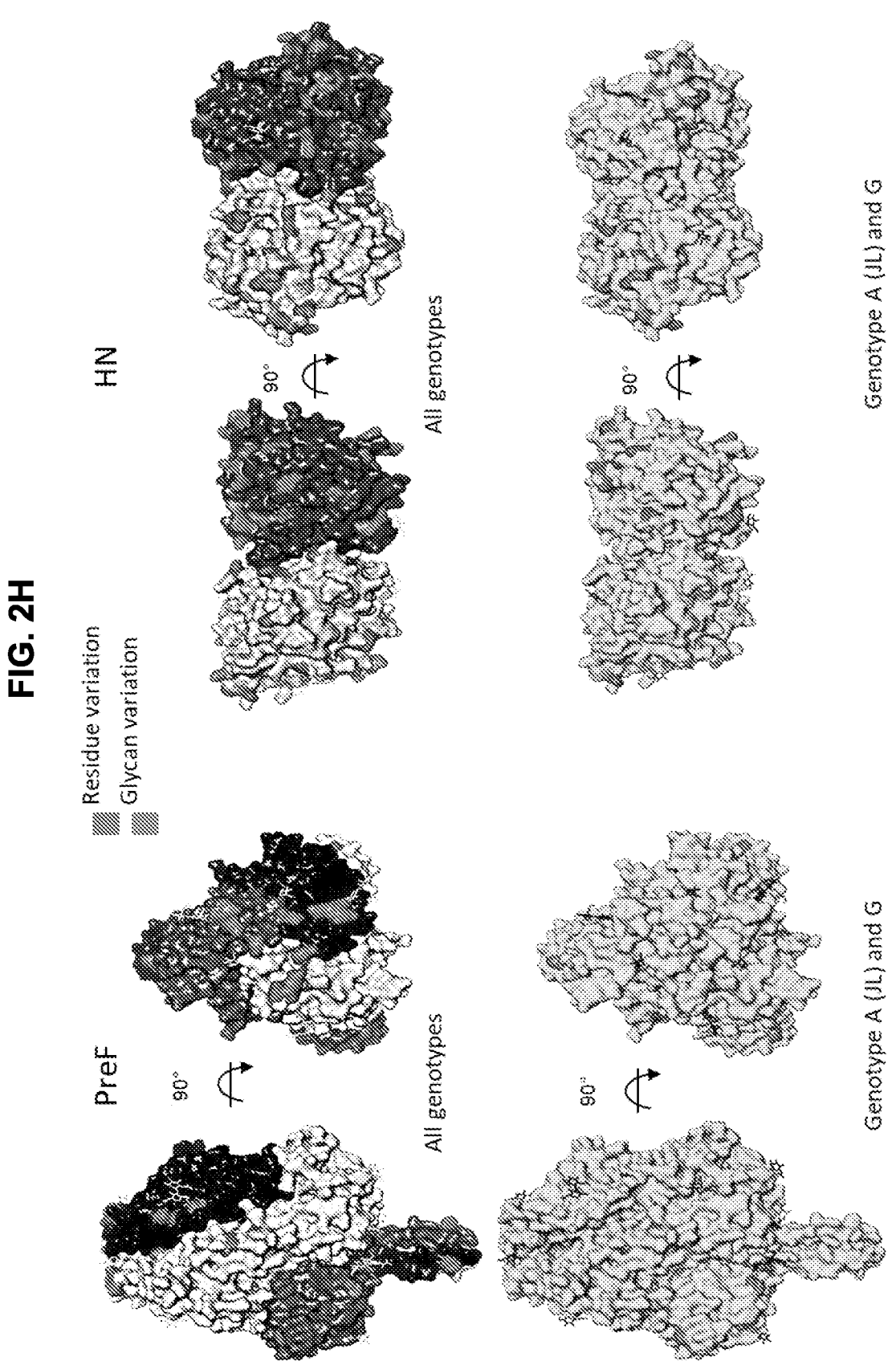

Crystal structure of prefusion mumps F glycoprotein trimer to 2.16 Å resolution reveals a stabilizing disulfide design and the location of polymorphic residues. Size-exclusion chromatography of the prefusion-stabilized mumps F protein trimer (MuV F V206C-A223C-GGG-476-GCN4, SEQ ID NO: 11) revealed a homogeneous peak (FIG. 1C), which when expressed in the presence of kifunensine, could be deglycosylated and crystallized. The 3-dimensional coordinates for the structure are provided herewith in Table 1. The x-ray structure to 2.16 Å resolution (FIGS. 1D and 1E) revealed a similar overall architecture to prefusion PIV5 and other paramyxovirus prefusion F trimers (Stewart-Jones et al., *Proc Natl Acad Sci USA* 115, 12265-12270, 2018; Welch, B. D. et al. *Proc Natl Acad Sci USA* 109, 16672-16677, 2012; Xu K. et al. *PLoS Pathog* 11(12): e1005322, 2015), however adopts a 'closed cap' structure comprising of loops N177-S184 at the trimer apex of the mumps prefusion F trimer, formed by interactions between side chains T178, Q179 and N181 (FIGS. 2A and 2B). The remaining N-acetyl glucosamine moieties from the six glycans at positions N73, N182, N352, N427, N433 and N457 were visible in the electron density and a glycosylated model built (FIG. 2C). The V206C-A223C disulfide was clearly defined by the electron density with a Cα-Cα atomic distance of 4.8 Å whereas in the homologous postfusion PIV3 F trimer structure [PDB ID 1ZTM], Cα-Cα atoms are positioned 5.8 Å apart. The DI-DIII domains enclosed a large aqueous cavity measuring ~20,000 Å³ in volume and protomers bury a 6,500 Å² interface, similar to that observed in PIV5, PIV3 and nipah prefusion F structures (Stewart-Jones et al., *Proc Natl Acad Sci USA* 115, 12265-12270, 2018; Welch, B. D. et al. *Proc Natl Acad Sci USA* 109, 16672-16677, 2012; Xu K. et al. *PLoS Pathog* 11(12): e1005322, 2015). The residues thought to undergo conformational change between prefusion and postfusion conformations (based on PIV5 pre-F structure [PDB ID 4WSG] and PIV3 post-F [PDB ID 1ZTM]) are shown in black in FIG. 1E and correspond to MuV F residues 92-253.

While the sequence identities of mumps F and HN are relatively high between genotypes (FIGS. 2A-2C), polymorphic variation to the structures of prefusion mumps F and HN was mapped (FIG. 2D). Mapping the variation to prefusion F for all genotypes and specifically between genotype G and Jeryl Lynn (genotype A), much of the protein surface exposed for antibody recognition was conserved, while numerous variable amino acids were located within the aqueous cavity in the core of the prefusion trimer (FIG. 2D, left). In contrast, the mumps HN dimer structures revealed that most polymorphic amino acids are exposed to the solvent (FIG. 2D, right), including a glycan variation at position N464 between Jeryl Lynn and genotype G HNs. The predominance of solvent-exposed polymorphic residues on HN versus prefusion F suggests that genotype G resistance to Jeryl Lynn vaccine-elicited humoral immunity could be accounted for more from HN than from prefusion F.

Cross-strain effectiveness of stabilizing mutations. To show that the prefusion stabilizing mutations were effective for F from across MuV strains, these mutations were tested in F from several different MuV strains. MuV F V206C-A223C-GGG-476-GCN4 (SEQ ID NO: 11) is based on a genotype C MuV F. Introduction of these prefusion-stabilizing mutations into a genotype A (Jeryl Lynn) MuV F protein (MuV-JL F 206C-A223C-GGG-476-GCN4 (SEQ ID NO: 26) and genotype G MuV F protein (MuV-IL17 F 206C-A223C-GGG-476-GCN4 (SEQ ID NO: 51) also provided prefusion stabilization. Further, introduction of these prefusion-stabilizing mutations into F protein from the following MuV stains also resulted in prefusion stabilization as measured by negative stain EM and/or prefusion specific antibody binding: Canada (URABE), Albany (genotype A), Hoshino (genotype B), India (genotype C), Netherlands (genotype D), China (genotype F), NethL11 (genotype G), NY14 (genotype G), IA14 (genotype G), MA16 (genotype G), LA17 (genotype G), IL17 (genotype G), Virginia (genotype H), Taiwan (genotype J), Taiwan (genotype K), Netherlands (genotype L), MG15 (genotype A)

Figures 4A, 4B, 4C:
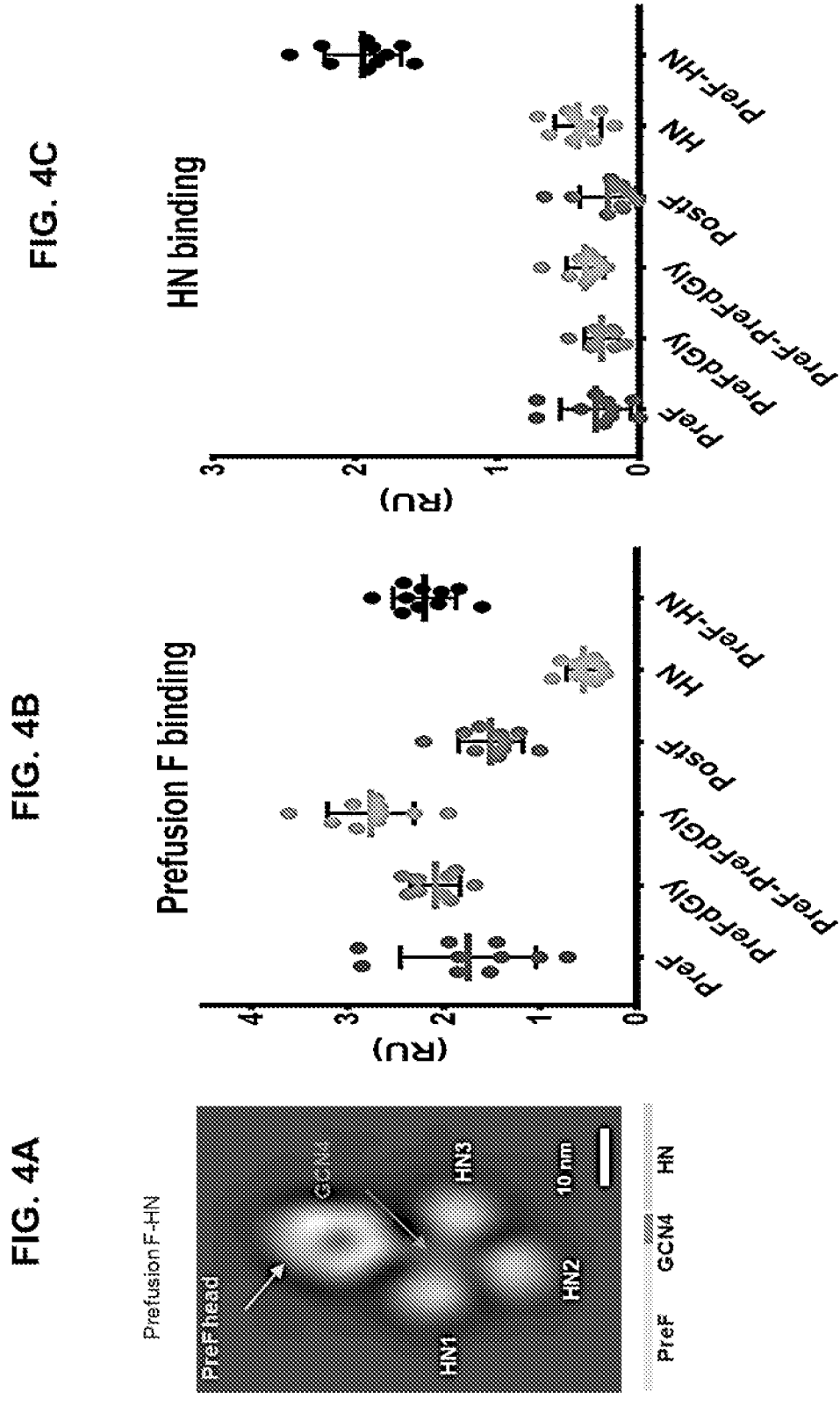

F-HN chimera. To increase the immunogenic footprint of the MuV F ectodomain trimer, a MuV HN ectodomain was genetically fused to the C-terminus of the trimerization domain of each protomer of the trimer. The format is illustrated in FIG. 4A. Corresponding sequences are shown below. Negative stain EM shows that the F ectodomain maintains the prefusion conformation, with the three HN ectodomains (one linked to each F protomer) arrayed C-terminal to the trimerization domain. This design yielded approximately 0.3 mg/L from Expi293 cells and was monodispersed on size exclusion chromatography and displayed expected assembly from negative-stain EM (FIG. 1C and FIG. 4A).

Figure 3A:
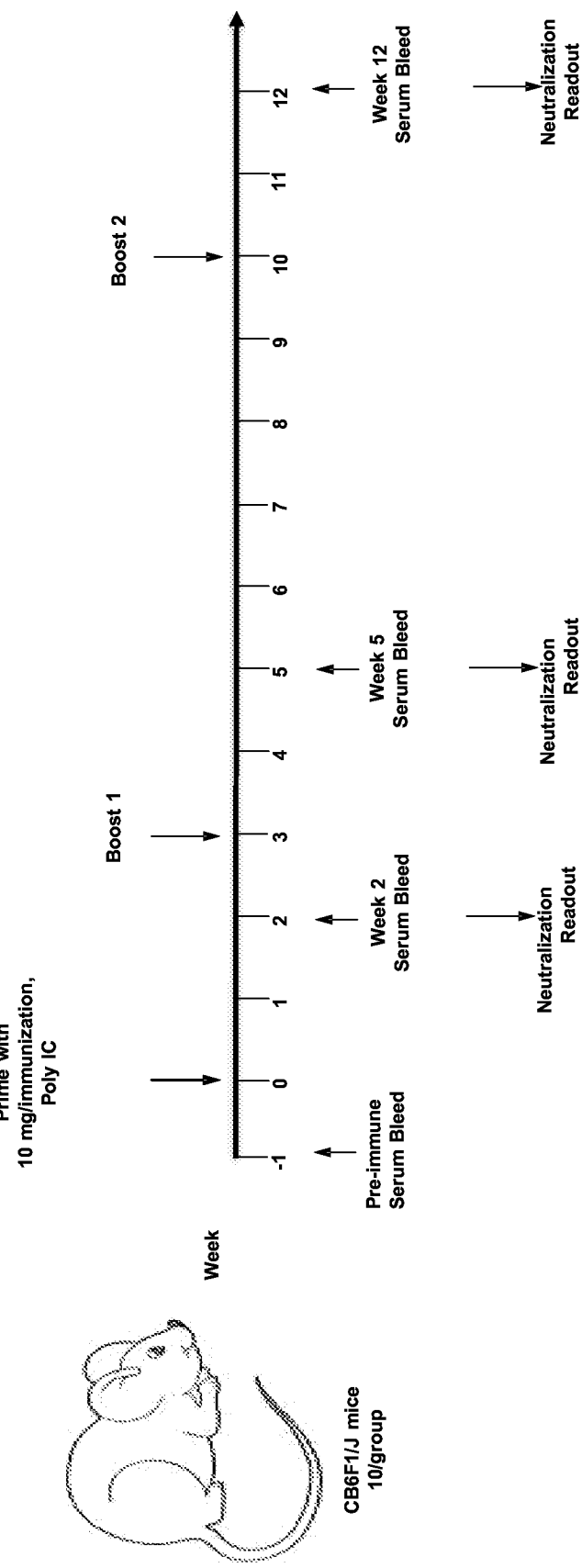
FIGS. 3A and 3B. Design and immunization scheme for mumps F and preF-HN immunogen variants.

Prefusion-stabilized mumps F and prefusion-stabilized F-HN chimeric trimers elicit high-titer neutralizing antibodies in mice. The ability of prefusion-stabilized mumps F to elicit neutralizing antibodies compared to other mumps immunogens was assessed. Groups of 10 CB6F1/J mice were immunized with 10 μg doses of mumps glycoproteins combined with 10 μg polyinosinic-polycytidylic acid (poly-I:C) adjuvant at weeks 0, 3 and 10 and the ability of sera to prevent mumps virus infection of HEp-2 cells was measured (FIG. 3A).

The immunogens assessed were a MuV F ectodomain trimer in a post-fusion conformation (native ectodomain with –476-GCN4), a MuV F ectodomain trimer in a pre-fusion conformation (MuV F V206C-A223C-GGG-476-GCN4, SEQ ID NO: 11), MuV HN ectodomain monomer, and a MuV F ectodomain trimer in a pre-fusion conformation with the protomers of the trimer fused to MuV HN ectodomain (MuV F 206C-223C-GGG-476+GCN4+MuV HN_G (SEQ ID NO: 27).

Where mice were immunized with prefusion mumps F-containing immunogens (preF or preF-HN), specific responses to preF were detected in sera, with lower levels of binding to postfusion-immunized mice (FIG. 4B). Recombinant HN monomer bound only HN-immunized mouse sera, however monomeric HN immunized mice showed little binding whereas sera from preF-HN immunized mice showed substantial levels of HN binding suggesting multi-valency of HN was driving a robust humoral responses (FIG. 4C).

Figure 3B:
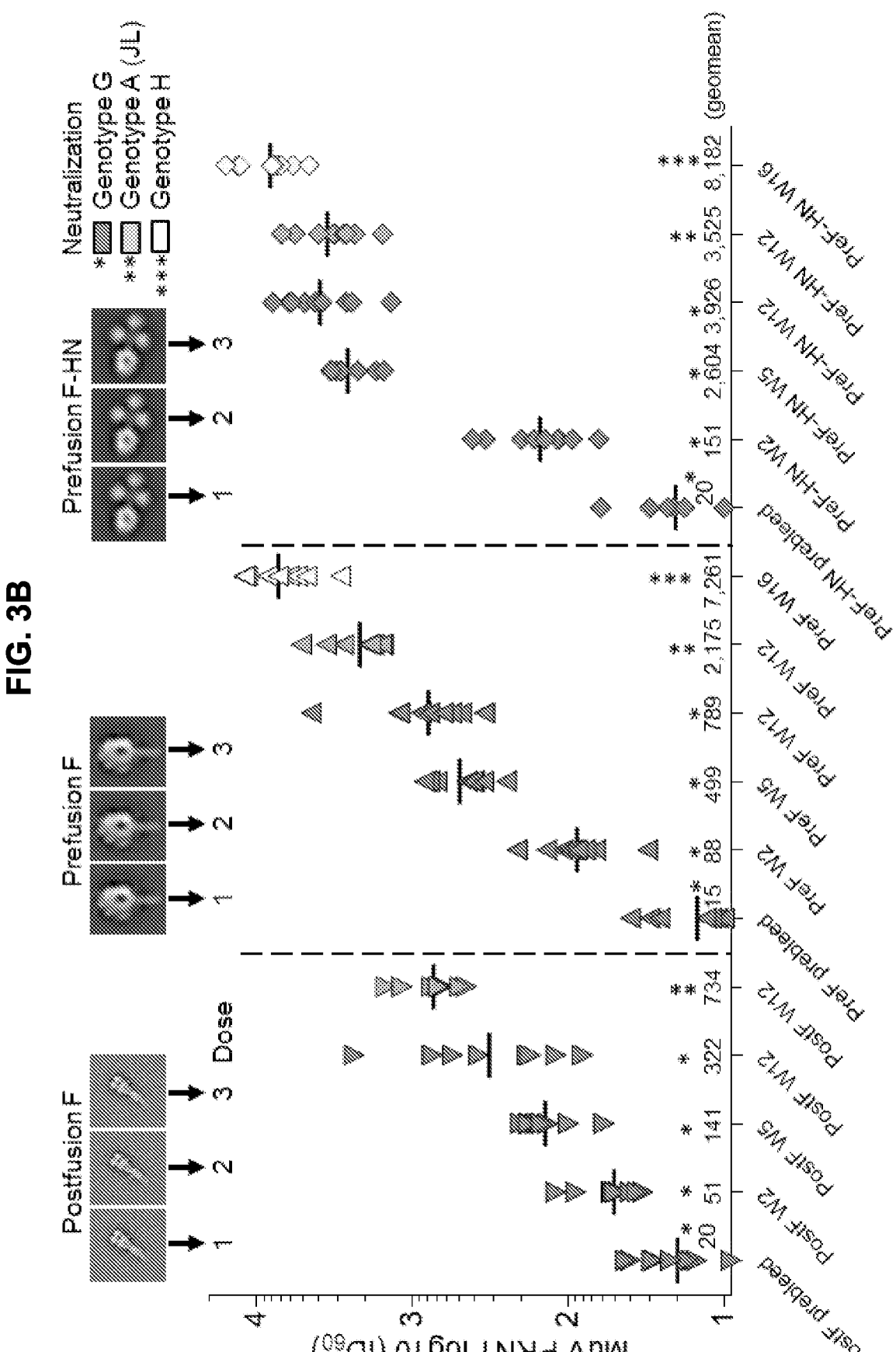

To analyze the elicitation of neutralizing antibody titers from three immunizations with either postfusion F, prefusion F or prefusion F-HN, the PRNT 2 weeks following each immunization was analyzed (FIG. 3B). Incremental increases in neutralizing titers were observed after each immunization, however the third immunization showed a more marginal increase than after the second immunization. Neutralizing antibodies were observed with postfusion immunization, however the prefusion F immunogen showed a 3.5 and 2.5-fold higher neutralization than postfusion F after the second and third immunization respectively (geometric mean infective dose (ID$_{60}$ values) of 322 and 789 respectively to genotype G mumps virus). The preF-HN chimeric variant elicited neutralizing titers after the third immunization 12-fold higher than postfusion F and 5-fold higher than prefusion F, with an ID$_{60}$ value of 3930 to genotype G virus.

Figure 4D:
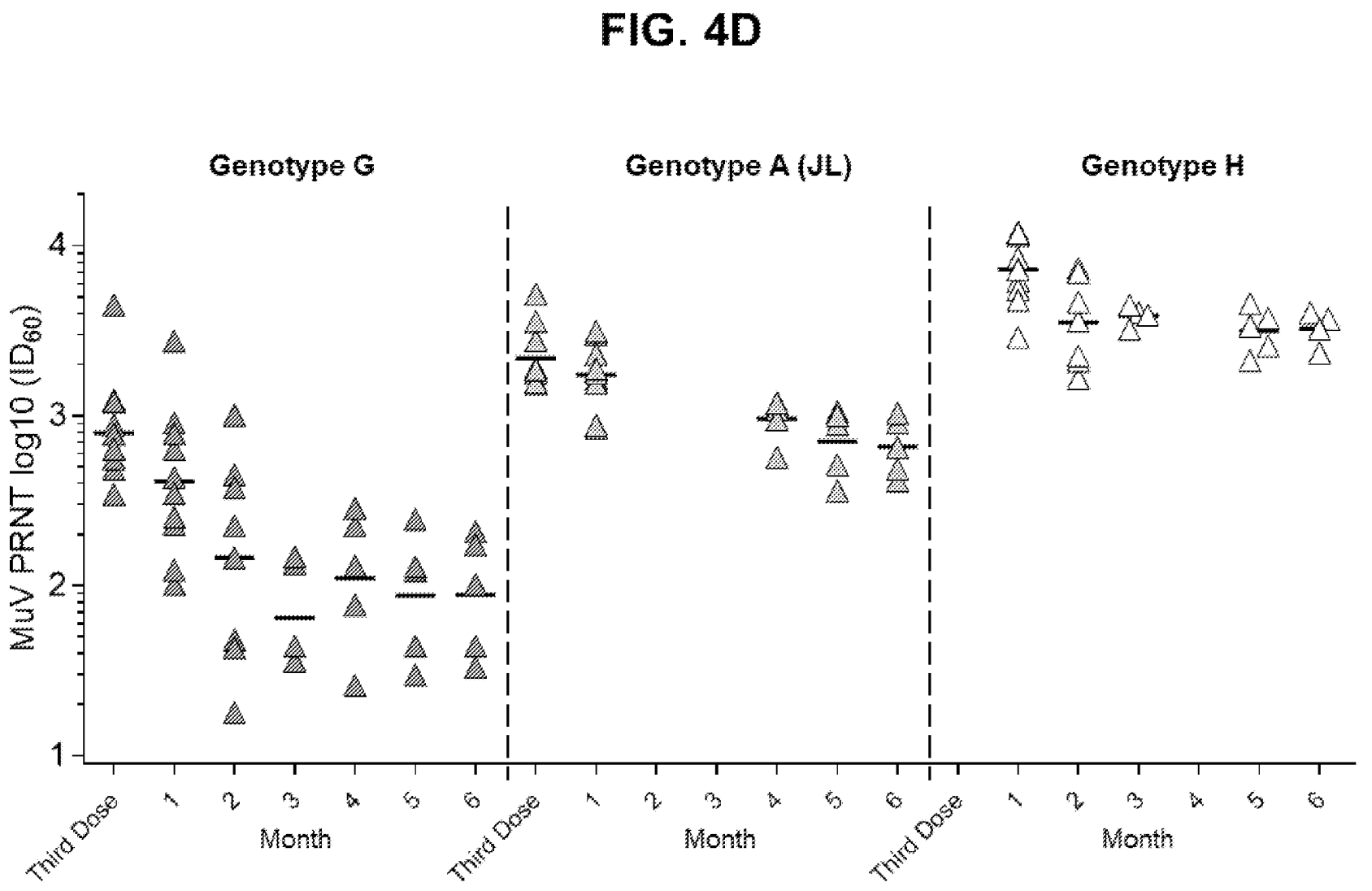
Figure 4E:
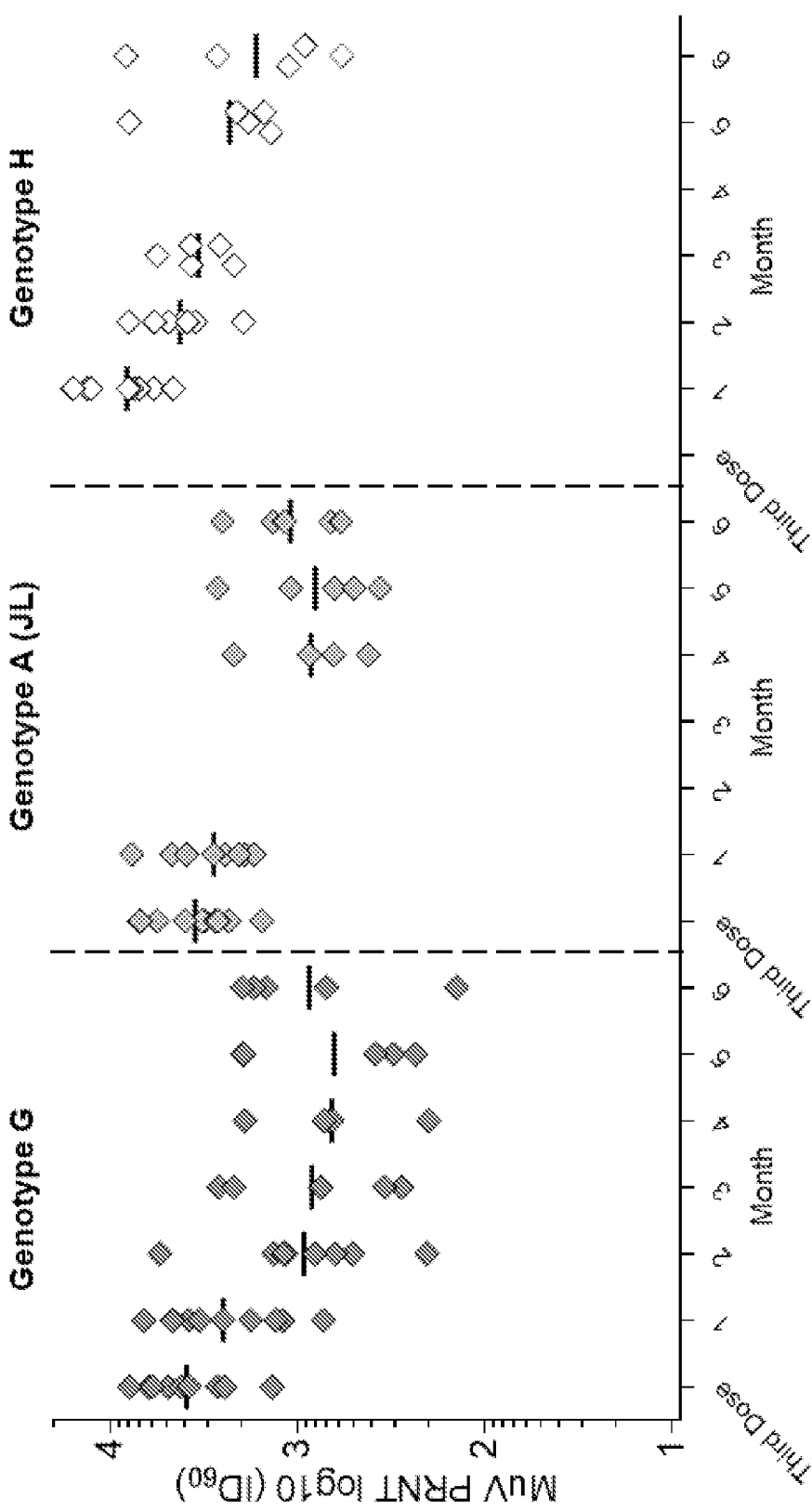

Next, the PRNT to Jeryl Lynn and genotype H viruses was evaluated to characterize cross-neutralizing antibodies elicited from the recombinant immunogens. For postfusion and prefusion F, a greater level of neutralization was observed for Jeryl Lynn virus than to genotype G virus, whereas for the prefusion F-HN chimera equivalent PRNTs were observed. At week 16, sera from both preF and preF-HN groups showed robust PRNT to genotype H virus. This indicates these recombinant immunogens can elicit antibodies that can cross-neutralize numerous mumps genotypes. the durability of PRNT to these three mumps viruses was monitored for an additional 6 months and it was found that while there is an a reduction in titers, ID$_{60}$ plateaus form after 3 months and the preF-HN had geometric mean PRNTs for genotype G, Jeryl Lynn and genotype H viruses of approximately 640, 800 and 1700 respectively (FIG. 4D). The ID$_{60}$ PRNT plateaus formed with the preF immunogen against genotype G, Jeryl Lynn and genotype H viruses were approximately 100, 660 and 3153 (FIG. 4E). Overall, prefusion stabilized F mumps linked to HN yielded neutralization titers that were higher than F alone and represents a design strategy to combine both viral surface antigens in a single immunogen stoichiometrically.

Discussion

Human immunity to mumps following MMR vaccination is characterized by PRNT typically around 220 for Jeryl Lynn and 40 for genotype G (Rasheed et al., *Proc Natl Acad Sci USA* 116(38):19071-19076, 2019). The results provided herein for the disclosed immunogens appear to provide increased effectiveness as measured by PNRT, assuming that the mouse model data correlated with response in a human.

Due to mumps outbreaks among two-dose vaccine recipients, improvements are needed to the current mumps vaccine to reduce disease incidence and the burden on public health resources. A third dose of mumps-containing vaccine has been recommended by the Advisory Committee on Immunization Practices (ACIP) to individuals at risk of contracting mumps in an outbreak setting. A third dose of live attenuated MMR has resulted in a temporary elevation of neutralization titers, lasting about 12 months (Fiebelkorn A. P. et al. Open Forum Infect Dis 1(3):ofu094, 2014). Additionally, there was a 78% reduced risk of contracting mumps infection after a third dose of MMR compared to individuals who had received two doses of MMR (Cardemil C. et al, Effectiveness of a Third Dose of MMR Vaccine for Mumps Outbreak Control. *N Engl J Med.* 377 (10): 947-956, 2017). The recombinant protein vaccine candidates described in this example provide an alternative vaccine modality than administration of MMR in a mumps outbreak setting and provide increased durability and effectiveness.

The prefusion F-HN chimera, comprising the two key neutralization targets on mumps virions is capable of eliciting potent cross-genotype neutralizing responses, including to the dominant mumps genotype G causing outbreaks and two other genotypes, A and H represents a universal vaccine candidate for global mumps strains.

Sequences:
MuV F A163C/V235C-GGG-483-GCN4

(SEQ ID NO: 2)

mkafsvtclsfavfsssicvninilqqigyikqqvrqlsyysqssssyivvkllpniqptddscefksvtqynktlsnll lpiaeninniaspspgsrrhGGGagiaigiaalgvataaqvtaavslvqaqtnaraiaamknsiqatnravfevkegtqq laCavqaiqdhintimntqlnnmscqildnqlatslglyltelttvfqpqltnpalspisiqalrsilgsmtpaCvqatl stsisaaeilsaglmegqiisvlldemqmivkiniptivtqsnalvidfysissfinnqesiiqlpdrileigneqwsyp aknckltrhhifcqyneaerlslesklclcagnisacvfspiagsymrrfvaldgtivancrsltclckspsypiyqpdhh avttidltacqtlsldgldfsivslsnityaenltislsqtintqpidistelskvnaslqnavkyikesnhqlqsvsvn Ski   IEDKIEEILSKIYHIENEIARIKKLIGEAP MuV F V206C/A223C-GGG-483-GCN4

(SEQ ID NO: 3)

mkafsvtclsfavfsssicvninilqqigyikqqvrqlsyysqssssyivvkllpniqptddscefksvtqynktlsnll lpiaeninniaspspgsrrhGGGagiaigiaalgvataaqvtaavslvqaqtnaraiaamknsiqatnravfevkegtqq laiavqaiqdhintimntqlnnmscqildnqlatslglyltelttCfqpqltnpalspisiqClrsllgsmtpavvqatl stsisaaeilsaglmegqiisvlldemqmivkiniptivtqsnalvidfysissfinnqesiiqlpdrileigneqwsyp aknckltrhhifcqyneaerlslesklclagnisacvfspiagsymrrfvaldgtivancrsltclckspsypiyqpdhh avttidltacqtlsldgldfsivslsnityaenltisisqtintqpidistelskvnaslqnavkyikesnhqlqsvsvn Ski   IEDKIEEILSKIYHIENEIARIKKLIGEAP MuV F N86C/A215C-GGG-483-GCN4

(SEQ ID NO: 4)

mkafsvtclsfavfsssicvninilqqiqyikqqvrqlsyysqssssyivvkllpniqptddscefksvtqynktlsnll lpiaeCinniaspspgsrrhGGGagiaigiaalgvataaqvtaavslvqaqtnaraiaamknsiqatnravfevkegtqq laiavqaiqdhintimntqlnnmscqildnqlatslglyltelttvfqpqltnpClspisiqalrsllgsmtpavvqatl stsisaaeilsaglmegqiisvlldemqmivkiniptivtqsnalvidfysissfinnqesiiqlpdrileigneqwsyp aknckltrhhifcqyneaerlslesklclagnisacvfspiagsymrrfvaldgtivancrsltclckspsypiyqpdhh avttidltacqtlsldgldfsivslsnityaenltisisqtintqpidistelskvnaslqnavkyikesnhqlqsvsvn Ski   IEDKIEEILSKIYHIENEIARIKKLIGEAP MuV F P209C/P214C-GGG-483-GCN4

(SEQ ID NO: 5)

mkafsvtclsfavfsssicvninilqqiqyikqqvrqlsyysqssssyivvkllpniqptddscefksvtqynktlsnll lpiaeninniaspspgsrrhGGGagiaigiaalgvataaqvtaavslvqaqtnaraiaamknsiqatnravfevkegtqq laiavqaiqdhintimntqlnnmscqildnqlatslglyltelttvfqCqltnCalspisiqalrsllgsmtpavvqatl stsisaaeilsaglmegqiisvlldemqmivkiniptivtqsnalvidfysissfinnqesiiqlpdrileigneqwsyp aknckltrhhifcqyneaerlslesklclagnisacvfspiagsymrrfvaldgtivancrsltclckspsypiyqpdhh avttidltacqtlsldgldfsivslsnityaenltisisqtintqpidistelskvnaslqnavkyikesnhqlqsvsvn Ski   IEDKIEEILSKIYHIENEIARIKKLIGEAP MuV F K155C/L161C-GGG-483-GCN4

(SEQ ID NO: 6)

mkafsvtclsfavfsssicvninilqqigyikqqvrqlsyysqssssyivvkllpniqptddscefksvtqynktlsnll lpiaeninniaspspgsrrhGGGagiaigiaalgvataaqvtaavslvqaqtnaraiaamknsiqatnravfevCegtqq

Caiavqaiqdhintimntqlnnmscqildnqlatslglyltelttvfqpqltnpalspisiqalrsllgsmtpavvqatl stsisaaeilsaglmegqiisvlldemqmivkiniptivtqsnalvidfysissfinnqesiiqlpdrileigneqwsyp aknckltrhhifcqyneaerlslesklclagnisacvfspiagsymrrfvaldgtivancrsltclckspsypiyqpdhh avttidltacqtlsldgldfsivslsnityaenltisisqtintqpidistelskvnaslqnavkyikesnhqlqsvsvn Ski   IEDKIEEILSKIYHIENEIARIKKLIGEAP MuV F V165C/M231C-GGG-483-GCN4

(SEQ ID NO: 7)

mkafsvtclsfavfsssicvninilqqiqyikqqvrqlsyysqssssyivvkllpniqptddscefksvtqynktlsnll lpiaeninniaspspgsrrhGGGagiaigiaalgvataaqvtaavslvqaqtnaraiaamknsiqatnravfevkegtqq laiaCqaiqdhintimntqlnnmscqildnqlatslglyltelttvfqpqltnpalspisiqalrsllgsCtpavvqatl stsisaaeilsaglmegqiisvlldemqmivkiniptivtqsnalvidfysissfinnqesiiqlpdrileigneqwsyp aknckltrhhifcqyneaerlslesklclagnisacvfspiagsymrrfvaldgtivancrsltclckspsypiyqpdhh avttidltacqtlsldgldfsivslsnityaenltisisqtintqpidistelskvnaslqnavkyikesnhqlqsvsvn Ski   IEDKIEEILSKIYHIENEIARIKKLIGEAP MuV F I221C/M255C-GGG-483-GCN4

(SEQ ID NO: 8)

mkafsvtclsfavfsssicvninilqqigyikqqvrqlsyysqssssyivvkllpniqptddscefksvtqynktlsnll lpiaeninniaspspgsrrhGGGagiaigiaalgvataaqvtaavslvqaqtnaraiaamknsiqatnravfevkegtqq laiavqaiqdhintimntqlnnmscqildnqlatslglyltelttvfqpqltnpalspisCqalrsllgsmtpavvqatl stsisaaeilsaglCegqiisvlldemqmivkiniptivtqsnalvidfysissfinnqesiiqlpdrileigneqwsyp aknckltrhhifcqyneaerlsleseklclagnisacvfspiagsymrrfvaldgtivancrsltclckspsypiyqpdhh avttidltacqtlsldgldfsivslsnityaenltisisqtintqpidistelskvnaslqnavkyikesnhqlqsvsvn Ski   IEDKIEEILSKIYHIENEIARIKKLIGEAP MuV F S184P/GGG-483-GCN4

(SEQ ID NO: 9)

<u>mkafsvtclsfavfsssic</u>vninilqqigyikqqvrqlsyysqssssyivvkllpniqptddscefksvtqynktlsnll lpiaeninniaspspgsrrhGGGagiaigiaalgvataaqvtaavslvqaqtnaraiaamknsiqatnravfevkegtqq laiavqaiqdhintimntqlnnm<u>P</u>cqildnqlatslglyltelttvfqpqltnpalspisiqalrsllgsmtpavvqatl stsisaaeilsaglmegqiisvlldemqmivkiniptivtqsnalvidfysissfinnqesiiqlpdrileigneqwsyp akncklctrhhifcqyneaerlsleseklclagnisacvfspiagsymrrfvaldgtivancrsltclckspsypiyqpdhh avttidltacqtlsldgldfsivslsnityaenltisisqtintqpidistelskvnaslqnavkyikesnhqlqsvsvn Ski   IEDKIEEILSKIYHIENEIARIKKLIGEAP MuV F A163C/V235C-GGG-476-GCN4

(SEQ ID NO: 10)

<u>mkafsvtclsfavfsssic</u>vninilqqiqyikqqvrqlsyysqssssyivvkllpniqptddscefksvtqynktlsnll lpiaeninniaspspgsrrhGGGagiaigiaalgvataaqvtaavslvqaqtnaraiaamknsiqatnravfevkegtqq la<u>C</u>avqaiqdhintimntqlnnmscqildnqlatslglyltelttvfqpqltnpalspisiqalrsllgsmtpa<u>C</u>vqatl stsisaaeilsaglmegqiisvlldemqmivkiniptivtqsnalvidfysissfinnqesiiqlpdrileigneqwsyp akncklctrhhifcqyneaerlsleseklclagnisacvfspiagsymrrfvaldgtivancrsltclckspsypiyqpdhh avttidltacqtlsldgldfsivslsnityaenltislsqtintqpidistelskvnaslqnavkyikesnhqlqs

IEDKIEEILSKIYHIENEIARIKKLIGEAP

MuV F V206C/A223C-GGG-476-GCN4

(SEQ ID NO: 11)

<u>mkafsvtclsfavfsssic</u>vninilqqigyikqqvrqlsyysqssssyivvkllpniqptddscefksvtqynktlsnll lpiaeninniaspspgsrrhGGGagiaigiaalgvataaqvtaavslvqaqtnaraiaamknsiqatnravfevkegtqq laiavqaiqdhintimntqlnnmscqildnqlatslglyltelttt<u>C</u>fqpqltnpalspisiq<u>C</u>lrsllgsmtpavvqatl stsisaaeilsaglmegqiisvlldemqmivkiniptivtqsnalvidfysissfinnqesiiqlpdrileigneqwsyp akncklctrhhifcqyneaerlsleseklclagnisacvfspiagsymrrfvaldgtivancrsltclckspsypiyqpdhh avttidltacqtlsldgldfsivslsnityaenltislsqtintqpidistelskvnaslqnavkyikesnhqlqs

IEDKIEEILSKIYHIENEIARIKKLIGEAP

MuV F N86C/A215C-GGG-476-GCN4

(SEQ ID NO: 12)

<u>mkafsvtclsfavfsssic</u>vninilqqigyikqqvrqlsyysqssssyivvkllpniqptddscefksvtqynktlsnll lpiae<u>C</u>inniaspspgsrrhGGGagiaigiaalgvataaqvtaavslvqaqtnaraiaamknsiqatnravfevkegtqq laiavqaiqdhintimntqlnnmscqildnqlatslglyltelttvfqpqltnp<u>C</u>lspisiqalrsllgsmtpavvqatl stsisaaeilsaglmegqiisvlldemqmivkiniptivtqsnalvidfysissfinnqesiiqlpdrileigneqwsyp akncklctrhhifcqyneaerlsleseklclagnisacvfspiagsymrrfvaldgtivancrsltclckspsypiyqpdhh avttidltacqtlsldgldfsivslsnityaenltislsqtintqpidistelskvnaslqnavkyikesnhqlqs

IEDKIEEILSKIYHIENEIARIKKLIGEAP

MuV F P209C/P214C-GGG-476-GCN4

(SEQ ID NO: 13)

<u>mkafsvtclsfavfsssic</u>vninilqqiqyikqqvrqlsyysqssssyivvkllpniqptddscefksvtqynktlsnll lpiaeninniaspspgsrrhGGGagiaigiaalgvataaqvtaavslvqaqtnaraiaamknsiqatnravfevkegtqq laiavqaiqdhintimntqlnnmscqildnqlatslglyltelttvfq<u>C</u>qltn<u>C</u>alspisiqalrsllgsmtpavvqatl stsisaaeilsaglmegqiisvlldemqmivkiniptivtqsnalvidfysissfinnqesiiqlpdrileigneqwsyp aknckltrhhifcqyneaerlsleklclagnisacvfspiagsymrrfvaldgtivancrsltclckspsypiyqpdhh avttidltacqtlsldgldfsivslsnityaenltislsqtintqpidistelskvnaslqnavkyikesnhqlqs

IEDKIEEILSKIYHIENEIARIKKLIGEAP

MuV F K155C/L161C-GGG-476-GCN4
                                                              (SEQ ID NO: 14)
mkafsvtclsfavfsssicvninilqqigyikqqvrqlsyysqssssyivvkllpniqptddscefksvtqynktlsnll lpiaeninniaspspgsrrhGGGagiaigiaalgvataaqvtaavslvqaqtnaraiaamknsiqatnravfevCegtqq Caiavqaiqdhintimntqlnnmscqildnqlatslglyltelttvfqpqltnpalspisiqalrsllgsmtpavvqatl stsisaaeilsaglmegqiisvlldemqmivkiniptivtqsnalvidfysissfinnqesiiqlpdrileigneqwsyp aknckltrhhifcqyneaerlsleklclagnisacvfspiagsymrrfvaldgtivancrsltclckspsypiyqpdhh avttidltacqtlsldgldfsivslsnityaenltislsqtintqpidistelskvnaslqnavkyikesnhqlqs

IEDKIEEILSKIYHIENEIARIKKLIGEAP

MuV F V165C/M231C-GGG-476-GCN4
                                                              (SEQ ID NO: 15)
mkafsvtclsfavfsssicvninilqqigyikqqvrqlsyysqssssyivvkllpniqptddscefksvtqynktlsnll lpiaeninniaspspgsrrhGGGagiaigiaalgvataaqvtaavslvqaqtnaraiaamknsiqatnravfevkegtqq laiaCqaiqdhintimntqlnnmscqildnqlatslglyltelttvfqpqltnpalspisiqalrsiIgsCtpavvqatl stsisaaeilsaglmegqiisvlldemqmivkiniptivtqsnalvidfysissfinnqesiiqlpdrileigneqwsyp aknckltrhhifcqyneaerlsleklclagnisacvfspiagsymrrfvaldgtivancrsltclckspsypiyqpdhh avttidltacqtlsldgldfsivslsnityaenltislsqtintqpidistelskvnaslqnavkyikesnhqlqs

IEDKIEEILSKIYHIENEIARIKKLIGEAP

MuV F 1221C/M255C-GGG-476-GCN4
                                                              (SEQ ID NO: 16)
mkafsvtclsfavfsssicvninilqqigyikqqvrqlsyysqssssyivvkllpniqptddscefksvtqynktlsnll lpiaeninniaspspgsrrhGGGagiaigiaalgvataaqvtaavslvqaqtnaraiaamknsiqatnravfevkegtqq laiavqaiqdhintimntqlnnmscqildnqlatslglyltelttvfqpqltnpalspisCqalrsllgsmtpavvqatl stsisaaeilsaglCegqiisvlldemqmivkiniptivtqsnalvidfysissfinnqesiiqlpdrileigneqwsyp aknckltrhhifcqyneaerlsleklclagnisacvfspiagsymrrfvaldgtivancrsltclckspsypiyqpdhh avttidltacqtlsldgldfsivslsnityaenltisisqtintqpidistelskvnaslqnavkyikesnhqlqs

IEDKIEEILSKIYHIENEIARIKKLIGEAP

MuV F S184P-GGG-476-GCN4
                                                              (SEQ ID NO: 17)
mkafsvtclsfavfsssicvninilqqiqyikqqvrqlsyysqssssyivvkllpniqptddscefksvtqynktlsnll lpiaeninniaspspgsrrhGGGagiaigiaalgvataaqvtaavslvqaqtnaraiaamknsiqatnravfevkegtqq laiavqaiqdhintimntqlnnmPcqildnqlatslglyltelttvfqpqltnpalspisiqalrsllgsmtpavvqatl stsisaaeilsaglmegqiisvlldemqmivkiniptivtqsnalvidfysissfinnqesiiqlpdrileigneqwsyp aknckltrhhifcqyneaerlsleklclagnisacvfspiagsymrrfvaldgtivancrsltclckspsypiyqpdhh avttidltacqtlsldgldfsivslsnityaenltislsqtintqpidistelskvnaslqnavkyikesnhqlqs

IEDKIEEILSKIYHIENEIARIKKLIGEAP

MuV F A163C/V235C-GGG-469-GCN4
                                                              (SEQ ID NO: 18)
mkafsvtclsfavfsssicvninilqqigyikqqvrqlsyysqssssyivvkllpniqptddscefksvtqynktlsnll lpiaeninniaspspgsrrhGGGagiaigiaalgvataaqvtaavslvqaqtnaraiaamknsiqatnravfevkegtqq laCavqaiqdhintimntqlnnmscqildnqlatslglyltelttvfqpqltnpalspisiqalrsllgsmtpaCvqatl -continued stsisaaeilsaglmegqiisvlldemqmivkiniptivtqsnalvidfysissfinnqesiiqlpdrileigneqwsyp aknckltrhhifcqyneaerlsleskltclagnisacvfspiagsymrrfvaldgtivancrsltclckspsypiyqpdhh avttidltacqtlsldgldfsivslsnityaenltislsqtintqpidistelskvnaslqnavkyike

IEDKIEEILSKIYHIENEIARIKKLIGEAP

MuV F V206C/A223C-GGG-469-GCN4

(SEQ ID NO: 19)

<u>mkafsvtclsfavfsssic</u>vninilqqigyikqqvrqlsyysqssssyivvkllpniqptddscefksvtqynktlsnll lpiaeninniaspspgsrrhGGGagiaigiaalgvataaqvtaavslvqaqtnaraiaamknsiqatnravfevkegtqq laiavqaiqdhintimntqlnnmscqildnqlatslglyltelttt<u>C</u>fqpqltnpalspisiq<u>C</u>lrsllgsmtpavvqatl stsisaaeilsaglmegqiisvlldemqmivkiniptivtqsnalvidfysissfinnqesiiqlpdrileigneqwsyp aknckltrhhifcqyneaerlsleskltclagnisacvfspiagsymrrfvaldgtivancrsltclckspsypiyqpdhh avttidltacqtlsldgldfsivslsnityaenltislsqtintqpidistelskvnaslqnavkyike

IEDKIEEILSKIYHIENEIARIKKLIGEAP

MuV F N86C/A215C-GGG-469-GCN4

(SEQ ID NO: 20)

<u>mkafsvtclsfavfsssic</u>vninilqqiqyikqqvrqlsyysqssssyivvkllpniqptddscefksvtqynktlsnll lpiae<u>C</u>inniaspspgsrrhGGGagiaigiaalgvataaqvtaavslvqaqtnaraiaamknsiqatnravfevkegtqq laiavqaiqdhintimntqlnnmscqildnqlatslglyltelttvfqpqltnp<u>C</u>lspisiqalrsllgsmtpavvqatl stsisaaeilsaglmegqiisvlldemqmivkiniptivtqsnalvidfysissfinnqesiiqlpdrileigneqwsyp aknckltrhhifcqyneaerlsleskltclagnisacvfspiagsymrrfvaldgtivancrsltclckspsypiyqpdhh avttidltacqtlsldgldfsivslsnityaenltislsqtintqpidistelskvnaslqnavkyike

IEDKIEEILSKIYHIENEIARIKKLIGEAP

MuV F P209C/P214C-GGG-469-GCN4

(SEQ ID NO: 21)

<u>mkafsvtclsfavfsssic</u>vninilqqiqyikqqvrqlsyysqssssyivvkllpniqptddscefksvtqynktlsnll lpiaeninniaspspgsrrhGGGagiaigiaalgvataaqvtaavslvqaqtnaraiaamknsiqatnravfevkegtqq laiavqaiqdhintimntqlnnmscqildnqlatslglyltelttvfq<u>C</u>qltn<u>C</u>alspisiqalrsllgsmtpavvqatl stsisaaeilsaglmegqiisvlldemqmivkiniptivtqsnalvidfysissfinnqesiiqlpdrileigneqwsyp aknckltrhhifcqyneaerlsleskltclagnisacvfspiagsymrrfvaldgtivancrsltclckspsypiyqpdhh avttidltacqtlsldgldfsivslsnityaenltislsqtintqpidistelskvnaslqnavkyike

IEDKIEEILSKIYHIENEIARIKKLIGEAP

MuV F K155C/L161C-GGG-469-GCN4

(SEQ ID NO: 22)

<u>mkafsvtclsfavfsssic</u>vninilqqigyikqqvrqlsyysqssssyivvkllpniqptddscefksvtqynktlsnll lpiaeninniaspspgsrrhGGGagiaigiaalgvataaqvtaavslvqaqtnaraiaamknsiqatnravfev<u>C</u>egtqq <u>C</u>aiavqaiqdhintimntqlnnmscqildnqlatslglyltelttvfqpqltnpalspisiqalrsllgsmtpavvqatl stsisaaeilsaglmegqiisvlldemqmivkiniptivtqsnalvidfysissfinnqesiiqlpdrileigneqwsyp aknckltrhhifcqyneaerlsleskltclagnisacvfspiagsymrrfvaldgtivancrsltclckspsypiyqpdhh avttidltacqtlsldgldfsivslsnityaenltislsqtintqpidistelskvnaslqnavkyike

IEDKIEEILSKIYHIENEIARIKKLIGEAP

MuV F V165C/M231C-GGG-469-GCN4

(SEQ ID NO: 23)

<u>mkafsvtclsfavfsssic</u>vninilqqiqyikqqvrqlsyysqssssyivvkllpniqptddscefksvtqynktlsnll lpiaeninniaspspgsrrhGGGagiaigiaalgvataaqvtaavslvqaqtnaraiaamknsiqatnravfevkegtqq laia<u>C</u>qaiqdhintimntqlnnmscqildnqlatslglyltelttvfqpqltnpalspisiqalrsilgs<u>C</u>tpavvqatl stsisaaeilsaglmegqiisvlldemqmivkiniptivtqsnalvidfysissfinnqesiiqlpdrileigneqwsyp -continued aknckltrhhifcqyneaerlslesklclagnisacvfspiagsymrrfvaldgtivancrsltclckspsypiyqpdhh avttidltacqtlsldgldfsivslsnityaenltisisqtintqpidistelskvnaslqnavkyike

IEDKIEEILSKIYHIENEIARIKKLIGEAP

MuV F I221C/M255C-GGG-469-GCN4

(SEQ ID NO: 24)

<u>mkafsvtclsfavfsssic</u>vninilqqiqyikqqvrqlsyysqssssyivvkllpniqptddscefksvtqynktlsnll lpiaeninniaspspgsrrhGGGagiaigiaalgvataaqvtaavslvqaqtnaraiaamknsiqatnravfevkegtqq laiavqaiqdhintimntqlnnmscqildnqlatslglyltelttvfqpqltnpalspis<u>C</u>qalrsllgsmtpavvqatl stsisaaeilsagl<u>C</u>egqiisvlldemqmivkiniptivtqsnalvidfysissfinnqesiiqlpdrileigneqwsyp aknckltrhhifcqyneaerlslesklclagnisacvfspiagsymrrfvaldgtivancrsltclckspsypiyqpdhh avttidltacqtlsldgldfsivslsnityaenltislsqtintqpidistelskvnaslqnavkyike

IEDKIEEILSKIYHIENEIARIKKLIGEAP

MuV F S184P-GGG-469-GCN4

(SEQ ID NO: 25)

<u>mkafsvtclsfavfsssic</u>vninilqqigyikqqvrqlsyysqssssyivvkllpniqptddscefksvtqynktlsnll lpiaeninniaspspgsrrhGGGagiaigiaalgvataaqvtaavslvqaqtnaraiaamknsiqatnravfevkegtqq laiavqaiqdhintimntqlnnm<u>P</u>cqildnqlatslglyitelttvfqpqltnpalspisiqalrsllgsmtpavvqatl stsisaaeilsaglmegqiisvlldemqmivkiniptivtqsnalvidfysissfinnqesiiqlpdrileigneqwsyp aknckltrhhifcqyneaerlslesklclagnisacvfspiagsymrrfvaldgtivancrsltclckspsypiyqpdhh avttidltacqtlsldgldfsivslsnityaenltislsqtintqpidistelskvnaslqnavkyike

IEDKIEEILSKIYHIENEIARIKKLIGEAP

MuV-JL F 206C/A223C-GGG-476-GCN4

(SEQ ID NO: 26)

<u>mkafsvtclsfavfsssic</u>vninilqqiqyikqqvrqlsyysqssssyVvvkllpniqptd<u>N</u>scefksvtqynktlsnll lpiaeninniaspspgsrrhGGGagiaigiaalgvataaqvtaavslvqaqtnaraiaamknsiqatnravfevkegtqq laiavqaiqdhintimntqlnnmscqildnqlatslglyltelttt<u>C</u>fqpqllnpalspisiq<u>C</u>lrsllgsmtpavvqatl stsisaaeilsaglmegqi<u>V</u>svlldemqmivkin<u>V</u>ptivtqsnalvidfysissfinnqesiiqlpdrileigneqw<u>R</u>yp anck<u>S</u>trhhifcqyneaeriske<u>T</u>klclagnisacvfspiagsymrrfvaldgtivancrsltclckspsypiyqpdhh avttidlt<u>S</u>cqtlsldgldfsivslsnityaenltislsqtintqpidistelskvnaslqnavkyikesnhqlqs

IEDKIEEILSKIYHIENEIARIKKLIGEAP

MuV-IL17 F 206C/A223C-GGG-476-GCN4

(SEQ ID NO: 51

<u>mkvslvtclgfavfsfsic</u>vninilqqiqyikqqvrqlsyysqssssyivvkllpniqptdnscefksvtqynktlsnll lpiaeninniaspspgsrrhGGGagiaigiaalgvataaqvtaavslvqaqtnaraiaamknsiqatnravfevkegtqq laiavqaiqnhintimntqlnnmscqildnqlatslglylte<u>LTTC</u>fqpqlinpalspisiq<u>CLRS</u>llgsmtpavvqatl stsisaaeilsaglmegqivsvlldemqmivkiniptivtqsnalvidfysissfingqesiiqlpdrileigneqwsyp aknckltrhhifcqyneaerlslesklclagnisacvfspiagsymrrfvaldgtivancrsltclckspsypiyqpdhh avttidltacqtlsldgldfsivslsnityaenltisisqtintqpidistelikvnaslqnavkyikesnhqlqs

IEDKIEEILSKIYHIENEIARIKKLIGEAP

Postfusion MuV F ectodomain (SEQ ID NO: 52)

mkafsvtclsfavfsssicvninilqqigyikqqvrqlsyysqssssyivvkllpniqptddscefksvtqynktlsnll lpiaeninniaspspgsrrhGGGagiaigiaalgvataaqvtaavslvqaqtnaraiaamknsiqatnravfev<u>C</u>egtqq <u>C</u>aiavqaiqdhintimntqlnnmscqildnqlatslglyltelttvfqpqltnpalspisiqalrsllgsmtpavvqatl stsisaaeilsaglmegqiisvlldemqmivkiniptivtqsnalvidfysissfinnqesiiqlpdrileigneqwsyp 95 96

-continued

```
aknckltrhhifcqyneaerlsleskiclagnisacvfspiagsymrrfvaldgtivancrsltclckspsypiyqpdhh avttidltacqtlsldgldfsivslsnityaenltislsqtintqpidistelskvnaslqnavkyikesnhqlqsvsvn skigailEDKIEEILSKIYHIENEIARIKKLIGEAP MuV F 206C/223C-GGG-476 + GCN4 + MuV HN_G
                                                       (SEQ ID NO: 27)
mkafsvtclsfavfsssicvninilqqigyikqqvrqlsyysqssssyivvkllpniqptddscefksvtqynktlsnll lpiaeninniaspspgsrrhGGGagiaigiaalgvataaqvtaavslvqaqtnaraiaamknsiqatnravfevkegtqq laiavqaiqdhintimntqlnnmscqildnqlatslglyltelttCfqpqltnpalspisiqClrsllgsmtpavvqatl stsisaaeilsaglmegqiisvlldemqmivkiniptivtqsnalvidfysissfinnqesiiqlpdrileigneqwsyp akncklrhhifcqyneaerlsleskiclagnisacvfspiagsymrrfvaldgtivancrsltclckspsypiyqpdhh avttidltacqtlsldgldfsivslsnityaenltisisqtintqpidistelskvnaslqnavkyikesnhqlqs

IEDKIEEILSKIYHIENEIARIKKLIGEAP GSGGGGGG niplvndlrfinginkfiiedyathdfsighpinmpsfiptatspngctripsfslgkthwcythnvinanckdhtssnq yvsmgilvqtasgypmfktikiqylsdglnrkscsiatvpdgcamycyvstqletddyagsspptqkltlifyndtvter tispsglegnwatlvpgvgsgiyfenklifpayggvlpnstigvksareffrpvnpynpcsgpqqdldqralrsyfpsyf snrriqsaflvcawnqilvtncelvvpssnqtmmgaegrvllinnrllyyqrstswwpyellyeisftftnsgpssvnms wipiysftrpgsgncsgenvcptacvsgvyldpwpltpyshqsginrnfyftgallnssttrvnptlyvsalnnlkvlap ygtqglfasyttttcfqdtgdasvycvyimelasnivgefqilpvltritit
```

The above sequences include an N-terminal signal peptide, a MuV F ectodomain, a GCN4 trimerization domain, optionally a MuV HN ectodomain, a thrombin cleavage site, a HIS tag and a Strep tag, as well as various linker residues between segments.

Example 2

MeV F Proteins Stabilized in a Prefusion Conformation and Fusions Thereof with MeV H Ectodomain or MuV HN Ectodomain The example illustrates embodiments of a MeV F ectodomain trimer stabilized in a prefusion conformation by one or more amino acid substitutions. Further provided are MeV F ectodomain trimers linked to a MeV H ectodomain. The prefusion-stabilized MeV F ectodomain trimers and corresponding fusions with MeV H ectodomain are useful, for example, for inducing a neutralizing immune response to MeV in a subject.

When produced in cells, the MeV F ectodomain linked to a C-terminal GCN4 trimerization domain forms trimers that spontaneously transition to the prefusion conformation. Unstabilized recombinant MeV F-GCN4 is so unstable, 100% of molecules have transitioned to the postfusion conformation at the point of evaluation (EM). Also protein expression is substantially reduced without stabilization.

Accordingly, structure-based vaccine design was used to identify mutations for the stabilization of the MeV F ectodomain in a prefusion conformation (based on prefusion PIV5 F structure PDB ID 4WSG and MeV F structure PDB ID 5YXW), and also to eliminate the F1/F2 cleavage site to produce a "single chain" MeV F protein with increased expression. Multiple stabilization strategies were employed to "lock" the MeV F ectodomain in the prefusion conformation, including introduction of disulfide bonds and proline substitutions. In total, approximately 40 different mutants were designed, expressed, purified, assessed for expression level, and assessed for prefusion conformation by negative stain EM.

The mutations were introduced into a MeV F ectodomain (based on C-terminal truncations at MeV F position 486, and linked to a C-terminal GCN4 trimerization domain, and the resulting mutants were screened as noted above. The ectodomain also included a mutation to remove the F1/F2 furin cleavage site. The prefusion stabilizing mutations assessed included: cysteine substitutions at one or more of MeV F positions 48 and 284, 90 and 225, 141 and 270, 165 and 171, 173 and 245, 175 and 241, 212 and 236, 216 and 233, and 219 and 224 that form a non-natural disulfide bond; and a proline substitution at MeV F position 194. Relevant sequences are shown below.

The expression and purification of the single chain and prefusion-stabilized MeV F proteins showed a substantial increase in expression level compared to the unmodified MeV F.

As illustrated in FIG. 5, negative EM can be used to distinguish MeV F ectodomain trimers that are in the prefusion conformation from those that are in the postfusion conformation. Also, MeV F R165C-M171C-486-GCN4 (SEQ ID NO: 38) showed an excellent combination of prefusion stabilization and protein expression, and purified as a monodispersed protein by 5200 gel filtration. This construct and others were analyzed by electron microscopy to further confirm the prefusion conformation.

Immunization assays were conducted with a MeV F ectodomain trimer in a post-fusion conformation and a MeV F ectodomain trimer in a pre-fusion conformation (MeV F R165C-M171C-486-GCN4 (SEQ ID NO: 38). The immunization protocol was according to that shown in FIG. 3A. Groups of 10 CB6F1/J mice were immunized with 10 μg/dose of protein in Poly IC adjuvant at weeks 0 and 3, and the neutralization titer of week 5 sera from the immunized mice were assessed. The immune sera were assessed in a MeV neutralization assay (FIG. 5C), which showed that immune sera from animals immunized with the MeV F R165C-M171C-486-GCN4 (SEQ ID NO: 38) neutralized MeV more than 200-fold higher than sera from animals immunized with the postfusion MeV F, and above a protective threshold.

Sequences:
MeV F A90C/I225C-GGG-486-GCN4
(SEQ ID NO: 37)

mysmqlascvtltlvllvnsqihwgnlskigvvgigsasykvmtrsshqslviklmpnitllnnctrveiaeyrrllrtv lepirdClnavtqnirpvqsvassrrhGGGagvvlagaalgvataaqitagialhqsmlnsqaidnlraslettnqaiea irqagqemilavqgvqdyinnelipsmnqlscdligqklglkllryytellsifgpslrdpCsaeisiqalsyalggdin kvleklgysggdllgilesrgikarithvdtesyfivlsiayptlseikgvivhrlegvsynigsqewyttvpkyvatqg ylisnfdesssctfmpegtvcsqnalypmspllqeclrgstkscartlvsgsfgnrfiisqgnllaneaslickcyttgti inqdpdkiltyiaadhcpvvevngvtiqvgsrrypdavylhridlgppislerldvgtnlgnaiakledakellessdqi lsa   IEDKIEEILSKIYHIENEIARIKKLIGEAP MeV F R165C/M171C-GGG-486-GCN4
(SEQ ID NO: 38)

mysmqlascvtitlvllvnsqihwgnlskigvvgigsasykvmtrsshqslviklmpnitllnnctrveiaeyrrllrtv lepirdalnavtqnirpvqsvassrrhGGGagvvlagaalgvataaqitagialhqsmlnsqaidnlraslettnqaiea iCqagqeCilavqgvqdyinnelipsmnqlscdligqklglkllryyteilslfgpslrdpisaeisiqalsyalggdin kvleklgysggdllgilesrgikarithvdtesyfivlsiayptlseikgvivhrlegvsynigsqewyttvpkyvatqg ylisnfdesssctfmpegtvcsqnalypmspllqeclrgstkscartlvsgsfgnrfilsqgniiancasilckcyttgti inqdpdkiltyiaadhcpvvevngvtiqvgsrrypdavylhridlgppisleridvgtnlgnaiakledakellessdqi lsa   IEDKIEEILSKIYHIENEIARIKKLIGEAP MeV F L173C/V245C-GGG-486-GCN4
(SEQ ID NO: 39)

mysmqlascvtltlvllvnsqihwgnlskiqvvgigsasykvmtrsshqslviklmpnitllnnctrveiaeyrrllrtv lepirdalnavtqnirpvqsvassrrhGGGagvvlagaalgvataaqitagiaihqsmlnsqaidnlraslettnqaiea irqagqemiCavqgvqdyinnelipsmnqlscdligqklglkllryytellsifgpslrdpisaeisiqalsyalggdin kCleklgysggdllgilesrgikarithvdtesyfivlsiayptlseikgvivhrlegvsynigsqewyttvpkyvatqg ylisnfdesssctfmpegtvcsqnalypmspllqeclrgstkscartlvsgsfgnrfilsqgnliancasilckcyttgti inqdpdkiltyiaadhcpvvevngvtiqvgsrrypdavylhridlgppislerldvgtnlgnaiakledakellessdqi lsa   IEDKIEEILSKIYHIENEIARIKKLIGEAP MeV F V175C/D241C-GGG-486-GCN4
(SEQ ID NO: 40)

mysmqlascvtltlvllvnsqihwgnlskiqvvqiqsasykvmtrsshqslviklmpnitllnnctrveiaeyrrllrtv lepirdalnavtqnirpvqsvassrrhGGGagvvlagaaigvataaqitagiaihqsmlnsqaidnlraslettnqaiea irqagqemilaCqgvqdyinnelipsmnqlscdligqklglkllryyteilslfgpslrdpisaeisiqalsyalggCin kvleklgysggdllgilesrgikarithvdtesyfivlsiayptlseikgvivhrlegvsynigsqewyttvpkyvatqg ylisnfdesssctfmpegtvcsqnalypmspllqeclrgstkscartlvsgsfgnrfilsqgnliancasilckcyttgti inqdpdkiltyiaadhcpvvevngvtiqvgsrrypdavylhridlgppislerldvgtnlgnaiakledakellessdqi lsa   IEDKIEEILSKIYHIENEIARIKKLIGEAP MeV F L216C/A233C-GGG-486-GCN4
(SEQ ID NO: 41)

mysmqlascvtltlvllvnsqihwgnlskigvvgigsasykvmtrsshqslviklmpnitllnnctrveiaeyrrllrtv lepirdalnavtqnirpvqsvassrrhGGGagvvlagaalgvataaqitagiaihqsmlnsqaidnlraslettnqaiea -continued irqagqqemilavqgvqdyinnelipsmnqlscdligqklglkllrryyteilsCfgpslrdpisaeisiqClsyalggdin kvleklgysggdllgilesrgikarithvdtesyfivlsiayptlseikgvivhrlegvsynigsqewyttvpkyvatqg ylisnfdessctfmpegtvcsqnalypmspllqeclrgstkscartlvsgsfgnrfilsqgnliancasilckcyttgti inqdpdkiltyiaadhcpvvevngvtiqvgsrrypdavylhridlgppislerldvgtnlgnaiakledakellessdqi lsa   IEDKIEEILSKIYHIENEIARIKKLIGEAP MeV F P219C/P224C-GGG-486-GCN4
                                                          (SEQ ID NO: 42)
<u>mysmqlascvtltlvllvns</u>qihwgnlskiqvvgigsasykvmtrsshqslviklmpnitllnnctrveiaeyrrllrtv lepirdalnavtqnirpvqsvassrrhGGGagvvlagaaigvataaqitagiaihqsmlnsqaidnlraslettnqaiea irqagqemilavqgvqdyinnelipsmnqlscdligqklglkllrryyteilslfgCslrdCisaeisiqalsyalggdin kvleklgysggdllgilesrgikarithvdtesyfivlsiayptlseikgvivhrlegvsynigsqewyttvpkyvatqg ylisnfdessctfmpegtvcsqnalypmspllqeclrgstkscartlvsgsfgnrfilsqgnliancasilckcyttgti inqdpdkiltyiaadhcpvvevngvtiqvgsrrypdavylhridlgppislerldvgtnlgnaiakledakellessdqi lsa   IEDKIEEILSKIYHIENEIARIKKLIGEAP MeV F S194P-GGG-486-GCN4
                                                          (SEQ ID NO: 43)
<u>mysmqlascvtltlvllvns</u>qihwgnlskiqvvgigsasykvmtrsshqslviklmpnitllnnctrveiaeyrrllrtv lepirdalnavtqnirpvqsvassrrhGGGagvvlagaaigvataaqitagiaihqsmlnsqaidnlraslettnqaiea irqagqemilavqgvqdyinnelipsmnqlPcdligqklglkllrryyteilslfgpslrdpisaeisiqalsyalggdin kvleklgysggdllgilesrgikarithvdtesyfivlsiayptlseikgvivhrlegvsynigsqewyttvpkyvatqg ylisnfdessctfmpegtvcsqnalypmspllqeclrgstkscartlvsgsfgnrfilsqgnliancasilckcyttgti inqdpdkiltyiaadhcpvvevngvtiqvgsrrypdavylhridlgppislerldvgtnlgnaiakledakellessdqi lsa   IEDKIEEILSKIYHIENEIARIKKLIGEAP Postfusion MeV F
                                                          (SEQ ID NO: 61)
MYSMQLASCVTLTLVLLVNSQIHWGNLSKIGVVGIGSASYKVMTRSSHQSLVIKLMPNITLLNNCTRVEIAEYRRLLRTV

LEPIRDALNAVTQNIRPVQSVASSGSGGGSAQITAGIALHQSMLNSQAIDNLRASLETTNQAIEAIRQAGQEMILAVQGV

QDYINNELIPSMNQLSCDLIGQKLGLKLLRYYTEILSLFGPSLRDPISAEISIQALSYALGGDINKVLEKLGYSGGDLLG

ILESRGIKARITHVDTESYFIVLSIAYPTLSEIKGVIVHRLEGVSYNIGSQEWYTTVPKYVATQGYLISNFDESSCTFMP

EGTVCSQNALYPMSPLLQECLRGSTKSCARTLVSGSFGNRFILSQGNLIANCASILCKCYTTGTIINQDPDKILTYIAAD

HCPVVEVNGVTIQVGSRRYPDAVYLHRIDLGPPISLERLDVGTNLGNAIAKLEDAKELLESSDQILSAIGGYIPEAPRDG

QAYVRKDGEWVLLSTFL

MeV F S103C/VH7C-GGG-486-GCN4
                                                          (SEQ ID NO: 62)
<u>mysmqlascvtltlvllvns</u>qihwgnlskigvvgigsasykvmtrsshqslviklmpnitllnnctrveiaeyrrllrtv lepirdalnavtqnirpvqCvassrrhGGGagvClagaaigvataaqitagiaihqsmlnsqaidnlraslettnqaiea irqagqemilavqgvqdyinnelipsmnqlscdligqklglkllrryyteilsifgpslrdpisaeisiqalsyalggdin kvleklgysggdllgilesrgikarithvdtesyfivlsiayptlseikgvivhrlegvsynigsqewyttvpkyvatqg ylisnfdessctfmpegtvcsqnalypmspllqeclrgstkscartlvsgsfgnrfilsqgnliancasilckcyttgti inqdpdkiltyiaadhcpvvevngvtiqvgsrrypdavylhridlgppislerldvgtnlgnaiakledakellessdqi lsa   IEDKIEEILSKIYHIENEIARIKKLIGEAP MeV F V175F-GGG-486-GCN4
                                                          (SEQ ID NO: 63)
<u>mysmqlascvtltlvllvns</u>qihwgnlskiqvvgigsasykvmtrsshqslviklmpnitllnnctrveiaeyrrllrtv lepirdalnavtqnirpvqsvassrrhGGGagvvlagaaigvataaqitagiaihqsmlnsqaidnlraslettnqaiea -continued irqagqemilaFqgvqdyinnelipsmnglscdligqklglkllryyteilslfgpslrdpisaeisiqalsyalggdin kvleklgysggdllgilesrgikarithvdtesyfivlsiayptlseikgvivhrlegvsynigsqewyttvpkyvatqg ylisnfdessctfmpegtvcsqnalypmspllqeclrgstkscartlvsgsfgnrfilsqgnliancasilckcyttgti inqdpdkiltyiaadhcpvvevngvtiqvgsrrypdavylhridlgppislerldvgtnlgnaiakledakellessdqi lsa   IEDKIEEILSKIYHIENEIARIKKLIGEAP MeV F S103C/V117C, V175F, S194P-GGG-486-GCN4

(SEQ ID NO: 64)

<u>mysmq</u>lascvtitlvllvnsqihwgnlskigvvgigsasykvmtrsshqslviklmpnitllnnctrveiaeyrrllrtv lepirdalnavtqnirpvq<u>C</u>vassrrhGGGagv<u>C</u>lagaaigvataaqitagiaihqsminsqaidnlraslettnqaiea irqagqemilaFqgvqdyinnelipsmnqlPcdligqklglkllryyteilslfgpslrdpisaeisiqalsyalggdin kvleklqysqqdllqilesrgikarithvdtesyfivlsiayptlseikqvivhrlegvsynigsqewyttvpkyvatqq ylisnfdessctfmpegtvcsqnalypmspllqeclrgstkscartlvsgsfgnrfilsqgnliancasilckcyttgti inqdpdkiltyiaadhcpvvevngvtiqvgsrrypdavylhridlgppislerldvgtnlgnaiakledakellessdqi lsa   IEDKIEEILSKIYHIENEIARIKKLIGEAP MeV F S103C/V117C, R165C/M171C, S194P-GGG-486-GCN4

(SEQ ID NO: 65)

<u>mysmq</u>lascvtltlvllvnsqihwgnlskigvvgigsasykvmtrsshqslviklmpnitllnnctrveiaeyrrllrtv lepirdalnavtqnirpvq<u>C</u>vassrrhGGGagv<u>C</u>lagaalgvataaqitagiaihqsminsqaidnlraslettnqaiea i<u>C</u>qagqe<u>C</u>ilaFqgvqdyinnelipsmnqlPcdligqklglkllryyteilsifgpslrdpisaeisiqalsyalggdin kvleklgysggdllgilesrgikarithvdtesyfivlsiayptlseikgvivhrlegvsynigsqewyttvpkyvatqg ylisnfdessctfmpegtvcsqnalypmspllqeclrgstkscartlvsgsfgnrfilsqgnliancasilckcyttgti inqdpdkiltyiaadhcpvvevngvtiqvgsrrypdavylhridlgppislerldvgtnlgnaiakledakellessdqi lsa   IEDKIEEILSKIYHIENEIARIKKLIGEAP MeV F R99C/V117C-GGG-486-GCN4

(SEQ ID NO: 66)

<u>mysmq</u>lascvtitlvllvnsqihwgnlskigvvgigsasykvmtrsshqslviklmpnitllnnctrveiaeyrrllrtv lepirdalnavtqni<u>C</u>pvqsvassrrhGGGagv<u>C</u>lagaaigvataaqitagiaihqsminsqaidnlraslettnqaiea irqagqemilavqgvqdyinnelipsmnqlscdligqklglkllryvteilsifgpslrdpisaeisiqalsyalggdin kvleklgysggdllgilesrgikarithvdtesyfivlsiayptlseikgvivhrlegvsynigsqewyttvpkyvatqg ylisnfdessctfmpegtvcsqnalypmspllqeclrgstkscartlvsgsfgnrfilsqgnliancasilckcyttgti inqdpdkiltyiaadhcpvvevngvtiqvgsrrypdavylhridlgppislerldvgtnlgnaiakledakellessdqi lsa   IEDKIEEILSKIYHIENEIARIKKLIGEAP MeV F R99C/V117C, V175F, S194P-GGG-486-GCN4

(SEQ ID NO: 67)

<u>mysmq</u>lascvtitlvllvnsqihwgnlskigvvgigsasykvmtrsshqslviklmpnitllnnctrveiaeyrrllrtv lepirdalnavtqni<u>C</u>pvqsvassrrhGGGagv<u>C</u>lagaaigvataaqitagiaihqsminsqaidnlraslettnqaiea irqagqemilaFqgvqdyinnelipsmnqlPcdligqklglkllryyteilsifgpslrdpisaeisiqalsyalggdin kvleklgysggdllgilesrgikarithvdtesyfivlsiayptlseikgvivhrlegvsynigsqewyttvpkyvatqg ylisnfdessctfmpegtvcsqnalypmspllqeclrgstkscartlvsgsfgnrfilsqgnliancasilckcyttgti inqdpdkiltyiaadhcpvvevngvtiqvgsrrypdavylhridlgppislerldvgtnlgnaiakledakellessdqi lsa   IEDKIEEILSKIYHIENEIARIKKLIGEAP MeV F R99C/V117C, R165C/M171C, S194P-GGG-486-GCN4

(SEQ ID NO: 68)

<u>mysmq</u>lascvtitlvllvnsqihwgnlskigvvgigsasykvmtrsshqslviklmpnitllnnctrveiaeyrrllrtv lepirdalnavtqni<u>C</u>pvqsvassrrhGGGagv<u>C</u>lagaalgvataaqitagialhqsminsqaidnlraslettnqaiea i<u>C</u>qagqe<u>C</u>ilaFqgvqdyinnelipsmnqlPcdligqklglkllryyteilsifgpslrdpisaeisiqalsyalggdin -continued kvleklgysggdllgilesrgikarithvdtesyfivlsiayptlseikgvivhrlegvsynigsqewyttvpkyvatqg ylisnfdessctfmpegtvcsqnalypmspllqeclrgstkscartlvsgsfgnrfilsqgnliancasilckcyttgti inqdpdkiltyiaadhcpvvevngvtiqvgsrrypdavylhridlgppislerldvgtnlgnaiakledakellessdqi lsa  IEDKIEEILSKIYHIENEIARIKKLIGEAP MeV F R99C/V117C-GGG-493-GCN4
                                                                    (SEQ ID NO: 69)
<u>mysmqlascvtitlvll</u>vnsqihwgnlskigvvgigsasykvmtrsshqslviklmpnitllnnctrveiaeyrrllrtv lepirdalnavtqniCpvqsvassrrhGGGagvClagaalgvataaqitagialhqsminsqaidnlraslettnqaiea irqagqemilavqgvqdyinnelipsmnqlscdligqklglkllrryyteilsifgpslrdpisaeisiqalsyalggdin kvleklgysggdllgilesrgikarithvdtesyfivlsiayptlseikgvivhrlegvsynigsqewyttvpkyvatqg ylisnfdessctfmpegtvcsqnalypmspllqeclrgstkscartlvsgsfgnrfilsqgnliancasilckcyttgti inqdpdkiltyiaadhcpvvevngvtiqvgsrrypdavylhridlgppislerldvgtnlgnaiakledakellessdqi l rsmkglssa IEDKIEEILSKIYHIENEIARIKKLIGEAP MeV F R99C/V117C, V175F, S194P-GGG-493-GCN4
                                                                    (SEQ ID NO: 70)
<u>mysmqlascvtltlvll</u>vnsqihwgnlskiqvvqiqsasykvmtrsshqslviklmpnitllnnctrveiaeyrrllrtv lepirdalnavtqniCpvqsvassrrhGGGagvClagaaigvataaqitagiaihqsminsqaidnlraslettnqaiea irqagqemilaFqgvqdyinnelipsmnqlPcdligqklglkllrryyteilslfgpslrdpisaeisiqalsyalggdin kvleklqysqqdllqilesrgikarithvdtesyfivlsiayptlseikqvivhrlegvsynigsqewyttvpkyvatqq ylisnfdessctfmpegtvcsqnalypmspllqeclrgstkscartlvsgsfgnrfilsqgnliancasilckcyttgti inqdpdkiltyiaadhcpvvevngvtiqvgsrrypdavylhridlgppislerldvgtnlgnaiakledakellessdqi l rsmkglssa IEDKIEEILSKIYHIENEIARIKKLIGEAP MeV F R99C/V117C, R165C/M171C, S194P-GGG-493-GCN4
                                                                    (SEQ ID NO: 71)
<u>mysmqlascvtitlvll</u>vnsqihwgnlskigvvgigsasykvmtrsshqslviklmpnitllnnctrveiaeyrrllrtv lepirdalnavtqniCpvqsvassrrhGGGagvClagaaigvataaqitagiaihqsminsqaidnlraslettnqaiea iCqagqeCilaFqgvqdyinnelipsmnqlPcdligqklglkllrryyteilsifgpslrdpisaeisiqalsyalggdin kvleklqysqqdllqilesrgikarithvdtesyfivlsiayptlseikqvivhrlegvsynigsqewyttvpkyvatqq ylisnfdessctfmpegtvcsqnalypmspllqeclrgstkscartlvsgsfgnrfilsqgnliancasilckcyttgti inqdpdkiltyiaadhcpvvevngvtiqvgsrrypdavylhridlgppisleridvgtnlgnaiakledakellessdqi l rsmkglssa IEDKIEEILSKIYHIENEIARIKKLIGEAP MeV F P100C/V117C, R165C/M171C, S194P-GGG-486-GCN4
                                                                    (SEQ ID NO: 72)
<u>mysmqlascvtltlvll</u>vnsqihwgnlskigvvgigsasykvmtrsshqslviklmpnitllnnctrveiaeyrrllrtv lepirdalnavtqnirCvqsvassrrhGGGagvClagaaigvataaqitagiaihqsminsqaidnlraslettnqaiea iCqagqeCilaFqgvqdyinnelipsmnqlPcdligqklglkllrryyteilsifgpslrdpisaeisiqalsyalggdin kvleklgysggdllgilesrgikarithvdtesyfivlsiayptlseikgvivhrlegvsynigsqewyttvpkyvatqg ylisnfdessctfmpegtvcsqnalypmspllqeclrgstkscartlvsgsfgnrfilsqgnliancasilckcyttgti inqdpdkiltyiaadhcpvvevngvtiqvgsrrypdavylhridlgppisleridvgtnlgnaiakledakellessdqi lsa  IEDKIEEILSKIYHIENEIARIKKLIGEAP MeV F V101C/V117C, R165C/M171C, S194P-GGG-486-GCN4
                                                                    (SEQ ID NO: 73)
<u>mysmqlascvtltlvll</u>vnsqihwgnlskiqvvgigsasykvmtrsshqslviklmpnitllnnctrveiaeyrrllrtv lepirdalnavtqnirpCqsvassrrhGGGagvClagaaigvataaqitagiaihqsminsqaidnlraslettnqaiea iCqagqeCilaFqgvqdyinnelipsmnqlPcdligqklglkllrryyteilsifgpslrdpisaeisiqalsyalggdin -continued kvleklgysggdllgilesrgikarithvdtesyfivlsiayptlseikgvivhrlegvsynigsqewyttvpkyvatqg ylisnfdessctfmpegtvcsqnalypmspllqeclrgstkscartlvsgsfgnrfilsqgnliancasilckcyttgti inqdpdkiltyiaadhcpvvevngvtiqvgsrrypdavylhridlgppisleridvgtnlgnaiakledakellessdqi lsa   IEDKIEEILSKIYHIENEIARIKKLIGEAP MeV F Q102C/V117C, R165C/M171C, S194P-GGG-486-GCN4

(SEQ ID NO: 74)
mysmqlascvtltlvllvnsqihwgnlskiqvvgigsasykvmtrsshqslviklmpnitllnnctrveiaeyrrllrtv lepirdalnavtqnirpvCsvassrrhGGGagvClagaaigvataaqitagiaihqsminsqaidnlraslettnqaiea iCqagqeCilaFqgvqdyinnelipsmnqlPcdligqklglkllrryyteilsifgpslrdpisaeisiqalsyalggdin kvleklgysggdllgilesrgikarithvdtesyfivlsiayptlseikgvivhrlegvsynigsqewyttvpkyvatqg ylisnfdessctfmpegtvcsqnalypmspllqeclrgstkscartlvsgsfgnrfilsqgnliancasilckcyttgti inqdpdkiltyiaadhcpvvevngvtiqvgsrrypdavylhridlgppisleridvgtnlgnaiakledakellessdqi lsa   IEDKIEEILSKIYHIENEIARIKKLIGEAP MeV F R165C/M171C, M141C/T270C-GGG-486-GCN4

(SEQ ID NO: 75)
mysmqlascvtltlvllvnsqihwgnlskigvvgigsasykvmtrsshqslviklmpnitllnnctrveiaeyrrllrtv lepirdalnavtqnirpvqsvassrrhGGGagvvlagaaigvataaqitagialhqsClnsqaidnlraslettnqaiea iCqagqeCllavqgvqdyinnelipsmnqlscdligqklglkllrryyteilsifgpslrdpisaeisiqalsyalggdin kvleklgysggdllgilesrgikarichvdtesyfivlsiayptlseikgvivhrlegvsynigsqewyttvpkyvatqg ylisnfdessctfmpegtvcsqnalypmspllqeclrgstkscartlvsgsfgnrfilsqgnliancasilckcyttgti inqdpdkiltyiaadhcpvvevngvtiqvgsrrypdavylhridlgppisleridvgtnlgnaiakledakellessdqi lsa   IEDKIEEILSKIYHIENEIARIKKLIGEAP MeV F R165C/M171C, E212C/Y236C-GGG-486-GCN4 (SEQ ID NO: 76)
mysmqlascvtltlvllvnsqihwgnlskiqvvgigsasykvmtrsshqslviklmpnitllnnctrveiaeyrrllrtv lepirdalnavtqnirpvqsvassrrhGGGagvvlagaaigvataaqitagiaihqsminsqaidnlraslettnqaiea iCqagqeCHavqgvqdyinnelipsmnqlscdligqklglkllrryytCllslf gpslrdpisaeisiqalsCalggdin kvleklgysggdllgilesrgikarithvdtesyfivlsiayptlseikgvivhrlegvsynigsqewyttvpkyvatqg ylisnfdessctfmpegtvcsqnalypmspllqeclrgstkscartlvsgsfgnrfilsqgnliancasilckcyttgti inqdpdkiltyiaadhcpvvevngvtiqvgsrrypdavylhridlgppisleridvgtnlgnaiakledakellessdqi lsa   IEDKIEEILSKIYHIENEIARIKKLIGEAP MeV F R165C/M171C, R48C/A284C-GGG-486-GCN4

(SEQ ID NO: 77)
mysmqlascvtltlvllvnsqihwgnlskiqvvgigsasykvmtCsshqslviklmpnitllnnctrveiaeyrrllrtv lepirdalnavtqnirpvqsvassrrhGGGagvvlagaalgvataaqitagialhqsmlnsqaidnlraslettnqaiea iCqagqeCilavqgvqdyinnelipsmnqlscdligqklglkllrryyteilsifgpslrdpisaeisiqalsyalggdin kvleklgysggdllgilesrgikarithvdtesyfivlsiCyptlseikgvivhrlegvsynigsqewyttvpkyvatqg ylisnfdessctfmpegtvcsqnalypmspllqeclrgstkscartlvsgsfgnrfilsqgnliancasilckcyttgti inqdpdkiltyiaadhcpvvevngvtiqvgsrrypdavylhridlgppisleridvgtnlgnaiakledakellessdqi lsa   IEDKIEEILSKIYHIENEIARIKKLIGEAP MeV F R99C/V117C, native furin-486-GCN4

(SEQ ID NO: 78)
mysmqlascvtitivllvnsqihwgnlskiqvvqiqsasykvmtrsshqslviklmpnitllnnctrveiaeyrrllrtv lepirdalnavtqniCpvqsvassrrhkrfagvClagaalgvataaqitagialhqsmlnsqaidnlraslettnqaiea irqagqemilavqgvqdyinnelipsmnqlscdligqklglkllrvvteilsifgpslrdpisaeisiqalsyalggdin kvleklgysggdllgilesrgikarithvdtesyfivlsiayptlseikgvivhrlegvsynigsqewyttvpkyvatqg -continued ylisnfdessctfmpegtvcsqnalypmspllqeclrgstkscartlvsgsfgnrfilsqgnliancasilckcyttgti inqdpdkiltyiaadhcpvvevngvtiqvgsrrypdavylhridlgppislerldvgtnlgnaiakledakellessdqi lsa  IEDKIEEILSKIYHIENEIARIKKLIGEAP MeV F R99C/V117C, V175F, S194P, native furin-486-GCN4
                                                                (SEQ ID NO: 79)
mysmqlascvtltlvllvnsqihwqnlskiqvvqiqsasykvmtrsshqslviklmpnitllnnctrveiaeyrrllrtv lepirdalnavtqniCpvqsvassrrhkrfagvClagaalgvataaqitagialhqsmlnsqaidnlraslettnqaiea irqagqemilaFqgvqdyinnelipsmnqlPcdligqklglkllryytellsifgpslrdpisaeisiqalsyalggdin kvleklgysggdllgilesrgikarithvdtesyfivlsiayptlseikgvivhrlegvsynigsqewyttvpkyvatqg ylisnfdessctfmpegtvcsqnalypmspllqeclrgstkscartlvsgsfgnrfilsqgnliancasilckcyttgti inqdpdkiltyiaadhcpvvevngvtiqvgsrrypdavylhridlgppislerldvgtnlgnaiakledakellessdqi lsa  IEDKIEEILSKIYHIENEIARIKKLIGEAP MeV F R99C/V117C, R165C/M171C, S194P, native furin-486-GCN4
                                                                (SEQ ID NO: 80)
mysmqlascvtitivllvnsqihwqnlskigvvgigsasykvmtrsshqslviklmpnitllnnctrveiaeyrrllrtv lepirdalnavtqniCpvqsvassrrhkrfagvClagaalgvataaqitagialhqsmlnsqaidnlraslettnqaiea lCqagqeCilaFqgvqdyinnelipsmnqlPcdligqklglkllryytellsifgpslrdpisaeisiqalsyalggdin kvleklgysggdllgilesrgikarithvdtesyfivlsiayptlseikgvivhrlegvsynigsqewyttvpkyvatqg ylisnfdessctfmpegtvcsqnalypmspllqeclrgstkscartlvsgsfgnrfilsqgnliancasilckcyttgti inqdpdkiltyiaadhcpvvevngvtiqvgsrrypdavylhridlgppislerldvgtnlgnaiakledakellessdqi lsa  IEDKIEEILSKIYHIENEIARIKKLIGEAP The above sequences include an N-terminal signal peptide, a MeV F ectodomain, a GCN4 trimerization domain, as well as various linker residues between segments.

Additionally, chimeric constructs with the MeV F ectodomain with amino acid substitutions for stabilization in a prefusion conformation linked to a MuV HN ectodomain or a MeV H ectodomain were designed as follows:

MeV F R165C/M171C-GGG-486-GCN4 + MeV_H
                                                                (SEQ ID NO: 56)
mysmqlascvtltlvllvnsqihwqnlskigvvgigsasykvmtrsshqslviklmpnitllnnctrveiaeyrrllrtv lepirdalnavtqnirpvqsvassrrhGGGagvvlagaalgvataaqitagialhqsmlnsqaidnlraslettnqaiea iCqagqeCilavqgvqdyinnelipsmnqlscdligqklglkllrryyteilslfgpslrdpisaeisiqalsyalggdin kvleklgysggdllgilesrgikarithvdtesyfivlsiayptlseikgvivhrlegvsynigsqewyttvpkyvatqg ylisnfdessctfmpegtvcsqnalypmspllqeclrgstkscartlvsgsfgnrfilsqgnliancasilckcyttgti inqdpdkiltyiaadhcpvvevngvtiqvgsrrypdavylhridlgppislerldvgtnlgnaiakledakellessdqi lsa  IEDKIEEILSKIYHIENEIARIKKLIGEAP  GSGGGGGG flavskgncsgpttirgqfsnmsislldlylgrgynvssivtmtsqgmyggtyivekpnlsskrselsqlsmyrvfevgv irnpglgapvfhmtnyleqpvsndlsncmvalgelklaalchgedsitipyqgsgkgvsfqlvklgvwkspadmqswvpl stddpvidrlyisshrgviadnqakwavpttrtddklrmetcfqqackgkiqticenpewaplkdnripsygvlsvdlsl tvelkikiasgfgplithgsgmdlyksnhnnvywltippmknlalgvintlewiprfkvspylftvpikeagedchapty ipaevdgdvklssnlvilpgqdlqyvlatydtsrvehavvyyvyspgrsfsyfypfripikgvpielqvecftwdqklwc rhfcvladsesgghithsgmvgmgvsctvtredgtnrr -continued MeV F R165C/M171C-GGG-486-GCN4 + MuV_HN
(SEQ ID NO: 57)
mysmqlascvtltlvllvnsqihwgnlskigvvgigsasykvmtrsshqslviklmpnitllnnctrveiaeyrrllrtv lepirdalnavtqnirpvqsvassrrhGGGagvvlagaalgvataaqitagialhqsmlnsqaidnlraslettnqaiea iCqagqeCilavqgvqdyinnelipsmnqlscdligqklglkllryyteilslfgpslrdpisaeisiqalsyalggdin kvleklgysggdllgilesrgikarithvdtesyfivlsiayptlseikgvivhrlegvsynigsqewyttvpkyvatqg ylisnfdessctfmpegtvcsqnalypmspllqeclrgstkscartlvsgsfgnrfilsqgnliancasilckcyttgti inqdpdkiltyiaadhcpvvevngvtiqvgsrrypdavylhridlgppislerldvgtnlgnaiakledakellessdqi lsa  IEDKIEEILSKIYHIENEIARIKKLIGEAPG  sgggggg niplvndlrfinginkfiiedyathdfsighpinmpsfiptatspngctripsfsigkthwcythnvinanckdhtssnq yvsmgilvqtasgypmfktikiqylsdglnrkscsiatvpdgcamycyvstqletddyagsspptqkltlllfyndtvter tispsglegnwatlvpgvgsgiyfenklifpayggvlpnstigvksareffrpvnpynpcsgpqqdldqralrsyfpsyf snrriqsaflvcawnqilvtncelvvpssnqtmmgaegrvllinnrllyyqrstswwpyellyeisftftnsgpssvnms wipiysftrpgsgncsgenvcptacvsgvyldpwpltpyshqsginrnfyftgallnssttrvnptlyvsalnnlkvlap ygtqglfasyttttcfqdtgdasvycvyimelasnivgefqilpvltritit MeV F R165C/M171C-GGG-486-GCN4/Fd + MeV_H
(SEQ ID NO: 81)
MYSMQLASCVTLTLVLLVNSQIHWGNLSKIGVVGIGSASYKVMTRSSHQSLVIKLMPNITLLNNCTRVEIAEYRRLLRTV

LEPIRDALNAVTQNIRPVQSVASSRRHGGGAGVVLAGAALGVATAAQITAGIALHQSMLNSQAIDNLRASLETTNQAIEA

ICQAGQECILAVQGVQDYINNELIPSMNQLSCDLIGQKLGLKLLRYYTEILSLFGPSLRDPISAEISIQALSYALGGDIN

KVLEKLGYSGGDLLGILESRGIKARITHVDTESYFIVLSIAYPTLSEIKGVIVHRLEGVSYNIGSQEWYTTVPKYVATQG

YLISNFDESSCTFMPEGTVCSQNALYPMSPLLQECLRGSTKSCARTLVSGSFGNRFILSQGNLIANCASILCKCYTTGTI

INQDPDKILTYIAADHCPVVEVNGVTIQVGSRRYPDAVYLHRIDLGPPISLERLDVGTNLGNAIAKLEDAKELLESSDQI

LSA  IEDKIEEILSKIYHIENEIARIKKLIGEAP  GS  GYIPEAPRDGQAYVRKDGEWVLLSTFL  GSGGGGGg

FLAVSKGNCSGPTTIRGQFSNMSLSLLDLYLGRGYNVSSIVTMTSQGMYGGTYLVEKPNLSSKRSELSQLSMYRVFEVGV

IRNPGLGAPVFHMTNYLEQPVSNDLSNCMVALGELKLAALCHGEDSITIPYQGSGKGVSFQLVKLGVWKSPADMQSWVPL

STDDPVIDRLYLSSHRGVIADNQAKWAVPTTRTDDKLRMETCFQQACKGKIQTLCENPEWAPLKDNRIPSYGVLSVDLSL

TVELKIKIASGFGPLITHGSGMDLYKSNHNNVYWLTIPPMKNLALGVINTLEWIPRFKVSPYLFTVPIKEAGEDCHAPTY

LPAEVDGDVKLSSNLVILPGQDLQYVLATYDTSRVEHAVVYYVYSPGRSFSYFYPFRLPIKGVPIELQVECFTWDQKLWC

RHFCVLADSESGGHITHSGMVGMGVSCTVTREDGTNRR

The above sequences include an N-terminal signal peptide, a MeV F ectodomain, a GCN4 trimerization domain, optionally a T4 Fibritin trimerization domain, a MeV H ectodomain, as well as various linker residues between segments.

Example 3

Multimeric MuV HN, Multimeric MeV H, and MuV Pre-F-MeV H Chimera

This example describes an embodiment of a recombinant MuV pre-F ectodomain trimer linked to MeV H ectodomain to provide a chimeric immunogen that elicits a cross-neutralizing immune response to MeV and MuV. Additionally, multimeric MuV HN and multimeric MeV H are described.

To increase the immunogenic footprint of the MuV F ectodomain trimer, a MeV H ectodomain was genetically fused to the C-terminus of the trimerization domain of each protomer of the trimer. The assessed construct included a MuV F ectodomain containing V206C-A223C, a mutation to eliminate the F1/F2 furin cleavage site, a trimerization domain fused to position 476 of the ectodomain, and a MeV H ectodomain linked to the C-terminus of the trimerization domain. In this embodiment, the trimerization domain included both a GCN4 trimerization domain and a T4 fibritin trimerization domain in series; however, either of these domains can also be used on their own. The format is illustrated in FIG. 6A. A corresponding sequence is shown below.

MuV F 206C/223C-476 + GCN4/Fd + MeV-H (SEQ ID NO: 28):
Mkafsvtclsfavfsssicvninilqqigyikqqvrqlsyysqssssyivvkllpniqptddscefksvtqynktlsnll lpiaeninniaspspgsrrhGGGagiaigiaalgvataaqvtaavslvqaqtnaraiaamknsiqatnravfevkegtqq laiavqaiqdhintimntqlnnmscqildnqlatslglyltelttCfqpqltnpalspisiqClrsllgsmtpavvqatl stsisaaeilsaglmegqiisvlldemqmivkiniptivtqsnalvidfysissfinnqesiiqlpdrileigneqwsyp anckltrhhifcqyneaerlslesklclagnisacvfspiagsymrrfvaldgtivancrsltclckspsypiyqpdhh avttidltacqtlsldgldfsivslsnityaenltislsqtintqpidistelskvnaslqnavkyikesnhqlqs IEDKIEEILSKIYHIENEIARIKKLIGEAP GS GYIPEAPRDGQAYVRKDGEWVLLSTFL GSGGGGGg Flavskgncsgpttirgqfsnmsislldlylgrgynvssivtmtsqgmyggtyivekpnlsskrselsqlsmyrvfevgv irnpglgapvfhmtnyleqpvsndlsncmvalgelklaalchgedsitipyqgsgkgvsfqlvklgvwkspadmqswvpl stddpvidrlylsshrgviadnqakwavpttrtddklrmetcfqqackgkiqticenpewaplkdnripsygvlsvdlsl tvelkikiasgfgplithgsgmdlyksnhnnvywltippmknlalgvintlewiprfkvspylftvpikeagedchapty ipaevdgdvklssnlvilpgqdlqyvlatydtsrvehavvyyvyspgrsfsyfypfripikgvpielqvecftwdqklwc rhfcvladsesgghithsgmvgmgvsctvtredgtnrr Negative stain EM of purified MuV F 206C-223C-476+ GCN4/Fd+MeV-H (SEQ ID NO: 28) shows that the F ectodomain maintains the prefusion conformation, with the three H ectodomains (one linked to each F protomer) arrayed C-terminal to the trimerization domain (FIG. 6A). The negative stain EM shows that this construct assembles with a conformation similar to MuV F-MuV HN descried in Example 1.

Additional immunogens were constructed containing multimers of the MeV H ectodomain head region, or the MuV HN ectodomain head region.

Trimeric MuV HN ectodomain head region and trimeric MeV H ectodomain head region were constructed by linking the N-terminus of the head region to a T4 fibritin trimerization domain. The sequences are provided as follows:

Fd-MuV HN (trimeric MuV HN, SEQ ID NO: 58)
mysmqlascvtltlvllvnsq GS GYIPEAPRDGQAYVRKDGEWVLLSTFL GSGGGGGg

NIPLVNDLRFINGINKFIIEDYATHDFSIGHPLNMPSFIPTATSPNGCTRIPSFSLGKTHWCYTHNVINANCKDHTSSNQ

YVSMGILVQTASGYPMFKTLKIQYLSDGLNRKSCSIATVPDGCAMYCYVSTQLETDDYAGSSPPTQKLTLLFYNDTVTER

TISPSGLEGNWATLVPGVGSGIYFENKLIFPAYGGVLPNSTLGVKSAREFFRPVNPYNPCSGPQQDLDQRALRSYFPSYF

SNRRIQSAFLVCAWNQILVTNCELVVPSSNQTMMGAEGRVLLINNRLLYYQRSTSWWPYELLYEISFTFTNSGPSSVNMS

WIPIYSFTRPGSGNCSGENVCPTACVSGVYLDPWPLTPYSHQSGINRNFYFTGALLNSSTTRVNPTLYVSALNNLKVLAP

YGTQGLFASYTTTTCFQDTGDASVYCVYIMELASNIVGEFQILPVLTRLTIT

Fd-MeV H (trimeric MeV H, SEQ ID NO: 59)
mysmqlascvtltlvllvnsq GS GYIPEAPRDGQAYVRKDGEWVLLSTFL GSGGGGGg

FLAVSKGNCSGPTTIRGQFSNMSLSLLDLYLGRGYNVSSIVTMTSQGMYGGTYLVEKPNLSSKRSELSQLSMYRVFEVGV

IRNPGLGAPVFHMTNYLEQPVSNDLSNCMVALGELKLAALCHGEDSITIPYQGSGKGVSFQLVKLGVWKSPADMQSWVPL

STDDPVIDRLYLSSHRGVIADNQAKWAVPTTRTDDKLRMETCFQQACKGKIQTLCENPEWAPLKDNRIPSYGVLSVDLSL

TVELKIKIASGFGPLITHGSGMDLYKSNHNNVYWLTIPPMKNLALGVINTLEWIPRFKVSPYLFTVPIKEAGEDCHAPTY

LPAEVDGDVKLSSNLVILPGQDLQYVLATYDTSRVEHAVVYVYYVYSPGRSFSYFYPFRLPIKGVPIELQVECFTWDQKLWC

RHFCVLADSESGGHITHSGMVGMGVSCTVTREDGTNRR

Dimeric MeV H was constructed by expressing the MeV H ectodomain head region in mammalian cells and purifying the resulting protein complex; the MeV H head dimerizes in physiological solution. The sequence of the MeV H head region is provided as follows:

```
Dimeric MeV H head region
                                        (SEQ ID NO: 60)
Mysmqlascvtltlvllvnsq flavskgncsgpttirgqfsnmslslld lylgrgynvssivtmtsqgmyggtylvekpnlsskrselsqlsmyrvfev gvirnpglgapvfhmtnyleqpvsndlsncmvalgelklaalchgedsit ipyqgsgkgvsfqlvklgvwkspadmqswvplstddpvidrlylsshrgv
```

-continued
```
iadngakwavpttrtddklrmetcfqqackgkiqtlcenpewaplkdnri psygvlsvdlsltvelkikiasgfgplithgsgmdlyksnhnnvywltip pmknlalgvintlewiprfkvspyiftvpikeagedchaptyipaevdgd vklssnlvilpgqdlqyvlatydtsrvehavvyyvyspgrsfsyfypfri pikgvpielqvecftwdqklwcrhfcvladsesgghithsgmvgmgvsct vtredgtnrr
```

Dimeric MeV H including the stalk and head regions can be constructed by expressing the MeV H ectodomain stalk and head regions in mammalian cells and purifying the resulting protein complex; the MeV H stalk and head dimerizes in physiological solution. Exemplary sequences of MeV H stalk and head regions are provided as follows:

```
MeV H stalk and head
                                                        (SEQ ID NO: 86)
mysmqlascvtltlvllvnsq  RLHraaiytaeihkslstnldvtnsiehqvkdvltplfkiiqdevqlrtpqrftdlv kfisdkikfinpdreydfrdltwcinpperikldydqycadvaaeelmnalvnstlletrttnqFLAVskgncsgpttir gqfsnmsislslldlylgrgynvssivtmtsqgmyggtyivekpnlsskrselsqlsmyrvfevgvirnpglgapvfhmtny leqpvsndlsncmvalgelklaalchgedsitipyqgsgkgvsfqlvklgvwksptdmqswvplstddpvidrlyisshr gviadnqakwavpttrtddklrmetcfqqackgkiqalcenpewaplkdnripsygvlsvdlsltvelkikiasgfgpli thgsgmdlyksnhnnvywltippmknlalgvintlewiprfkvspylfnvpikeagedchaptylpaevdgdvklssnlv ilpgqdlqyvlatydtsrvehavvyyvyspsrsfsyfypfripikgvpielqvecftwdqklwcrhfcvladsesgghit hsgmegmgvsctvtredgtnrr MeV H stalk and head 2
                                                        (SEQ ID NO: 87)
mysmqlascvtltlvllvnsq  raaiytaeihksistnldvtnsiehqvkdvltplfkiiqdevqlrtpqrftdivkfi sdkikfinpdreydfrdltwcinpperikldydqycadvaaeelmnalvnstlletrttnqFLAVskgncsgpttirgqf snmslslldlylgrgynvssivtmtsqgmyggtylvekpnlsskrselsqlsmyrvfevgvirnpglgapvfhmtnyleq pvsndlsncmvalgelklaalchgedsitipyqgsgkgvsfqlvklgvwksptdmqswvplstddpvidrlylsshrgvi adnqakwavpttrtddklrmetcfqqackgkiqalcenpewaplkdnripsygvlsvdlsitvelkikiasgfgplithg sgmdlyksnhnnvywltippmknlaigvintlewiprfkvspylfnvpikeagedchaptyipaevdgdvkissnlviip gqdiqyviatydtsrvehavvyyvyspsrsfsyfypfripikgvpielqvecftwdqklwcrhfcvladsesgghithsg megmgvsctvtredgtnrr MeV H stalk and head 3
                                                        (SEQ ID NO: 88)
mysmqlascvtltlvllvnsq  LHraaiytaeihksistnldvtnsiehqvkdvltplfkligdevglrtpqrftdivk fisdkikfinpdreydfrdltwcinpperikldydqycadvaaeelmnalvnstlletrttnqFLAVskgncsgpttirg qfsnmslslldlylgrgynvssivtmtsqgmyggtylvekpnlsskrselsqlsmyrvfevgvirnpglgapvfhmtnyl eqpvsndlsncmvalgelklaalchgedsitipyqgsgkgvsfqlvklgvwksptdmqswvplstddpvidrlylsshrg viadnqakwavpttrtddklrmetcfqqackgkiqalcenpewaplkdnripsygvlsvdlsitvelkikiasgfgplit hgsgmdlyksnhnnvywltippmknlalgvintlewiprfkvspylfnvpikeagedchaptylpaevdgdvkissnlvi lpgqdlqyvlatydtsrvehavvyyvyspsrsfsyfypfripikgvpielqvecftwdqklwcrhfcvladsesgghith sgmegmgvsctvtredgtnrr MeV H stalk and head 4
                                                        (SEQ ID NO: 89)
mysmqlascvtltlvllvnsq  taeihkslstnldvtnsiehqvkdvltplfkligdevglrtpqrftdivkfisdkik flnpdreydfrdltwcinpperikldydqycadvaaeelmnalvnstlletrttnqFLAVskgncsgpttirgqfsnmsl
```

-continued

```
slldlylgrgynvssivtmtsqgmyggtyivekpnlsskrselsqlsmyrvfevgvirnpglgapvfhmtnyleqpvsnd lsncmvalgelklaalchgedsitipyqgsgkgvsfqlvklgvwksptdmqswvplstddpvidrlyisshrgviadnqa kwavpttrtddklrmetcfqqackgkiqalcenpewaplkdnripsygvlsvdlsltvelkikiasgfgplithgsgmdl yksnhnnvywltippmknlalgvintlewiprfkvspylfnvpikeagedchaptyipaevdgdvkissnlviipgqdlq yvlatydtsrvehavvyvvyspsrsfsyfypfripikgvpielqvecftwdqklwcrhfcvladsesgghithsgmegmg vsctvtredgtnrr
```

MuV HN including the stalk and head regions can be constructed by expressing the MuV HN ectodomain stalk and head regions in mammalian cells and purifying the resulting protein. Exemplary sequences of MuV HN stalk [15] and head regions are provided as follows:

MuV HN stalk and head (SEQ ID NO: 90)

```
mysmqlascvtltlvllvnsq ELVRmindqglsnqlssitdkiresatmiasavgvmnqvihgvtvslplqiegnqnq llatlatictsqkqvsncstNIPlvndlrfinginkfiiedyathdfsighpinmpsfiptatspngctripsfslgkth wcythnvinanckdhtssnqyvsmgilvqtasgypmfktikiqylsdglnrkscsiatvpdgcamycyvstqletddyag sspptqkltllfyndtvtertispsglegnwativpgvgsgiyfenklifpayggvlpnstigvksareffrpvnpynpc sgpqqdldqralrsyfpsyfsnrriqsafivcawnqilvtncelvvpssnqtmmgaegrvllinnrllyyqrstswwpye llyeisftftnsgpssvnmswipiysftrpgsgncsgenvcptacvsgvyidpwpltpyshqsginrnfyftgallnsst trvnptlyvsalnnlkvlapygtqglfasyttttcfqdtgdasvycvyimelasnivgefqilpvltritit
```

MuV HN stalk and head 2

(SEQ ID NO: 91)

```
mysmqlascvtltlvllvnsq dqglsnqlssitdkiresatmiasavgvmnqvihgvtvslplqiegnqnqllatlat ictsqkqvsncstNIPlvndlrfinginkfiiedyathdfsighpinmpsfiptatspngctripsfslgkthwcythnv inanckdhtssnqyvsmgilvqtasgypmfktikiqylsdglnrkscsiatvpdgcamycyvstqletddyagsspptqk itllfyndtvtertispsglegnwatlvpgvgsgiyfenklifpayggvlpnstlgvksareffrpvnpynpcsgpqqdl dqrairsyfpsyfsnrriqsaflvcawnqilvtnceivvpssnqtmmgaegrvllinnrllyyqrstswwpyellyeisf tftnsgpssvnmswipiysftrpgsgncsgenvcptacvsgvyidpwpltpyshqsginrnfyftgallnssttrvnptl yvsalnnlkvlapygtqglfasyttttcfqdtgdasvycvyimelasnivgefqilpvltritit
```

MuV HN stalk and head 3

(SEQ ID NO: 92)

```
mysmqlascvtltlvllvnsq qlsnqlssitdkiresatmiasavgvmnqvihqvtvslplqieqnqnqllatlatic tsqkqvsncstNIPlvndlrfinginkfiiedyathdfsighpinmpsfiptatspngctripsfslgkthwcythnvin anckdhtssnqyvsmgilvqtasgypmfktikiqylsdglnrkscsiatvpdgcamycyvstqletddyagsspptqklt llfyndtvtertispsglegnwatlvpgvgsgiyfenklifpayggvlpnstigvksareffrpvnpynpcsgpqqdldq rairsyfpsyfsnrriqsaflvcawnqilvtnceivvpssnqtmmgaegrvllinnrllyyqrstswwpyellyeisftf tnsgpssvnmswipiysftrpgsgncsgenvcptacvsgvyidpwpltpyshqsginrnfyftgallnssttrvnptlyv salnnlkvlapygtqglfasyttttcfqdtgdasvycvyimelasnivgefqilpvltritit
```

MuV HN stalk and head 4

(SEQ ID NO: 93)

```
mysmqlascvtltlvllvnsq LVRmindqqlsnqlssitdkiresatmiasavqvmnqvihqvtvslplqieqnqnql latlatictsqkqvsncstNIPlvndlrfinginkfiiedyathdfsighpinmpsfiptatspngctripsfslgkthw cythnvinanckdhtssnqyvsmgilvqtasgypmfktikiqylsdglnrkscsiatvpdgcamycyvstqletddyags spptqkltllfyndtvtertispsglegnwativpgvgsgiyfenklifpayggvlpnstlgvksareffrpvnpynpcs gpqqdldqrairsyfpsyfsnrriqsafivcawnqlivtnceivvpssnqtmmgaegrvllinnrllyyqrstswwpyel
```

-continued

```
lyeisftftnsgpssvnmswipiysftrpgsgncsgenvcptacvsgvyidpwpltpyshqsginrnfyftgallnsstt rvnptlyvsalnnlkvlapygtqglfasyttttcfqdtgdasvycvyimelasnivgefqilpvltritit
```

5

Additionally, chimeric versions of the trimeric MuV HN ectodomain head region and trimeric MeV H ectodomain head region were constructed by linking these molecules to the N- and C-termini of a T4 fibritin trimerization domain and/or GCN4 trimerization domain. The sequences are provided as follows:

```
MuV HN-Fd-MeV H
                                                            (SEQ ID NO: 82)
mysmqlascvtltlvllvnsq NIPlvndlrfinginkfiiedyathdfsighpinmpsfiptatspngctripsfsig kthwcythnvinanckdhtssnqyvsmgilvqtasgypmfktikiqyisdglnrkscsiatvpdgcamycyvstqletdd yagsspptqkltllfyndtvtertispsglegnwatlvpgvgsgiyfenklifpayggvlpnstlgvksareffrpvnpy npcsgpqqdldqrairsyfpsyfsnrriqsafivcawnqilvtncelvvpssnqtmmgaegrvllinnrllyyqrstsww pyellyeisftftnsgpssvnmswipiysftrpgsgncsgenvcptacvsgvyidpwpltpyshqsginrnfyftgalln ssttrvnptlyvsalnnlkvlapygtqglfasyttttcfqdtgdasvycvyimelasnivgefqilpvltrltit  gg GSGYIPEAPRDGQAYVRKDGEWVLLSTFLGSGGGGGg flavskgncsgpttirgqfsnmsislldlylgrgynvssivtmtsqgmyggtyivekpnlsskrselsqlsmyrvfevgv irnpglgapvfhmtnyleqpvsndlsncmvalgelklaalchgedsitipyqgsgkgvsfqlvklgvwksptdmqswvpl stddpvidrlyisshrgviadnqakwavpttrtddklrmetcfqqackgkiqalcenpewaplkdnripsygvlsvdlsl tvelkikiasgfgplithgsgmdlyksnhnnvywltippmknlalgvintlewiprfkvspylfnvpikeagedchapty lpaevdgdvklssnlvilpgqdlqyvlatydtsrvehavvyyvyspsrsfsyfypfripikgvpielqvecftwdqklwc rhfcvladsesgghithsgmegmgvsctvtredgtnrr MuV HN-GCN4/Fd-MeV H
                                                            (SEQ ID NO: 83)
mysmqlascvtltlvllvnsq NIPlvndlrfinginkfiiedyathdfsighpinmpsfiptatspngctripsfsig kthwcythnvinanckdhtssnqyvsmgilvqtasgypmfktikiqyIsdglnrkscsiatvpdgcamycyvstqletdd yagsspptqkltllfyndtvtertispsglegnwatlvpgvgsgiyfenklifpayggvlpnstlgvksareffrpvnpy npcsgpqqdldqralrsyfpsyfsnrriqsaflvcawngilvtncelvvpssnqtmmgaegrvllinnrllyyqrstsww pyellyeisftftnsgpssvnmswipiysftrpgsgncsgenvcptacvsgvyldpwpltpyshqsginrnfyftgalln ssttrvnptlyvsalnnlkvlapygtqglfasyttttcfqdtgdasvycvyimelasnivgefqilpvltrltit  gg KLMKQIEDKIEEILSKIYHIENEIARIKKLIGEAP GSGYIPEAPRDGQAYVRKDGEWVLLSTFL GSGGGGGg flavskgncsgpttirgqfsnmsislldlylgrgynvssivtmtsqgmyggtyivekpnlsskrselsqlsmyrvfevgv irnpglgapvfhmtnyleqpvsndlsncmvalgeiklaalchgedsitipyqgsgkgvsfqlvklgvwksptdmqswvpl stddpvidrlyisshrgviadnqakwavpttrtddklrmetcfqqackgkiqalcenpewaplkdnripsygvlsvdlsl tvelkikiasgfgplithgsgmdlyksnhnnvywltippmknlalgvintlewiprfkvspylfnvpikeagedchapty ipaevdgdvklssnlvilpgqdlqyvlatydtsrvehavvyyvyspsrsfsyfypfripikgvpielqvecftwdqklwc rhfcvladsesgghithsgmegmgvsctvtredgtnrr MeV H-Fd-MuV HN
                                                            (SEQ ID NO: 84)
mysmqlascvtltlvllvnsq FLAvskgncsgpttirgqfsnmslslldlylgrgynvssivtmtsqgmyggtylvek pnlsskrselsqlsmyrvfevgvirnpglgapvfhmtnyleqpvsndlsncmvalgeiklaalchgedsitipyqgsgkg vsfqlvklgvwksptdmqswvplstddpvidrlyisshrgviadnqakwavpttrtddklrmetcfqqackgkiqalcen pewaplkdnripsygvlsvdlsitvelkikiasgfgplithgsgmdlyksnhnnvywltippmknlalgvintlewiprf kvspylfnvpikeagedchaptylpaevdgdvklssnlvilpgqdlqyvlatydtsrvehavvyyvyspsrsfsyfypfr ipikgvpielqvecftwdqklwcrhfcvladsesgghithsgmegmgvsctvtredgtnrr
```

-continued
GSGYIPEAPRDGQAYVRKDGEWVLLSTFL  GSGGGGGg

NIPlvndlrfinginkfiiedyathdfsighpinmpsfiptatspngctripsfslgkthwcythnvinanckdhtssnq yvsmgilvqtasgypmfktikiqylsdglnrkscsiatvpdgcamycyvstqletddyagsspptqkltlifyndtvter tispsglegnwativpgvgsgiyfenklifpayggvlpnstigvksareffrpvnpynpcsgpqqdldqralrsyfpsyf snrriqsaflvcawnqilvtncelvvpssnqtmmgaegrvllinnrllyyqrstswwpyellyeisftftnsgpssvnms wipiysftrpgsgncsgenvcptacvsgvyldpwpltpyshqsginrnfyftgallnssttrvnptlyvsalnnlkvlap ygtqglfasyttttcfqdtgdasvycvyimelasnivgefqilpvltrltit MeV H-GCN4/Fd-MuV HN
                                                                    (SEQ ID NO: 85)
mysmqlascvtltlvllvnsq  FLAvskgncsgpttirgqfsnmslslldlylgrgynvssivtmtsqgmyggtylvek pnlsskrselsqlsmyrvfevgvirnpglgapvfhmtnyleqpvsndlsncmvalgeiklaalchgedsitipyqgsgkg vsfqlvklgvwksptdmqswvplstddpvidrlyisshrgviadnqakwavpttrtddklrmetcfqqackgkiqalcen pewaplkdnripsygvlsvdlsltvelkikiasgfgplithgsgmdlyksnhnnvywltippmknlalgvintlewiprf kvspylfnvpikeagedchaptyIpaevdgdvkissnlvilpgqdlqyvlatydtsrvehawyyvyspsrsfsyfypfr lpikgvpielqvecftwdqklwcrhfcvladsesgghithsgmegmgvsctvtredgtnrr MKQIEDKIEEILSKIYHIENEIARIKKLIGEAP  GSGYIPEAPRDGQAYVRKDGEWVLLSTFL  GSGGGGGg NIPlvndlrfinginkfiiedyathdfsighpinmpsfiptatspngctripsfslgkthwcythnvinanckdhtssnq yvsmgilvqtasgypmfktikiqylsdglnrkscsiatvpdgcamycyvstqletddyagsspptqkltlifyndtvter tispsglegnwativpgvgsgiyfenklifpayggvlpnstigvksareffrpvnpynpcsgpqqdldqralrsyfpsyf snrriqsaflvcawnqilvtncelvvpssnqtmmgaegrvllinnrllyyqrstswwpyellyeisftftnsgpssvnms wipiysftrpgsgncsgenvcptacvsgvyldpwpltpyshqsginrnfyftgallnssttrvnptlyvsalnnlkvlap ygtqglfasyttttcfqdtgdasvycvyimelasnivgefqilpvltrltit

35

The MeV H ectodomain head dimer (SEQ ID NO: 60), MeV H ectodomain head trimer (SEQ ID NO: 59), and MuV HN ectodomain head trimer (SEQ ID NO: 58) were designed, expressed, purified and characterized by negative stain EM (see FIG. 6A).

Mice were immunized with the purified constructs and sera assessed for MeV and MuV neutralization by PRNT. The immunogens assessed were the MeV H dimer or trimer (SEQ ID NO: 59 or 60), prefusion MuV F ectodomain trimer (MuV F V206C-A223C-GGG-476-GCN4, SEQ ID NO: 11), MuV pre-F-MeV H chimera (MuV F 206C-223C-476+GCN4/Fd+MeV_H_3INB-tHS (SEQ ID NO: 28), and MuV HN trimer (SEQ ID NO: 58).

For MeV neutralization (FIG. 6B), the MeV H dimer elicited PRNT $ID_{60}$ averaging 66,000, the MeV H trimer 30,000, and the trimerized H on the C-terminus of prefusion MuV F 35,000. These results were quite surprising given the much lower neutralization titers observed from immunization with prefusion MeV F trimer (PRNT of 873; see FIG. 5C). Human PRNT titers following 2×MMR vaccination average approximately 650. The very high MeV PRNT titer for the MeV H designs was not expected since the prefusion F ectodomain trimer was initially believed to provide a better immune response (similar to other paramyxoviruses, such as RSV). Unexpectedly, the multimeric MeV H immunogens showed very good immunogenicity, being up to 75-fold more potent than prefusion-stabilized MeV F ectodomain trimer and approximately 100-fold higher than human responses following MMR vaccination.

For MuV neutralization (FIG. 6C), each of the assessed immunogens elicited an immune response above the protective threshold, and the soluble trimerized MuV HN elicited a very potent immune response, which is quite surprising given the minimal response elicited by soluble MuV HN monomer (FIG. 4C). Surprisingly, there was a 13.4-fold increase in neutralization potency between the MuV HN ectodomain monomer and the trimeric MuV HN ectodomain.

Protein production, analysis and immunization were performed as noted above.

It will be apparent that the precise details of the methods or compositions described may be varied or modified without departing from the spirit of the described embodiments. We claim all such modifications and variations that fall within the scope and spirit of the claims below.

It is claimed is:

1. An immunogen, comprising:
a recombinant Mumps virus (MuV) F ectodomain trimer stabilized in a prefusion conformation by one or more amino acid substitutions in protomers of the trimer, the amino acid substitutions comprising cysteine substitutions that form a non-natural disulfide bond to stabilize the MuV F ectodomain trimer in the prefusion conformation, wherein the cysteine substitutions are located at one or more of MuV F positions 86 and 215, positions 155 and 161, positions 165 and 231, positions 206 and 223, positions 209 and 214, and positions 221 and 255, according to a reference MuV F amino acid sequence set forth as SEQ ID NO: 1.

2. The immunogen of claim 1, wherein the cysteine substitutions are located at one or more of MuV F positions 86 and 215, positions 155 and 161, positions 165 and 231, positions 206 and 223, and positions 221 and 255.

3. The immunogen of claim 1, wherein the cysteine substitutions are located at MuV F positions 206 and 223.

4. The immunogen of claim 1, wherein the cysteine substitutions at:
MuV F positions 86 and 215 are N86C and A215C substitutions;
MuV F positions 155 and 161 are K155C and L161C substitutions;
MuV F positions 165 and 231 are V165C and M231C substitutions;
MuV F positions 206 and 223 are V206C and A223C substitutions;
MuV F positions 209 and 214 are P209C and P214C substitutions; or
MuV F positions 221 and 255 are I221C and M255C substitutions.

5. The immunogen of claim 1, wherein the protomers of the recombinant MuV F ectodomain trimer comprise a $F_2$ protein comprising or consisting of MuV F positions 20-100 and a $F_1$ ectodomain comprising or consisting of MuV F positions 104-469, 104-476, or 104-483.

6. The immunogen of claim 1, wherein the protomers of the trimer further comprise a mutation to remove a F1/F2 furin cleavage site of the MuV F ectodomain and optionally a first residue of a fusion peptide of a F1 ectodomain.

7. The immunogen of claim 6, wherein the mutation to remove the $F_1/F_2$ furin cleavage site and the first residue of the fusion peptide comprise a deletion of MuV F positions 101-103 with positions 100 and 104 fused by a peptide linker.

8. The immunogen of claim 7, wherein the peptide linker is a Gly-Gly-Gly linker.

9. The immunogen of claim 1, wherein the protomers of the MuV F ectodomain trimer comprise an amino acid sequence at least 90% identical to:
residues 20-483 of any one of SEQ ID NOs: 3-8,
residues 20-476 of any one of SEQ ID NOs: 11-16, 26, or 51, or residues 20-469 of any one of SEQ ID NOs: 19-24; and wherein the protomers comprise the one or more amino acid substitutions that stabilize the MuV F ectodomain trimer in the prefusion conformation.

10. The immunogen of claim 9, wherein the protomers of the MuV F ectodomain trimer comprise or consist of the amino acid sequence set forth as:
residues 20-483 of any one of SEQ ID NOs: 3-8,
residues 20-476 of any one of SEQ ID NOs: 11-16, 26, or 51, or
residues 20-469 of any one of SEQ ID NOs: 19-24.

11. The immunogen of claim 1, wherein the protomers of the recombinant MuV F ectodomain trimer are fused C-terminally to a trimerization domain.

12. The immunogen of claim 11, wherein the trimerization domain comprises a GCN4 trimerization domain, a T4 fibritin trimerization domain, or both.

13. The immunogen of claim 12, wherein:
the GCN4 trimerization domain comprises an amino acid sequence set forth as

```
                              (SEQ ID NO: 33)
        IEDKIEEILSKIYHIENEIARIKKLIGEAP.
``` the T4 fibritin trimerization domain comprises an amino acid sequence set forth as

```
                              SEQ ID NO: 34)
        GYIPEAPRDGQAYVRKDGEWVLLSTFL.
``` the trimerization domain comprising both the GCN4 and T4 fibritin trimerization domains comprises an amino acid sequence set forth as

```
                              (SEQ ID NO: 35)
IEDKIEEILSKIYHIENEIARIKKLIGEAPGSGYIPEAPRDGQAYVRKD

GEWVLLSTFL.
```

14. The immunogen of claim 11, wherein the protomers of the MuV F ectodomain trimer fused to the trimerization domain comprise an amino acid sequence at least 90% identical to:
residues 20-513 of any one of SEQ ID NOs: 3-8,
residues 20-506 of any one of SEQ ID NOs: 11-16, 26, or 51, or
residues 20-499 of any one of SEQ ID NOs: 19-24; and wherein the protomers comprise the one or more amino acid substitutions that stabilize the MuV F ectodomain trimer in the prefusion conformation.

15. The immunogen of claim 14, wherein the protomers of the MuV F ectodomain trimer fused to the trimerization domain comprise or consist of the amino acid sequence set forth as:

residues 20-513 of any one of SEQ ID NOs: 3-8,
residues 20-506 of any one of SEQ ID NOs: 11-16, 26, or
   51, or
residues 20-499 of any one of SEQ ID NOs: 19-24.

16. The immunogen of claim 1, wherein the protomers of the recombinant MuV F ectodomain trimer are linked to a heterologous protein.

17. The immunogen of claim 16, wherein the heterologous protein is an ectodomain head or ectodomain stalk and head of a MeV H protein or a MuV HN protein.

18. The immunogen of claim 17, wherein the ectodomain head or ectodomain stalk and head of the MeV H protein or the MuV HN protein is fused C-terminally to a trimerization domain that is fused C-terminally to the protomer of the recombinant MuV F ectodomain trimer.

19. The immunogen of claim 18, wherein the protomers of the MuV F ectodomain trimer linked to the trimerization domain and the ectodomain of the MeV H protein or the ectodomain of a MuV HN protein comprise an amino acid sequence set forth as residues 20-966 of SEQ ID NO: 27, residues 21-981 of SEQ ID NO: 28, or residues 20-1006 of SEQ ID NO: 29.

20. The immunogen of claim 1, wherein the protomers of the recombinant MeV F ectodomain trimer or the recombinant MuV F ectodomain trimer further comprise one or more additional amino acid substitutions that increase stabilization of the prefusion conformation, increase solubility, or reduce an unwanted immune response.

21. The immunogen of claim 1, conjugated to a heterologous carrier.

22. The immunogen of claim 1, wherein the immunogen is soluble.

23. The immunogen of claim 1, wherein the protomers of the recombinant MuV F ectodomain trimer are fused to a transmembrane domain by a peptide linker, or directly fused to the transmembrane domain.

24. The immunogen of claim 23, wherein the protomers of the recombinant MuV F ectodomain trimer comprise a full-length $F_1$ protein.

25. A virus-like particle comprising the immunogen of claim 1.

26. A self-assembling protein nanoparticle comprising the immunogen of claim 1.

27. A nucleic acid molecule encoding the immunogen of claim 1.

28. The nucleic acid molecule of claim 27, operably linked to a promoter.

29. A vector comprising the nucleic acid molecule of claim 27.

30. The vector of claim 29, wherein the vector is an RNA vector.

31. A method of producing an immunogen, comprising:
   expressing the nucleic acid molecule of claim 27 in a host cell; and
   purifying the immunogen.

32. An immunogenic composition, comprising the immunogen of claim 1, a nucleic acid molecule encoding the immunogen, a vector comprising the nucleic acid molecule, a virus like particle comprising the immunogen, or a self-assembling protein nanoparticle comprising the immunogen, and a pharmaceutically acceptable carrier.

33. A method of eliciting an immune response to MuV in a subject, comprising administering to the subject an effective amount of the immunogenic composition of claim 32 to elicit the immune response.

34. The immunogen of claim 1, wherein the cysteine substitutions are located at one or more of MuV F positions 86 and 215, positions 165 and 231, positions 206 and 223, and positions 221 and 255, and
   (i) the protomers of the MuV F ectodomain trimer are fused to a trimerization domain or transmembrane domain at one of MuV F positions 469-483, or
   (ii) the protomers of the recombinant MuV F ectodomain trimer comprise a $F_2$ protein comprising or consisting of MuV F positions 20-100, a $F_1$ ectodomain comprising or consisting of MuV F positions 104-483, and a MuV F transmembrane domain and cytoplasmic tail comprising or consisting of positions 484-538,
   wherein the amino acid positions are according to the reference MuV F amino acid sequence set forth as SEQ ID NO: 1.

35. The immunogen of claim 34, wherein the protomers of the MuV F ectodomain trimer are fused to the trimerization domain, and the transmembrane domain is fused at one of MuV F positions 469, 476, or 483.

* * * * *